(12) United States Patent
Shelton, IV et al.

(10) Patent No.: US 11,963,683 B2
(45) Date of Patent: Apr. 23, 2024

(54) METHOD FOR OPERATING TIERED OPERATION MODES IN A SURGICAL SYSTEM

(71) Applicant: Cilag GmbH International, Zug (CH)

(72) Inventors: Frederick E. Shelton, IV, New Vienna, OH (US); Patrick L. Creamer, New Orleans, LA (US); Shane R. Adams, Lebanon, OH (US); Jason L. Harris, Lebanon, OH (US); Kevin M. Fiebig, Cincinnati, OH (US); Michael J. Vendely, Lebanon, OH (US)

(73) Assignee: Cilag GmbH International, Zug (CH)

( * ) Notice: Subject to any disclaimer, the term of this patent is extended or adjusted under 35 U.S.C. 154(b) by 35 days.

(21) Appl. No.: 17/062,504

(22) Filed: Oct. 2, 2020

(65) Prior Publication Data

US 2022/0104822 A1 Apr. 7, 2022

(51) Int. Cl.
*A61B 34/10* (2016.01)
*A61B 17/115* (2006.01)
(Continued)

(52) U.S. Cl.
CPC .......... *A61B 17/1155* (2013.01); *A61B 34/10* (2016.02); *A61B 34/25* (2016.02);
(Continued)

(58) Field of Classification Search
CPC ..... A61B 17/1155; A61B 34/30; A61B 90/36; A61B 90/98; A61B 34/20; A61B 90/30;
(Continued)

(56) References Cited

U.S. PATENT DOCUMENTS 5,518,164 A 5/1996 Hooven
5,754,192 A 5/1998 Sugaya
(Continued)

FOREIGN PATENT DOCUMENTS

CA 3089858 A1 8/2019
CN 114625037 A 6/2022
(Continued)

OTHER PUBLICATIONS

U.S. Appl. No. 16/182,290, filed Nov. 6, 2018, Ethicon LLC.
(Continued)

*Primary Examiner* — Nathaniel C Chukwurah
(74) *Attorney, Agent, or Firm* — Condo Roccia Koptiw LLP

(57) ABSTRACT

A surgical system may include tiered-access features. The surgical system may be used to analyze at least a portion of a surgical field. Based on a control parameter, the system may scale up or down various capabilities, such as visualization processing, endocutter communication, endocutter algorithm updates, smart cartridge connectivity, smart motor control for circular stapler, smart energy control, cloud analytics, hub connectivity control, and/or hub visualization and control interactions. The control parameter may include system aspects such as processing capability or bandwidth for example and/or the identification of an appropriate service tier.

15 Claims, 216 Drawing Sheets

(51) Int. Cl.
*A61B 34/00* (2016.01)
*A61B 90/00* (2016.01)
*A61B 90/92* (2016.01)
*A61B 90/98* (2016.01)
*A61B 17/00* (2006.01)

(52) U.S. Cl.
CPC .............. *A61B 90/36* (2016.02); *A61B 90/92* (2016.02); *A61B 90/98* (2016.02); *A61B 2017/00199* (2013.01); *A61B 2034/107* (2016.02); *A61B 2090/365* (2016.02)

(58) Field of Classification Search
CPC ............ A61B 17/07207; A61B 90/361; A61B 34/10; A61B 34/25; A61B 90/92; A61B 1/000094; A61B 5/0075; A61B 18/00; A61B 2017/00398; A61B 2017/0046; A61B 2017/00061; A61B 2562/0219; A61B 2034/107; A61B 2034/256; A61B 2090/0803; A61B 2217/007; A61B 2017/00473; A61B 2034/2065; A61B 2090/065; A61B 2090/365; A61B 50/13; A61B 2034/2059; A61B 2034/254; A61B 2562/0223; A61B 2017/0003; A61B 2017/00026; A61B 2217/005; A61B 2090/0808; A61B 34/37; A61B 2017/00199; A61B 2017/00128; A61B 2017/07271; A61B 2017/00017; A61B 2090/371; A61B 2034/2048; A61B 2017/07285; A61B 2017/00119; G16H 40/67; G16H 40/40; G06K 7/10297; G06K 17/00

See application file for complete search history.

(56) References Cited

U.S. PATENT DOCUMENTS

| | | |
|---|---|---|
| 6,352,532 B1 | 3/2002 | Kramer et al. |
| 6,443,973 B1 | 9/2002 | Whitman |
| 6,451,015 B1 | 9/2002 | Rittman, III et al. |
| 6,847,336 B1 | 1/2005 | Lemelson et al. |
| 7,032,798 B2 | 4/2006 | Whitman et al. |
| 7,164,940 B2 | 1/2007 | Hareyama et al. |
| 7,496,395 B2 | 2/2009 | Serov et al. |
| 7,667,592 B2 | 2/2010 | Ohyama et al. |
| 7,670,334 B2 | 3/2010 | Hueil et al. |
| 7,803,151 B2 | 9/2010 | Whitman |
| 7,833,219 B2 | 11/2010 | Tashiro et al. |
| 7,839,354 B2 | 11/2010 | Moriwaki |
| 8,157,145 B2 | 4/2012 | Shelton, IV et al. |
| 8,210,411 B2 | 7/2012 | Yates et al. |
| 8,255,045 B2 | 8/2012 | Gharib et al. |
| 8,476,227 B2 | 7/2013 | Kaplan et al. |
| 8,523,043 B2 | 9/2013 | Ullrich et al. |
| 8,608,045 B2 | 12/2013 | Smith et al. |
| 8,851,354 B2 | 10/2014 | Swensgard et al. |
| 8,918,207 B2 | 12/2014 | Prisco |
| 8,960,519 B2 | 2/2015 | Whitman et al. |
| 9,011,427 B2 | 4/2015 | Price et al. |
| 9,072,535 B2 | 7/2015 | Shelton et al. |
| 9,123,155 B2 | 9/2015 | Cunningham et al. |
| 9,250,172 B2 | 2/2016 | Harris et al. |
| 9,283,054 B2 | 3/2016 | Morgan et al. |
| 9,345,481 B2 | 5/2016 | Hall et al. |
| 9,516,239 B2 | 12/2016 | Blanquart et al. |
| 9,538,962 B1 | 1/2017 | Hannaford et al. |
| 9,582,055 B2 | 2/2017 | De Jong et al. |
| 9,700,292 B2 | 7/2017 | Nawana et al. |
| 9,743,016 B2 | 8/2017 | Nestares et al. |
| 9,777,913 B2 | 10/2017 | Talbert et al. |
| 9,913,642 B2 | 3/2018 | Leimbach et al. |
| 9,993,305 B2 | 6/2018 | Andersson |
| 10,095,942 B2 | 10/2018 | Mentese et al. |
| 10,244,991 B2 | 4/2019 | Shademan et al. |
| 10,492,783 B2 | 12/2019 | Shelton et al. |
| 10,639,037 B2 | 5/2020 | Shelton, IV et al. |
| 10,695,081 B2 | 6/2020 | Shelton et al. |
| 10,881,399 B2 | 1/2021 | Shelton, IV et al. |
| 10,912,567 B2 | 2/2021 | Shelton, IV et al. |
| 10,987,178 B2 | 4/2021 | Shelton, IV et al. |
| 11,123,074 B2 | 9/2021 | Adams et al. |
| 11,185,331 B2 | 11/2021 | Adams et al. |
| 11,284,963 B2 | 3/2022 | Shelton, IV et al. |
| 11,304,763 B2 | 4/2022 | Shelton, IV et al. |
| 2004/0108825 A1 | 6/2004 | Lee et al. |
| 2005/0033117 A1 | 2/2005 | Ozaki et al. |
| 2005/0128184 A1 | 6/2005 | Mcgreevy |
| 2005/0134525 A1 | 6/2005 | Tanghe et al. |
| 2005/0187576 A1 | 8/2005 | Whitman et al. |
| 2005/0206583 A1 | 9/2005 | Lemelson et al. |
| 2006/0004286 A1 | 1/2006 | Chang et al. |
| 2006/0076385 A1 | 4/2006 | Etter et al. |
| 2006/0082542 A1 | 4/2006 | Morita et al. |
| 2006/0109238 A1 | 5/2006 | Lau et al. |
| 2006/0184160 A1 | 8/2006 | Ozaki et al. |
| 2006/0273135 A1 | 12/2006 | Beetel |
| 2007/0013336 A1 | 1/2007 | Nowlin et al. |
| 2007/0055304 A1 | 3/2007 | Whitman |
| 2007/0151390 A1 | 7/2007 | Blumenkranz et al. |
| 2007/0173689 A1 | 7/2007 | Ozaki et al. |
| 2007/0225690 A1 | 9/2007 | Sekiguchi et al. |
| 2008/0058593 A1 | 3/2008 | Gu et al. |
| 2008/0135736 A1 | 6/2008 | Koiwai et al. |
| 2008/0319275 A1 | 12/2008 | Chiu et al. |
| 2009/0036750 A1 | 2/2009 | Weinstein et al. |
| 2009/0046146 A1 | 2/2009 | Hoyt |
| 2009/0090763 A1 | 4/2009 | Zemlok et al. |
| 2009/0128084 A1 | 5/2009 | Johnson et al. |
| 2009/0248022 A1 | 10/2009 | Falkenstein et al. |
| 2010/0089970 A1 | 4/2010 | Smith et al. |
| 2010/0096431 A1 | 4/2010 | Smith et al. |
| 2010/0131482 A1 | 5/2010 | Linthicum et al. |
| 2010/0312575 A1 | 12/2010 | Witt |
| 2011/0017801 A1 | 1/2011 | Zemlok et al. |
| 2011/0095067 A1 | 4/2011 | Ohdaira |
| 2011/0144640 A1 | 6/2011 | Heinrich et al. |
| 2011/0181394 A1 | 7/2011 | Blair |
| 2012/0069131 A1 | 3/2012 | Abelow |
| 2012/0116365 A1 | 5/2012 | Price et al. |
| 2012/0138658 A1 | 6/2012 | Ullrich et al. |
| 2012/0182409 A1 | 7/2012 | Moriyama et al. |
| 2012/0205419 A1 | 8/2012 | Weir et al. |
| 2012/0211542 A1 | 8/2012 | Racenet |
| 2012/0248167 A1 | 10/2012 | Flanagan et al. |
| 2012/0253329 A1 | 10/2012 | Zemlok et al. |
| 2013/0116218 A1 | 5/2013 | Kaplan et al. |
| 2013/0197531 A1 | 8/2013 | Boukhny et al. |
| 2013/0245456 A1 | 9/2013 | Ferguson, Jr. et al. |
| 2014/0018637 A1 | 1/2014 | Bennett et al. |
| 2014/0066700 A1 | 3/2014 | Wilson et al. |
| 2014/0087999 A1 | 3/2014 | Kaplan |
| 2014/0160002 A1 | 6/2014 | Dent |
| 2014/0160259 A1 | 6/2014 | Blanquart et al. |
| 2014/0160260 A1 | 6/2014 | Blanquart et al. |
| 2014/0160318 A1 | 6/2014 | Blanquart et al. |
| 2014/0160319 A1 | 6/2014 | Nestares et al. |
| 2014/0166728 A1 | 6/2014 | Swayze et al. |
| 2014/0175150 A1 | 6/2014 | Shelton, IV et al. |
| 2014/0201126 A1 | 7/2014 | Zadeh et al. |
| 2014/0214311 A1 | 7/2014 | Stevens et al. |
| 2014/0224856 A1 | 8/2014 | Smith et al. |
| 2014/0246479 A1 | 9/2014 | Baber et al. |
| 2014/0258917 A1 | 9/2014 | Greif et al. |
| 2014/0263541 A1 | 9/2014 | Leimbach et al. |
| 2014/0263551 A1 | 9/2014 | Hall et al. |
| 2014/0263552 A1 | 9/2014 | Hall et al. |
| 2014/0267655 A1 | 9/2014 | Richardson et al. |
| 2014/0268860 A1 | 9/2014 | Talbert et al. |
| 2014/0305994 A1 | 10/2014 | Parihar et al. |
| 2015/0053749 A1 | 2/2015 | Shelton, IV et al. |
| 2015/0125447 A1 | 5/2015 | Heider |

(56) References Cited

U.S. PATENT DOCUMENTS

| | | |
|---|---|---|
| 2015/0157416 A1 | 6/2015 | Andersson |
| 2015/0181629 A1 | 6/2015 | Jun |
| 2015/0182220 A1 | 7/2015 | Yates et al. |
| 2015/0223890 A1 | 8/2015 | Miller et al. |
| 2015/0272575 A1 | 10/2015 | Leimbach et al. |
| 2015/0342621 A1 | 12/2015 | Jackson, III |
| 2016/0038253 A1 | 2/2016 | Piron et al. |
| 2016/0045661 A1 | 2/2016 | Gray et al. |
| 2016/0066915 A1 | 3/2016 | Baber et al. |
| 2016/0066916 A1 | 3/2016 | Overmyer et al. |
| 2016/0081598 A1 | 3/2016 | Fern et al. |
| 2016/0100839 A1 | 4/2016 | Marczyk et al. |
| 2016/0148052 A1 | 5/2016 | Tsuda et al. |
| 2016/0154620 A1 | 6/2016 | Tsuda et al. |
| 2016/0171330 A1 | 6/2016 | Mentese et al. |
| 2016/0171947 A1 | 6/2016 | Chen |
| 2016/0174969 A1 | 6/2016 | Kerr et al. |
| 2016/0249915 A1 | 9/2016 | Beckman et al. |
| 2016/0249919 A1 | 9/2016 | Savage et al. |
| 2016/0253472 A1 | 9/2016 | Pedersen et al. |
| 2016/0256156 A1 | 9/2016 | Shelton et al. |
| 2016/0256184 A1 | 9/2016 | Shelton, IV et al. |
| 2016/0265938 A1 | 9/2016 | Hryb et al. |
| 2016/0302210 A1 | 10/2016 | Thornton et al. |
| 2016/0310134 A1 | 10/2016 | Contini et al. |
| 2016/0332296 A1 | 11/2016 | Kurnianto |
| 2017/0000551 A1 | 1/2017 | Ward et al. |
| 2017/0000575 A1 | 1/2017 | Griffiths et al. |
| 2017/0086914 A1 | 3/2017 | Wiener et al. |
| 2017/0172381 A1 | 6/2017 | Morimoto |
| 2017/0199632 A1 | 7/2017 | Ohmura |
| 2017/0227754 A1 | 8/2017 | Huang |
| 2017/0249431 A1 | 8/2017 | Shelton, IV et al. |
| 2017/0272838 A1 | 9/2017 | Glazer et al. |
| 2017/0296169 A1 | 10/2017 | Yates et al. |
| 2017/0296178 A1 | 10/2017 | Miller et al. |
| 2017/0296213 A1 | 10/2017 | Swensgard et al. |
| 2017/0311777 A1 | 11/2017 | Hirayama et al. |
| 2017/0323062 A1 | 11/2017 | Djajadiningrat et al. |
| 2017/0333033 A1 | 11/2017 | Valentine et al. |
| 2018/0032130 A1 | 2/2018 | Meglan |
| 2018/0064352 A1 | 3/2018 | Homyk et al. |
| 2018/0098049 A1 | 4/2018 | Sugano et al. |
| 2018/0098768 A1 | 4/2018 | Zhang et al. |
| 2018/0165051 A1 | 6/2018 | Kim et al. |
| 2018/0182281 A1 | 6/2018 | Charrad et al. |
| 2018/0197624 A1 | 7/2018 | Robaina et al. |
| 2018/0256025 A1 | 9/2018 | Yi et al. |
| 2018/0270474 A1 | 9/2018 | Liu |
| 2018/0329504 A1 | 11/2018 | Ziraknejad et al. |
| 2018/0353186 A1 | 12/2018 | Mozdzierz et al. |
| 2018/0360449 A1 | 12/2018 | Shelton, IV et al. |
| 2018/0360460 A1 | 12/2018 | Mozdzierz et al. |
| 2018/8360452 | 12/2018 | Shelton et al. |
| 2019/0000446 A1 | 1/2019 | Shelton, IV et al. |
| 2019/0000464 A1 | 1/2019 | Shelton, IV et al. |
| 2019/0000478 A1 | 1/2019 | Messerly et al. |
| 2019/0020420 A1 | 1/2019 | Zocher et al. |
| 2019/0099180 A1 | 4/2019 | Leimbach et al. |
| 2019/0104919 A1 | 4/2019 | Shelton et al. |
| 2019/0117070 A1 | 4/2019 | Muhsin et al. |
| 2019/0123978 A1 | 4/2019 | Shaw et al. |
| 2019/0125361 A1* | 5/2019 | Shelton, IV ........... A61B 90/30 |
| 2019/0125432 A1 | 5/2019 | Shelton, IV et al. |
| 2019/0125454 A1* | 5/2019 | Stokes ................... A61B 90/98 |
| 2019/0183591 A1 | 6/2019 | Johnson et al. |
| 2019/0200844 A1 | 7/2019 | Shelton et al. |
| 2019/0200905 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0200996 A1 | 7/2019 | Shelton et al. |
| 2019/0200997 A1 | 7/2019 | Shelton et al. |
| 2019/0200998 A1 | 7/2019 | Shelton et al. |
| 2019/0201025 A1 | 7/2019 | Shelton, IV et al. |
| 2019/0201029 A1 | 7/2019 | Shelton, IV et al. |
| 2019/0201033 A1 | 7/2019 | Yates et al. |
| 2019/0201034 A1 | 7/2019 | Shelton et al. |
| 2019/0201044 A1 | 7/2019 | Shelton, IV et al. |
| 2019/0201102 A1 | 7/2019 | Shelton et al. |
| 2019/0201104 A1 | 7/2019 | Shelton et al. |
| 2019/0201105 A1 | 7/2019 | Shelton, IV et al. |
| 2019/0201115 A1* | 7/2019 | Shelton, IV ........... A61B 34/76 |
| 2019/0201119 A1 | 7/2019 | Harris et al. |
| 2019/0201122 A1 | 7/2019 | Shelton, IV et al. |
| 2019/0201129 A1 | 7/2019 | Shelton et al. |
| 2019/0201136 A1* | 7/2019 | Shelton, IV ........... A61M 1/79 |
| 2019/0201137 A1 | 7/2019 | Shelton et al. |
| 2019/0201140 A1 | 7/2019 | Yates et al. |
| 2019/0201141 A1 | 7/2019 | Shelton et al. |
| 2019/0201144 A1 | 7/2019 | Shelton et al. |
| 2019/0201146 A1 | 7/2019 | Shelton et al. |
| 2019/0204201 A1 | 7/2019 | Shelton, IV et al. |
| 2019/0205001 A1 | 7/2019 | Messerly et al. |
| 2019/0206003 A1 | 7/2019 | Harris et al. |
| 2019/0206050 A1 | 7/2019 | Yates et al. |
| 2019/0206555 A1* | 7/2019 | Morgan ................. G16H 40/40 |
| 2019/0206562 A1 | 7/2019 | Shelton et al. |
| 2019/0206563 A1 | 7/2019 | Shelton et al. |
| 2019/0206564 A1* | 7/2019 | Shelton, IV ....... G06K 7/10316 |
| 2019/0206565 A1 | 7/2019 | Shelton, IV |
| 2019/0206569 A1 | 7/2019 | Shelton et al. |
| 2019/0250873 A1 | 8/2019 | Blume et al. |
| 2019/0314000 A1 | 10/2019 | Du et al. |
| 2019/0314015 A1 | 10/2019 | Shelton et al. |
| 2019/0388137 A1 | 12/2019 | Henrywood et al. |
| 2020/0030044 A1 | 1/2020 | Wang et al. |
| 2020/0046208 A1 | 2/2020 | Kasai et al. |
| 2020/0078078 A1 | 3/2020 | Henderson et al. |
| 2020/0078079 A1 | 3/2020 | Morgan et al. |
| 2020/0090412 A1 | 3/2020 | Harviainen |
| 2020/0120308 A1 | 4/2020 | Mcmillan et al. |
| 2020/0162664 A1 | 5/2020 | Maeda et al. |
| 2020/0188057 A1 | 6/2020 | Brandao et al. |
| 2020/0214571 A1 | 7/2020 | Bradbury et al. |
| 2020/0219319 A1 | 7/2020 | Lashmar et al. |
| 2020/0281790 A1 | 9/2020 | Augustine et al. |
| 2020/0342228 A1 | 10/2020 | Prevrhal et al. |
| 2020/0350063 A1 | 11/2020 | Thornton et al. |
| 2020/0356255 A1 | 11/2020 | Qing et al. |
| 2020/0405304 A1 | 12/2020 | Mozdzierz et al. |
| 2020/0405311 A1 | 12/2020 | Shelton, IV et al. |
| 2020/0405439 A1 | 12/2020 | Shelton et al. |
| 2021/0007574 A1 | 1/2021 | Hirayama et al. |
| 2021/0015461 A1 | 1/2021 | Karasawa |
| 2021/0060243 A1 | 3/2021 | Dave et al. |
| 2021/0077111 A1 | 3/2021 | Adams et al. |
| 2021/0092007 A1 | 3/2021 | Danilchenko et al. |
| 2021/0113269 A1 | 4/2021 | Vilsmeier et al. |
| 2021/0137581 A1 | 5/2021 | Reid et al. |
| 2021/0169578 A1 | 6/2021 | Calloway et al. |
| 2021/0196384 A1 | 7/2021 | Shelton, IV et al. |
| 2021/0196423 A1 | 7/2021 | Shelton, IV et al. |
| 2021/0205027 A1 | 7/2021 | Leist |
| 2021/0212770 A1 | 7/2021 | Messerly et al. |
| 2021/0220058 A1 | 7/2021 | Messerly et al. |
| 2021/0240279 A1 | 8/2021 | Harviainen et al. |
| 2021/0307833 A1 | 10/2021 | Farley et al. |
| 2021/0315579 A1 | 10/2021 | Shelton, IV et al. |
| 2021/0401533 A1 | 12/2021 | Im |
| 2022/0022982 A1 | 1/2022 | Hares et al. |
| 2022/0025258 A1 | 1/2022 | Ichikawa et al. |
| 2022/0104694 A1 | 4/2022 | Shelton, IV et al. |
| 2022/0104713 A1 | 4/2022 | Shelton, IV |
| 2022/0104765 A1 | 4/2022 | Shelton, IV et al. |
| 2022/0104806 A1 | 4/2022 | Shelton, IV et al. |
| 2022/0104807 A1 | 4/2022 | Shelton, IV et al. |
| 2022/0104813 A1 | 4/2022 | Shelton, IV et al. |
| 2022/0104814 A1 | 4/2022 | Shelton, IV et al. |
| 2022/0104820 A1 | 4/2022 | Shelton, IV et al. |
| 2022/0104821 A1 | 4/2022 | Shelton, IV et al. |
| 2022/0104843 A1 | 4/2022 | Shelton, IV et al. |
| 2022/0104867 A1 | 4/2022 | Shelton, IV et al. |
| 2022/0104889 A1 | 4/2022 | Shelton, IV et al. |
| 2022/0104896 A1 | 4/2022 | Shelton, IV et al. |

(56) References Cited

U.S. PATENT DOCUMENTS

| | | | |
|---|---|---|---|
| 2022/0104897 A1 | 4/2022 | Shelton, IV et al. |
| 2022/0104908 A1 | 4/2022 | Shelton, IV et al. |
| 2022/0104910 A1 | 4/2022 | Shelton, IV et al. |
| 2022/0104911 A1 | 4/2022 | Shelton, IV et al. |
| 2022/0104912 A1 | 4/2022 | Shelton, IV et al. |
| 2022/0108783 A1 | 4/2022 | Shelton, IV et al. |
| 2022/0108788 A1 | 4/2022 | Shelton, IV et al. |
| 2022/0108789 A1 | 4/2022 | Shelton, IV et al. |
| 2022/0246287 A1 | 8/2022 | Dawson et al. |

FOREIGN PATENT DOCUMENTS

| | | | |
|---|---|---|---|
| EP | 2491872 A1 | 8/2012 |
| EP | 2659852 A2 | 11/2013 |
| EP | 2789299 A1 | 10/2014 |
| EP | 3061405 A1 | 8/2016 |
| EP | 3064141 A1 | 9/2016 |
| EP | 3412225 A1 | 12/2018 |
| EP | 3449800 A1 | 3/2019 |
| EP | 3466348 A2 | 4/2019 |
| EP | 3506273 A1 | 7/2019 |
| EP | 3506299 A1 | 7/2019 |
| EP | 3547324 A1 | 10/2019 |
| EP | 3628207 A1 | 4/2020 |
| KR | 20010001630 A | 1/2001 |
| WO | 0070529 A2 | 11/2000 |
| WO | 2008-135736 | 11/2008 |
| WO | 2015125447 A1 | 8/2015 |
| WO | 2016171947 A1 | 10/2016 |
| WO | 2019130088 A1 | 7/2019 |
| WO | 2019133056 A1 | 7/2019 |
| WO | WO 2019-130108 A1 | 7/2019 |
| WO | 2019133140 A9 | 9/2019 |
| WO | 2020101283 A1 | 5/2020 |
| WO | 2020129916 A1 | 6/2020 |
| WO | WO 2020-129916 A1 | 6/2020 |
| WO | 2020154351 A1 | 7/2020 |

OTHER PUBLICATIONS

U.S. Appl. No. 16/209,478, filed Dec. 4, 2018, Ethicon LLC.
U.S. Appl. No. 16/458,117, filed Jun. 30, 2019, Ethicon LLC.
U.S. Appl. No. 16/574,773, filed Sep. 18, 2019, Ethicon LLC.
U.S. Appl. No. 16/574,797, filed Sep. 18, 2019, Ethicon LLC.
U.S. Appl. No. 16/574,281, filed Sep. 18, 2019, Ethicon LLC.
U.S. Appl. No. 16/729,747, filed Dec. 31, 2019, Ethicon LLC.
U.S. Appl. No. 16/729,778, filed Dec. 31, 2019, Ethicon LLC.
U.S. Appl. No. 16/729,807, filed Dec. 31, 2019, Ethicon LLC.
U.S. Appl. No. 17/062,521, filed Oct. 2, 2020, Shelton, et al.
U.S. Appl. No. 17/062,522, filed Oct. 2, 2020, Shelton, et al.
U.S. Appl. No. 17/062,523, filed Oct. 2, 2020, Shelton, et al.
U.S. Appl. No. 17/062,511, filed Oct. 2, 2020, Shelton, et al.
U.S. Appl. No. 17/062,524, filed Oct. 2, 2020, Shelton, et al.
U.S. Appl. No. 17/062,501, filed Oct. 2, 2020, Shelton, et al.
U.S. Appl. No. 17/062,502, filed Oct. 2, 2020, Shelton, et al.
U.S. Appl. No. 17/062,499, filed Oct. 2, 2020, Shelton, et al.
U.S. Appl. No. 17/062,496, filed Oct. 2, 2020, Shelton, et al.
U.S. Appl. No. 17/062,525, filed Oct. 2, 2020, Shelton, et al.
U.S. Appl. No. 17/062,526, filed Oct. 2, 2020, Shelton, et al.
U.S. Appl. No. 17/062,530, filed Oct. 2, 2020, Shelton, et al.
U.S. Appl. No. 17/062,512, filed Oct. 2, 2020, Shelton, et al.
U.S. Appl. No. 17/062,508, filed Oct. 2, 2020, Shelton, et al.
U.S. Appl. No. 17/062,509, filed Oct. 2, 2020, Shelton, et al.
U.S. Appl. No. 17/062,507, filed Oct. 2, 2020, Shelton, et al.
U.S. Appl. No. 17/062,513, filed Oct. 2, 2020, Shelton, et al.
U.S. Appl. No. 17/062,517, filed Oct. 2, 2020, Shelton, et al.
U.S. Appl. No. 17/062,520, filed Oct. 2, 2020, Shelton, et al.
U.S. Appl. No. 17/062,519, filed Oct. 2, 2020, Shelton, et al.
U.S. Appl. No. 17/062,516, filed Oct. 2, 2020, Shelton, et al.
George Slade, "The Fast Fourier Transform in Hardware: A Tutorial Based on an FPGA Implementation", http://web.mit.edu/, Mar. 21, 2013, accessed Sep. 8, 2020, 28 pages.
"FPGA Fundamentals", https://www.ni.com/en-us.html, Jun. 17, 2020, accessed Sep. 8, 2020, 9 pages.
Google scholar search, Jun. 17, 2022.
Alsos, "Interaction Techniques for Using Handhelds and PCs Together in a Clinical Setting", Dept of Computer and Information Science; Norwegian University of Science and Technology, Oct. 14-18, 2006, 10 pages.
Qamar, Rahil, "Semantic Mapping of Clinical Model Data to Biomedical Terminologies to Facilitate Interoperability", A these submitted to the University of Manchester, 2008, 260 pages.
Shankland, Stephen , "Adobe kills Creative Suite, goes subscription- only", CNET; https://www.cnet.com/tech/tech-industry/adobe-kills-creative-suite-goes-subscription-only/, May 6, 2013, 7 pages.
Alberta Health Services, "Surgical Aseptic Technique and Sterile Field, Recommendations for Asepsis for Invasive Surgical Procedures conducted outside if Operating Rooms or in Community-Based Healthcare Settings", Jan. 2013, 19 pages.

* cited by examiner

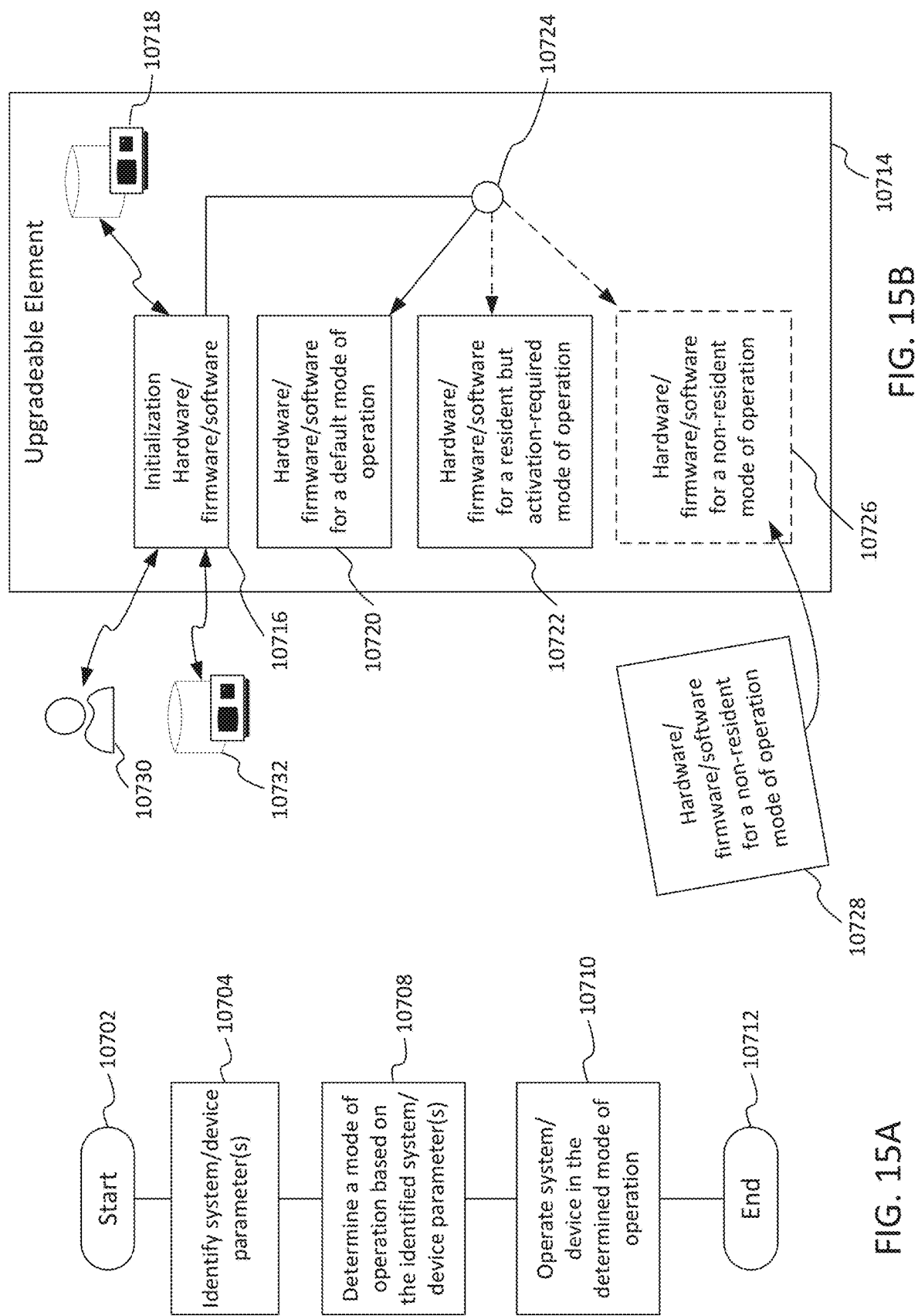

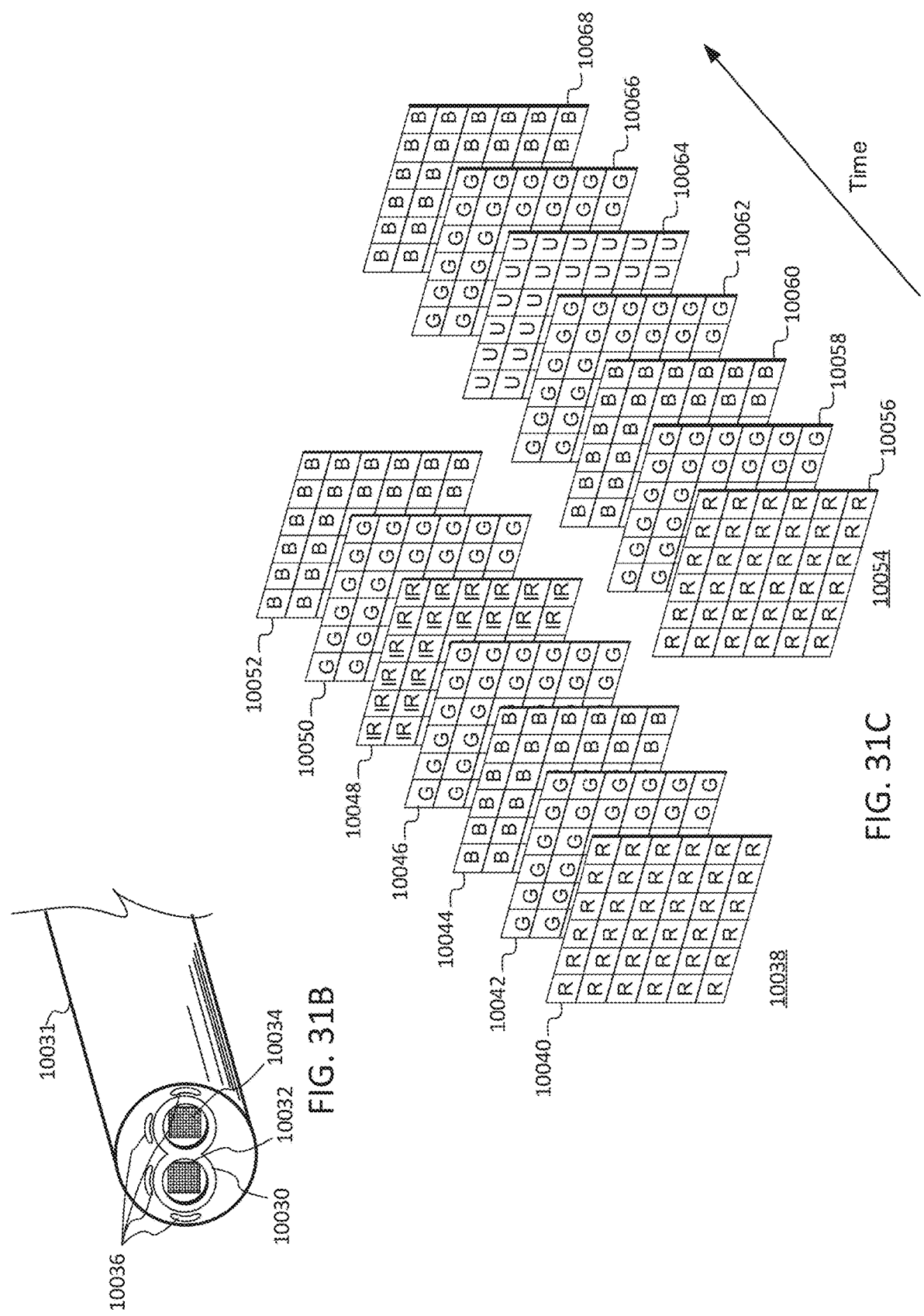

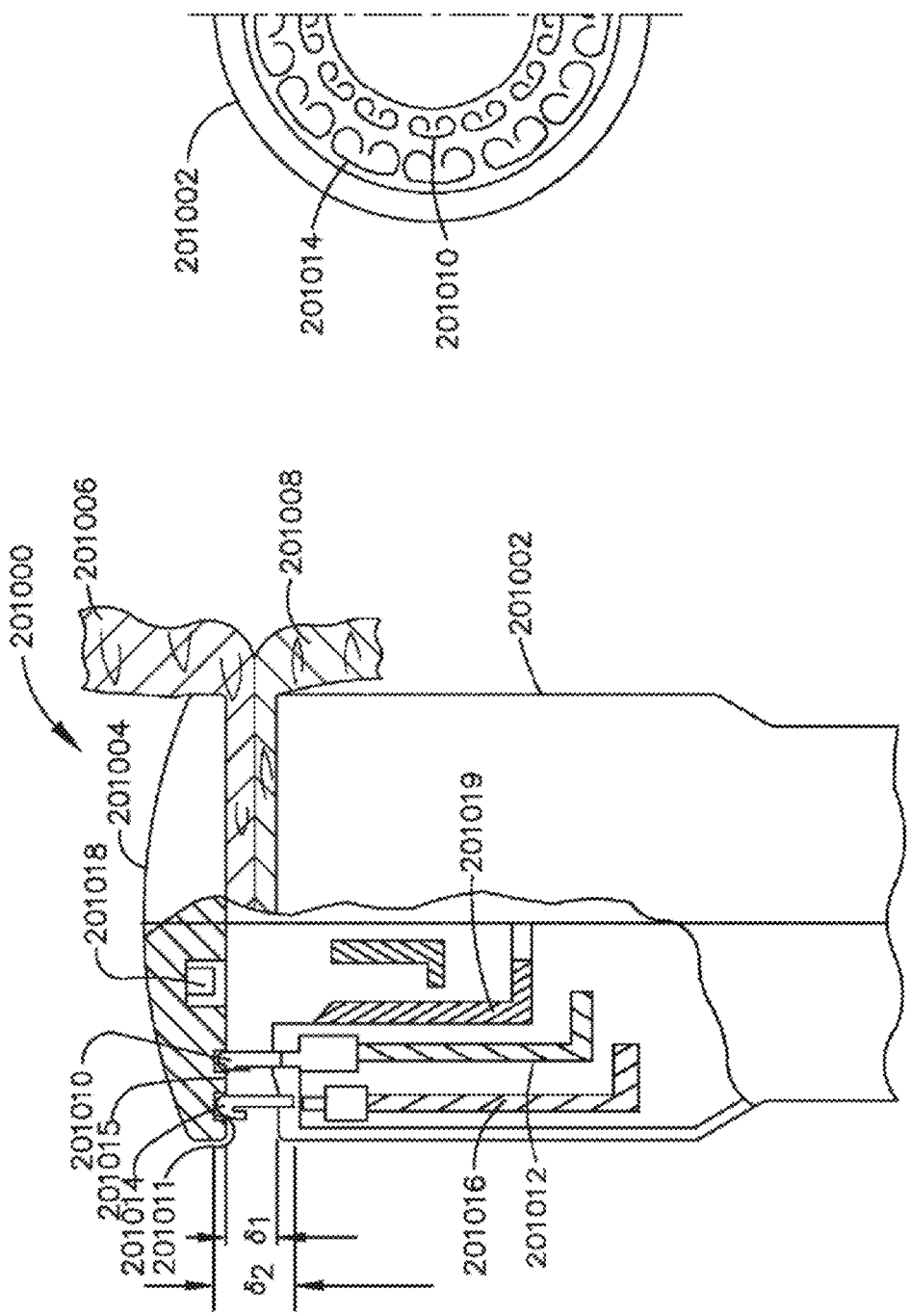

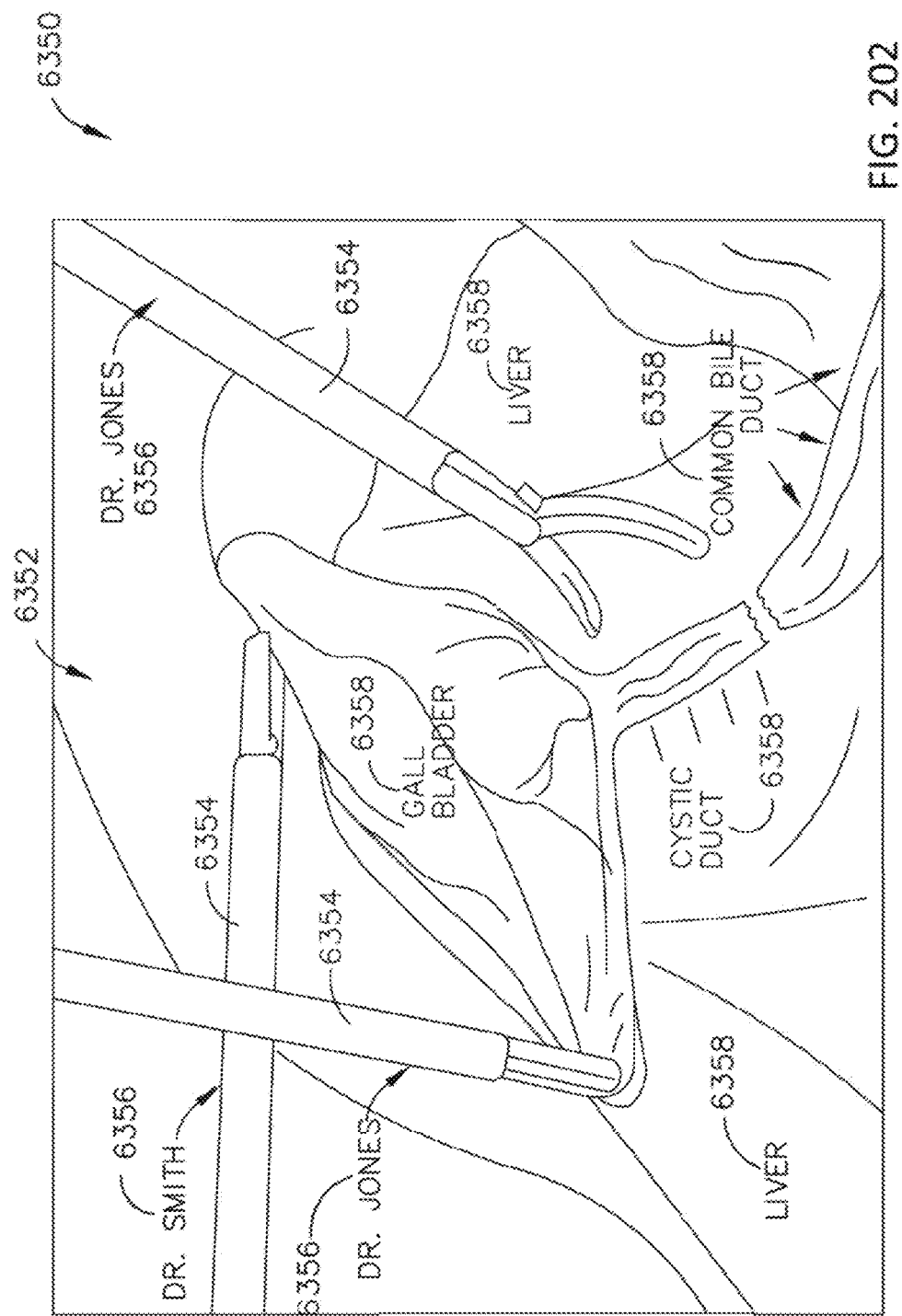

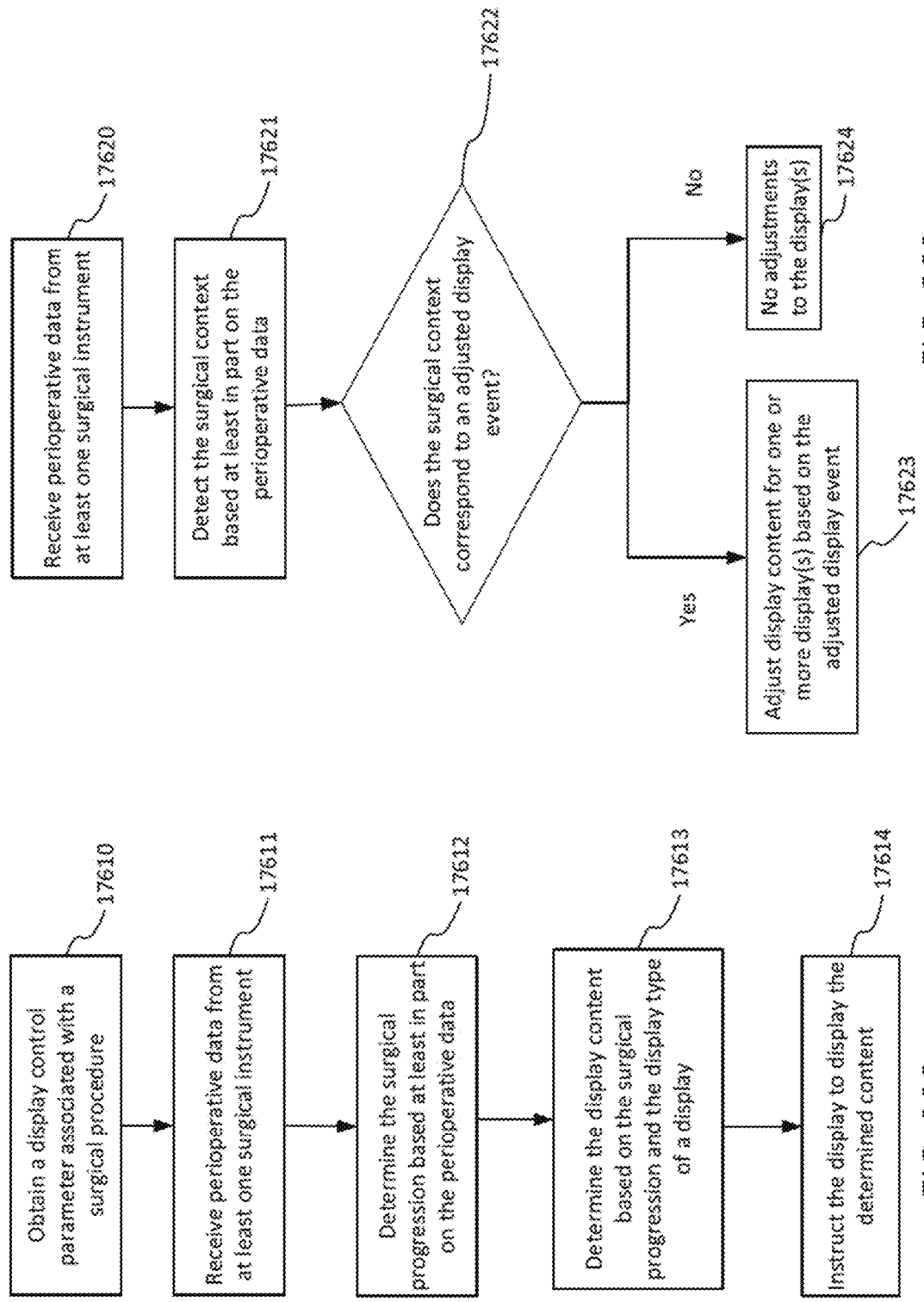

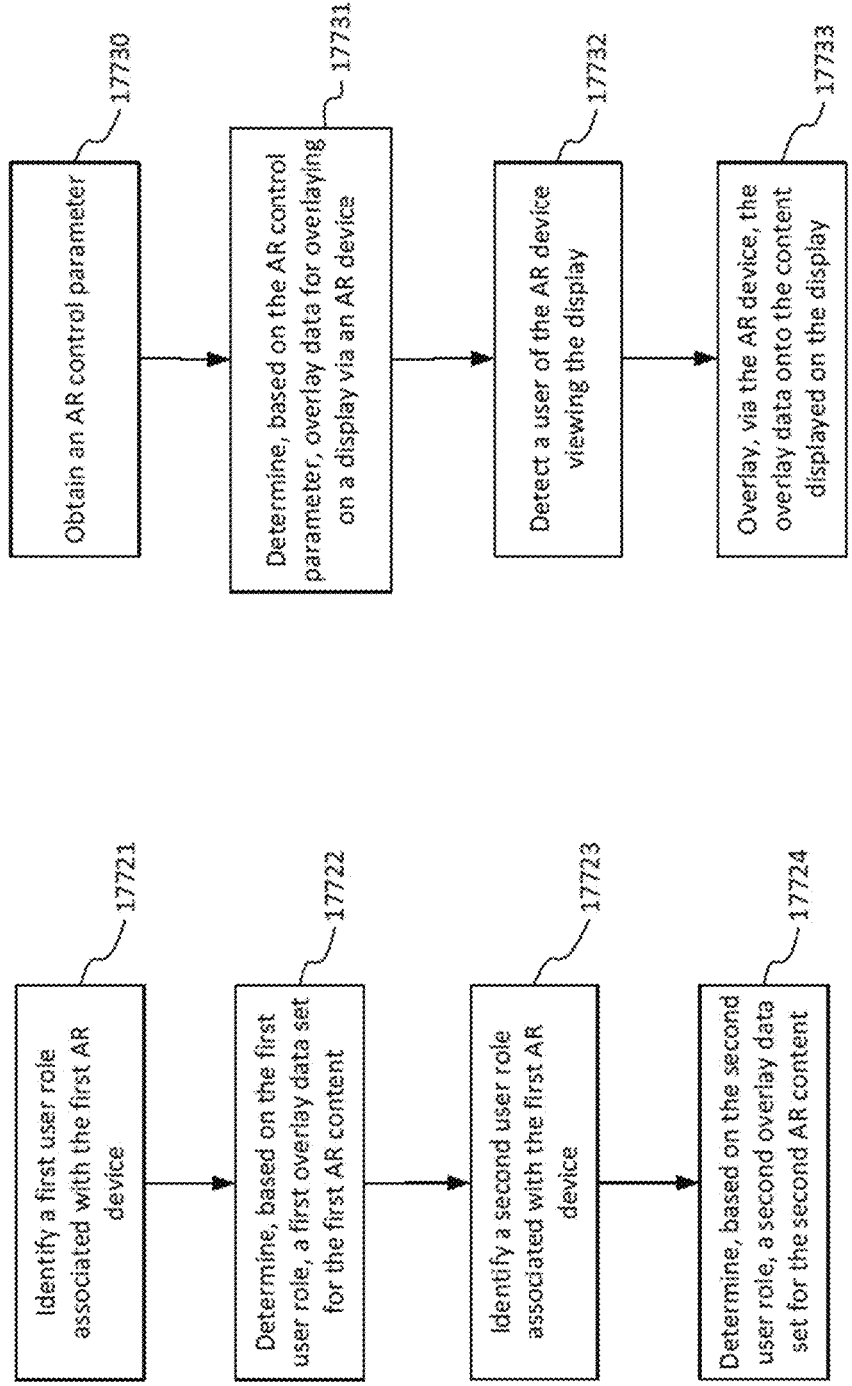

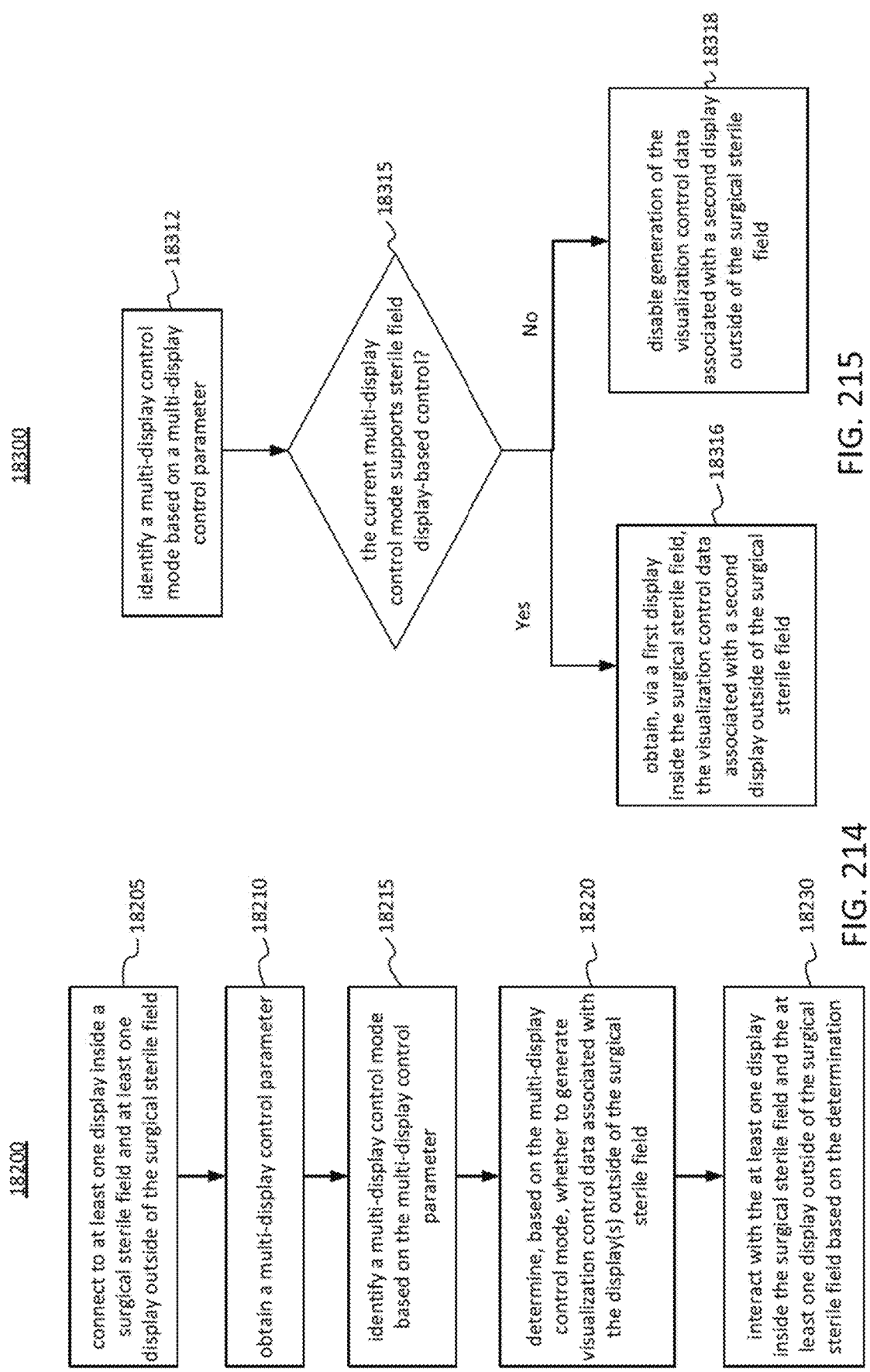

METHOD FOR OPERATING TIERED OPERATION MODES IN A SURGICAL SYSTEM

CROSS-REFERENCE TO RELATED APPLICATIONS

This application is related to the following, the contents of each of which are incorporated by reference herein:

U.S. patent application Ser. No. 17/062,521 filed Oct. 2, 2020, entitled Tiered-Access Surgical Visualization System;

U.S. patent application Ser. No. 17/062,522 filed Oct. 2, 2020, entitled Surgical Visualization and Particle Trend Analysis System;

U.S. patent application Ser. No. 17/062,523 filed Oct. 2, 2020, entitled Field Programmable Surgical Visualization System;

U.S. patent application Ser. No. 17/062,511 filed Oct. 2, 2020, entitled Communication Capability of a Smart Stapler;

U.S. patent application Ser. No. 17/062,524 filed Oct. 2, 2020, entitled End Effector Updates;

U.S. patent application Ser. No. 17/062,501 filed Oct. 2, 2020, entitled Communication Capability of a Surgical Device with Component;

U.S. patent application Ser. No. 17/062,502 filed Oct. 2, 2020, entitled Surgical Instrument with Adaptative Function Controls;

U.S. patent application Ser. No. 17/062,499 filed Oct. 2, 2020, entitled Surgical Instrument with Adaptative Motor Control;

U.S. patent application Ser. No. 17/062,496 filed Oct. 2, 2020, entitled Surgical Instrument with Adaptative Configuration Control;

U.S. patent application Ser. No. 17/062,525 filed Oct. 2, 2020, entitled Smart Energy Combo Control Options;

U.S. patent application Ser. No. 17/062,526 filed Oct. 2, 2020, entitled Cloud Analytics Packages;

U.S. patent application Ser. No. 17/062,530 filed Oct. 2, 2020, entitled Surgical Hub Having Variable Interconnectivity Capabilities;

U.S. patent application Ser. No. 17/062,512 filed Oct. 2, 2020, entitled Tiered System Display Control Based on Capacity and User Operation;

U.S. patent application Ser. No. 17/062,508 filed Oct. 2, 2020, entitled Cooperative Surgical Displays;

U.S. patent application Ser. No. 17/062,509 filed Oct. 2, 2020, entitled Interactive Information Overlay on Multiple Surgical Displays;

U.S. patent application Ser. No. 17/062,507 filed Oct. 2, 2020, entitled Communication Control for A Surgeon Controlled Secondary Display and Primary Display;

U.S. patent application Ser. No. 17/062,513 filed Oct. 2, 2020, entitled Situational Awareness of Instruments Location and Individualization of Users to Control Displays;

U.S. patent application Ser. No. 17/062,517 filed Oct. 2, 2020, entitled Shared Situational Awareness of The Device Actuator Activity to Prioritize Certain Aspects of Displayed Information;

U.S. patent application Ser. No. 17/062,520 filed Oct. 2, 2020, entitled Monitoring of User Visual Gaze to Control Which Display System Displays the Primary Information;

U.S. patent application Ser. No. 17/062,519 filed Oct. 2, 2020, entitled Reconfiguration of Display Sharing; and U.S. patent application Ser. No. 17/062,516 filed Oct. 2, 2020, entitled Control A Display Outside the Sterile Field from A Device Within the Sterile Field.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

A surgical system may include tiered-access features. The surgical system may be used to analyze at least a portion of a surgical field. Based on a control parameter, the system may scale up or down various capabilities, such as visualization processing, endocutter communication, endocutter algorithm updates, smart cartridge connectivity, smart motor control for circular stapler, smart energy control, cloud analytics, hub connectivity control, and/or hub visualization and control interactions. The control parameter may include system aspects such as processing capability or bandwidth for example and/or the identification of an appropriate service tier.

For example, a surgical system may operate in a first mode of operation, receive a control parameter, and determine to operate in a second mode of operation based on the received control parameter.

For example, a surgical system may receive a control parameter. Based on the control parameter, the surgical system may operate in a first mode of operation or a second mode of operation. For example, the control parameter may be or may include a parameter indicative of any of power capacity, memory capacity, bandwidth capacity, and processing compatibility. For example, the control parameter may be or may include a parameter indicative of processing compatibility, wherein processing compatibility indicates a purchased functional tier associated with any of a user or instrument.

BRIEF DESCRIPTION OF THE DRAWINGS

FIG. 15A illustrates an example flow for determining a mode of operation and operating in the determined mode.

FIG. 15B illustrates an example flow for changing a mode of operation.

FIG. 31B shows an example laser-light sensor; and FIG. 31C shows an example operation of a pixel array.

FIG. 103 is a partial cutaway view of a powered circular stapling device comprising a circular stapling head assembly and an anvil, in accordance with at least one aspect of the present disclosure.

FIG. 104 is a partial top view of the circular stapling head assembly shown herein showing a first row of staples (inner staples) and a second row of staples (outer staples), in accordance with at least one aspect of the present disclosure.

FIG. 117 is a partial schematic diagram of a circular powered stapling device showing anvil closure on the left side and knife 201616 actuation on the right side, in accordance with at least one aspect of the present disclosure.

FIG. 118 is a graphical representation of anvil displacement ($\delta$Anvil) along the vertical axis as a function of force to close (FTC) a clamp along the horizontal axis, in accordance with at least one aspect of the present disclosure.

FIG. 119 is a graphical representation 201630 of knife 201616 displacement ($\delta$Knife) along the vertical axis as a function of knife 201616 velocity (VK mm/sec) along the horizontal axis on the left and also as a function of knife 201616 force (FK lbs) along the horizontal axis on the right, in accordance with at least one aspect of the present disclosure.

FIG. 120 is a logic flow diagram of a process depicting a control program or a logic configuration to detect the tissue gap and force-to-fire to adjust the knife stroke and speed, in accordance with at least one aspect of the present disclosure.

FIG. 121 is a logic flow diagram of a process depicting a control program or a logic configuration to advance the knife 201616 under a heavy tissue toughness velocity profile with a velocity spike as shown in FIG. 119, in accordance with at least one aspect of the present disclosure.

FIG. 122 illustrates a partial perspective view of a circular stapler showing a circular stapler trocar including a staple cartridge, which has four predetermined zones, in accordance with at least one aspect of the present disclosure.

FIG. 123 illustrates a partial perspective view of a circular stapler showing a circular stapler trocar including a staple cartridge, which has eight predetermined zones, in accordance with at least one aspect of the present disclosure.

FIG. 124 illustrates, on the left, two tissues including previously deployed staples properly disposed onto the staple cartridge of FIG. 122, and on the right, two tissues including previously deployed staples properly disposed onto the staple cartridge of FIG. 122, in accordance with at least one aspect of the present disclosure.

FIG. 125 illustrates two tissues including previously deployed staples properly disposed onto the staple cartridge of FIG. 123, in accordance with at least one aspect of the present disclosure.

FIG. 126 illustrates two tissues including previously deployed staples improperly disposed onto the staple cartridge of FIG. 123, in accordance with at least one aspect of the present disclosure.

FIG. 127 is a graph depicting a tissue impedance signature of the properly disposed tissues of FIG. 125, in accordance with at least one aspect of the present disclosure.

FIG. 128 is a graph depicting a tissue impedance signature of the improperly disposed tissues of FIG. 126, in accordance with at least one aspect of the present disclosure.

Figure 129:
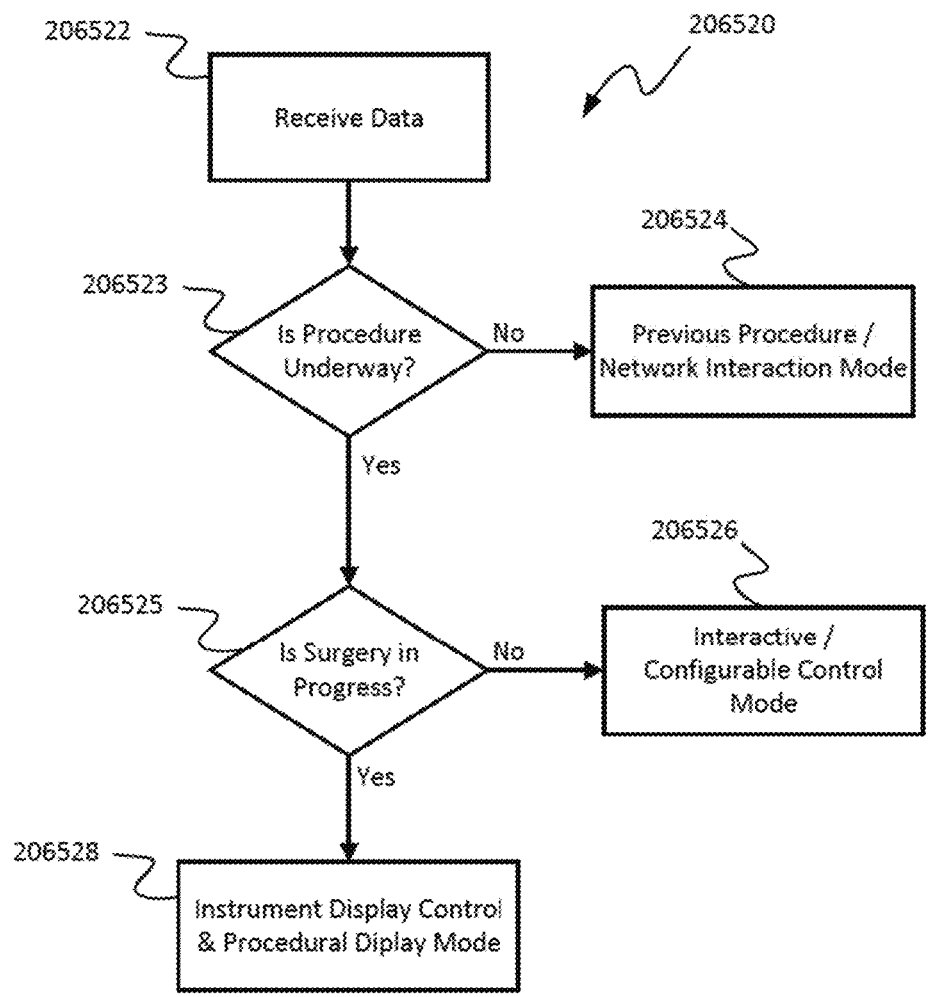

FIG. 129 is a logic flow diagram of a process depicting a control program or a logic configuration for selecting operational modes of a surgical hub, in accordance with at least one aspect of the present disclosure.

Figure 130:
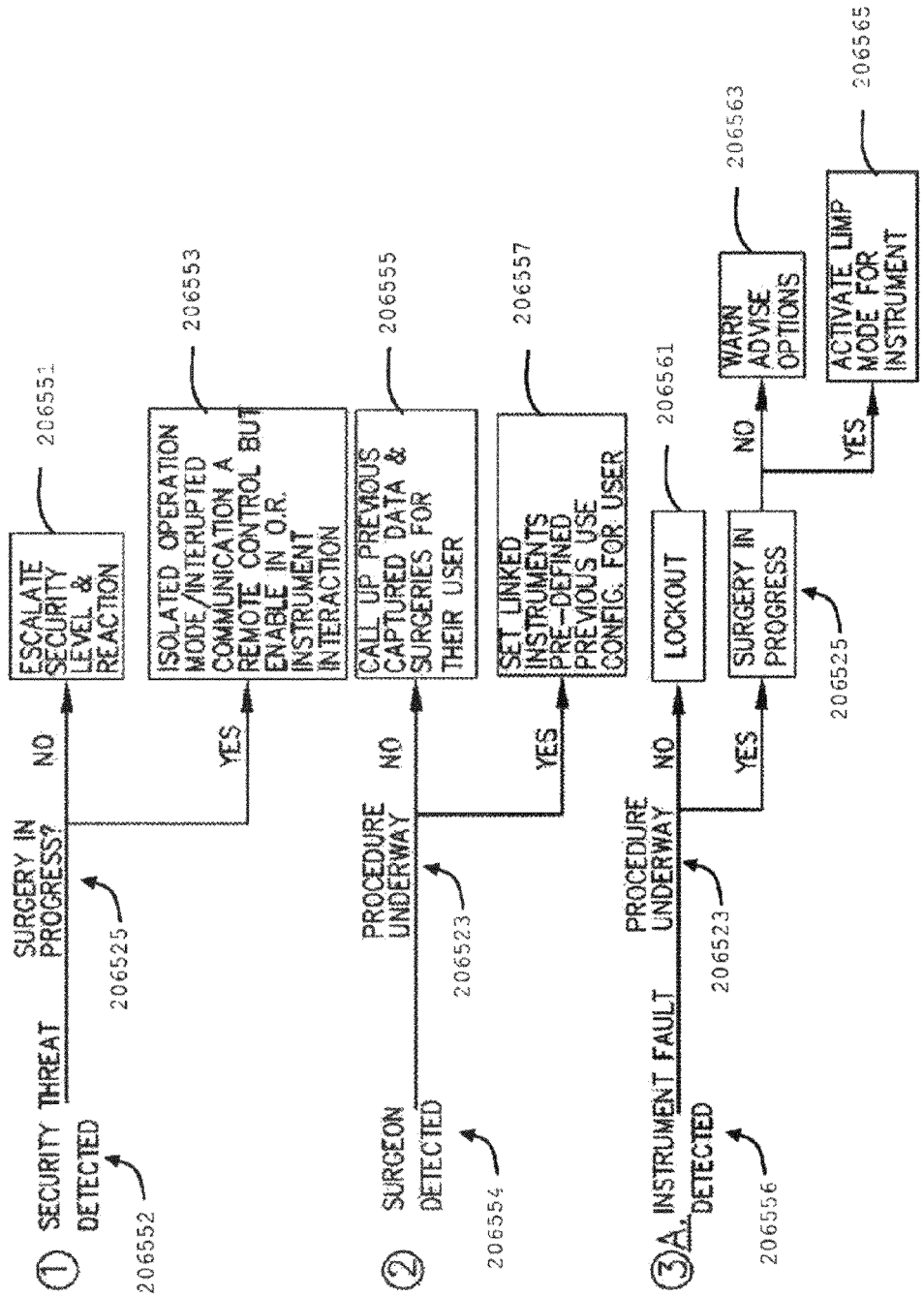

FIG. 130 is a logic flow diagram of a process depicting a control program or a logic configuration for responding to sensed parameters, in accordance with at least one aspect of the present disclosure.

Figure 131:
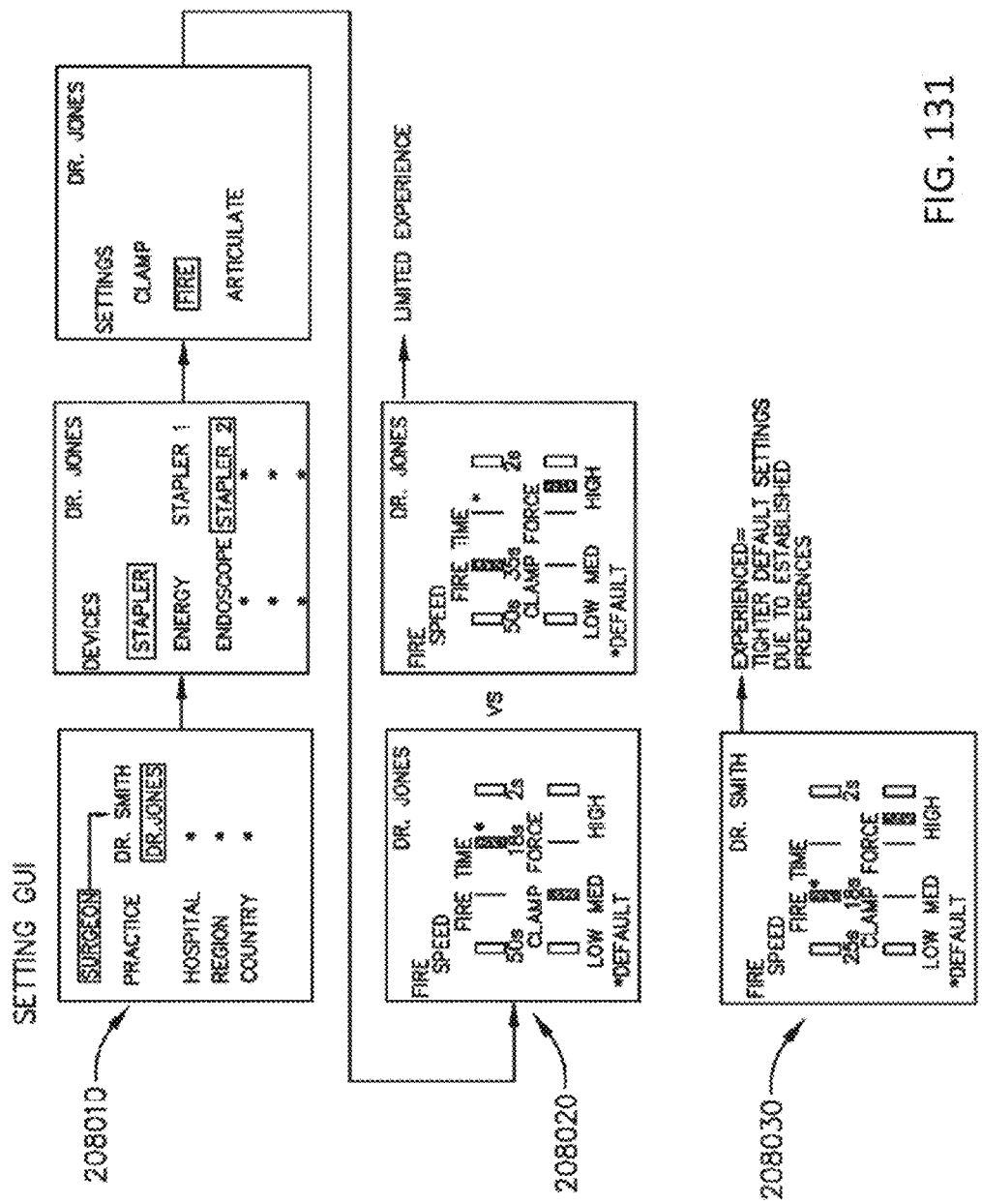

FIG. 131 is a diagram of a graphical user interface (GUI) for controlling various device parameters in accordance with at least one aspect of the present disclosure.

Figure 132:
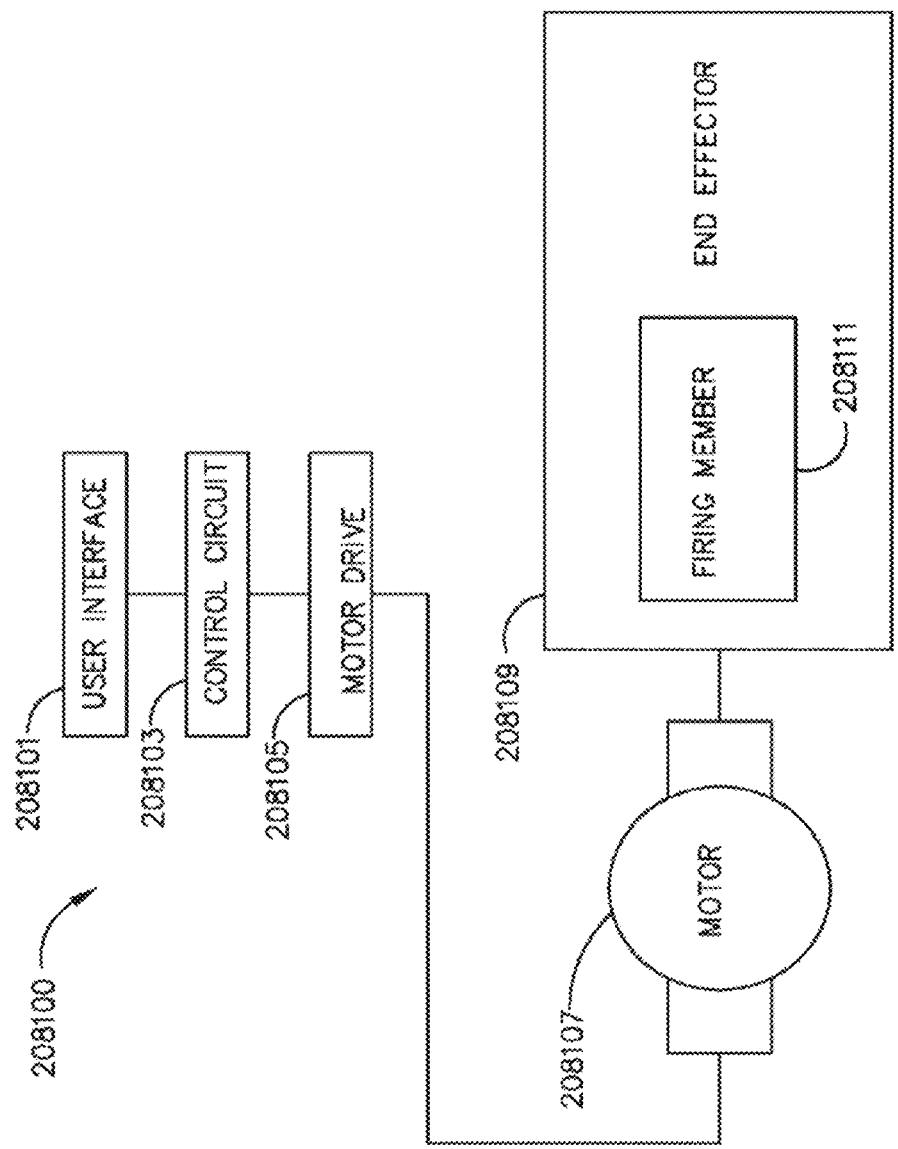

FIG. 132 is a block diagram depicting a surgical system in accordance with at least one aspect of the present disclosure.

Figure 133:
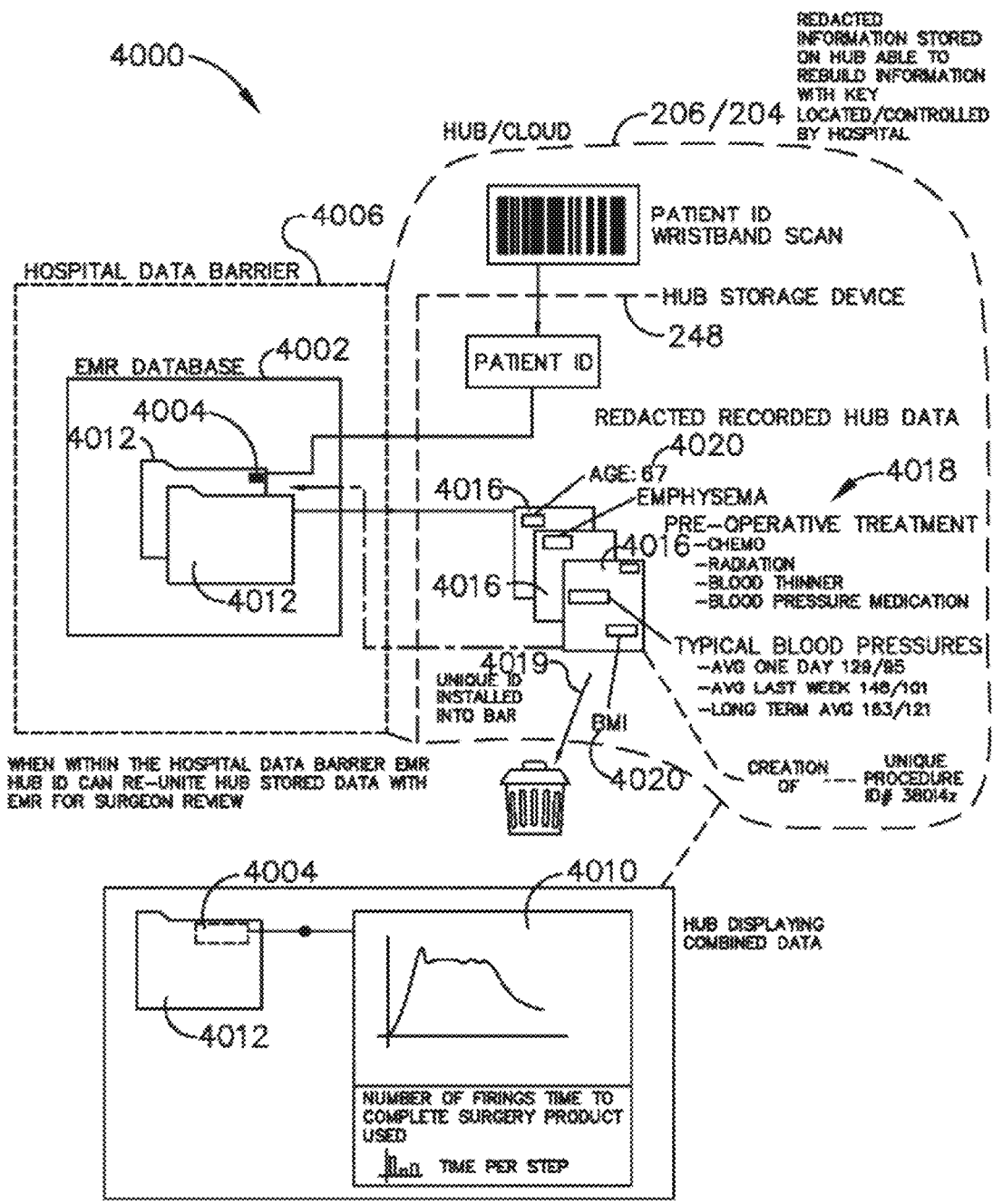
Figure 134:
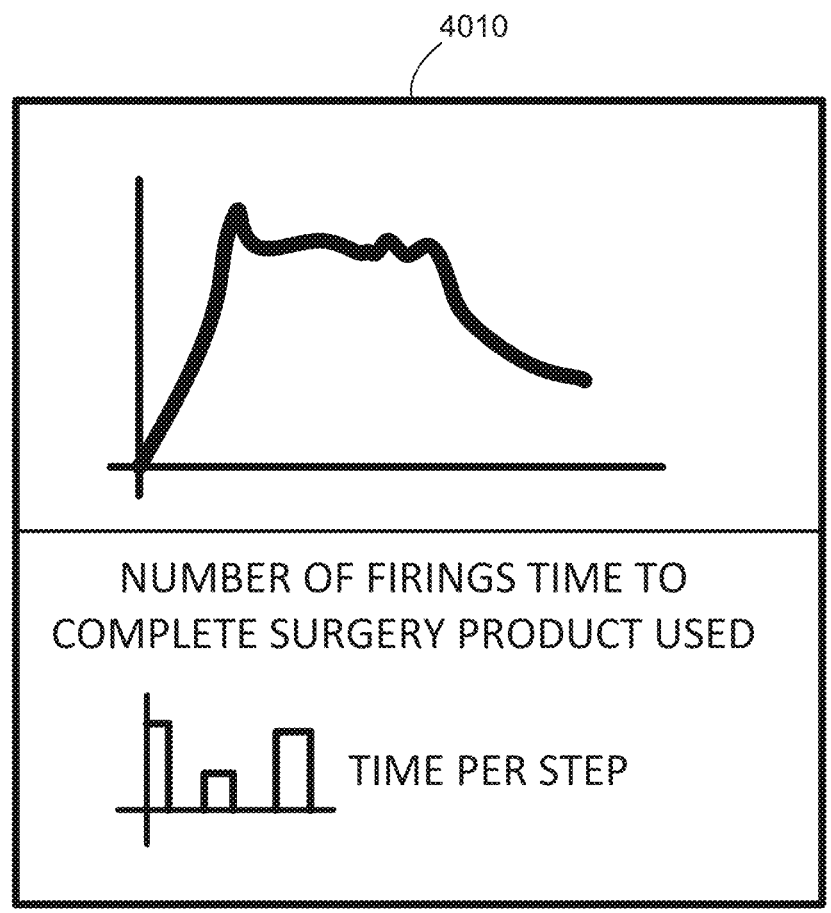

FIGS. 133 and 134 illustrate a technique for interacting with a patient Electronic Medical Record (EMR) database, in accordance with at least one aspect of the present disclosure.

Figure 135:
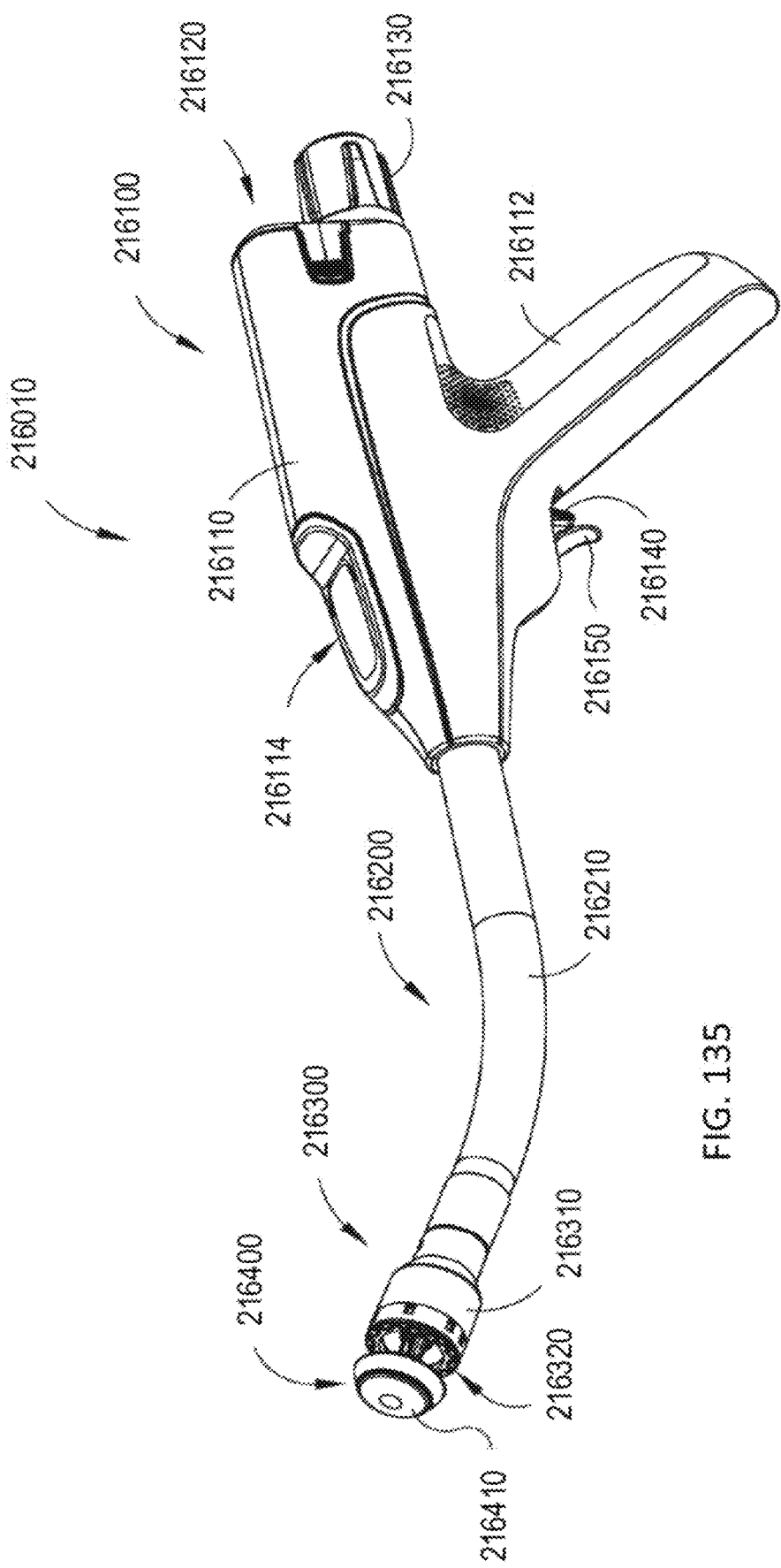
Figure 136:
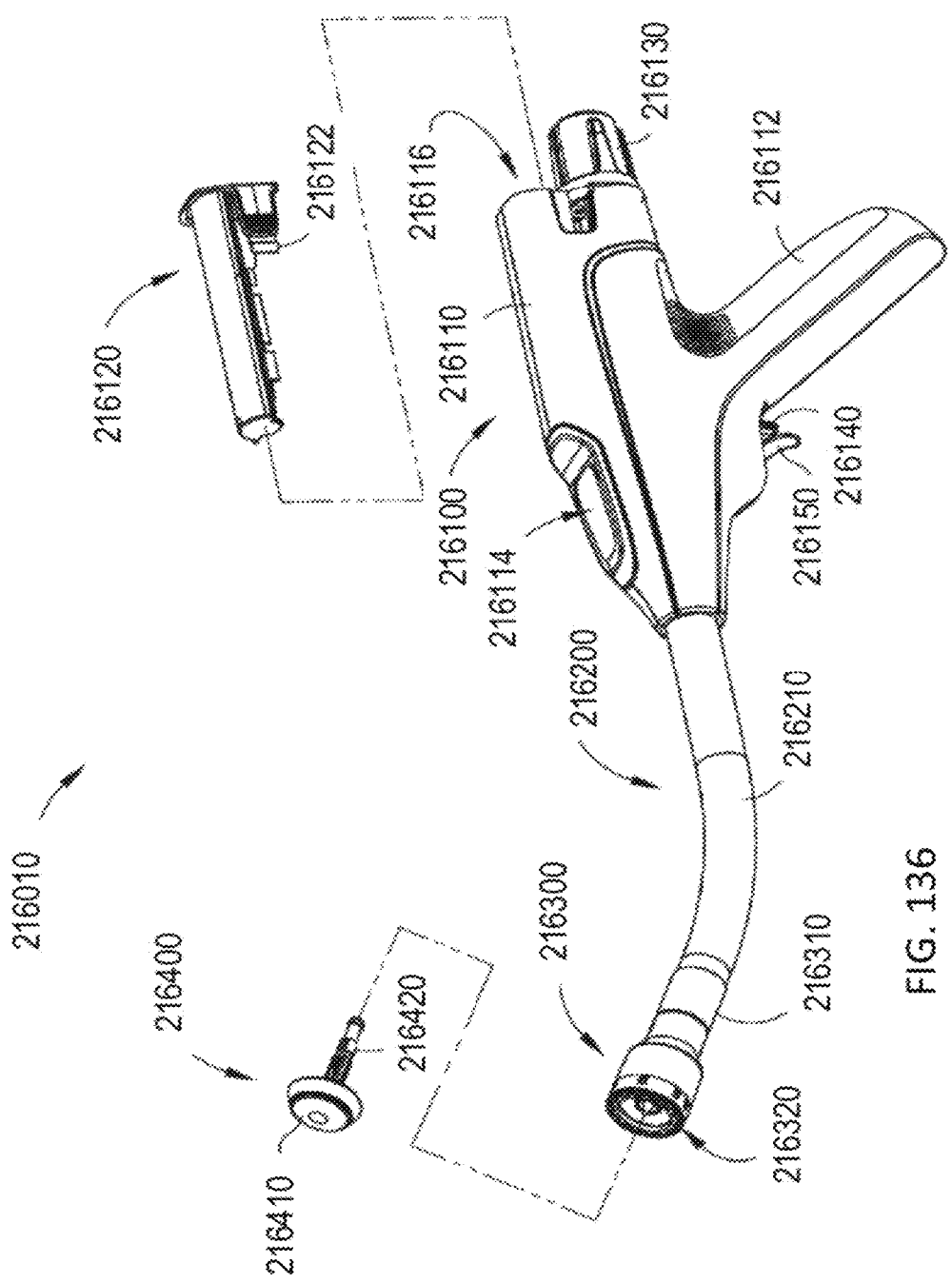
Figure 137:
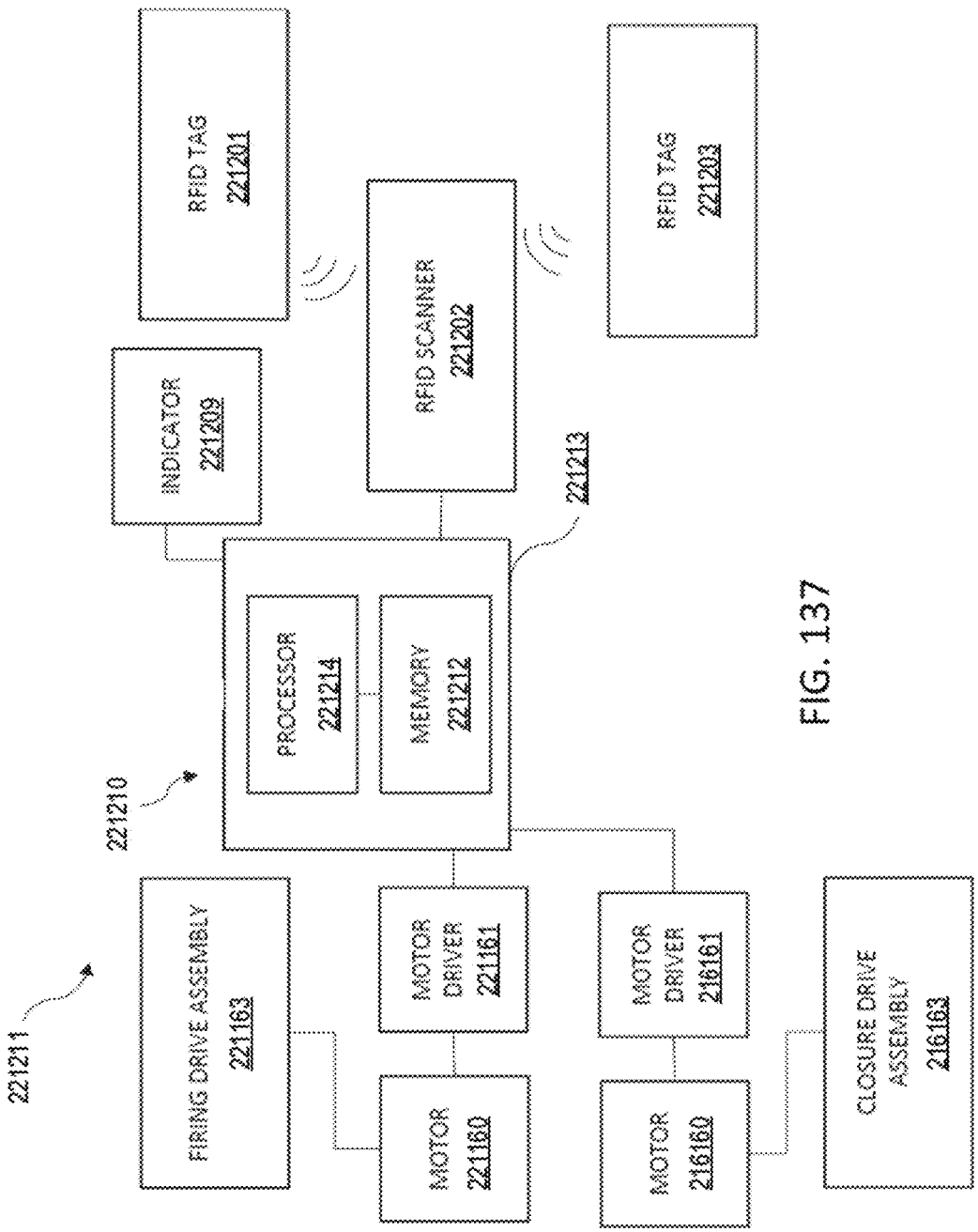

FIG. 135 depicts a perspective view of an exemplary circular stapler, in accordance with at least one aspect of the present disclosure FIG. 136 depicts a perspective view of the circular stapler of FIG. 135, with a battery pack removed from a housing assembly and an anvil removed from a stapling head assembly, in accordance with at least one aspect of the present disclosure FIG. 137 depicts a control system of a surgical stapling instrument, in accordance with at least one aspect of the present disclosure.

Figure 138:
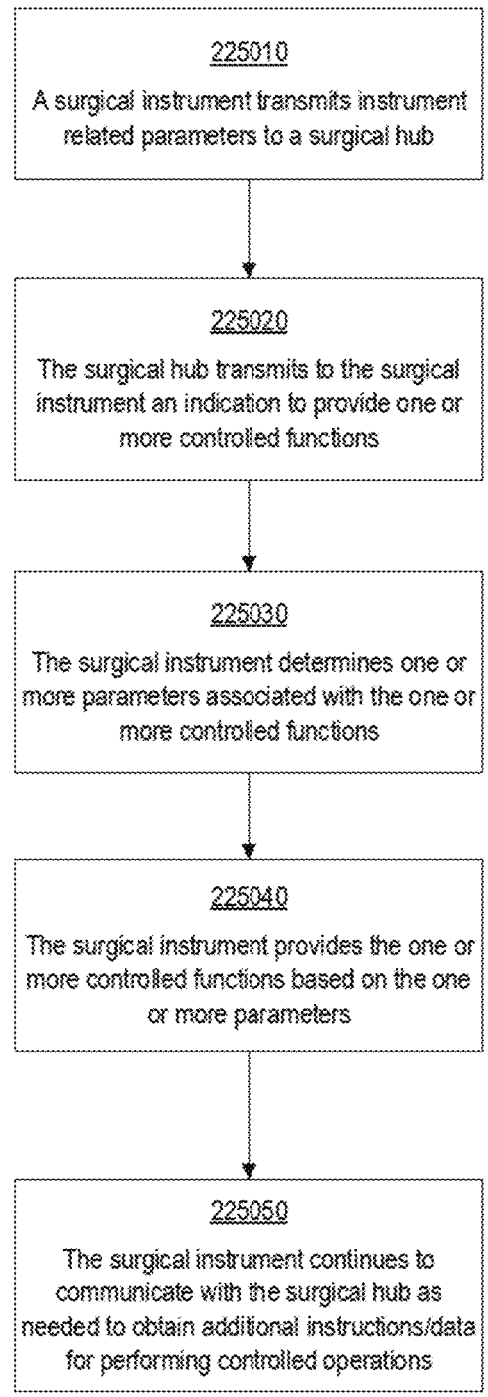

FIG. 138 depicts a flow chart of example processing for adaptive control of surgical instrument functions.

Figure 139:
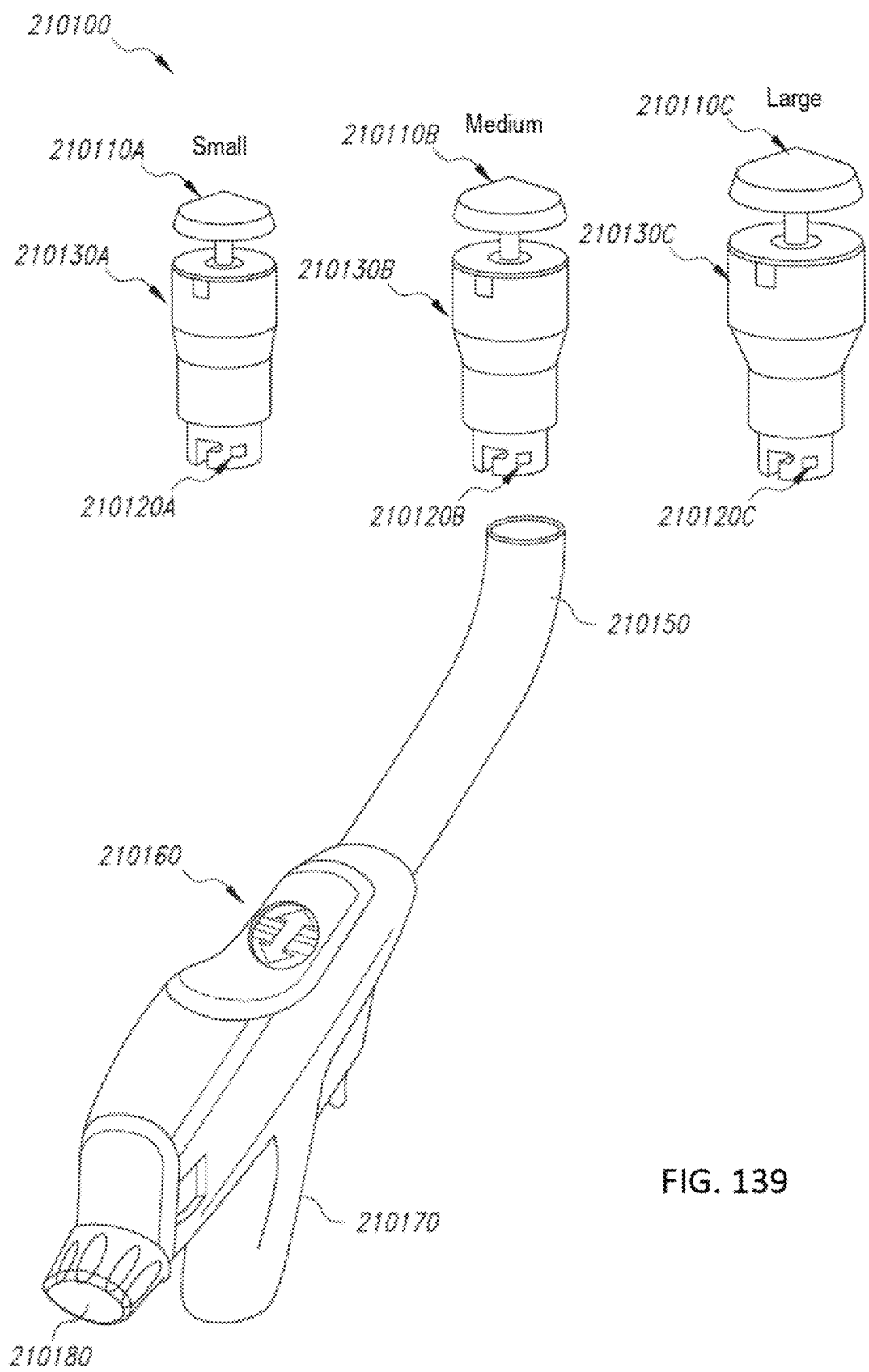

FIG. 139 illustrates an example motorized circular stapling instrument in accordance with at least one aspect of the present disclosure.

Figure 140:
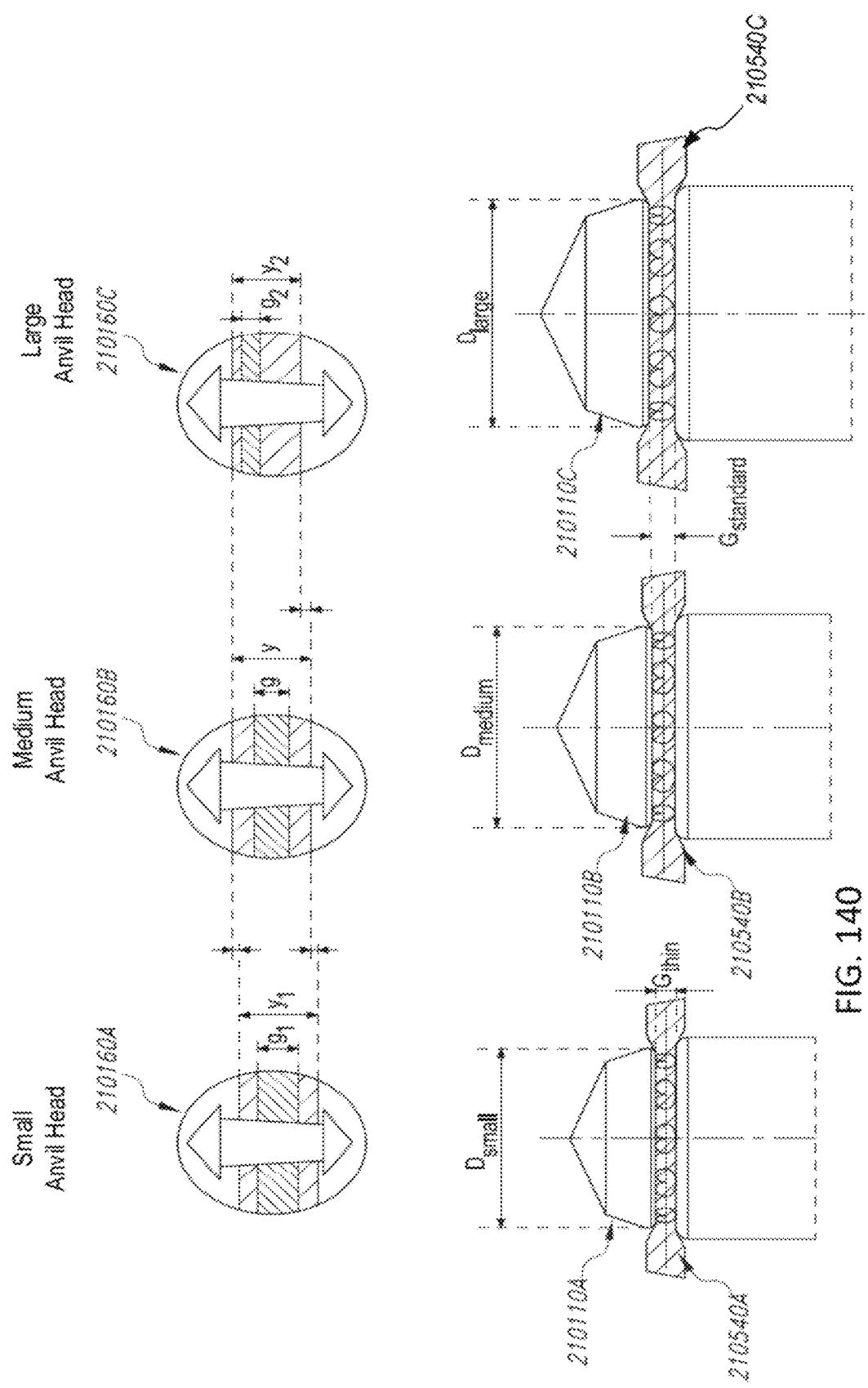

FIG. 140 illustrates an example representation of an adaptable staple height operating range displaying on an example motorized circular stapling instrument.

Figure 141:
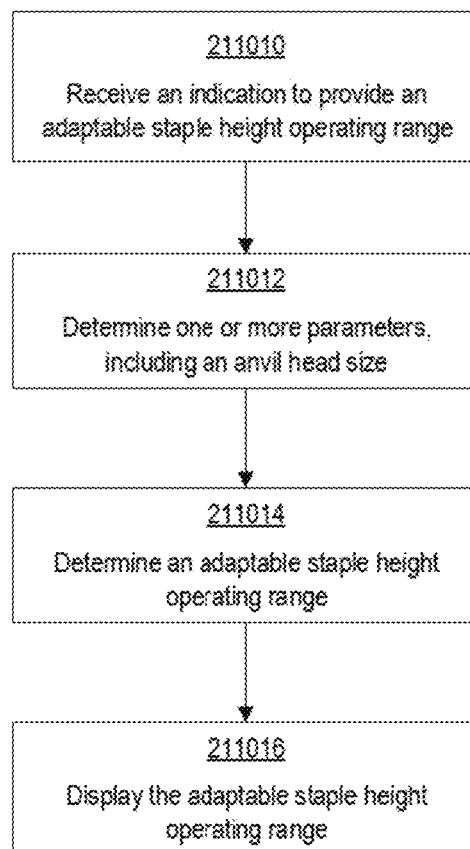

FIG. 141 is an example flow diagram of an example motorized circular stapling instrument operating in a stroke control operation mode.

Figure 142:
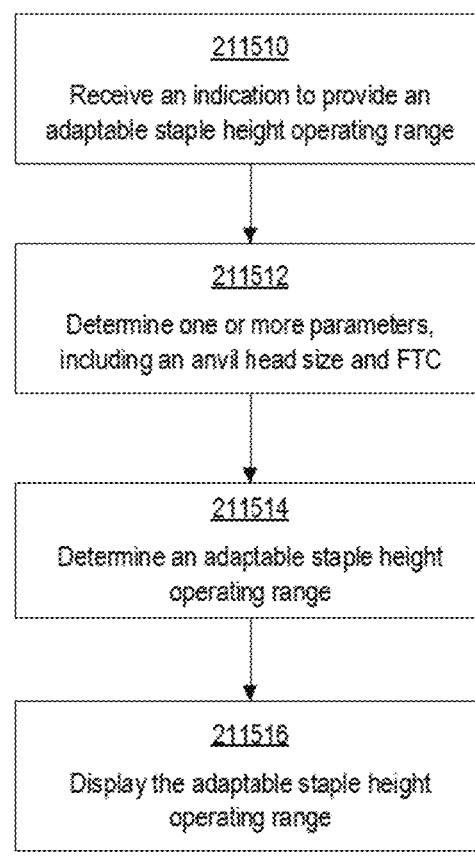

FIG. 142 is an example flow diagram of an example motorized circular stapling instrument operating in a load control operation mode.

Figure 143:
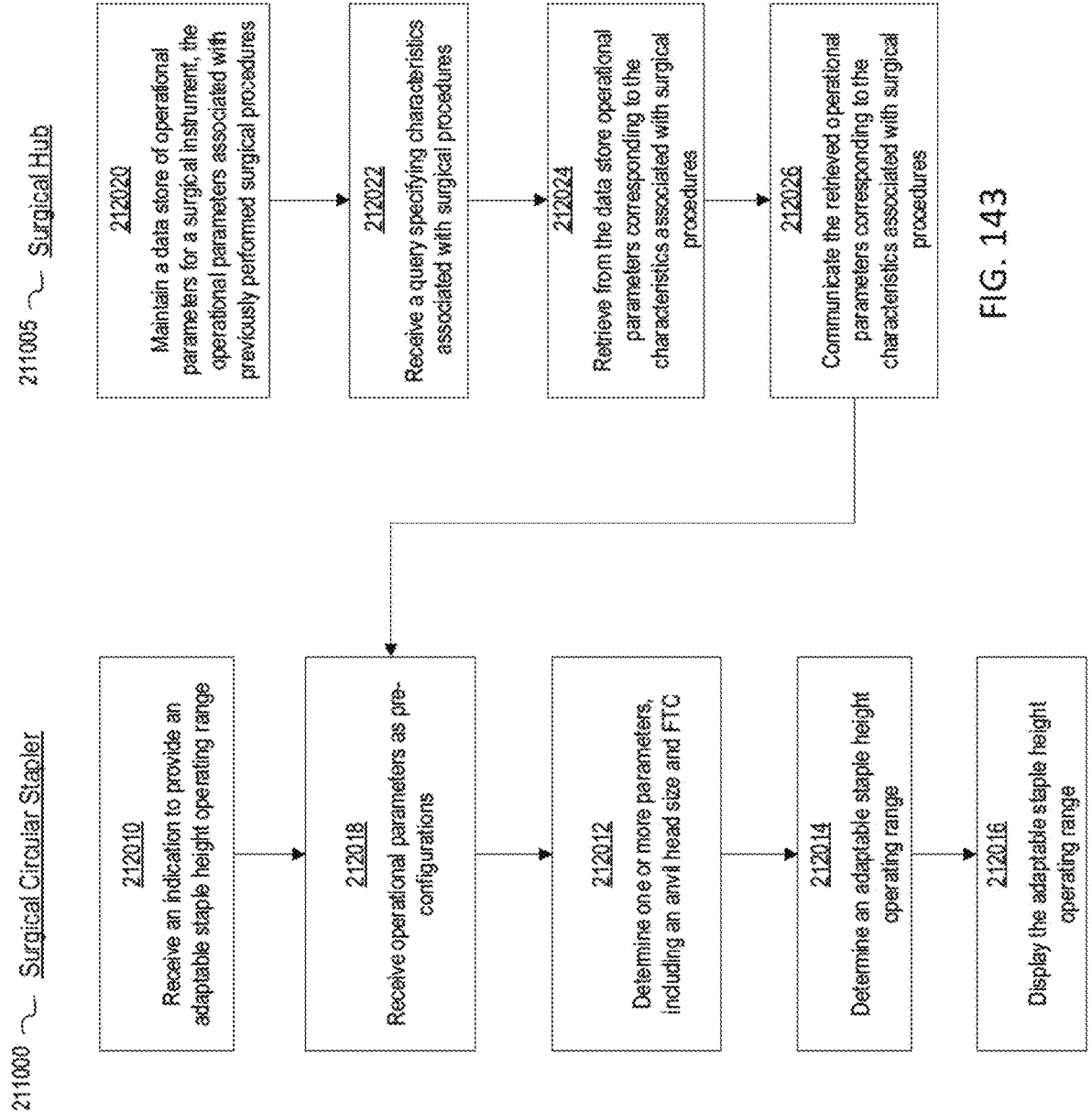

FIG. 143 is an example flow diagram of an example motorized circular stapling instrument operating in a previous-configuration control operation mode.

Figure 144:
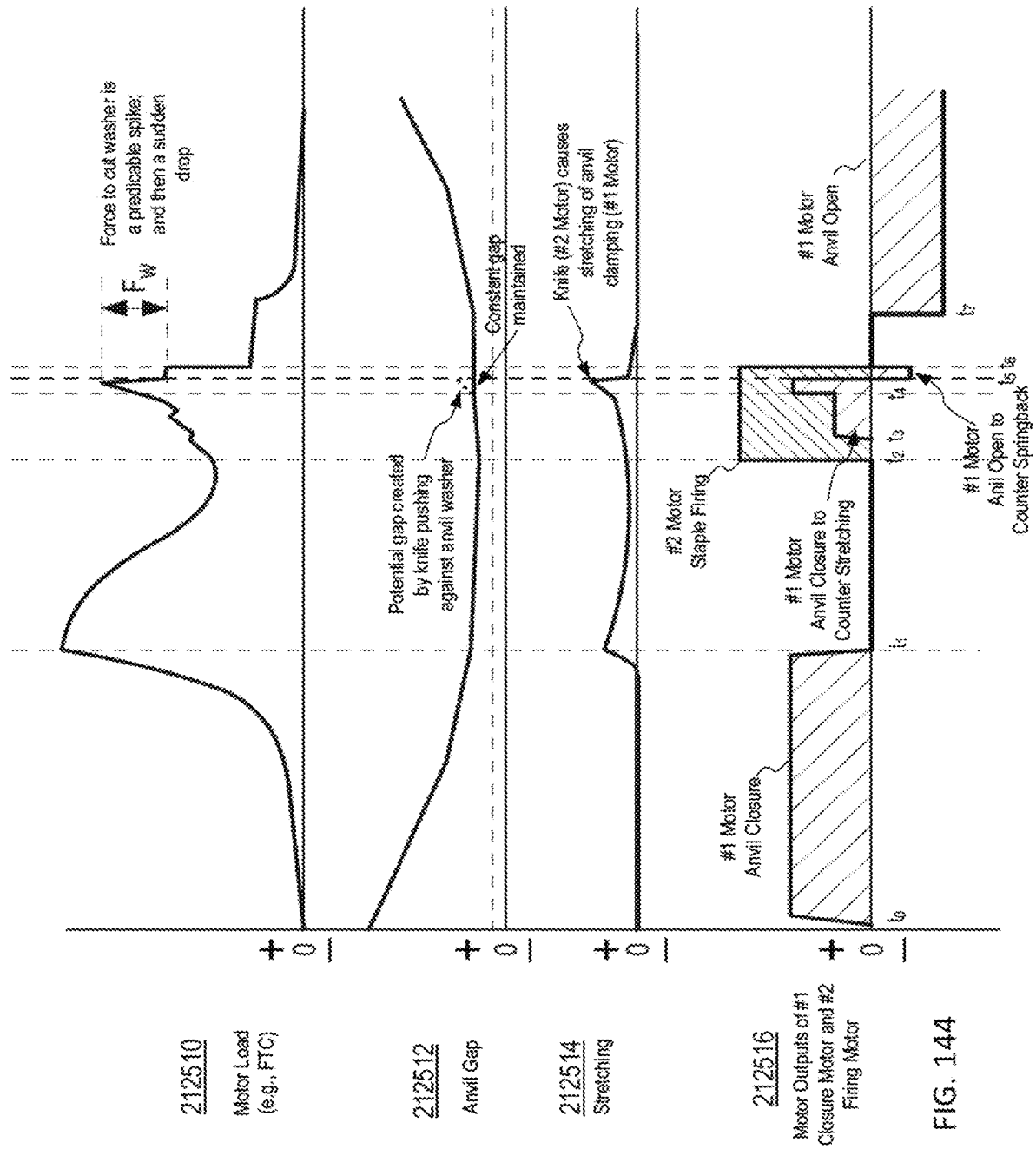

FIG. 144 is an example diagram illustrating various aspects of an example motorized circular stapling instrument operating using adaptive motor control in a load control operation mode.

Figure 145:
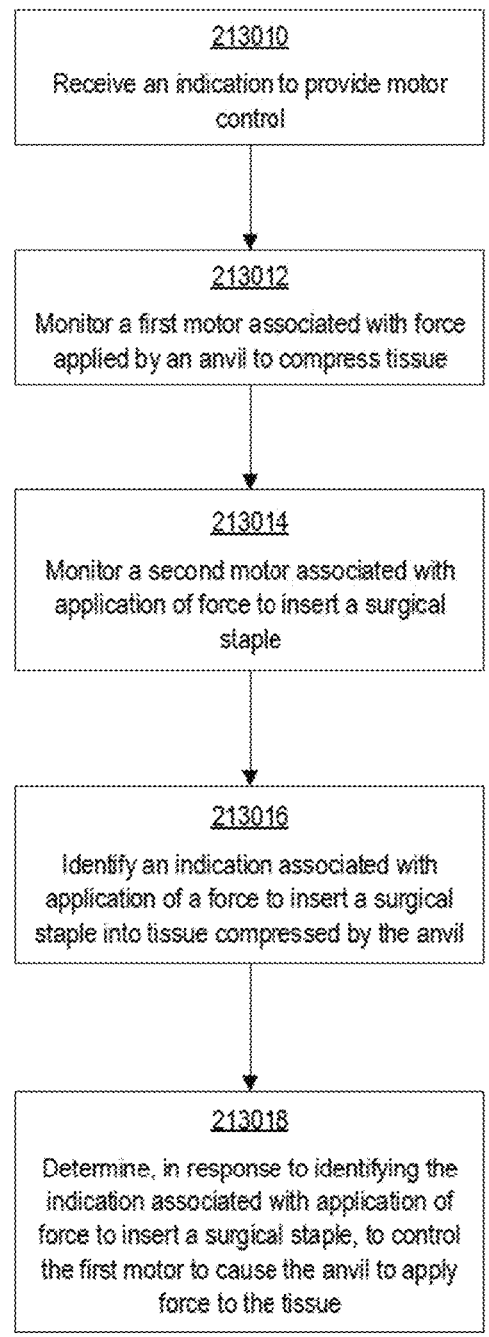

FIG. 145 is an example flow diagram of an example motorized circular stapling instrument operating with adaptive motor control in a load control operation mode.

Figure 146:
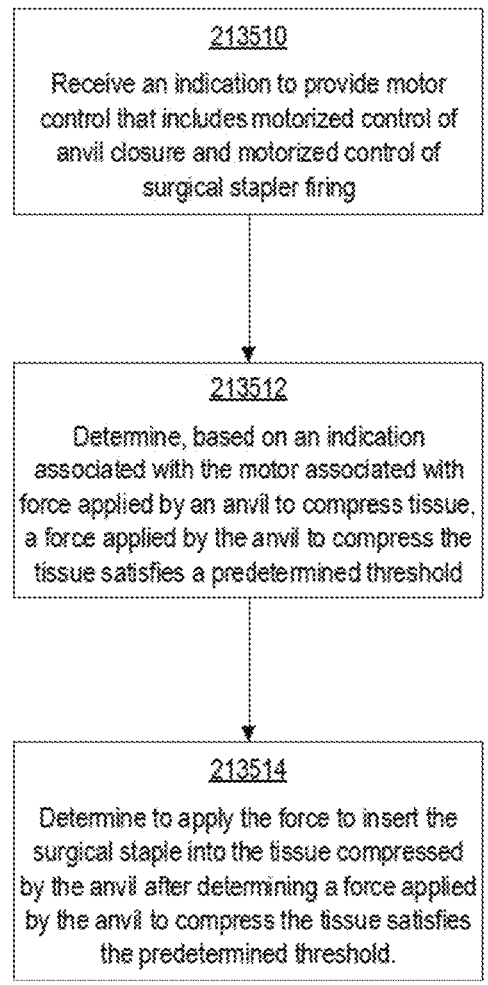

FIG. 146 is another example flow diagram of an example motorized circular stapling instrument operating in a load control operation mode.

Figure 147:
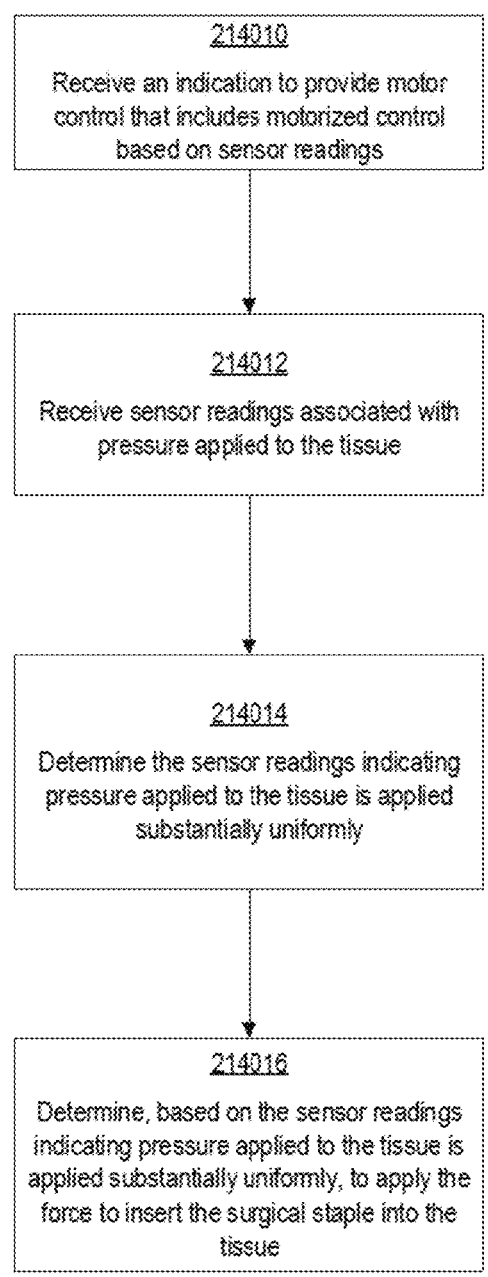

FIG. 147 is another example flow diagram of an example motorized circular stapling instrument operating in a load control operation mode.

Figure 148:
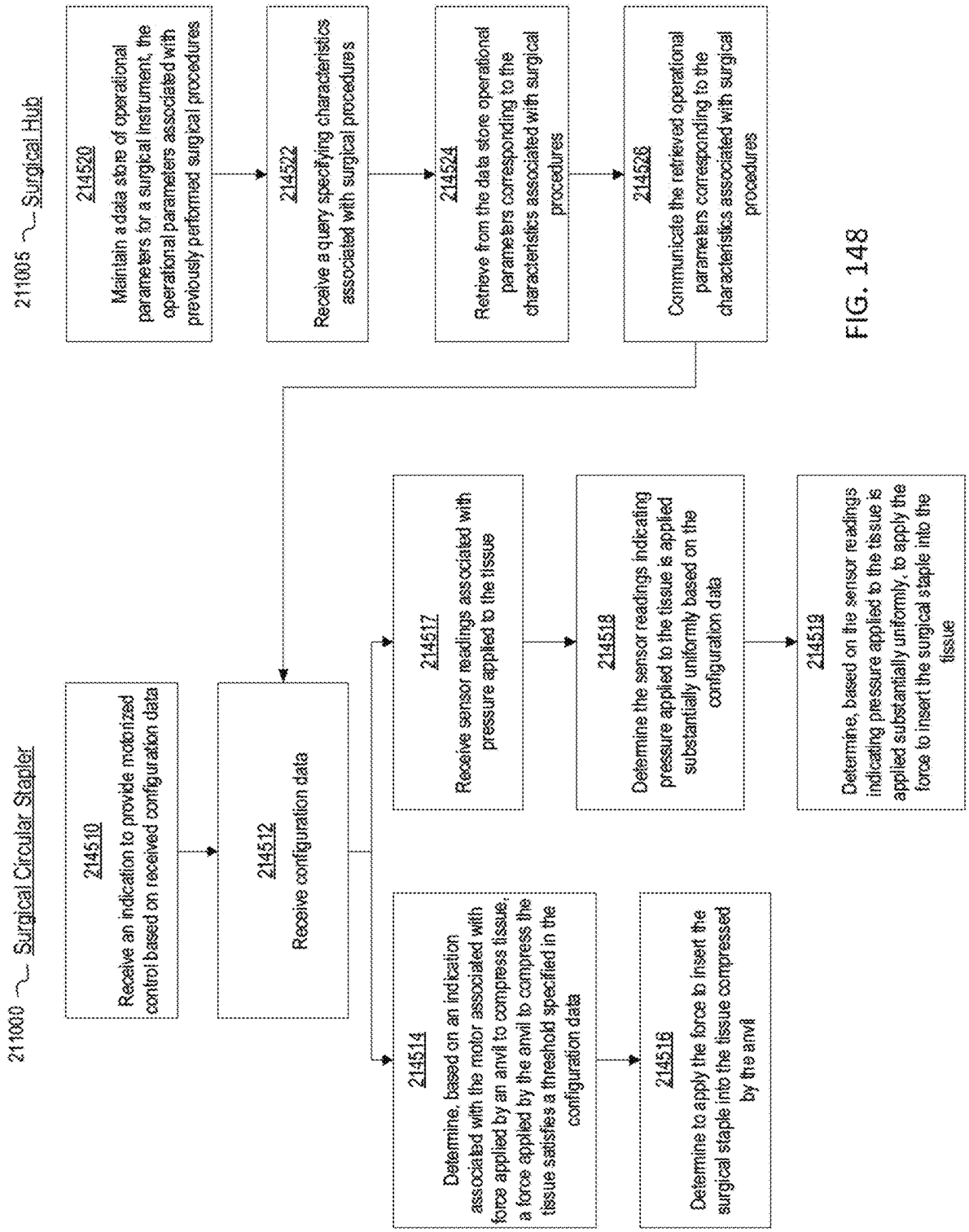

FIG. 148 is another example flow diagram of an example motorized circular stapling instrument operating in a previous-configuration control operation mode.

Figure 149:
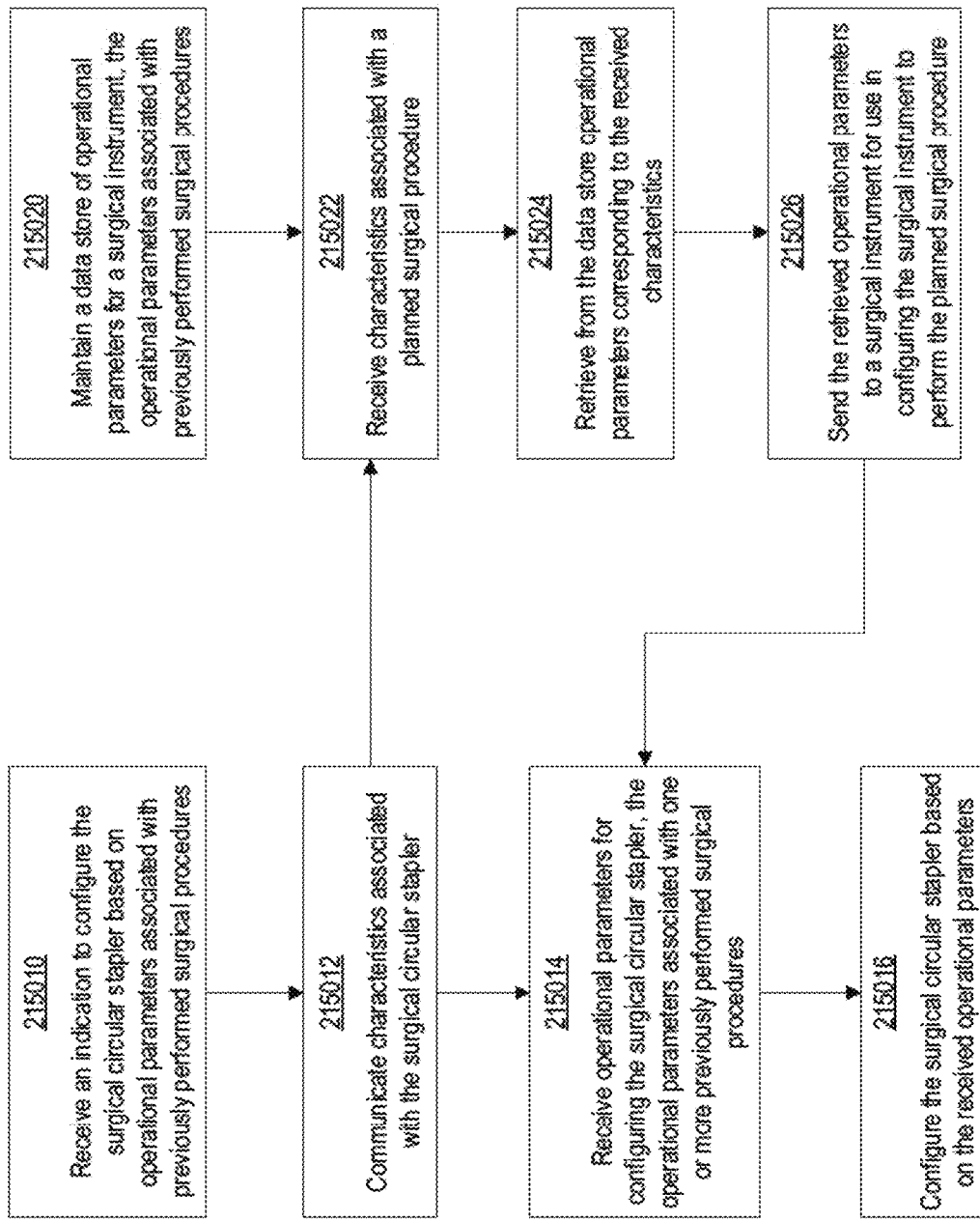

FIG. 149 is another example flow diagram of an example motorized circular stapling instrument operating in a previous-configuration control operation mode.

Figure 150:
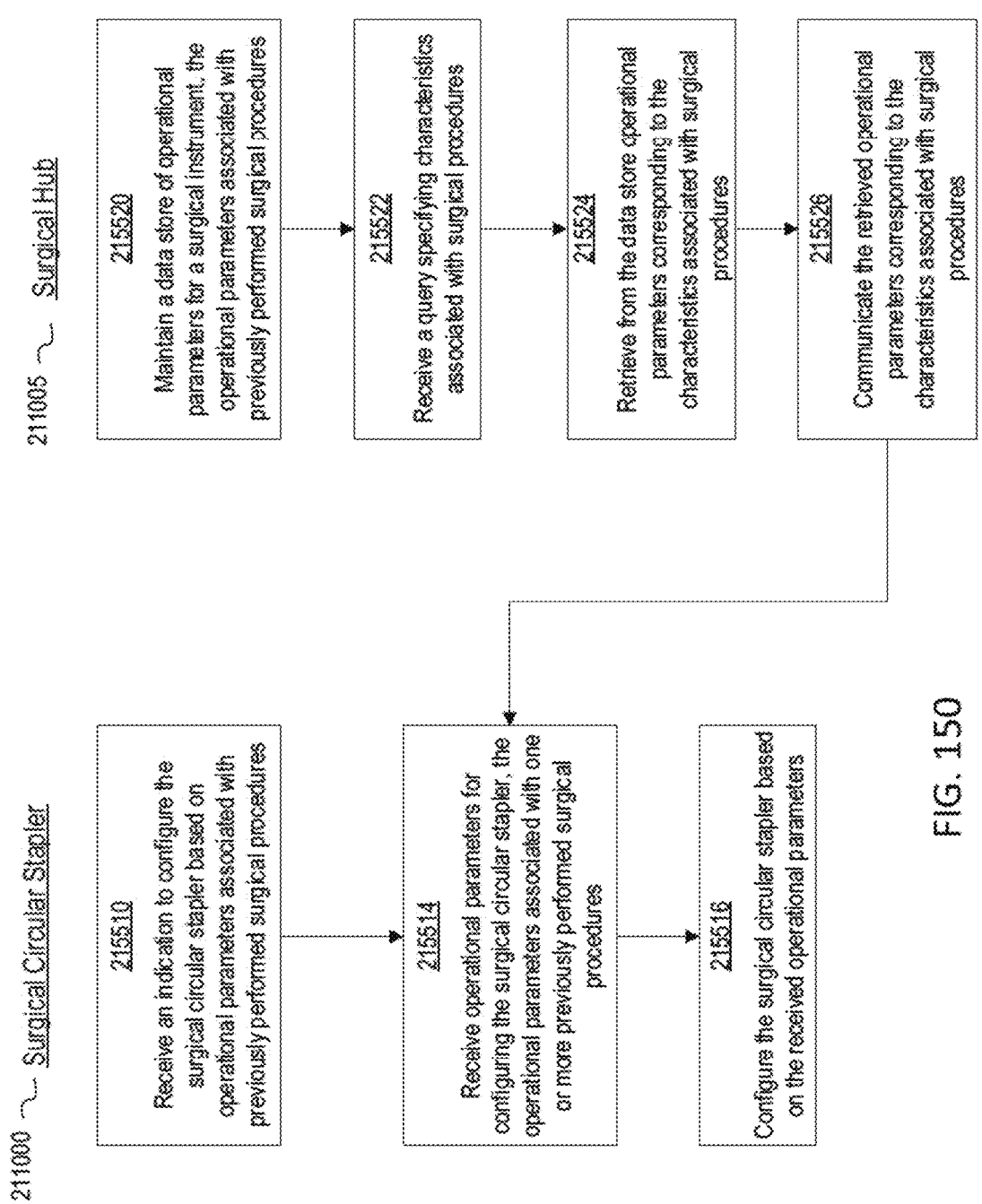

FIG. 150 is another example flow diagram of an example motorized circular stapling instrument operating in a previous-configuration control operation mode.

Figure 151:
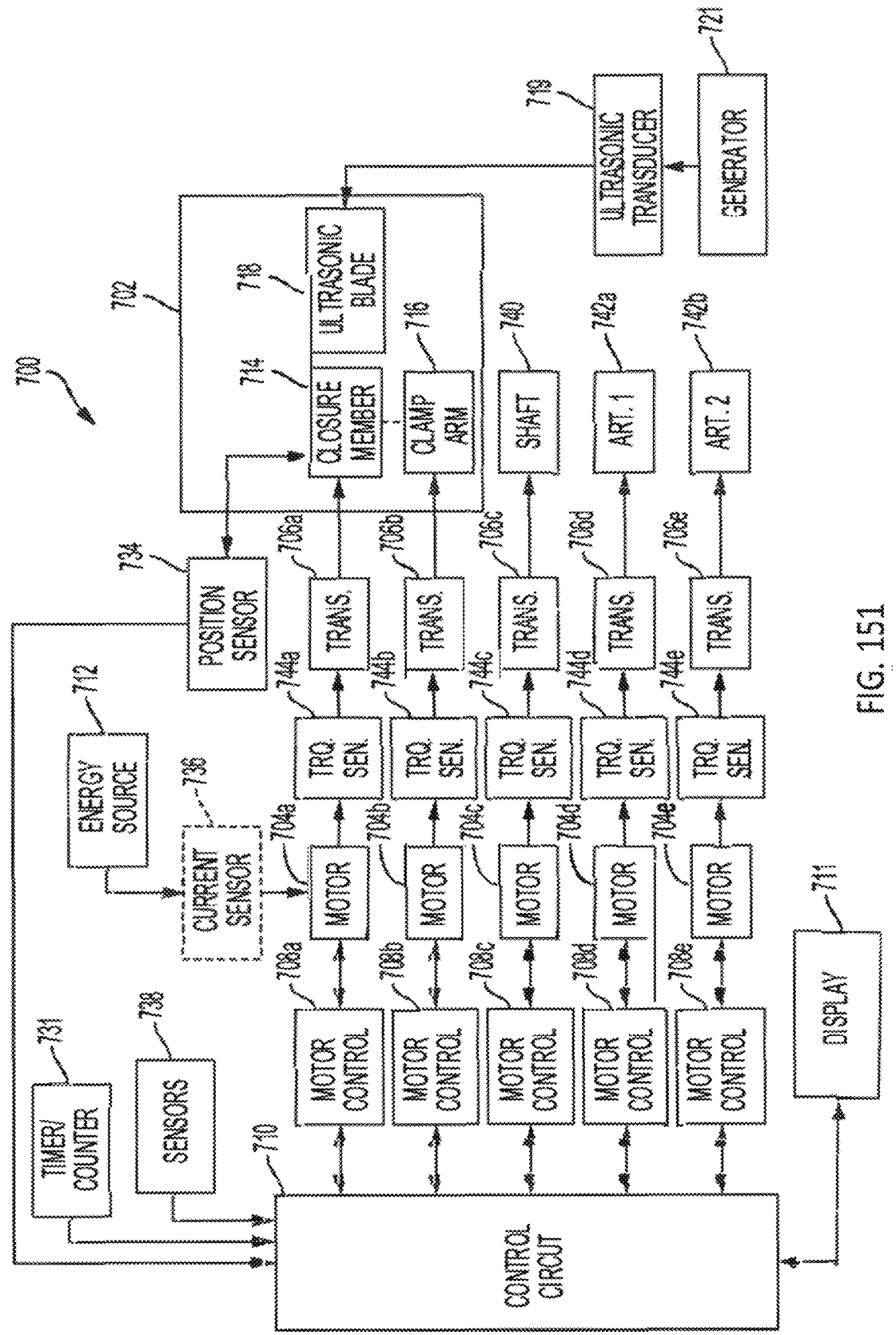

FIG. 151 is a schematic diagram of a robotic surgical instrument configured to operate a surgical tool described herein, in accordance with at least one aspect of the present disclosure.

Figure 152:
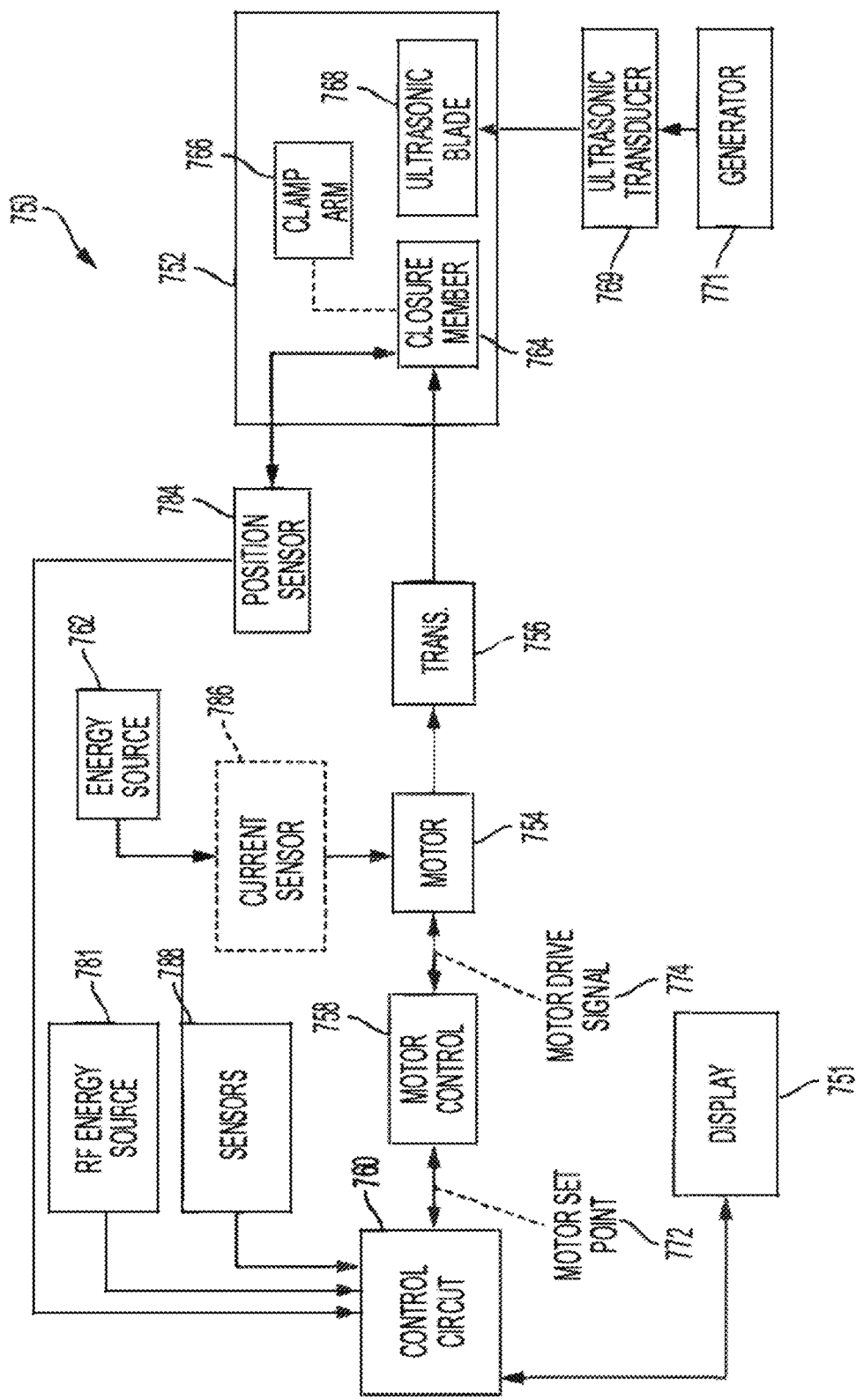

FIG. 152 illustrates a block diagram of a surgical instrument programmed to control the distal translation of a displacement member, in accordance with at least one aspect of the present disclosure.

Figure 153:
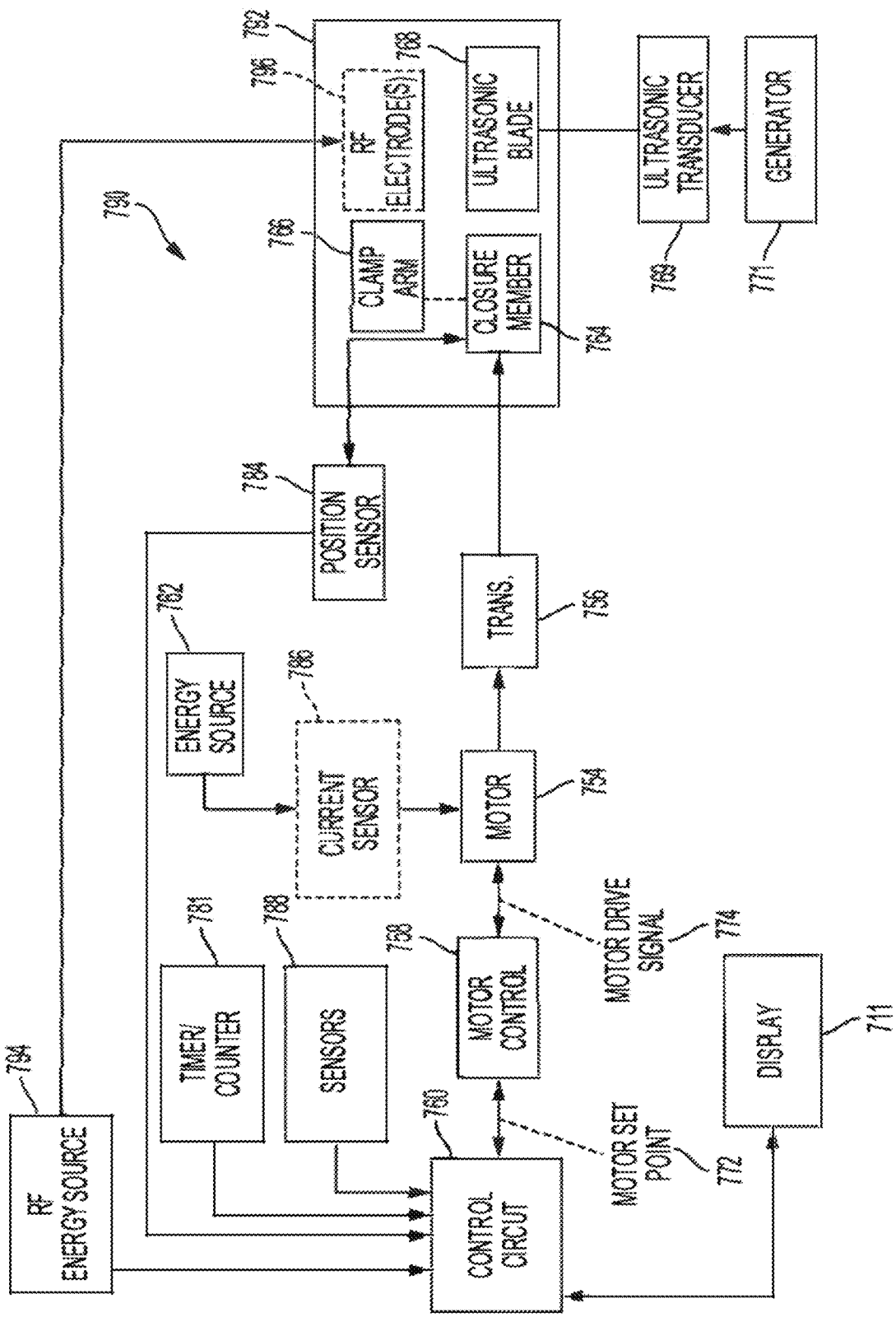

FIG. 153 is a schematic diagram of a surgical instrument configured to control various functions, in accordance with at least one aspect of the present disclosure.

Figure 154:
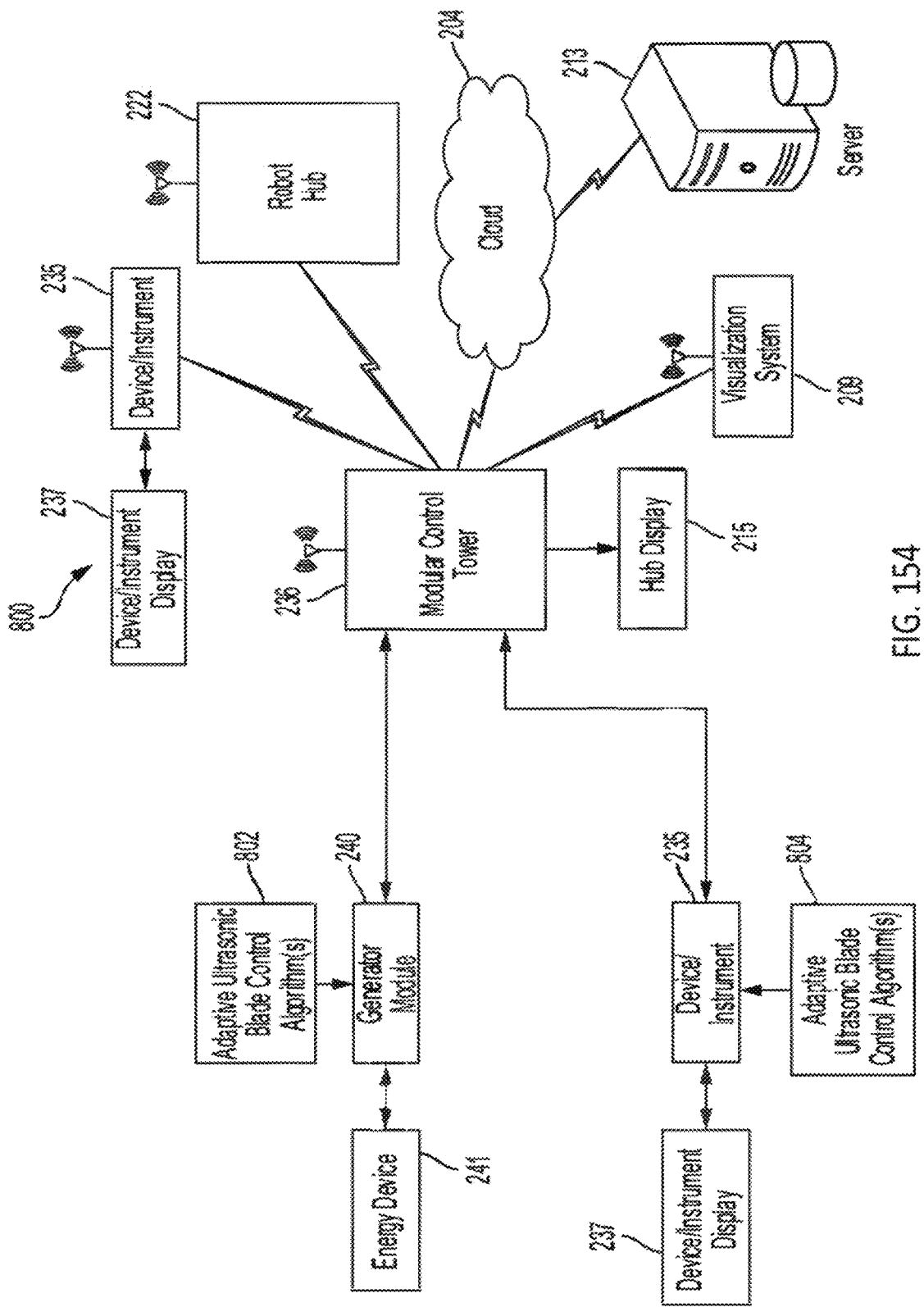

FIG. 154 is a system configured to execute adaptive ultrasonic blade control algorithms in a surgical data network comprising a modular communication hub, in accordance with at least one aspect of the present disclosure.

Figure 155:
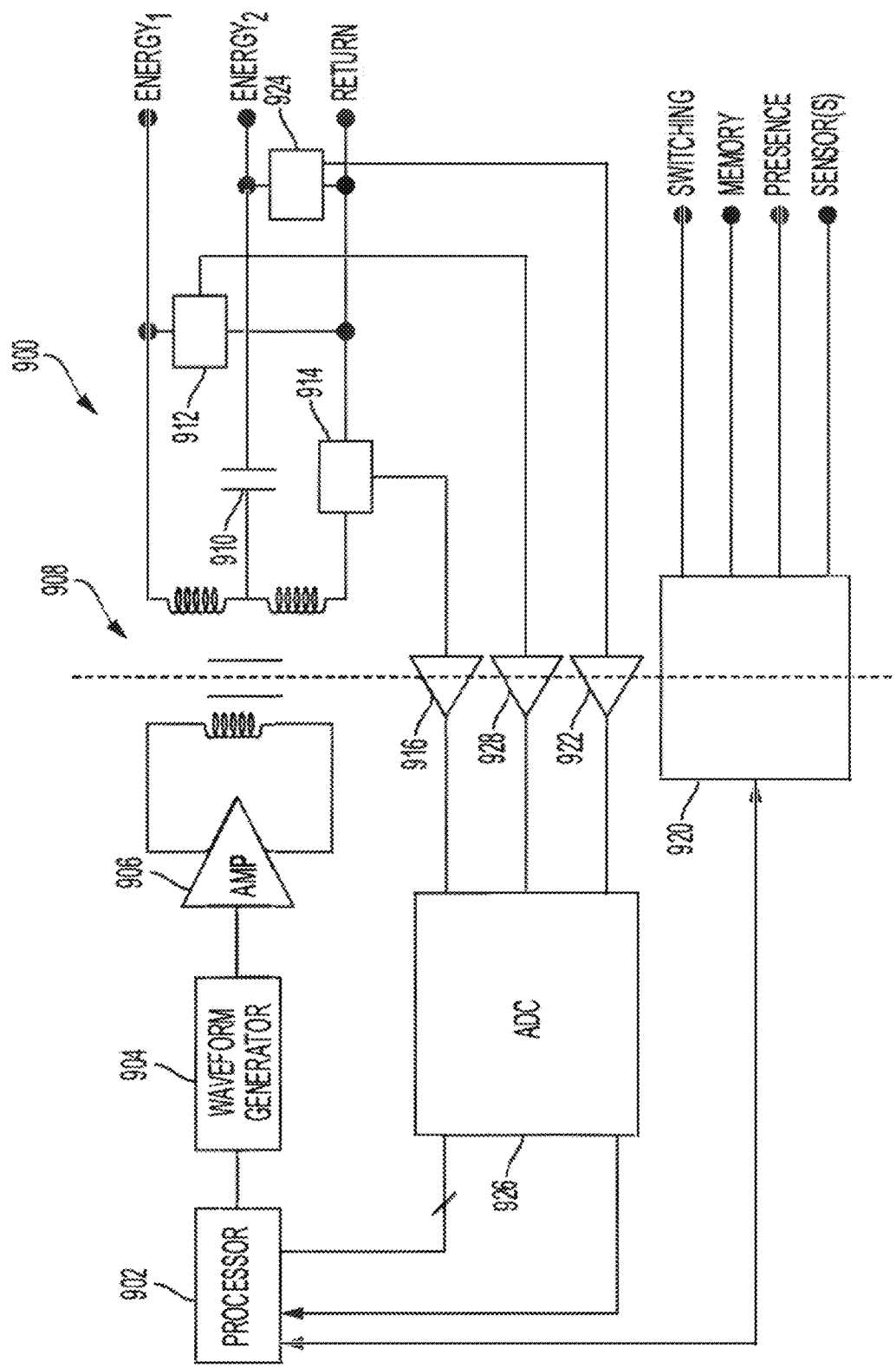

FIG. 155 illustrates an example of a generator, in accordance with at least one aspect of the present disclosure.

Figure 156:
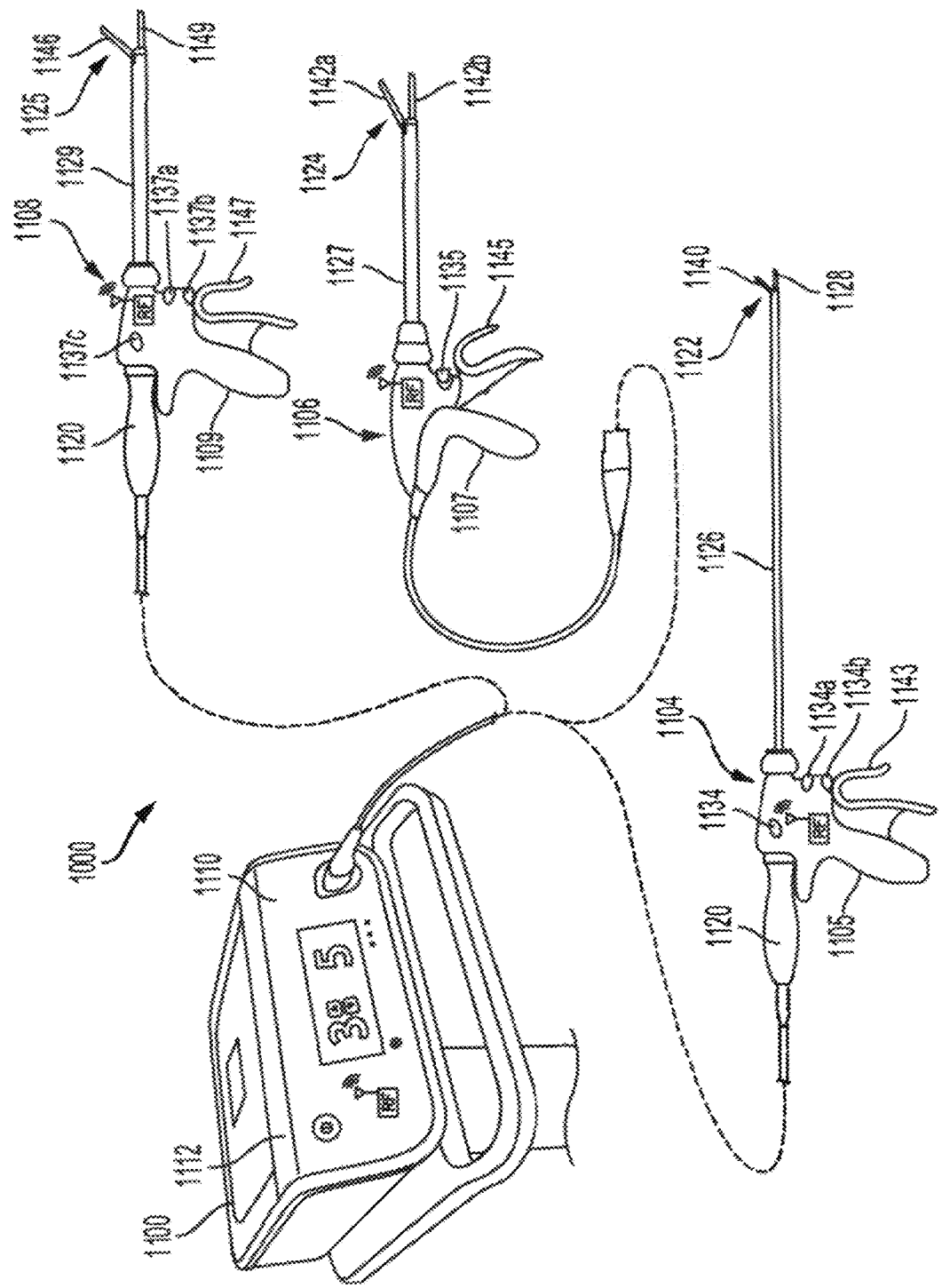

FIG. 156 is a surgical system comprising a generator and various surgical instruments usable therewith, in accordance with at least one aspect of the present disclosure.

Figure 157:
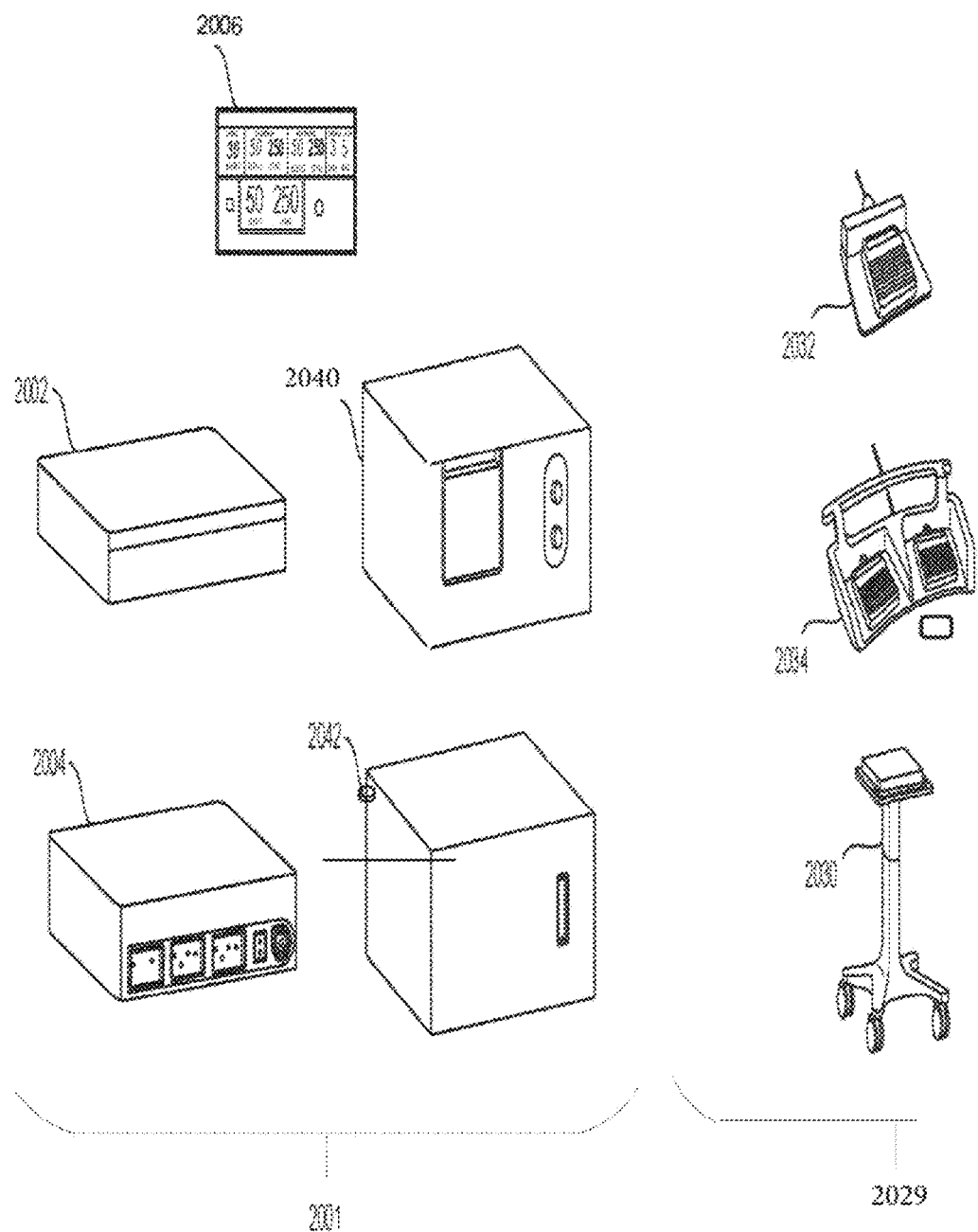

FIG. 157 is a diagram of a situationally aware surgical system, in accordance with at least one aspect of the present disclosure.

Figure 158B:
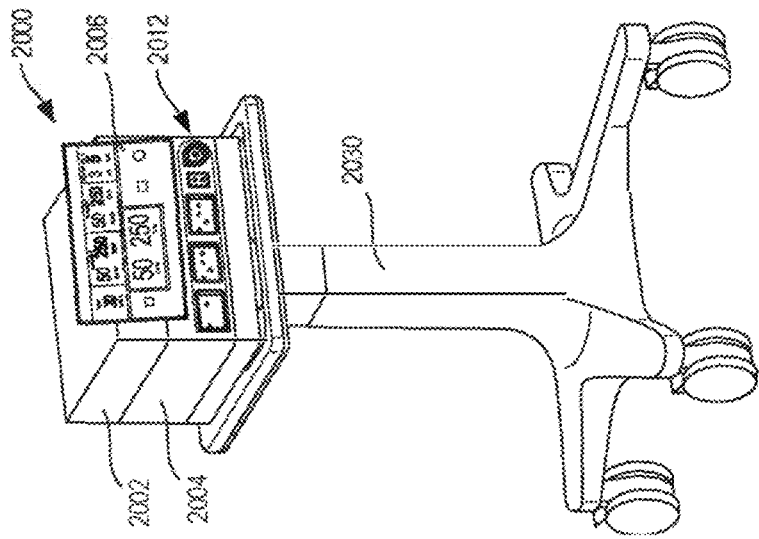
Figure 158A:
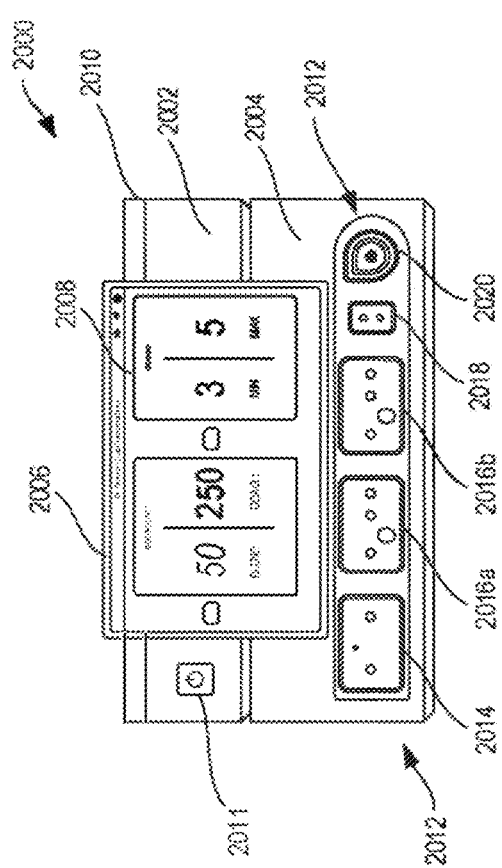

FIG. 158A is a first illustrative modular energy system configuration including a header module and a display screen that renders a graphical user interface (GUI) for relaying information regarding modules connected to the header module, in accordance with at least one aspect of the present disclosure.

Figure 159A:
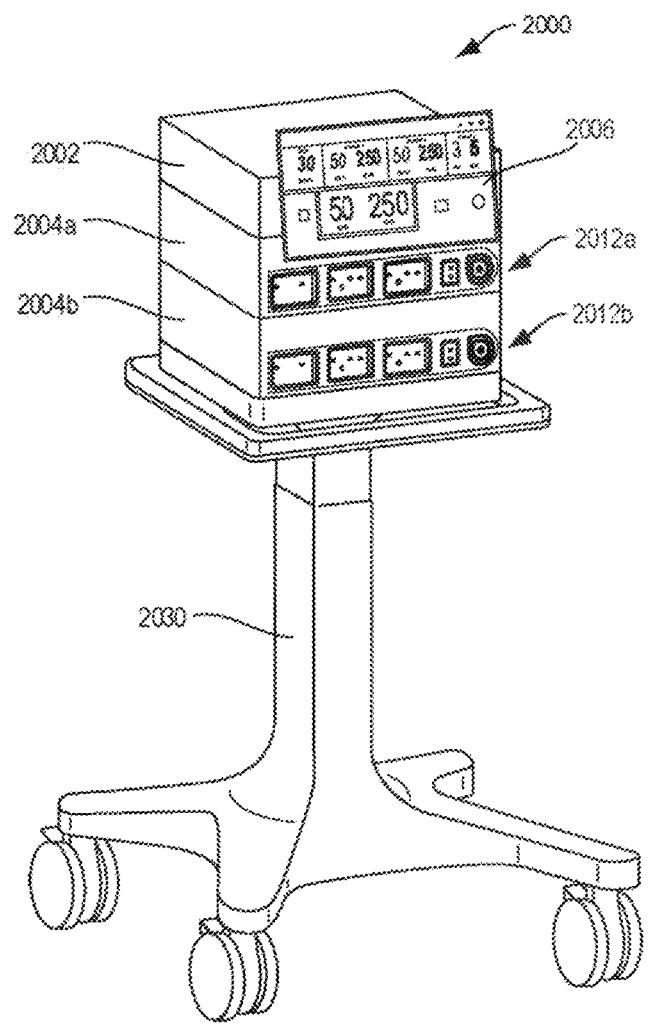

FIG. 158B is the modular energy system shown in FIG. 159A mounted to a cart, in accordance with at least one aspect of the present disclosure.

FIG. 159A is a second illustrative modular energy system configuration including a header module, a display screen, an energy module, and an expanded energy module connected together and mounted to a cart, in accordance with at least one aspect of the present disclosure.

Figure 159B:
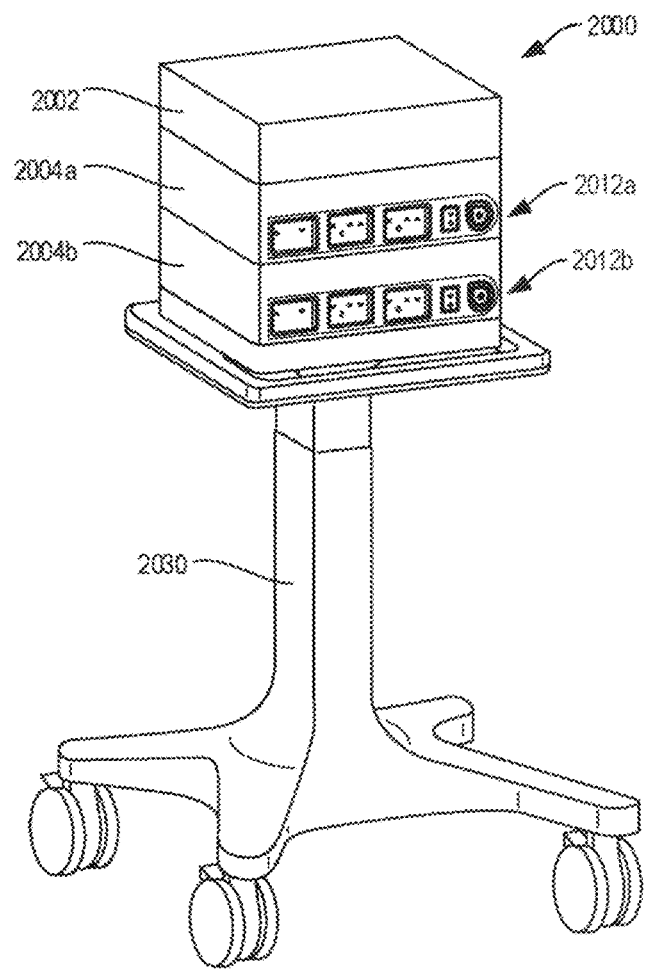

FIG. 159B is a third illustrative modular energy system configuration that is similar to the second configuration shown in FIG. 160A, except that the header module lacks a display screen, in accordance with at least one aspect of the present disclosure.

Figure 160:
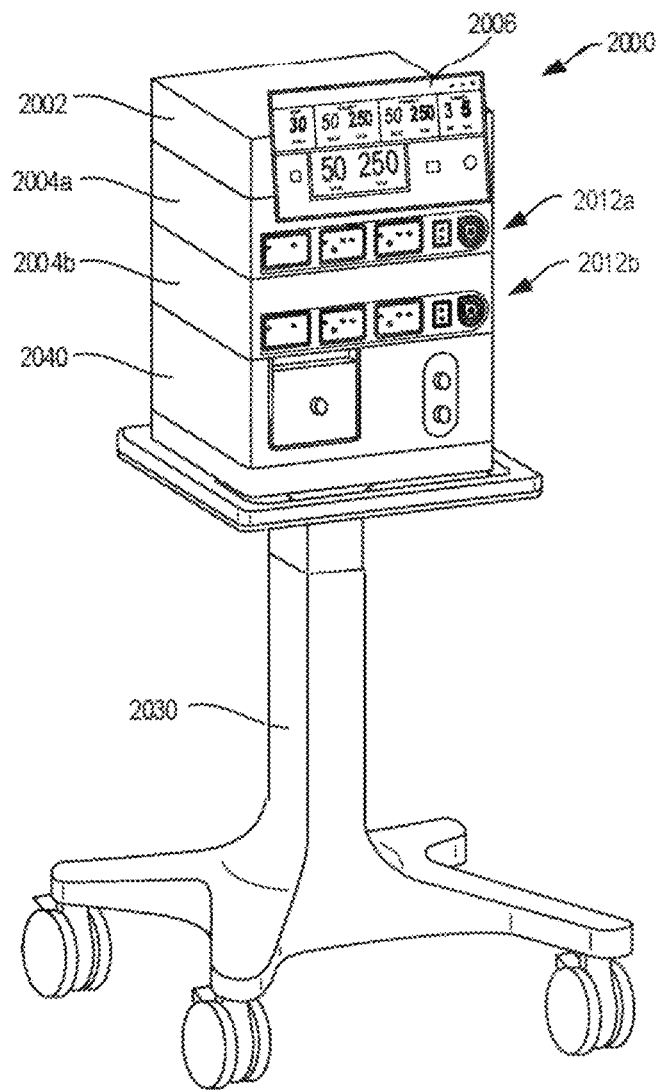

FIG. 160 is a fourth illustrative modular energy stem configuration including a header module, a display screen, an energy module, an expanded energy module, and a technology module connected together and mounted to a cart, in accordance with at least one aspect of the present disclosure.

Figure 161:
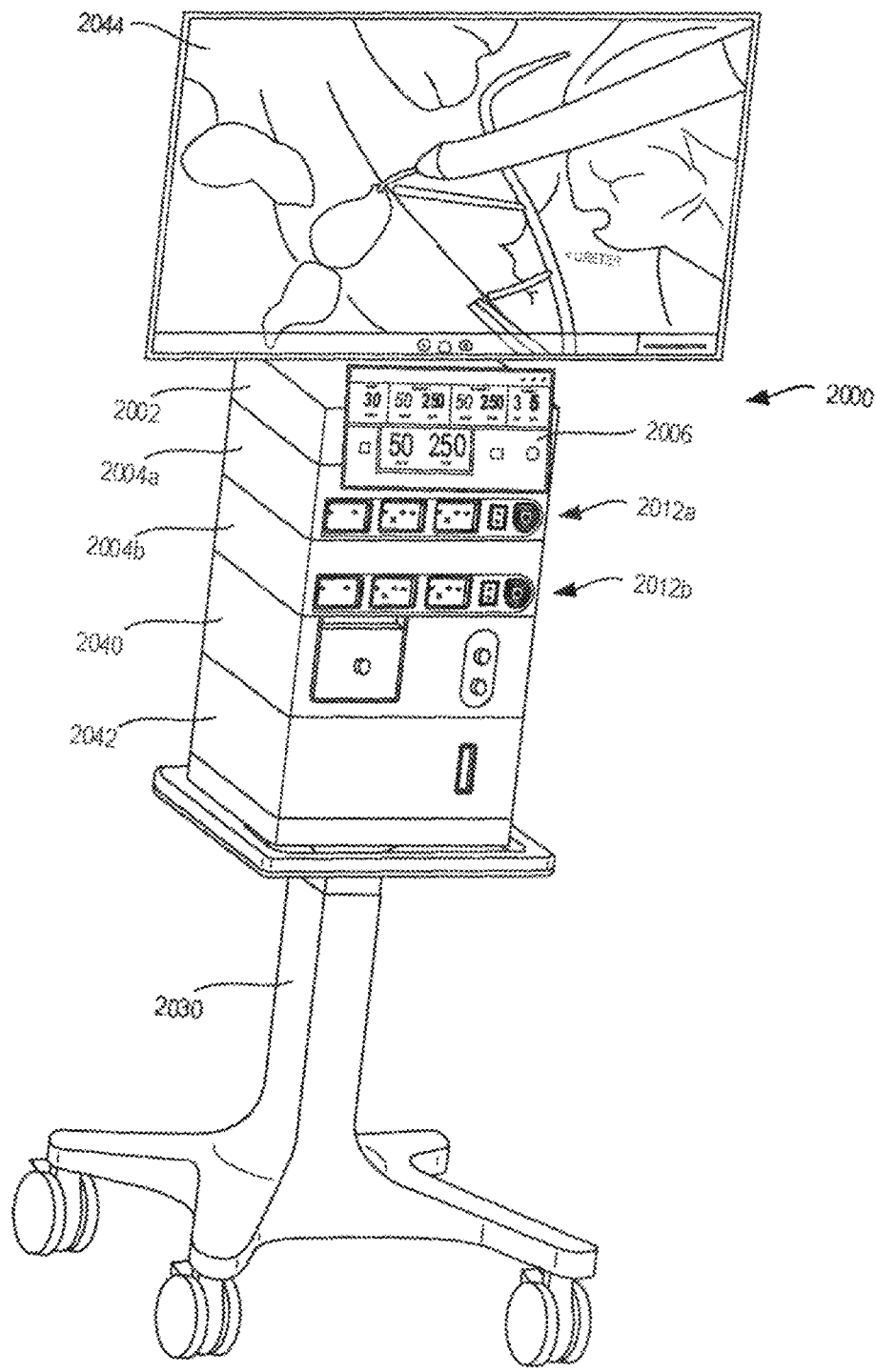

FIG. 161 is a fifth illustrative modular energy system configuration including a header module, a display screen, an energy module, an expanded energy module, a technology module, and a visualization module connected together and mounted to a cart, in accordance with at least one aspect of the present disclosure.

Figure 162:
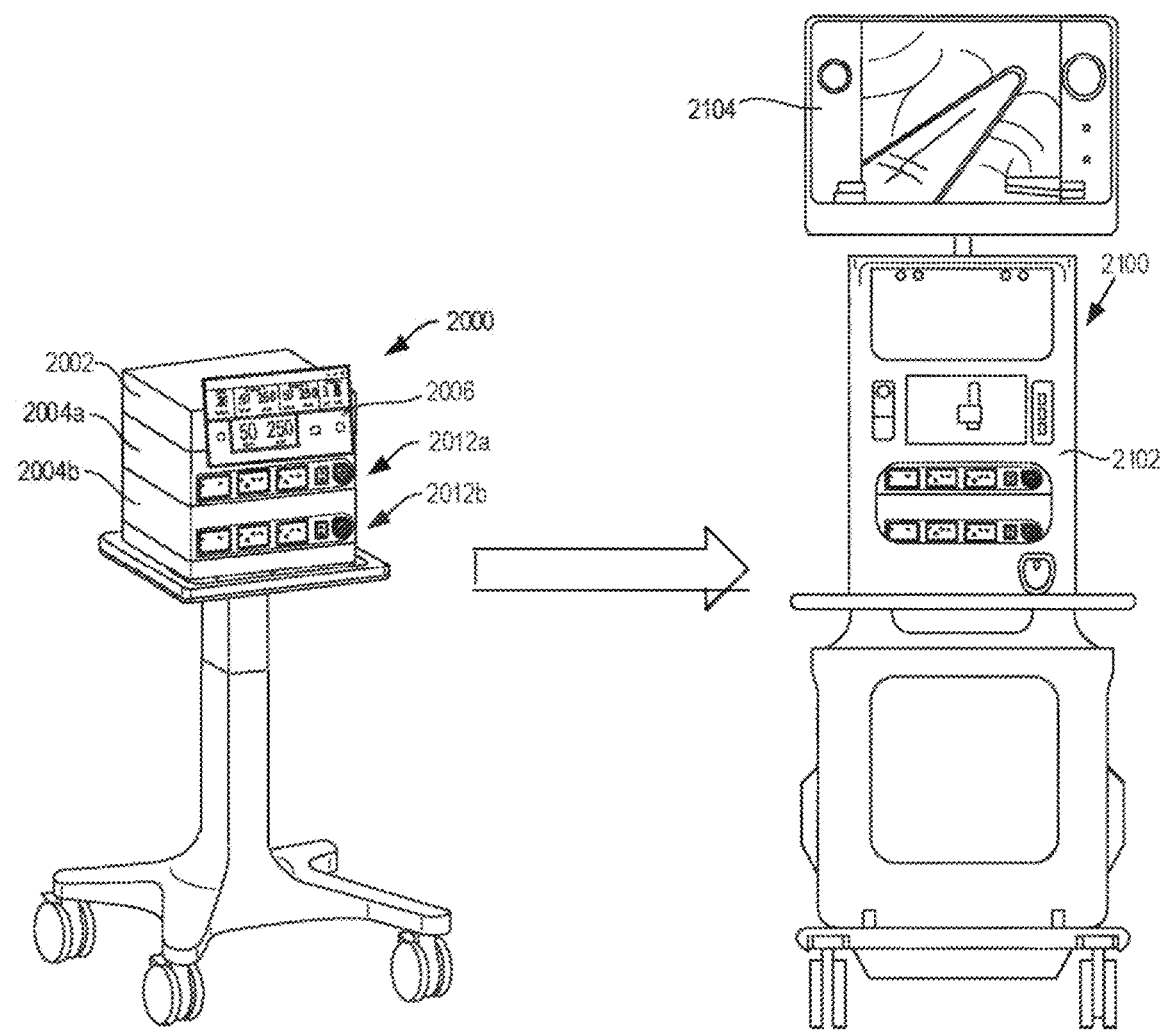

FIG. 162 is a diagram of a modular energy system including communicably connectable surgical platforms, in accordance with at least one aspect of the present disclosure.

Figure 163:
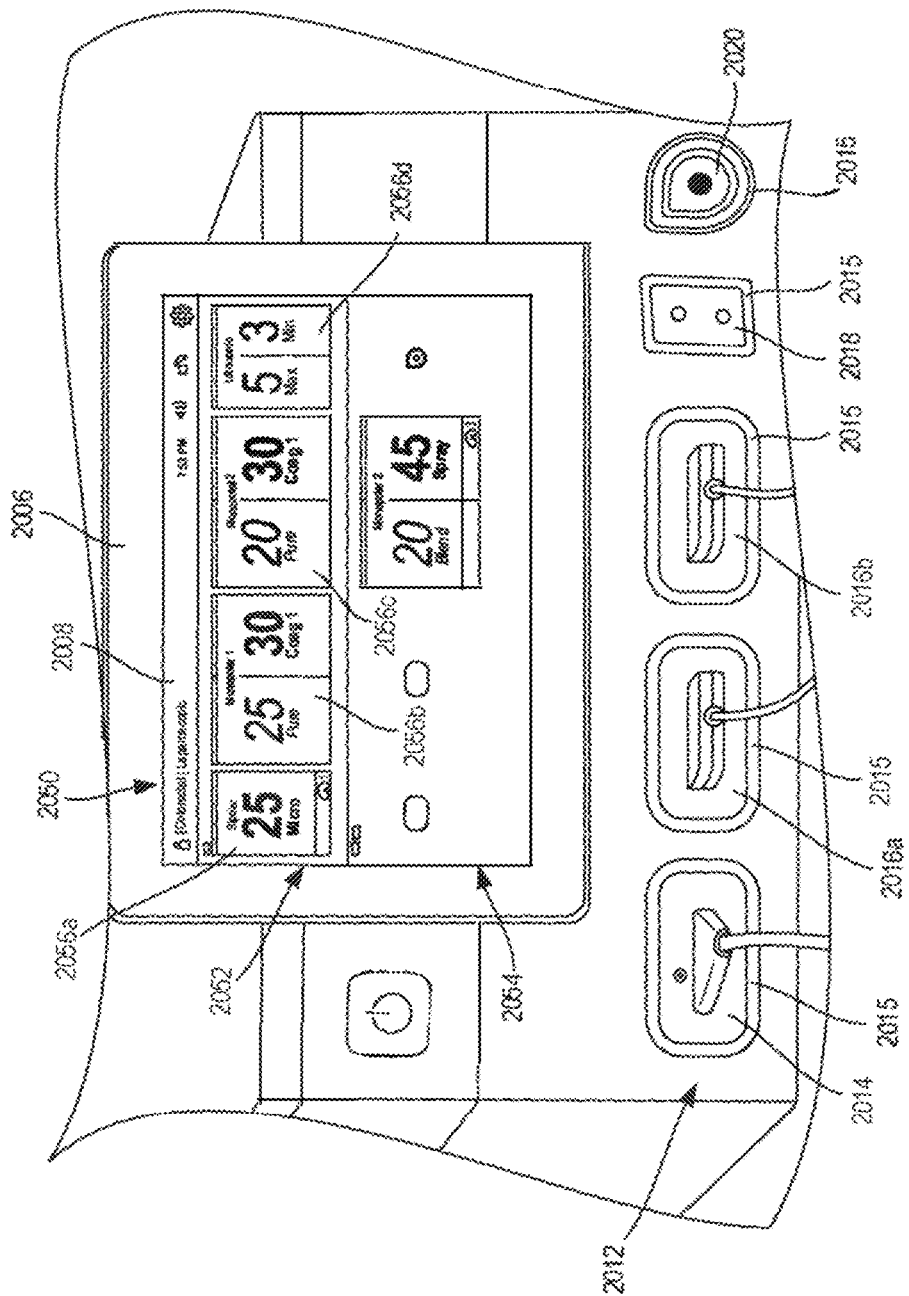

FIG. 163 is a perspective view of a header module of a modular energy system including a user interface, in accordance with at least one aspect of the present disclosure.

Figure 164:
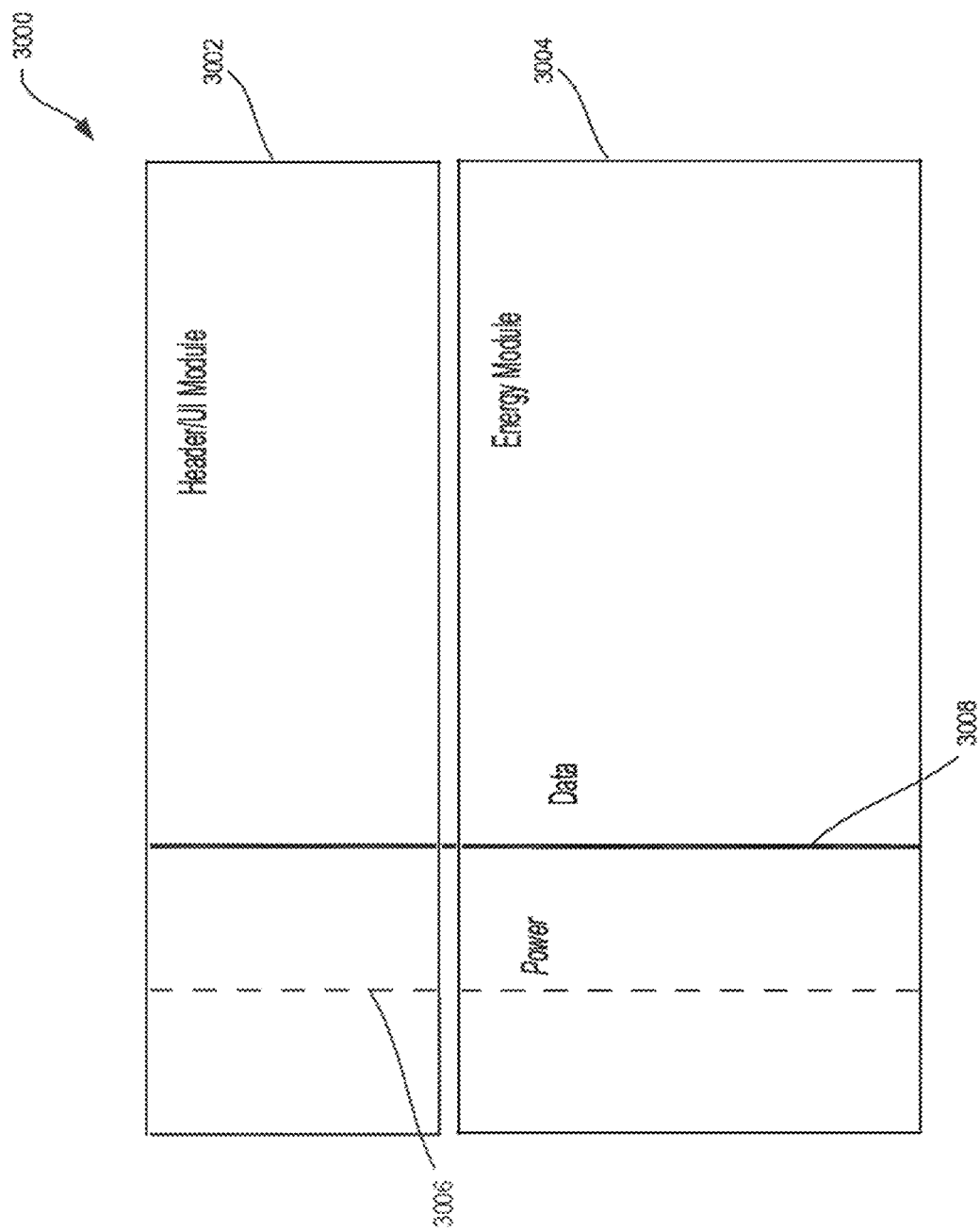

FIG. 164 is a block diagram of a stand-alone hub configuration of a modular energy system, in accordance with at least one aspect of the present disclosure.

Figure 165:
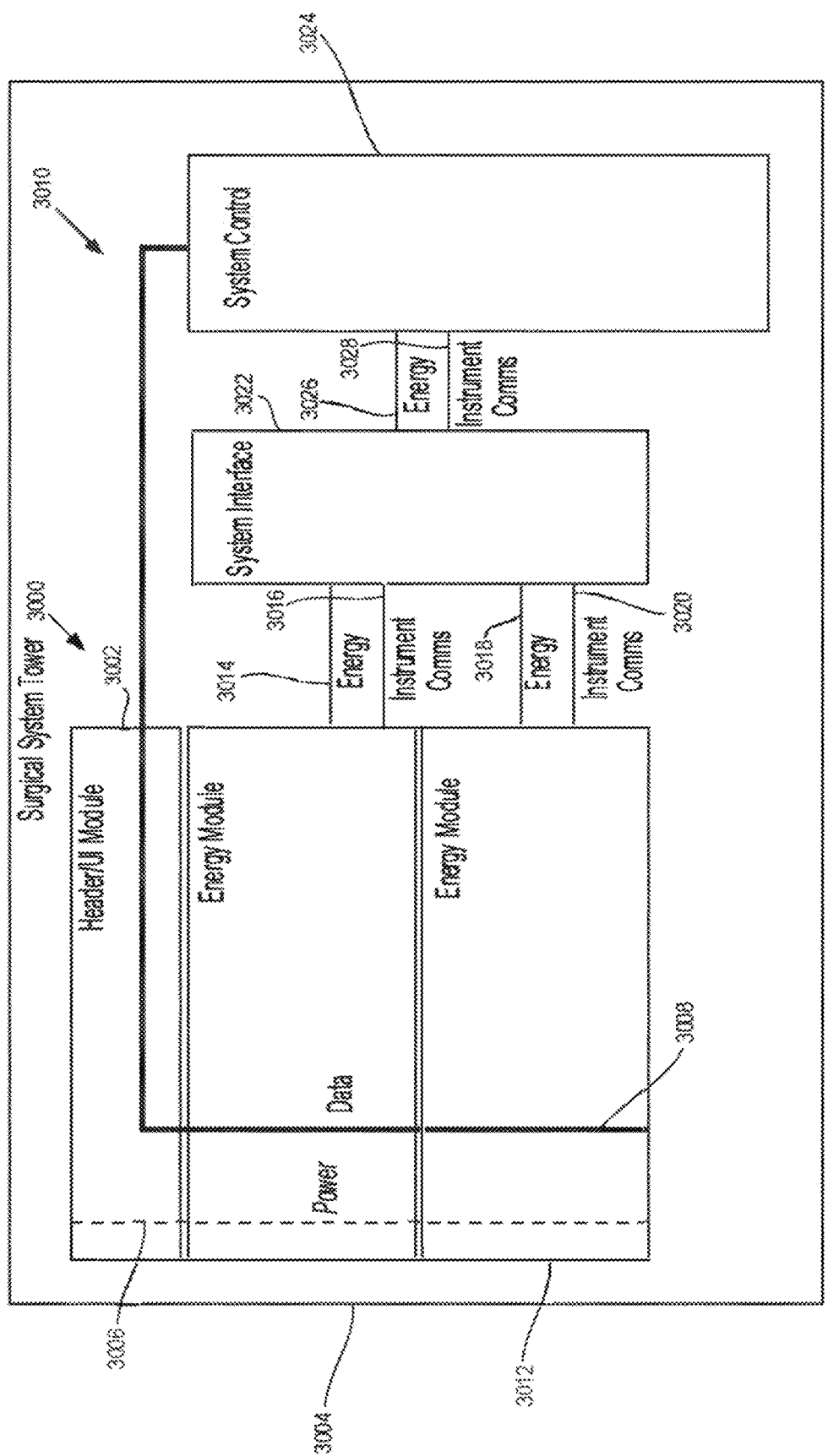

FIG. 165 is a block diagram of a hub configuration of a modular energy system integrated with a surgical control system, in accordance with at least one aspect of the present disclosure.

Figure 166:
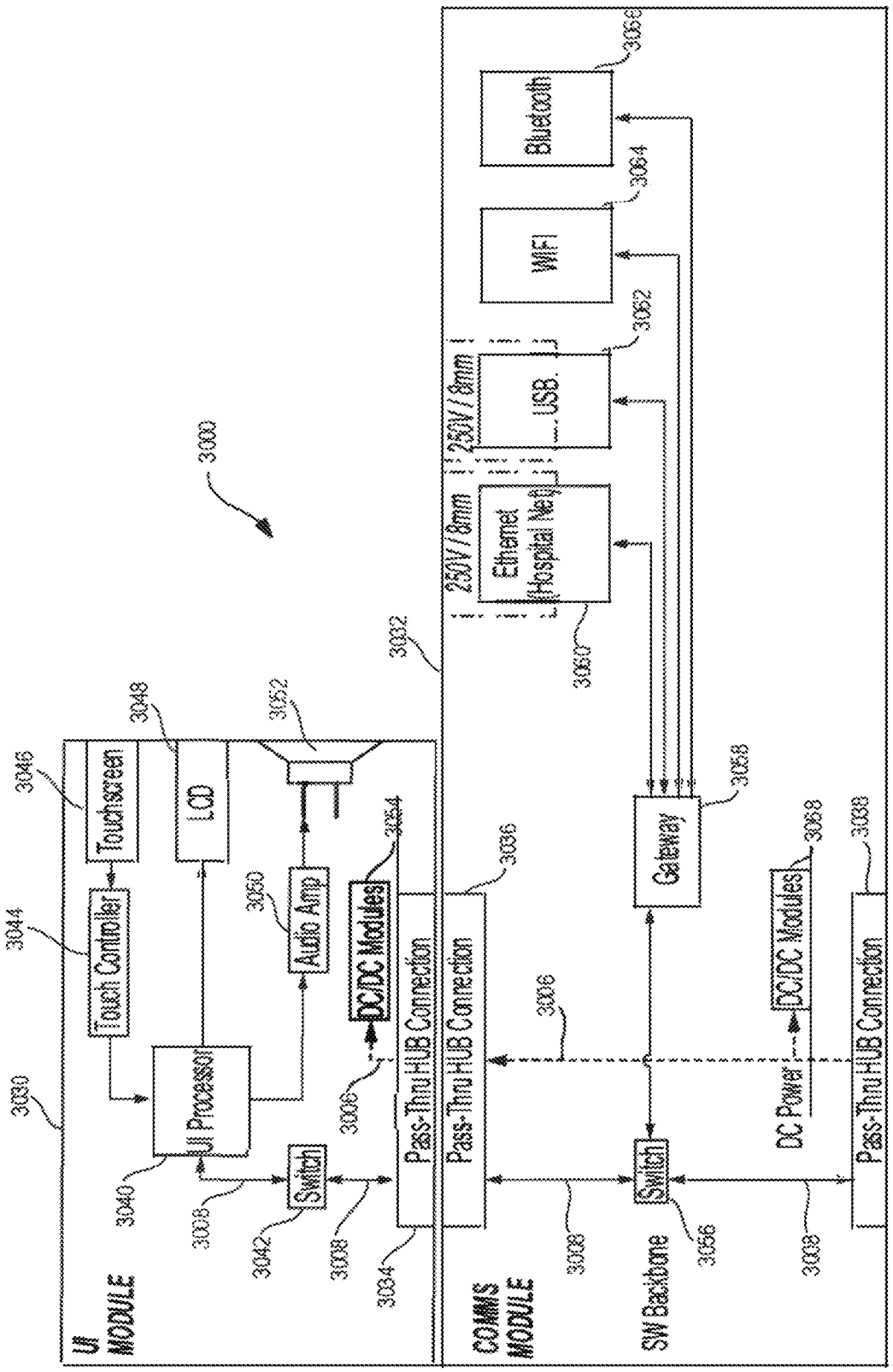

FIG. 166 is a block diagram of a user interface module coupled to a communications module of a modular energy system, in accordance with at least one aspect of the present disclosure.

Figure 167:
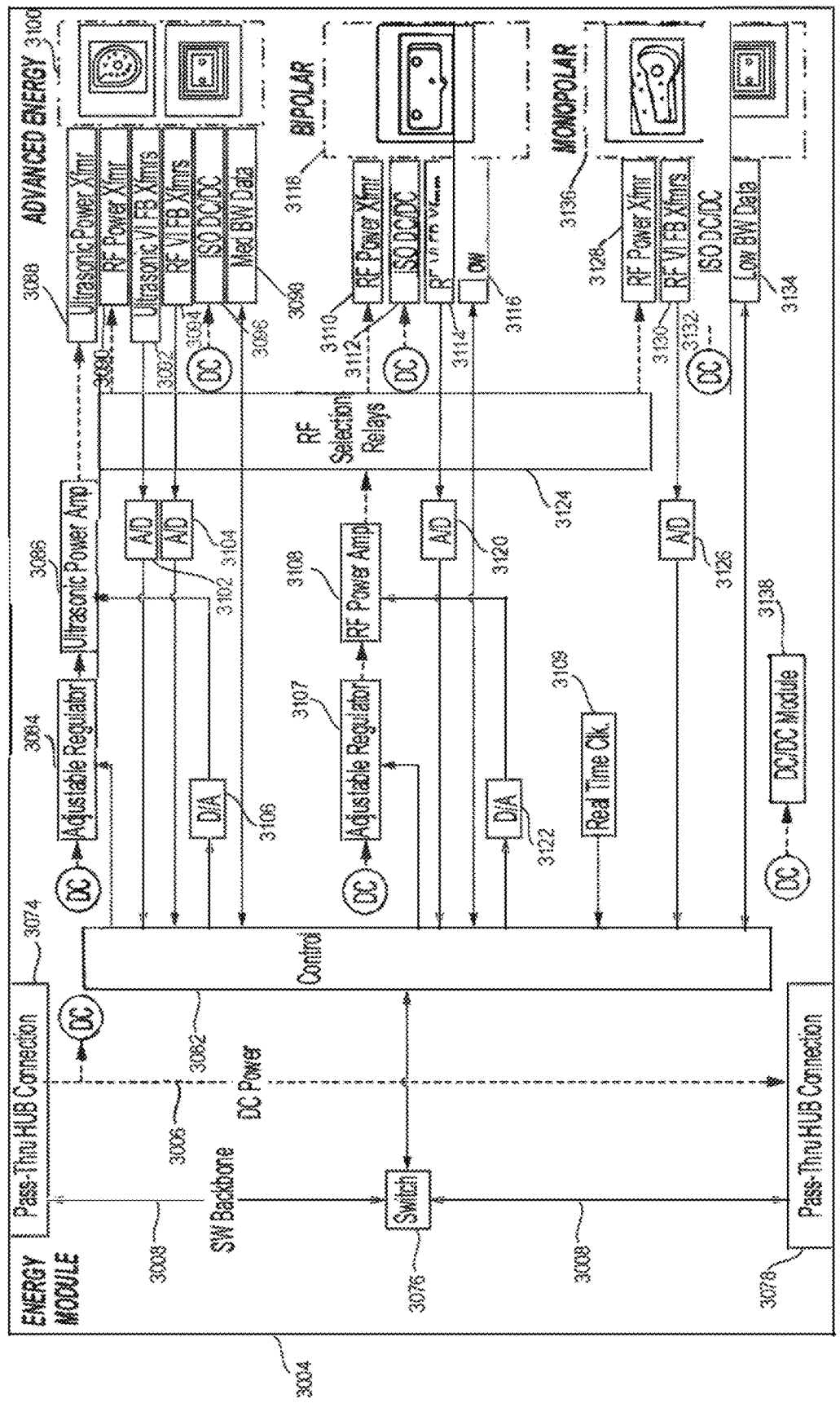

FIG. 167 is a block diagram of an energy module of a modular energy system, in accordance with at least one aspect of the present disclosure.

Figure 168A:
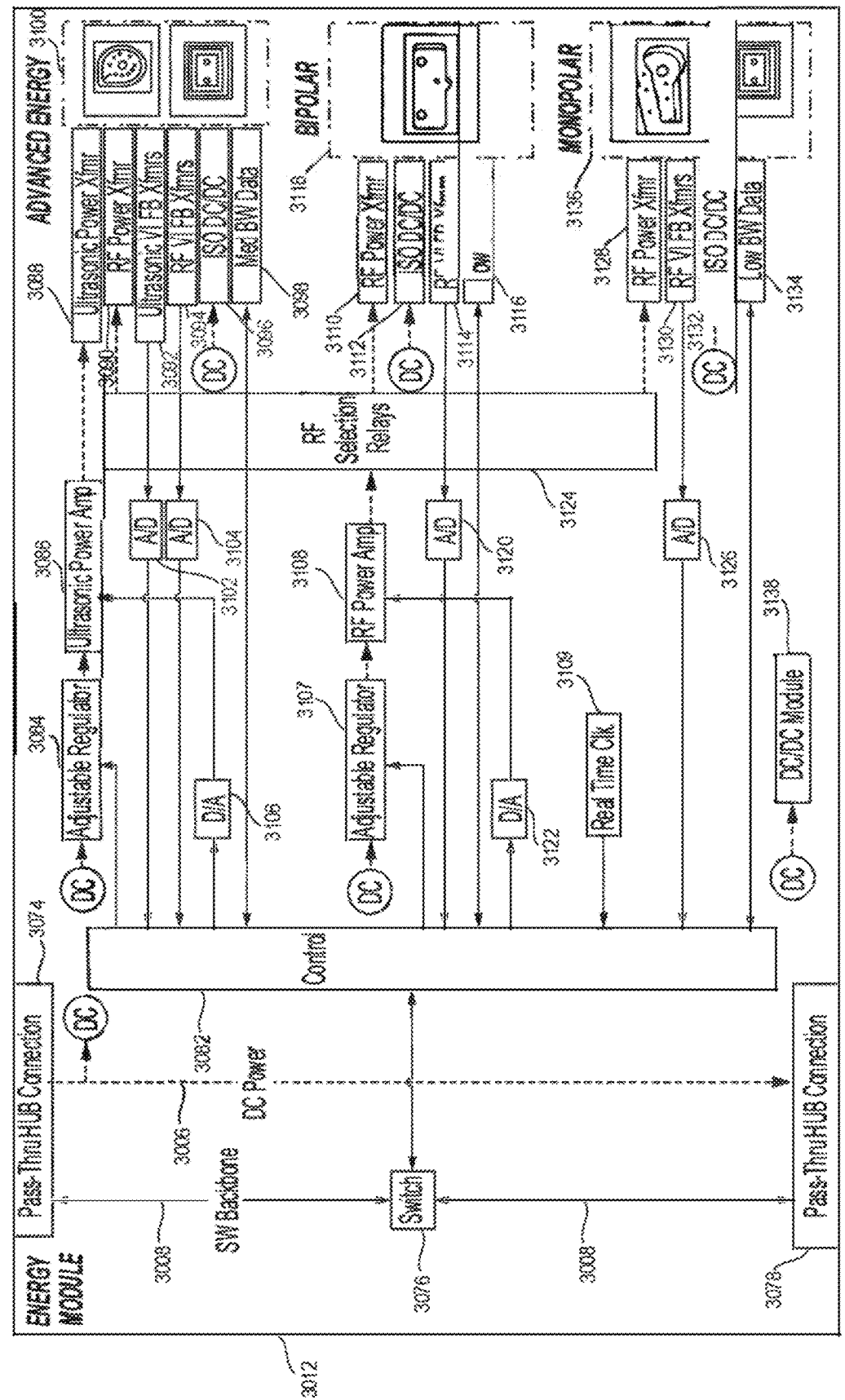
Figure 168B:
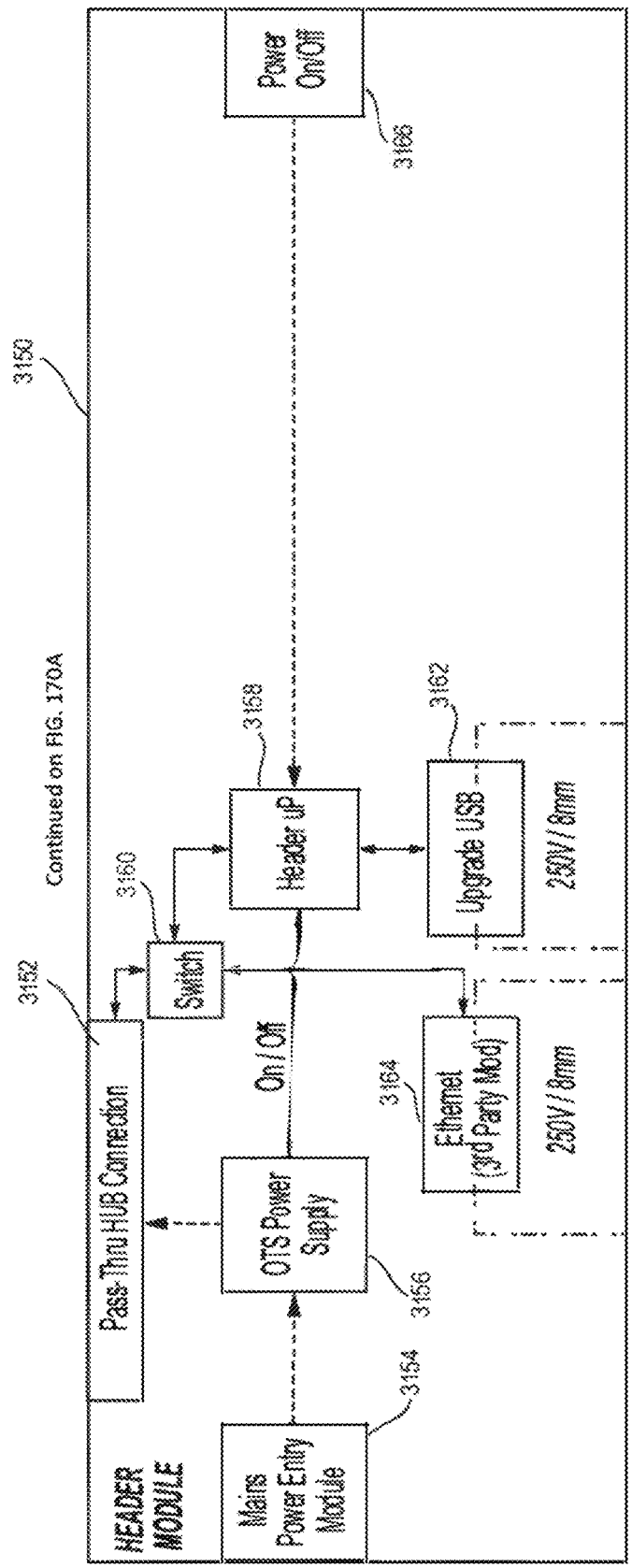

FIGS. 168A and 168B illustrate a block diagram of an energy module coupled to a header module of a modular energy system, in accordance with at least one aspect of the present disclosure.

Figure 169A:
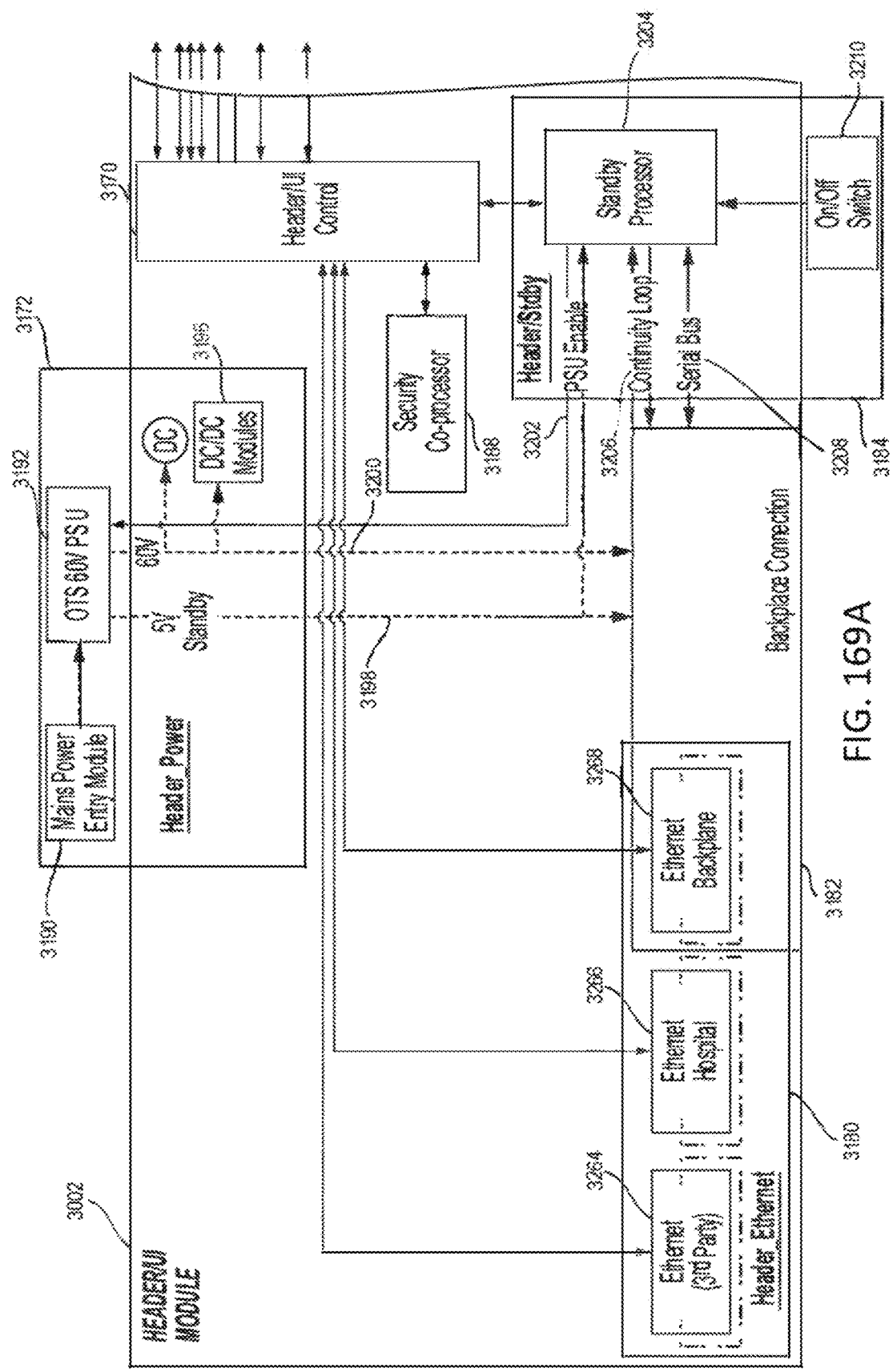
Figure 169B:
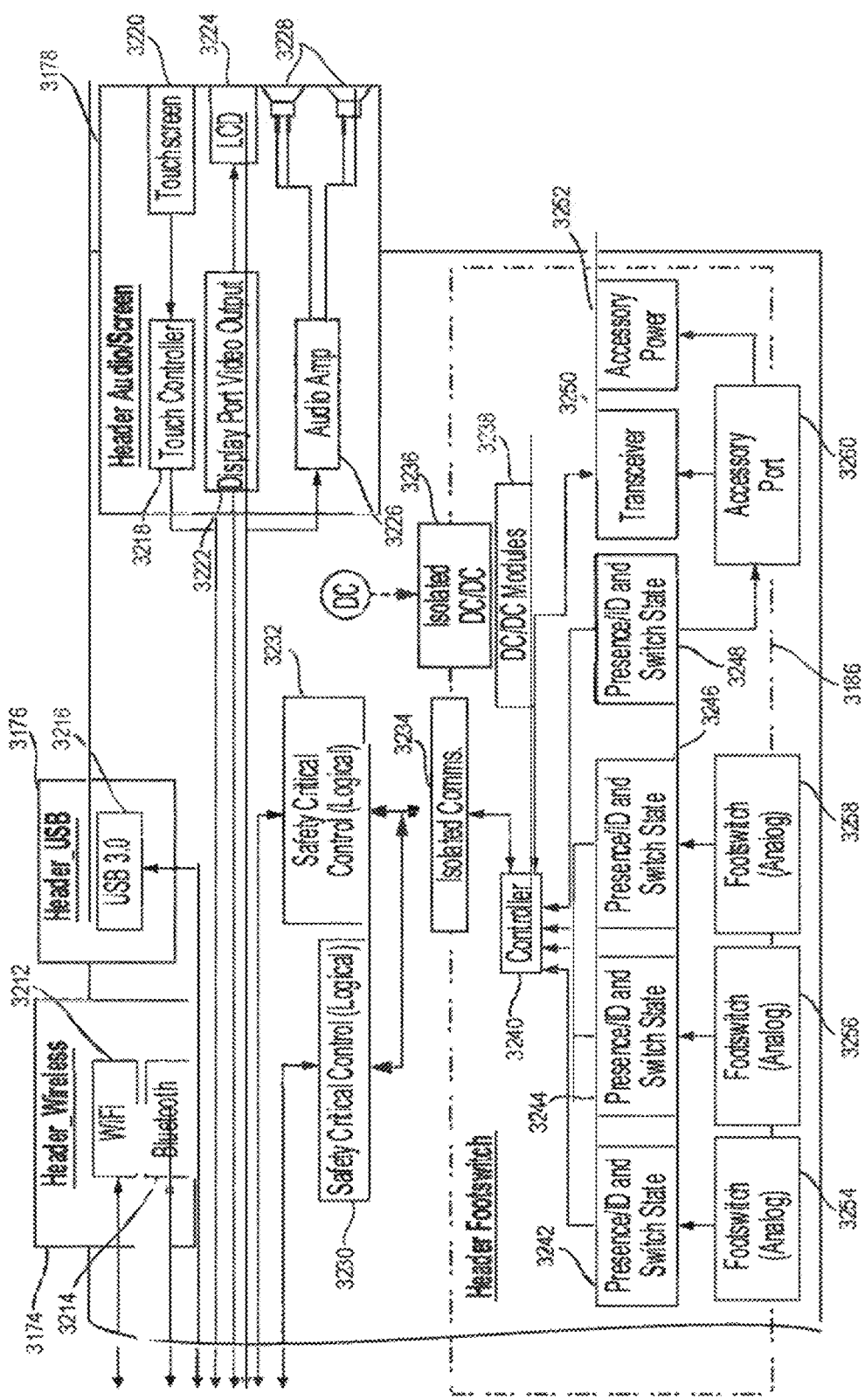

FIGS. 169A and 169B illustrate a block diagram of a header/user interface (UI) module of a modular energy system for a hub, in accordance with at least one aspect of the present disclosure.

Figure 170:
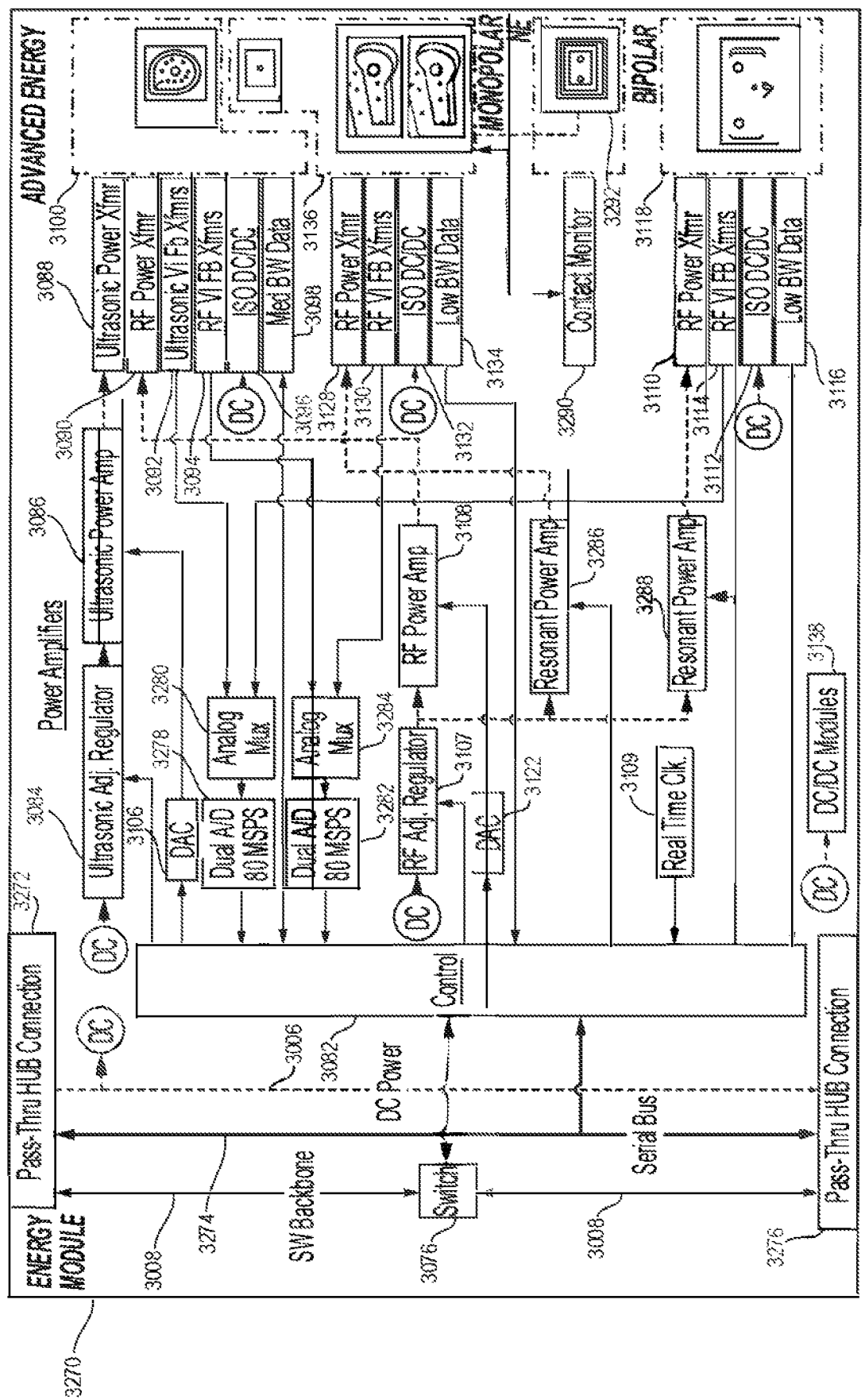

FIG. 170 is a block diagram of an energy module for a hub, in accordance with at least one aspect of the present disclosure.

Figure 171:
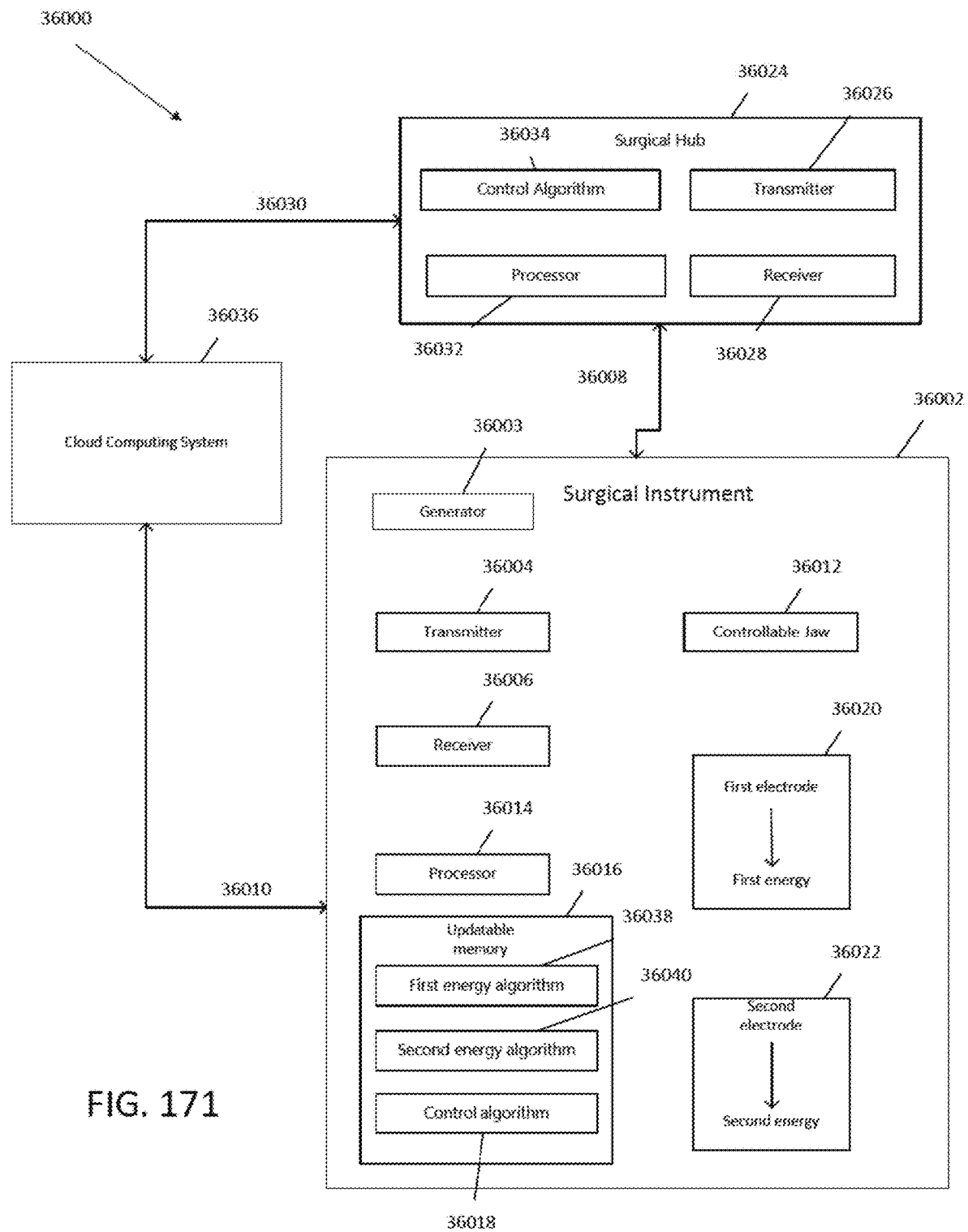

FIG. 171 illustrates a system for communication between a surgical instrument, a surgical hub, and a cloud computing system, in accordance with at least one aspect of the present disclosure.

Figure 172:
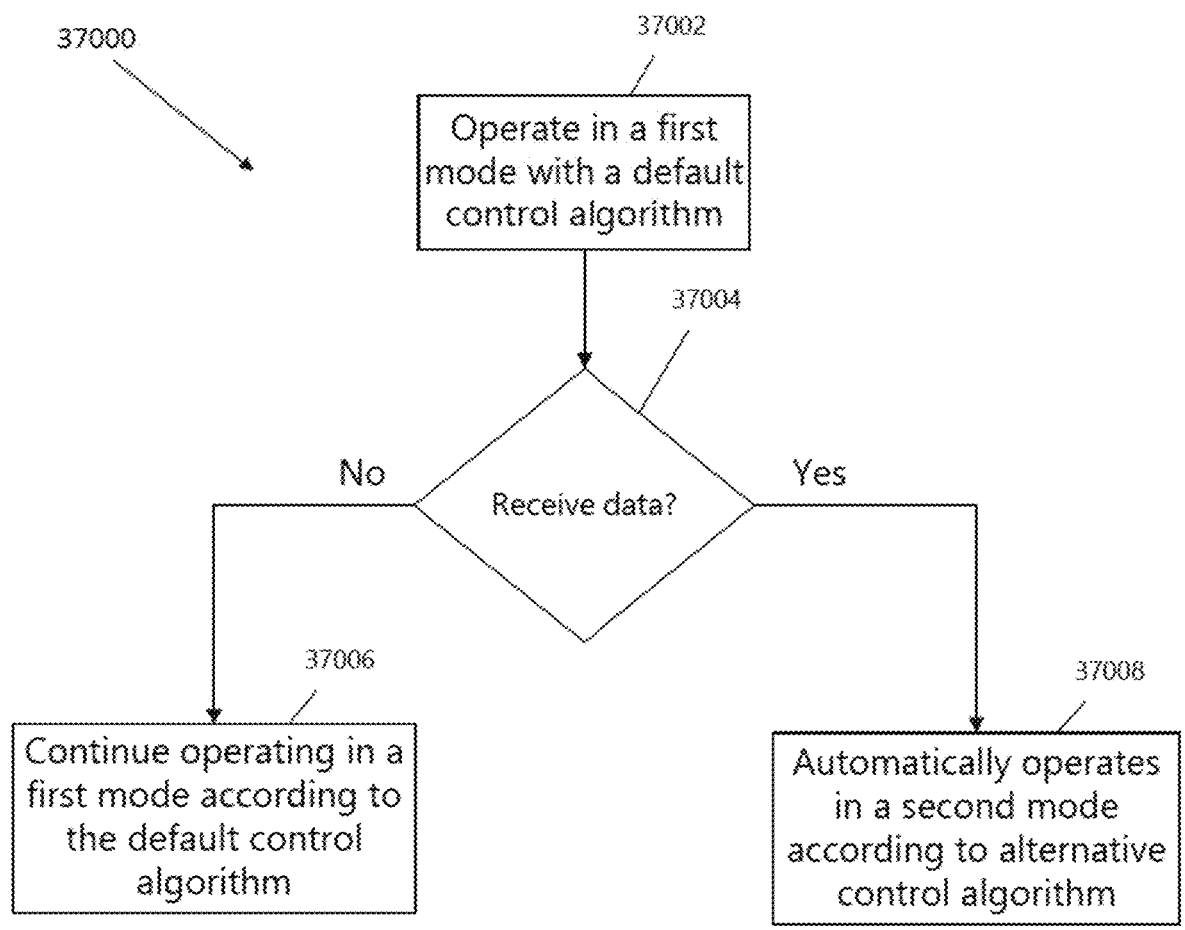

FIG. 172 illustrates a logic flow diagram of a process for updating the algorithm of a surgical instrument, in accordance with at least one aspect of the present disclosure.

Figure 173:
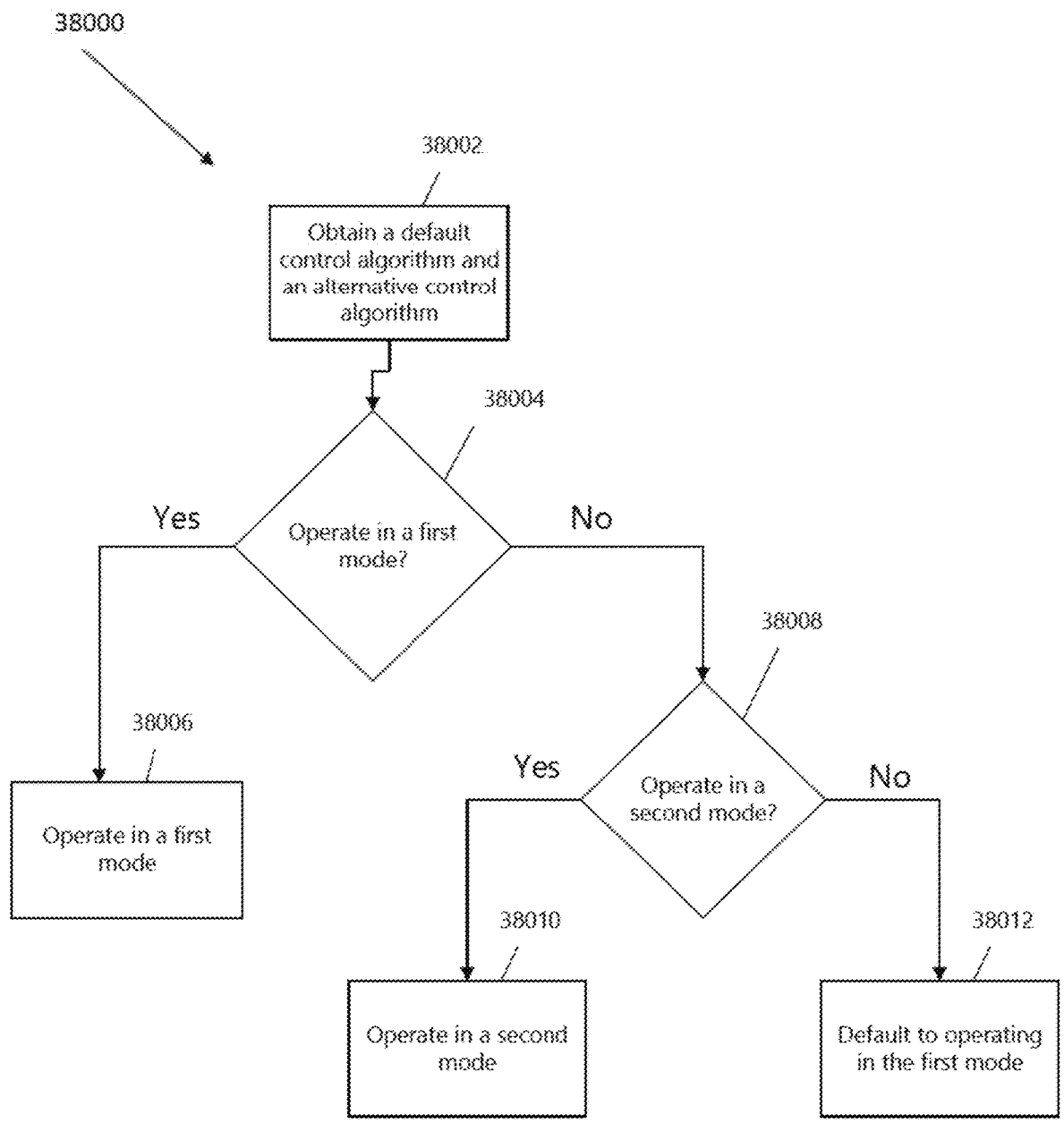

FIG. 173 illustrates another logic flow diagram of a process for updating an algorithm of a surgical instrument, in accordance with at least one aspect of the present disclosure.

Figure 174:
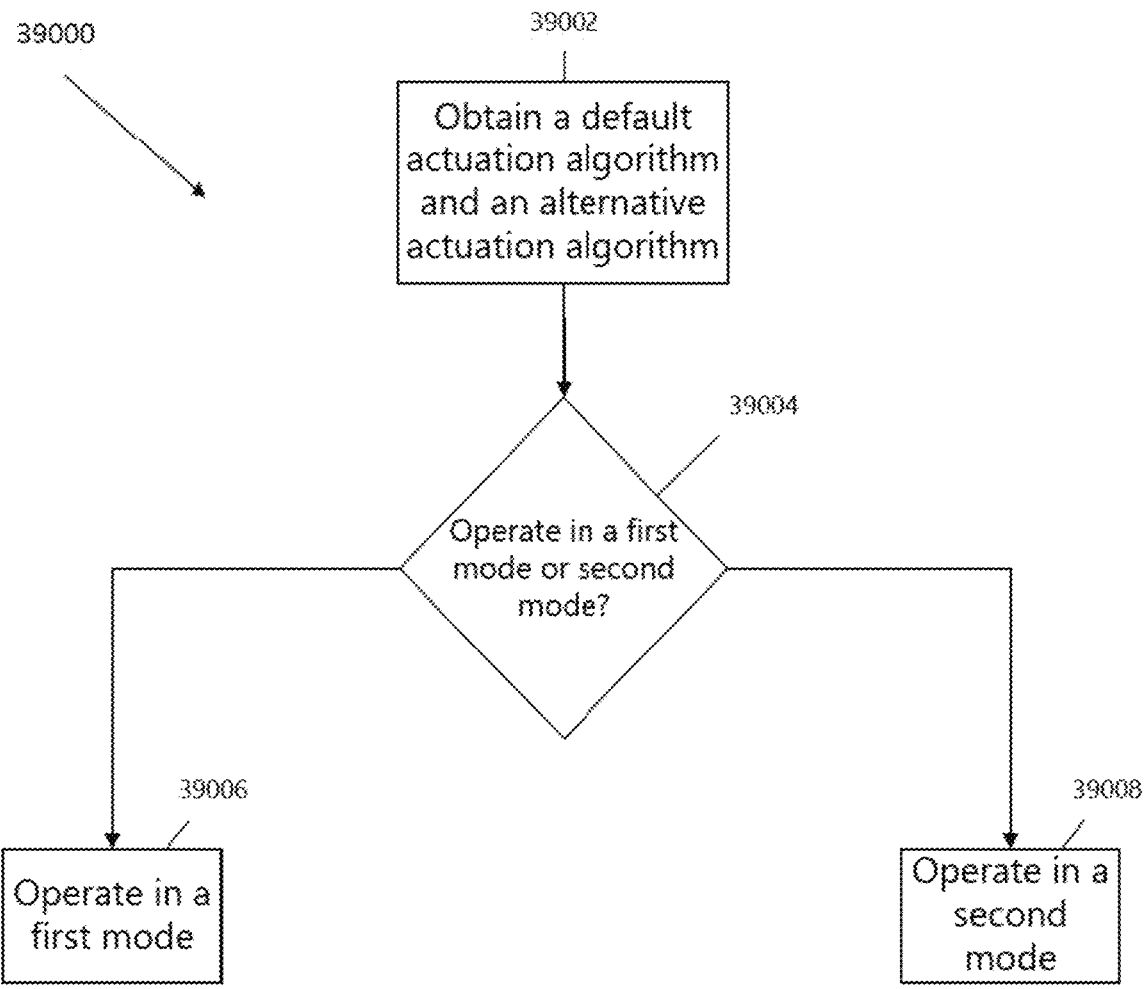

FIG. 174 illustrates another logic flow diagram of a process for updating an algorithm of a surgical instrument, in accordance with at least one aspect of the present disclosure.

Figure 175:
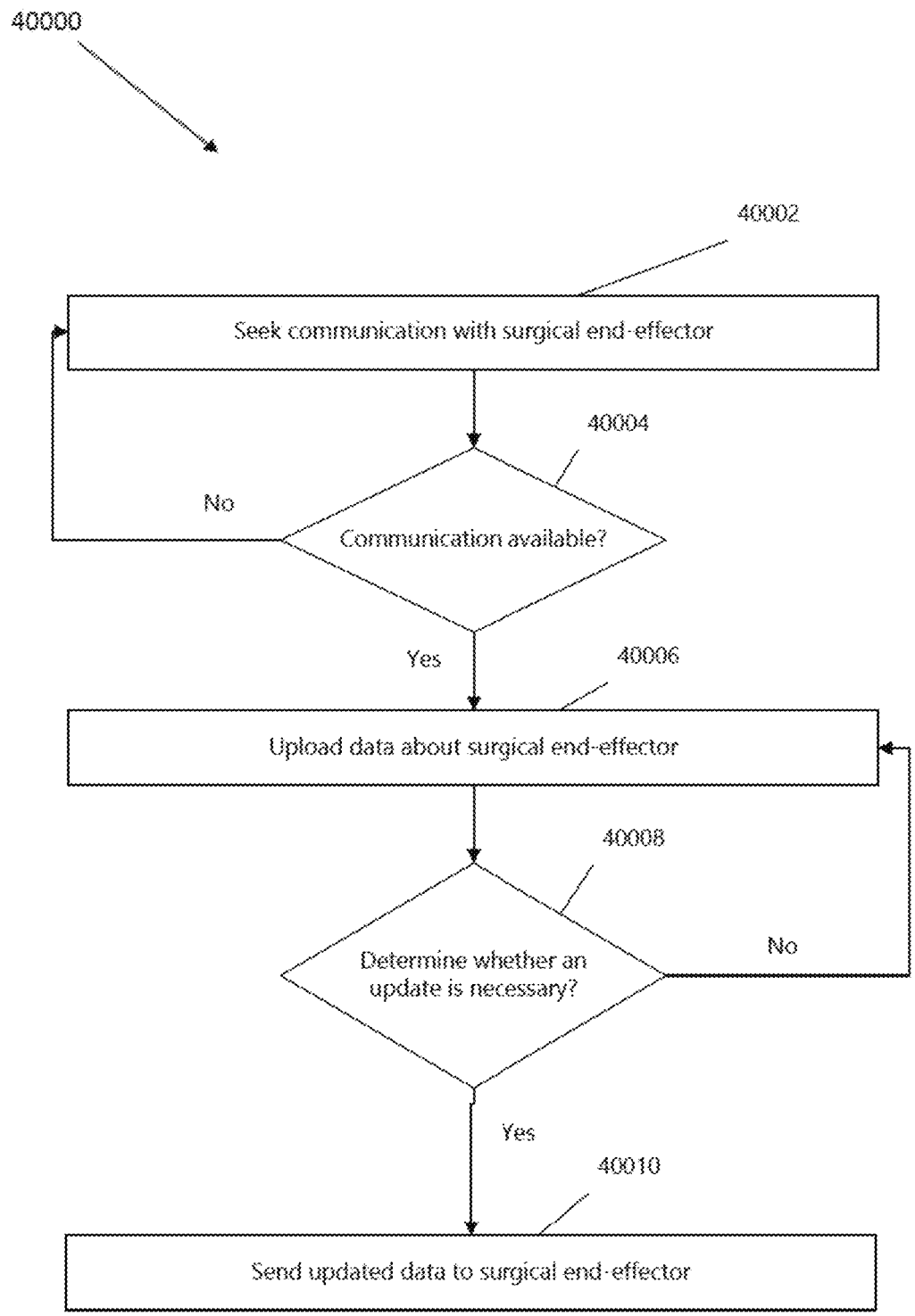

FIG. 175 illustrates a logic flow diagram of a process for a surgical hub updating an algorithm of a surgical instrument, in accordance with at least one aspect of the present disclosure.

Figure 176:
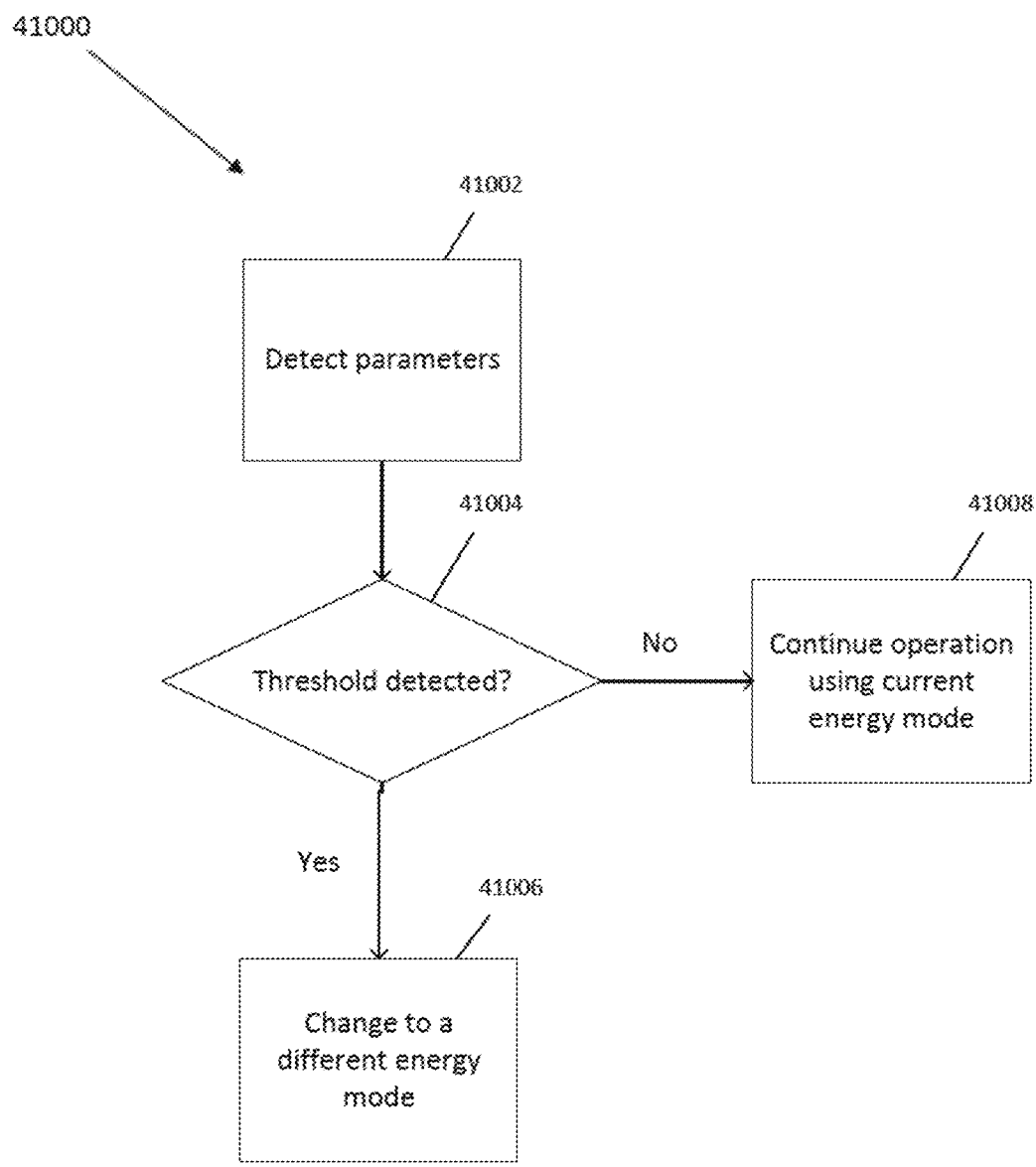

FIG. 176 illustrates a logic flow diagram of a process for changing or blending energy modalities of a surgical instrument based on detected threshold parameters, in accordance with at least one aspect of the present disclosure.

Figure 177:
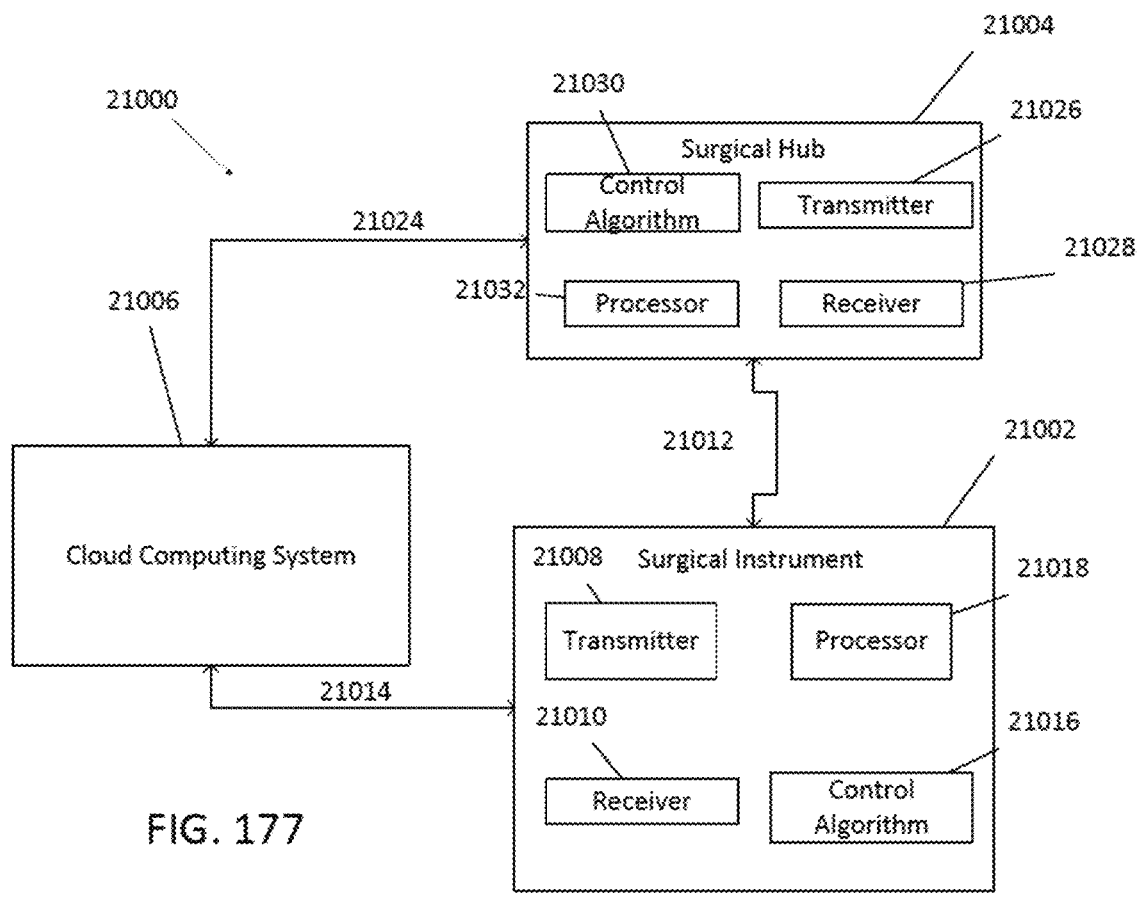

FIG. 177 illustrates a system for communication between a surgical instrument, a surgical hub, and a cloud computing system, in accordance with at least one aspect of the present disclosure.

Figure 178:
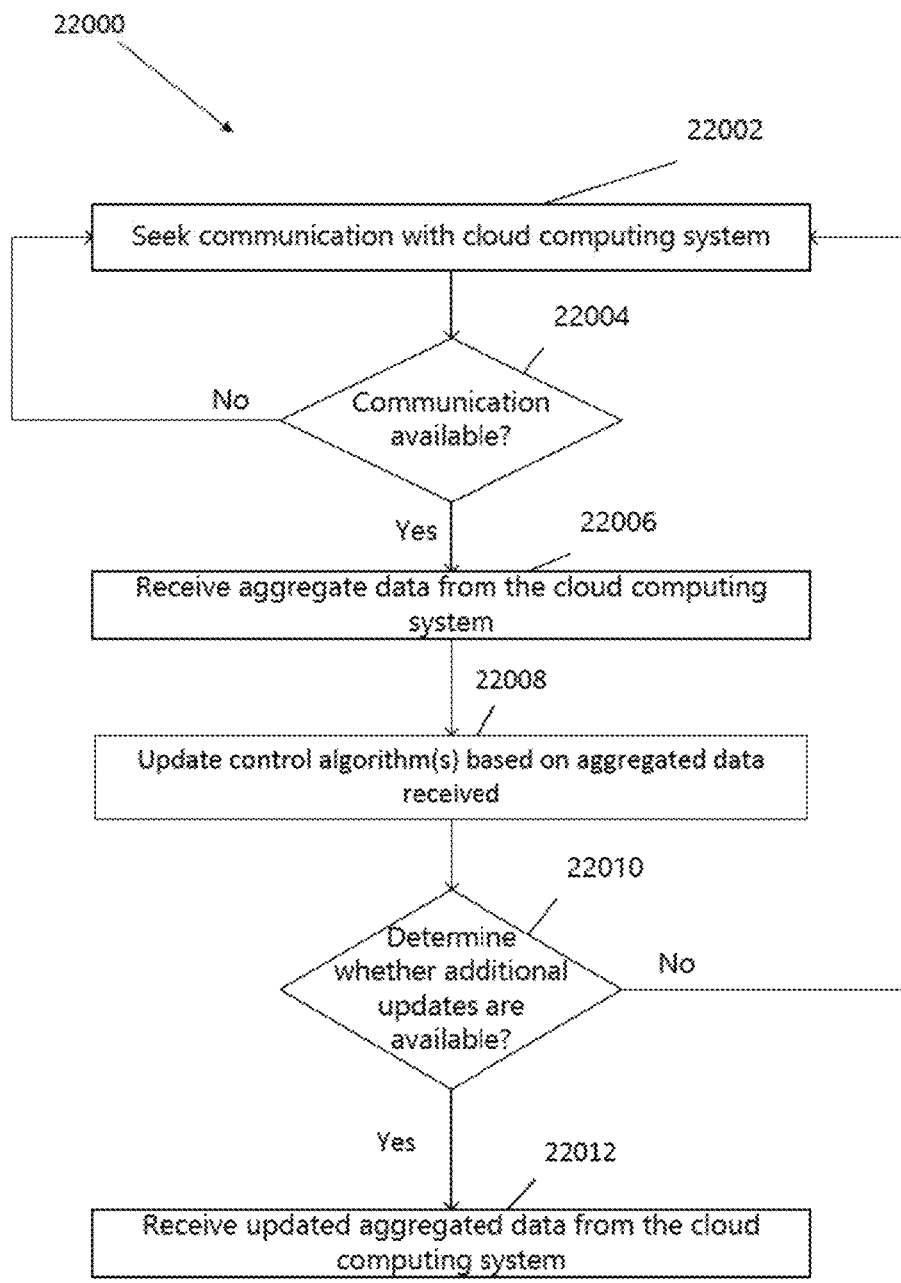

FIG. 178 illustrates a logic flow diagram of a process for updating the control algorithm of a surgical hub, in accordance with at least one aspect of the present disclosure.

Figure 179:
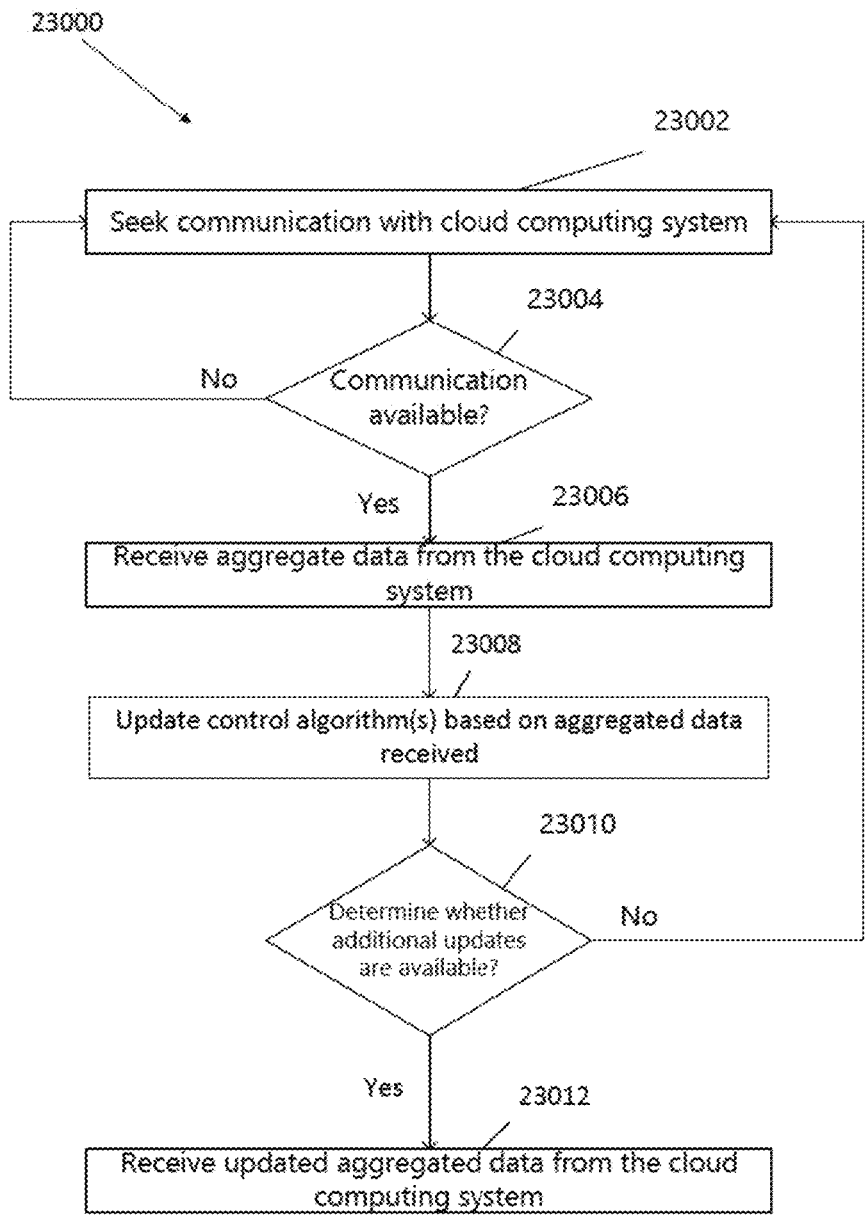

FIG. 179 illustrates a logic flow diagram of a process for updating the algorithm of a surgical instrument, in accordance with at least one aspect of the present disclosure.

Figure 180:
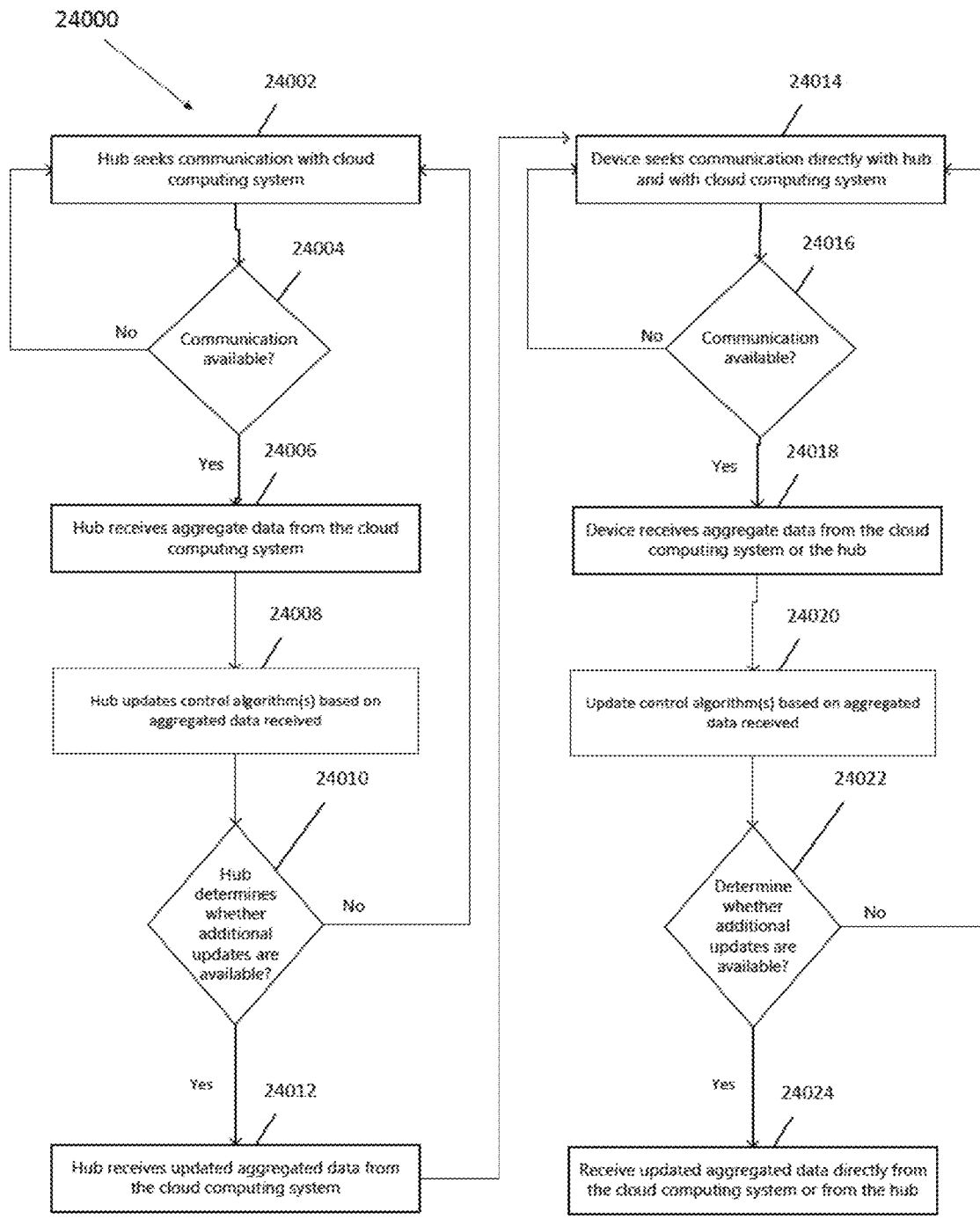

FIG. 180 illustrates a logic flow diagram of a process for updating a surgical system, in accordance with at least one aspect of the present disclosure.

Figures 180A, 180B, 180C:
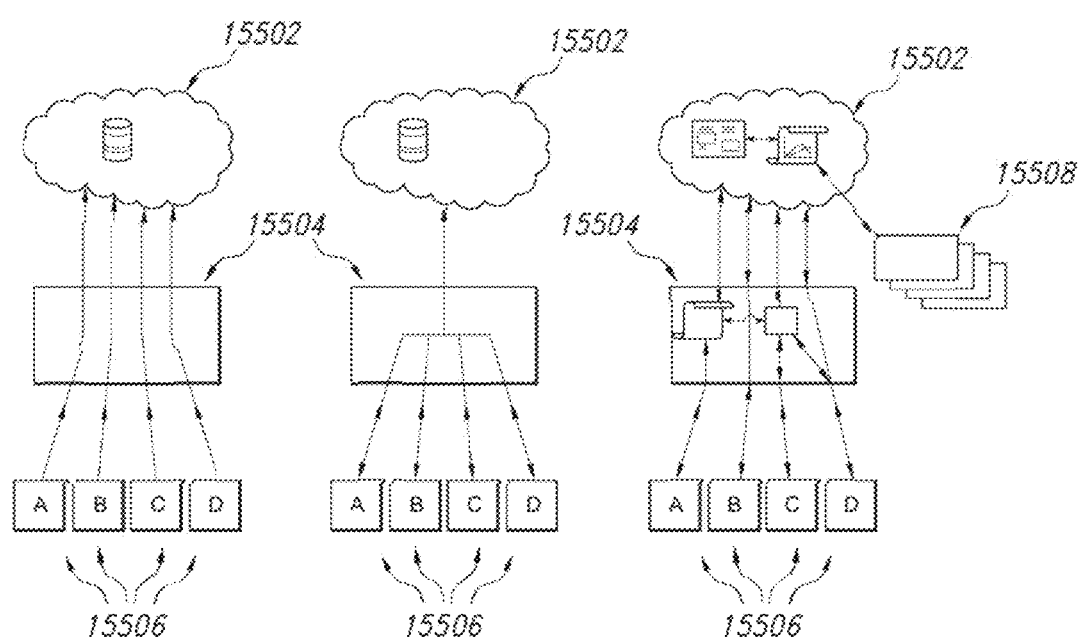

FIGS. 180A-C illustrate example hub connectivity modes.

Figures 181, 182A:
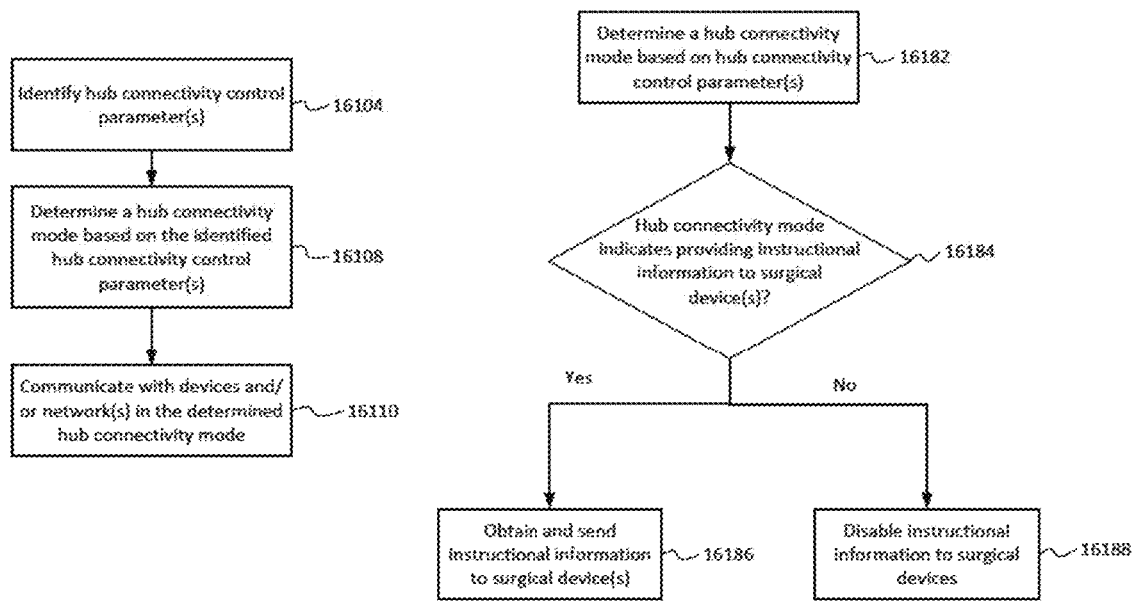

FIG. 181 shows an example flow for operating under tiered hub communication modes.

Figure 182B:
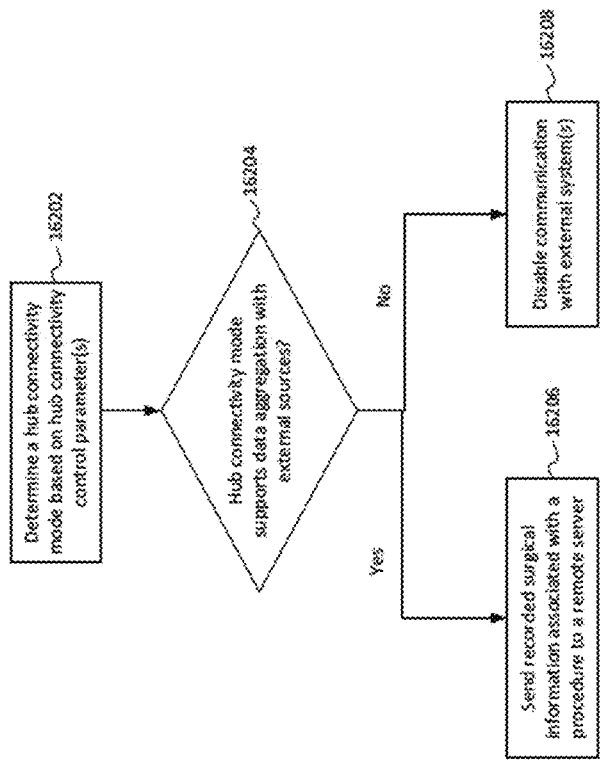
Figure 182C:
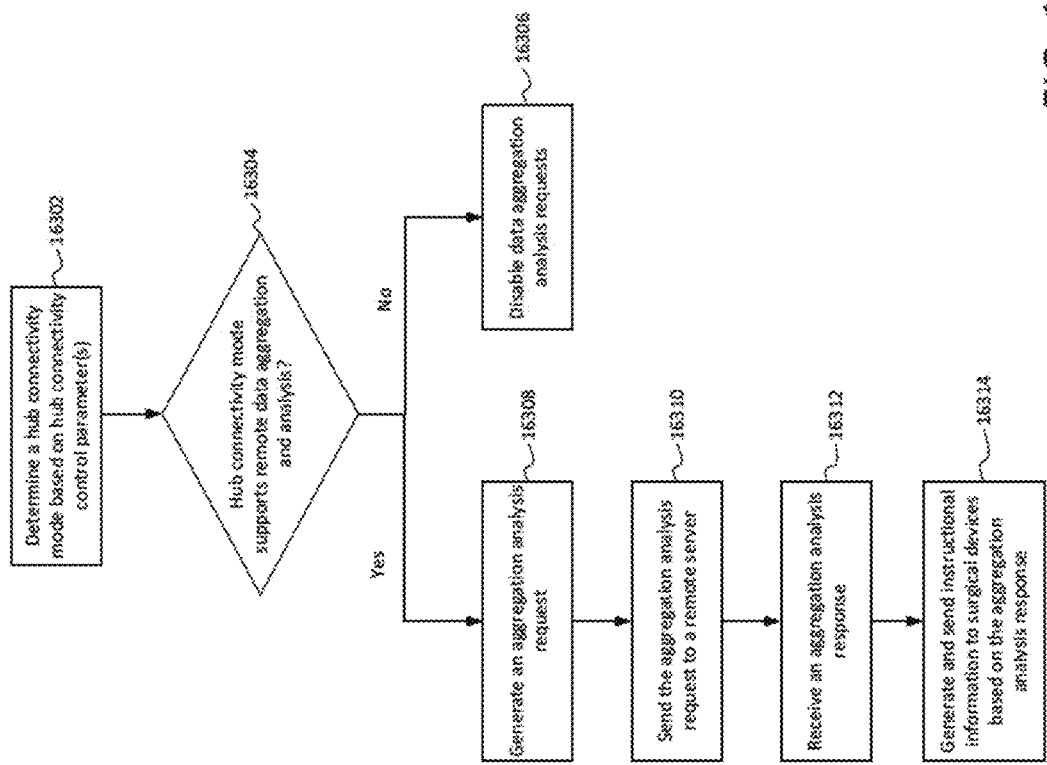

FIGS. 182A-C show example flows for operating under tiered hub communication modes.

Figure 183A:
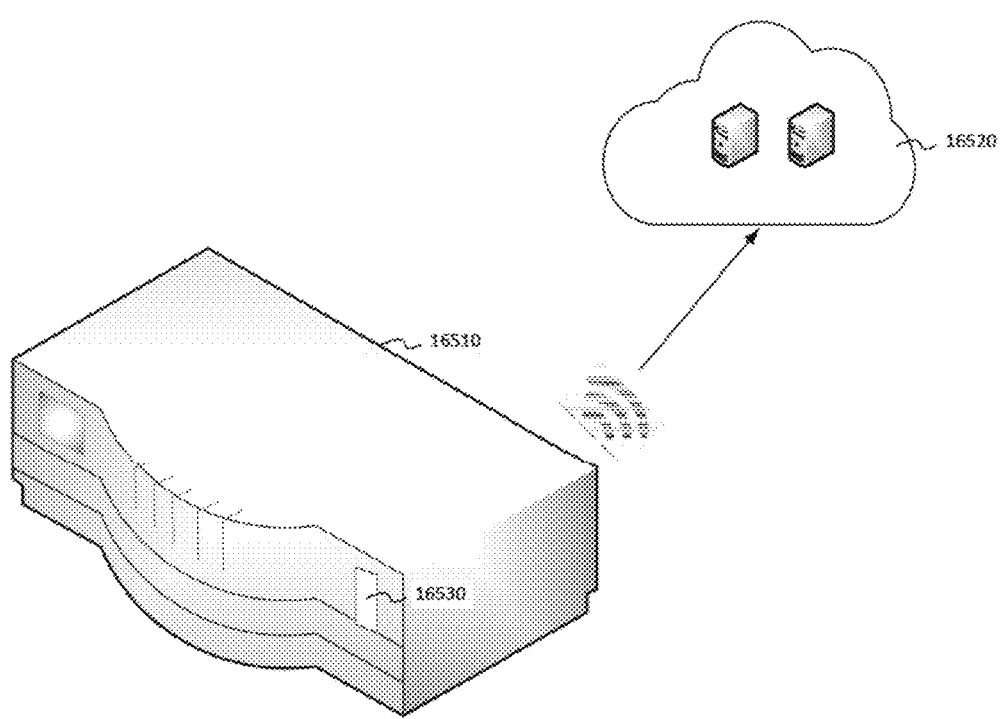

FIG. 183A illustrates an example surgical supply packaged with an RFID NFC chip.

Figure 183B:
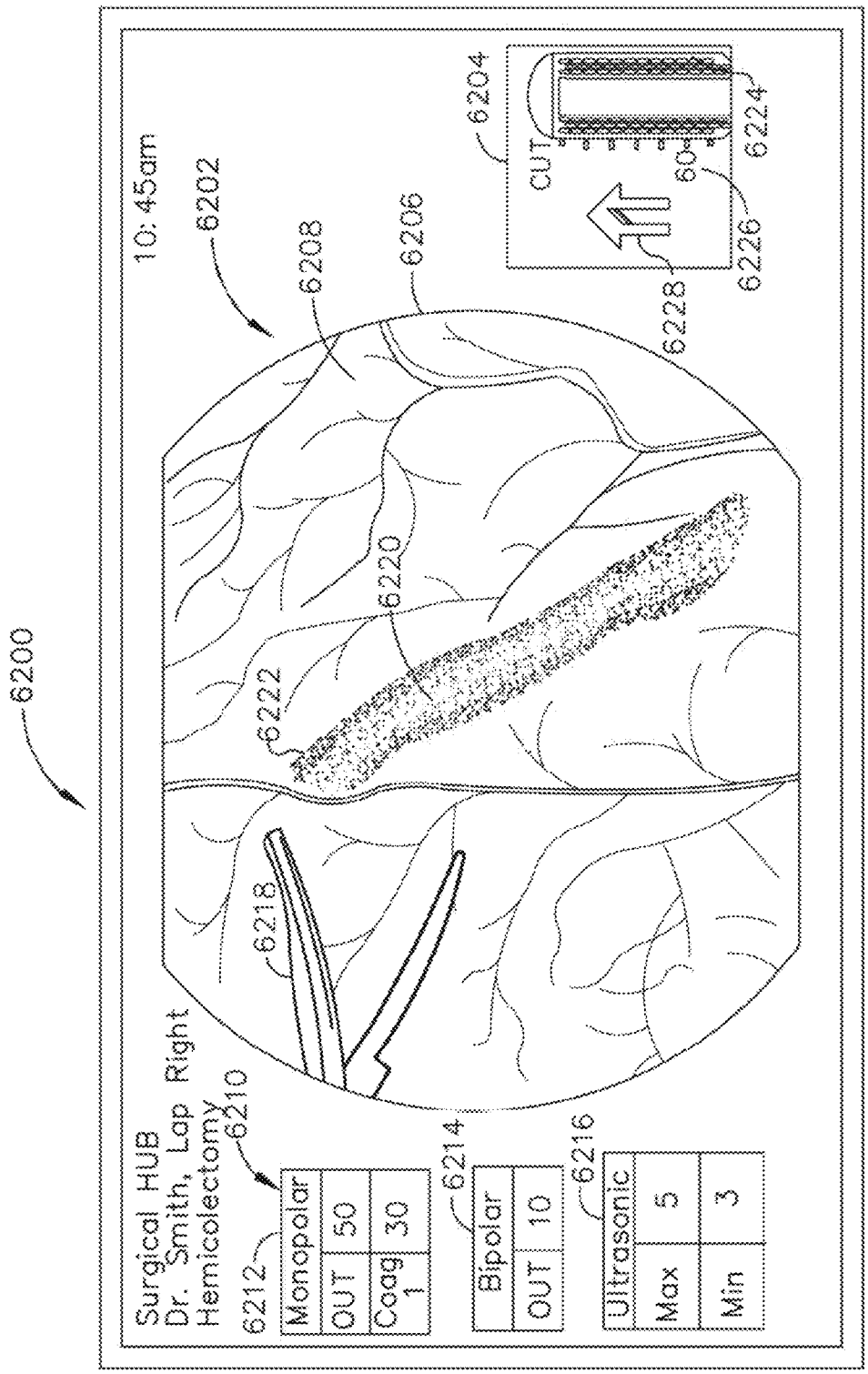

FIG. 183B illustrates a primary display of the surgical hub comprising a global and local display.

Figure 184:
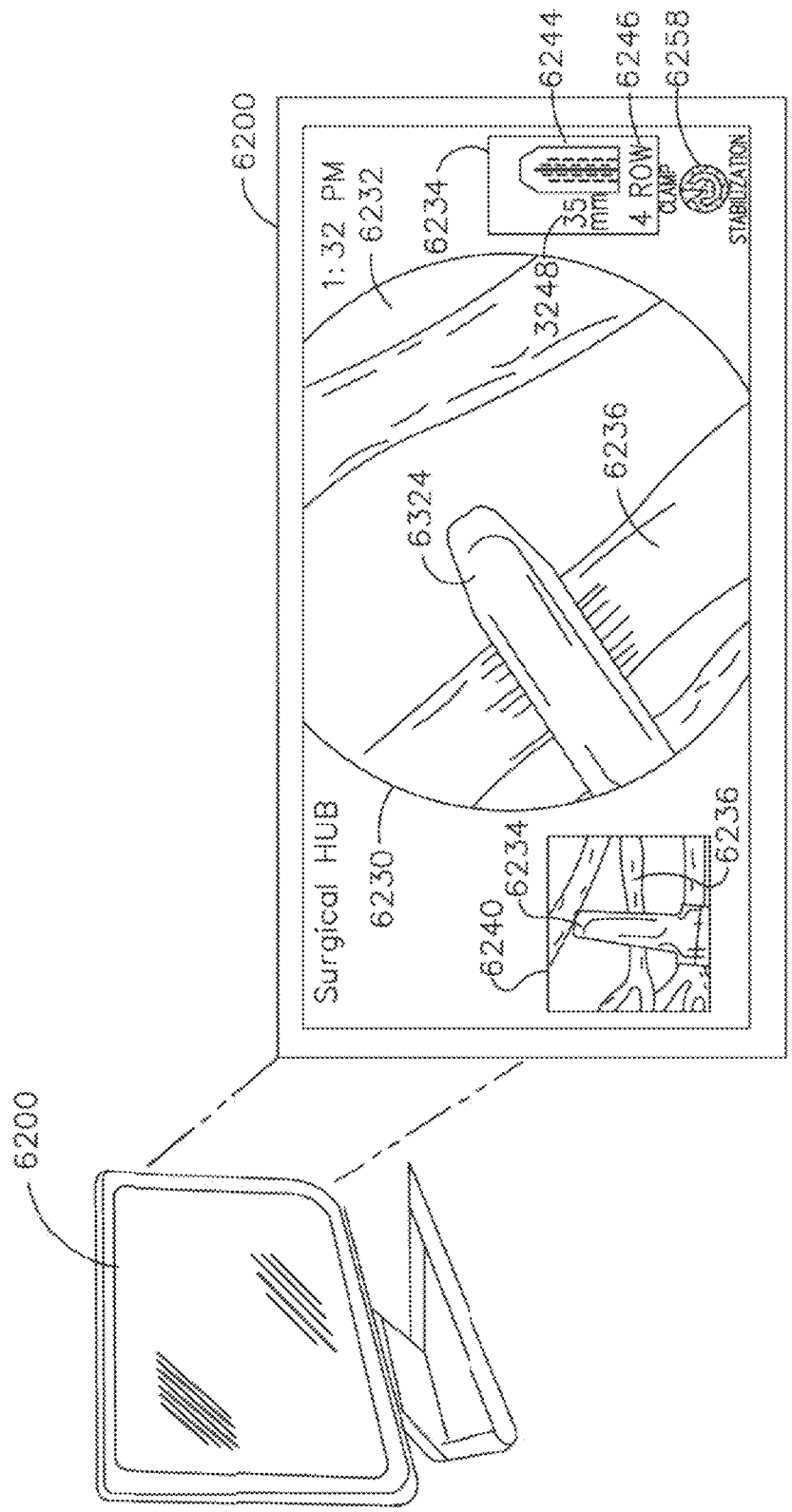

FIG. 184 illustrates an example a primary display of the surgical hub.

Figure 185:
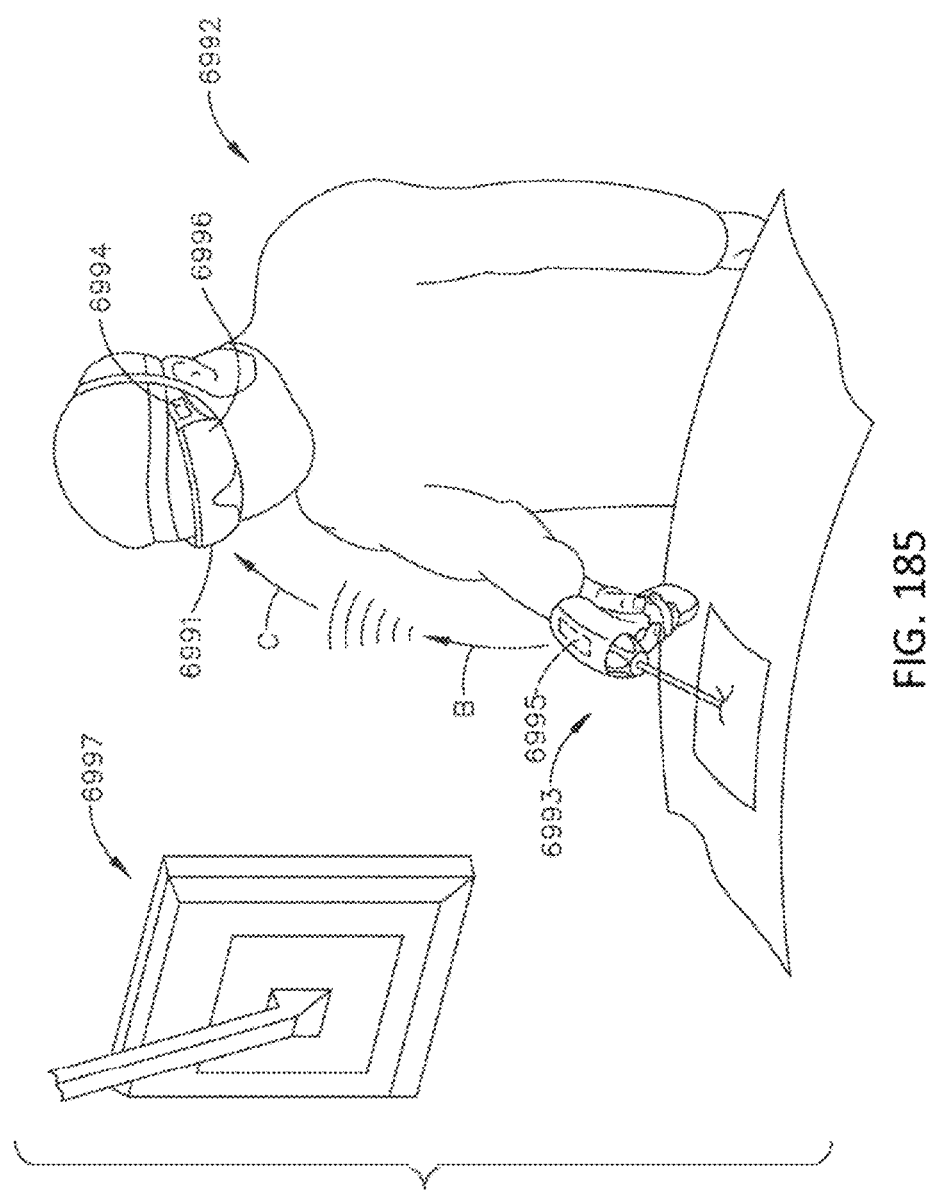

FIG. 185 depicts a perspective view of a surgeon using a surgical instrument that includes a handle assembly housing and a wireless circuit board during a surgical procedure, with the surgeon wearing a set of safety glasses.

Figure 186:
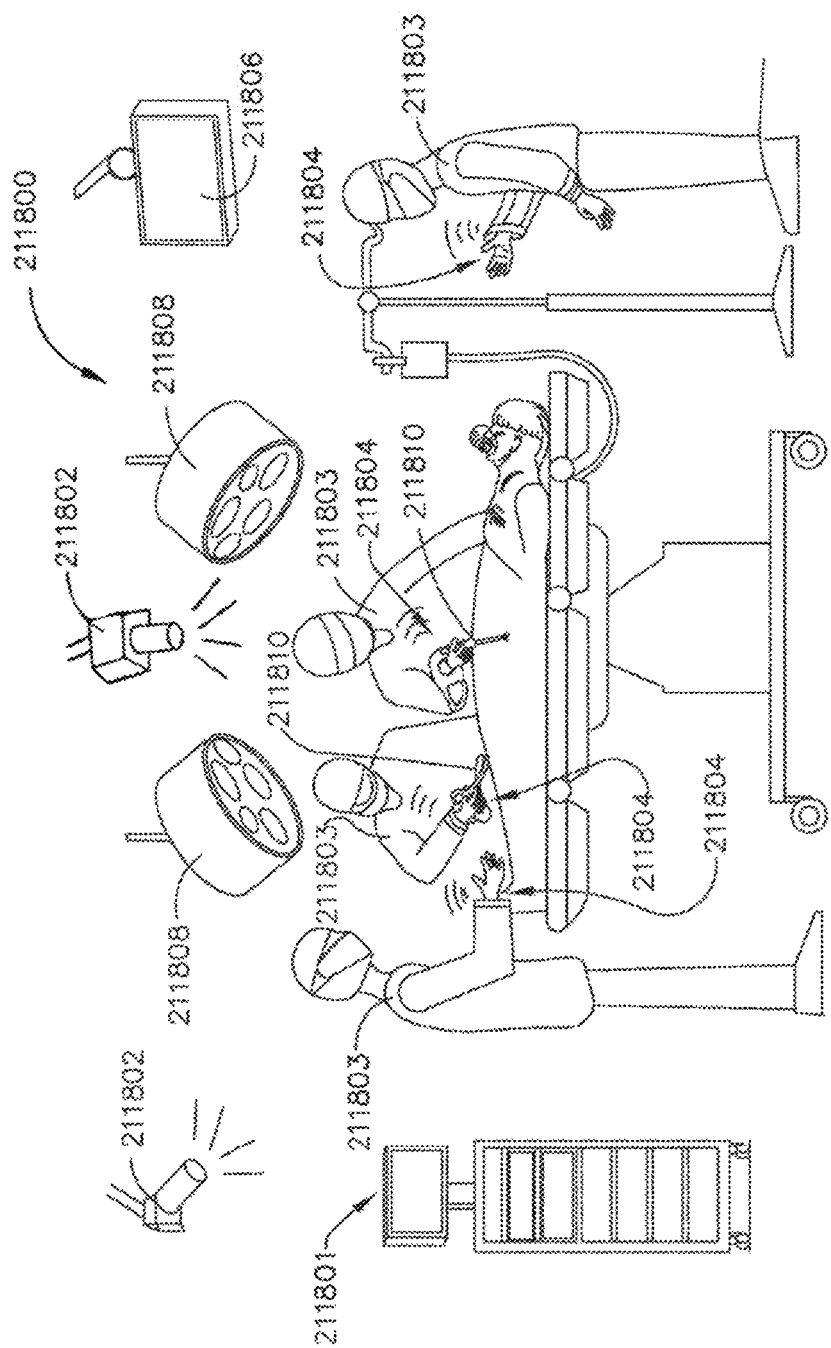

FIG. 186 is a diagram of an illustrative operating room (OR) setup.

Figure 187:
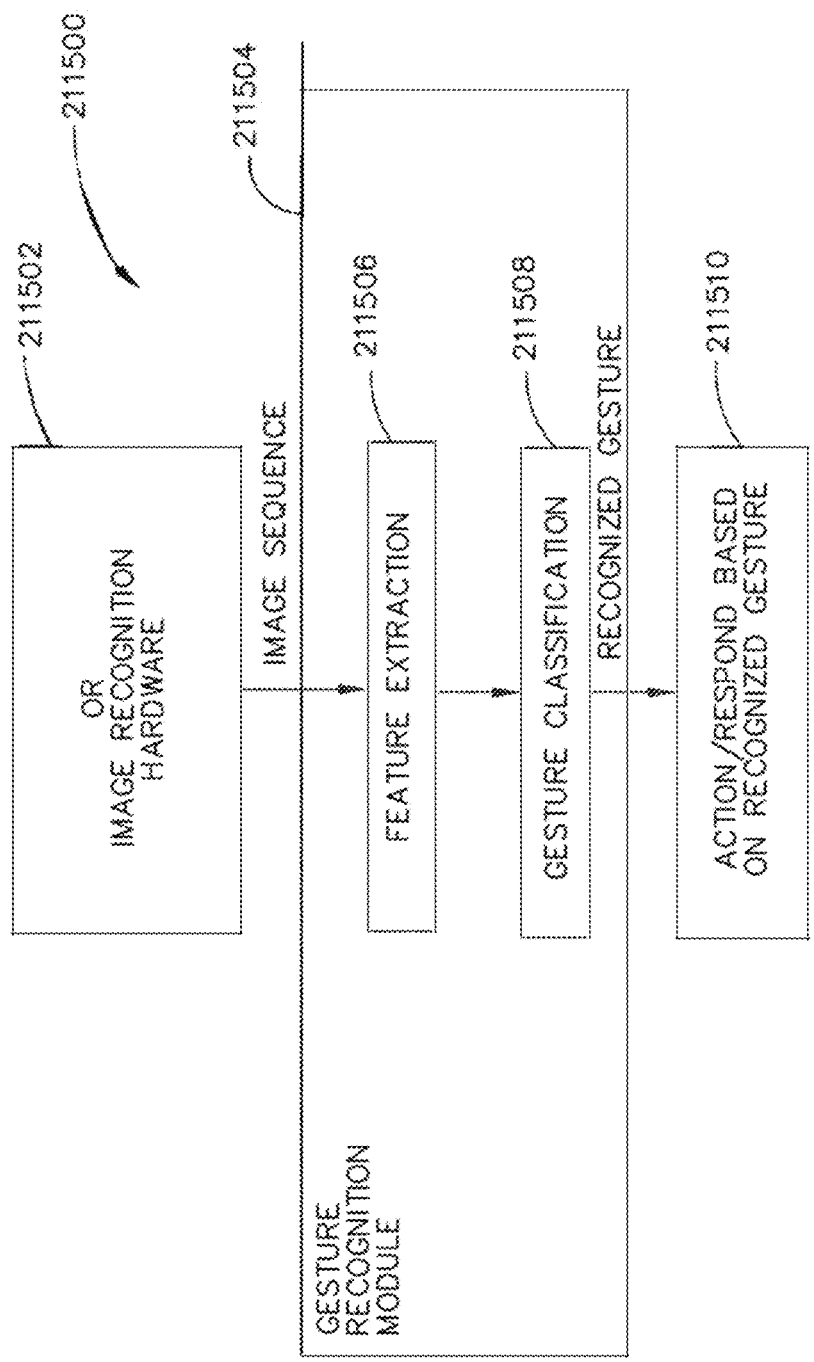

FIG. 187 is a block diagram of a gesture recognition system.

Figure 188:
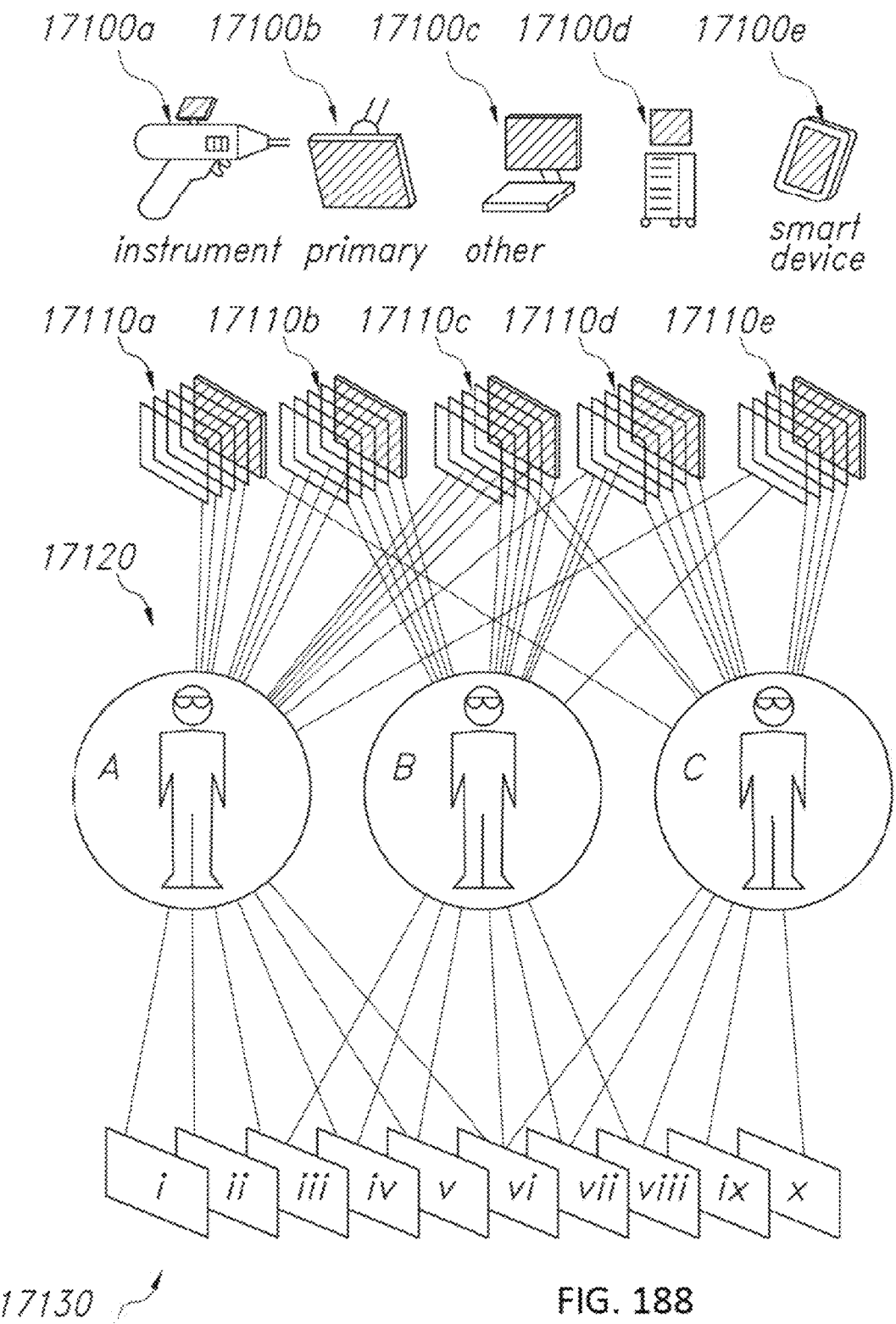

FIG. 188 illustrates example role-based interaction and control related to augmented reality and deviceless control system.

Figure 189:
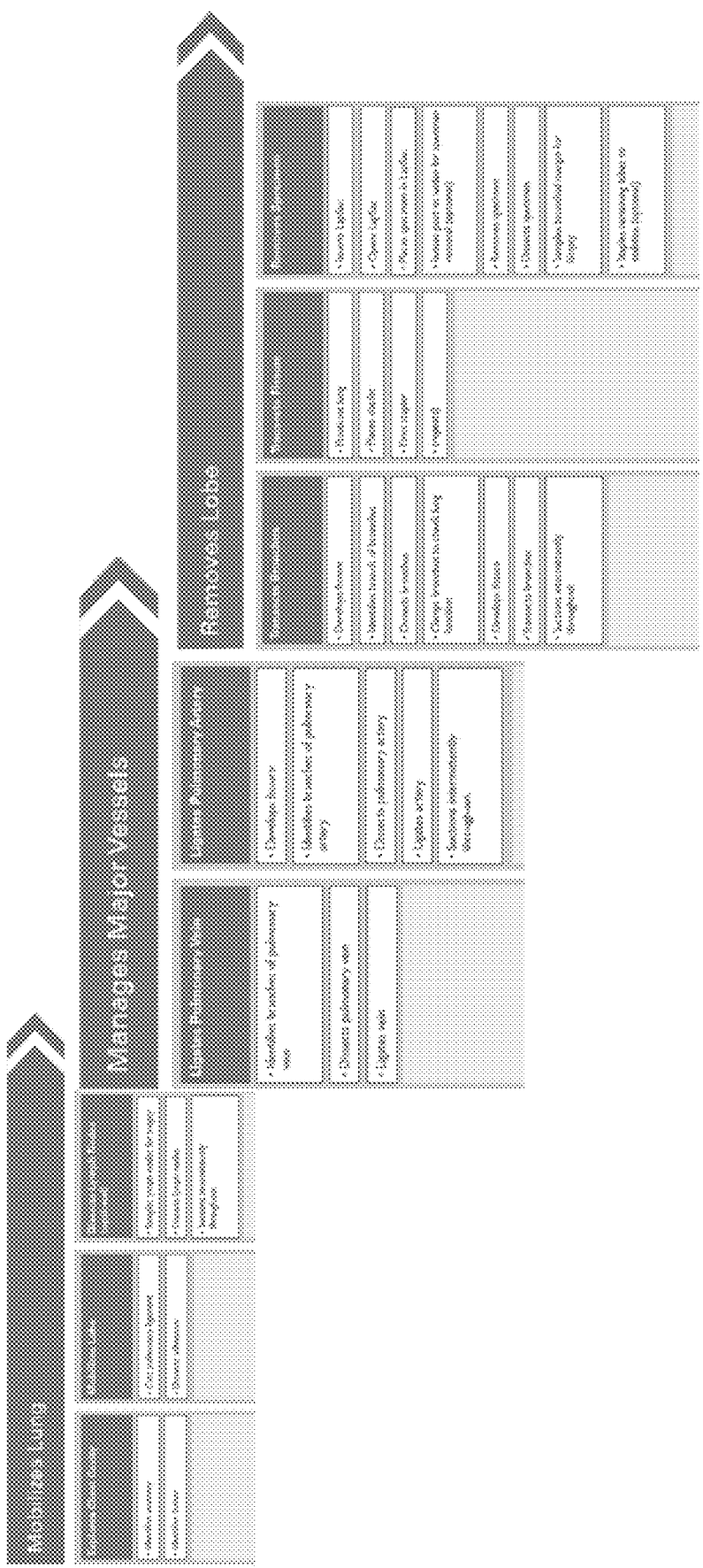

FIG. 189 illustrates example procedural step-based interactions and control related to augmented reality and deviceless control system.

Figure 190:
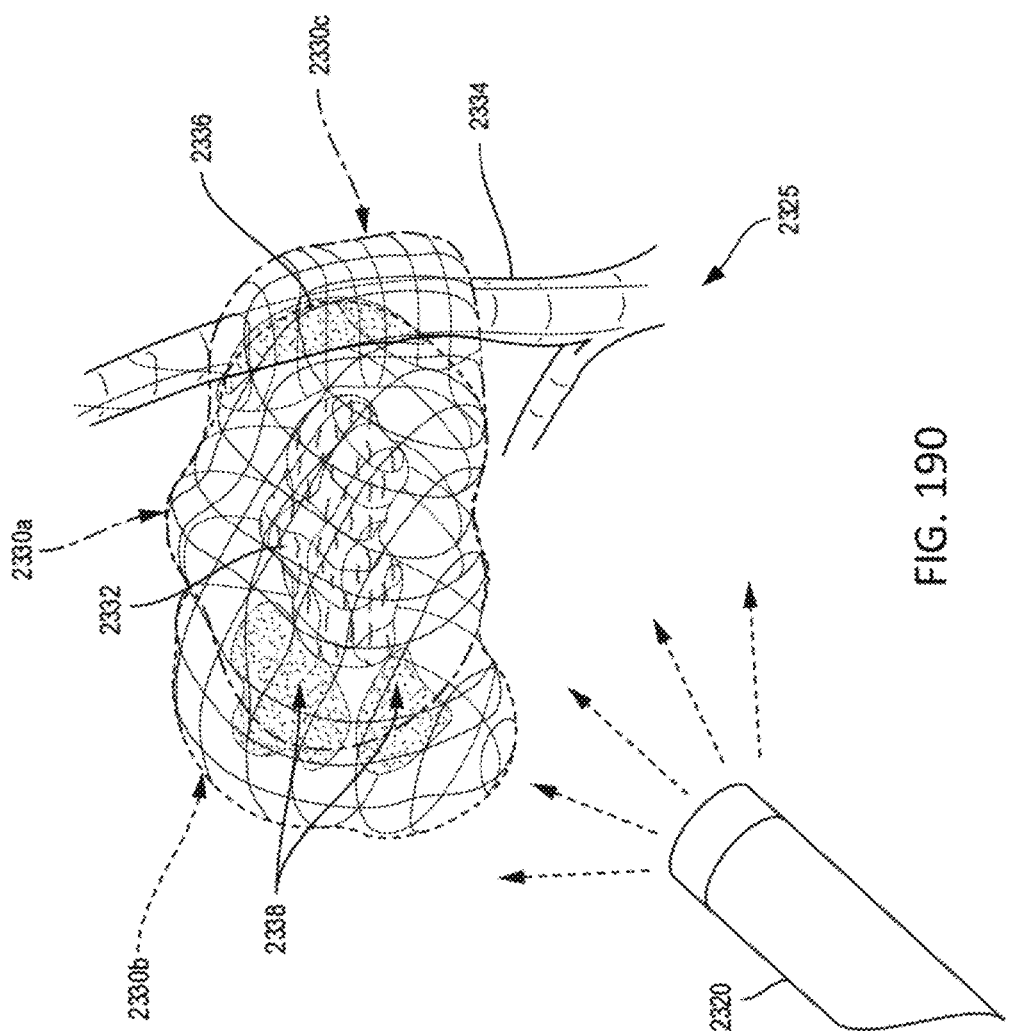

FIG. 190 is a schematic of an example visualization of anatomical structures via a spectral surgical visualization system.

Figure 191:
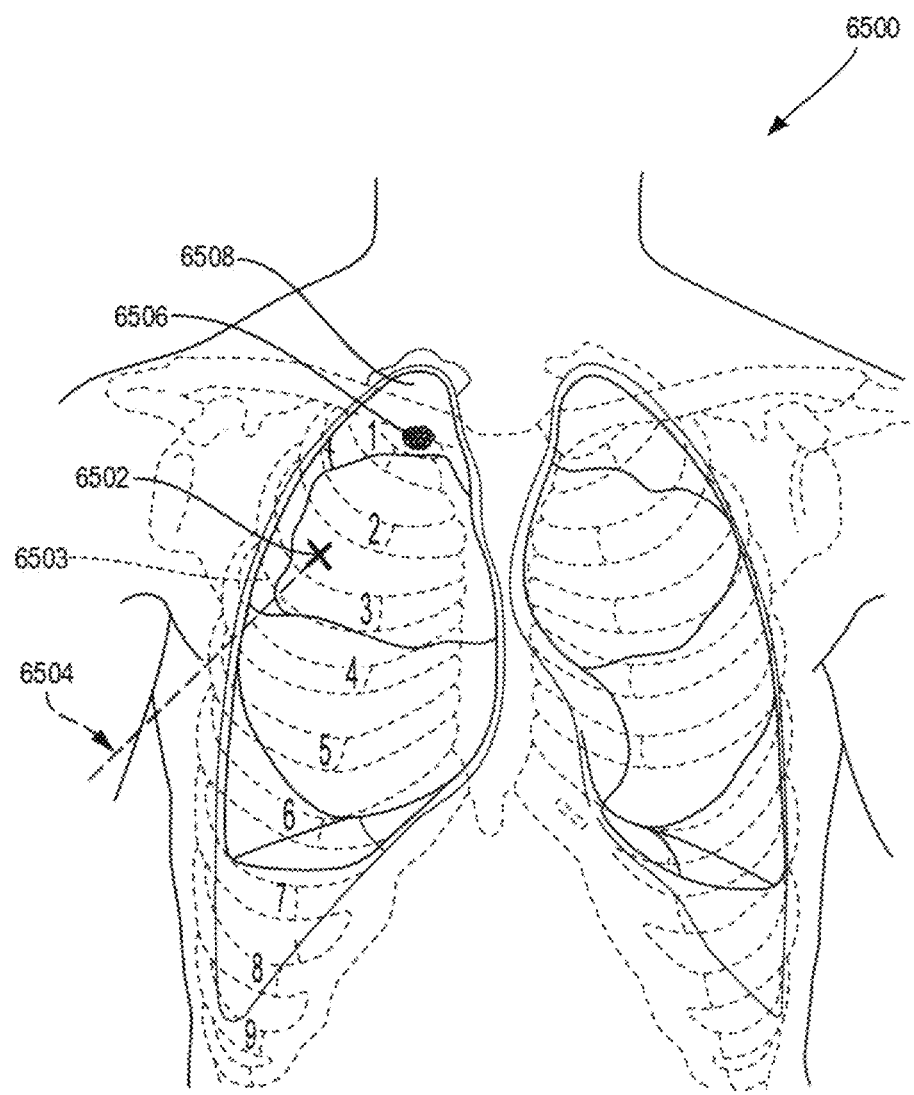

FIG. 191 is a diagram of a surgical instrument access path for a video-assisted thoracoscopic surgery (VATS) procedure, in accordance with at least one aspect of the present disclosure.

Figure 192:
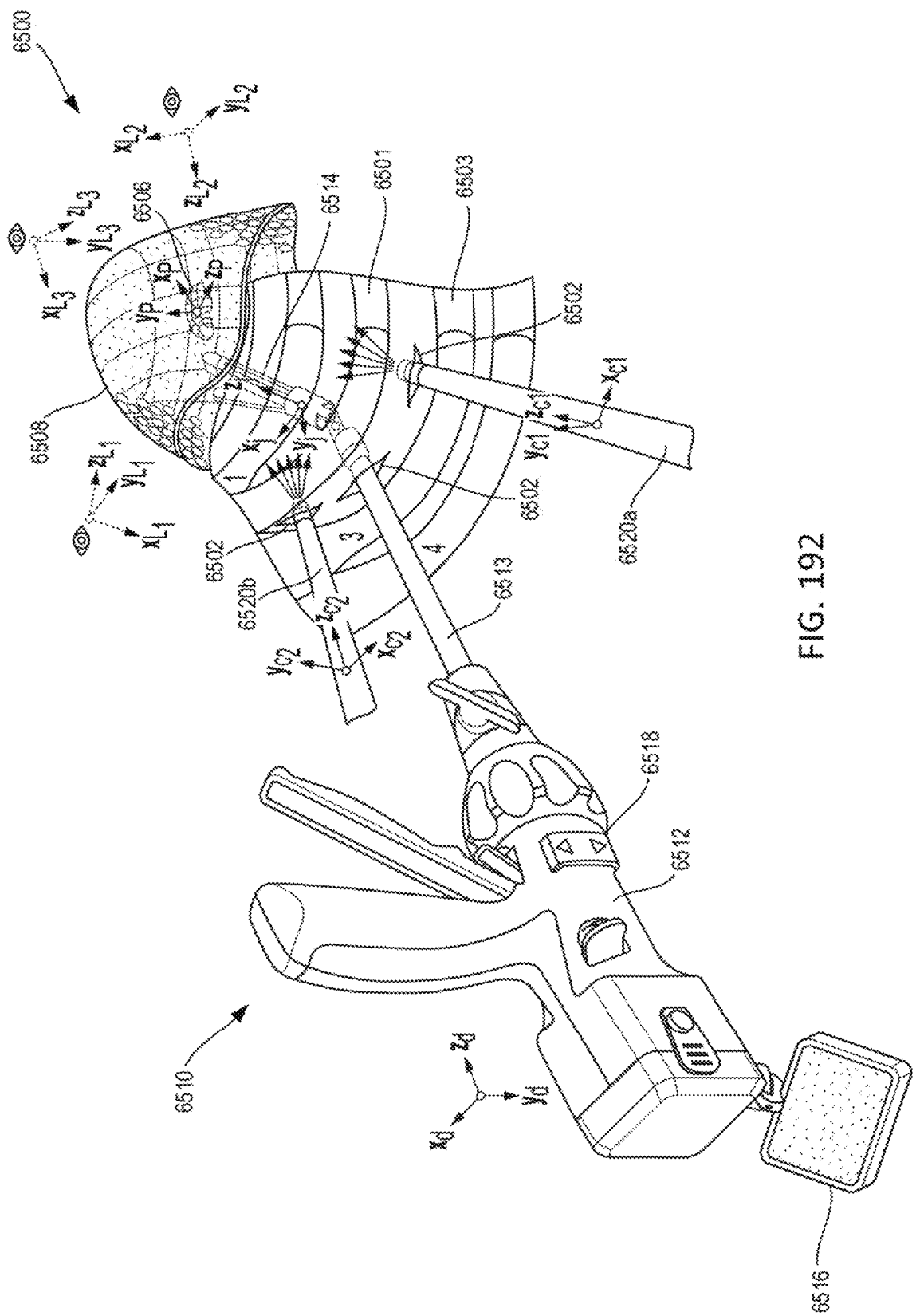

FIG. 192 is a diagram of various coordinate systems associated with a VATS procedure, in accordance with at least one aspect of the present disclosure.

Figure 193:
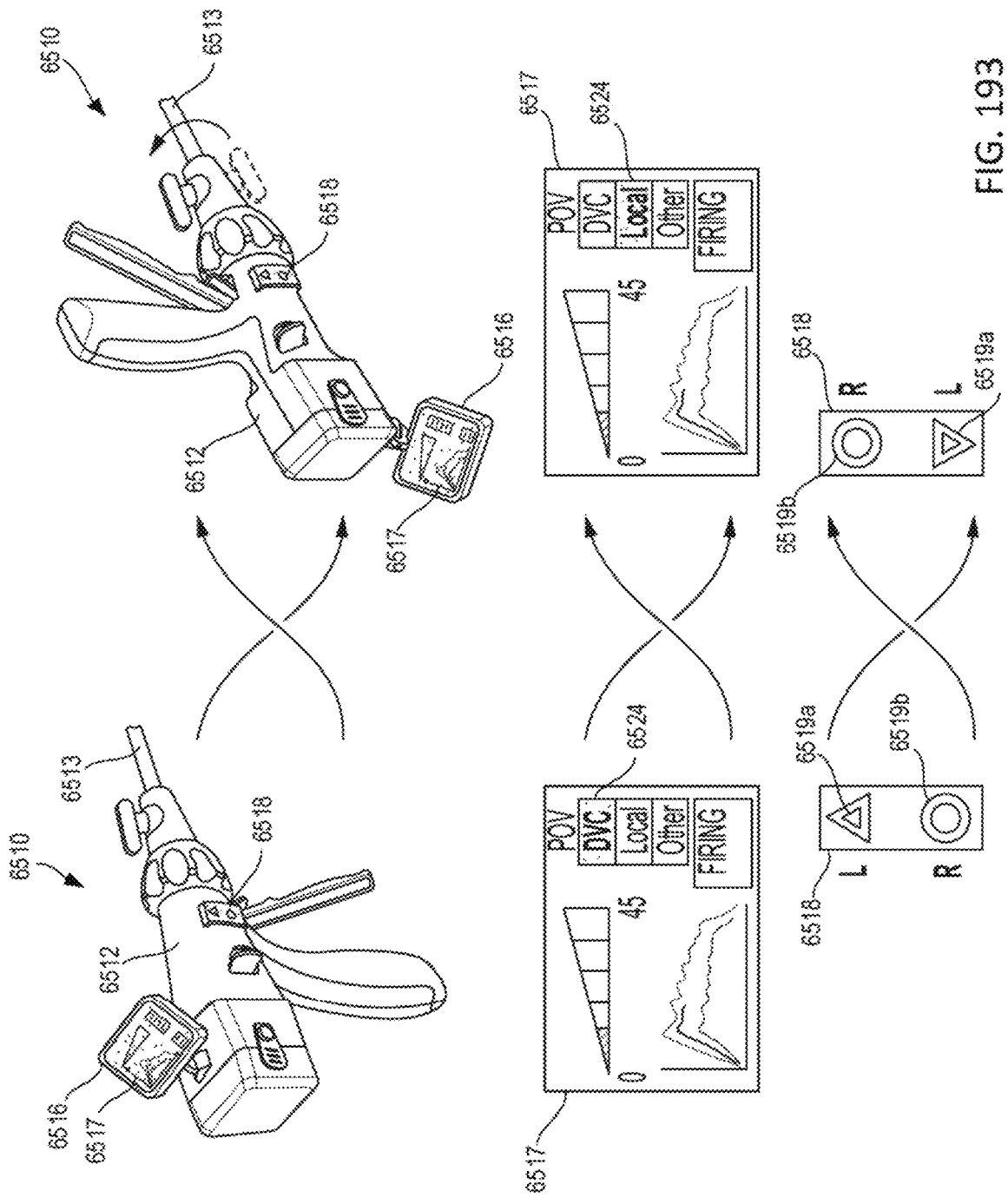

FIG. 193 is a diagram depicting an example change in orientation of a display and user controls in response to a change in orientation of the surgical instrument.

Figure 194:
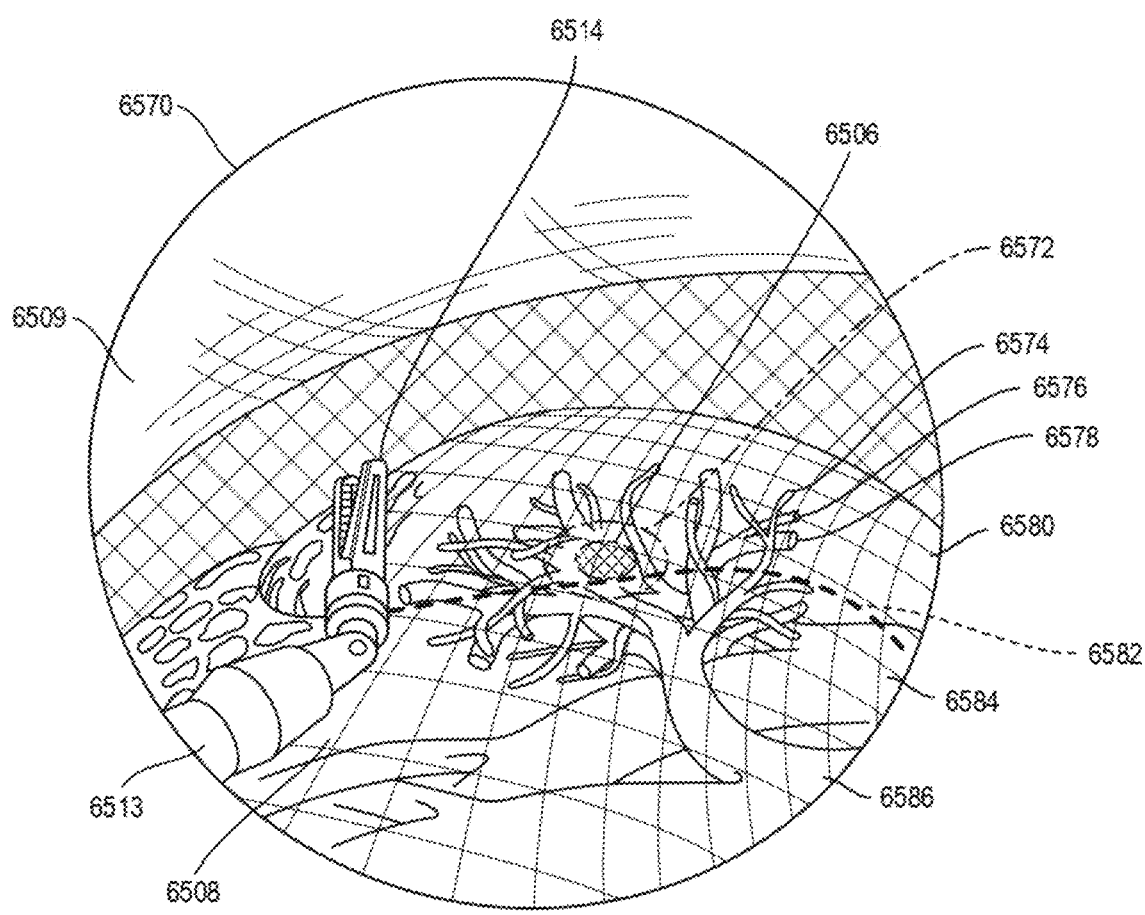

FIG. 194 depicts an example camera view of a surgical procedure.

Figure 195:
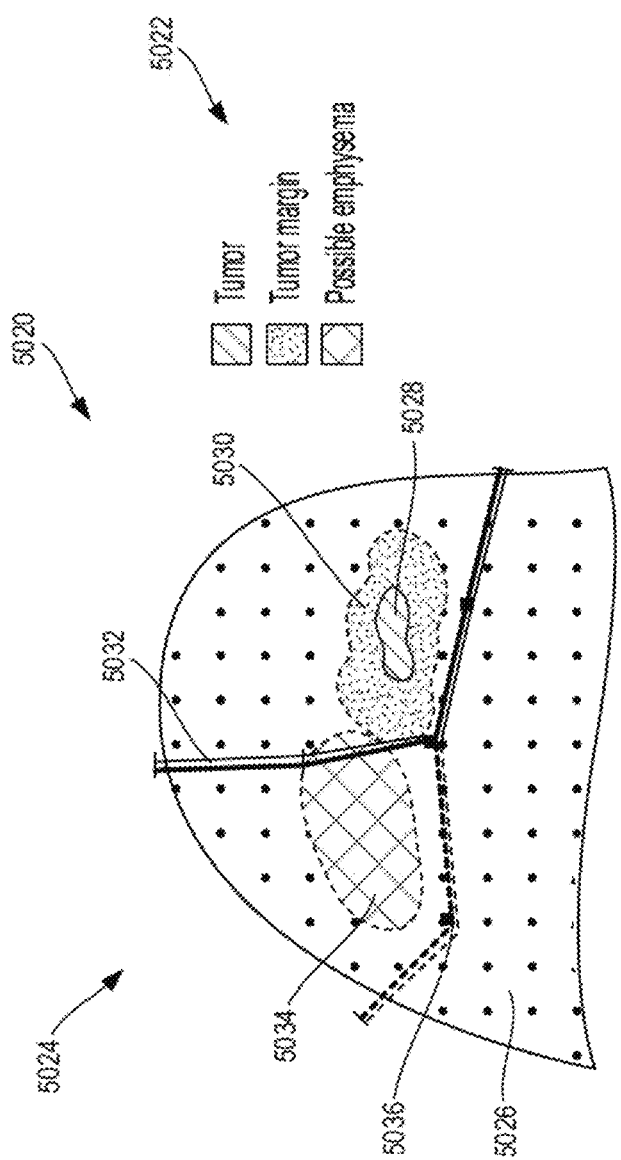

FIG. 195 shows an example display of a surgical visualization system shown in accordance with at least one aspect of the present disclosure.

Figure 196:
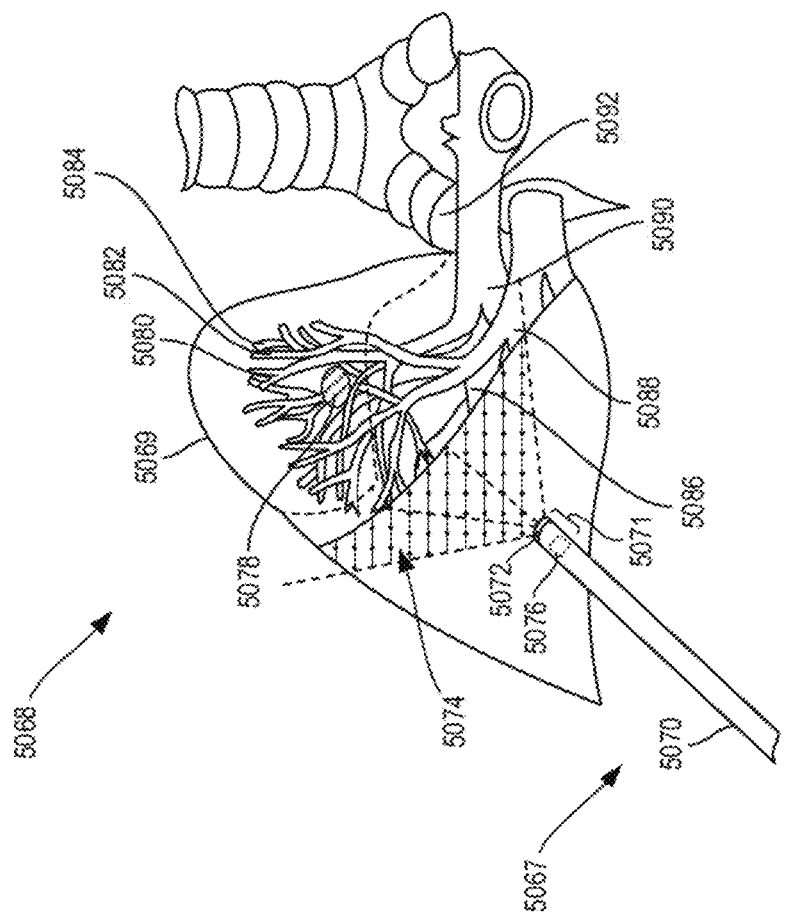

FIG. 196 shows an example model of an anatomical structure generated by an example surgical visualization system.

Figure 197:
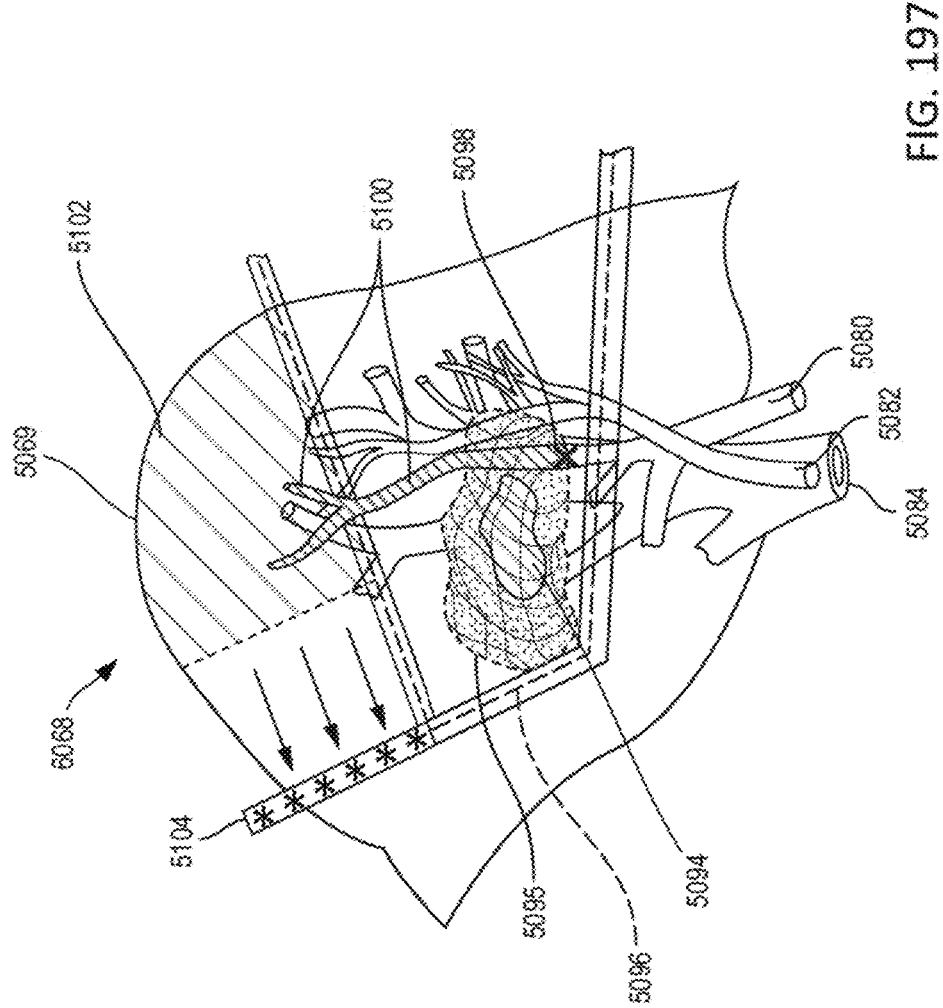

FIG. 197 shows n example display of an example model in accordance with at least one aspect of the present disclosure.

Figure 198:
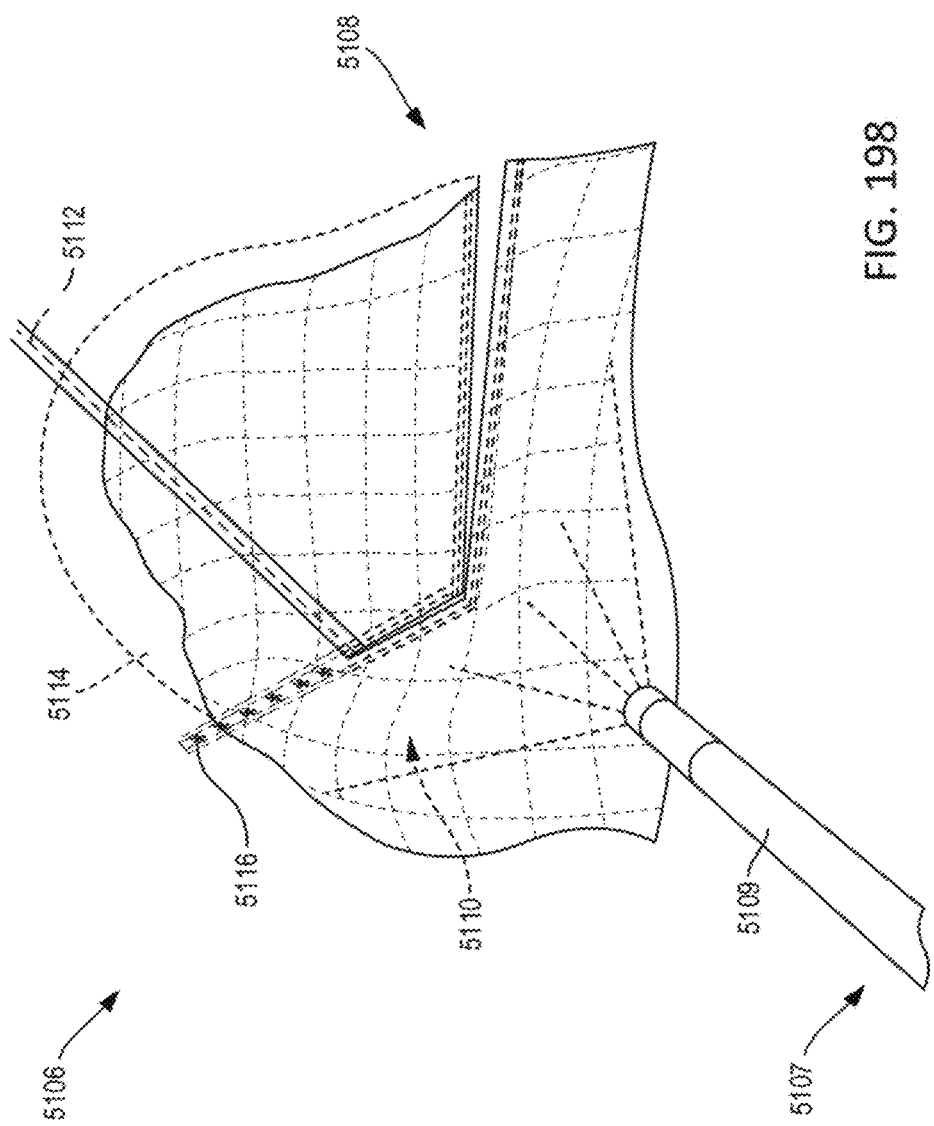

FIG. 198 shows an example display of an example model of an anatomical structure generated by an example surgical visualization system.

Figure 199:
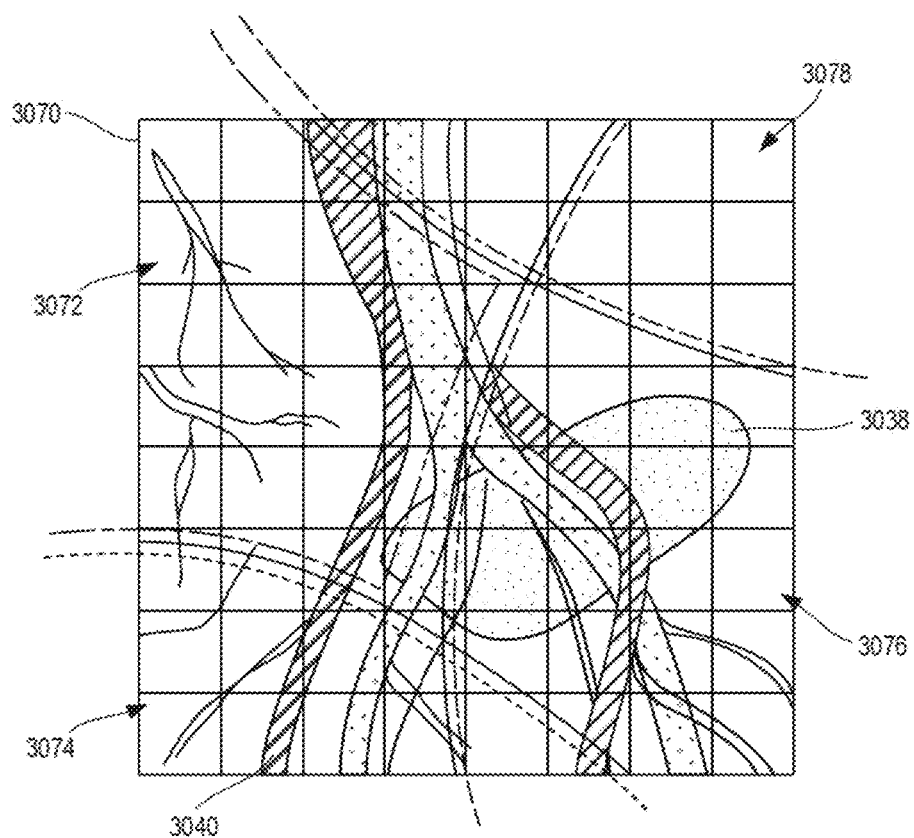

FIG. 199 is a diagram of an example fused image generated from a multispectral EMR source.

Figure 200:
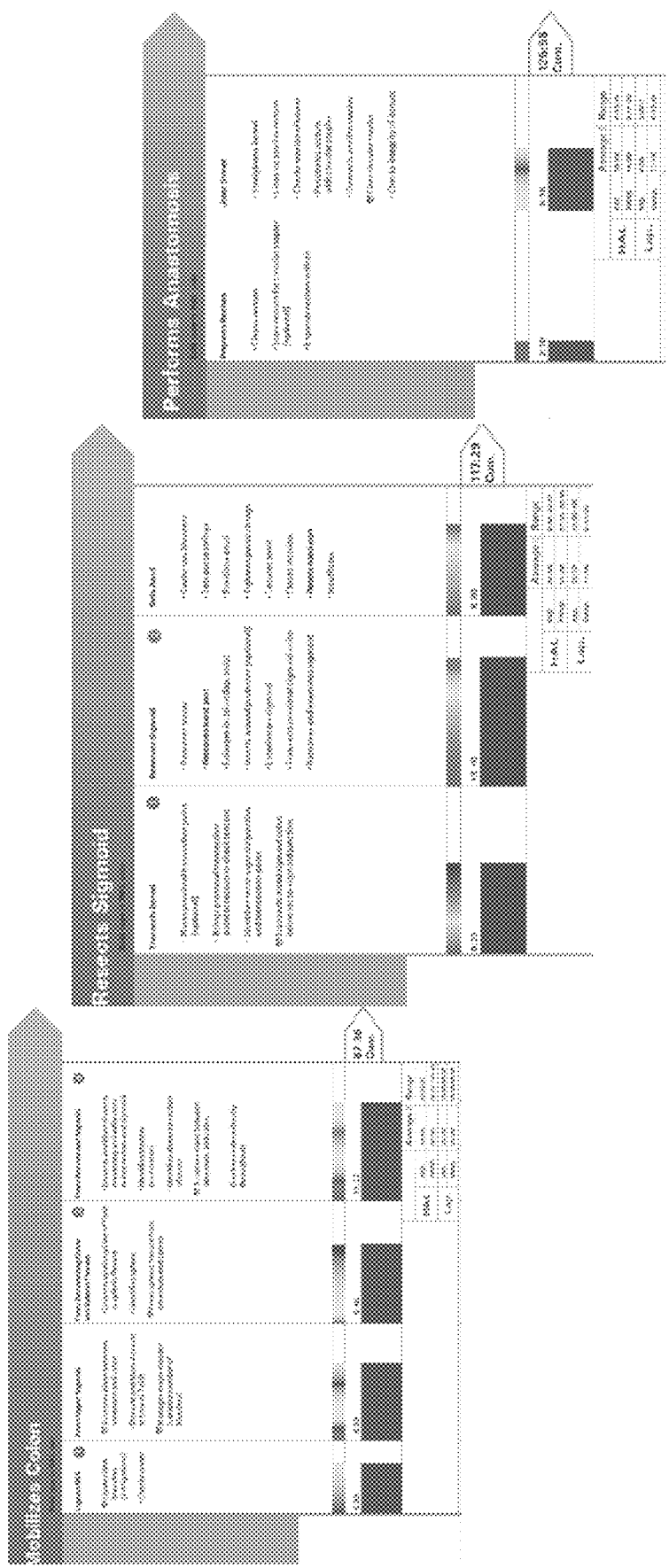

FIG. 200 illustrates example procedural steps and progression that may be detected by example situation awareness capabilities of the system.

Figure 201A:
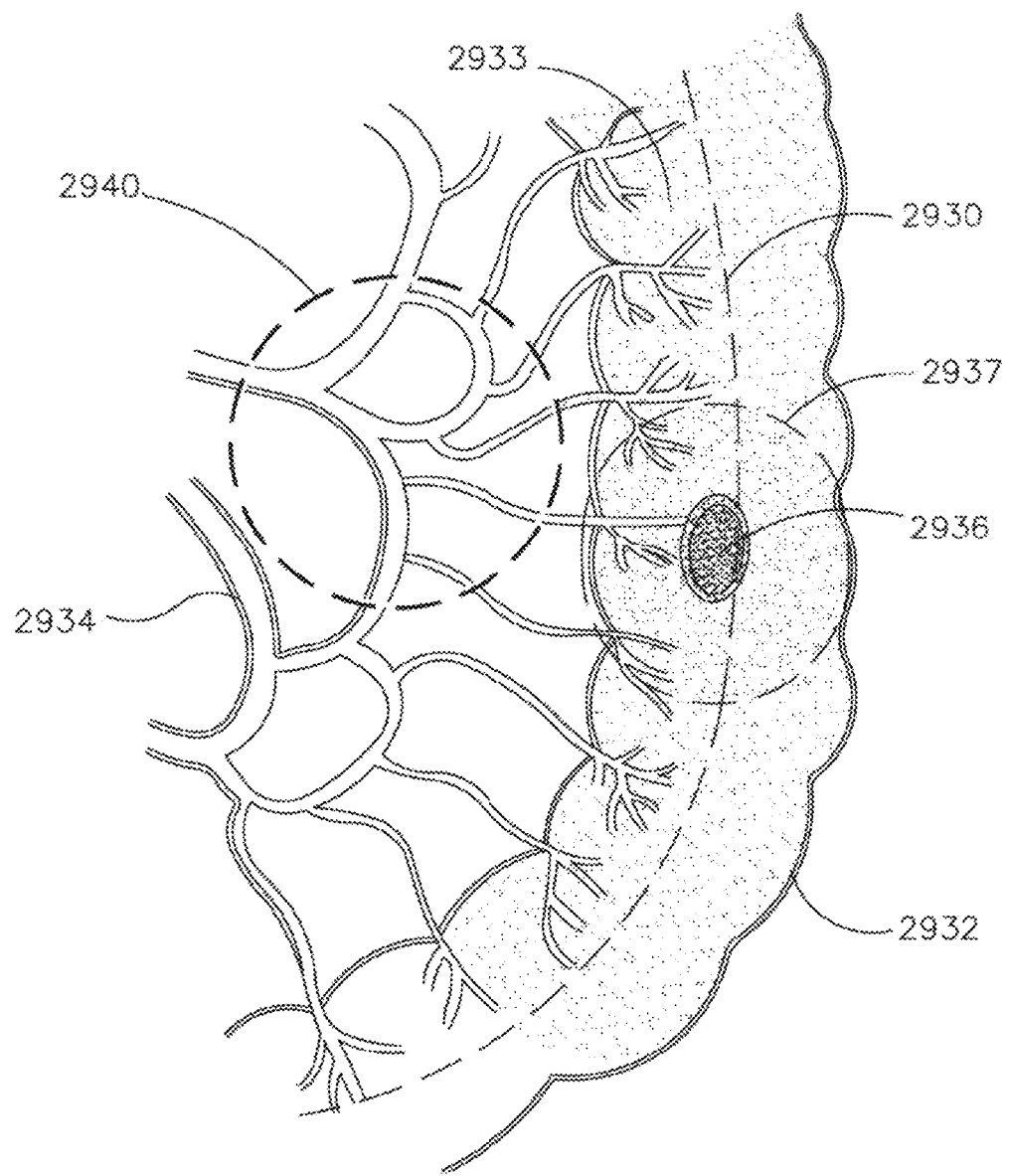
Figure 201B:
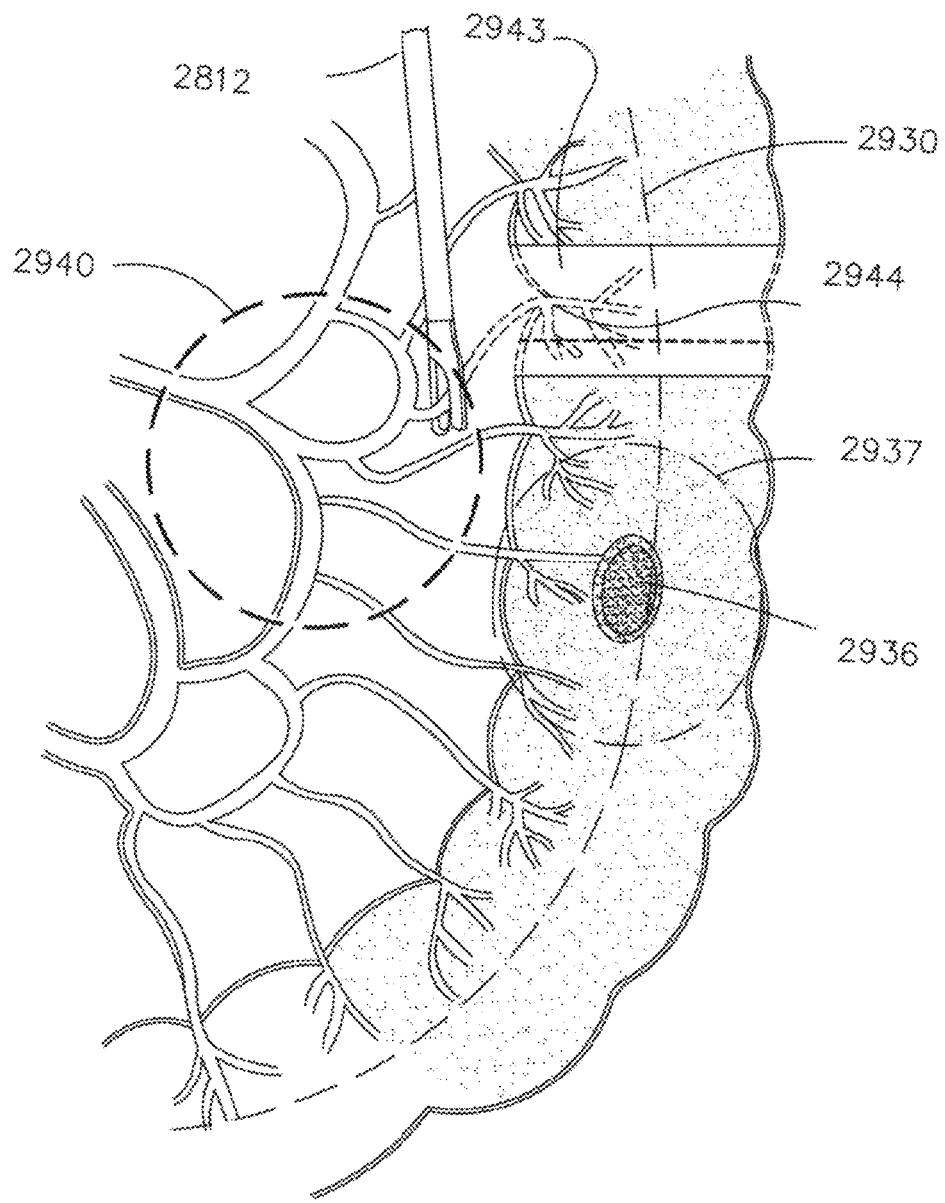
Figure 201C:
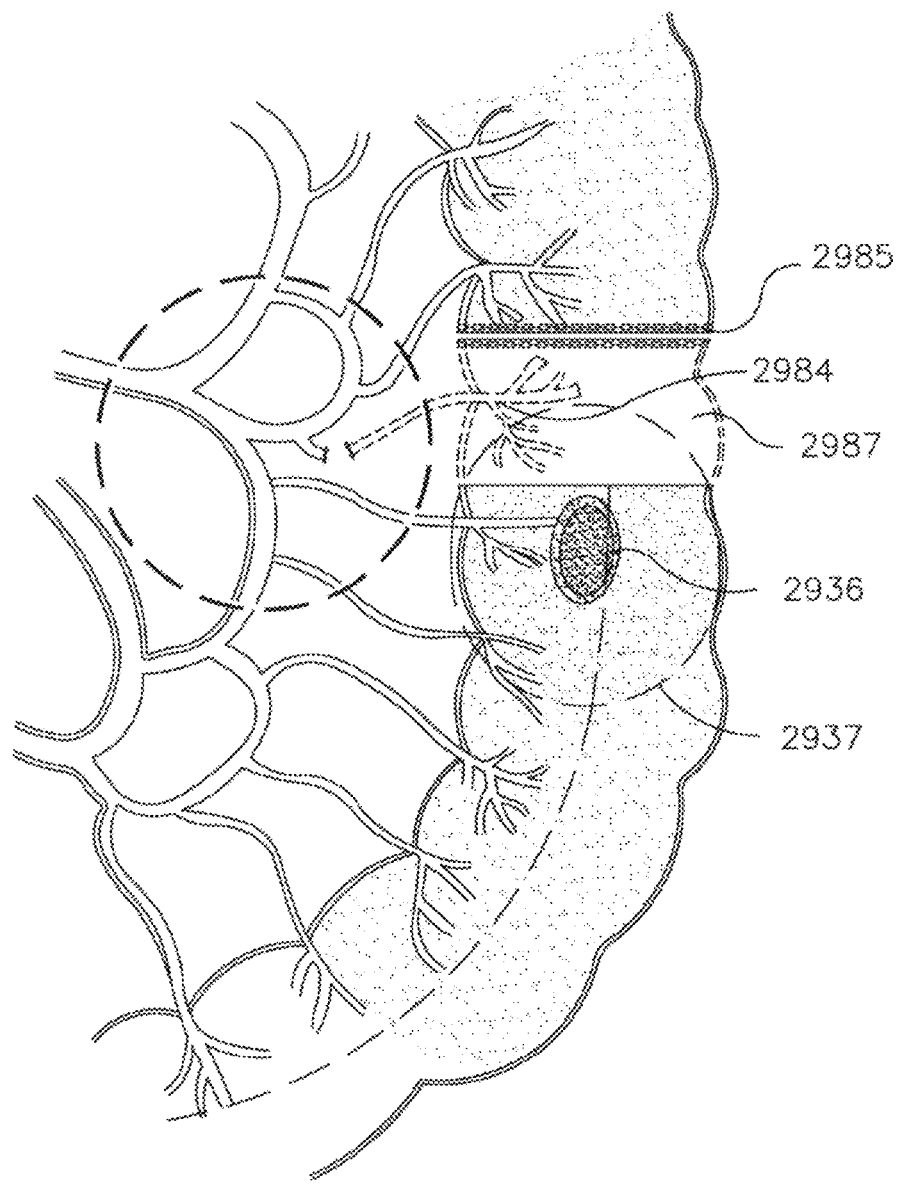

FIG. 201A-C illustrate examples of a sequence of surgical steps with multi-image analysis at the surgical site.

FIG. 202 illustrates an example of an augmented video image of a pre-operative video image augmented with data identifying displayed elements.

Figure 203:
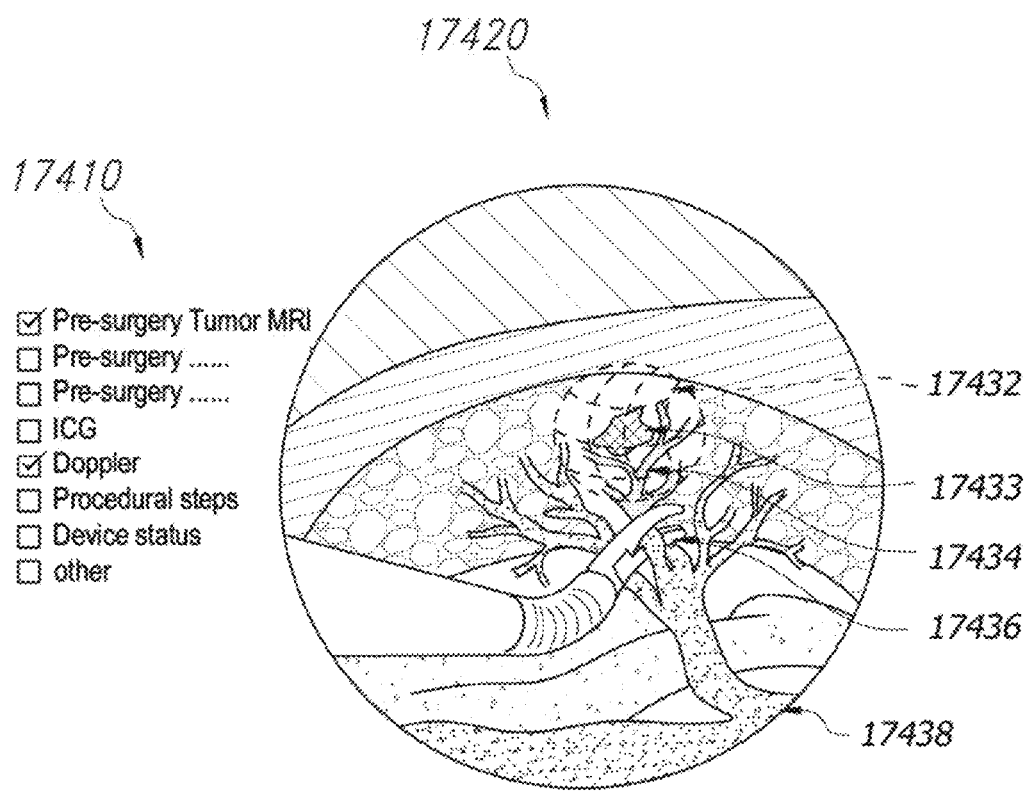

FIG. 203 illustrates an example of am augmented reality overlay for a targeted area with pre-surgery tumor data and real time doppler monitoring.

Figure 204:
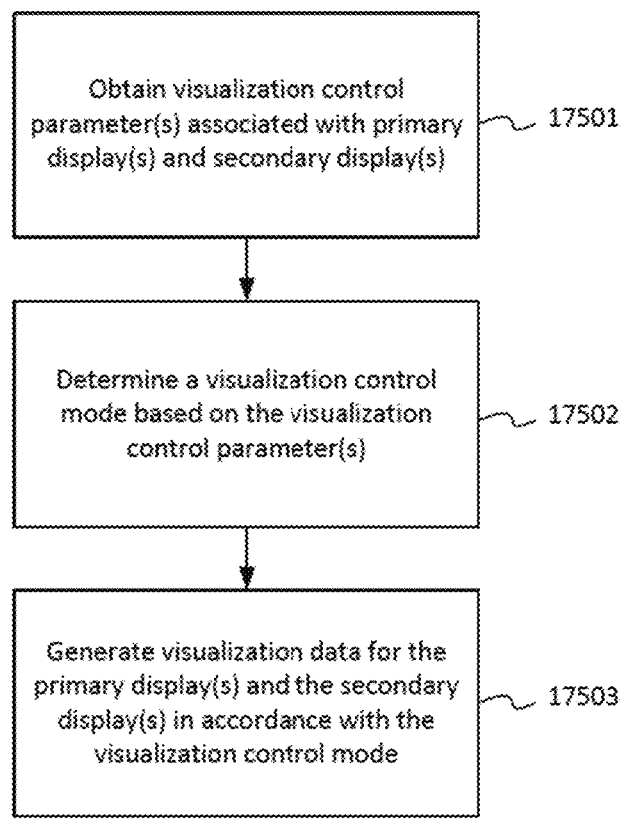

FIG. 204 shows an example flow for a hub operating under tiered visualization control modes.

Figure 205:
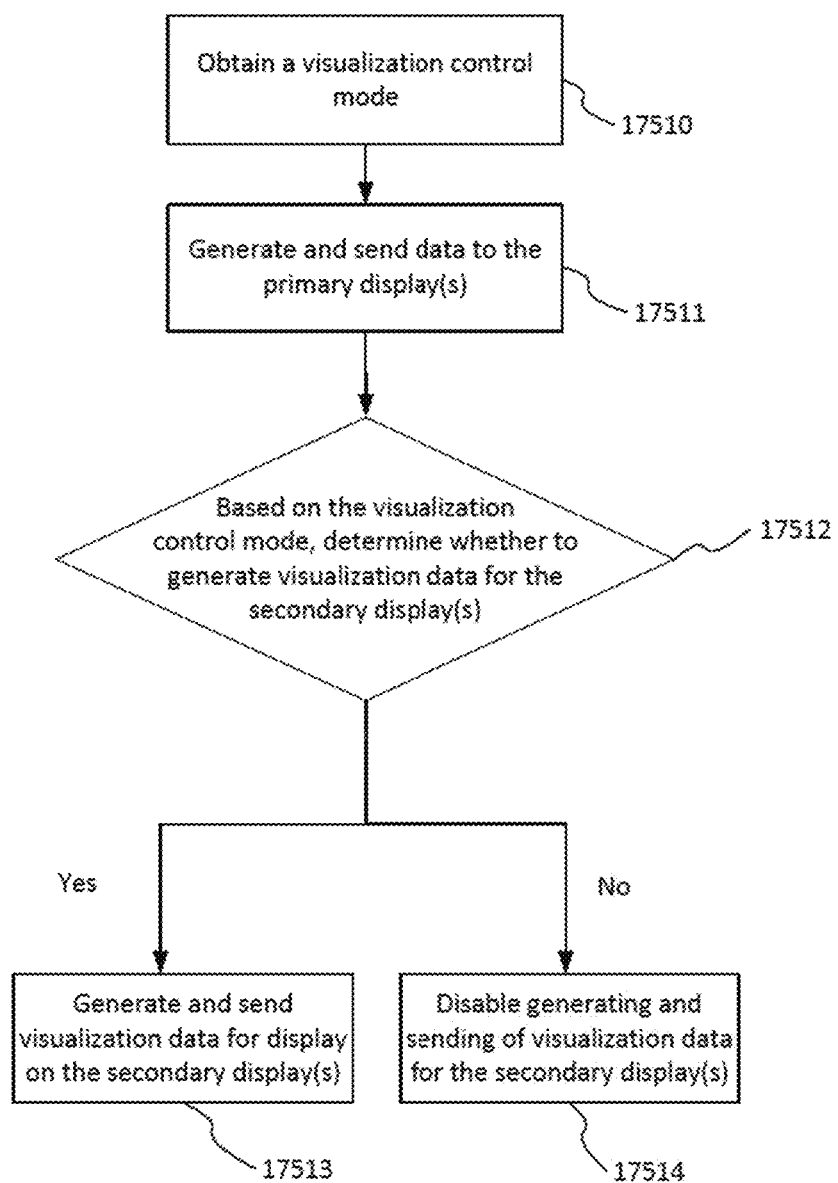

FIG. 205 shows an example flow for a hub operating under tiered visualization control modes.

Figure 206:
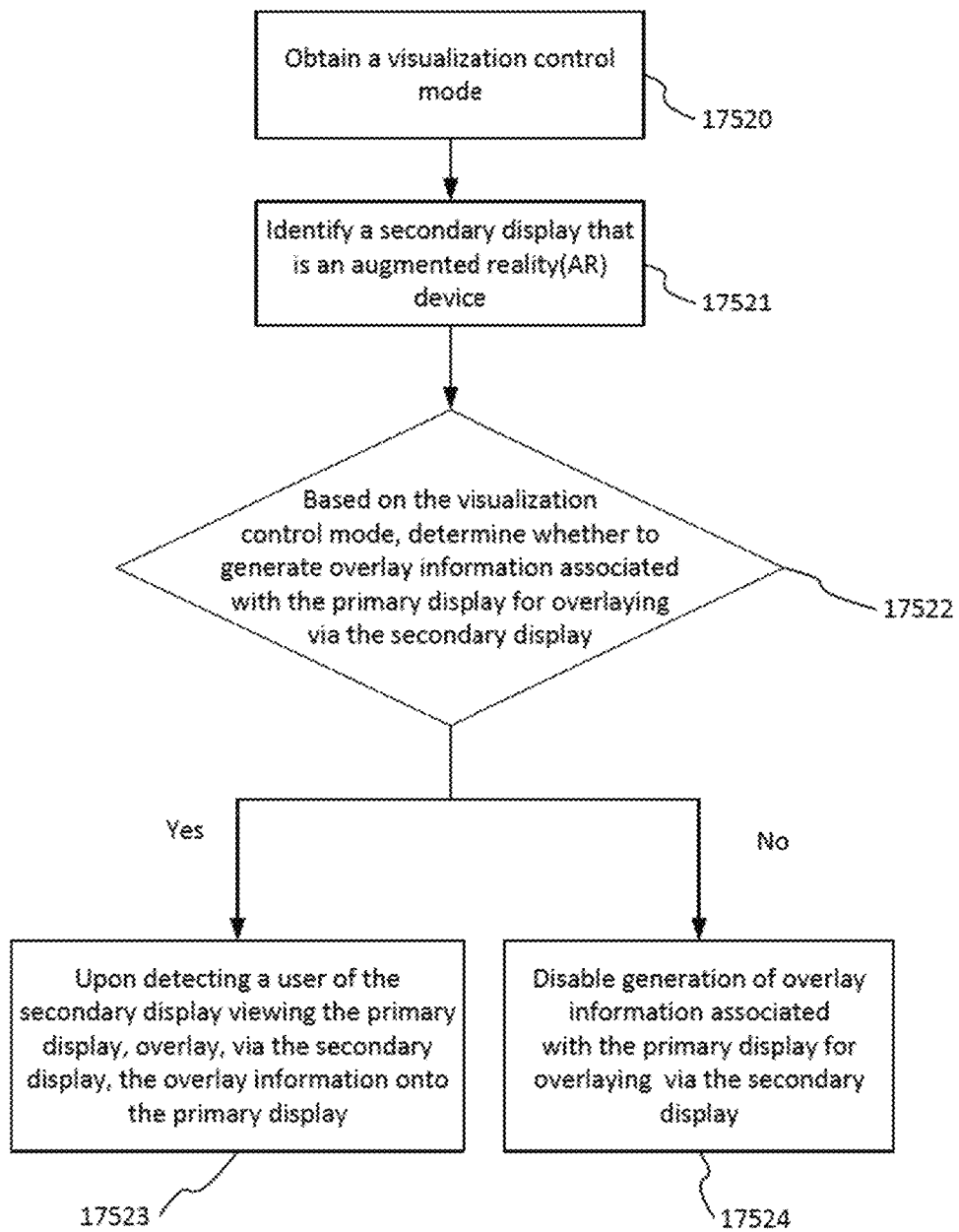

FIG. 206 shows a detailed example flow for a hub operating under a visualization control mode where the secondary display is an augmented reality (AR) device.

Figure 207:
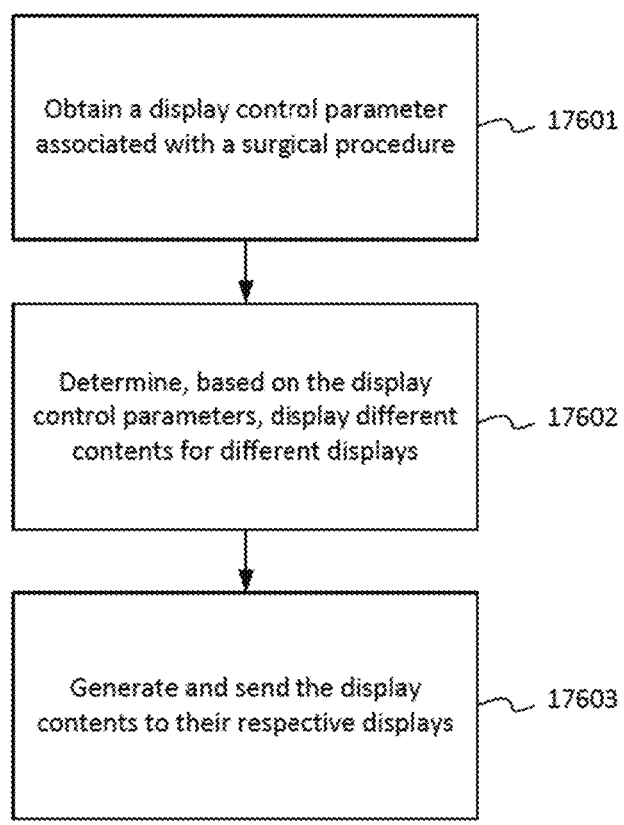

FIG. 207 shows an example flow for a hub operating under a visualization control mode that supports situational awareness capabilities.

FIG. 208 shows an example flow for a hub operating under a visualization control mode that supports situational awareness capabilities.

FIG. 209 shows an example flow of a hub operating under a visualization control mode that supports adjusting display based on an adjusted display event.

Figure 210:
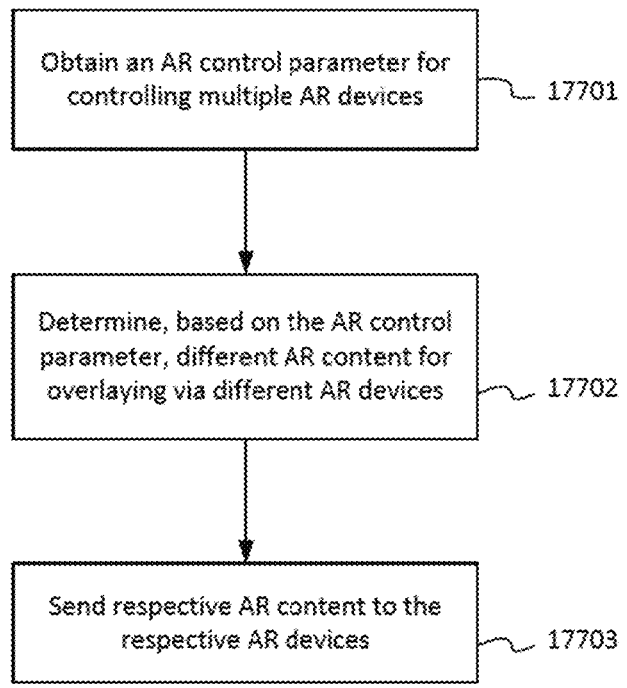

FIG. 210 shows an example flow of a hub operating under a visualization control mode that support AR capabilities.

Figure 211:
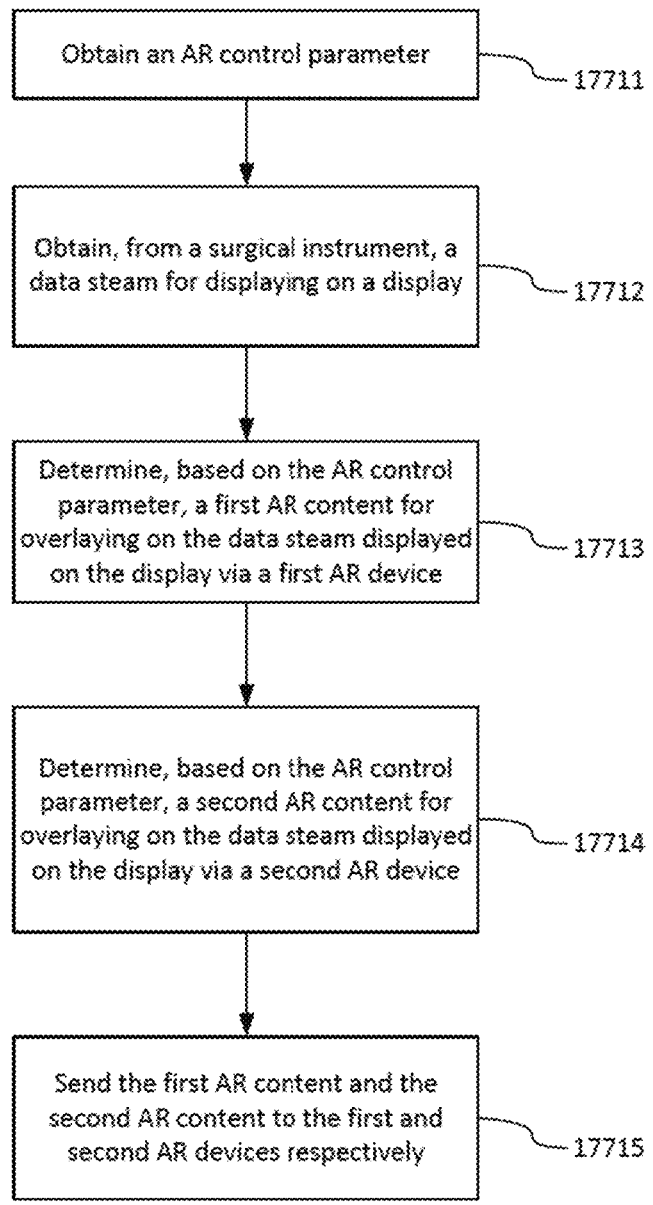

FIG. 211 shows an example flow of a hub operating on under a visualization control mode that support AR capabilities.

FIG. 212 shows an example flow of a hub operating under a visualization control mode that support role-based AR capabilities.

FIG. 213 shows an example flow of a hub operating under a visualization control mode with AR capabilities that support overlays on various displays.

FIG. 214 shows example flow for operating under a multi-display control mode.

FIG. 215 shows an example flow for operating under tiered multi-display control mode(s).

Figure 216:
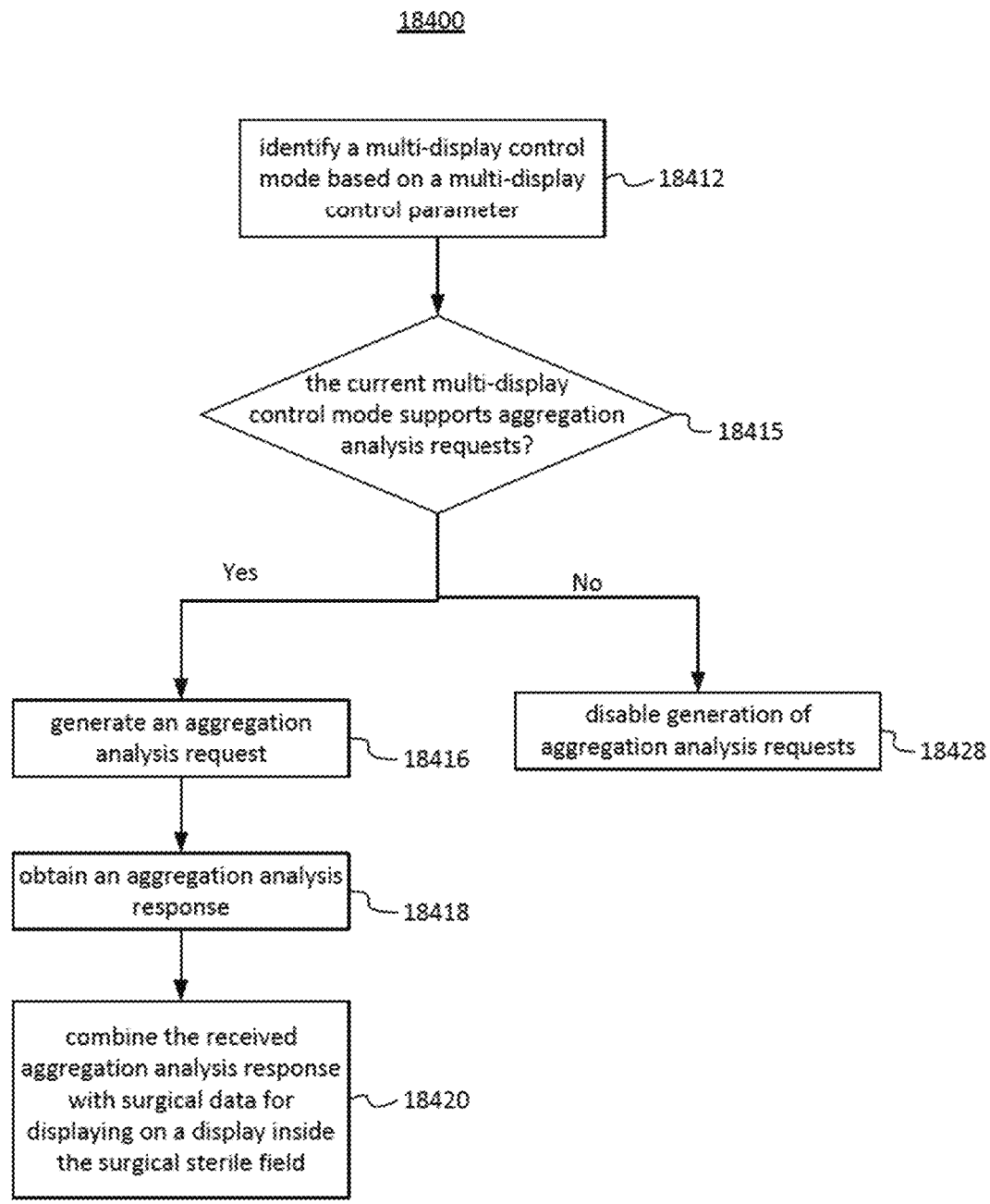

FIG. 216 shows an example flow for operating under tiered multi-display control mode(s).

Figure 217:
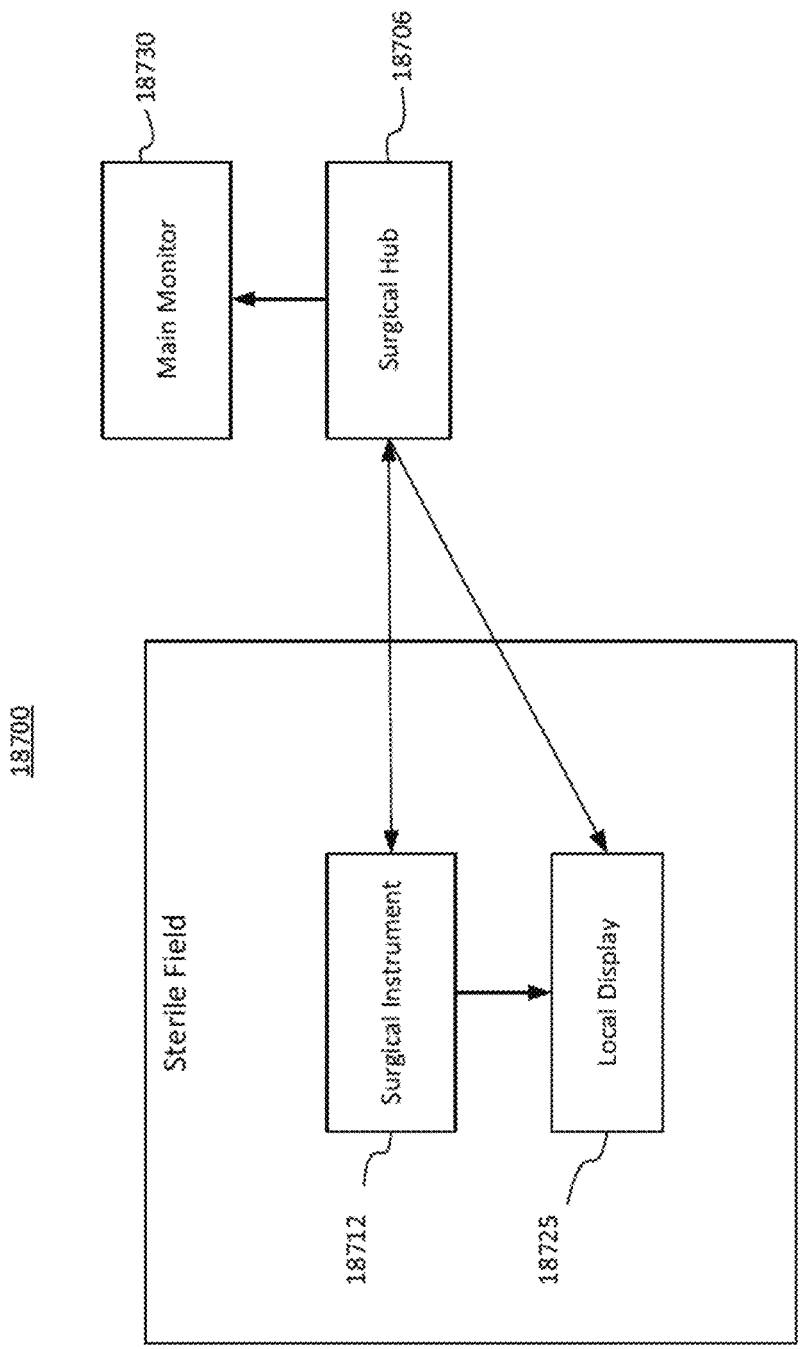

FIG. 217 shows an example multi-display control mode such as a one-way communication mode.

Figure 218:
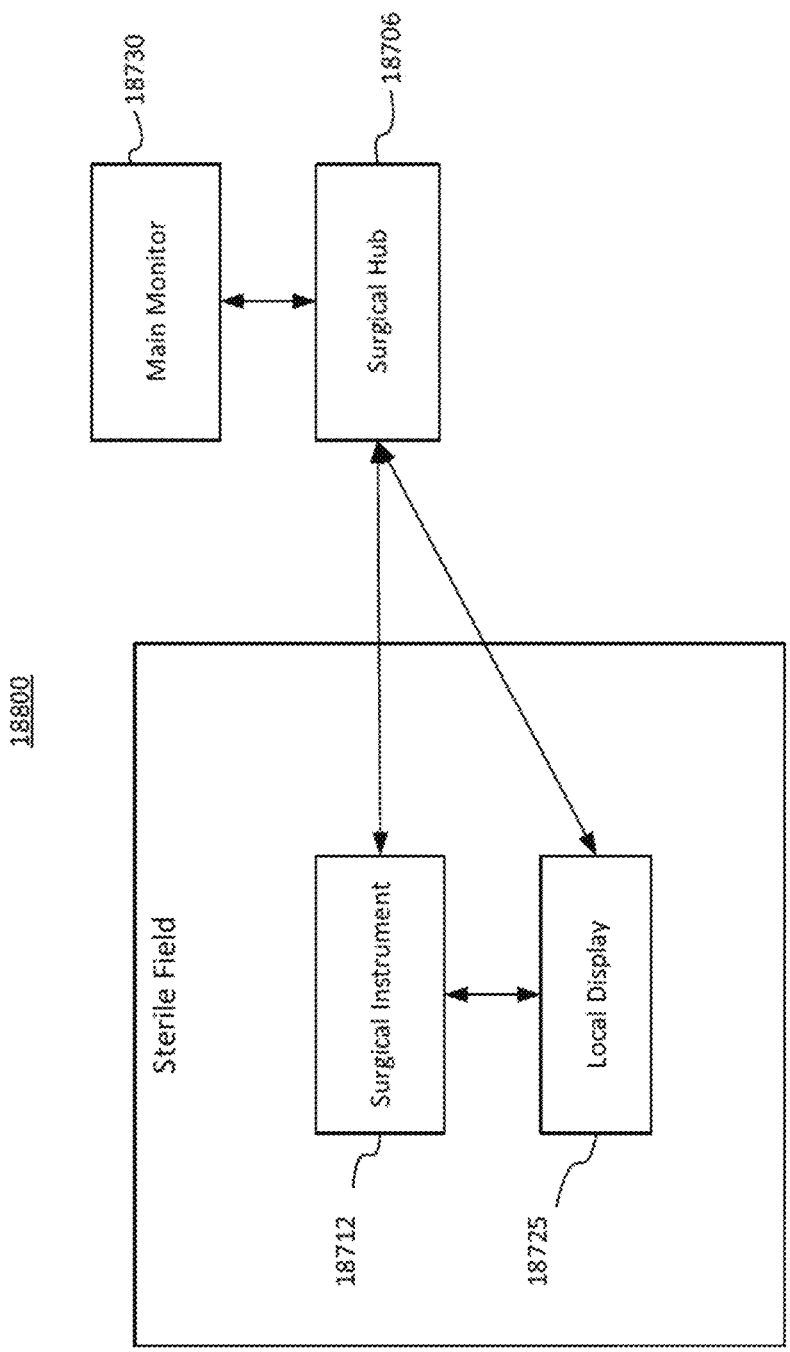

FIG. 218 shows an example multi-display control mode that may support sterile field display-based control.

Figure 219:
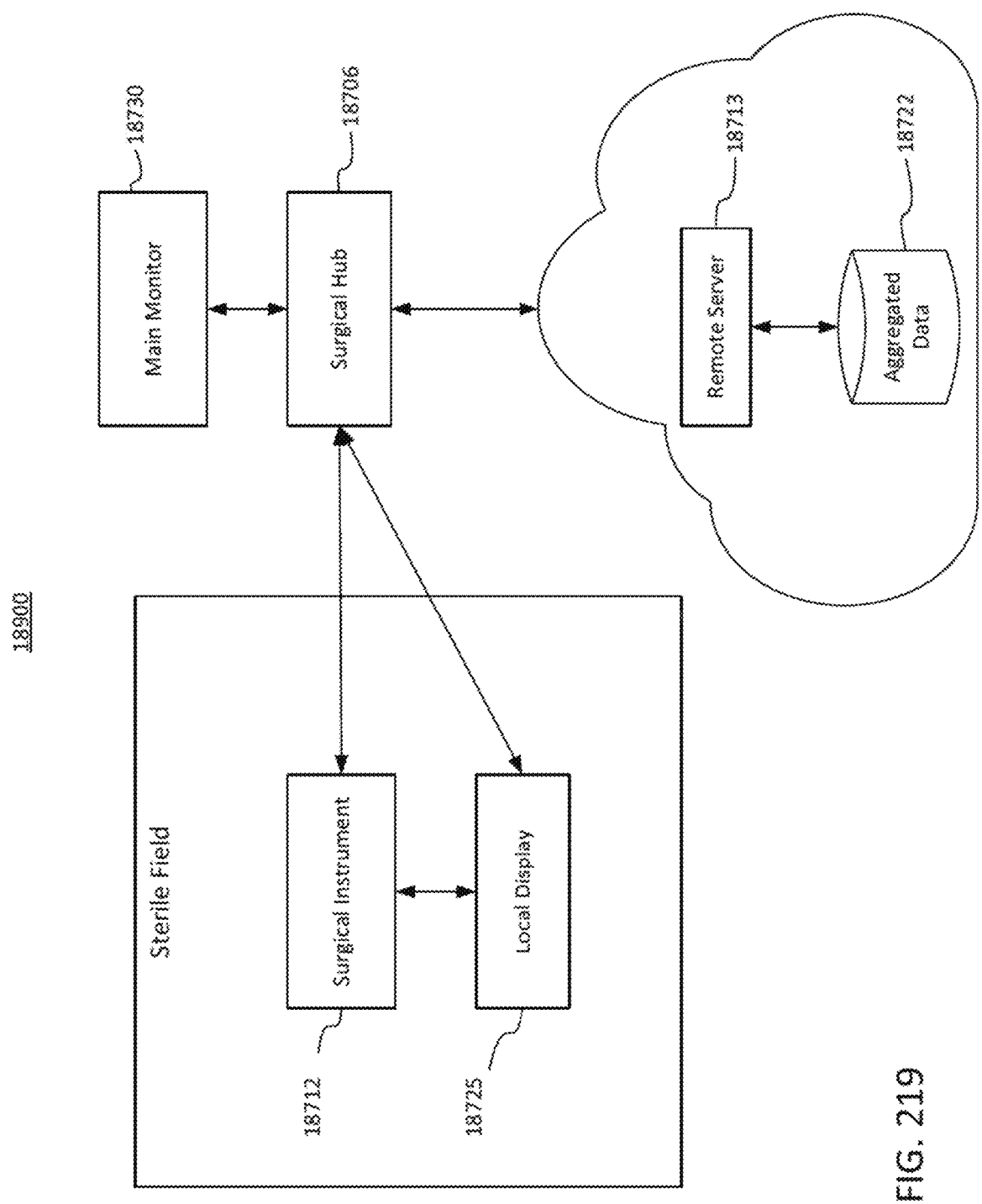

FIG. 219 shows an example multi-display control mode that may support remote data aggregation analysis.

Figure 220:
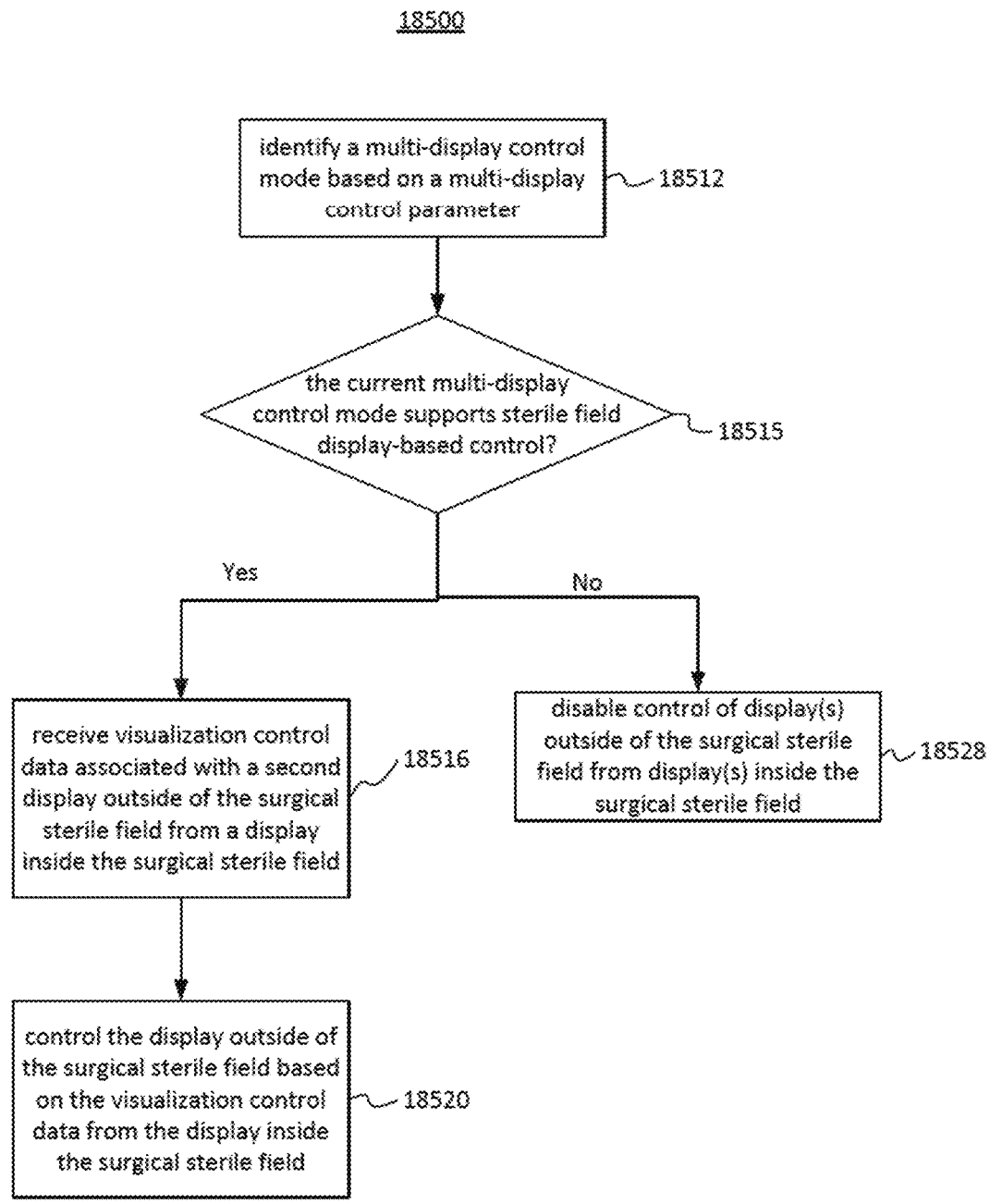

FIG. 220 shows an example flow for operating under tiered multi-display control mode(s).

Figure 221:
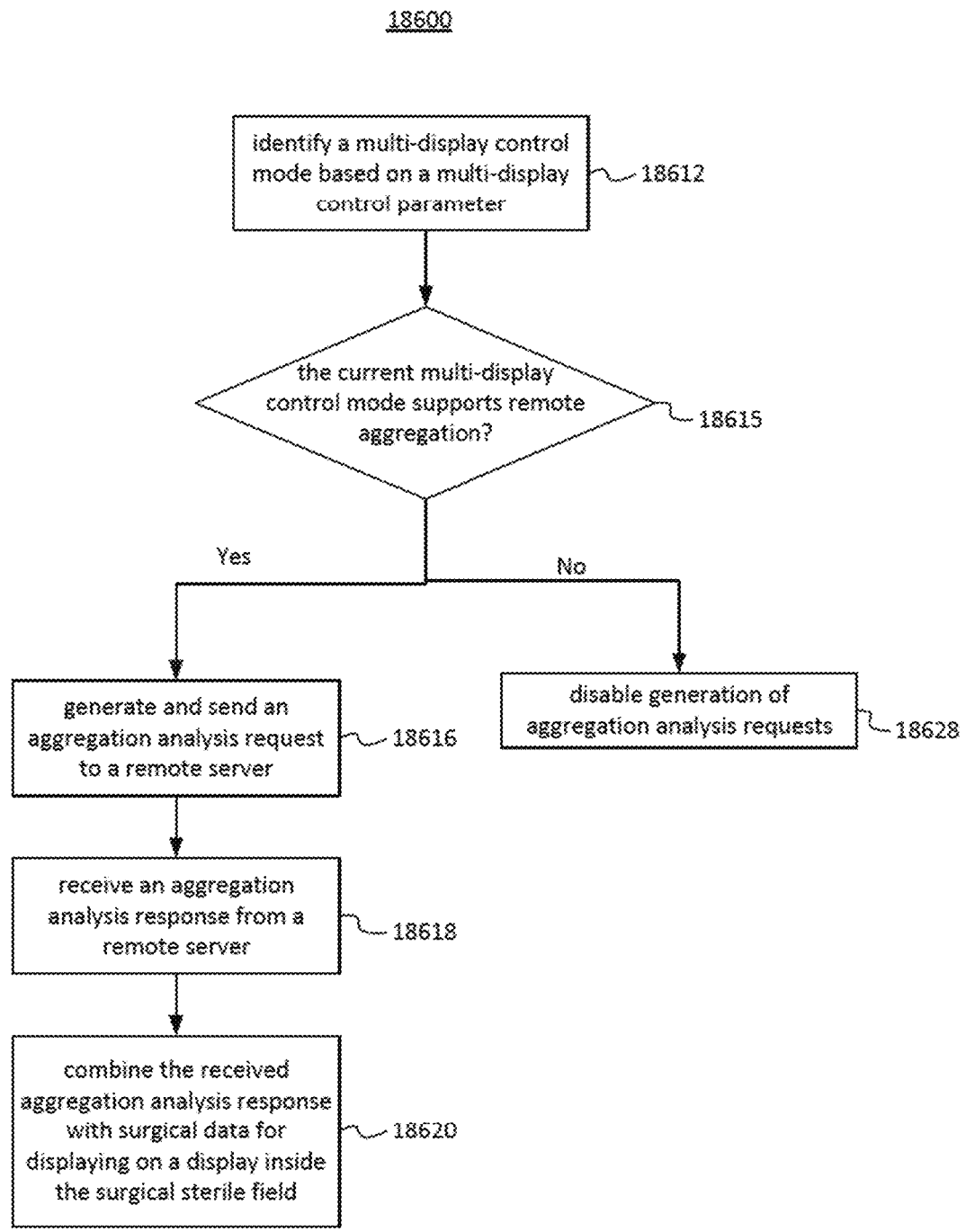

FIG. 221 shows an example flow for operating under tiered multi-display control mode(s).

DETAILED DESCRIPTION

Applicant of the present application owns the following U.S. Patent Applications, filed contemporaneously, each of which is herein incorporated by reference in its entirety:

U.S. patent application Ser. No. 15/940,656, entitled "SURGICAL HUB COORDINATION OF CONTROL AND COMMUNICATION OF OPERATING ROOM DEVICES," filed on Mar. 29, 2018, now U.S. Patent Application Publication No. 2019/0201141;

U.S. patent application Ser. No. 16/361,793, entitled "SURGICAL INSTRUMENT COMPRISING AN ADAPTIVE CONTROL SYSTEM," filed Mar. 22, 2019, now U.S. Patent Application Publication No. 20190314015;

U.S. patent application Ser. No. 13/803,086, entitled "ARTICULATABLE SURGICAL INSTRUMENT COMPRISING AN ARTICULATION LOCK," now U.S. Patent Application Publication No. 2014/0263541;

U.S. patent application Ser. No. 13/800,067, entitled "STAPLE CARTRIDGE TISSUE THICKNESS SENSOR SYSTEM," filed on Mar. 13, 2013, now U.S. Patent Application Publication No. 2014/0263552;

U.S. patent application Ser. No. 16/024,075, entitled "SAFETY SYSTEMS FOR SMART POWERED SURGICAL STAPLING," filed on Jun. 29, 2018, now U.S. Patent Application Publication No. 2019/0201146;

U.S. patent application Ser. No. 15/940,679, entitled "CLOUD-BASED MEDICAL ANALYTICS FOR LINKING OF LOCAL USAGE TRENDS WITH THE RESOURCE ACQUISITION BEHAVIORS OF LARGER DATA SET," filed on Mar. 29, 2018, now U.S. Patent Application Publication No. 2019/0201144;

U.S. patent application Ser. No. 15/940,668, entitled "AGGREGATION AND REPORTING OF SURGICAL HUB DATA," filed on Mar. 29, 2018, now U.S. Patent Application Publication No. 2019/0201115; and U.S. Patent Application Publication No. US 20190200981 (U.S. application Ser. No. 16/209,423, filed Dec. 4, 2018), titled "METHOD OF COMPRESSING TISSUE WITHIN A STAPLING DEVICE AND SIMULTANEOUSLY DISPLAYING THE LOCATION OF THE TISSUE WITHIN THE JAWS," published Jul. 4, 2019;

U.S. Pat. No. 9,072,535, titled "SURGICAL STAPLING INSTRUMENTS WITH ROTATABLE STAPLE DEPLOYMENT ARRANGEMENTS," issued Jul. 5, 2015;

U.S. Patent Application Publication No. US 20140263551 (U.S. application Ser. No. 13/800,025, filed Mar. 13, 2013), titled "STAPLE CARTRIDGE TISSUE THICKNESS SENSOR SYSTEM," published Sep. 18, 2014;

U.S. Patent Application Publication No. US 20190000478 (U.S. application Ser. No. 15/636,096, filed Jun. 28, 2017), titled "SURGICAL SYSTEM COUPLABLE WITH STAPLE CARTRIDGE AND RADIO FREQUENCY CARTRIDGE, AND METHOD OF USING SAME," published Jan. 3, 2019;

U.S. Patent Application Publication No. US 20160256156 (applications Ser. No. 14/852,982, filed Sep. 14, 2015), titled "TIME DEPENDENT EVALUATION OF SENSOR DATA TO DETERMINE STABILITY, CREEP, AND VISCOELASTIC ELEMENTS OF MEASURES," published Sep. 8, 2016; and U.S. Pat. No. 10,695,081, titled "CONTROLLING A SURGICAL INSTRUMENT ACCORDING TO SENSED CLOSURE PARAMETERS," issued Jun. 30, 2020.

U.S. Patent Application Publication No. US 2019-0200844 A1 (U.S. patent application Ser. No. 16/209,385 filed Dec. 4, 2018), titled "METHOD OF HUB COMMUNICATION, PROCESSING, STORAGE AND DISPLAY," published Jul. 4, 2019;

U.S. Patent Application Publication No. US 2019-0201137 A1 (U.S. patent application Ser. No. 16/209,407, filed Dec. 4, 2018), titled "METHOD OF ROBOTIC HUB COMMUNICATION, DETECTION, AND CONTROL," published Jul. 4, 2019;

U.S. Patent Application Publication No. US 2019-0206569 A1 (U.S. patent application Ser. No. 16/209,403 filed Dec. 4, 2018), titled "METHOD OF CLOUD BASED DATA ANALYTICS FOR USE WITH THE HUB," published Jul. 4, 2019;

U.S. Patent Application Publication No. US 2017-0296213 A1 (U.S. patent application Ser. No. 15/130,590 filed Apr. 15, 2016), titled "SYSTEMS AND METHODS FOR CONTROLLING A SURGICAL STAPLING AND CUTTING INSTRUMENT," published Oct. 19, 2017;

U.S. Pat. No. 9,345,481, titled "STAPLE CARTRIDGE TISSUE THICKNESS SENSOR SYSTEM," issued May 24, 2016;

U.S. Patent Application Publication No. US 2018/0360452 (U.S. patent application Ser. No. 15/628,175, filed Jun. 20, 2017), titled "TECHNIQUES FOR ADAPTIVE CONTROL OF MOTOR VELOCITY OF A SURGICAL STAPLING AND CUTTING INSTRUMENT," published Dec. 20, 2018

U.S. patent application Ser. No. 16/209,416, entitled "METHOD OF HUB COMMUNICATION, PROCESSING, DISPLAY, AND CLOUD ANALYTICS," filed Dec. 4, 2018;

U.S. patent application Ser. No. 15/940,671, entitled "SURGICAL HUB SPATIAL AWARENESS TO DETERMINE DEVICES IN OPERATING THEATER," filed Mar. 29, 2018;

U.S. patent application Ser. No. 16/182,269 entitled "IMAGE CAPTURING OF THE AREAS OUTSIDE THE ABDOMEN TO IMPROVE PLACEMENT AND CONTROL OF A SURGICAL DEVICE IN USE," filed Nov. 6, 2018;

U.S. patent application Ser. No. 16/729,747 entitled "DYNAMIC SURGICAL VISUALIZATION SYSTEMS," filed Dec. 31, 2019;

U.S. Patent Application Ser. No. 16/729,778 entitled "SYSTEM AND METHOD FOR DETERMINING, ADJUSTING, AND MANAGING RESECTION MARGIN ABOUT A SUBJECT TISSUE," filed Dec. 31, 2019;

U.S. patent application Ser. No. 16/729,807 entitled METHOD OF USING IMAGING DEVICES IN SURGERY, filed Dec. 31, 2019;

U.S. patent application Ser. No. 15/940,654, entitled SURGICAL HUB SITUATIONAL AWARENESS, filed Mar. 29, 2018;

U.S. patent application Ser. No. 15/940,704, titled USE OF LASER LIGHT AND RED-GREEN-BLUE COLORATION TO DETERMINE PROPERTIES OF BACK SCATTERED LIGHT, which was filed on Mar. 29, 2018;

U.S. patent application Ser. No. 16/182,290, entitled "SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION," filed Nov. 6, 2018;

U.S. Pat. No. 9,011,427, entitled SURGICAL INSTRUMENT WITH SAFETY GLASSES, issued on Apr. 21, 2015;

U.S. Pat. No. 9,123,155, titled APPARATUS AND METHOD FOR USING AUGMENTED REALITY VISION SYSTEM IN SURGICAL PROCEDURES, which issued on Sep. 1, 2015;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Dec. 4, 2018;

U.S. Patent Application Publication No. US20190206563A1 (U.S. patent application Ser. No. 16/209,465), titled Method for adaptive control schemes for surgical network control and interaction, filed Dec. 4, 2018;

U.S. Patent Application Publication No. US20190201034A1 (U.S. patent application Ser. No. 16/182,240), titled Powered stapling device configured to adjust force, advancement speed, and overall stroke of cutting member based on sensed parameter of firing or clamping, filed Nov. 6, 2018;

U.S. Patent Application Publication No. US20190200996A1 (U.S. patent application Ser. No. 16/182,229), titled ADJUSTMENT OF STAPLE HEIGHT OF AT LEAST ONE ROW OF STAPLES BASED ON THE SENSED TISSUE THICKNESS OR FORCE IN CLOSING, filed Nov. 6, 2018;

U.S. Patent Application Publication No. US20190200997A1 (U.S. patent application Ser. No. 16/182,234), titled Stapling device with both compulsory and discretionary lockouts based on sensed parameters, filed Nov. 6, 2018;

U.S. patent application Ser. No. 16/458,117, titled SURGICAL SYSTEM WITH RFID TAGS FOR UPDATING MOTOR ASSEMBLY PARAMETERS, filed Jun. 30, 2019;

U.S. Patent Application Publication No. 2017/0296213 (U.S. patent application Ser. No. 15/130,590), titled SYSTEMS AND METHODS FOR CONTROLLING A SURGICAL STAPLING AND CUTTING INSTRUMENT, published on Oct. 19, 2017;

U.S. Patent Application Publication No. US20190099180A1 (U.S. patent application Ser. No. 15/720,852), titled SYSTEM AND METHODS FOR CONTROLLING A DISPLAY OF A SURGICAL INSTRUMENT, filed Sep. 29, 2017;

U.S. Patent Application Publication No. 2014/0166728 (U.S. patent application Ser. No. 13/716,318), entitled "Motor Driven Rotary Input Circular Stapler with Modular End Effector," published Jun. 19, 2014;

U.S. Pat. No. 9,250,172, titled Systems and methods for predicting metabolic and bariatric surgery outcomes, issued on Feb. 2, 2016;

U.S. Patent Application Publication No. US20130116218A1 (U.S. patent application Ser. No. 13/631,095), titled Methods and compositions of bile acids, published May 9, 2013;

U.S. Patent Application Publication No. US20140087999A1 (U.S. patent application Ser. No. 13/828,809), titled Clinical predictors of weight loss, published Mar. 27, 2014;

U.S. Pat. No. 8,476,227, titled Methods of activating a melanocortin-4 receptor pathway in obese subjects, issued Jul. 2, 2013;

U.S. patent application Ser. No. 16/574,773, titled METHOD FOR CALIBRATING MOVEMENTS OF ACTUATED MEMBERS OF POWERED SURGICAL STAPLER, filed Sep. 18, 2019;

U.S. patent application Ser. No. 16/574,797, titled METHOD FOR CONTROLLING CUTTING MEMBER ACTUATION FOR POWERED SURGICAL STAPLER, filed Sep. 18, 2019;

U.S. patent application Ser. No. 16/574,281, titled METHOD FOR CONTROLLING END EFFECTOR CLOSURE FOR POWERED SURGICAL STAPLER, filed Sep. 18, 2019;

U.S. Patent Application Publication No. US20190201119A1 (U.S. patent application Ser. No. 15/940,694), titled CLOUD-BASED MEDICAL ANALYTICS FOR MEDICAL FACILITY SEGMENTED INDIVIDUALIZATION OF INSTRUMENT FUNCTION, filed Mar. 29, 2018;

U.S. Pat. No. 10,492,783, titled SURGICAL INSTRUMENT WITH IMPROVED STOP/START CONTROL DURING A FIRING MOTION, issued on Dec. 3, 2019;

U.S. Patent Application Publication No. US20190200998A1 (U.S. patent application Ser. No. 16/209,491), titled METHOD FOR CIRCULAR STA- PLER CONTROL ALGORITHM ADJUSTMENT BASED ON SITUATIONAL AWARENESS, filed Dec. 4, 2018;

U.S. patent application Ser. No. 15/940,636, entitled "ADAPTIVE CONTROL PROGRAM UPDATES FOR SURGICAL DEVICES," filed Mar. 29, 2018, now U.S. Patent Application Publication No. 2019/0206003;

U.S. patent application Ser. No. 16/562,170, entitled "MANAGING SIMULTANEOUS MONOPOLAR OUTPUTS USING DUTY CYCLE AND SYNCHRONIZATION," filed on Sep. 5, 2019, now U.S. Patent Application Publication No. 2020/0078079;

U.S. patent application Ser. No. 16/209,490, entitled "METHOD FOR FACILITY DATA COLLECTION AND INTERPRETATION," filed Dec. 4, 2018, now U.S. Patent Application Publication No. 2019/0206564; and U.S. patent application Ser. No. 16/182,246, titled ADJUSTMENTS BASED ON AIRBORNE PARTICLE PROPERTIES, filed Nov. 6, 2018.

Figure 1:
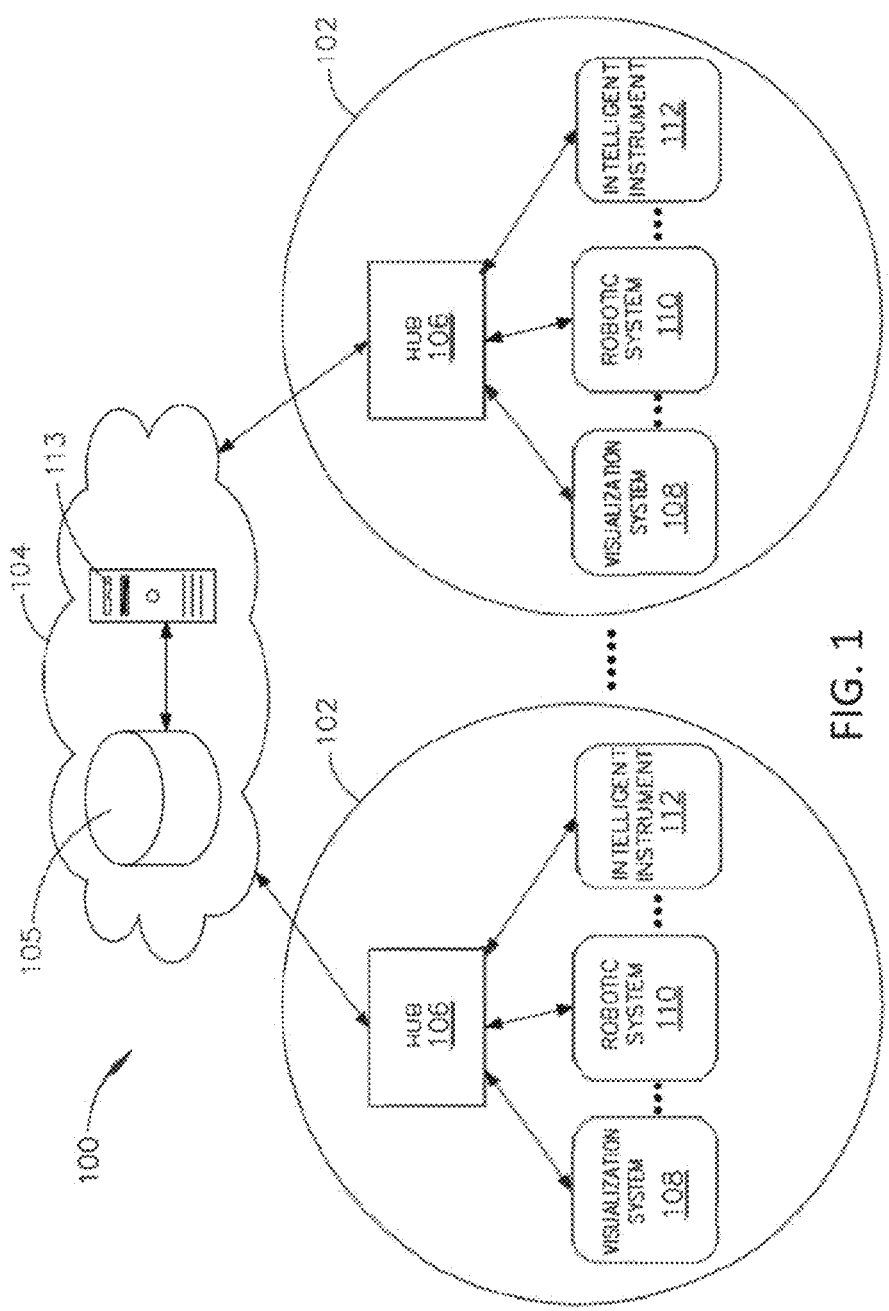
FIG. 1 is a block diagram of a computer-implemented interactive surgical system.

Referring to FIG. 1, a computer-implemented interactive surgical system 100 may include one or more surgical systems 102 and a cloud-based system (e.g., the cloud 104 that may include a remote server 113 coupled to a storage device 105). Each surgical system 102 may include at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P may be integers greater than or equal to one.

Figure 2:
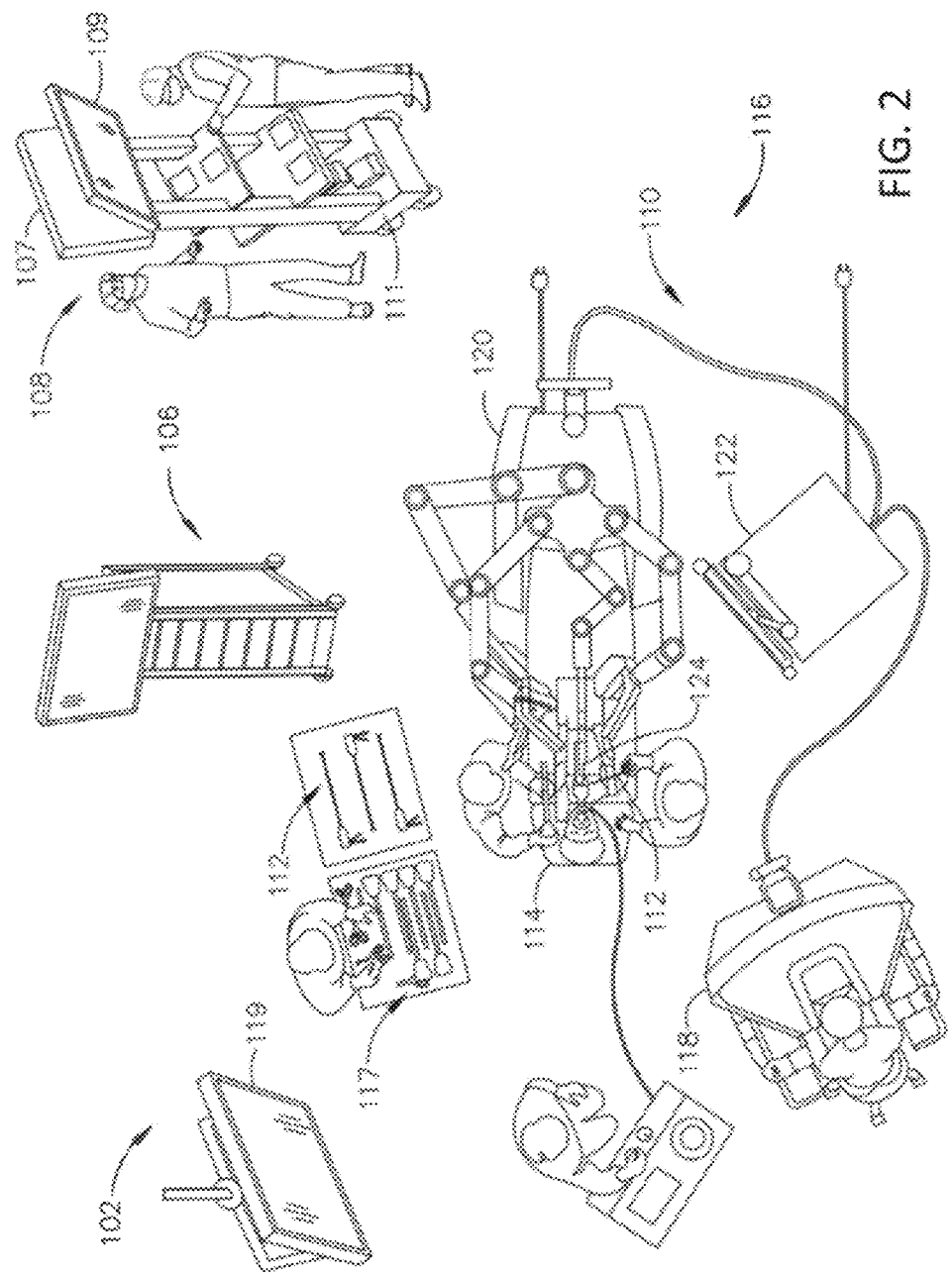
FIG. 2 shows an example surgical system being used to perform a surgical procedure in an operating room.

In various aspects, the visualization system 108 may include one or more imaging sensors, one or more image-processing units, one or more storage arrays, and one or more displays that are strategically arranged with respect to the sterile field, as illustrated in FIG. 2. In one aspect, the visualization system 108 may include an interface for HL7, PACS, and EMR. Various components of the visualization system 108 are described under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 may include a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 may also be configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 may also be configured to coordinate information flow to a display of the surgical instrument 112. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 depicts an example of a surgical system 102 being used to perform a surgical procedure on a patient who is lying down on an operating table 114 in a surgical operating room 116. A robotic system 110 may be used in the surgical procedure as a part of the surgical system 102. The robotic system 110 may include a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud 104, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 124 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209, 385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 3:
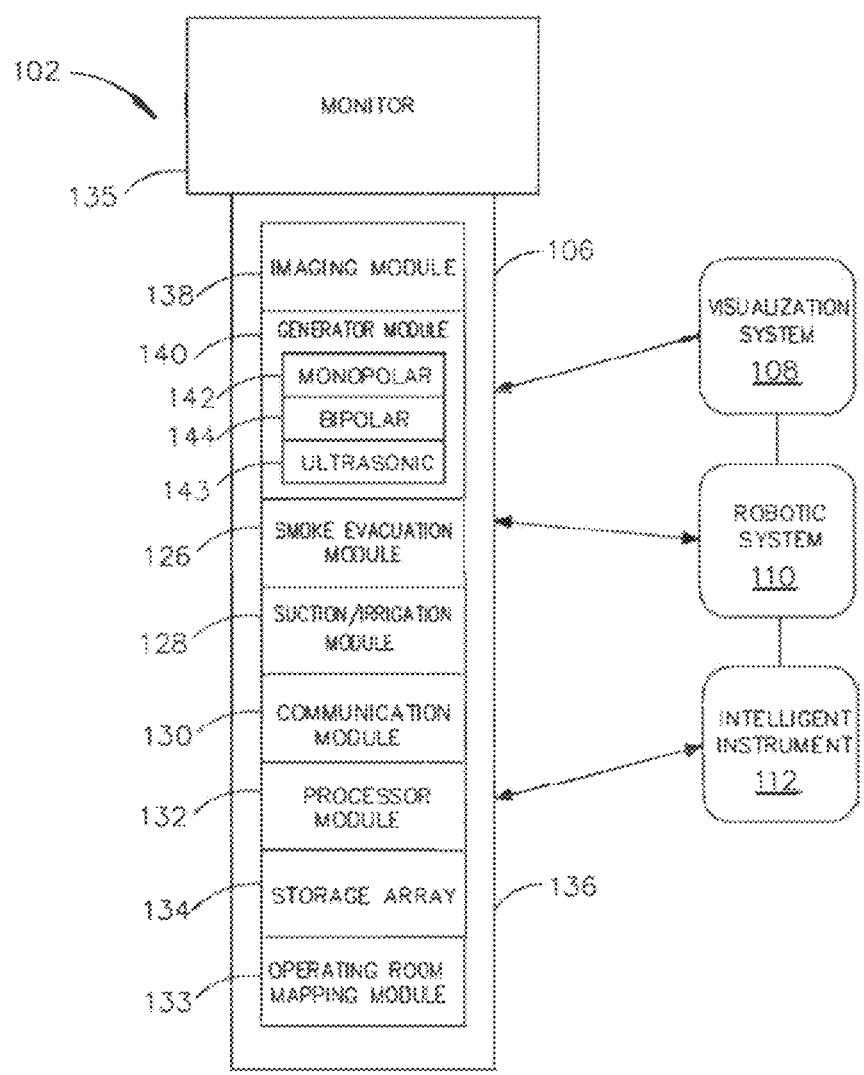
FIG. 3 shows an example surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, a storage array 134, and an operating-room mapping module 133. In certain aspects, as illustrated in FIG. 3, the hub 106 further includes a smoke evacuation module 126 and/or a suction/irrigation module 128. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines. Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line is a first fluid line and a second fluid line extends from the remote surgical site to a suction and irrigation module slidably received in the hub enclosure. In one aspect, the hub enclosure comprises a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module con-figured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 146. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

Figure 4:
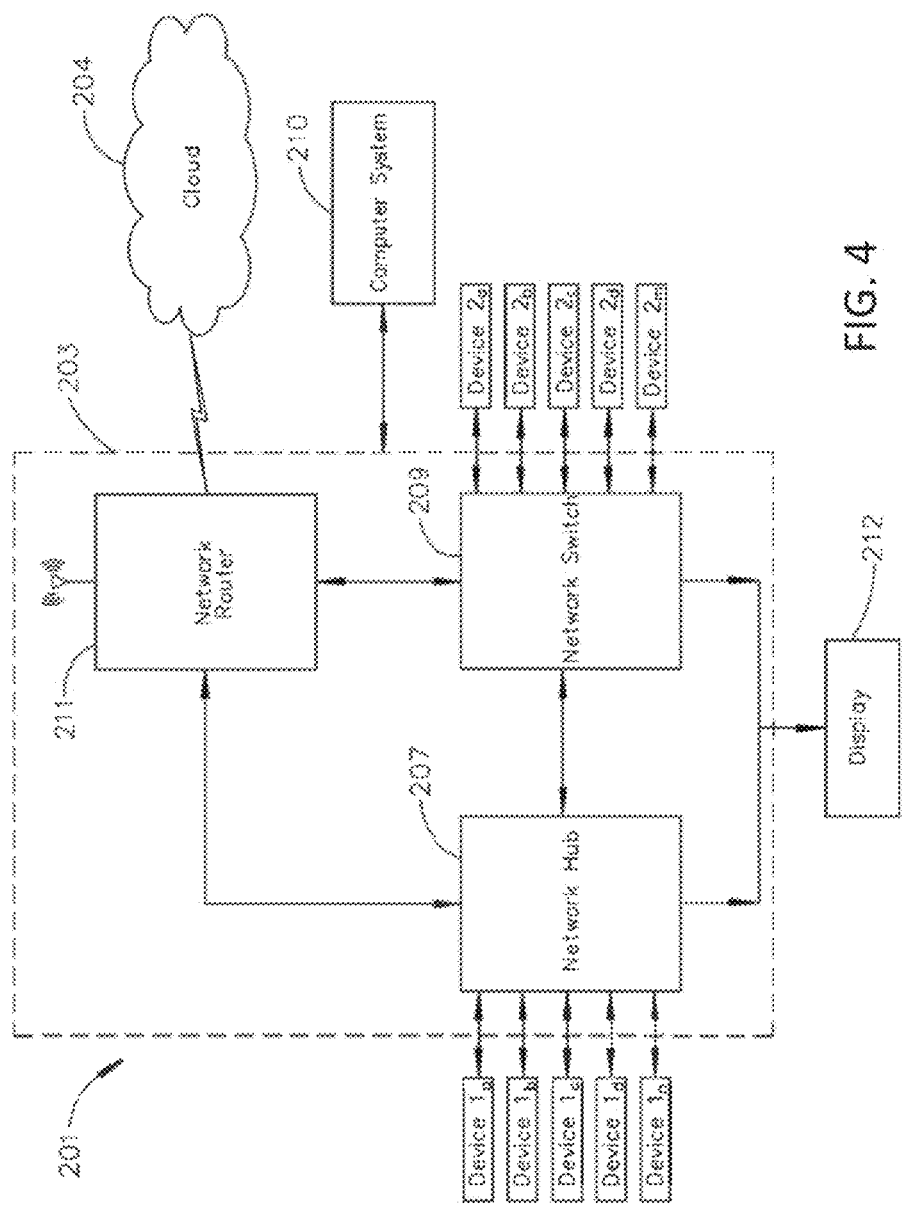
FIG. 4 illustrates a surgical data network having a communication hub configured to connect modular devices located in or more operating theaters of a healthcare facility, or any room in a healthcare facility specially equipped for surgical operations, to the cloud, in accordance with at least one aspect of the present disclosure.

FIG. 4 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

The operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub may provide connectivity to the devices 1a-1n located in the same operating theater network. The network hub 207 may collect data in the form of packets and sends them to the router in half duplex mode. The network hub 207 may not store any media access control/Internet Protocol (MAC/IP) to transfer the device data. Only one of the devices 1a-1n can send data at a time through the network hub 207. The network hub 207 may not have routing tables or intelligence regarding where to send information and broadcasts all network data across each connection and to a remote server 213 (FIG. 4) over the cloud 204. The network hub 207 can detect basic network errors such as collisions, but having all information broadcast to multiple ports can be a security risk and cause bottlenecks.

The operating theater devices 2a-2m may be connected to a network switch 209 over a wired channel or a wireless channel. The network switch 209 works in the data link layer of the OSI model. The network switch 209 may be a multicast device for connecting the devices 2a-2m located in the same operating theater to the network. The network switch 209 may send data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 may be coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 may send data in the form of packets to the cloud 204 and works in full duplex mode. Multiple devices can send data at the same time. The network router 211 uses IP addresses to transfer data.

In an example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and may handle a data type known as frames. Frames may carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 can be generally easy to install, configure, and maintain, making it a good option for networking the operating theater devices 1a-1n/2a-2m.

Figure 5:
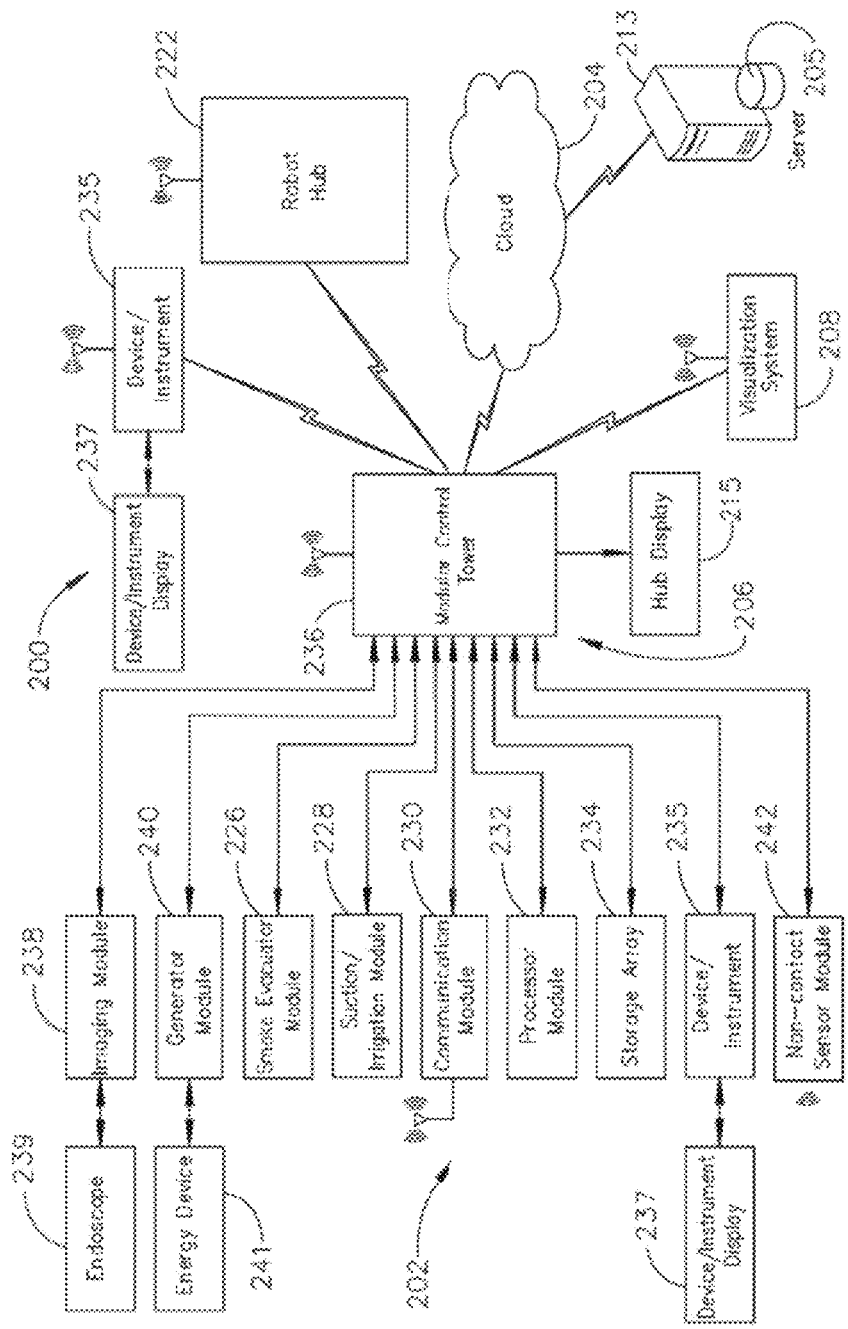
FIG. 5 illustrates an example computer-implemented interactive surgical system.
Figure 6:
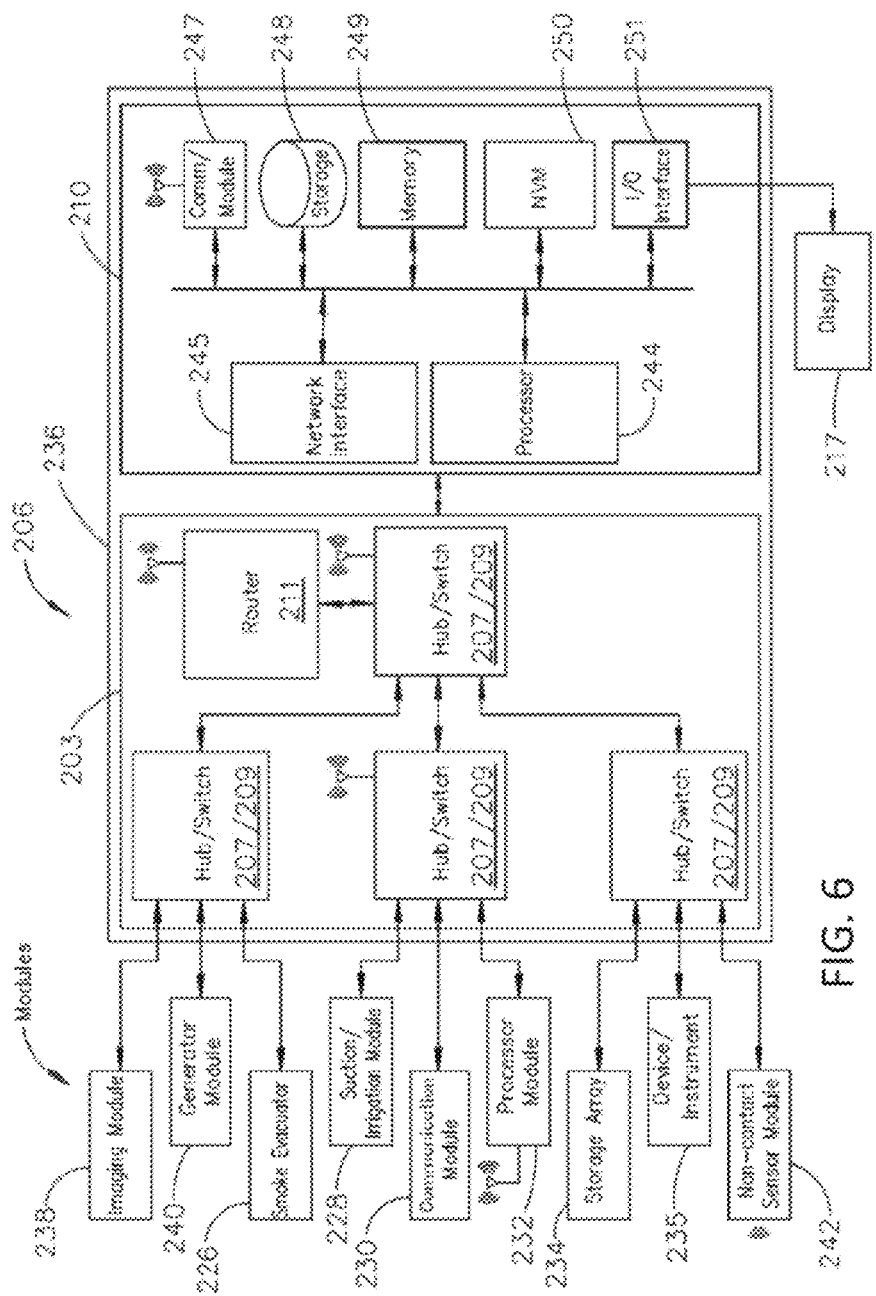
FIG. 6 illustrates an example surgical hub comping a plurality of modules coupled to the modular control tower.

FIG. 5 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 6, the modular control tower 236 comprises a modular communication hub 203 coupled to a computer system 210.

As illustrated in the example of FIG. 5, the modular control tower 236 may be coupled to an imaging module 238 that may be coupled to an endoscope 239, a generator module 240 that may be coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices may be coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 6 illustrates a surgical hub 206 comprising a plurality of modules coupled to the modular control tower 236. The modular control tower 236 may comprise a modular communication hub 203, e.g., a network connectivity device, and a computer system 210 to provide local processing, visualization, and imaging, for example. As shown in FIG. 6, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 6, each of the network hubs/switches in the modular communication hub 203 may include three downstream ports and one upstream port. The upstream network hub/switch may be connected to a processor to provide a communication connection to the cloud computing resources and a local display 217. Communication to the cloud 204 may be made either through a wired or a wireless communication channel.

The surgical hub 206 may employ a non-contact sensor module 242 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 may comprise a processor 244 and a network interface 245. The processor 244 can be coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charnel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 210 through input device(s) coupled to the I/O interface 251. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5 and the like. WAN technologies may include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 6, the imaging module 238 and/or visualization system 208, and/or the processor module 232 of FIGS. 5-6, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system, it can also be external to the computer system 210. The hardware/software necessary for connection to the network interface may include, for illustrative purposes only, internal and external technologies such as modems, including regular telephone-grade modems, cable modems, and DSL modems, ISDN adapters, and Ethernet cards.

Figure 7:
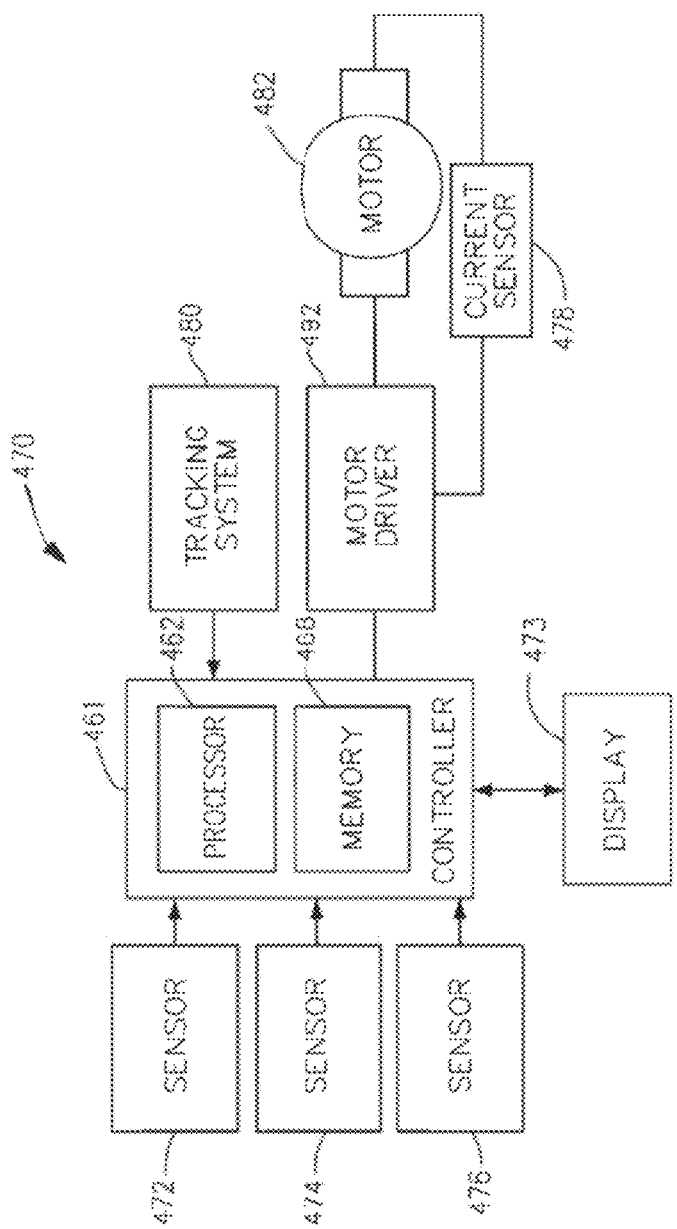
FIG. 7 shows an example surgical instrument or tool.

FIG. 7 illustrates a logic diagram of a control system 470 of a surgical instrument or tool in accordance with one or more aspects of the present disclosure. The system 470 may comprise a control circuit. The control circuit may include a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 may be configured to determine the position of the longitudinally movable displacement member. The position information may be provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 may display a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 may include a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In some examples, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 may be a frill-bridge controller for use with external N-channel power metal-oxide semiconductor field-effect transistors (MOSFETs) specifically designed for inductive loads, such as brush DC motors. The driver 492 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the lowside FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 may comprise a controlled motor drive circuit arrangement comprising a position sensor 472 according to one aspect of this disclosure. The position sensor 472 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 472 may be equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches may be fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system may comprise a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 may be a low-voltage and low-power component and includes four Hall-effect elements in an area of the position sensor 472 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bitshift, and table lookup operations. The angle position, alarm bits, and magnetic field information may be transmitted over a standard serial communication interface, such as a serial peripheral interface (SPI) interface, to the microcontroller 461. The position sensor 472 may provide 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertial, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force may be converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 474, such as, for example, a micro-strain gauge, that can be configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain can be converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub 203 as shown in FIGS. 5 and 6.

Figure 8:
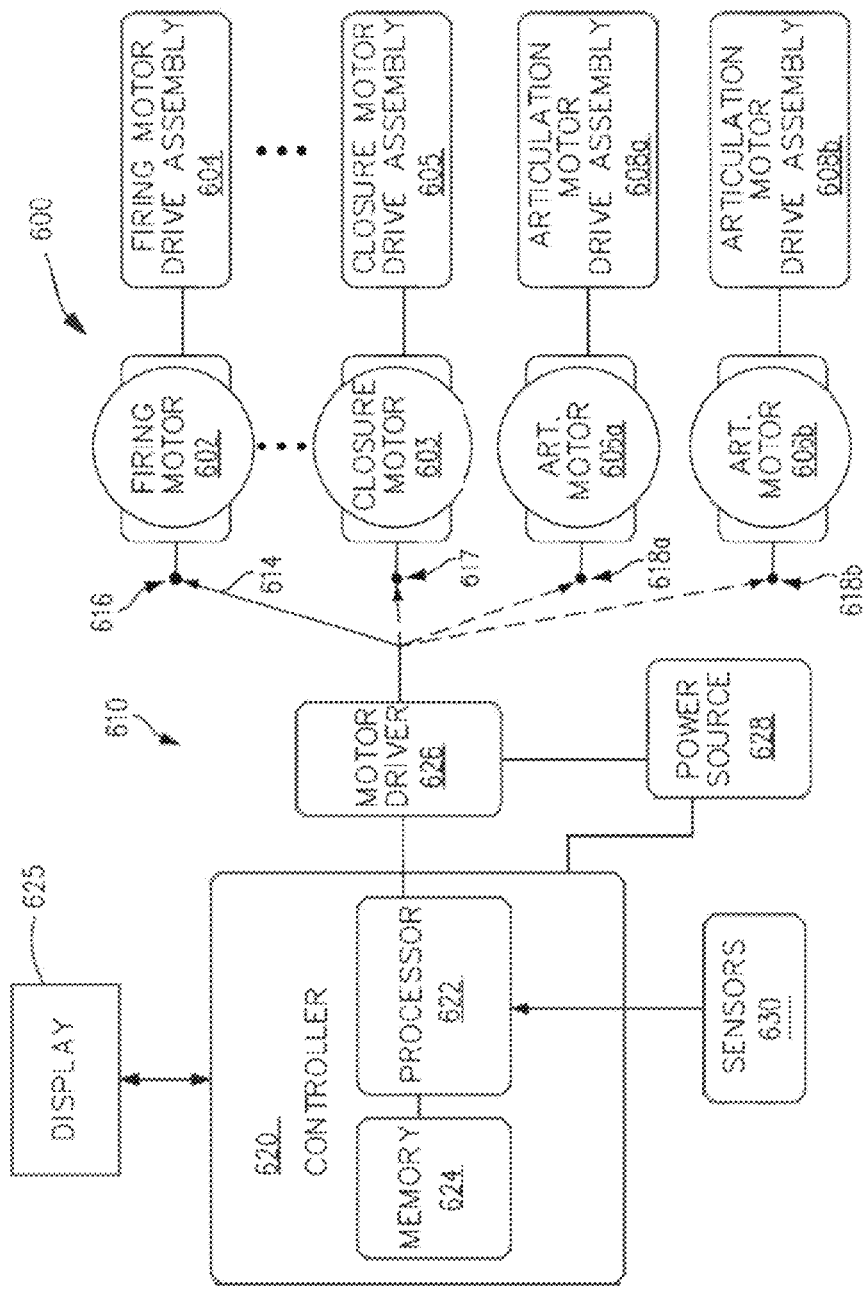
FIG. 8 illustrates an example surgical instrument or tool having motors that an be activated to perform various functions.

FIG. 8 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described herein, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 8, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606*a*, 606*b* may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 8, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described herein.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor can be a multipurpose, programmable device that accepts digital data as input, processes it according to instructions stored in its memory, and provides results as output. It can be an example of sequential digital logic, as it may have internal memory. Processors may operate on numbers and symbols represented in the binary numeral system.

The processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

The memory 624 may include program instructions for controlling each of the motors of the surgical instrument 600 that are couplable to the common control module 610. For example, the memory 624 may include program instructions for controlling the firing motor 602, the closure motor 603, and the articulation motors 606*a*, 606*b*. Such program instructions may cause the processor 622 to control the firing, closure, and articulation functions in accordance with inputs from algorithms or control programs of the surgical instrument or tool.

One or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618*a*, 618*b*.

Figure 9:
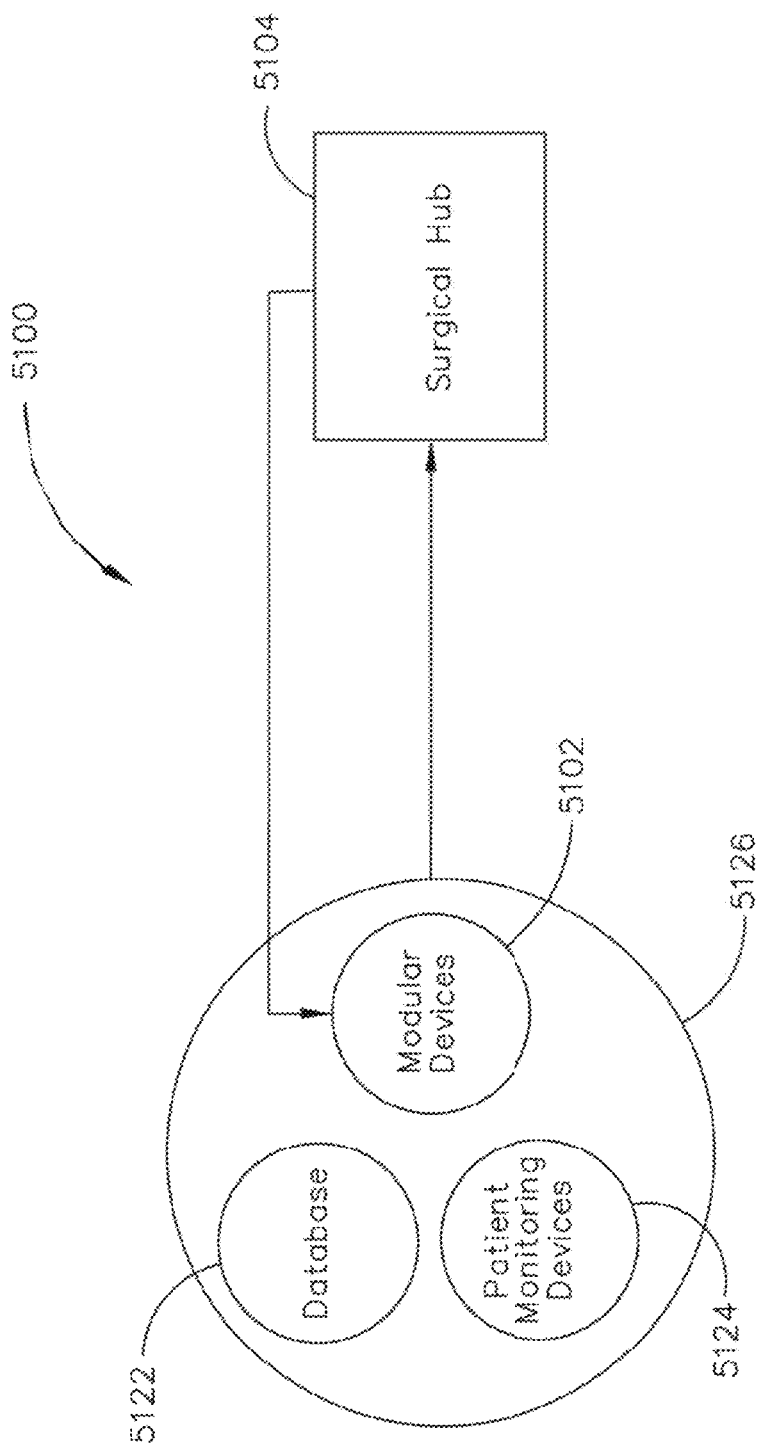
FIG. 9 is a diagram of an example situationally aware surgical system.

FIG. 9 illustrates a diagram of a situationally aware surgical system 5100, in accordance with at least one aspect of the present disclosure. In some exemplifications, the data sources 5126 may include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In an exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In an exemplification, the situational awareness system can include a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in an exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use a soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can be configured to compare the list of items for the procedure and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In some exemplifications, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In some exemplifications, the surgical hub 5104 can be configured to provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Figure 10:
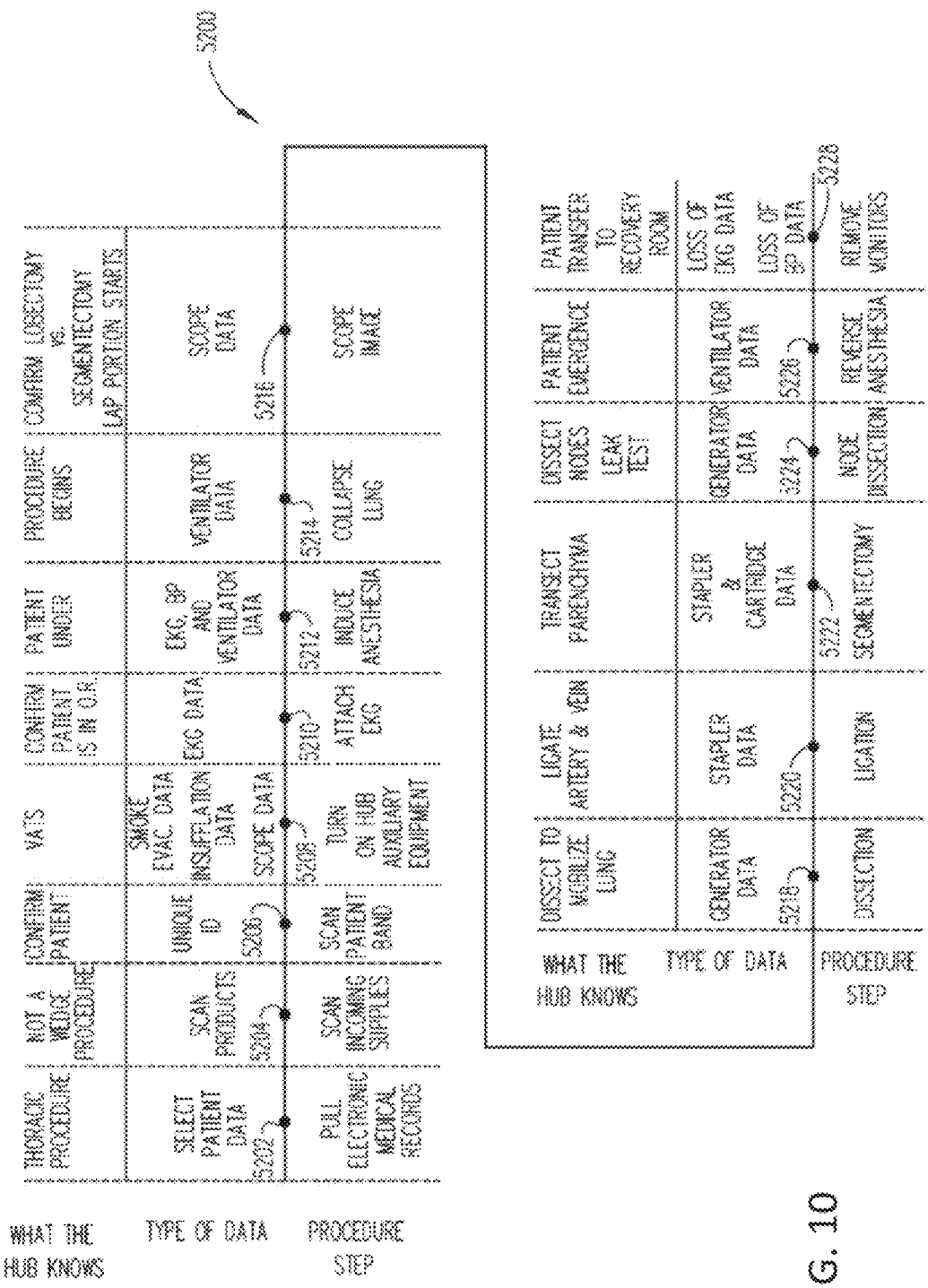
FIG. 10 illustrates an example timeline of an illustrative surgical procedure and the inferences that the surgical hub can make from the data detected at each step in the surgical procedure.

FIG. 10 illustrates a timeline 5200 of an illustrative surgical procedure and the contextual information that a surgical hub 5104 can derive from the data received from the data sources 5126 at each step in the surgical procedure. In the following description of the timeline 5200 illustrated in FIG. 9, reference should also be made to FIG. 9. The timeline 5200 may depict the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 may receive data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 can be able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described herein.

As the first step 5202 in this illustrative procedure, the hospital staff members may retrieve the patient's EMR from the hospital's EMR database. Based on select patient data in the EMR, the surgical hub 5104 determines that the procedure to be performed is a thoracic procedure. Second 5204, the staff members may scan the incoming medical supplies for the procedure. The surgical hub 5104 cross-references the scanned supplies with a list of supplies that can be utilized in various types of procedures and confirms that the mix of supplies corresponds to a thoracic procedure. Further, the surgical hub 5104 may also be able to determine that the procedure is not a wedge procedure (because the incoming supplies either lack certain supplies that are necessary for a thoracic wedge procedure or do not otherwise correspond to a thoracic wedge procedure). Third 5206, the medical personnel may scan the patient band via a scanner 5128 that is communicably connected to the surgical hub 5104. The surgical hub 5104 can then confirm the patient's identity based on the scanned data. Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that may be located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 may determine that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing. Fifth 5210, the staff members attach the EKG electrodes and other patient monitoring devices 5124 to the patient. The EKG electrodes and other patient monitoring devices 5124 may pair with the surgical hub 5104. As the surgical hub 5104 begins receiving data from the patient monitoring devices 5124, the surgical hub 5104 may confirm that the patient is in the operating theater, as described in the process 5207, for example. Sixth 5212, the medical personnel may induce anesthesia in the patient. The surgical hub 5104 can infer that the patient is under anesthesia based on data from the modular devices 5102 and/or patient monitoring devices 5124, including EKG data, blood pressure data, ventilator data, or combinations thereof. for example. Upon completion of the sixth step 5212, the pre-operative portion of the lung segmentectomy procedure is completed and the operative portion begins.

Seventh 5214, the patient's lung that is being operated on may be collapsed (while ventilation is switched to the contralateral lung). The surgical hub 5104 can infer from the ventilator data that the patient's lung has been collapsed, for example. The surgical hub 5104 can infer that the operative portion of the procedure has commenced as it can compare the detection of the patient's lung collapsing to the expected steps of the procedure (which can be accessed or retrieved previously) and thereby determine that collapsing the lung can be the first operative step in this particular procedure. Eighth 5216, the medical imaging device 5108 (e.g., a scope) may be inserted and video from the medical imaging device may be initiated. The surgical hub 5104 may receive the medical imaging device data (i.e., video or image data) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized. For example, one technique for performing a VATS lobectomy may place the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. An example technique for performing a VATS lobectomy may utilize a single medical imaging device. An example technique for performing a VATS segmentectomy utilizes multiple cameras. An example technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team may begin the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step. Tenth 5220, the surgical team may proceed to the ligation step of the procedure. The surgical hub 5104 can infer that the surgeon is ligating arteries and veins because it may receive data from the surgical stapling and cutting instrument indicating that the instrument is being fired. Similar to the prior step, the surgical hub 5104 can derive this inference by cross-referencing the receipt of data from the surgical stapling and cutting instrument with the retrieved steps in the process. Eleventh 5222, the segmentectomy portion of the procedure can be performed. The surgical hub 5104 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 5104 to infer that the segmentectomy portion of the procedure is being performed. Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (e.g., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure may begin.

Thirteenth 5226, the patient's anesthesia can be reversed. The surgical hub 5104 can infer that the patient is emerging from the anesthesia based on the ventilator data (i.e., the patient's breathing rate begins increasing), for example. Lastly, the fourteenth step 5228 may be that the medical personnel remove the various patient monitoring devices 5124 from the patient. The surgical hub 5104 can thus infer that the patient is being transferred to a recovery room when the hub loses EKG, BP, and other data from the patient monitoring devices 5124. As can be seen from the description of this illustrative procedure, the surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 10, the patient data can also be utilized by a situationally aware surgical hub 5104 to generate control adjustments for the paired modular devices 5102.

Figure 11:
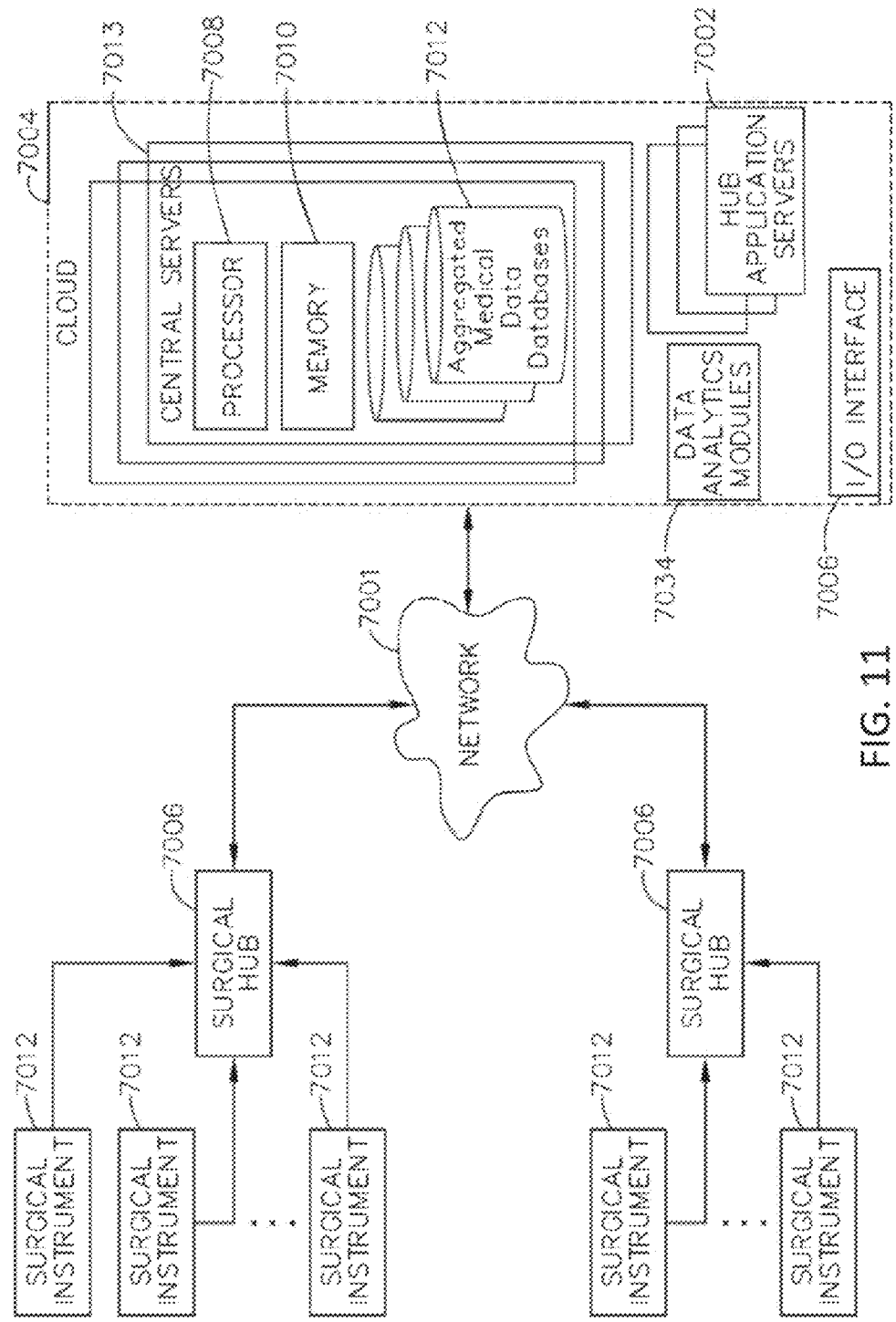
FIG. 11 is a block diagram of the computer-implemented interactive surgical system.

FIG. 11 is a block diagram of the computer-implemented interactive surgical system, in accordance with at least one aspect of the present disclosure. In one aspect, the computer-implemented interactive surgical system may be configured to monitor and analyze data related to the operation of various surgical systems that include surgical hubs, surgical instruments, robotic devices and operating theaters or healthcare facilities. The computer-implemented interactive surgical system may comprise a cloud-based analytics system. Although the cloud-based analytics system may be described as a surgical system, it may not be necessarily limited as such and could be a cloud-based medical system generally. As illustrated in FIG. 11, the cloud-based analytics system may comprise a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 may be communicatively coupled to one or more surgical instruments 7012. The hubs 7006 may also be communicatively coupled to the cloud 7004 of the computer-implemented interactive surgical system via the network 7001. The cloud 7004 may be a remote centralized source of hardware and software for storing, manipulating, and communicating data generated based on the operation of various surgical systems. As shown in FIG. 11, access to the cloud 7004 may be achieved via the network 7001, which may be the Internet or some other suitable computer network. Surgical hubs 7006 that may be coupled to the cloud 7004 can be considered the client side of the cloud computing system (i.e., cloud-based analytics system). Surgical instruments 7012 may be paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 11, the cloud 7004 comprises central servers 7013 (may be same or similar to remote server 7013), hub application servers 7002, data analytics modules 7034, and an input/output ("I/O") interface 7006. The central servers 7013 of the cloud 7004 collectively administer the cloud computing system, which includes monitoring requests by client surgical hubs 7006 and managing the processing capacity of the cloud 7004 for executing the requests. Each of the central servers 7013 may comprise one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also may comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7012 of the cloud 7004. In particular, the cloud 7004 may advantageously perform data analysis and operations on the aggregated data to yield insights and/or perform functions that individual hubs 7006 could not achieve on their own. To this end, as shown in FIG. 11, the cloud 7004 and the surgical hubs 7006 are communicatively coupled to transmit and receive information. The I/O interface 7006 is connected to the plurality of surgical hubs 7006 via the network 7001. In this way, the I/O interface 7006 can be configured to transfer information between the surgical hubs 7006 and the aggregated medical data databases 7011. Accordingly, the I/O interface 7006 may facilitate read/write operations of the cloud-based analytics system. Such read/write operations may be executed in response to requests from hubs 7006. These requests could be transmitted to the hubs 7006 through the hub applications. The I/O interface 7006 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 may be configured to host and supply shared capabilities to software applications (e.g., hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 12.

The particular cloud computing system configuration described in the present disclosure may be specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch-controlled user interfaces such that clinicians may control aspects of interaction between the surgical instruments 7012 and the cloud 7004. Other suitable user interfaces for control such as auditory controlled user interfaces can also be used.

Figure 12:
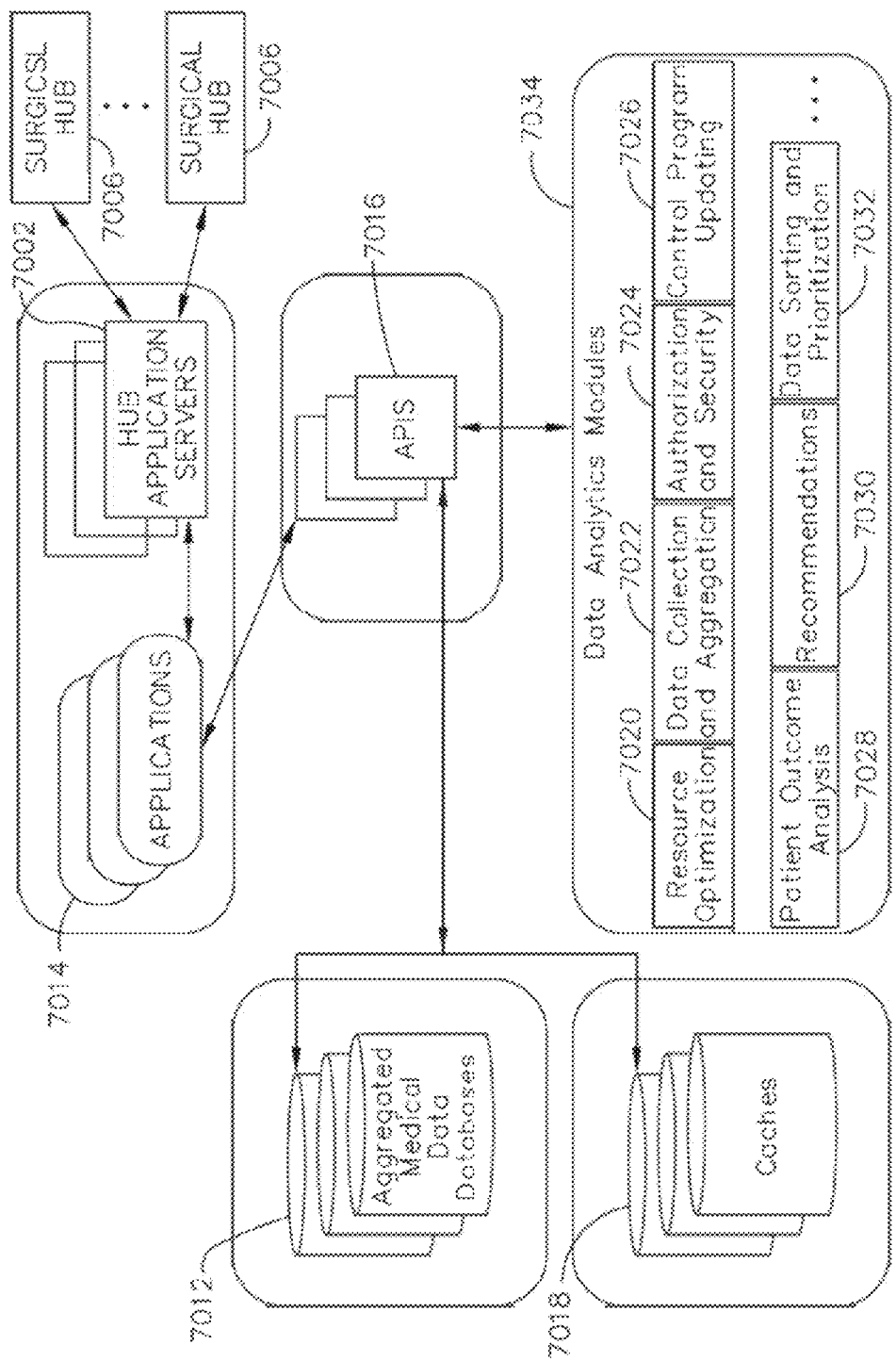
FIG. 12 illustrates the functional architecture of an example computer-implemented interactive surgical system.

FIG. 12 is a block diagram which illustrates the functional architecture of the computer-implemented interactive surgical system, in accordance with at least one aspect of the present disclosure. The cloud-based analytics system may include a plurality of data analytics modules 7034 that may be executed by the processors 7008 of the cloud 7004 for providing data analytic solutions to problems specifically arising in the medical field. As shown in FIG. 12, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 may define the set of protocols and routines corresponding to the hub applications 7014. Additionally, the APIs 7016 may manage the storing and retrieval of data into and from the aggregated medical databases 7012 for the operations of the applications 7014. The caches 7018 may also store data (e.g., temporarily) and may be coupled to the APIs 7016 for more efficient retrieval of data used by the applications 7014. The data analytics modules 7034 in FIG. 12 may include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules may be used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently. The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that may be transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004. Furthermore, for security purposes, the cloud could maintain a database of hubs 7006, instruments 7012, and other devices that may comprise a "black list" of prohibited devices. In particular, a surgical hubs 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally, or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash-based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described herein to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g., a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

Additional example details for the various functions described are provided in the ensuing descriptions below. Each of the various descriptions may utilize the cloud architecture as described in FIGS. 11 and 12 as one example of hardware and software implementation.

Figure 13:
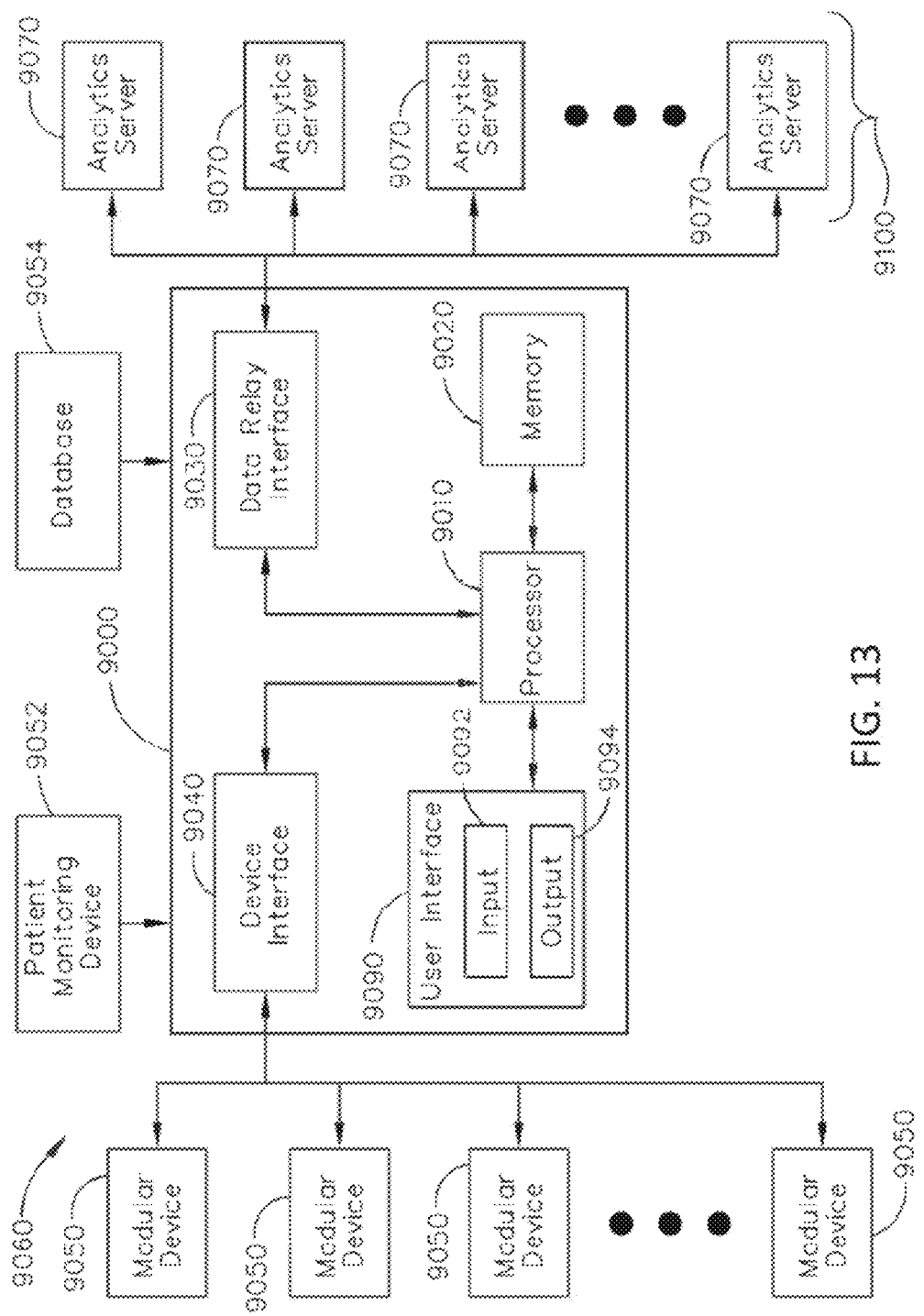
FIG. 13 illustrates an example computer-implemented interactive surgical system at configured to adaptively generate control program updates for modular devices.

FIG. 13 illustrates a block diagram of a computer-implemented adaptive surgical system 9060 that is configured to adaptively generate control program updates for modular devices 9050, in accordance with at least one aspect of the present disclosure. In some exemplifications, the surgical system may include a surgical hub 9000, multiple modular devices 9050 communicably coupled to the surgical hub 9000, and an analytics system 9100 communicably coupled to the surgical hub 9000. Although a single surgical hub 9000 may be depicted, it should be noted that the surgical system 9060 can include any number of surgical hubs 9000, which can be connected to form a network of surgical hubs 9000 that are communicably coupled to the analytics system 9010. In some exemplifications, the surgical hub 9000 may include a processor 9010 coupled to a memory 9020 for executing instructions stored thereon and a data relay interface 9030 through which data is transmitted to the analytics system 9100. In some exemplifications, the surgical hub 9000 further may include a user interface 9090 having an input device 9092 (e.g., a capacitive touchscreen or a keyboard) for receiving inputs from a user and an output device 9094 (e.g., a display screen) for providing outputs to a user. Outputs can include data from a query input by the user, suggestions for products or mixes of products to use in a given procedure, and/or instructions for actions to be carried out before, during, or after surgical procedures. The surgical hub 9000 further may include an interface 9040 for communicably coupling the modular devices 9050 to the surgical hub 9000. In one aspect, the interface 9040 may include a transceiver that is communicably connectable to the modular device 9050 via a wireless communication protocol. The modular devices 9050 can include, for example, surgical stapling and cutting instruments, electrosurgical instruments, ultrasonic instruments, insufflators, respirators, and display screens. In some exemplifications, the surgical hub 9000 can further be communicably coupled to one or more patient monitoring devices 9052, such as EKG monitors or BP monitors. In some exemplifications, the surgical hub 9000 can further be communicably coupled to one or more databases 9054 or external computer systems, such as an EMR database of the medical facility at which the surgical hub 9000 is located.

When the modular devices 9050 are connected to the surgical hub 9000, the surgical hub 9000 can sense or receive perioperative data from the modular devices 9050 and then associate the received perioperative data with surgical procedural outcome data. The perioperative data may indicate how the modular devices 9050 were controlled during the course of a surgical procedure. The procedural outcome data includes data associated with a result from the surgical procedure (or a step thereof), which can include whether the surgical procedure (or a step thereof) had a positive or negative outcome. For example, the outcome data could include whether a patient suffered from postoperative complications from a particular procedure or whether there was leakage (e.g., bleeding or air leakage) at a particular staple or incision line. The surgical hub 9000 can obtain the surgical procedural outcome data by receiving the data from an external source (e.g., from an EMR database 9054), by directly detecting the outcome (e.g., via one of the connected modular devices 9050), or inferring the occurrence of the outcomes through a situational awareness system. For example, data regarding postoperative complications could be retrieved from an EMR database 9054 and data regarding staple or incision line leakages could be directly detected or inferred by a situational awareness system. The surgical procedural outcome data can be inferred by a situational awareness system from data received from a variety of data sources, including the modular devices 9050 themselves, the patient monitoring device 9052, and the databases 9054 to which the surgical hub 9000 is connected.

The surgical hub 9000 can transmit the associated modular device 9050 data and outcome data to the analytics system 9100 for processing thereon. By transmitting both the perioperative data indicating how the modular devices 9050 are controlled and the procedural outcome data, the analytics system 9100 can correlate the different manners of controlling the modular devices 9050 with surgical outcomes for the particular procedure type. In some exemplifications, the analytics system 9100 may include a network of analytics servers 9070 that are configured to receive data from the surgical hubs 9000. Each of the analytics servers 9070 can include a memory and a processor coupled to the memory that is executing instructions stored thereon to analyze the received data. In some exemplifications, the analytics servers 9070 may be connected in a distributed computing architecture and/or utilize a cloud computing architecture. Based on this paired data, the analytics system 9100 can then learn optimal or preferred operating parameters for the various types of modular devices 9050, generate adjustments to the control programs of the modular devices 9050 in the field, and then transmit (or "push") updates to the modular devices' 9050 control programs.

Additional detail regarding the computer-implemented interactive surgical system 9060, including the surgical hub 9000 and various modular devices 9050 connectable thereto, are described in connection with FIGS. 5-6.

Figure 14:
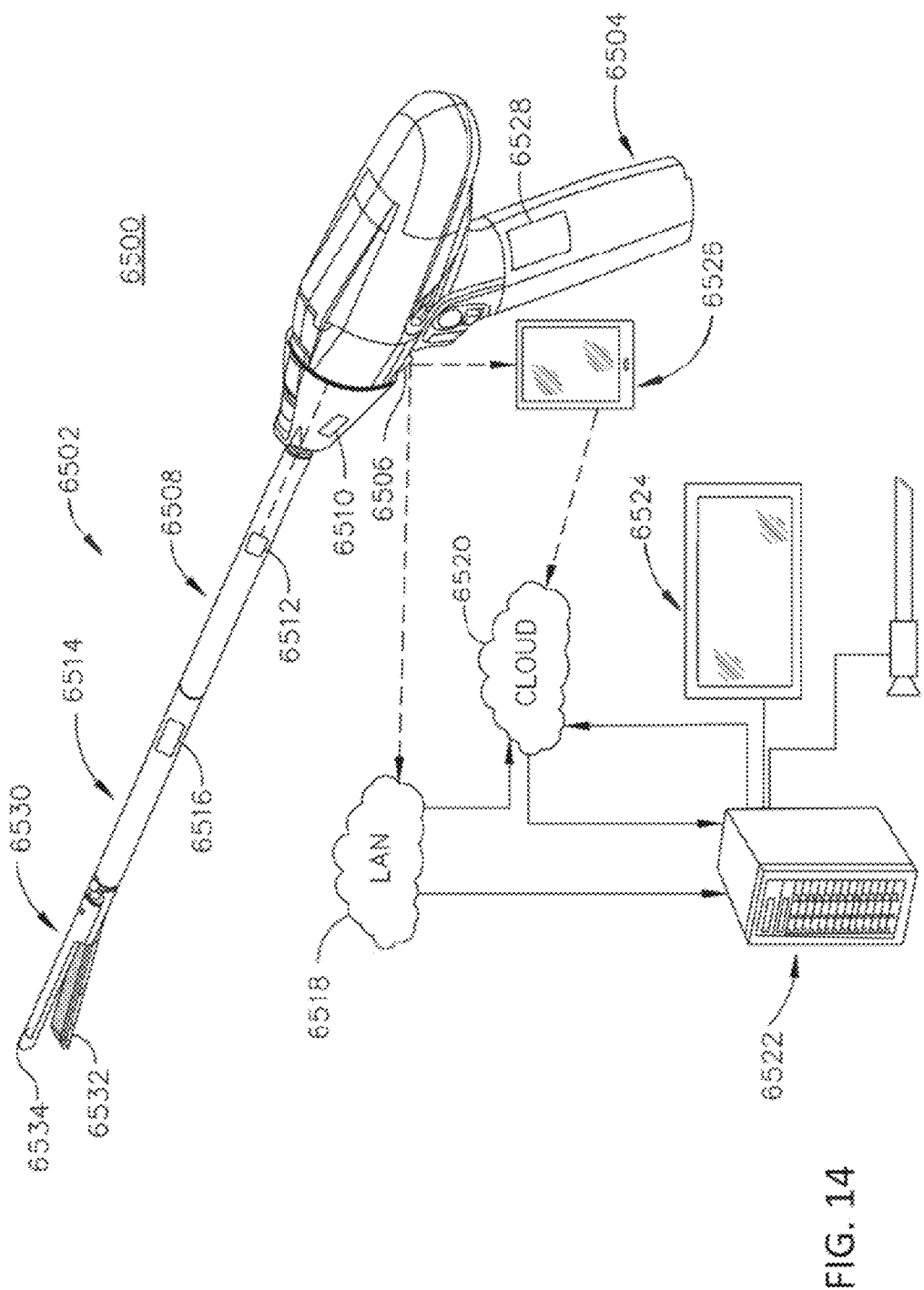
FIG. 14 illustrates an example surgical system that includes a handle having a controller and a motor, an adapter releasably coupled to the handle, and a loading unit releasably coupled to tape adapter.

FIG. 14 provides a surgical system 6500 in accordance with the present disclosure and may include a surgical instrument 6502 that can be in communication with a console 6522 or a portable device 6526 through a local area network 6518 or a cloud network 6520 via a wired or wireless connection. In various aspects, the console 6522 and the portable device 6526 may be any suitable computing device. The surgical instrument 6502 may include a handle 6504, an adapter 6508, and a loading unit 6514. The adapter 6508 releasably couples to the handle 6504 and the loading unit 6514 releasably couples to the adapter 6508 such that the adapter 6508 transmits a force from a drive shaft to the loading unit 6514. The adapter 6508 or the loading unit 6514 may include a force gauge (not explicitly shown) disposed therein to measure a force exerted on the loading unit 6514. The loading unit 6514 may include an end effector 6530 having a first jaw 6532 and a second jaw 6534. The loading unit 6514 may be an in-situ loaded or multi-firing loading unit (MFLU) that allows a clinician to fire a plurality of fasteners multiple times without requiring the loading unit 6514 to be removed from a surgical site to reload the loading unit 6514.

The first and second jaws 6532, 6534 may be configured to clamp tissue therebetween, fire fasteners through the clamped tissue, and sever the clamped tissue. The first jaw 6532 may be configured to fire at least one fastener a plurality of times, or may be configured to include a replaceable multi-fire fastener cartridge including a plurality of fasteners (e.g., staples, clips, etc.) that may be fired more than one time prior to being replaced. The second jaw 6534 may include an anvil that deforms or otherwise secures the fasteners about tissue as the fasteners are ejected from the multi-fire fastener cartridge.

The handle 6504 may include a motor that is coupled to the drive shaft to affect rotation of the drive shaft. The handle 6504 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 6504 may be in communication with a controller 6528 of the handle 6504 to selectively activate the motor to affect rotation of the drive shafts. The controller 6528 may be disposed within the handle 6504 and is configured to receive input from the control interface and adapter data from the adapter 6508 or loading unit data from the loading unit 6514. The controller 6528 may analyze the input from the control interface and the data received from the adapter 6508 and/or loading unit 6514 to selectively activate the motor. The handle 6504 may also include a display that is viewable by a clinician during use of the handle 6504. The display may be configured to display portions of the adapter or loading unit data before, during, or after firing of the instrument 6502.

The adapter 6508 may include an adapter identification device 6510 disposed therein and the loading unit 6514 includes a loading unit identification device 6516 disposed therein. The adapter identification device 6510 may be in communication with the controller 6528, and the loading unit identification device 6516 may be in communication with the controller 6528. It will be appreciated that the loading unit identification device 6516 may be in communication with the adapter identification device 6510, which relays or passes communication from the loading unit identification device 6516 to the controller 6528.

The adapter 6508 may also include a plurality of sensors 6512 (one shown) disposed thereabout to detect various conditions of the adapter 6508 or of the environment (e.g., if the adapter 6508 is connected to a loading unit, if the adapter 6508 is connected to a handle, if the drive shafts are rotating, the torque of the drive shafts, the strain of the drive shafts, the temperature within the adapter 6508, a number of firings of the adapter 6508, a peak force of the adapter 6508 during firing, a total amount of force applied to the adapter 6508, a peak retraction force of the adapter 6508, a number of pauses of the adapter 6508 during firing, etc.). The plurality of sensors 6512 may provide an input to the adapter identification device 6510 in the form of data signals. The data signals of the plurality of sensors 6512 may be stored within, or be used to update the adapter data stored within, the adapter identification device 6510. The data signals of the plurality of sensors 6512 may be analog or digital. The plurality of sensors 6512 may include a force gauge to measure a force exerted on the loading unit 6514 during firing.

The handle 6504 and the adapter 6508 can be configured to interconnect the adapter identification device 6510 and the loading unit identification device 6516 with the controller 6528 via an electrical interface. The electrical interface may be a direct electrical interface (i.e., include electrical contacts that engage one another to transmit energy and signals therebetween). Additionally or alternatively, the electrical interface may be a non-contact electrical interface to wirelessly transmit energy and signals therebetween (e.g., inductively transfer). It is also contemplated that the adapter identification device 6510 and the controller 6528 may be in wireless communication with one another via a wireless connection separate from the electrical interface.

The handle 6504 may include a transmitter 6506 that is configured to transmit instrument data from the controller 6528 to other components of the system 6500 (e.g., the LAN 6518, the cloud 6520, the console 6522, or the portable device 6526). The transmitter 6506 also may receive data (e.g., cartridge data, loading unit data, or adapter data) from the other components of the system 6500. For example, the controller 6528 may transmit instrument data including a serial number of an attached adapter (e.g., adapter 6508) attached to the handle 6504, a serial number of a loading unit (e.g., loading unit 6514) attached to the adapter, and a serial number of a multi-fire fastener cartridge (e.g., multi-fire fastener cartridge), loaded into the loading unit, to the console 6528. Thereafter, the console 6522 may transmit data (e.g., cartridge data, loading unit data, or adapter data) associated with the attached cartridge, loading unit, and adapter, respectively, back to the controller 6528. The controller 6528 can display messages on the local instrument display or transmit the message, via transmitter 6506, to the console 6522 or the portable device 6526 to display the message on the display 6524 or portable device screen, respectively.

FIG. 15A illustrates an example flow for determining a mode of operation and operating in the determined mode. The computer-implemented interactive surgical system and/or components and/or subsystems of the computer-implemented interactive surgical system may be configured to be updated. Such updates may include the inclusions of features and benefits that were not available to the user before the update. These updates may be established by any method of hardware, firmware, and software updates suitable for introducing the feature to the user. For example, replaceable/swappable (e.g., hot swappable) hardware components, flashable firmware devices, and updatable software systems may be used to update computer-implemented interactive surgical system and/or components and/or subsystems of the computer-implemented interactive surgical system.

The updates may be conditioned on any suitable criterion or set of criteria. For example, an update may be conditioned on one or more hardware capabilities of the system, such as processing capability, bandwidth, resolution, and the like. For example, the update may be conditioned on one or more software aspects, such as a purchase of certain software code. For example, the update may be conditioned on a purchased service tier. The service tier may represent a feature and/or a set of features the user is entitled to use in connection with the computer-implemented interactive surgical system. The service tier may be determined by a license code, an e-commerce server authentication interaction, a hardware key, a username/password combination, a biometric authentication interaction, a public/private key exchange interaction, or the like.

At 10704, a system/device parameter may be identified. The system/device parameter may be any element or set of elements on which an update in conditioned. For example, the computer-implemented interactive surgical system may detect a certain bandwidth of communication between a modular device and a surgical hub. For example, the computer-implemented interactive surgical system may detect an indication of the purchase of certain service tier.

At 10708, a mode of operation may be determined based on the identified system/device parameter. This determination may be made by a process that maps system/device parameters to modes of operation. The process may be a manual and/or an automated process. The process may be the result of local computation and/or remote computation. For example, a client/server interaction may be used to determine the mode of operation based on the on the identified system/device parameter. For example, local software and/or locally embedded firmware may be used to determine the mode of operation based on the identified system/device parameter. For example, a hardware key, such as a secure microprocessor for example, may be used to determine the mode of operation based on the identified system/device parameter.

At 10710, operation may proceed in accordance with the determined mode of operation. For example, a system or device may proceed to operate in a default mode of operation. For example, a system or device may proceed to operate in an alternate mode of operation. The mode of operation may be directed by control hardware, firmware, and/or software already resident in the system or device. The mode of operation may be directed by control hardware, firmware, and/or software newly installed/updated.

FIG. 15B illustrates an example functional block diagram for changing a mode of operation. An upgradeable element 10714 may include an initialization component 10716. The initialization component 10716 may include any hardware, firmware, and/or software suitable determining a mode of operation. For example, the initialization component 10716 may be portion of a system or device start-up procedure. The initialization component 10716 may engage in an interaction to determine a mode of operation for the upgradeable element 10714. For example, the initialization component 10716 may interact with a user 10730, an external resource 10732, and/or a local resource 10718 for example. For example, the initialization component 10716 may receive a licensing key from the user 10730 to determine a mode of operation. The initialization component 10716 may query an external resource 10732, such as a server for example, with a serial number of the upgradable device 10714 to determine a mode of operation. For example, the initialization component 10716 may query a local resource 10718, such as a local query to determine an amount of available bandwidth and/or a local query of a hardware key for example, to determine a mode of operation.

The upgradeable element 10714 may include one or more operation components 10720, 10722, 10726, 10728 and an operational pointer 10724. The initialization component 10716 may direct the operational pointer 10724 to direct the operation of the upgradable element 10741 to the operation component 10720, 10722, 10726, 10728 that corresponds with the determined mode of operation. The initialization component 10716 may direct the operational pointer 10724 to direct the operation of the upgradable element to a default operation component 10720. For example, the default operation component 10720 may be selected on the condition of no other alternate mode of operation being determined. For example, the default operation component 10720 may be selected on the condition of a failure of the initialization component and/or interaction failure. The initialization component 10716 may direct the operational pointer 10724 to direct the operation of the upgradable element 10714 to a resident operation component 10722. For example, certain features may be resident in the upgradable component 10714 but require activation to be put into operation. The initialization component 10716 may direct the operational pointer 10724 to direct the operation of the upgradable element 10714 to install a new operation component 10728 and/or a new installed operation component 10726. For example, new software and/or firmware may be downloaded. The new software and or firmware may contain code to enable the features represented by the selected mode of operation. For example, a new hardware component may be installed to enable the selected mode of operation.

A surgical visualization system may include tiered-access to certain capabilities. The surgical visualization system may be used to analyze at least a portion of a surgical field. The surgical visualization system may include a processor which is configured to operate in first mode of operation. The processor may receive a control parameter and, based on that control parameter, determine to operate in a second mode of operation. The first mode of operation may relate to determining and/or displaying a metric that represents the present state of moving particles that portion of the surgical field. The second mode of operation may relate to determining and/or displaying a metric that represents an aggregated state of moving particles in that portion of the surgical field and/or a metric that represents a state of moving particles at a selectable tissue depth. The control parameter on which the mode of operation is determined may include system aspects such as processing capability or bandwidth for example and/or the identification of an appropriate service tier for the surgical visualization system.

A surgical visualization system may include tiered-access features. The surgical visualization system may be used to analyze at least a portion of a surgical field. Based on a control parameter, the system may assess the present state of moving particles that portion of the surgical field, assess an aggregated state of the moving particles, and/or assess moving particles at a selectable tissue depth. The control parameter may include system aspects such as processing capability or bandwidth for example and/or the identification of an appropriate service tier.

FIGS. 16A-D and FIGS. 17A-F depict various aspects of one example of a visualization system 2108 that may be incorporated into a surgical system. The visualization system 2108 may include an imaging control unit 2002 and a hand unit 2020. The imaging control unit 2002 may include one or more illumination sources, a power supply for the one or more illumination sources, one or more types of data communication interfaces (including USB, Ethernet, or wireless interfaces 2004), and one or more a video outputs 2006. The imaging control unit 2002 may further include an interface, such as a USB interface 2010, configured to transmit integrated video and image capture data to a USB enabled device. The imaging control unit 2002 may also include one or more computational components including, without limitation, a processor unit, a transitory memory unit, a non-transitory memory unit, an image processing unit, a bus structure to form data links among the computational components, and any interface (e.g. input and/or output) devices necessary to receive information from and transmit information to components not included in the imaging control unit. The non-transitory memory may further contain instructions that when executed by the processor unit, may perform any number of manipulations of data that may be received from the hand unit 2020 and/or computational devices not included in the imaging control unit.

The illumination sources may include a white light source 2012 and one or more laser light sources. The imaging control unit 2002 may include one or more optical and/or electrical interfaces for optical and/or electrical communication with the hand unit 2020. The one or more laser light sources may include, as non-limiting examples, any one or more of a red laser light source, a green laser light source, a blue laser light source, an infrared laser light source, and an ultraviolet laser light source. In some non-limiting examples, the red laser light source may source illumination having a peak wavelength that may range between 635 nm and 660 nm, inclusive. Non-limiting examples of a red laser peak wavelength may include about 635 nm, about 640 nm, about 645 nm, about 650 nm, about 655 nm, about 660 nm, or any value or range of values therebetween. In some non-limiting examples, the green laser light source may source illumination having a peak wavelength that may range between 520 nm and 532 nm, inclusive. Non-limiting examples of a green laser peak wavelength may include about 520 nm, about 522 nm, about 524 nm, about 526 nm, about 528 nm, about 530 nm, about 532 nm, or any value or range of values therebetween. In some non-limiting examples, the blue laser light source may source illumination having a peak wavelength that may range between 405 nm and 445 nm, inclusive. Non-limiting examples of a blue laser peak wavelength may include about 405 nm, about 410 nm, about 415 nm, about 420 nm, about 425 nm, about 430 nm, about 435 nm, about 440 nm, about 445 nm, or any value or range of values therebetween. In some non-limiting examples, the infrared laser light source may source illumination having a peak wavelength that may range between 750 nm and 3000 nm, inclusive. Non-limiting examples of an infrared laser peak wavelength may include about 750 nm, about 1000 nm, about 1250 nm, about 1500 nm, about 1750 nm, about 2000 nm, about 2250 nm, about 2500 nm, about 2750 nm, 3000 nm, or any value or range of values therebetween. In some non-limiting examples, the ultraviolet laser light source may source illumination having a peak wavelength that may range between 200 nm and 360 nm, inclusive. Non-limiting examples of an ultraviolet laser peak wavelength may include about 200 nm, about 220 nm, about 240 nm, about 260 nm, about 280 nm, about 300 nm, about 320 nm, about 340 nm, about 360 nm, or any value or range of values therebetween.

In one non-limiting aspect, the hand unit 2020 may include a body 2021, a camera scope cable 2015 attached to the body 2021, and an elongated camera probe 2024. The body 2021 of the hand unit 2020 may include hand unit control buttons 2022 or other controls to permit a health professional using the hand unit 2020 to control the operations of the hand unit 2020 or other components of the imaging control unit 2002, including, for example, the light sources. The camera scope cable 2015 may include one or more electrical conductors and one or more optical fibers. The camera scope cable 2015 may terminate with a camera head connector 2008 at a proximal end in which the camera head connector 2008 is configured to mate with the one or more optical and/or electrical interfaces of the imaging control unit 2002. The electrical conductors may supply power to the hand unit 2020, including the body 2021 and the elongated camera probe 2024, and/or to any electrical components internal to the hand unit 2020 including the body 2021 and/or elongated camera probe 2024. The electrical conductors may also serve to provide bi-directional data communication between any one or more components the hand unit 2020 and the imaging control unit 2002. The one or more optical fibers may conduct illumination from the one or more illumination sources in the imaging control unit 2002 through the hand unit body 2021 and to a distal end of the elongated camera probe 2024. In some non-limiting aspects, the one or more optical fibers may also conduct light reflected or refracted from the surgical site to one or more optical sensors disposed in the elongated camera probe 2024, the hand unit body 2021, and/or the imaging control unit 2002.

Figure 16A:
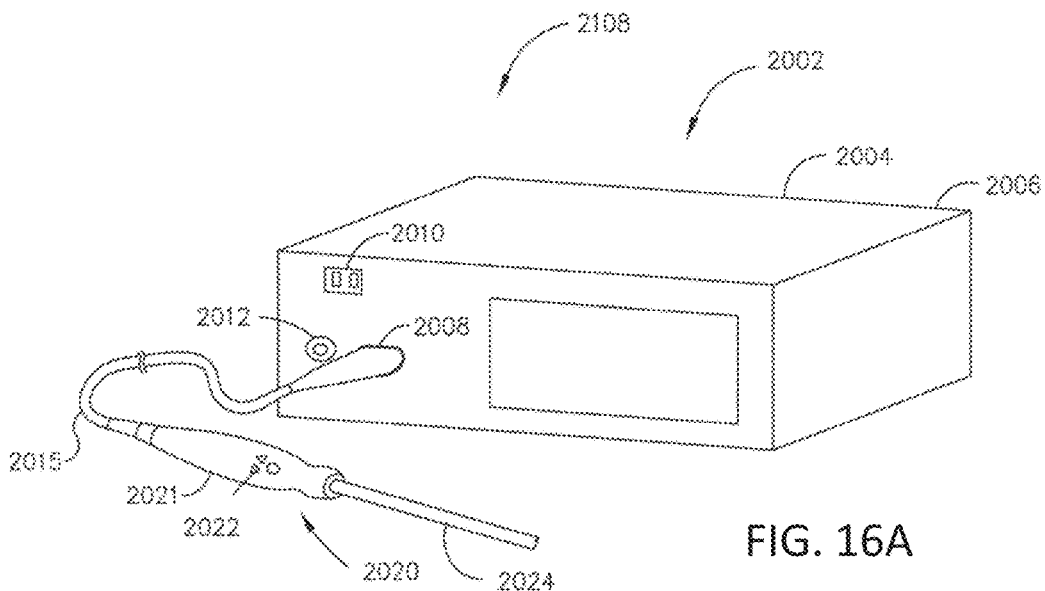
FIGS. 16A-D illustrate an example visualization system.
Figure 16B:
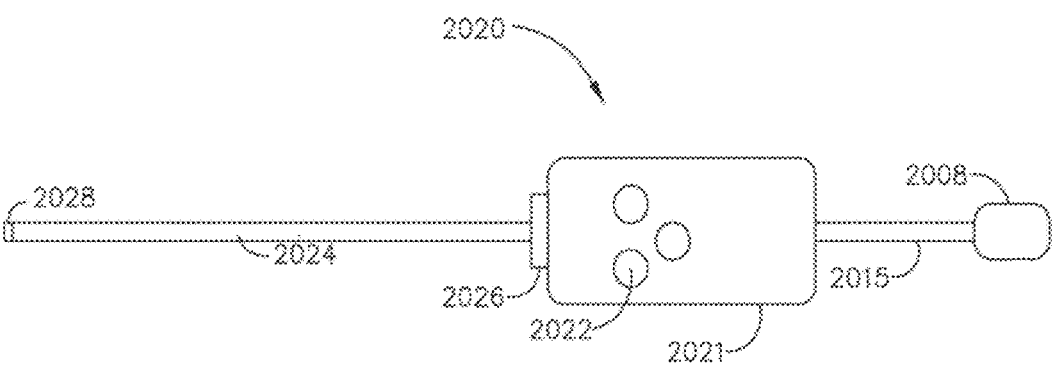

FIG. 16B (a top plan view) depicts in more detail some aspects of a hand unit 2020 of the visualization system 2108. The hand unit body 2021 may be constructed of a plastic material. The hand unit control buttons 2022 or other controls may have a rubber overmolding to protect the controls while permitting them to be manipulated by the surgeon. The camera scope cable 2015 may have optical fibers integrated with electrical conductors, and the camera scope cable 2015 may have a protective and flexible overcoating such as PVC. In some non-limiting examples, the camera scope cable 2015 may be about 10 ft. long to permit ease of use during a surgical procedure. The length of the camera scope cable 2015 may range from about 5 ft. to about 15 ft. Non-limiting examples of a length of the camera scope cable 2015 may be about 5 ft., about 6 ft., about 7 ft., about 8 ft., about 9 ft., about 10 ft., about 11 ft., about 12 ft., about 13 ft., about 14 ft., about 15 ft., or any length or range of lengths therebetween. The elongated camera probe 2024 may be fabricated from a rigid material such as stainless steel. In some aspects, the elongated camera probe 2024 may be joined with the hand unit body 2021 via a rotatable collar 2026. The rotatable collar 2026 may permit the elongated camera probe 2024 to be rotated with respect to the hand unit body 2021. In some aspects, the elongated camera probe 2024 may terminate at a distal end with a plastic window 2028 sealed with epoxy.

Figure 16C:
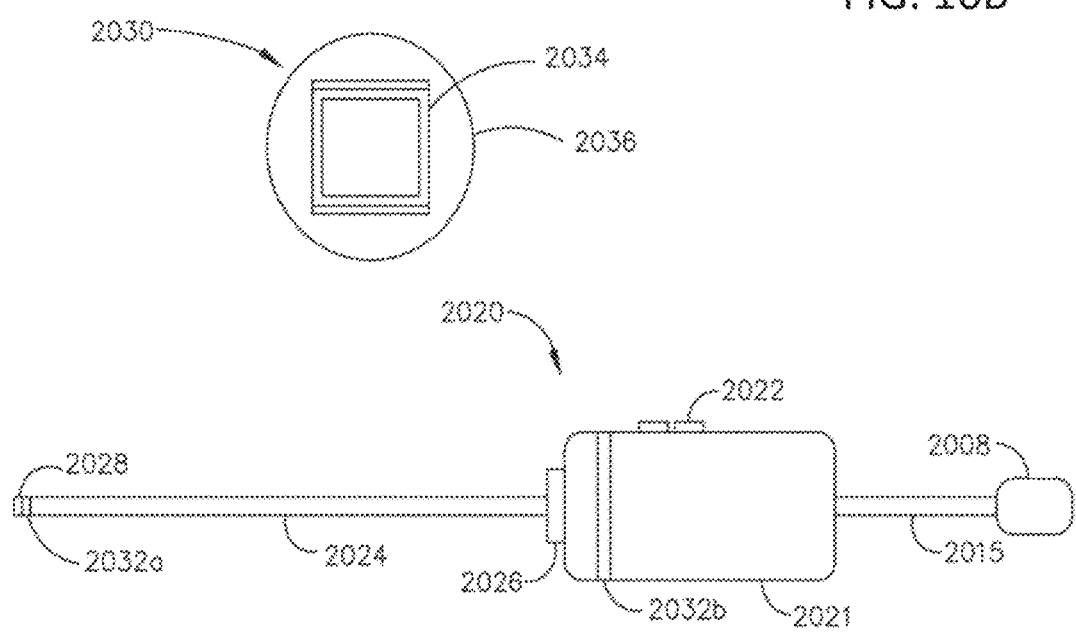
Figure 16D:
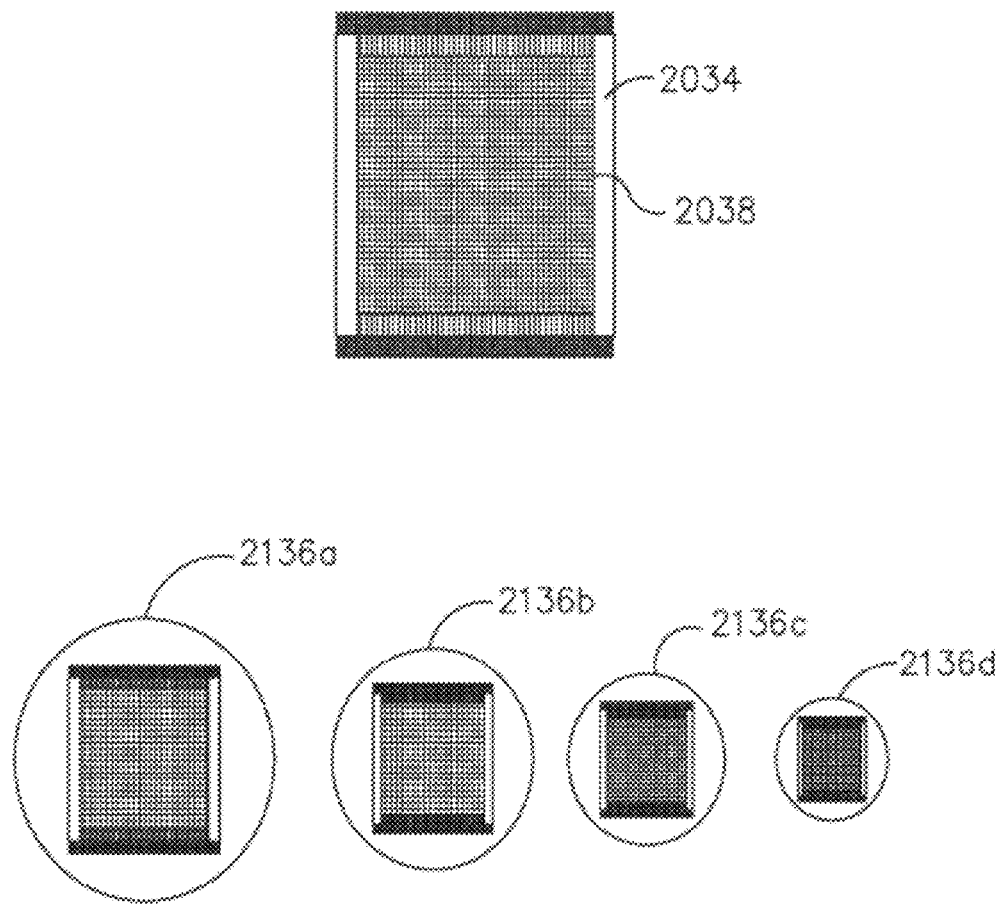

The side plan view of the hand unit, depicted in FIG. 16C illustrates that a light or image sensor 2030 maybe disposed at a distal end 2032*a* of the elongated camera probe or within the hand unit body 2032*b*. In some alternative aspects, the light or image sensor 2030 may be dispose with additional optical elements in the imaging control unit 2002. FIG. 16C further depicts an example of a light sensor 2030 comprising a CMOS image sensor 2034 disposed within a mount 2036 having a radius of about 4 mm. FIG. 16D illustrates aspects of the CMOS image sensor 2034, depicting the active area 2038 of the image sensor. Although the CMOS image sensor in FIG. 16C is depicted to be disposed within a mount 2036 having a radius of about 4 mm, it may be recognized that such a sensor and mount combination may be of any useful size to be disposed within the elongated camera probe 2024, the hand unit body 2021, or in the image control unit 2002. Some non-limiting examples of such alternative mounts may include a 5.5 mm mount 2136*a*, a 4 mm mount 2136*b*, a 2.7 mm mount 2136*c*, and a 2 mm mount 2136*d*. It may be recognized that the image sensor may also comprise a CCD image sensor. The CMOS or CCD sensor may comprise an array of individual light sensing elements (pixels).

FIGS. 17A-F depict various aspects of some examples of illumination sources and their control that may be incorporated into the visualization system 2108.

Figure 17A:
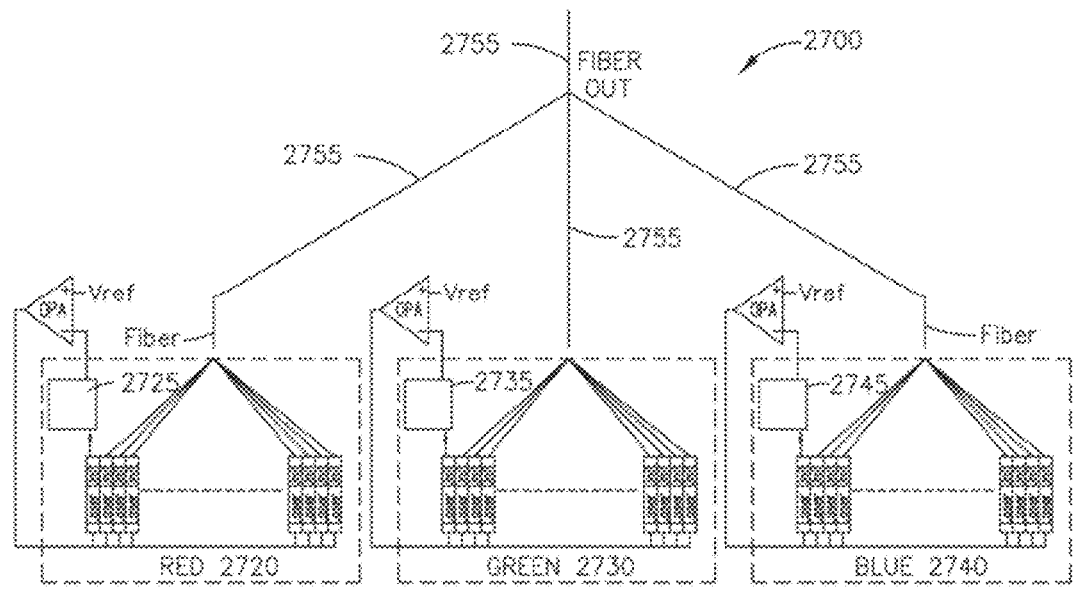
FIGS. 17A-F illustrate a plurality of laser emitters that may be incorporated in an example visualization system, an illumination of an image sensor having a Bayer pattern of color filters, a graphical representation of the operation of a pixel array for a plurality of frames, a schematic of an example of an operation sequence of chrominance and luminance frames, an example of sensor and emitter patterns, and a graphical representation of the operation of a pixel array, respectively.

FIG. 17A illustrates an aspect of a laser illumination system having a plurality of laser bundles emitting a plurality of wavelengths of electromagnetic energy. As can be seen in the figure, the illumination system 2700 may comprise a red laser bundle 2720, a green laser bundle 2730, and a blue laser bundle 2740 that are all optically coupled together though fiber optics 2755. As can be seen in the figure, each of the laser bundles may have a corresponding light sensing element or electromagnetic sensor 2725, 2735, 2745 respectively, for sensing the output of the specific laser bundle or wavelength.

Additional disclosures regarding the laser illumination system depicted in FIG. 17A for use in a surgical visualization system 2108 may be found in U.S. Patent Application Publication No. 2014/0268860, titled CONTROLLING THE INTEGRAL LIGHT ENERGY OF A LASER PULSE filed on Mar. 15, 2014, which issued on Oct. 3, 2017 as U.S. Pat. No. 9,777,913, the contents thereof being incorporated by reference herein in its entirety and for all purposes.

Figure 17B:
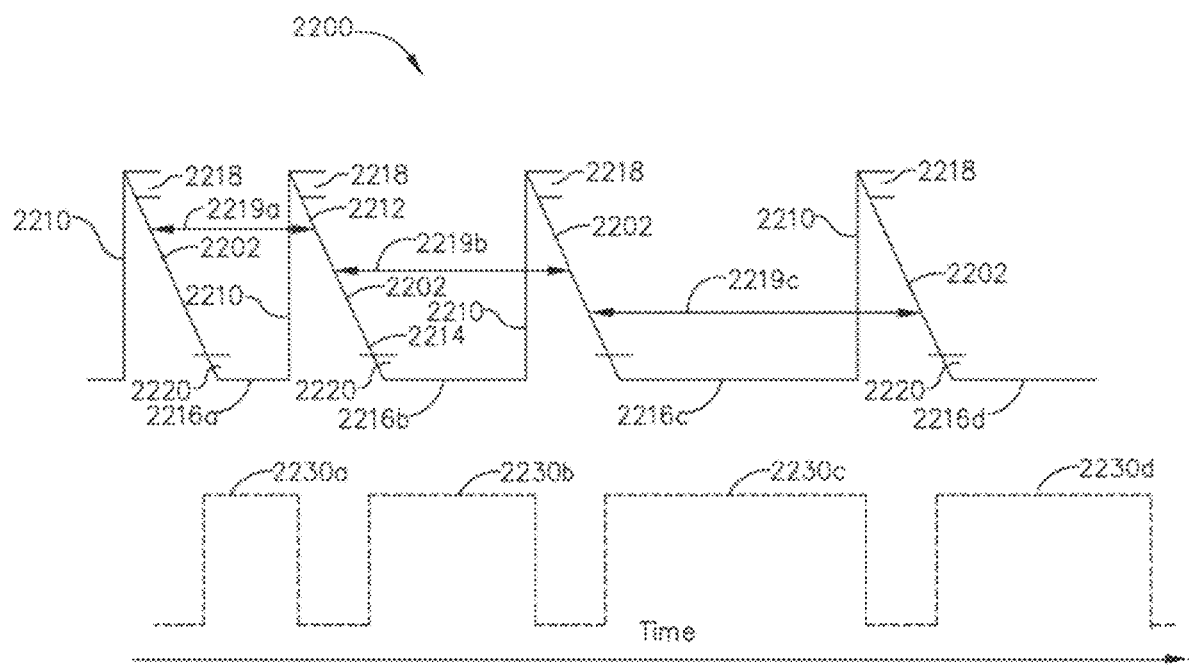

FIG. 17B illustrates the operational cycles of a sensor used in rolling readout mode. It will be appreciated that the x direction corresponds to time and the diagonal lines 2202 indicate the activity of an internal pointer that reads out each frame of data, one line at time. The same pointer is responsible for resetting each row of pixels for the next exposure period. The net integration time for each row 2219*a-c* is equivalent, but they are staggered in time with respect to one another due to the rolling reset and read process. Therefore, for any scenario in which adjacent frames are required to represent different constitutions of light, the only option for having each row be consistent is to pulse the light between the readout cycles 2230*a-c*. More specifically, the maximum available period corresponds to the sum of the blanking time plus any time during which optical black or optically blind (OB) rows (2218, 2220) are serviced at the start or end of the frame.

FIG. 17B illustrates the operational cycles of a sensor used in rolling readout mode or during the sensor readout 2200. The frame readout may start at and may be represented by vertical line 2210. The read out period is represented by the diagonal or slanted line 2202. The sensor may be read out on a row by row basis, the top of the downwards slanted edge being the sensor top row 2212 and the bottom of the downwards slanted edge being the sensor bottom row 2214. The time between the last row readout and the next readout cycle may be called the blanking time 2216*a-d*. It may be understood that the blanking time 2216*a-d* may be the same between success readout cycles or it may differ between success readout cycles. It should be noted that some of the sensor pixel rows might be covered with a light shield (e.g., a metal coating or any other substantially black layer of another material type). These covered pixel rows may be referred to as optical black rows 2218 and 2220. Optical black rows 2218 and 2220 may be used as input for correction algorithms.

As shown in FIG. 17B, these optical black rows 2218 and 2220 may be located on the top of the pixel array or at the bottom of the pixel array or at the top and the bottom of the pixel array. In some aspects, it may be desirable to control the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. In some aspects, an electronic shutter or rolling shutter may be used to start the integration time (2219a-c) by resetting the pixel. The light will then integrate until the next readout phase. In some aspects, the position of the electronic shutter can be moved between two readout cycles 2202 in order to control the pixel saturation for a given amount of light. In some alternative aspects lacking an electronic shutter, the integration time 2219a-c of the incoming light may start during a first readout cycle 2202 and may end at the next readout cycle 2202, which also defines the start of the next integration. In some alternative aspects, the amount of light accumulated by each pixel may be controlled by a time during which light is pulsed 2230a-d during the blanking times 2216a-d. This ensures that all rows see the same light issued from the same light pulse 2230a-c. In other words, each row will start its integration in a first dark environment 2231, which may be at the optical black back row 2220 of read out frame (m) for a maximum light pulse width, and will then receive a light strobe and will end its integration in a second dark environment 2232, which may be at the optical black front row 2218 of the next succeeding read out frame (m+1) for a maximum light pulse width. Thus, the image generated from the light pulse 2230a-c will be solely available during frame (m+1) readout without any interference with frames (m) and (m+2).

It should be noted that the condition to have a light pulse 2230a-c to be read out only in one frame and not interfere with neighboring frames is to have the given light pulse 2230a-c firing during the blanking time 2216. Because the optical black rows 2218, 2220 are insensitive to light, the optical black back rows 2220 time of frame (m) and the optical black front rows 2218 time of frame (m+1) can be added to the blanking time 2216 to determine the maximum range of the firing time of the light pulse 2230.

Figure 17C:
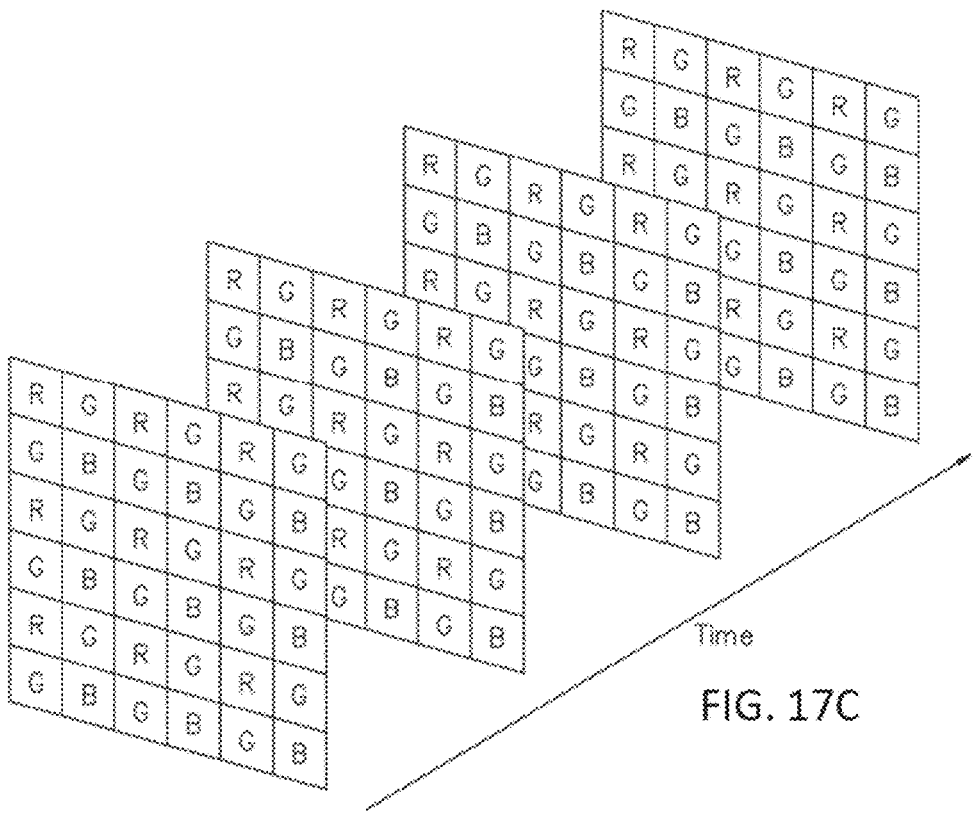

In some aspects, FIG. 17B depicts an example of a timing diagram for sequential frame captures by a conventional CMOS sensor. Such a CMOS sensor may incorporate a Bayer pattern of color filters, as depicted in FIG. 17C. It is recognized that the Bayer pattern provides for greater luminance detail than chrominance. It may further be recognized that the sensor has a reduced spatial resolution since a total of 4 adjacent pixels are required to produce the color information for the aggregate spatial portion of the image. In an alternative approach, the color image may be constructed by rapidly strobing the visualized area at high speed with a variety of optical sources (either laser or light-emitting diodes) having different central optical wavelengths.

The optical strobing system may be under the control of the camera system, and may include a specially designed CMOS sensor with high speed readout. The principal benefit is that the sensor can accomplish the same spatial resolution with significantly fewer pixels compared with conventional Bayer or 3-sensor cameras. Therefore, the physical space occupied by the pixel array may be reduced. The actual pulse periods (2230a-c) may differ within the repeating pattern, as illustrated in FIG. 17B. This is useful for, e.g., apportioning greater time to the components that require the greater light energy or those having the weaker sources. As long as the average captured frame rate is an integer multiple of the requisite final system frame rate, the data may simply be buffered in the signal processing chain as appropriate.

The facility to reduce the CMOS sensor chip-area to the extent allowed by combining all of these methods is particularly attractive for small diameter (about 3-10 mm) endoscopy. In particular, it allows for endoscope designs in which the sensor is located in the space-constrained distal end, thereby greatly reducing the complexity and cost of the optical section, while providing high definition video. A consequence of this approach is that to reconstruct each final, full color image, requires that data be fused from three separate snapshots in time. Any motion within the scene, relative to the optical frame of reference of the endoscope, will generally degrade the perceived resolution, since the edges of objects appear at slightly different locations within each captured component. In this disclosure, a means of diminishing this issue is described which exploits the fact that spatial resolution is much more important for luminance information, than for chrominance.

Figure 17D:
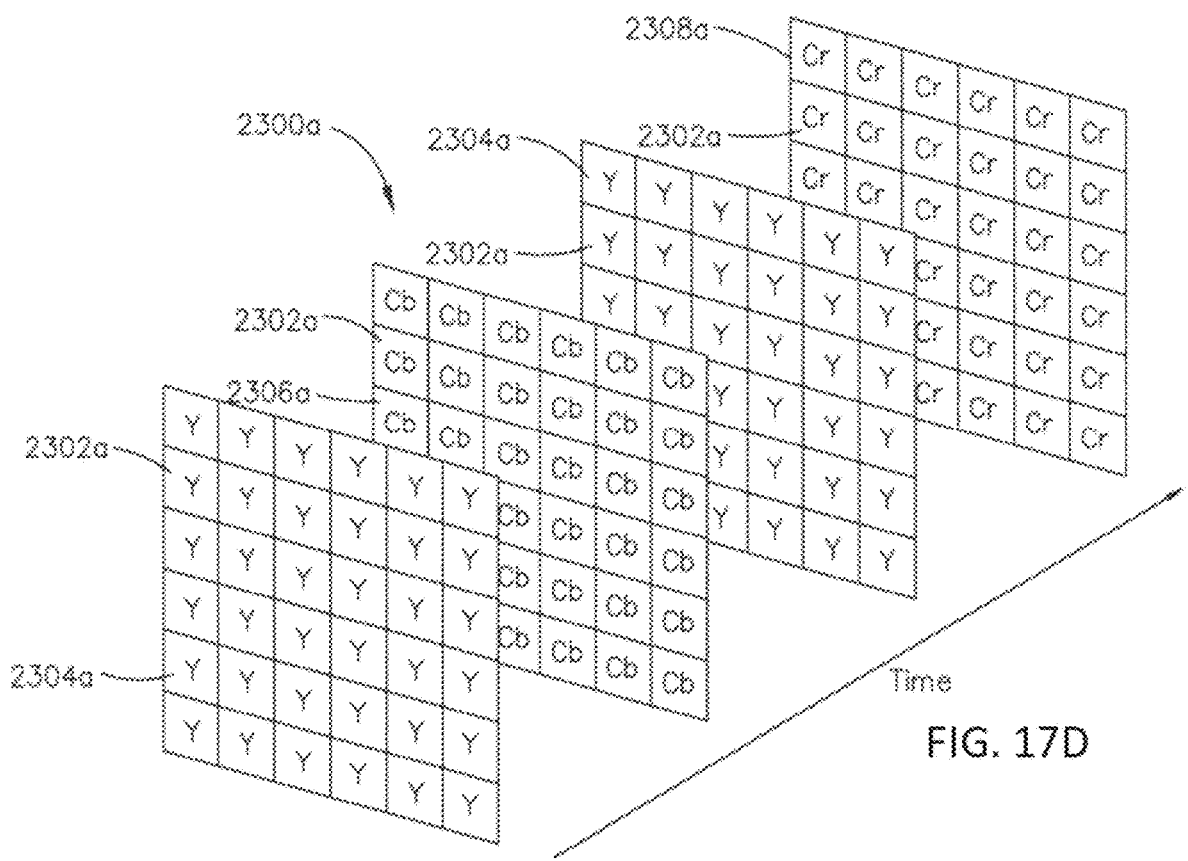

The basis of the approach is that, instead of firing monochromatic light during each frame, combinations of the three wavelengths are used to provide all of the luminance information within a single image. The chrominance information is derived from separate frames with, e.g., a repeating pattern such as Y-Cb-Y-Cr (FIG. 17D). While it is possible to provide pure luminance data by a shrewd choice of pulse ratios, the same is not true of chrominance.

In one aspect, as illustrated in FIG. 17D, an endoscopic system 2300a may comprise a pixel array 2302a having uniform pixels and the system 2300a may be operated to receive Y (luminance pulse) 2304a, Cb (ChromaBlue) 2306a and Cr (ChromaRed) 2308a pulses.

To complete a full color image requires that the two components of chrominance also be provided. However, the same algorithm that was applied for luminance cannot be directly applied for chrominance images since it is signed, as reflected in the fact that some of the RGB coefficients are negative. The solution to this is to add a degree of luminance of sufficient magnitude that all of the final pulse energies become positive. As long as the color fusion process in the ISP is aware of the composition of the chrominance frames, they can be decoded by subtracting the appropriate amount of luminance from a neighboring frame. The pulse energy proportions are given by:

$$Y=0.183 \cdot R+0.614 \cdot G+0.062 \cdot B$$

$$Cb=\lambda \cdot Y-0.101 \cdot R-0.339 \cdot G+0.439 \cdot B$$

$$Cr=\delta \cdot Y+0.439 \cdot R-0.399 \cdot G-0.040 \cdot B$$

$$\lambda \geq 0.399/0.614=0.552$$

$$\delta \geq 0.399/0.614=0.650$$

Figure 17E:
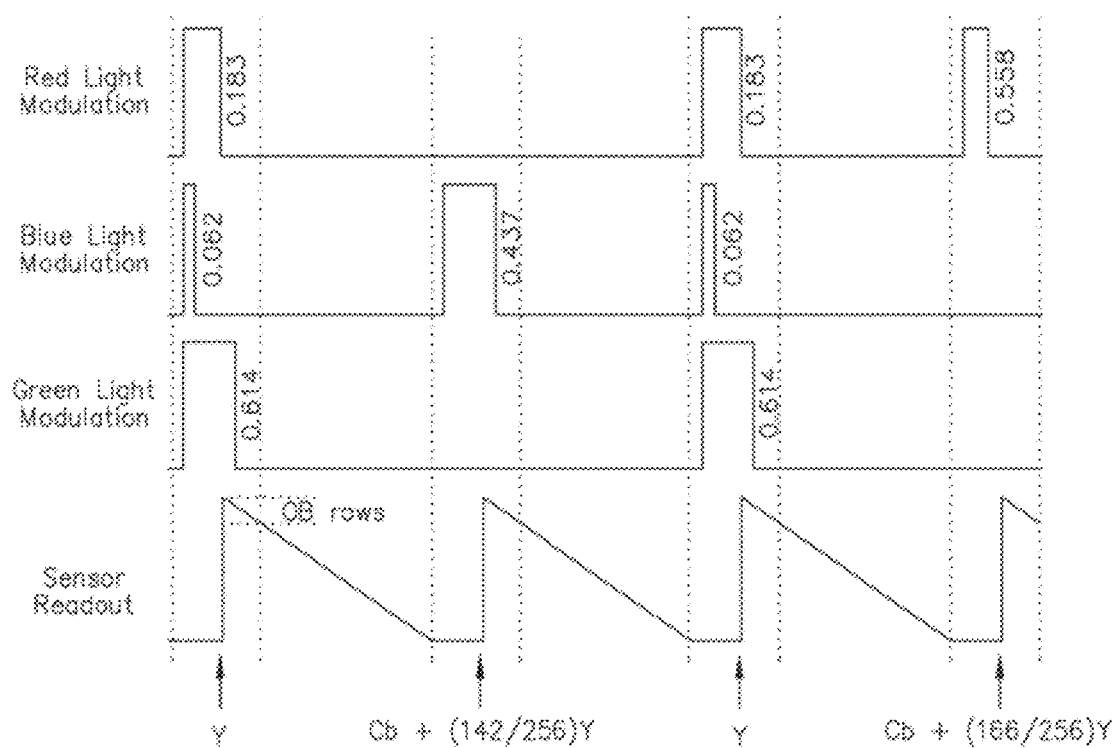

It turns out that if the $\lambda$ factor is equal to 0.552; both the red and the green components are exactly cancelled, in which case the Cb information can be provided with pure blue light. Similarly, setting $\delta=0.650$ cancels out the blue and green components for Cr which becomes pure red. This particular example is illustrated in FIG. 17E, which also depicts λ and δ as integer multiples of (½)⁸. This is a convenient approximation for the digital frame reconstruction.

In the case of the Y-Cb-Y-Cr pulsing scheme, the image data is already in the YCbCr space following the color fusion. Therefore, in this case it makes sense to perform luminance and chrominance-based operations up front, before converting back to linear RGB to perform the color correction etc.

Figure 17F:
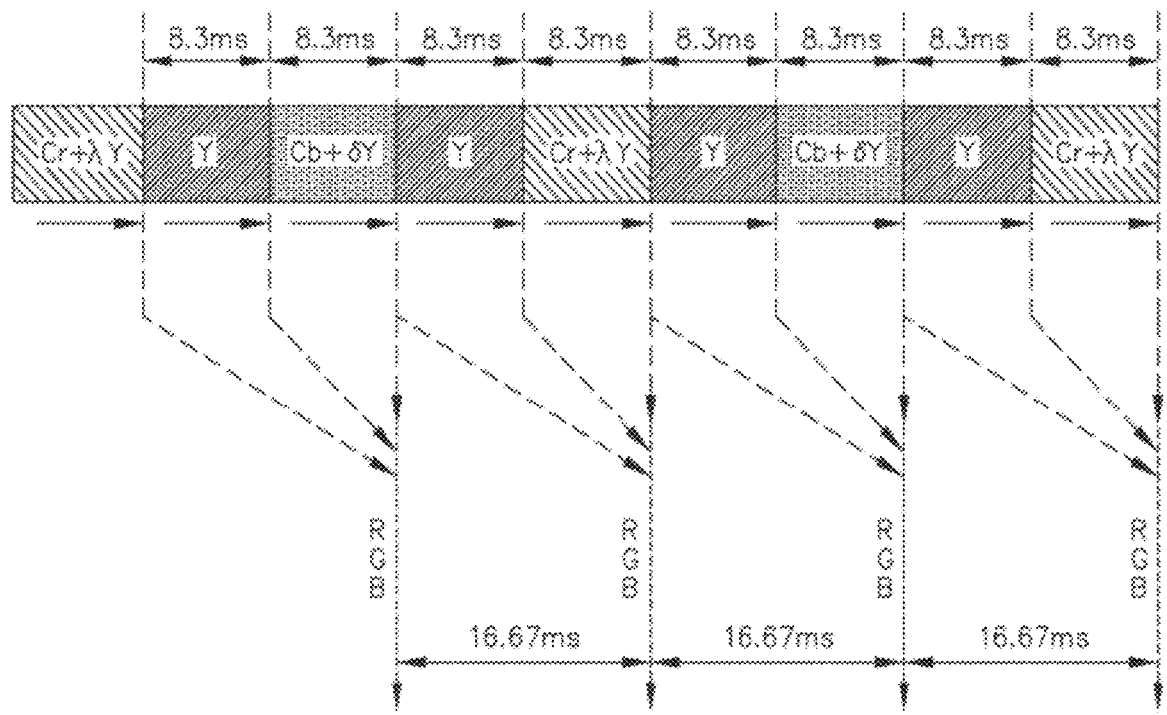

The color fusion process is more straightforward than de-mosaic, which is necessitated by the Bayer pattern (see FIG. 17C), since there is no spatial interpolation. It does require buffering of frames though in order to have all of the necessary information available for each pixel. In one general aspect, data for the Y-Cb-Y-Cr pattern may be pipelined to yield one full color image per two raw captured images. This is accomplished by using each chrominance sample twice. In FIG. 17F the specific example of a 120 Hz frame capture rate providing 60 Hz final video is depicted.

Additional disclosures regarding the control of the laser components of an illumination system as depicted in FIGS. 17B-F for use in a surgical visualization system 108 may be found in U.S. Patent Application Publication No. 2014/0160318, titled YCBCR PULSED ILLUMINATION SCHEME IN A LIGHT DEFICIENT ENVIRONMENT, filed on Jul. 26, 2013, which issued on Dec. 6, 2016 as U.S. Pat. No. 9,516,239, and U.S. Patent Application Publication No. 2014/0160319, titled CONTINUOUS VIDEO IN A LIGHT DEFICIENT ENVIRONMENT, filed on Jul. 26, 2013, which issued on Aug. 22, 2017 as U.S. Pat. No. 9,743,016, the contents thereof being incorporated by reference herein in their entirety and for all purposes.

Subsurface Vascular Imaging

During a surgical procedure, a surgeon may be required to manipulate tissues to effect a desired medical outcome. The actions of the surgeon are limited by what is visually observable in the surgical site. Thus, the surgeon may not be aware, for example, of the disposition of vascular structures that underlie the tissues being manipulated during the procedure.

Since the surgeon is unable to visualize the vasculature beneath a surgical site, the surgeon may accidentally sever one or more critical blood vessels during the procedure.

Therefore, it is desirable to have a surgical visualization system that can acquire imaging data of the surgical site for presentation to a surgeon in which the presentation can include information related to the presence of vascular structures located beneath the surface of a surgical site.

Some aspects of the present disclosure further provide for a control circuit configured to control the illumination of a surgical site using one or more illumination sources such as laser light sources and to receive imaging data from one or more image sensors. In some aspects, the present disclosure provides for a non-transitory computer readable medium storing computer readable instructions that, when executed, cause a device to detect a blood vessel in a tissue and determine its depth below the surface of the tissue.

In some aspects, a surgical image acquisition system may include a plurality of illumination sources wherein each illumination source is configured to emit light having a specified central wavelength, a light sensor configured to receive a portion of the light reflected from a tissue sample when illuminated by the one or more of the plurality of illumination sources, and a computing system. The computing system may be configured to: receive data from the light sensor when the tissue sample is illuminated by each of the plurality of illumination sources; determine a depth location of a structure within the tissue sample based on the data received by the light sensor when the tissue sample is illuminated by each of the plurality of illumination sources, and calculate visualization data regarding the structure and the depth location of the structure. In some aspects, the visualization data may have a data format that may be used by a display system, and the structure may comprise one or more vascular tissues.

Vascular Imaging Using NIR Spectroscopy

In one aspect, a surgical image acquisition system may include an independent color cascade of illumination sources comprising visible light and light outside of the visible range to image one or more tissues within a surgical site at different times and at different depths. The surgical image acquisition system may further detect or calculate characteristics of the light reflected and/or refracted from the surgical site. The characteristics of the light may be used to provide a composite image of the tissue within the surgical site as well as provide an analysis of underlying tissue not directly visible at the surface of the surgical site. The surgical image acquisition system may determine tissue depth location without the need for separate measurement devices.

In one aspect, the characteristic of the light reflected and/or refracted from the surgical site may be an amount of absorbance of light at one or more wavelengths. Various chemical components of individual tissues may result in specific patterns of light absorption that are wavelength dependent.

In one aspect, the illumination sources may comprise a red laser source and a near infrared laser source, wherein the one or more tissues to be imaged may include vascular tissue such as veins or arteries. In some aspects, red laser sources (in the visible range) may be used to image some aspects of underlying vascular tissue based on spectroscopy in the visible red range. In some non-limiting examples, a red laser light source may source illumination having a peak wavelength that may range between 635 nm and 660 nm, inclusive. Non-limiting examples of a red laser peak wavelength may include about 635 nm, about 640 nm, about 645 nm, about 650 nm, about 655 nm, about 660 nm, or any value or range of values therebetween. In some other aspects, near infrared laser sources may be used to image underlying vascular tissue based on near infrared spectroscopy. In some non-limiting examples, a near infrared laser source may emit illumination have a wavelength that may range between 750-3000 nm, inclusive. Non-limiting examples of an infrared laser peak wavelength may include about 750 nm, about 1000 nm, about 1250 nm, about 1500 nm, about 1750 nm, about 2000 nm, about 2250 nm, about 2500 nm, about 2750 nm, 3000 nm, or any value or range of values therebetween. It may be recognized that underlying vascular tissue may be probed using a combination of red and infrared spectroscopy. In some examples, vascular tissue may be probed using a red laser source having a peak wavelength at about 660 nm and a near IR laser source having a peak wavelength at about 750 nm or at about 850 nm.

Near infrared spectroscopy (NIRS) is a non-invasive technique that allows determination of tissue oxygenation based on spectro-photometric quantitation of oxy- and deoxyhemoglobin within a tissue. In some aspects, NIRS can be used to image vascular tissue directly based on the difference in illumination absorbance between the vascular tissue and non-vascular tissue. Alternatively, vascular tissue can be indirectly visualized based on a difference of illumination absorbance of blood flow in the tissue before and after the application of physiological interventions, such as arterial and venous occlusions methods.

Instrumentation for near-IR (NIR) spectroscopy may be similar to instruments for the UV-visible and mid-IR ranges. Such spectroscopic instruments may include an illumination source, a detector, and a dispersive element to select a specific near-IR wavelength for illuminating the tissue sample. In some aspects, the source may comprise an incandescent light source or a quartz halogen light source. In some aspects, the detector may comprise semiconductor (for example, an InGaAs) photodiode or photo array. In some aspects, the dispersive element may comprise a prism or, more commonly, a diffraction grating. Fourier transform NIR instruments using an interferometer are also common, especially for wavelengths greater than about 1000 nm. Depending on the sample, the spectrum can be measured in either reflection or transmission mode.

Figure 18:
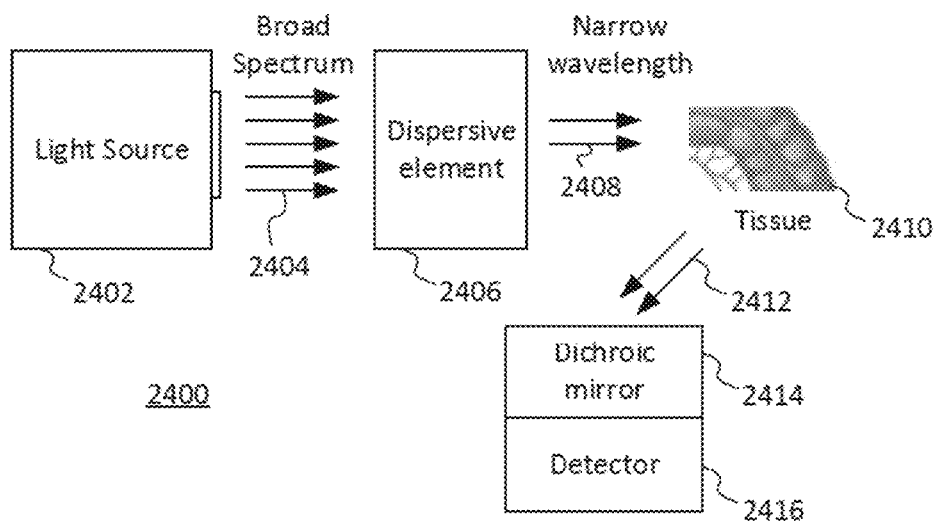
FIG. 18 illustrates example instrumentation for NIR spectroscopy.

FIG. 18 depicts schematically one example of instrumentation 2400 similar to instruments for the UV-visible and mid-IR ranges for NIR spectroscopy. A light source 2402 may emit a broad spectral range of illumination 2404 that may impinge upon a dispersive element 2406 (such as a prism or a diffraction grating). The dispersive element 2406 may operate to select a narrow wavelength portion 2408 of the light emitted by the broad spectrum light source 2402, and the selected portion 2408 of the light may illuminate the tissue 2410. The light reflected from the tissue 2412 may be directed to a detector 2416 (for example, by means of a dichroic mirror 2414) and the intensity of the reflected light 2412 may be recorded. The wavelength of the light illuminating the tissue 2410 may be selected by the dispersive element 2406. In some aspects, the tissue 2410 may be illuminated only by a single narrow wavelength portion 2408 selected by the dispersive element 2406 form the light source 2402. In other aspects, the tissue 2410 may be scanned with a variety of narrow wavelength portions 2408 selected by the dispersive element 2406. In this manner, a spectroscopic analysis of the tissue 2410 may be obtained over a range of NIR wavelengths.

Figure 19:
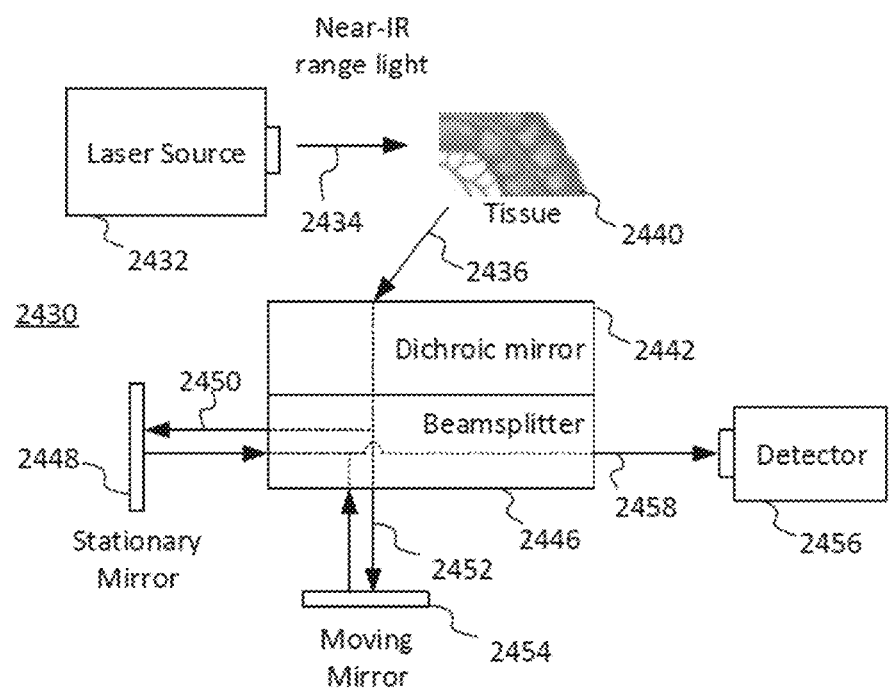
FIG. 19 illustrates example instrumentation for determining NIRS based on Fourier transform infrared imaging.

FIG. 19 depicts schematically one example of instrumentation 2430 for determining NIRS based on Fourier transform infrared imaging. In FIG. 19, a laser source emitting 2432 light in the near IR range 2434 illuminates a tissue sample 2440. The light reflected 2436 by the tissue 2440 is reflected by a mirror, such as a dichroic mirror 2444, to a beam splitter 2446. The beam splitter 2446 directs one portion of the light 2448 reflected by the tissue 2440 to a stationary mirror 2450 and one portion of the light 2452 reflected 2436 by the tissue 2440 a moving mirror 2454. The moving mirror 2454 may oscillate in position based on an affixed piezoelectric transducer activated by a sinusoidal voltage having a voltage frequency. The position of the moving mirror 2454 in space corresponds to the frequency of the sinusoidal activation voltage of the piezoelectric transducer. The light reflected from the moving mirror and the stationary mirror may be recombined 2458 at the beam splitter 2446 and directed to a detector 2456. Computational components may receive the signal output of the detector 2456 and perform a Fourier transform (in time) of the received signal. Because the wavelength of the light received from the moving mirror 2454 varies in time with respect to the wavelength of the light received from the stationary mirror 2450, the time-based Fourier transform of the recombined light corresponds to a wavelength-based Fourier transform of the recombined light 2458. In this manner, a wavelength-based spectrum of the light reflected from the tissue 2440 may be determined and spectral characteristics of the light reflected 2436 from the tissue 2440 may be obtained. Changes in the absorbance of the illumination in spectral components from the light reflected from the tissue 2440 may thus indicate the presence or absence of tissue having specific light absorbing properties (such as hemoglobin).

An alternative to near infrared light to determine hemoglobin oxygenation would be the use of monochromatic red light to determine the red light absorbance characteristics of hemoglobin. The absorbance characteristics of red light having a central wavelength of about 660 nm by the hemoglobin may indicate if the hemoglobin is oxygenated (arterial blood) or deoxygenated (venous blood).

In some alternative surgical procedures, contrasting agents can be used to improve the data that is collected on oxygenation and tissue oxygen consumption. In one non-limiting example, NIRS techniques may be used in conjunction with a bolus injection of a near-IR contrast agent such as indocyanine green (ICG) which has a peak absorbance at about 800 nm. ICG has been used in some medical procedures to measure cerebral blood flow.

Vascular Imaging Using Laser Doppler Flowmetry

In one aspect, the characteristic of the light reflected and/or refracted from the surgical site may be a Doppler shift of the light wavelength from its illumination source.

Laser Doppler flowmetry may be used to visualize and characterized a flow of particles moving relative to an effectively stationary background. Thus, laser light scattered by moving particles, such as blood cells, may have a different wavelength than that of the original illuminating laser source. In contrast, laser light scattered by the effectively stationary background (for example, the vascular tissue) may have the same wavelength of that of the original illuminating laser source. The change in wavelength of the scattered light from the blood cells may reflect both the direction of the flow of the blood cells relative to the laser source as well as the blood cell velocity.

Figure 20A:
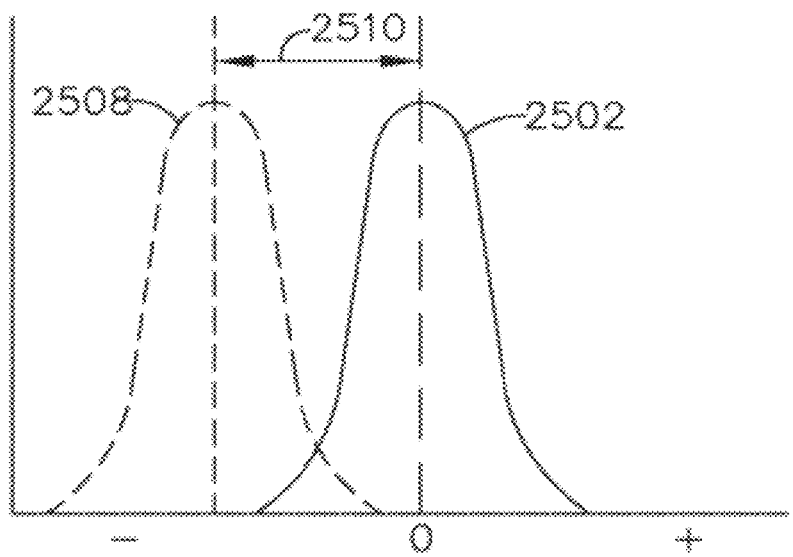
FIGS. 20A-C illustrate a change in wavelength of light scattered from moving blood cells.
Figure 20B:
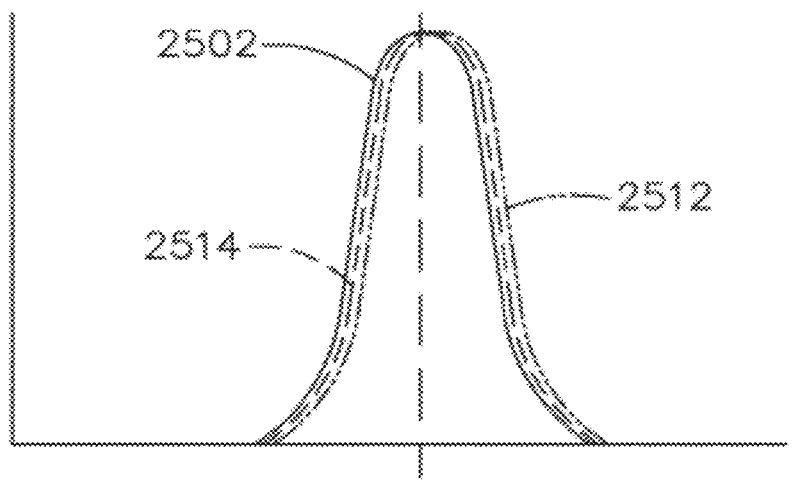
Figure 20C:
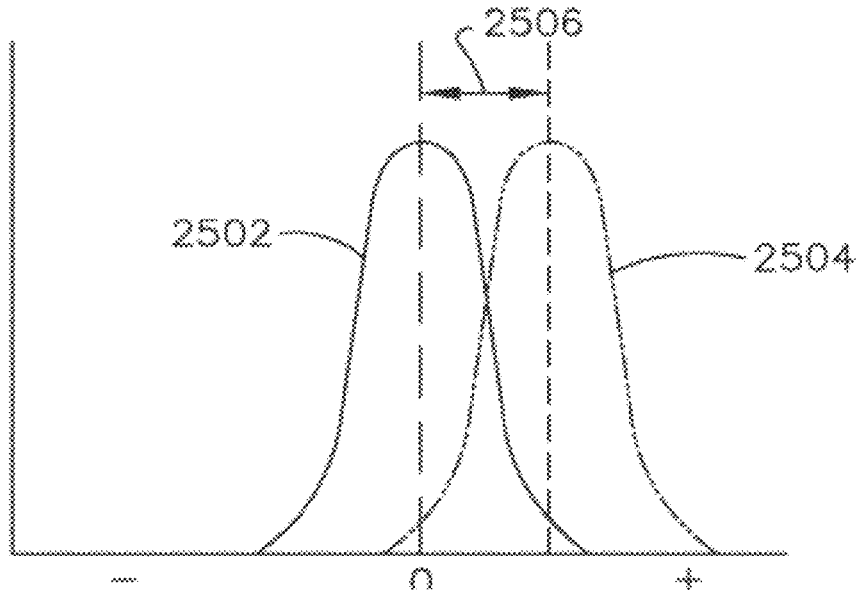

FIGS. 20A-C illustrate the change in wavelength of light scattered from blood cells that may be moving away from (FIG. 20A) or towards (FIG. 20C) the laser light source.

In each of FIGS. 20A-C, the original illuminating light 2502 is depicted having a relative central wavelength of 0. It may be observed from FIG. 20A that light scattered from blood cells moving away from the laser source 2504 has a wavelength shifted by some amount 2506 to a greater wavelength relative to that of the laser source (and is thus red shifted). It may also be observed from FIG. 20C that light scattered from blood cells moving towards from the laser source 2508 has a wavelength shifted by some amount 2510 to a shorter wavelength relative to that of the laser source (and is thus blue shifted). The amount of wavelength shift (for example 2506 or 2510) may be dependent on the velocity of the motion of the blood cells. In some aspects, an amount of a red shift (2506) of some blood cells may be about the same as the amount of blue shift (2510) of some other blood cells. Alternatively, an amount of a red shift (2506) of some blood cells may differ from the amount of blue shift (2510) of some other blood cells Thus, the velocity of the blood cells flowing away from the laser source as depicted in FIG. 20A may be less than the velocity of the blood cells flowing towards the laser source as depicted in FIG. 26C based on the relative magnitude of the wavelength shifts (2506 and 2510). In contrast, and as depicted in FIG. 26B, light scattered from tissue not moving relative to the laser light source (for example blood vessels 2512 or non-vascular tissue 2514) may not demonstrate any change in wavelength.

Figure 21:
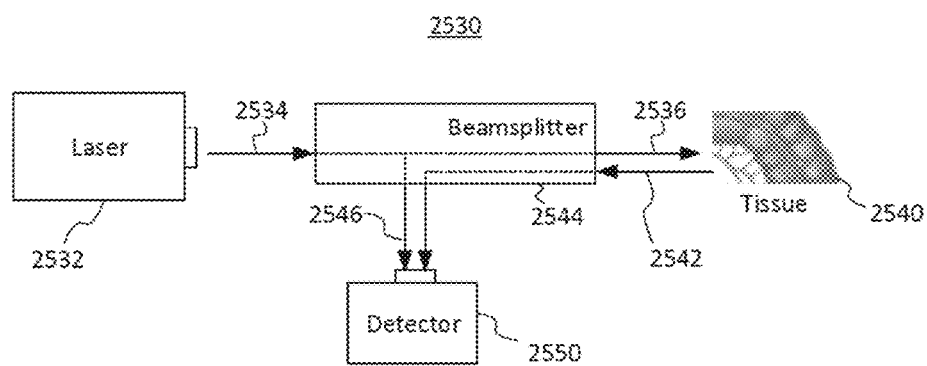
FIG. 21 illustrates example instrumentation that may be used to detect a Doppler shift in laser light scattered from portions of a tissue.

FIG. 21 depicts an aspect of instrumentation 2530 that may be used to detect a Doppler shift in laser light scattered from portions of a tissue 2540. Light 2534 originating from a laser 2532 may pass through a beam splitter 2544. Some portion of the laser light 2536 may be transmitted by the beam splitter 2544 and may illuminate tissue 2540. Another portion of the laser light may be reflected 2546 by the beam splitter 2544 to impinge on a detector 2550. The light back-scattered 2542 by the tissue 2540 may be directed by the beam splitter 2544 and also impinge on the detector 2550. The combination of the light 2534 originating from the laser 2532 with the light back-scattered 2542 by the tissue 2540 may result in an interference pattern detected by the detector 2550. The interference pattern received by the detector 2550 may include interference fringes resulting from the combination of the light 2534 originating from the laser 2532 and the Doppler shifted (and thus wavelength shifted) light back-scattered 2452 from the tissue 2540.

It may be recognized that back-scattered light 2542 from the tissue 2540 may also include back scattered light from boundary layers within the tissue 2540 and/or wavelength-specific light absorption by material within the tissue 2540. As a result, the interference pattern observed at the detector 2550 may incorporate interference fringe features from these additional optical effects and may therefore confound the calculation of the Doppler shift unless properly analyzed.

Figure 22:
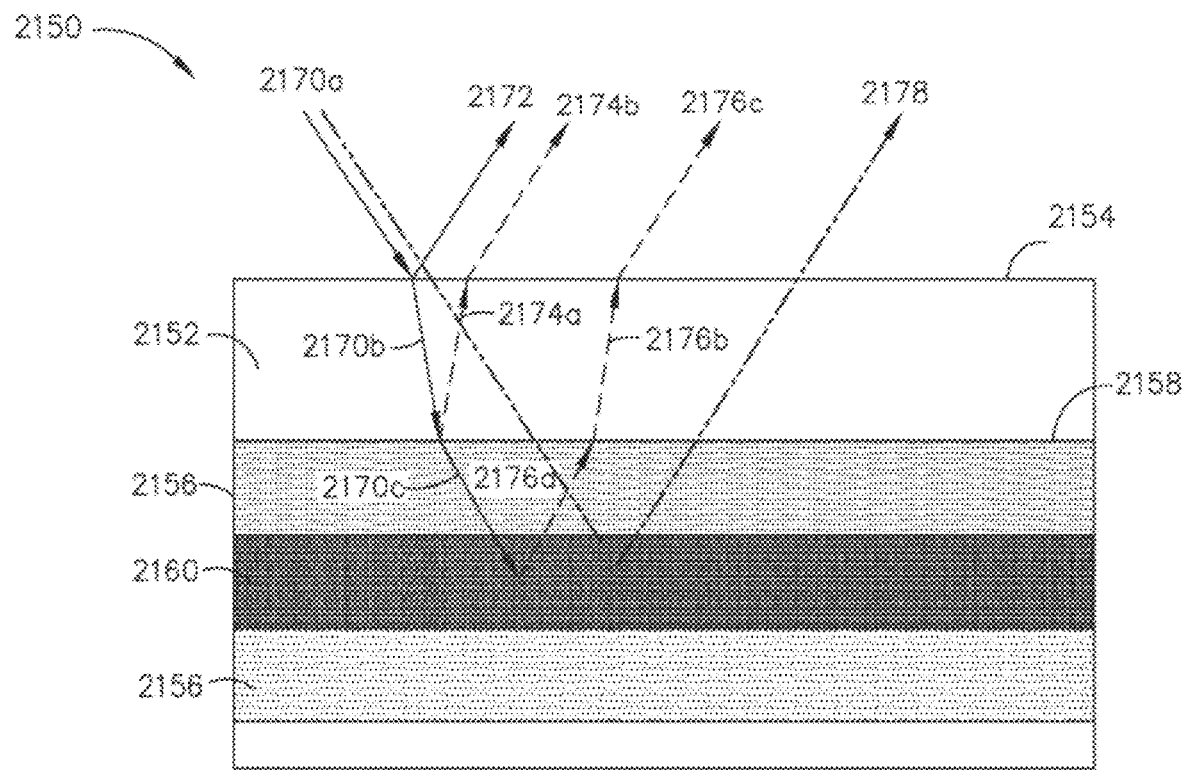
FIGS. 22 and 23 illustrate example optical effects on light impinging on a tissue having subsurface structures.

FIG. 22 depicts some of these additional optical effects. It is well known that light traveling through a first optical medium having a first refractive index, n1, may be reflected at an interface with a second optical medium having a second refractive index, n2. The light transmitted through the second optical medium will have a transmission angle relative to the interface that differs from the angle of the incident light based on a difference between the refractive indices n1 and n2 (Snell's Law). FIG. 22 illustrates the effect of Snell's Law on light impinging on the surface of a multi-component tissue 2150, as may be presented in a surgical field. The multi-component tissue 2150 may be composed of an outer tissue layer 2152 having a refractive index n1 and a buried tissue, such as a blood vessel having a vessel wall 2156. The blood vessel wall 2156 may be characterized by a refractive index n2. Blood may flow within the lumen of the blood vessel 2160. In some aspects, it may be important during a surgical procedure to determine the position of the blood vessel 2160 below the surface 2154 of the outer tissue layer 2152 and to characterize the blood flow using Doppler shift techniques.

An incident laser light 2170a may be used to probe for the blood vessel 2160 and may be directed on the top surface 2154 of the outer tissue layer 2152. A portion 2172 of the incident laser light 2170a may be reflected at the top surface 2154. Another portion 2170b of the incident laser light 2170a may penetrate the outer tissue layer 2152. The reflected portion 2172 at the top surface 2154 of the outer tissue layer 2152 has the same path length of the incident light 2170a, and therefore has the same wavelength and phase of the incident light 2170a. However, the portion 2170b of light transmitted into the outer tissue layer 2152 will have a transmission angle that differs from the incidence angle of the light impinging on the tissue surface because the outer tissue layer 2152 has an index of refraction n1 that differs from the index of refraction of air.

If the portion of light transmitted through the outer tissue layer 2152 impinges on a second tissue surface 2158, for example of the blood vessel wall 2156, some portion 2174a,b of light will be reflected back towards the source of the incident light 2170a. The light thus reflected 2174a at the interface between the outer tissue layer 2152 and the blood vessel wall 2156 will have the same wavelength as the incident light 2170a, but will be phase shifted due to the change in the light path length. Projecting the light reflected 2174a,b from the interface between the outer tissue layer 2152 and the blood vessel wall 2156 along with the incident light on the sensor, will produce an interference pattern based on the phase difference between the two light sources.

Further, a portion of the incident light 2170c may be transmitted through the blood vessel wall 2156 and penetrate into the blood vessel lumen 2160. This portion of the incident light 2170c may interact with the moving blood cells in the blood vessel lumen 2160 and may be reflected back 2176a-c towards the source of the impinging light having a wavelength Doppler shifted according to the velocity of the blood cells, as disclosed above. The Doppler shifted light reflected 2176a-c from the moving blood cells may be projected along with the incident light on the sensor, resulting in an interference pattern having a fringe pattern based on the wavelength difference between the two light sources.

In FIG. 22, a light path 2178 is presented of light impinging on the red blood cells in the blood vessel lumen 2160 if there are no changes in refractive index between the emitted light and the light reflected by the moving blood cells. In this example, only a Doppler shift in the reflected light wavelength can be detected. However, the light reflected by the blood cells (2176a-c) may incorporate phase changes due to the variation in the tissue refractive indices in addition to the wavelength changes due to the Doppler Effect.

Thus, it may be understood that if the light sensor receives the incident light, the light reflected from one or more tissue interfaces (2172, and 2174a,b) and the Doppler shifted light from the blood cells (2176a-c), the interference pattern thus produced on the light sensor may include the effects due to the Doppler shift (change in wavelength) as well as the effects due to the change in refractive index within the tissue (change in phase). As a result, a Doppler analysis of the light reflected by the tissue sample may produce erroneous results if the effects due to changes in the refractive index within the sample are not compensated for.

Figure 23:
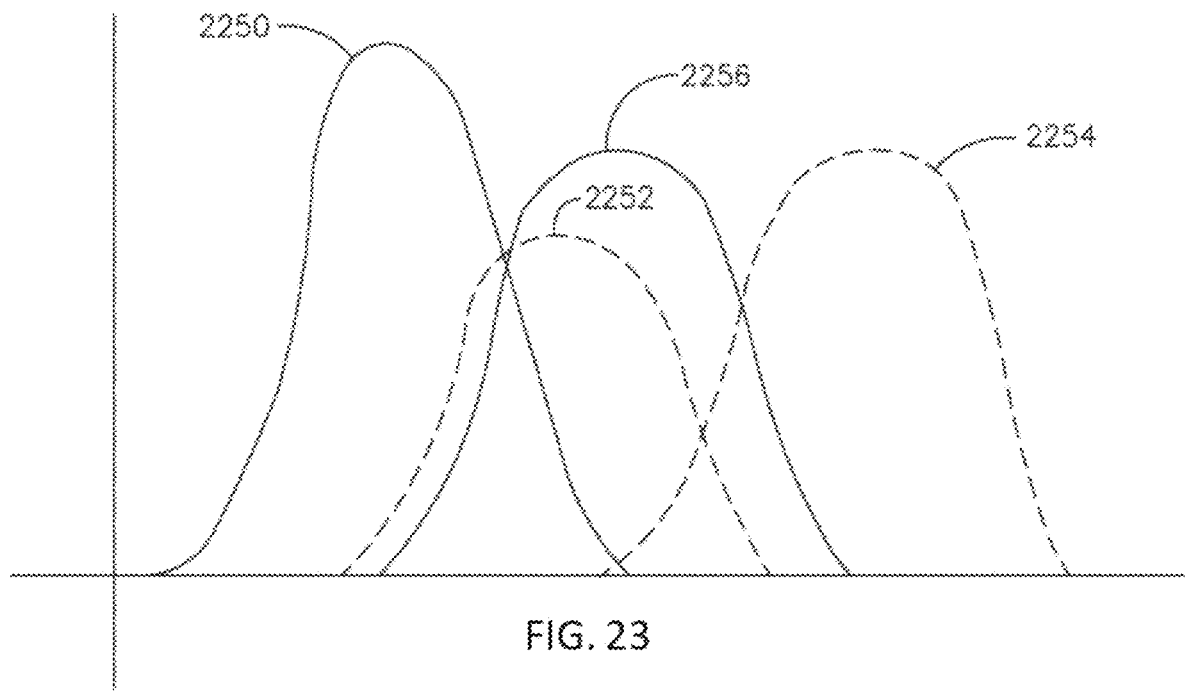

FIG. 23 illustrates an example of the effects on a Doppler analysis of light that impinge 2250 on a tissue sample to determine the depth and location of an underlying blood vessel. If there is no intervening tissue between the blood vessel and the tissue surface, the interference pattern detected at the sensor may be due primarily to the change in wavelength reflected from the moving blood cells. As a result, a spectrum 2252 derived from the interference pattern may generally reflect only the Doppler shift of the blood cells. However, if there is intervening tissue between the blood vessel and the tissue surface, the interference pattern detected at the sensor may be due to a combination of the change in wavelength reflected from the moving blood cells and the phase shift due to the refractive index of the intervening tissue. A spectrum 2254 derived from such an interference pattern, may result in the calculation of the Doppler shift that is confounded due to the additional phase change in the reflected light. In some aspects, if information regarding the characteristics (thickness and refractive index) of the intervening tissue is known, the resulting spectrum 2256 may be corrected to provide a more accurate calculation of the change in wavelength.

It is recognized that the tissue penetration depth of light is dependent on the wavelength of the light used. Thus, the wavelength of the laser source light may be chosen to detect particle motion (such a blood cells) at a specific range of tissue depth.

Figure 24C:
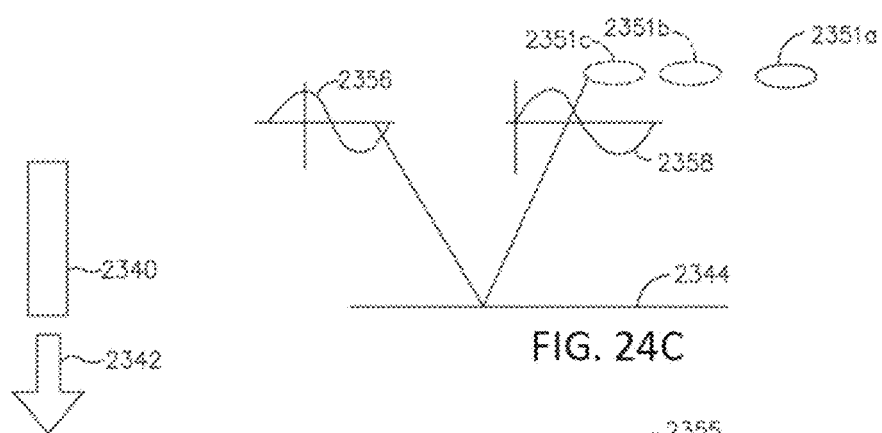
FIGS. 24A-D illustrate the detection of moving blood cells at a tissue depth based on a laser Doppler analysis at a variety of laser wavelengths.
Figure 24A:
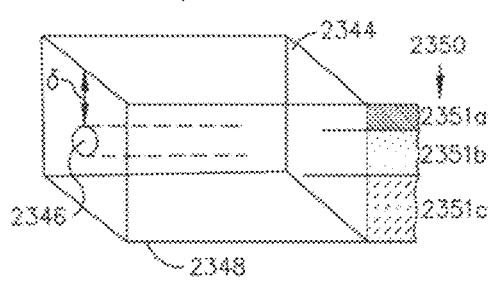
Figure 24B:
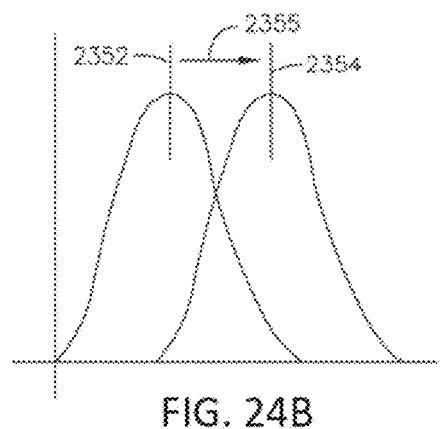

FIGS. 24A-C depict schematically a means for detect moving particles such as blood cells at a variety of tissue depths based on the laser light wavelength. As illustrated in FIG. 24A, a laser source 2340 may direct an incident beam of laser light 2342 onto a surface 2344 of a surgical site. A blood vessel 2346 (such as a vein or artery) may be disposed within the tissue 2348 at some depth.delta. from the tissue surface. The penetration depth 2350 of a laser into a tissue 2348 may be dependent at least in part on the laser wavelength. Thus, laser light having a wavelength in the red range of about 635 nm to about 660 nm, may penetrate the tissue 2351a to a depth of about 1 mm. Laser light having a wavelength in the green range of about 520 nm to about 532 nm may penetrate the tissue 2351b to a depth of about 2-3 mm. Laser light having a wavelength in the blue range of about 405 nm to about 445 nm may penetrate the tissue 2351c to a depth of about 4 mm or greater. In the example depicted in FIGS. 30A-C, a blood vessel 2346 may be located at a depth.delta. of about 2-3 mm below the tissue surface. Red laser light will not penetrate to this depth and thus will not detect blood cells flowing within this vessel. However, both green and blue laser light can penetrate this depth. Therefore, scattered green and blue laser light from the blood cells within the blood vessel 2346 may demonstrate a Doppler shift in wavelength.

FIG. 24B illustrates how a Doppler shift 2355 in the wavelength of reflected laser light may appear. The emitted light (or laser source light 2342) impinging on a tissue surface 2344 may have a central wavelength 2352. For example, light from a green laser may have a central wavelength 2352 within a range of about 520 nm to about 532 nm. The reflected green light may have a central wavelength 2354 shifted to a longer wavelength (red shifted) if the light was reflected from a particle such as a red blood cell that is moving away from the detector. The difference between the central wavelength 2352 of the emitted laser light and the central wavelength 2354 of the emitted laser light comprises the Doppler shift 2355.

As disclosed above with respect to FIGS. 22 and 23, laser light reflected from structures within a tissue 2348 may also show a phase shift in the reflected light due to changes in the index of refraction arising from changes in tissue structure or composition. The emitted light (or laser source light 2342) impinging on a tissue surface 2344 may have a first phase characteristic 2356. The reflected laser light may have a second phase characteristic 2358. It may be recognized that blue laser light that can penetrate tissue to a depth of about 4 mm or greater 2351c may encounter a greater variety of tissue structures than red laser light (about 1 mm 2351a) or green laser light (about 2-3 mm 2351b). Consequently, as illustrated in FIG. 30C, the phase shift 2358 of reflected blue laser light may be significant at least due to the depth of penetration.

Figure 24D:
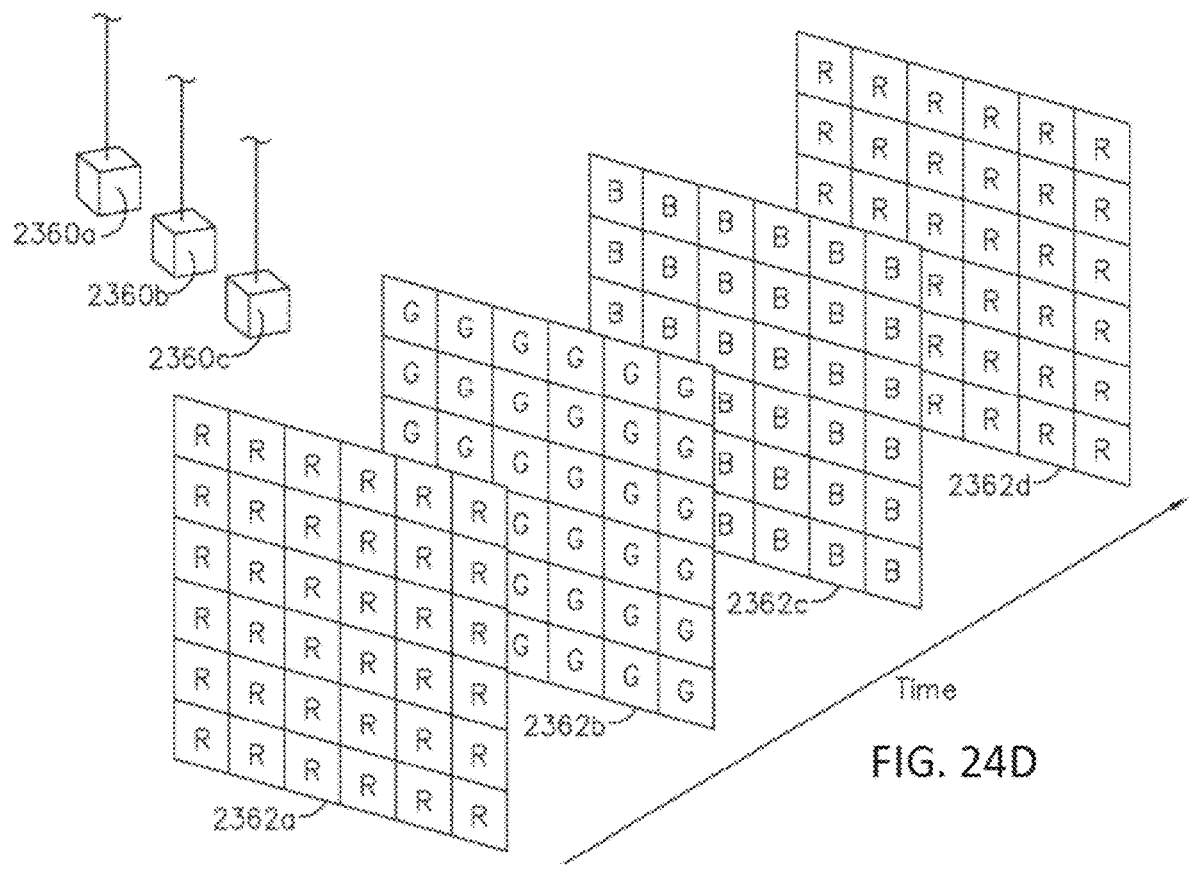

FIG. 24D illustrates aspects of illuminating tissue by red 2360a, green 2360b and blue 2360c laser light in a sequential manner. In some aspects, a tissue may be probed by red 2360a, green 2360b and blue 2360c laser illumination in a sequential manner. In some alternative examples, one or more combinations of red 2360a, green 2360b, and blue 2360c laser light, as depicted in FIG. 17D-F and disclosed above, may be used to illuminate the tissue according to a defined illumination sequence. 24D illustrates the effect of such illumination on a CMOS imaging sensor 2362a-d over time. Thus, at a first time t.sub.1, the CMOS sensor 2362a may be illuminated by the red 2360a laser. At a second time t.sub.2 the CMOS sensor 2362b may be illuminated by the green 2360b laser. At a third time t.sub.3, the CMOS sensor 2362c may be illuminated by the blue 2360c laser. The illumination cycle may then be repeated starting at a fourth time t.sub.4 in which the CMOS sensor 2362d may be illuminated by the red 2360a lase again. It may be recognized that sequential illumination of the tissue by laser illumination at differing wavelengths may permit a Doppler analysis at varying tissue depths over time. Although red 2360a, green 2360b and blue 2360c laser sources may be used to illuminate the surgical site, it may be recognized that other wavelengths outside of visible light (such as in the infrared or ultraviolet regions) may be used to illuminate the surgical site for Doppler analysis.

Figure 25:
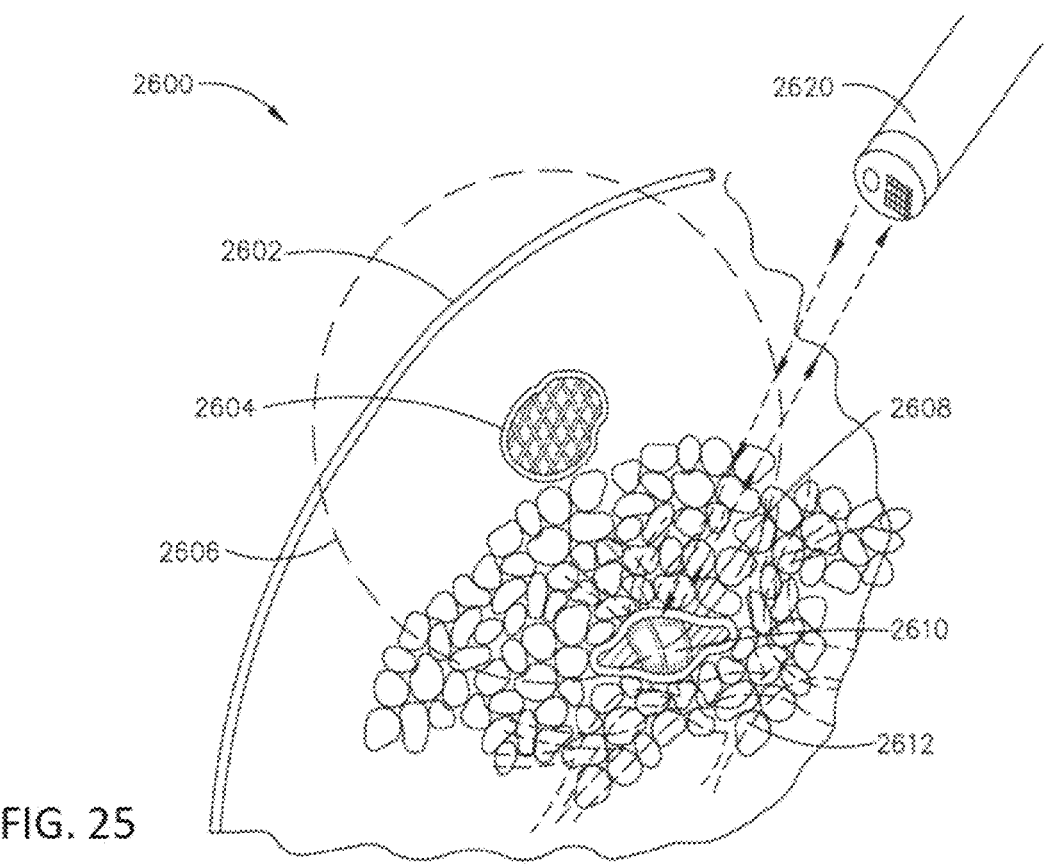
FIG. 25 illustrates an example of a use of Doppler imaging to detect the present of subsurface blood vessels.

FIG. 25 illustrates an example of a use of Doppler imaging to detect the present of blood vessels not otherwise viewable at a surgical site 2600. In FIG. 25, a surgeon may wish to excise a tumor 2602 found in the right superior posterior lobe 2604 of a lung. Because the lungs are highly vascular, care must be taken to identify only those blood vessels associate with the tumor and to seal only those vessels without compromising the blood flow to the non-affected portions of the lung. In FIG. 25, the surgeon has identified the margin 2606 of the tumor 2604. The surgeon may then cut an initial dissected area 2608 in the margin region 2606, and exposed blood vessels 2610 may be observed for cutting and sealing. The Doppler imaging detector 2620 may be used to locate and identify blood vessels not observable 2612 in the dissected area. An imaging system may receive data from the Doppler imaging detector 2620 for analysis and display of the data obtained from the surgical site 2600. In some aspects, the imaging system may include a display to illustrate the surgical site 2600 including a visible image of the surgical site 2600 along with an image overlay of the hidden blood vessels 2612 on the image of the surgical site 2600.

Figure 26:
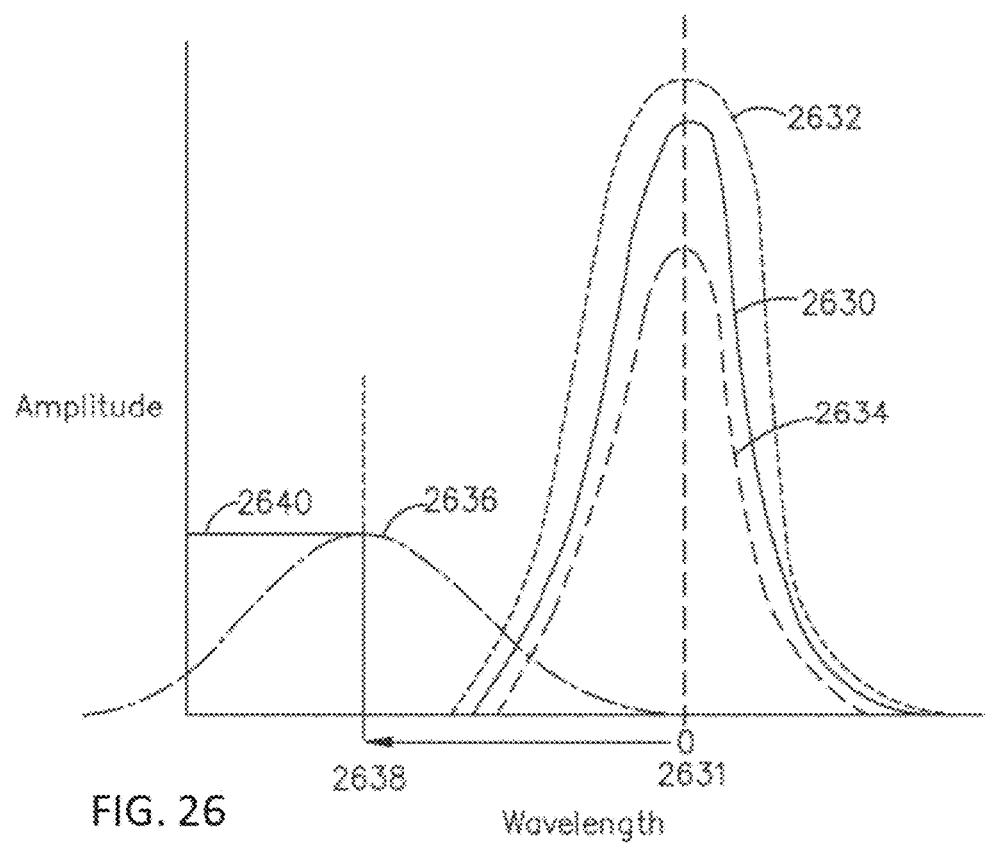
FIG. 26 illustrates a Doppler shift of blue light due to blood cells flowing through a subsurface blood vessel.

In the scenario disclosed above regarding FIG. 25, a surgeon wishes to sever blood vessels that supply oxygen and nutrients to a tumor while sparing blood vessels associated with non-cancerous tissue. Additionally, the blood vessels may be disposed at different depths in or around the surgical site 2600. The surgeon must therefore identify the position (depth) of the blood vessels as well as determine if they are appropriate for resection. FIG. 26 illustrates one method for identifying deep blood vessels based on a Doppler shift of light from blood cells flowing therethrough. As disclosed above, red laser light has a penetration depth of about 1 mm and green laser light has a penetration depth of about 2-3 mm. However, a blood vessel having a below-surface depth of 4 mm or more will be outside the penetration depths at these wavelengths. Blue laser light, however, can detect such blood vessels based on their blood flow.

FIG. 26 depicts the Doppler shift of laser light reflected from a blood vessel at a specific depth below a surgical site. The site may be illuminated by red laser light, green laser light, and blue laser light. The central wavelength 2630 of the illuminating light may be normalized to a relative central 3631. If the blood vessel lies at a depth of 4 or more mm below the surface of the surgical site, neither the red laser light nor the green laser light will be reflected by the blood vessel. Consequently, the central wavelength 2632 of the reflected red light and the central wavelength 2634 of the reflected green light will not differ much from the central wavelength 2630 of the illuminating red light or green light, respectively. However, if the site is illuminated by blue laser light, the central wavelength 2638 of the reflected blue light 2636 will differ from the central wavelength 2630 of the illuminating blue light. In some instances, the amplitude of the reflected blue light 2636 may also be significantly reduced from the amplitude of the illuminating blue light. A surgeon may thus determine the presence of a deep lying blood vessel along with its approximate depth, and thereby avoiding the deep blood vessel during surface tissue dissection.

Figure 27:
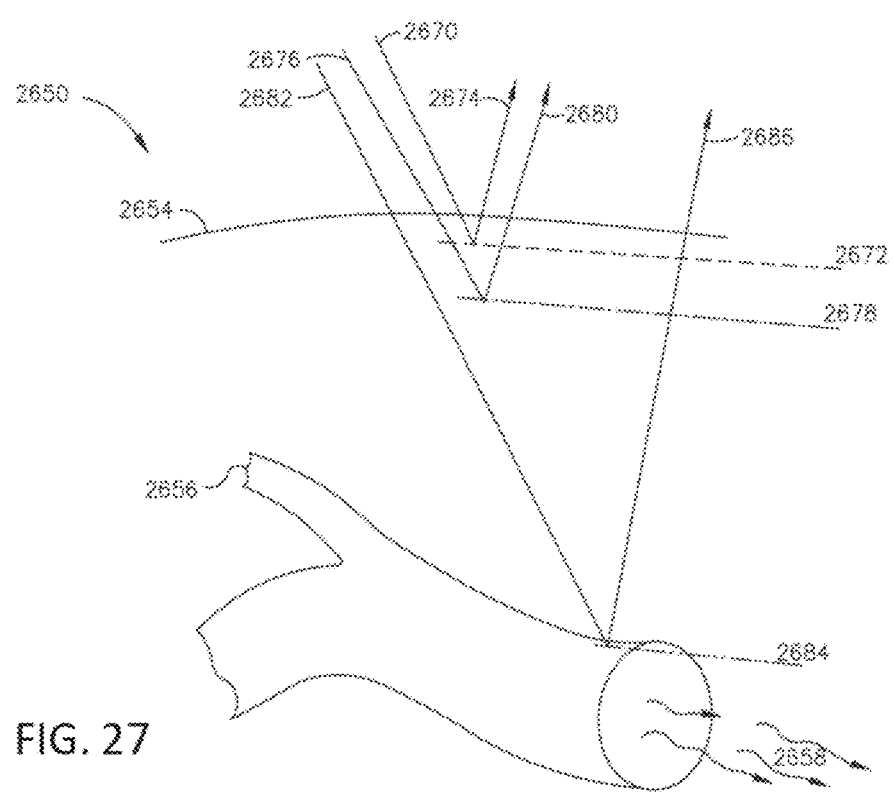
FIG. 27 illustrates example localization of a deep subsurface blood vessel.
Figure 28:
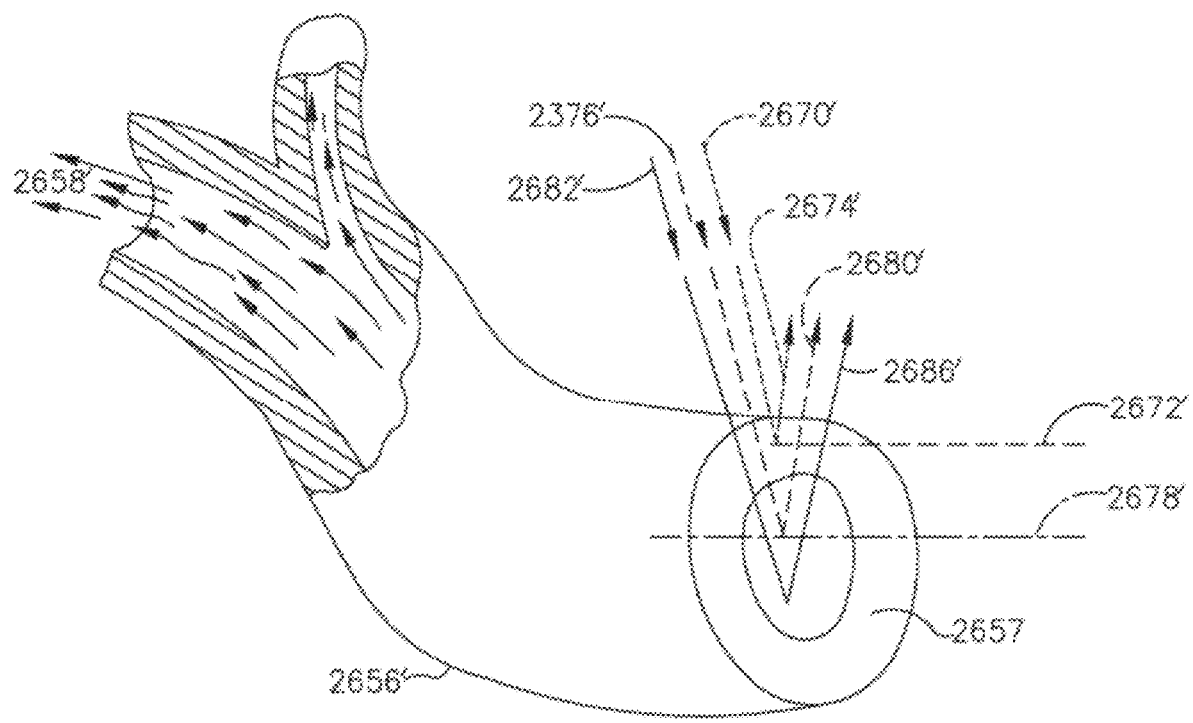
FIG. 28 illustrates example localization of a shallow subsurface blood vessel.

FIGS. 27 and 28 illustrates schematically the use of laser sources having differing central wavelengths (colors) for determining the approximate depth of a blood vessel beneath the surface of a surgical site. FIG. 27 depicts a first surgical site 2650 having a surface 2654 and a blood vessel 2656 disposed below the surface 2654. In one method, the blood vessel 2656 may be identified based on a Doppler shift of light impinging on the flow 2658 of blood cells within the blood vessel 2656. The surgical site 2650 may be illuminated by light from a number of lasers 2670, 2676, 2682, each laser being characterized by emitting light at one of several different central wavelengths. As noted above, illumination by a red laser 2670 can only penetrate tissue by about 1 mm. Thus, if the blood vessel 2656 was located at a depth of less than 1 mm 2672 below the surface 2654, the red laser illumination would be reflected 2674 and a Doppler shift of the reflected red illumination 2674 may be determined. Further, as noted above, illumination by a green laser 2676 can only penetrate tissue by about 2-3 mm. If the blood vessel 2656 was located at a depth of about 2-3 mm 2678 below the surface 2654, the green laser illumination would be reflected 2680 while the red laser illumination 2670 would not, and a Doppler shift of the reflected green illumination 2680 may be determined. However, as depicted in FIG. 27, the blood vessel 2656 is located at a depth of about 4 mm 2684 below the surface 2654. Therefore, neither the red laser illumination 2670 nor the green laser illumination 2676 would be reflected. Instead, only the blue laser illumination would be reflected 2686 and a Doppler shift of the reflected blue illumination 2686 may be determined.

In contrast to the blood vessel 2656 depicted in FIG. 27, the blood vessel 2656' depicted in FIG. 28 is located closer to the surface of the tissue at the surgical site. Blood vessel 2656' may also be distinguished from blood vessel 2656 in that blood vessel 2656' is illustrated to have a much thicker wall 2657. Thus, blood vessel 2656' may be an example of an artery while blood vessel 2656 may be an example of a vein because arterial walls are known to be thicker than venous walls. In some examples, arterial walls may have a thickness of about 1.3 mm. As disclosed above, red laser illumination 2670' can penetrate tissue to a depth of about 1 mm 2672'. Thus, even if a blood vessel 2656' is exposed at a surgical site (see 2610 at FIG. 25), red laser light that is reflected 2674' from the surface of the blood vessel 2656', may not be able to visualize blood flow 2658' within the blood vessel 2656' under a Doppler analysis due to the thickness of the blood vessel wall 2657. However, as disclosed above, green laser light impinging 2676' on the surface of a tissue may penetrate to a depth of about 2-3 mm 2678'. Further, blue laser light impinging 2682' on the surface of a tissue may penetrate to a depth of about 4 mm 2684'. Consequently, green laser light may be reflected 2680' from the blood cells flowing 2658' within the blood vessel 2656' and blue laser light may be reflected 2686' from the blood cells flowing 2658' within the blood vessel 2656'. As a result, a Doppler analysis of the reflected green light 2680' and reflected blue light 2686' may provide information regarding blood flow in near-surface blood vessel, especially the approximate depth of the blood vessel.

As disclosed above, the depth of blood vessels below the surgical site may be probed based on wavelength-dependent Doppler imaging. The amount of blood flow through such a blood vessel may also be determined by speckle contrast (interference) analysis. Doppler shift may indicate a moving particle with respect to a stationary light source. As disclosed above, the Doppler wavelength shift may be an indication of the velocity of the particle motion. Individual particles such as blood cells may not be separately observable. However, the velocity of each blood cell will produce a proportional Doppler shift. An interference pattern may be generated by the combination of the light back-scattered from multiple blood cells due to the differences in the Doppler shift of the back-scattered light from each of the blood cells. The interference pattern may be an indication of the number density of blood cells within a visualization frame. The interference pattern may be termed speckle contrast. Speckle contrast analysis may be calculated using a full frame 300.times.300 CMOS imaging array, and the speckle contrast may be directly related to the amount of moving particles (for example blood cells) interacting with the laser light over a given exposure period.

A CMOS image sensor may be coupled to a digital signal processor (DSP). Each pixel of the sensor may be multiplexed and digitized. The Doppler shift in the light may be analyzed by looking at the source laser light in comparison to the Doppler shifted light. A greater Doppler shift and speckle may be related to a greater number of blood cells and their velocity in the blood vessel.

Figure 29:
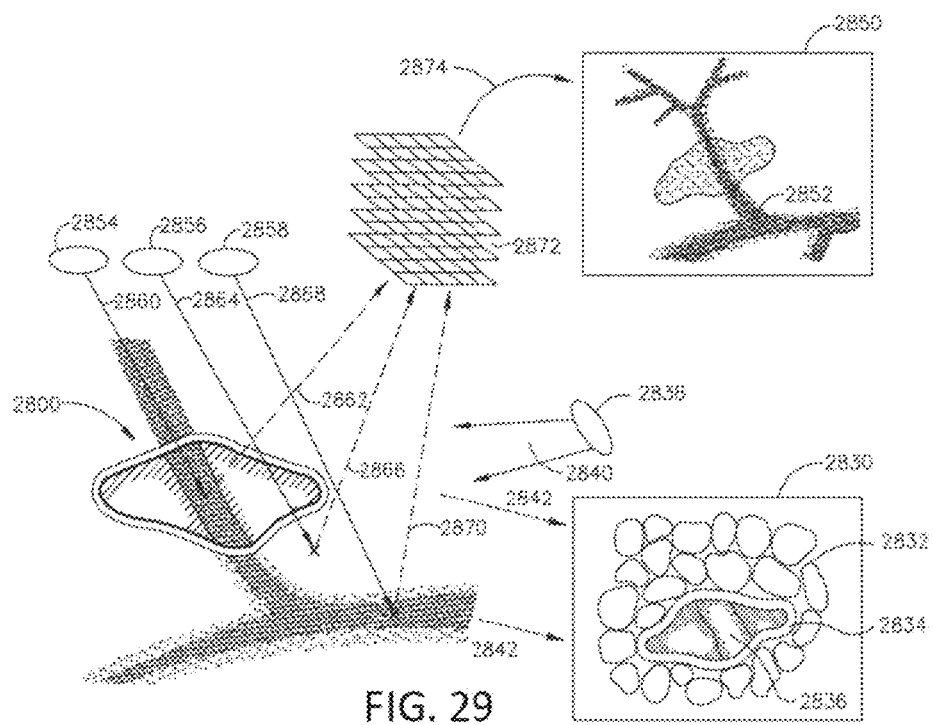
FIG. 29 illustrates an example composite image comprising a surface image and an image of a subsurface blood vessel.

FIG. 29 depicts an aspect of a composite visual display 2800 that may be presented a surgeon during a surgical procedure. The composite visual display 2800 may be constructed by overlaying a white light image 2830 of the surgical site with a Doppler analysis image 2850.

In some aspects, the white light image 2830 may portray the surgical site 2832, one or more surgical incisions 2834, and the tissue 2836 readily visible within the surgical incision 2834. The white light image 2830 may be generated by illuminating 2840 the surgical site 2832 with a white light source 2838 and receiving the reflected white light 2842 by an optical detector. Although a white light source 2838 may be used to illuminate the surface of the surgical site, in one aspect, the surface of the surgical site may be visualized using appropriate combinations of red 2854, green 2856, and blue 2858 laser light as disclosed above with respect to FIGS. 17C-F.

In some aspects, the Doppler analysis image 2850 may include blood vessel depth information along with blood flow information 2852 (from speckle analysis). As disclosed above, blood vessel depth and blood flow velocity may be obtained by illuminating the surgical site with laser light of multiple wavelengths, and determining the blood vessel depth and blood flow based on the known penetration depth of the light of a particular wavelength. In general, the surgical site 2832 may be illuminated by light emitted by one or more lasers such as a red leaser 2854, a green laser 2856, and a blue laser 2858. A CMOS detector 2872 may receive the light reflected back (2862, 2866, 2870) from the surgical site 2832 and its surrounding tissue. The Doppler analysis image 2850 may be constructed 2874 based on an analysis of the multiple pixel data from the CMOS detector 2872.

In one aspect, a red laser 2854 may emit red laser illumination 2860 on the surgical site 2832 and the reflected light 2862 may reveal surface or minimally subsurface structures. In one aspect, a green laser 2856 may emit green laser illumination 2864 on the surgical site 2832 and the reflected light 2866 may reveal deeper subsurface characteristics. In another aspect, a blue laser 2858 may emit blue laser illumination 2868 on the surgical site 2832 and the reflected light 2870 may reveal, for example, blood flow within deeper vascular structures. In addition, the speckle contrast analysis my present the surgeon with information regarding the amount and velocity of blood flow through the deeper vascular structures.

Although not depicted in FIG. 29, it may be understood that the imaging system may also illuminate the surgical site with light outside of the visible range. Such light may include infra red light and ultraviolet light. In some aspects, sources of the infra red light or ultraviolet light may include broad-band wavelength sources (such as a tungsten source, a tungsten-halogen source, or a deuterium source). In some other aspects, the sources of the infra red or ultraviolet light may include narrow-band wavelength sources (IR diode lasers, UV gas lasers or dye lasers).

Figure 30:
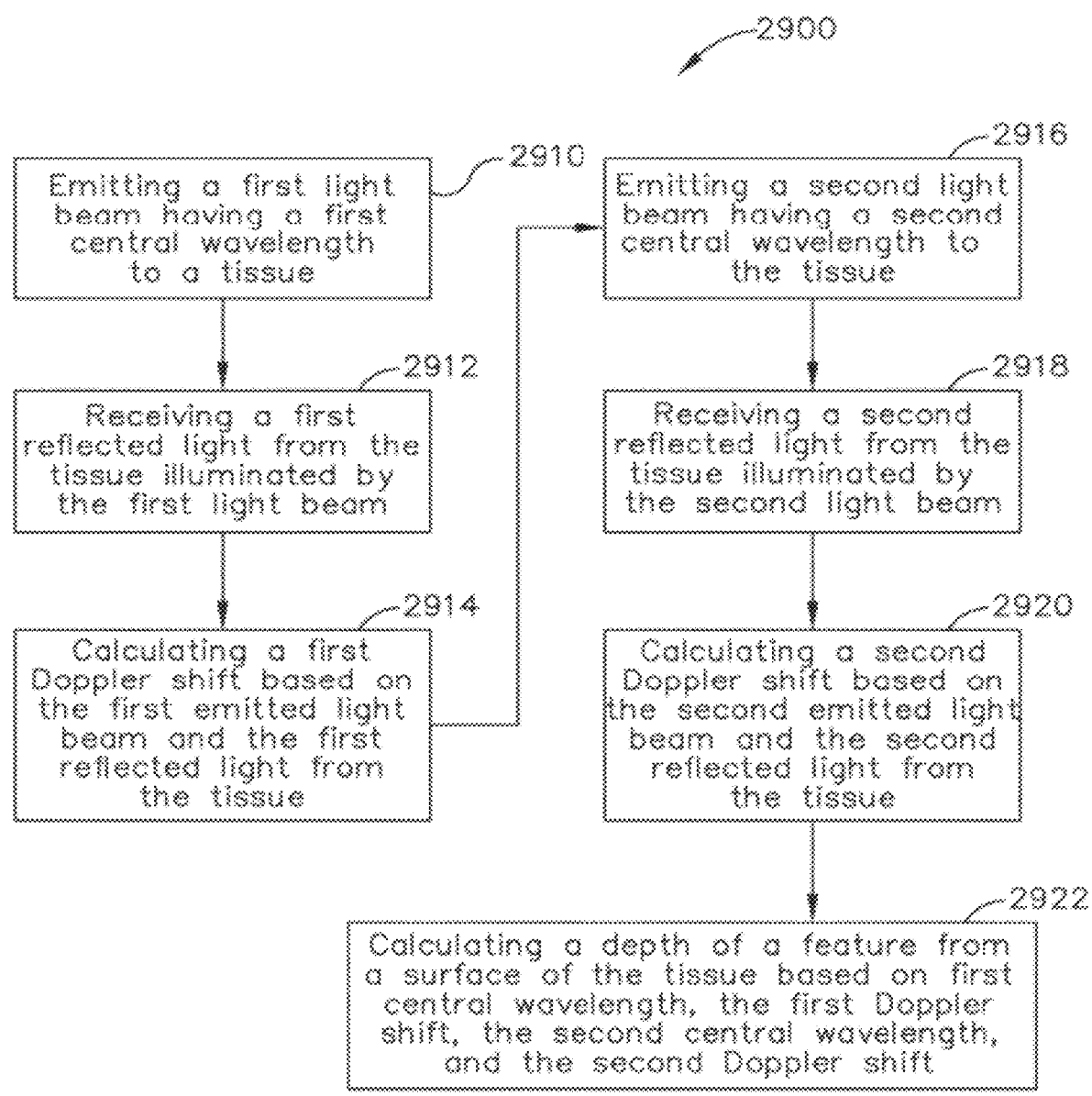
FIG. 30 illustrates an example method for determining a depth of a surface feature in a piece of tissue.

FIG. 30 is a flow chart 2900 of a method for determining a depth of a surface feature in a piece of tissue. An image acquisition system may illuminate 2910 a tissue with a first light beam having a first central frequency and receive 2912 a first reflected light from the tissue illuminated by the first light beam. The image acquisition system may then calculate 2914 a first Doppler shift based on the first light beam and the first reflected light. The image acquisition system may then illuminate 2916 the tissue with a second light beam having a second central frequency and receive 2918 a second reflected light from the tissue illuminated by the second light beam. The image acquisition system may then calculate 2920 a second Doppler shift based on the second light beam and the second reflected light. The image acquisition system may then calculate 2922 a depth of a tissue feature based at least in part on the first central wavelength, the first Doppler shift, the second central wavelength, and the second Doppler shift. In some aspects, the tissue features may include the presence of moving particles, such as blood cells moving within a blood vessel, and a direction and velocity of flow of the moving particles. It may be understood that the method may be extended to include illumination of the tissue by any one or more additional light beams. Further, the system may calculate an image comprising a combination of an image of the tissue surface and an image of the structure disposed within the tissue.

In some aspects, multiple visual displays may be used. For example, a 3D display may provide a composite image displaying the combined white light (or an appropriate combination of red, green, and blue laser light) and laser Doppler image. Additional displays may provide only the white light display or a displaying showing a composite white light display and an NIRS display to visualize only the blood oxygenation response of the tissue. However, the NIRS display may not be required every cycle allowing for response of tissue.

Subsurface Tissue Characterization Using Multispectral OCT

During a surgical procedure, the surgeon may employ "smart" surgical devices for the manipulation of tissue. Such devices may be considered "smart" in that they include automated features to direct, control, and/or vary the actions of the devices-based parameters relevant to their uses. The parameters may include the type and/or composition of the tissue being manipulated. If the type and/or composition of the tissue being manipulated is unknown, the actions of the smart devices may be inappropriate for the tissue being manipulated. As a result, tissues may be damaged or the manipulation of the tissue may be ineffective due to inappropriate settings of the smart device.

The surgeon may manually attempt to vary the parameters of the smart device in a trial-and-error manner, resulting in an inefficient and lengthy surgical procedure.

Therefore, it is desirable to have a surgical visualization system that can probe tissue structures underlying a surgical site to determine their structural and compositional characteristics, and to provide such data to smart surgical instruments being used in a surgical procedure.

Some aspects of the present disclosure further provide for a control circuit configured to control the illumination of a surgical site using one or more illumination sources such as laser light sources and to receive imaging data from one or more image sensors. In some aspects, the present disclosure provides for a non-transitory computer readable medium storing computer readable instructions that, when executed, cause a device to characterize structures below the surface at a surgical site and determine the depth of the structures below the surface of the tissue.

In some aspects, a surgical image acquisition system may comprise a plurality of illumination sources wherein each illumination source is configured to emit light having a specified central wavelength, a light sensor configured to receive a portion of the light reflected from a tissue sample when illuminated by the one or more of the plurality of illumination sources, and a computing system. The computing system may be configured to receive data from the light sensor when the tissue sample is illuminated by each of the plurality of illumination sources, calculate structural data related to a characteristic of a structure within the tissue sample based on the data received by the light sensor when the tissue sample is illuminated by each of the illumination sources, and transmit the structural data related to the characteristic of the structure to be received by a smart surgical device. In some aspects, the characteristic of the structure is a surface characteristic or a structure composition.

In one aspect, a surgical system may include multiple laser light sources and may receive laser light reflected from a tissue. The light reflected from the tissue may be used by the system to calculate surface characteristics of components disposed within the tissue. The characteristics of the components disposed within the tissue may include a composition of the components and/or a metric related to surface irregularities of the components.

In one aspect, the surgical system may transmit data related to the composition of the components and/or metrics related to surface irregularities of the components to a second instrument to be used on the tissue to modify the control parameters of the second instrument.

In some aspects, the second device may be an advanced energy device and the modifications of the control parameters may include a clamp pressure, an operational power level, an operational frequency, and a transducer signal amplitude.

As disclosed above, blood vessels may be detected under the surface of a surgical site base on the Doppler shift in light reflected by the blood cells moving within the blood vessels.

Laser Doppler flowmetry may be used to visualize and characterized a flow of particles moving relative to an effectively stationary background. Thus, laser light scattered by moving particles, such as blood cells, may have a different wavelength than that of the original illuminating laser source. In contrast, laser light scattered by the effectively stationary background (for example, the vascular tissue) may have the same wavelength of that of the original illuminating laser source. The change in wavelength of the scattered light from the blood cells may reflect both the direction of the flow of the blood cells relative to the laser source as well as the blood cell velocity. As previously disclosed, FIGS. 20A-C illustrate the change in wavelength of light scattered from blood cells that may be moving away from (FIG. 20A) or towards (FIG. 20C) the laser light source.

In each of FIGS. 20A-C, the original illuminating light 2502 is depicted having a relative central wavelength of 0. It may be observed from FIG. 20A that light scattered from blood cells moving away from the laser source 2504 has a wavelength shifted by some amount 2506 to a greater wavelength relative to that of the laser source (and is thus red shifted). It may also be observed from FIG. 18C that light scattered from blood cells moving towards from the laser source 2508 has a wavelength shifted by some amount 2510 to a shorter wavelength relative to that of the laser source (and is thus blue shifted). The amount of wavelength shift (for example 2506 or 2510) may be dependent on the velocity of the motion of the blood cells. In some aspects, an amount of a red shift (2506) of some blood cells may be about the same as the amount of blue shift (2510) of some other blood cells. Alternatively, an amount of a red shift (2506) of some blood cells may differ from the amount of blue shift (2510) of some other blood cells Thus, the velocity of the blood cells flowing away from the laser source as depicted in FIG. 24A may be less than the velocity of the blood cells flowing towards the laser source as depicted in FIG. 20C based on the relative magnitude of the wavelength shifts (2506 and 2510). In contrast, and as depicted in FIG. 20B, light scattered from tissue not moving relative to the laser light source (for example blood vessels 2512 or non-vascular tissue 2514) may not demonstrate any change in wavelength.

As previously disclosed, FIG. 21 depicts an aspect of instrumentation 2530 that may be used to detect a Doppler shift in laser light scattered from portions of a tissue 2540. Light 2534 originating from a laser 2532 may pass through a beam splitter 2544. Some portion of the laser light 2536 may be transmitted by the beam splitter 2544 and may illuminate tissue 2540. Another portion of the laser light may be reflected 2546 by the beam splitter 2544 to impinge on a detector 2550. The light back-scattered 2542 by the tissue 2540 may be directed by the beam splitter 2544 and also impinge on the detector 2550. The combination of the light 2534 originating from the laser 2532 with the light back-scattered 2542 by the tissue 2540 may result in an interference pattern detected by the detector 2550. The interference pattern received by the detector 2550 may include interference fringes resulting from the combination of the light 2534 originating from the laser 2532 and the Doppler shifted (and thus wavelength shifted) light back-scattered 2452 from the tissue 2540.

It may be recognized that back-scattered light 2542 from the tissue 2540 may also include back scattered light from boundary layers within the tissue 2540 and/or wavelength-specific light absorption by material within the tissue 2540. As a result, the interference pattern observed at the detector 2550 may incorporate interference fringe features from these additional optical effects and may therefore confound the calculation of the Doppler shift unless properly analyzed.

It may be recognized that light reflected from the tissue may also include back scattered light from boundary layers within the tissue and/or wavelength-specific light absorption by material within the tissue. As a result, the interference pattern observed at the detector may incorporate fringe features that may confound the calculation of the Doppler shift unless properly analyzed.

As previously disclosed, FIG. 22 depicts some of these additional optical effects. It is well known that light traveling through a first optical medium having a first refractive index, n1, may be reflected at an interface with a second optical medium having a second refractive index, n2. The light transmitted through the second optical medium will have a transmission angle relative to the interface that differs from the angle of the incident light based on a difference between the refractive indices n1 and n2 (Snell's Law). FIG. 20 illustrates the effect of Snell's Law on light impinging on the surface of a multi-component tissue 2150, as may be presented in a surgical field. The multi-component tissue 2150 may be composed of an outer tissue layer 2152 having a refractive index n1 and a buried tissue, such as a blood vessel having a vessel wall 2156. The blood vessel wall 2156 may be characterized by a refractive index n2. Blood may flow within the lumen of the blood vessel 2160. In some aspects, it may be important during a surgical procedure to determine the position of the blood vessel 2160 below the surface 2154 of the outer tissue layer 2152 and to characterize the blood flow using Doppler shift techniques.

An incident laser light 2170a may be used to probe for the blood vessel 2160 and may be directed on the top surface 2154 of the outer tissue layer 2152. A portion 2172 of the incident laser light 2170a may be reflected at the top surface 2154. Another portion 2170b of the incident laser light 2170a may penetrate the outer tissue layer 2152. The reflected portion 2172 at the top surface 2154 of the outer tissue layer 2152 has the same path length of the incident light 2170a, and therefore has the same wavelength and phase of the incident light 2170a. However, the portion 2170b of light transmitted into the outer tissue layer 2152 will have a transmission angle that differs from the incidence angle of the light impinging on the tissue surface because the outer tissue layer 2152 has an index of refraction n1 that differs from the index of refraction of air.

If the portion of light transmitted through the outer tissue layer 2152 impinges on a second tissue surface 2158, for example of the blood vessel wall 2156, some portion 2174a,b of light will be reflected back towards the source of the incident light 2170a. The light thus reflected 2174a at the interface between the outer tissue layer 2152 and the blood vessel wall 2156 will have the same wavelength as the incident light 2170a, but will be phase shifted due to the change in the light path length. Projecting the light reflected 2174a,b from the interface between the outer tissue layer 2152 and the blood vessel wall 2156 along with the incident light on the sensor, will produce an interference pattern based on the phase difference between the two light sources.

Further, a portion of the incident light 2170c may be transmitted through the blood vessel wall 2156 and penetrate into the blood vessel lumen 2160. This portion of the incident light 2170c may interact with the moving blood cells in the blood vessel lumen 2160 and may be reflected back 2176a-c towards the source of the impinging light having a wavelength Doppler shifted according to the velocity of the blood cells, as disclosed above. The Doppler shifted light reflected 2176a-c from the moving blood cells may be projected along with the incident light on the sensor, resulting in an interference pattern having a fringe pattern based on the wavelength difference between the two light sources.

In FIG. 22, a light path 2178 is presented of light impinging on the red blood cells in the blood vessel lumen 2160 if there are no changes in refractive index between the emitted light and the light reflected by the moving blood cells. In this example, only a Doppler shift in the reflected light wavelength can be detected. However, the light reflected by the blood cells (2176*a-c*) may incorporate phase changes due to the variation in the tissue refractive indices in addition to the wavelength changes due to the Doppler Effect.

Thus, it may be understood that if the light sensor receives the incident light, the light reflected from one or more tissue interfaces (2172, and 2174*a,b*) and the Doppler shifted light from the blood cells (2176*a-c*), the interference pattern thus produced on the light sensor may include the effects due to the Doppler shift (change in wavelength) as well as the effects due to the change in refractive index within the tissue (change in phase). As a result, a Doppler analysis of the light reflected by the tissue sample may produce erroneous results if the effects due to changes in the refractive index within the sample are not compensated for.

As previously disclosed, FIG. 23 illustrates an example of the effects on a Doppler analysis of light that impinge 2250 on a tissue sample to determine the depth and location of an underlying blood vessel. If there is no intervening tissue between the blood vessel and the tissue surface, the interference pattern detected at the sensor may be due primarily to the change in wavelength reflected from the moving blood cells. As a result, a spectrum 2252 derived from the interference pattern may generally reflect only the Doppler shift of the blood cells. However, if there is intervening tissue between the blood vessel and the tissue surface, the interference pattern detected at the sensor may be due to a combination of the change in wavelength reflected from the moving blood cells and the phase shift due to the refractive index of the intervening tissue. A spectrum 2254 derived from such an interference pattern, may result in the calculation of the Doppler shift that is confounded due to the additional phase change in the reflected light. In some aspects, if information regarding the characteristics (thickness and refractive index) of the intervening tissue is known, the resulting spectrum 2256 may be corrected to provide a more accurate calculation of the change in wavelength.

It may be recognized that the phase shift in the reflected light from a tissue may provide additional information regarding underlying tissue structures, regardless of Doppler effects.

A surgical visualization systems using the imaging technologies disclosed herein may benefit from ultrahigh sampling and display frequencies. Sampling rates may be associated with the capabilities of the underlying device performing the sampling. A general-purpose computing system with software may be associated with a first range of achievable sampling rates. A pure-hardware implementation (e.g., a dedicated application specific integrated circuit, ASIC) may be associated with a second range of achievable sampling rates. The second range, associated with the pure-hardware implementation, will generally be higher (e.g., much higher) than the first range, associated with general-purpose computing software implementation.

A surgical visualization systems using the imaging technologies disclosed herein may benefit from adaptable and/or updatable imaging algorithms (such as transforms and imaging processing for example). A general-purpose computing system with software may be associated with high degree of adaptability and/or upgradability. A pure-hardware implementation (e.g., a dedicated application specific integrated circuit, ASIC) may be associated with generally lower degree of adaptability and/or upgradability than that of general-purpose computing system with software. This may be due, in part, to the general ease at which software may be adapted and/or updated (which may include compiling and loading different software and/or updating modular components) compared to pure-hardware implementations (in which new hardware components are designed, built, added and/or swapped, physically).

A surgical visualization system using the imaging technologies disclosed herein may benefit from solutions that balance the higher sampling rates, associated with hardware-based implementations, with the adaptability and/or updatability of software systems. Such a surgical visualization systems may employ a mix of hardware and software solutions. For example, a surgical visualization system may employ various hardware-implemented transforms with a software selector. A surgical visualization system may also employ a field programmable gate array (FPGA). An FPGA may include a hardware device that may include one or more logic elements. These logic elements may be configured by a bitstream to implement various functions. For example, the logic elements may be configured to perform certain individual logic functions and configured to perform them with a certain order and interconnection. Once configured, the FPGA may perform its function using the hardware logic elements without further configuration. Also once configured, the FPGA may be reconfigured with a different bitstream to implement a different function. And similarly, once reconfigured, the FPGA may perform this different function using the hardware logic elements.

FIG. 31 illustrates an example surgical visualization system 10000. The surgical visualization system 10000 may be used to analyze at least a portion of a surgical field. For example, the surgical visualization system 10000 may be used to analyze tissue 10002 within the at least a portion of the surgical field. The surgical visualization system 10000 may include a field programmable gate array (FPGA) 10004, a processor (for example, a processor 10006 local to the FPGA 10004, a memory 10008, a laser-light illumination source 10010, a light sensor 10012, a display 10014, and/or a processor 10016 remote to the FGPA. The surgical visualization system 10000 may include components and functionality described in connection with FIGS. 16A-D for example.

The system 10000 may use an FPGA 10004 to convert the reflected laser light thru a transform of frequency to identify a Doppler shift, for example, of the light to determine moving particles. This transformed data may be displayed (e.g., displayed in real-time). It may be displayed, for example, as a graphic and/or metric 10020, representing the number of moving particles each second. The system 10000 may include communication between the processor 10006 local to the FPGA 10004 and the processor 10016 remote to the FGPA. For example, the processor 10016 remote to the FGPA 10004 may aggregate data (e.g., multiple seconds of data). And the system may be able to display that aggregation of data. For example, it may be displayed as a graphic and/or metric 10026 representing a moving trend. This graphic and/or metric 10026 may be superimposed on the real-time data. Such trend information may be used to identify occlusions, instrument vascular sealing/clamping efficiency, vascular tree overviews, even oscillating magnitudes of motion over time. The FPGA 10004 may be configured to be on-the-fly updateable, for example, updatable with different (e.g., more sophisticated) transformations. These updates may come from local or remote communication servers. These updates may, for example, change the transform's analysis from refractivity (e.g., analysis of cellular irregularities), to blood flow, to multiple simultaneous depth analysis, and the like.

The FPGA updates may include transforms that implement a variety of imaging options for the user. These imaging options may include standard combined visual light, tissue refractivity, doppler shift, motion artifact correction, improved dynamic range, improved local clarity, super resolution, NIR florescence, multi-spectral imaging, confocal laser endomicroscopy, optical coherence tomography, raman spectroscopy, photoacoustic imaging, or any combination. The imaging options may include any of the options presented in any of the following: U.S. patent application Ser. No. 15/940,742, entitled "DUAL CMOS ARRAY IMAGING," filed Mar. 29, 2018; U.S. patent application Ser. No. 13/952,564, entitled "WIDE DYNAMIC RANGE USING MONOCHROMATIC SENSOR," FILED Jul. 26, 2013; U.S. patent application Ser. No. 14/214,311, entitled "SUPER RESOLUTION AND COLOR MOTION ARTIFACT CORRECTION IN A PULSED COLOR IMAGING SYSTEM," filed Mar. 14, 2014; U.S. patent application Ser. No. 13/952,550, entitled "CAMERA SYSTEM WITH MINIMAL AREA MONOLITIC CMOS IMAGE SENSOR," filed Jul. 26, 2013, each of which is incorporated herein by reference in its entirety. Doppler wavelength shifting may be used to identify the number, size, speed, and/or directionality of moving particles, for example. Doppler wavelength shifting may be used with multiple laser wavelengths to interrelate the tissue depth and moving particles, for example. Tissue refractivity may be used for identification of irregular or variability of tissue superficial and sub-surface aspects, for example. In surgical practice, it may benefit identifying tumor margins, infection, broken surface tissue, adhesions, changes in tissue composition, and the like. NIR fluorescence may include techniques in which systemically-injected drugs are preferentially absorbed by targeted tissue. When illuminated with the appropriate wavelength of light, they fluoresce and can be imaged through a NIR-capable scope/camera. Hyperspectral imaging and/or multispectral imaging may include the illumination and assessment of tissue across many wavelengths throughout the electromagnetic spectrum to provide real-time images. It may be used to differentiate between target tissues. It may also enable an imaging depth of 0-10 mm for example. Confocal laser endomicroscopy (CLE) may uses light to capture high-resolution, cellular level resolution without penetrating into tissue. It may provide a real-time histopathology of tissue. Technology that uses light to capture micrometer-resolution, 3D images from within tissues. Optical coherence tomography (OCT) may employ NIR light. OCT may enable imaging of tissue at depths of 1-2 mm, for example. Raman spectroscopy may include techniques that measure photon shifts caused by monochromatic laser illumination of tissue. It may be used to identify certain molecules. Photoacoustic imaging may include subjecting tissue to laser pulses such that a portion of the energy causes thermoelastic expansion and ultrasonic emission. These resulting ultrasonic waves may be detected and analyzed to form images.

These updates could be automatic based on user input or system compatibility checks. These real-time, aggregation, and updateable features of the system 10000 may be selectively enabled based on any aspect of the system's configuration, for example system capacity, power availability, free memory access, communication capacity, software level, tiered purchase levels, and/or the like.

The laser-light illumination source 10010 may include any illumination source of laser light suitable for analyzing human tissue. The laser-light illumination source 10010 may include a device such as the source laser emitters illustrated in FIGS. 17A-F, for example. The laser light illumination source 10010 may use one or more wavelengths of laser light to illuminate the tissue 10002. For example, the laser-light illumination source 10010 may use a red-blue-green-ultraviolet 1-ultraviolet 2-infrared combination. This combination with a 360-480 Hz sampling and actuation rate, for example, would allow for each light source to have multiple frames at an end user 60 Hz combined frame rate. A laser light wavelength combination with independent sources may increase resolution from a single array and may enable various depth penetration.

The tissue 10002 may be human tissue within a portion of a surgical field, for example. The laser light may reflect from the tissue 10002, resulting in reflected laser light. The reflected laser light may be received by the light sensor 10012. The light sensor 10012 may be configured to receive reflected laser light from a least a portion of the surgical field. The light sensor 10012 may be configured to receive laser light from the entirety of the surgical field. The light sensor may be configured to receive reflected laser light from a selectable portion of the surgical field. For example, a user, such as a surgeon, may direct the light sensor and the light laser light illumination source and/or the laser light illumination source to analyze specific portions of the surgical field.

The light sensor 10012 may be any device suitable for sensing reflected laser light and outputting corresponding information. For example, the light sensor 10012 may detect one or more characteristics of the reflected laser light, such as amplitude, frequency, wavelength, doppler shift, and/or other time domain or frequency domain qualities, for example. The laser-light sensor 10012 source may include a device such as the light sensor disclosed in connection with FIGS. 16A-D for example.

The laser-light sensor 10012 may include one or more sensor modules 10013. The sensor modules 10013 may be configured to measure a wide range of wavelengths. The sensor modules 10013 may be tuned and/or filtered to measure specific wavelengths for example. The sensor modules 10013 may include discrete sensors, a collection of sensors, a sensor array, a combination of sensor arrays, or the like, for example. For example, the sensor modules 10013 may include semiconductor components such as photodiodes, CMOS (complementary metal oxide semiconductor) image sensors, CCD (charge coupled device) image sensors, or the like.

The laser-light sensor 10012 may include a dual CMOS arrays. FIG. 31B shows an example laser-light sensor 10030. The laser-light sensor 10030 may include two sensor modules 10032, 10034. The sensor modules 10032, 10034 may be implemented as a dual side-by-side CMOS arrays. For example, the laser-light sensor 10030 be incorporated into the form factor of a surgical scope 10031 (e.g., a 7 mm diameter surgical scope) with two sensor modules 10032, 10034 (e.g., 2 side-by-side 4 mm sensors). The laser-light sensor 10030 may be configured to enable shifting between and/or among imaging modes. The modes may include three-dimensional stereoscopic and two-dimensional, simultaneous imaging (e.g., visual imaging together with imaging for refractivity analysis and/or Doppler analysis), for example. The modes may include imaging with a narrower or broader visualization range, for example. The modes may include imaging with lower or higher resolution and/or artifact correction, for example. The sensor modules 10032, 10034 may include different types of sensors. For example, a first sensor module 10032 may be a CMOS device. And the second sensor module 10034 may be a different CMOS device. The difference in CMOS devices may enable greater diversity of light collection capabilities. For example, different CMOS devices may enable broader light contrast and/or better light collection. For example, the first sensor array 10032 may have a higher quantity of pixel detectors relative to the second sensor array 10034. The surgical scope 10031 may include one or more light sources 10036, such as laser-light illumination sources for example.

FIG. 31C is a graphical representation of an example operation of a pixel array for a plurality of frames. Sensor modules (such as CMOS sensor modules, for example) may incorporate a pattern and/or technique for light sensing. The light sensing technique associated with operation of the sensor modules may incorporate filtering. The light sensing technique associated with the sensor modules may incorporate strobing of the light source. Examples of these techniques may include those disclosed herein in association with FIGS. 17C and 17D for example. A pattern of strobing light source may be used in connection with the sensor modules to measure the reflected light and to generate information indicative of the reflected light. Pixel arrays may be captured by rapidly strobing the visualized area at high speed with a variety of optical sources (either laser or light-emitting diodes) having different central optical wavelengths.

The strobing may cause the sensor to capture a respective pixel array associated with a corresponding wavelength. For example, in a first pattern 10038 red, green, and blue, and infrared (near-infrared for example) wavelength light may be strobed. Such a strobing may cause the sensor to capture a first pixel 10040 array of associated with the red wavelength, a second pixel array 10042 associated with the green wavelength, a third pixel array 10044 associated with the blue wavelength, a fourth pixel array 4046 associated with the green wavelength, a fifth pixel array 10048 associated with the infrared (near-infrared for example) wavelength, a sixth pixel array 10050 associated with the green wavelength, and a seventh pixel 10052 array associated with the blue wavelength, for example. For example, in a second pattern 10054 red, green, and blue, and infrared (near-infrared for example) wavelength light may be strobed. Such a strobing may cause the sensor to capture a eighth pixel 10056 array of associated with the red wavelength, a ninth pixel array 10058 associated with the green wavelength, a tenth pixel array 10060 associated with the blue wavelength, a eleventh pixel array 10062 associated with the green wavelength, a twelfth pixel array 10064 associated with the ultraviolet wavelength, a thirteenth pixel array 10066 associated with the green wavelength, and a fourteenth pixel array 10068 associated with the blue wavelength, for example.

Patterns, such as first pattern 10038 and second pattern 10054 for example, may be associated with one or more sensor modules. Patterns, such as first pattern 10038 and second pattern 10054 for example, may be associated with a mode of operation, as disclosed herein. Patterns, such as first pattern 10038 and second pattern 10054 for example, may be operated serially. Patterns, such as first pattern 10038 and second pattern 10054 for example, may be operated in parallel (with appropriate blanking for example). Patterns, such as first pattern 10038 and second pattern 10054 for example, may each be associated with a respective sensor module. Patterns, such as first pattern 10038 and second pattern 10054 for example, may be associated with sensor modules jointly.

Figure 31A:
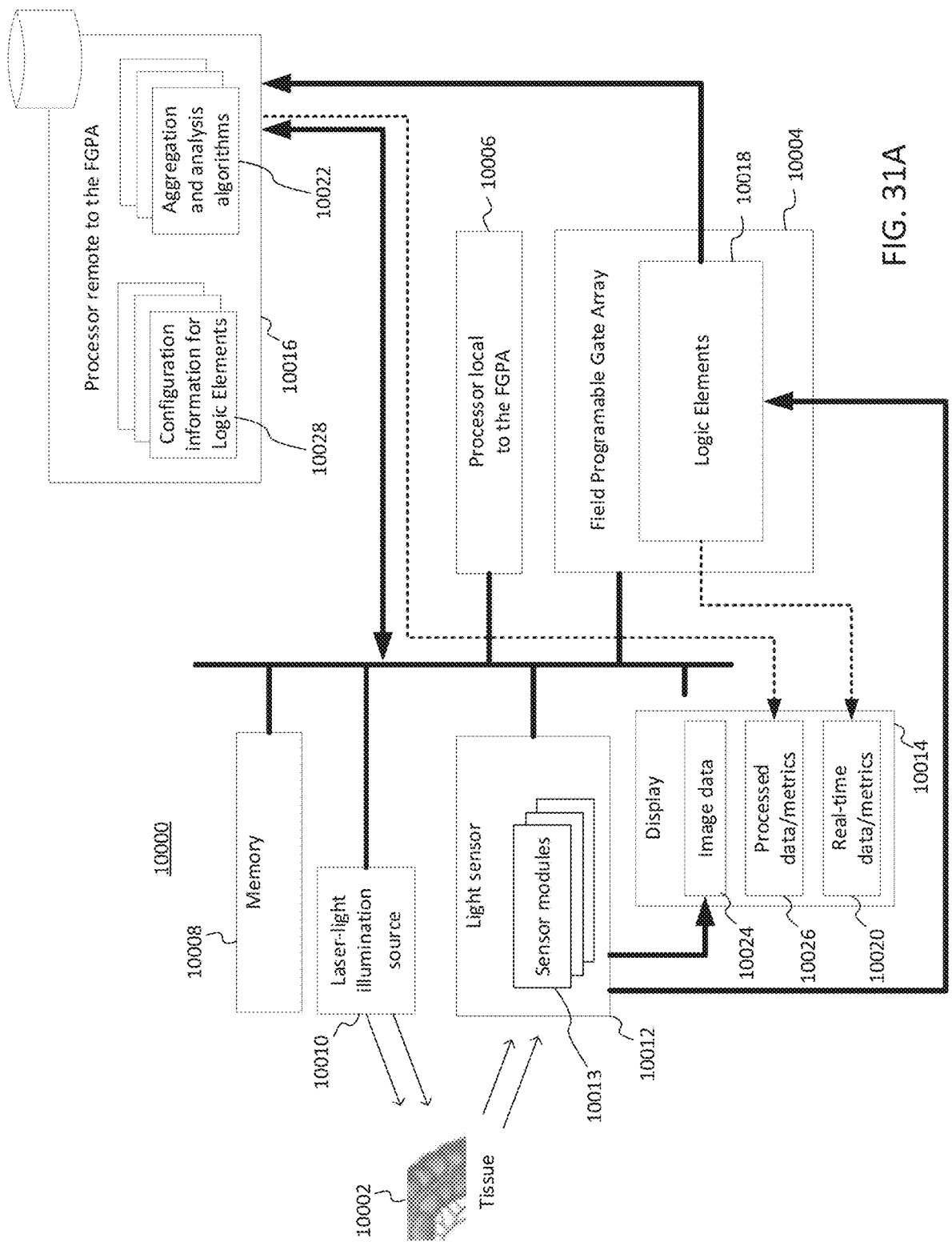
FIG. 31A illustrates an example visualization system.

As shown in FIG. 31A, the information collected by the light sensor 10012 may be communicated to the FPGA 10004. The FPGA 10004 may include any updatable gate array device suitable for analyzing data from a light sensor 10012. The FPGA 10004 may include one or more logic elements 10018. The logic elements 10018 may be configured to perform a transform on the incoming information. The FPGA 10004 may include an output suitable for passing analyzed and/or processed data representative of the tissue to the processor remote to the FPGA 10016 and/or the display 10014.

For example, the logic elements 10018 of the FPGA 10004 may provide information that may be passed to the display 10014 and displayed as a real-time data or a metric 10020 representative of a transform of reflected laser light information received by the light sensor 10012. The transform may include any mathematical and/or logical operation to transform data received from the light sensor 10012 to information indicative of partial motion. For example, the transform may include a Fast Fourier Transform (FFT).

The logic elements 10018 of the FGPA 10004 may provide a real-time data or metric 10020 to the display 10014 directly and/or in concert with the processor 10006 local to the field programmable gate array, for example. The real-time data and/or metric 10020 may include a representation of the motion of particles, such as particles per second for example. The real-time data and/or metric 10020 may be displayed on the display 10014. The real-time data and/or metric 10020 may be displayed as superimposed over a visualization of the tissue 10002.

For example, the logic elements 10018 of the FPGA 10004 may provide information that may be passed to the processor 10016 remote to the FPGA 10004 for aggregation and/or processing. The processor 10016 remote to the FPGA 10004 may provide an aggregation and analysis of this data. For example, the processor 10016 remote to the FPGA 10004 may provide running averages and other aggregation techniques. The processor 10016 remote to the FPGA 10004 may develop time aggregated data with variable time granularity. For example, the processor 10016 remote to the FPGA 10004 may aggregate several seconds of data from the field programmable gate array 10004. The processor 10016 remote to the FPGA 10004 may include other algorithms 10022 suitable for aggregating and analyzing data, such as least-squares regression techniques, polynomial fit techniques, other statistics such as average, mean, mode, max, min, variance and/or the like. The processor 10016 remote to the FPGA 10004 may include correlation algorithms correlating data received from the light sensor 10012 and/or data transformed by the FPGA 10004 with other aspects of the surgery, including for example, situational awareness data, procedure state, medical information, patient outcomes, other aggregated data such as adverse events like bleeding events. The processor 10016 remote to the FPGA 10004 may include certain artificial intelligence and/or machine learning-based algorithms. For example, previously acquired data may be used as a training set to one or more artificial intelligence and/or machine learning algorithms to provide further correlation between various surgical events and input received from the light sensor 10012 and input transformed by the FPGA 10004. Information resulting from an aggregation and analysis algorithm may be sent to the display 10014 (for example, sent in concert with the processor 10006 local to the FPGA 10004) for display to the user.

The display 10014 may include any device suitable for displaying information to a user. The display 10014 may include monitor 135 in connection with FIG. 3, for example. For example, display 10014 may include a traditional computer monitor. For example, the display 10014 may include any device suitable for displaying image and/or text data to a user. For example, the display 10014 may display image data 10024 received from the light sensor 10012 and/or other image sensors to depict a visual representation of the tissue 10002. The display 10014 may also be suitable for providing contextual information to the user including one or more displayed data elements. The data elements may include numerical or graphical representations of data and/or metrics. For example, the metrics may include one or more numbers accompanied by a graphical representation of the units. For example, the display 10014 may display a real-time metric 10020, such as the number of particles per second being detected according to the output of the FPGA 10004, for example. The display 10014 may display a processed metric 10026 (such as the rate of change of particles per second as determined over duration of time, for example) from an aggregation and analysis algorithm of the processor 10016 remote to the FPGA 10006.

The processor 10006 included local to the FPGA 10004 may include any device suitable for handling control processing of the surgical visualization system 10000. For example, the processor 10006 local to the FPGA may include a microprocessor, a microcontroller, a FPGA, and an application-specific integrated circuit (ASIC), a system-on-a-chip (SOIC), a digital signal processing (DSP) platform, a real-time computing system, or the like.

The processor 10006 local to the FPGA 10004 may provide control operation of any of the subcomponents of the surgical visualization system 10000. For example, the processor 10006 local to the FPGA 10004 may control operation of the laser light illumination source 10010. The processor 10006 local to the FPGA 10004 may provide timing for various laser light sequences, for example. The processor 10006 local to the FPGA 10004 may provide a modulation of frequency and/or amplitude of the laser light illumination source, for example. The processor 10006 local to the FPGA 10004 may direct the laser light illumination source to illuminate in any of the techniques disclosed in FIGS. 17A-F for example.

The processor 10006 local to the FPGA 10004 may be suitable for controlling operation of the light sensor 10012. For example, the processor 10006 local to the FPGA 10004 may direct the light sensor 10012 to provide certain sequences of shuttering such that certain light sensors are turned on or off at certain times for example. The processor 10006 local to the FPGA 10004 direct certain configurations of the light sensor 10012, such as local exposure, contrast, resolution, bandwidth, field-of-view, and imaging processing, for example.

The processor 10006 local to the FPGA 10004 may provide an internal networking function to direct dataflow between components of the surgical visualization system. For example, the processor 10006 local to the FPGA 10004 may direct data received from the light sensor 10012 to the FPGA 10004. The processor 10006 local to the FPGA 10004 may provide a switching fabric and/or direct a switching fabric to enable the appropriate communication of data from the light sensor 10012 to one or more logic elements 10018 of the FPGA 10004.

The processor 10006 local to the FPGA 10004 may control all or part of the operation of the display 10014. For example, the processor 10006 local to the FPGA 10004 may provide instructions for certain image data 10024, processed data and/or metrics 10026, and/or real-time data and/or metrics 10020 to be displayed on the display 10014.

The processor 10006 local to the FPGA 10004 may receive information from a user interface (not depicted in the figure). For example, processor 10006 local to the FPGA 10004 may receive certain selections of areas of interest on the image data 10024. To illustrate, if a surgeon were interested in the flow of particles in a specific area of the surgical field, the surgeon may select an area of interest on the display using a user interface (e.g., a keyboard and mouse) and processor 10006 local to the FPGA 10004 would respond accordingly. For example, by causing the surgical visualization system to determine and display one or more metrics associated with the selection made by the surgeon.

The processor 10006 local to the FPGA 10004 and/or the processor 10016 remote to the FPGA 10004 may operate either individually or in concert to enable configuration changes of the FPGA 10004. For example, the FPGA 10004 may include a first arrangement of logic elements to perform a first transform of the data. The FPGA 10004 may be configured to transition from the first arrangement of logic elements to a second arrangement of logic elements to perform a second transform of the data. For example, the processor 10006 local the FPGA 10004 and/or the processor 10016 remote to the FPGA 10004 may be suitable for adjusting, reconfiguring, and/or rearranging the arrangement or configuration of the logic elements 10018 of the FPGA 10004 such that the logic elements 10018 perform the second transform. The second transform may be different than the first transform. The second transform may be variant of the first transform. To illustrate this feature, an example first transform may include a 32-point Cooly-Tukey Radix-2 implemented Fast Fourier Transform (FFT) using an 11-bit signed integer input and the second transform may include a 1024-point Cooly-Tukey Radix-2 implemented FFT using a 12-bit signed integer input.

Data representative of various configurations of logic elements 10028 implementing different transforms may be available to the surgical visualization system. For example, the processor 10016 remote to the FPGA 10004 may have stored in a database one or more configuration configurations of logic elements 10028. These configurations 10028 may be updated from time to time. These configurations 10028 may represent various transforms. These configurations 10028 may represent transforms requiring different levels of hardware and processing resources. For example, they may include transforms that may be implemented by less sophisticated FPGAs and/or more sophisticated FPGAs. The configuration information 10028 may include configurations for transforms associated with various procedures and/or tissues. For example, the configuration information 10028 may include newly developed transforms and/or transforms developed in accordance with an analysis of the aggregated data over time. To illustrate this aspect and in one example, certain transforms may be determined to be better predictors of bleeding events in certain surgical procedures; such correlations may be used to further refine said transforms and then to promote the use of said transforms when similar patient data and/or procedural data dictates.

The upgradability of the transform may be associated with a purchased functional tier (e.g., a purchased software tier). For example, a purchased functional tier may enable the FGPA 10004 to be updatable and/or may make certain transforms available to the surgical visualization system 10000. The purchased functional tier be associated with a hospital, an operating room, a surgeon, a procedure, set of instrumentation, and/or a specific instrument, for example.

To illustrate, a surgical visualization system 10000 may be installed at a hospital for use with a default transform. The default transform may include a generalized transform that is suitable for many procedures. Upon the purchase of an upgraded functional tier, the FPGA 10004 may be a reconfigured to implement an alternate transform, which may be more tailored for a specific procedure, tissue type, or surgeon's preference, for example.

Adaptive FPGA updates may enable variable overlays. Such overlays may include data and/or metrics from alternative sourced datasets. These datasets may be used to give context to the real-time particle movement and the aggregated trend data. For example, environment parameters may be controlled to affect blood flow and/or inflammation at a local surgical site. Monitoring the flow of fluids, the processor remote to the FPGA may recommend (or automatically alter, for example) room and/or patient settings. These setting changes may optimize the surgical location and/or improve device performance. For example, by monitoring the flow of blood, the user may receive visualization feedback to understand the outcome of an action (e.g., a staple and/or seal) prior to preforming. Settings such as an increase or decrease the body temperature, a raise/lower of bed angle, pressure and placement of compression cuffs, may be used, with visual feedback, to direct blood towards or away from a monitored location.

The memory 10008 may include any device suitable for storing and providing stored data. The memory may include read-only memory (ROM) and/or random-access memory (RAM). The memory 10008 may an include electrically erasable programmable read-only memory (EEPROM) for example. The memory 10008 may be suitable for an embedded system, for example. The memory 10008 be suitable for storing any intermediate data products in the operation of the surgical visualization system for example. The memory 10008 may be suitable for storing configuration information surgical visualization system, including one or more command parameters, and/or configuration information for the said logical elements. The memory 10008 may be suitable for storing system parameters. The memory 10008 may be suitable for providing one or more buffers, registers, and/or temporary storage of information.

Figure 32:
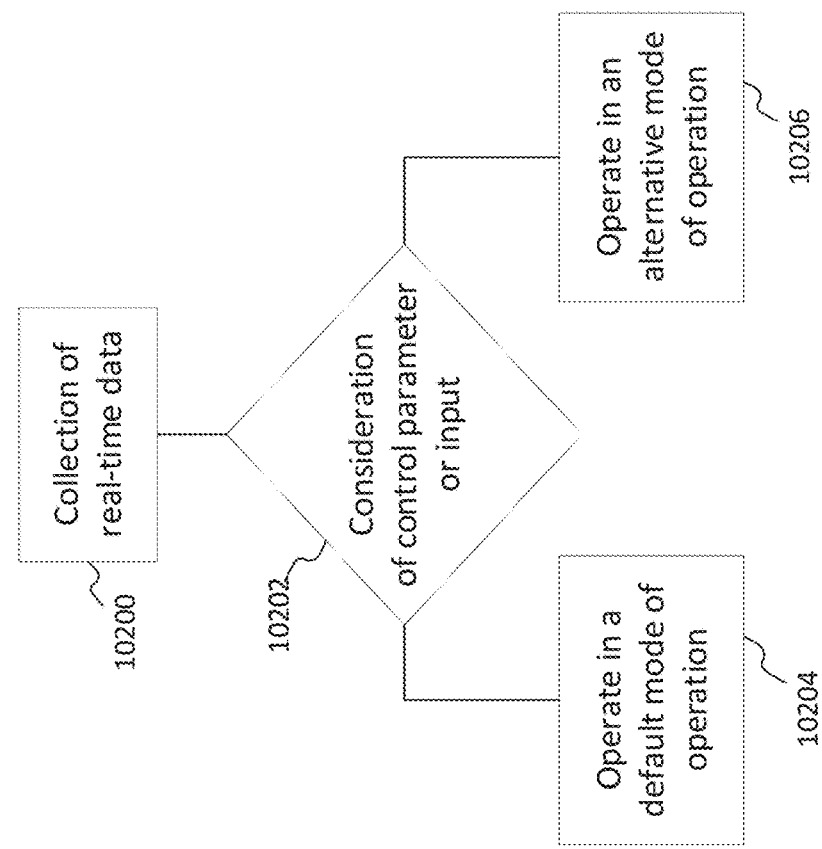
FIG. 32 illustrates an example method for determining an operating mode.

FIG. 32 illustrates an example method for determining an operating mode. At 10200 real-time data may be collected. For example, a surgical visualization system may collect real-time data associated with a tissue. For example, a laser light illumination source may illuminate a tissue resulting in a reflected laser light which may be sensed by a light sensor and transformed according to a transform implemented in an arrangement of logical elements in a Field Programmable Gate Array (FPGA). This collection of real-time data may be presented to a user. This collection of real-time data may be processed and/or stored and/or aggregated by a processor local to the field programmable gate array and/or a processor remote to the field programmable gate array for example.

At 10202, a control parameter and/or input may be considered for logical processing. For example, this consideration of a control parameter and/or input may be used to determine whether operation is to continue in a default mode of operation and/or an alternate mode of operation. For example, there may be determination of system lockout status on local processing and trending based on system parameters.

An input from the user and/or control parameter the control parameter may include any number of parameters or any information suitable for helping determine whether to operate in operation in a default mode or an alternate mode. For example, data exchange with a locally located control system may be used as a control parameter. For example, a local control system in two-way communication with remote system may be used. For example, the control parameter may include any of band with processing capability memory capability. The control parameter may include a purchasing of a software tier. The input may include the input from a user such as a surgeon to select an alternate transform rather than the default transform. For example, the input may be a user input selecting a portion of the surgical field for specific analysis for example. The control parameter and/or input may include a control parameter and input suitable for indicating the enablement of an aggregation and/or analysis of aggregated data.

The determination of whether to operate in a default mode or an alternate mode may include displaying to user max capabilities of the data. The determination of whether to operate in a default mode or an alternate mode may include a notification and confirmation interaction with the user via a display and user interface. In accordance with the determination of whether to operate in a default mode or an alternate mode, operation may continue at 10204 in a default mode or at 10206 in an alternate mode. For example, operation in a default mode of operation may include the collection and processing of real-time data according to a default transform. And, operation in an alternate mode of operation may include operating in accordance with a transform or a second transform or an alternate transform for the collection of real-time data for example.

In a surgical visualization system with light generation and an imaging sensor array, transform of detected light may transform that information into moving particle size, rate, and volume. The result of the transform may be displayed on a monitor. The default transform and/or the alternate transform may include various program parameters. Output from the default transform and/or the alternate transform may be coupled to exterior processing to determine trending and aggregation of data. Whether to operate in the default mode of operation and the alternate mode of operation may include a choice to display particle data, trending data, layered data, etc. The choice may be dependent on a system control parameter.

Figure 33:
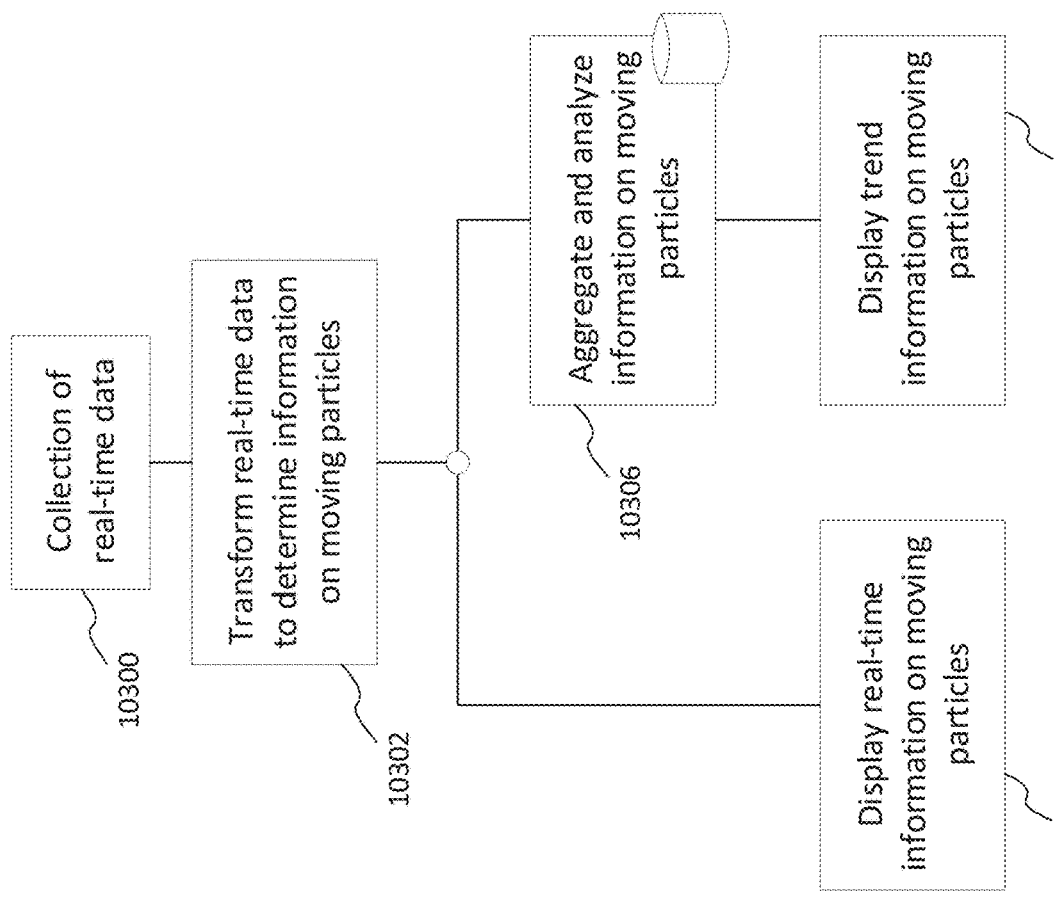
FIG. 33 illustrates an example method for displaying real-time and trending information to a user.

FIG. 33 illustrates an example method for displaying real-time and trending information to a user. The real-time transformations of the Doppler shift of a light wavelength may be exported to a processor component. The processor component may be capable of storing an amount of previous seconds of datasets. These datasets may be used as a reference to aggregate motion data into trending data. And, the trending data may be superimposed on a display to show both real-time movement and moving trends.

The moving trends may be compared with historic data (e.g., local historic data from previous minutes and/or hours within the same procedure, longer-term historic data), for example. The moving trends may be compared with data from local and/or external sources, for example. Comparisons may provide context of the trending, for example trending relative to a baseline. For example, comparisons may be made from the same patient at a different time. For example, comparisons may be made from one or more similar patients (e.g., patients with similar relevant traits). Comparisons may be used to inform surgeon decisions.

At 10300, real-time data may be collected. Laser light may be shown onto tissue in a surgical field and reflected back towards a light sensor. The real-time data may include data received by the light sensor. The real-time data may include a representation of the frequency and/or wavelength of the reflected light.

Moving particles in the surgical field may cause a Doppler shift in the wavelength of the reflected light. At 10302, the real-time data may be transformed by a transform to assess the Doppler shift. The resulting information may represent an aspect of the moving particles, such as speed, velocity, volume, for example. This resulting information may be displayed to a user, at 10304.

In addition, the max capabilities of the data and/or system may be displayed to the user. And, at 10306, the resulting information and/or the real-time data may be aggregated and/or further analyzed. For example, it may be processed with the situational awareness. For example, this may enable the separation and/or identification of blood flow, interstitial fluids, smoke, particulates, mist, aerosols and/or the like. And it may enable display of selected data without noise from other data types. For example, user selection of highlighted particle tracking may engage further processing and analysis to focus the display to the desired real-time data, resulting information, etc. For example, the user may select a type of data to be displayed, such as size of particles, volume, rate of increase, velocity of particle groups, and/or movement over time of a tagged group, etc. The resulting information and/or the real-time data may be aggregated and/or further analyzed to determine, for example, trends over time, transformations to time rate of change aspects (e.g., acceleration, etc.), calibrations and/or adjustments for temperature, insufflation gas types, laser source, combined laser data set, and the like. The aggregation and analysis may occur concurrently with displaying the real-time information. The aggregation and analysis of information on moving particles may occur at some time after displaying the real-time data on moving particles. The aggregation and analysis information on moving particles may occur without the display of real-time information on moving particles. The aggregation and analysis of information on moving particles may include any number of algorithms and our analysis suitable for analyzing visualization data.

At 10308, the information resulting from the aggregation and further analysis (e.g., trending information) may be displayed to the user. The trending information may be combined into graphical trend animations. The trending information may be shown as a metric. The trending information may be superimposed on the raw moving particle data.

Figure 34:
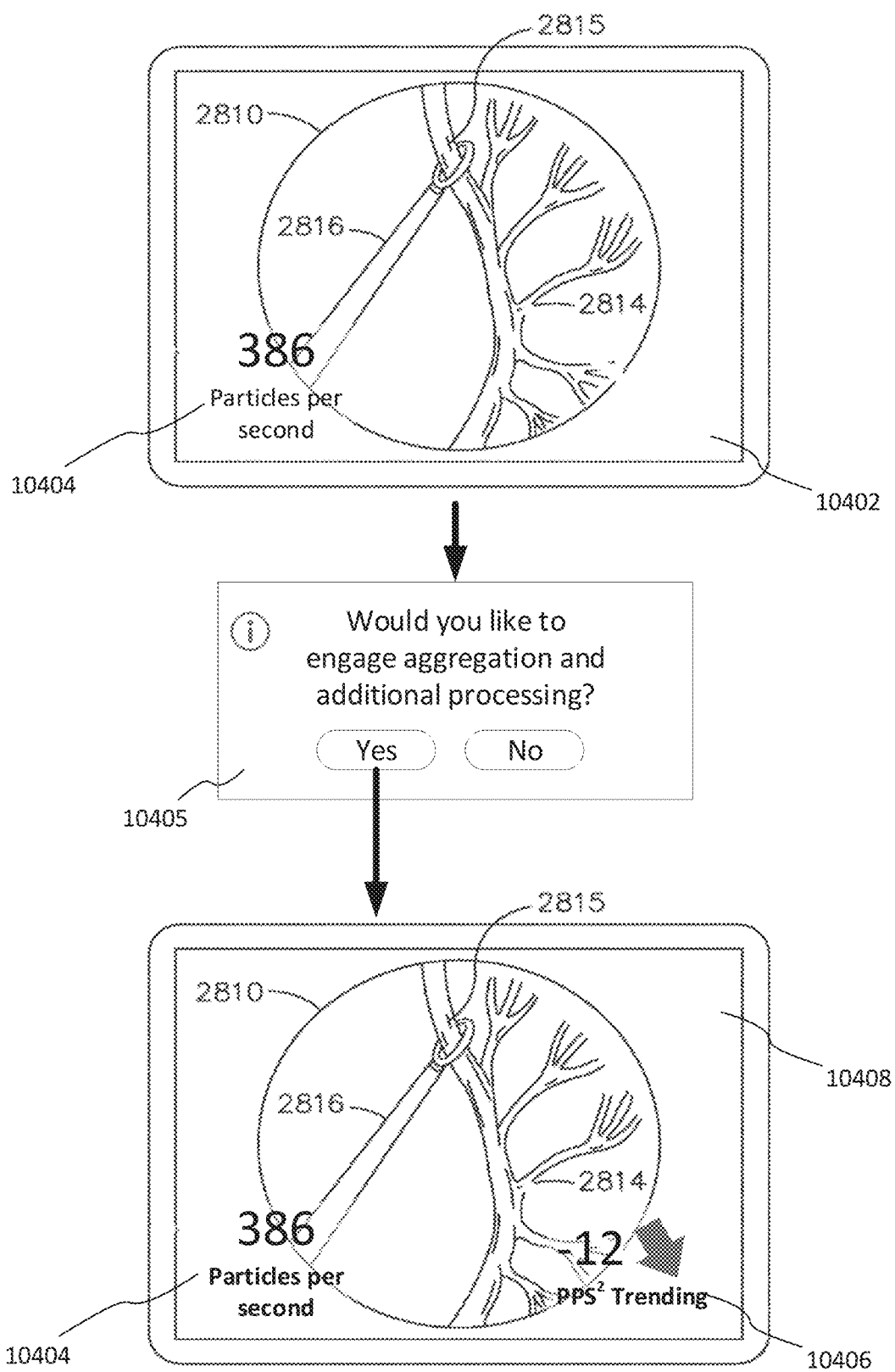
FIG. 34 depicts an example user interface with real-time and/or trending information being displayed.

FIG. 34 depicts an example user interface with real-time and/or trending information being displayed. A first user interface 10402 includes image data. This image data may represent an image portion 2810 of a surgical field. The image portion 2810 may present a close-up view of the vascular tree 2814 so that the surgeon can focus on dissecting only the blood vessel of interest 2815. For resecting the blood vessel of interest 2815, a surgeon may use a smart RF cautery device 2816. The image data may be developed by way of a CMOS image sensor and/or a light sensor. Data may also be collected by wideband light and/or laser light impinged on this tissue, being received by a light sensor, and being processed in real-time by way of a transform. The output of this transform may be a metric 10404 and/or other representation of the number of particles per second of motion within a certain portion of the field-of-view. For example, this metric may represent particles of smoke, liquid, blood cells, or the like for example. The metric 10404 may be displayed on the first user interface 10402.

A user interface element 10405 may be displayed to the user. For example, the user interface element 10405 may include a text box indicating whether or not the surgeon would like to engage local and/or remote processing for further analysis of the data. Certain conditions may be required to be satisfied to engage such processing. For example, engagement may be conditioned on the purchase of a software tier. For example, engagement may be conditioned on bandwidth and/or processing capabilities.

In view of the engagement, trend information 10406 may be displayed on second user interface 10408. The second user interface 10408 may be displayed on a display. For example, the trend data may include a metric of particles per second squared and/or an info graphic or other visualization, such as a chart, icon, graph or the like.

The real-time metric 10404, such as particles per second for example, and the trend information 10406, such as particle acceleration for example, may be included on the second user interface. These information elements may be displayed to the user. For example, real-time metric 10404 and the trend information 10406 they may be superimposed over the image data. Such real-time metric 10404, such as particles per second for example, and/or the trend information 10406, such as particle acceleration for example, may be useful to a surgeon performing a resection of the blood vessel 2815.

Figure 35:
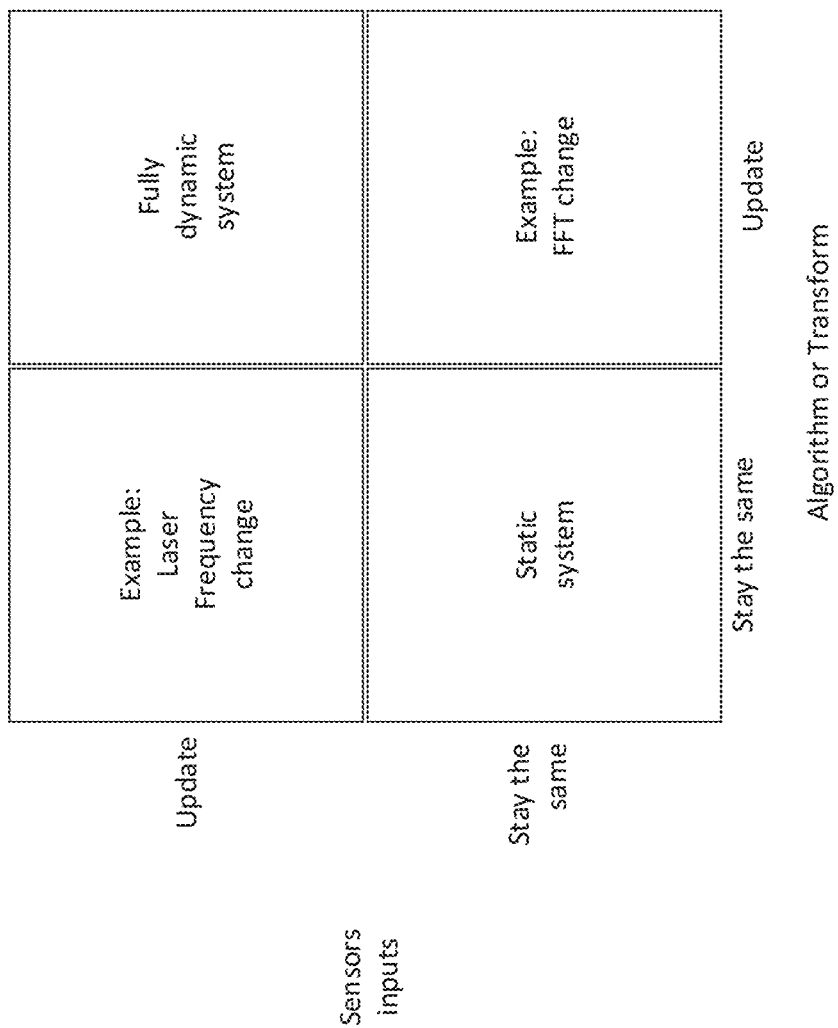
FIG. 35 depicts an example upgrade framework.

FIG. 35 depicts an example upgrade framework for a surgical visualization system. The framework includes a two-by-two. The left axis represents inputs. The bottom access represents transforms and/or algorithms. When performing an update to a surgical visualization system, the update may include a change to the inputs, such as changing the wavelength, pattern, intensity of light for example. The change to the inputs may include a change from a single wavelength to a multispectral input for example. When performing an update to a surgical visualization system, the update may include a change to the transforms and/or algorithms. The transform may include a new adjusting the transform for processing efficiency, responsiveness, energy usage, bandwidth, or the like.

As illustrated, an update may take the form of any box within the grid. An update may include a change of the inputs with the transform and/or algorithm remaining the same. An update may include a change of the transform and/or algorithm with the inputs being the same. An update may include a change of the transform and/or algorithm and a change to the inputs.

Figure 36:
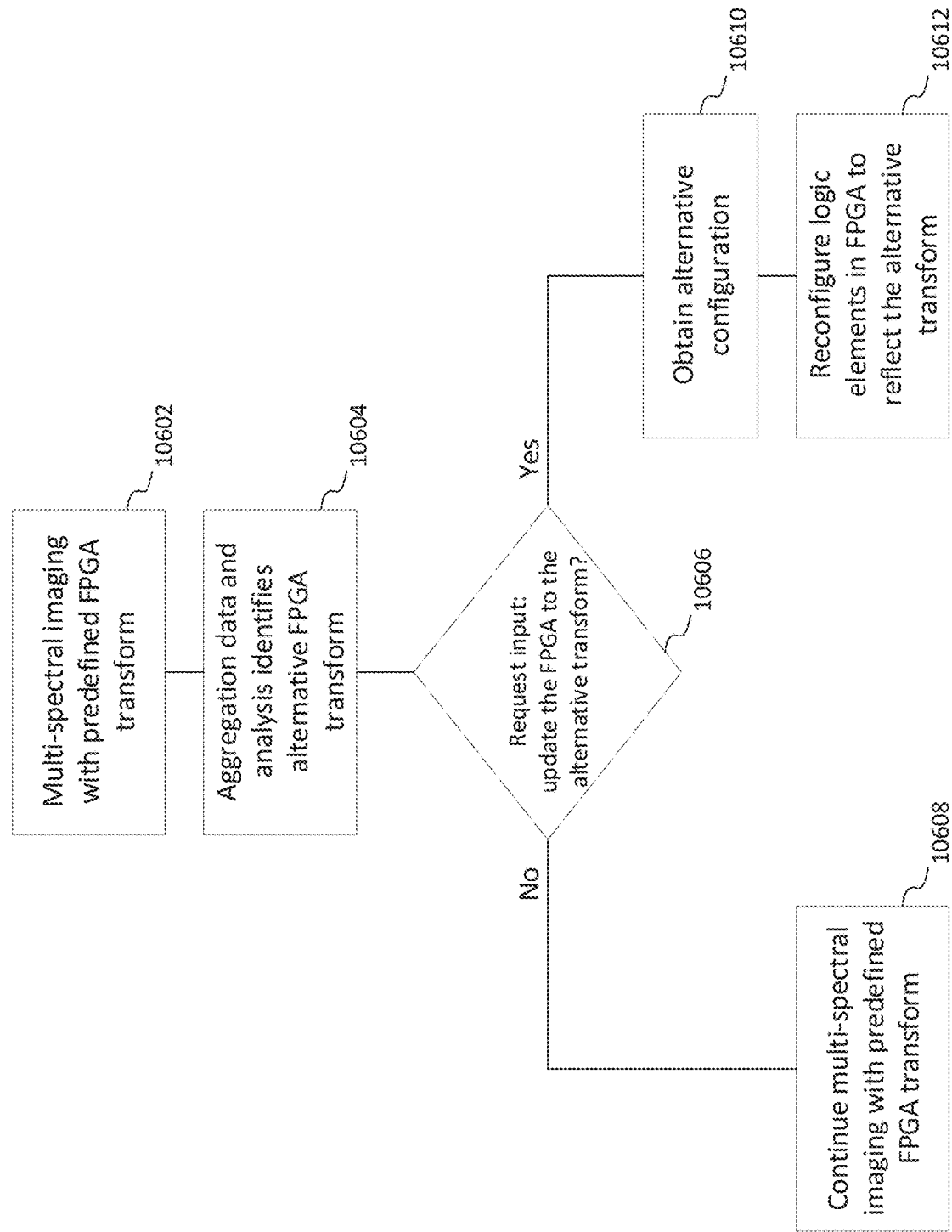
FIG. 36 illustrates an example method for reconfiguring a field programmable gate array.

FIG. 36 illustrates an example method for reconfiguring a FPGA. At 10602 a predefined FPGA transform may be used to transform multispectral imaging data. At 10604, information generated from this transform may be subject to aggregation and/or further analysis. The aggregation and further analysis may identify an alternative transform that is more suitable for a particular purpose. The system may request and/or receive input (such as a control parameter, for example) associated with an update to the transform, at 10606. If such an input and/or control parameter is indicative of not updating, the system may continue with existing transform, at 10608. If the system is upgradable, the system may obtain an alternate configuration, at 10610. The logic elements in the FPGA may be reconfigured in accordance with the alternate configuration to reflect the updated transform, at 10612. The system may resume multispectral imaging with the updated FPGA transform.

A surgical instrument, such as a surgical stapler, may have multiple operating modes, which may provide different combinations of communication, interaction, support and/or other capabilities. An instrument operation mode may be selected from multiple operation modes, which may be preconfigured, dynamically updated, semi-dynamically updated, periodically updated, or preset. Multi-modal instrument operation may control the availability, access, level of use, level of interaction and/or support for one or more capabilities available through an instrument. Instrument operation modes may variously allow or restrict instrument capabilities. Instrument capabilities authorized by a mode of operation may be variously unlocked, configured, or downloaded and installed. Resident capabilities of a surgical instrument not authorized by a mode of operation may be unutilized, locked or otherwise blocked. Instrument capabilities that vary by mode of operation may include, for example, sensors, communications, displays, data storage, data access, data aggregation, data analyses, feedback, recommendations, etc. In some implementations, a multi-modal surgical instrument may be fully operational in multiple modes of operation. Modes may vary in terms of communication capabilities, such as recordkeeping, data access and recall, data analyses, surgical recommendations, and so on.

An instrument may be configured to determine an instrument operation mode based on one or more instrument operation control parameters, such as one or more of the following: system capabilities (e.g., hardware capabilities, firmware capabilities and/or software capabilities), system capacity parameters (e.g., a wired and/or wireless connectivity capability); system condition parameters (e.g., bandwidth, interference, conductivity, current load level); system authorization parameters (e.g., parameters indicating compatibility, authorized (purchased or subscription) mode of instrument operation, instrument authenticity) and/or external control parameters (e.g., provided by a surgical hub or remote/cloud server), such as software version, revision or update level, subscription level, interconnectivity with an external/outside system, region of use, user input(s), or (e.g., secure) communication with an external database system.

Instrument operation mode control parameter(s) may include a consumer-controlled parameter, such as a subscription level. For example, a medical facility may purchase a subscription for selected instrument capabilities, which may be grouped into one or more modes of instrument operation.

For example, a surgical instrument may determine whether to obtain a sensed parameter associated with a sensor signal from a sensor based on the surgical instrument operation mode. A surgical instrument may determine whether to receive an instrument usage instruction based on the surgical instrument operation mode. The surgical instrument may communicate with a surgical hub based on the determination(s).

For example, a surgical instrument may determine, based on the instrument operation mode, whether to receive recommended instrument usage information (e.g., stapler cartridge selection) generated based on aggregated historical instrument usage data. A surgical instrument may determine, based on the instrument operation mode, whether to receive a stapler cartridge selection recommendation generated based on aggregated cartridge usage data associated with a surgical procedural step. The surgical instrument may communicate with a surgical hub based on the determination(s).

For example, a remote server may, based on the surgical instrument operation mode, receive instrument usage information associated with a medical procedure performed by a surgeon, aggregate the received instrument usage information with historic instrument usage information associated with the surgeon, and send the aggregated instruction usage information to the surgical instrument (e.g., directly or via a surgical hub). The remote server may, based on the surgical instrument operation mode, correlate the received instrument usage information to an outcome of the medical procedure and to an instrument operation status during the medical procedure; and send the correlated information to the surgical instrument (e.g., directly or via a surgical hub). The remote server may, based on the surgical instrument operation mode, determine a recommended instrument usage information associated with an upcoming medical procedure based on the correlated information; and send the recommended instrument usage information to the surgical instrument (e.g., directly or via a surgical hub).

In an example surgical instrument operation mode, a surgical instrument may engage in unidirectional communication during operation (e.g., following initialization, which may support limited bidirectional communication) by sending information (e.g., surgical procedure information, such as staple cartridge type and/or ID, errors, instrument status) to a surgical hub. The surgical hub may send the received information to a remote server (e.g., a remote processing server and/or a remote database in the cloud).

In an example surgical instrument operation mode, a surgical instrument may engage in bidirectional communication by sending information to and receiving information from a surgical hub, which may send the received information to a remote server (e.g., a remote processing server and/or a remote database in the cloud). The surgical instrument may receive information (e.g., surgical procedure recommendations) based on the information sent to the surgical hub and/or remote server (e.g., surgical procedure, sensed parameter(s), instrument usage information). The surgical hub and/or remote server may analyze historical information to render recommendations (e.g., force to fire, wait time, display information on one or more displays).

In an example surgical instrument operation mode, a surgical instrument may engage in bidirectional communication by sending information to and receiving information from a surgical hub. The surgical hub may send the received information to a remote server (e.g., a remote processing server and/or a remote database in the cloud). The surgical instrument may receive information (e.g., surgical procedure recommendations) based on the information sent to the surgical hub and/or remote server (e.g., surgical procedure, sensed parameter(s), instrument usage information), which may analyze historical information to render recommendations (e.g., force to fire, wait time, display information on one or more displays). The surgical instrument may determine, based on a surgical instrument operation mode, whether to send various surgical information to a surgical hub and/or remote server for archiving, subsequent retrieval, data aggregation, analyses and/or recommendations. The archived surgical information may be aggregated with historical information by a particular user (e.g., surgeon) and/or information received from other surgical hub(s), and/or surgical information associated with other medical facilities. The aggregated information may be accessed to generate instructional information for one or more surgical instrument(s). In an example, information aggregated may include information received from smart surgical devices, information associated with multiple surgeries, surgical information and corresponding outcomes associated with multiple patients. The aggregated information may be stored in a remote database. In an example, the surgical information may be aggregated at a remote server. A surgical instrument may determine, for example, based on a surgical instrument operation mode, whether to receive historical data, aggregated data, recommendations based on aggregated historical data, etc.

A surgical instrument may have multiple operating modes. An instrument operation mode may be selected from multiple operation modes, which may be preconfigured, dynamically updated, semi-dynamically updated, periodically updated, or preset. Multi-modal instrument operation may control the availability, access, level of use, level of interaction and/or support for one or more capabilities available through an instrument. A multi-modal surgical instrument may be fully operational in multiple modes of operation while varying one or more capabilities based on a mode of operation, such as one or more of sensors, communications, user-instrument interaction, displays, data storage, data access, data aggregation, data analytics, surgical support, feedback, surgical recommendations, etc. An instrument may be configured to determine an operation mode based on one or more instrument operation control parameters, such as system capabilities, system capacity parameters, system condition parameters, system authorization parameters, and/or external control parameters.

Figure 37:
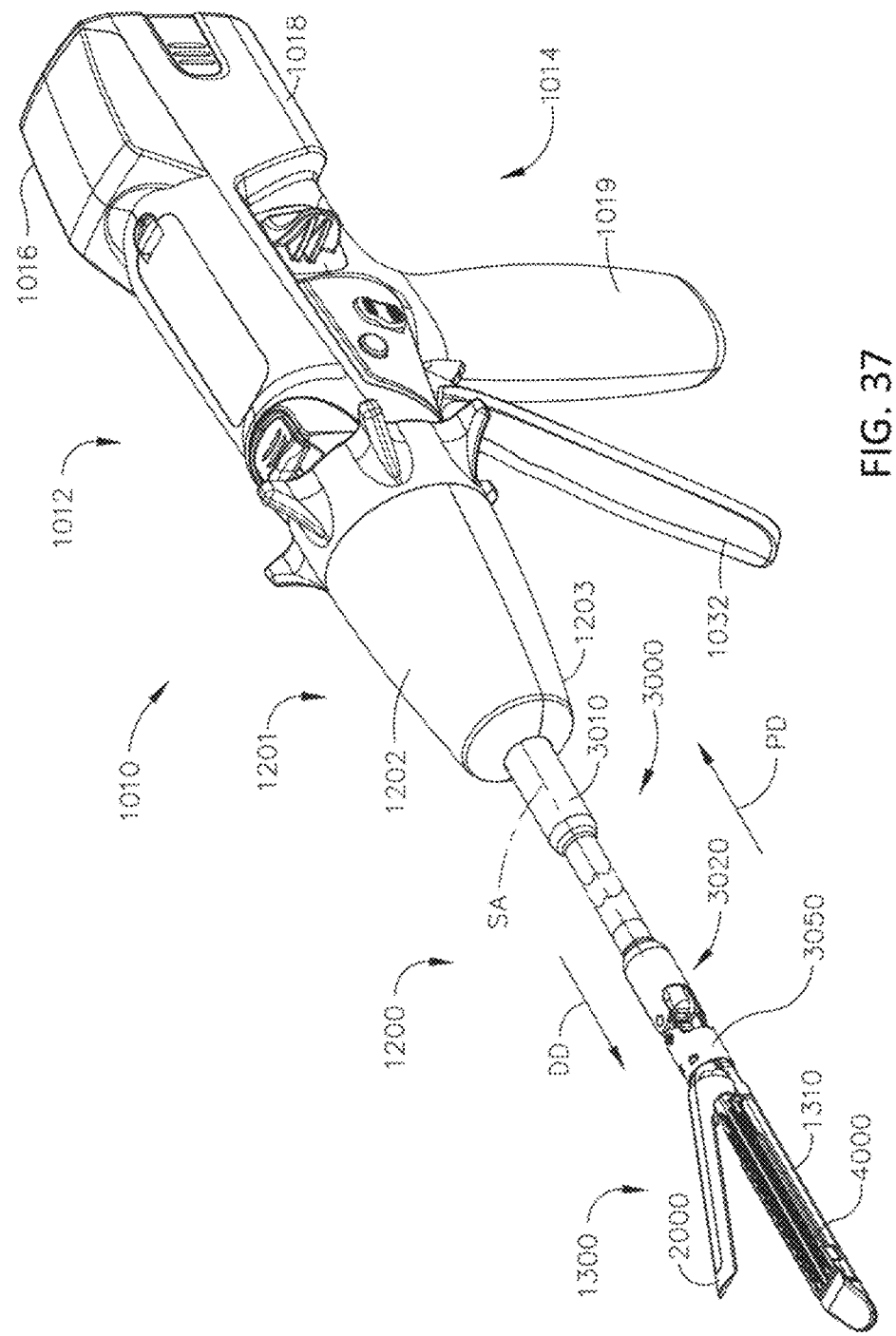
FIG. 37 is a perspective view of a powered surgical stapling system.
Figure 38:
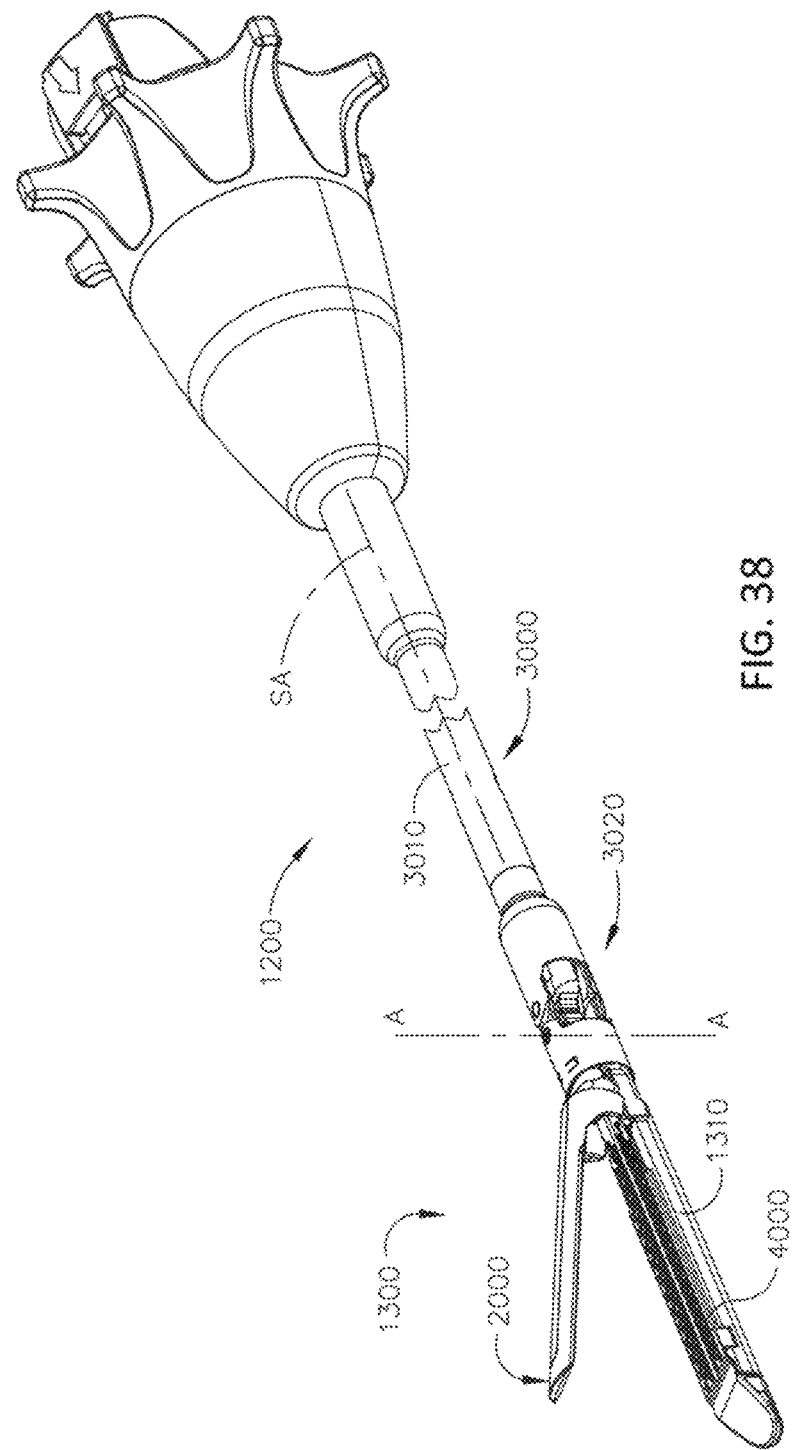
FIG. 38 is a perspective view of an interchangeable surgical shaft assembly of the powered surgical stapling system of FIG. 37.
Figure 39:
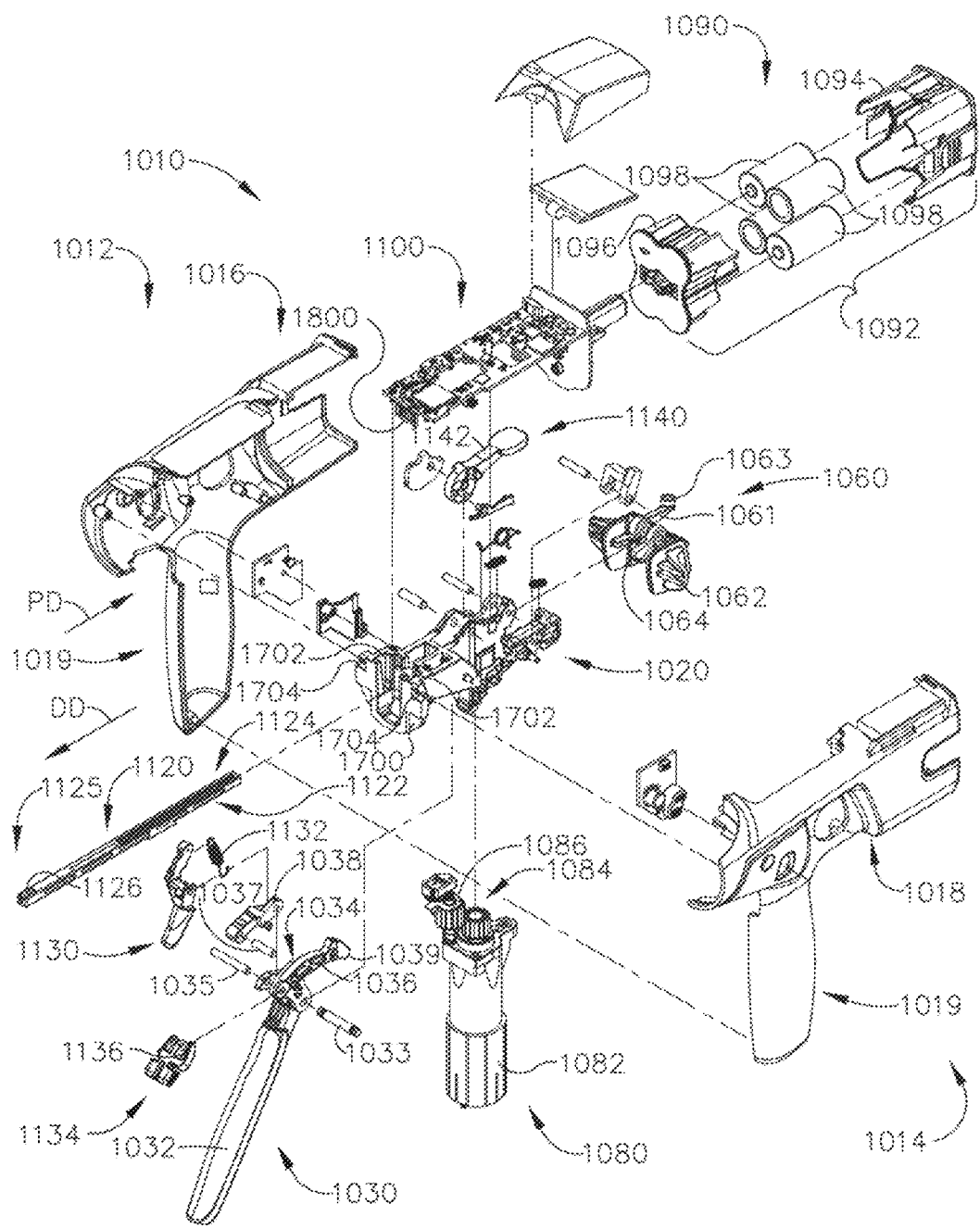
FIG. 39 is an exploded assembly view of portions of a handle assembly of the powered surgical stapling system of FIG. 37.

FIG. 37 is a perspective view of a powered surgical stapling system. FIG. 37 illustrates the surgical instrument 1010 (e.g., an endocutter) that includes an interchangeable shaft assembly 1200 operably coupled to a housing 1012. FIG. 38 is a perspective view of an interchangeable surgical shaft assembly of the powered surgical stapling system of FIG. 37. FIG. 38 illustrates the interchangeable shaft assembly 1200 detached from the housing 1012 or handle 1014. FIG. 18 is an exploded assembly view of portions of a handle assembly of the powered surgical stapling system of FIG. 37. As can be seen in FIG. 39, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019. FIGS. 16 and 18 depict a motor-driven surgical cutting and fastening instrument 1010 that may or may not be reused. In the illustrated embodiment, the instrument 1010 includes a previous housing 1012 that comprises a handle 1014 that is configured to be grasped, manipulated and actuated by the clinician. The housing 1012 can be configured for operable attachment to an interchangeable shaft assembly 1200 that has a surgical end effector 1300 operably coupled thereto that can be configured to perform one or more surgical tasks or procedures. As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. In addition, various components may be "housed" or contained in the housing or various components may be "associated with" a housing. In such instances, the components may not be contained within the housing or supported directly by the housing. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in which is hereby incorporated by reference herein in its entirety.

The previous housing 1012 depicted in FIG. 37 is shown in connection with an interchangeable shaft assembly 1200 (FIGS. 17, 19 and 20) that includes an end effector 1300 that comprises a surgical cutting and fastening device that is configured to operably support a surgical staple cartridge 4000 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener that can be gripped and manipulated by the clinician. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 39, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. More specifically, as illustrated in FIG. 39, the closure trigger 1032 can be pivotally coupled to the handle 1014 by a pin 1033. Such arrangement enables the closure trigger 1032 to be manipulated by a clinician such that when the clinician grips the pistol grip portion 1019 of the handle 1014, the closure trigger 1032 may be easily pivoted from a starting or "unactuated" position to an "actuated" position and more particularly to a fully compressed or fully actuated position. The closure trigger 1032 may be biased into the unactuated position by spring or other biasing arrangement (not shown). In various forms, the closure drive system 1030 further includes a closure linkage assembly 1034 that can be pivotally coupled to the closure trigger 1032. As can be seen in FIG. 39, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 39, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position towards the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 may serve to lock the closure trigger 1032 in the fully actuated position. When the clinician desires to unlock the closure trigger 1032 to permit it to be biased to the unactuated position, the clinician may simply pivot the closure release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the closure release button 1062. A magnetic element 1063, such as a permanent magnet, for example, may be mounted to the arm 1061. When the closure release button 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a "Hall Effect" sensor (not shown) can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the closure release button 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system 1080 may also be referred to herein as a "second drive system". The firing drive system 1080 may employ an electric motor 1082 that may be located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 3, for example, the power pack 1092 may comprise a proximal housing portion 1094 that is configured for attachment to a distal housing portion 1096. The proximal housing portion 1094 and the distal housing portion 1096 may be configured to operably support a plurality of batteries 1098 therein. Batteries 1098 may each comprise, for example, a Lithium Ion ("LI") or other suitable battery. The distal housing portion 1096 may be configured for removable operable attachment to the circuit board 1100 which may also be operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a with a set, or rack, of drive teeth 1122 on a longitudinally-movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counter-clockwise direction. When the electric motor 1082 is rotated in one direction, the drive member 1120 will be axially driven in the distal direction "DD". When the motor 82 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014. The firing trigger 1130 may be pivoted between an unactuated position and an actuated position. The firing trigger 1130 may be biased into the unactuated position by a spring 1132 or other biasing arrangement such that when the clinician releases the firing trigger 1130, it may be pivoted or otherwise returned to the unactuated position by the spring 1132 or biasing arrangement. In at least one form, the firing trigger 1130 can be positioned "outboard" of the closure trigger 1032 as was discussed above. In at least one form, a firing trigger safety button 1134 may be pivotally mounted to the closure trigger 1032 by the pin 1035. The safety button 1134 may be positioned between the firing trigger 1130 and the closure trigger 1032 and have a pivot arm 1136 protruding therefrom. When the closure trigger 1032 is in the unactuated position, the safety button 1134 can be contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that may be configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with teeth 1124 also provided in the drive member 1120. Thus, the clinician can manually retract the drive member 1120 by using the bailout handle assembly 1142 to ratchet the drive member 1120 in the proximal direction "PD". U.S. Pat. No. 8,608,045, entitled "POWERED SURGICAL CUTTING AND STAPLING APPARATUS WITH MANUALLY RETRACTABLE FIRING SYSTEM," discloses bailout arrangements and other components, arrangements and systems that may also be employed with the various instruments disclosed herein. U.S. Pat. No. 8,608,045 is hereby incorporated by reference herein in its entirety.

Figure 40:
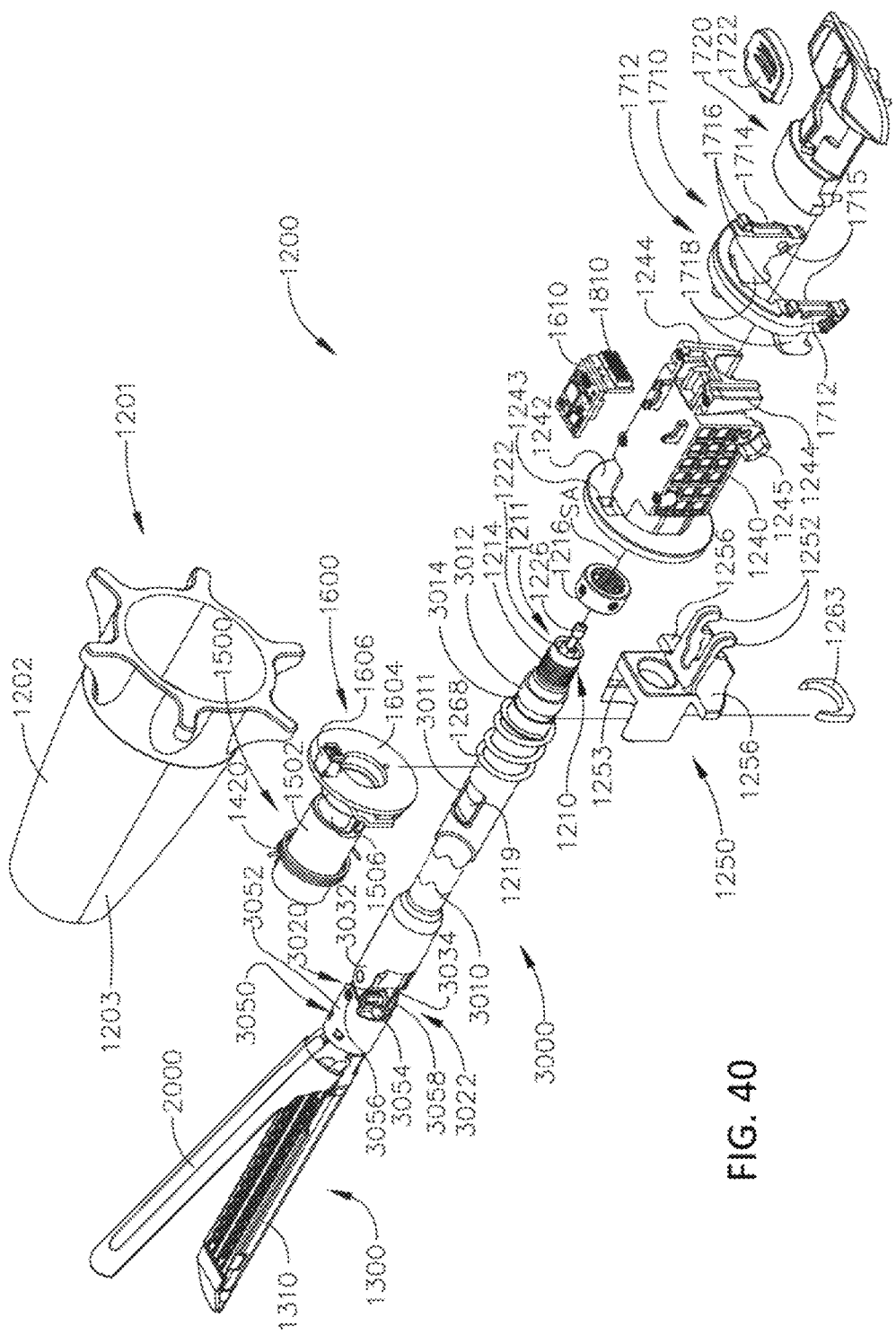
FIG. 40 is an exploded assembly view of the interchangeable surgical shaft assembly of FIG. 37.
Figure 41:
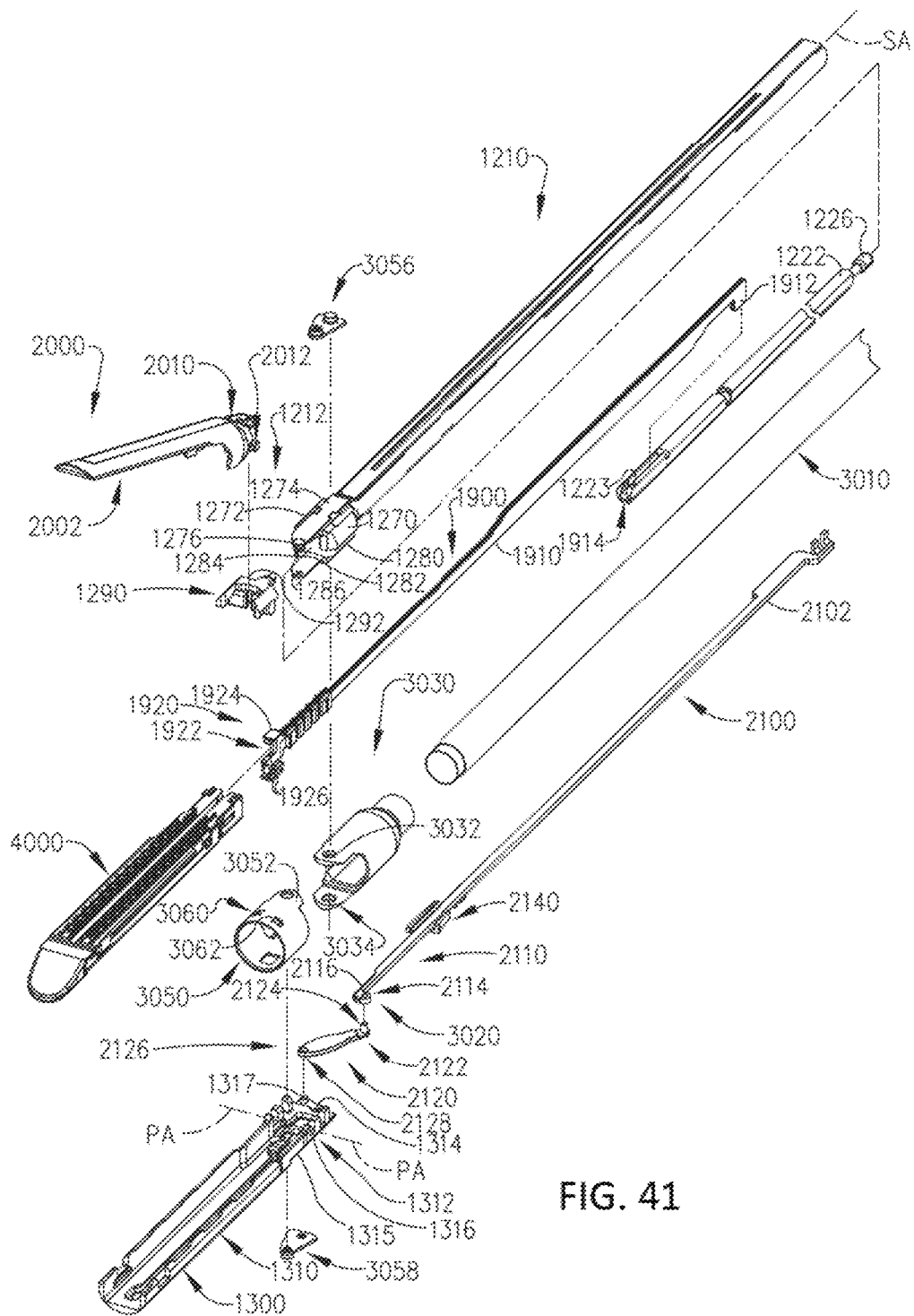
FIG. 41 is another partial exploded assembly view of a portion of the interchangeable surgical shaft assembly of FIG. 37.

Turning now to FIGS. 38 and 41, the interchangeable shaft assembly 1200 may include a surgical end effector 1300 that comprises an elongate channel 1310 that can be configured to operably support a staple cartridge 4000 therein. The end effector 1300 may further include an anvil 2000 that is pivotally supported relative to the elongate channel 1310. The interchangeable shaft assembly 1200 may further include an articulation joint 3020 and an articulation lock 2140 which can be configured to releasably hold the end effector 1300 in a desired position relative to a shaft axis SA. Examples of various features of at least one form of the end effector 1300, the articulation joint 3020 and articulation locks may be found in U.S. patent application Ser. No. 13/803,086, filed Mar. 14, 2013, entitled "ARTICULATABLE SURGICAL INSTRUMENT COMPRISING AN ARTICULATION LOCK," now U.S. Patent Application Publication No. 2014/0263541, which is hereby incorporated by reference herein in its entirety. FIG. 40 is an exploded assembly view of the interchangeable surgical shaft assembly of FIG. 38. As can be seen in FIG. 40, the interchangeable shaft assembly 1200 can further include a proximal housing or nozzle 1201 comprised of nozzle portions 1202 and 1203.

The interchangeable shaft assembly 1200 can further include a closure system or closure member assembly 3000 which can be utilized to close and/or open the anvil 2000 of the end effector 1300. The shaft assembly 1200 can include a spine 1210 that may be configured to, one, slidably support a firing member therein and, two, slidably support the closure member assembly 3000 which extends around the spine 1210. FIG. 41 shows partial exploded assembly view of a portion of the interchangeable surgical shaft assembly of FIG. 40. As can be seen in FIG. 41, a distal end 1212 of spine 1210 terminates in an upper lug mount feature 1270 and in a lower lug mount feature 1280. The upper lug mount feature 1270 can be formed with a lug slot 1272 therein that is adapted to mountingly support an upper mounting link 1274 therein. Similarly, the lower lug mount feature 1280 is formed with a lug slot 1282 therein that may be adapted to mountingly support a lower mounting link 1284 therein. The upper mounting link 1274 may include a pivot socket 1276 therein that can be adapted to rotatably receive therein a pivot pin 1292 that is formed on a channel cap or anvil retainer 1290 that is attached to a proximal end portion 1312 of the elongate channel 1310. The lower mounting link 1284 may include lower pivot pin 1286 that adapted to be received within a pivot hole 1314 formed in the proximal end portion 1312 of the elongate channel 1310. See FIG. 41. The lower pivot pin 1286 can be vertically aligned with the pivot socket 1276 to define an articulation axis AA about which the surgical end effector 1300 may articulate relative to the shaft axis SA. See FIG. 38.

In the illustrated example, the surgical end effector 1300 can be selectively articulatable about the articulation axis AA by an articulation system 2100. In one form, the articulation system 2100 may include proximal articulation driver 2102 that can be pivotally coupled to an articulation link 2120. As can be most particularly seen in FIG. 41, an offset attachment lug 2114 may be formed on a distal end 2110 of the proximal articulation driver 2102. A pivot hole 2116 can be formed in the offset attachment lug 2114 and is configured to pivotally receive therein a proximal link pin 2124 formed on the proximal end 2122 of the articulation link 2120. A distal end 2126 of the articulation link 2120 may include a pivot hole 2128 that is configured to pivotally receive therein a channel pin 1317 formed on the proximal end portion 1312 of the elongate channel 1310. Thus, axial movement of proximal articulation driver 2102 will thereby apply articulation motions to the elongate channel 1310 to thereby cause the surgical end effector 1300 to articulate about the articulation axis AA relative to the spine 1210. Further details concerning the construction and operation of the articulation system 2100 may be found in various references incorporated by reference herein including U.S. patent application Ser. No. 15/635,631, filed Jun. 28, 2017, entitled "SURGICAL INSTRUMENT WITH AXIALLY MOVABLE CLOSURE MEMBER," now U.S. Patent Application Publication No. 2019/0000464, which is hereby incorporated by reference herein in its entirety. In various circumstances, the proximal articulation driver 2102 can be held in position by an articulation lock 2140 when the proximal articulation driver 2102 is not being moved in the proximal or distal directions. Additional details regarding an example of an articulation lock 2140 may be found in U.S. Patent Application Publication No. 2019/0000464, as well as in other references incorporated by reference herein.

In various circumstances, the spine 1210 can comprise a proximal end 1211 which can be rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 40. Such an arrangement facilitates rotatable attachment of the spine 1210 to the chassis 1240 such that the spine 1210 may be selectively rotated about a shaft axis SA relative to the chassis 1240.

Referring primarily to FIG. 40, the interchangeable shaft assembly 1200 may include a closure shuttle 1250 that is slidably supported within the chassis 1240 such that it may be axially moved relative thereto. The closure shuttle 1250 may include a pair of proximally protruding hooks 1252 that may be configured for attachment to the attachment pin 1037 (FIG. 3) that can be attached to the second closure link 1038 as will be discussed in further detail below. In at least one example, the closure member assembly 3000 can comprise a proximal closure member segment 3010 that may have a proximal end 3012 that may be coupled to the closure shuttle 1250 for relative rotation thereto. For example, a U-shaped connector 1263 can be inserted into an annular slot 3014 in the proximal end 3012 of the proximal closure member segment 3010 and can be retained within vertical slots 1253 in the closure shuttle 1250. Such an arrangement may serve to attach the proximal closure member segment 3010 to the closure shuttle 1250 for axial travel therewith while enabling the proximal closure member segment 3010 to rotate relative to the closure shuttle 1250 about the shaft axis SA. A closure spring 1268 may be journaled on the proximal closure member segment 3010 and serves to bias the proximal closure member segment 3010 in the proximal direction "PD" which can serve to pivot the closure trigger 1032 into the unactuated position when the shaft assembly is operably coupled to the handle 1014.

In at least one form, the interchangeable shaft assembly 1200 may further include an articulation joint 3020. Other interchangeable shaft assemblies, however, may not be capable of articulation. As can be seen in FIG. 41, for example, a distal closure member or distal closure tube segment 3030 may be coupled to the distal end of the proximal closure member segment 3010. The articulation joint 3020 includes a double pivot closure sleeve assembly 3022. According to various forms, the double pivot closure sleeve assembly 3022 includes an end effector closure tube 3050 having upper and lower distally projecting tangs 3052, 3054. An upper double pivot link 3056 includes upwardly projecting distal and proximal pivot pins that engage respectively an upper distal pin hole in the upper proximally projecting tang 3052 and an upper proximal pin hole in an upper distally projecting tang 3032 on the distal closure tube segment 3030. A lower double pivot link 3058 includes upwardly projecting distal and proximal pivot pins that engage respectively a lower distal pin hole in the lower proximally projecting tang 3054 and a lower proximal pin hole in the lower distally projecting tang 3034. See FIGS. 19 and 20. As will be discussed in further detail below, the closure member assembly 3000 is translated distally (direction "DD") to close the anvil 2000, for example, in response to the actuation of the closure trigger 1032. The anvil 2000 is opened by proximally translating the closure member assembly 3000 which causes the end effector closure sleeve to interact with the anvil 2000 and pivot it to an open position.

As was also indicated above, the interchangeable shaft assembly 1200 further includes a firing member 1900 that is supported for axial travel within the spine 1210. The firing member 1900 includes an intermediate firing shaft portion 1222 that is configured for attachment to a distal cutting portion or knife bar 1910. The intermediate firing shaft portion 1222 may include a longitudinal slot 1223 in the distal end thereof which can be configured to receive a tab 1912 on the proximal end of the distal knife bar 1910. The longitudinal slot 1223 and the proximal end tab 1912 can be sized and configured to permit relative movement therebetween and can comprise a slip joint 1914. The slip joint 1914 can permit the intermediate firing shaft portion 1222 of the firing member 1900 to be moved to articulate the end effector 1300 without moving, or at least substantially moving, the knife bar 1910. Once the end effector 1300 has been suitably oriented, the intermediate firing shaft portion 1222 can be advanced distally until a proximal sidewall of the longitudinal slot 1223 comes into contact with the tab 1912 in order to advance the knife bar 1910 and fire the staple cartridge 4000 positioned within the channel 1310. The knife bar 1910 can include a knife portion 1920 that can include a blade or tissue cutting edge 1922 and includes an upper anvil engagement tab 1924 and lower channel engagement tabs 1926. Various firing member configurations and operations can be disclosed in various other references incorporated herein by reference.

As can be seen in FIG. 40, the shaft assembly 1200 further may include a switch drum 1500 that can be rotatably received on proximal closure member segment 3010. The switch drum 1500 may comprise a hollow shaft segment 1502 that may have a shaft boss formed thereon for receive an outwardly protruding actuation pin therein. In various circumstances, the actuation pin may extend through a longitudinal slot provided in the lock sleeve to facilitate axial movement of the lock sleeve when it is engaged with the articulation driver. A rotary torsion spring 1420 can be configured to engage the boss on the switch drum 1500 and a portion of the nozzle housing 1203 to apply a biasing force to the switch drum 1500. The switch drum 1500 can further comprise at least partially circumferential openings 1506 defined therein which can be configured to receive circumferential mounts extending from the nozzle portions 1202, 1203 and permit relative rotation, but not translation, between the switch drum 1500 and the nozzle 1201. The mounts may also extend through openings 3011 in the proximal closure member segment 3010 to be seated in recesses 1219 in the spine 1210. Rotation of the switch drum 1500 about the shaft axis SA will ultimately result in the rotation of the actuation pin and the lock sleeve between its engaged and disengaged positions. In one arrangement, the rotation of the switch drum 1500 may be linked to the axial advancement of the closure tube or closure member. Thus, in essence, actuation of the closure system may operably engage and disengage the articulation drive system with the firing drive system in the various manners described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, and U.S. Pat. No. 9,913,642, entitled "SURGICAL INSTRUMENT COMPRISING A SENSOR SYSTEM," which is hereby incorporated by reference herein in its entirety. For example, when the closure tube is in its proximal-most position corresponding to a "jaws open" position, the closure member segment 3010 will have positioned the switch drum 1500 so as to link the articulation system with the firing drive system. When, the closure tube has been moved to its distal position corresponding to a "jaws closed" position, the closure tube has rotated the switch drum 1500 to a position wherein the articulation system is delinked from the firing drive system.

As also illustrated in FIG. 40, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that can be mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement may permit relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis flange 1242. See FIG. 40. Further details regarding slip ring assembly 1600 may be found, for example, in U.S. patent application Ser. No. 13/803,086, entitled "ARTICULATABLE SURGICAL INSTRUMENT COMPRISING AN ARTICULATION LOCK," now U.S. Patent Application Publication No. 2014/0263541, U.S. patent application Ser. No. 13/800,067, entitled "STAPLE CARTRIDGE TISSUE THICKNESS SENSOR SYSTEM," filed on Mar. 13, 2013, now U.S. Patent Application Publication No. 2014/0263552, which is hereby incorporated by reference herein in its entirety, and U.S. Pat. No. 9,345,481, entitled "STAPLE CARTRIDGE TISSUE THICKNESS SENSOR SYSTEM," which is hereby incorporated by reference herein in its entirety.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to distal connector flange. In various instances, the shaft assembly 1200 can comprise at least one sensor configured to detect the position of the switch drum 1500.

Referring again to FIG. 40, the chassis 1240 may include at least one, and preferably two, tapered attachment portions 1244 formed thereon that are adapted to be received within corresponding dovetail slots 1702 formed within a distal attachment flange portion 1700 of the frame 1020. See FIG. 39. Each dovetail slot 1702 may be tapered or, stated another way, be somewhat V-shaped to seatingly receive the attachment portions 1244 therein. As can be further seen in FIG. 40, a shaft attachment lug 1226 is formed on the proximal end of the intermediate firing shaft portion 1222. As will be discussed in further detail below, when the interchangeable shaft assembly 1200 can be coupled to the handle 1014, the shaft attachment lug 1226 can be received in a firing shaft attachment cradle 1126 formed in a distal end 1125 of the longitudinal drive member 1120. See FIG. 39.

Various shaft assembly embodiments can employ a latch system 1710 for removably coupling the shaft assembly 1200 to the housing 1012 and more specifically to the frame 1020. As can be seen in FIG. 4, for example, in at least one form, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each may have a pivot lug 1715 formed thereon that are adapted to be received in corresponding holes 1245 formed in the chassis 1240. Such arrangement may facilitate pivotal attachment of the lock yoke 1712 to the chassis 1240. The lock yoke 1712 may include two proximally protruding lock lugs 1716 that are configured for releasable engagement with corresponding lock detents or grooves 1704 in the distal attachment flange portion 1700 of the frame 1020. See FIG. 39. In various forms, the lock yoke 1712 may be biased in the proximal direction by spring or biasing member (not shown). Actuation of the lock yoke 1712 may be accomplished by a latch button 1722 that is slidably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button in the distal direction which also may cause the lock yoke 1712 to pivot out of retaining engagement with the distal attachment flange portion 1700 of the frame 1020. When the lock yoke 1712 is in "retaining engagement" with the distal attachment flange portion 1700 of the frame 1020, the lock lugs 1716 may be retainingly seated within the corresponding lock detents or grooves 1704 in the distal attachment flange portion 1700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 1032 to grasp and manipulate the target tissue into a desired position. Once the target tissue may be positioned within the end effector 1300 in a desired orientation, the clinician may then fully actuate the closure trigger 1032 to close the anvil 2000 and clamp the target tissue in position for cutting and stapling. In that instance, the first drive system 1030 may have been fully actuated. After the target tissue has been clamped in the end effector 1300, it may be desirable to prevent the inadvertent detachment of the shaft assembly 1200 from the housing 1012. One form of the latch system 1710 may be configured to prevent such inadvertent detachment.

As can be most particularly seen in FIG. 40, the lock yoke 1712 may include at least one and preferably two lock hooks 1718 that are adapted to contact corresponding lock lug portions 1256 that may be formed on the closure shuttle 1250. When the closure shuttle 1250 is in an unactuated position (i.e., the first drive system 1030 is unactuated and the anvil 2000 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 2000 is in the closed position), the lock yoke 1712 may be prevented from being pivoted to an unlocked position. Stated another way, if the clinician were to attempt to pivot the lock yoke 1712 to an unlocked position or, for example, the lock yoke 1712 may be inadvertently bumped or contacted in a manner that might otherwise cause it to pivot distally, the lock hooks 1718 on the lock yoke 1712 will contact the lock lug portions 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange 1700 of the frame 1020 such that the tapered attachment portions 1244 formed on the chassis 1240 may be aligned with the dovetail slots 1702 in the frame 1020. The clinician may then move the shaft assembly 1200 along an installation axis that may be perpendicular to the shaft axis SA to seat the attachment portions 1244 in "operable engagement" with the corresponding dovetail receiving slots 1702. In doing so, the shaft attachment lug 1226 on the intermediate firing shaft portion 1222 will also be seated in the cradle 1126 in the longitudinally movable drive member 1120 and the portions of the pin 1037 on the second closure link 1038 will be seated in the corresponding hooks 1252 in the closure shuttle 1250. As used herein, the term "operable engagement" in the context of two components may mean that the two components are sufficiently engaged with each other so that upon application of an actuation motion thereto, the components may carry out their intended action, function and/or procedure.

At least five systems of the interchangeable shaft assembly 1200 can be operably coupled with at least five corresponding systems of the handle 1014. A first system can comprise a frame system which couples and/or aligns the frame or spine of the shaft assembly 1200 with the frame 1020 of the handle 1014. Another system can comprise a closure drive system 1030 which can operably connect the closure trigger 1032 of the handle 1014 and the closure tube 1260 and the anvil 2000 of the shaft assembly 1200. As outlined above, the closure shuttle 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft portion 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 can be configured for mating engagement with a corresponding electrical connector 1800 on the handle control board 1100. Further details pertaining to the circuitry and control systems may be found in U.S. patent application Ser. No. 13/803,086, now U.S. Patent Application Publication No. 2014/0263541, and U.S. Pat. No. 9,913,642. The fifth system may include the latching system for releasably locking the shaft assembly 1200 to the handle 1014.

The anvil 2000 in the illustrated example may include an anvil body 2002 that terminates in an anvil mounting portion 2010. The anvil mounting portion 2010 may be movably or pivotably supported on the elongate channel 1310 for selective pivotal travel relative thereto about a fixed anvil pivot axis PA that may be transverse to the shaft axis SA. In the illustrated arrangement, a pivot member or anvil trunnion 2012 may extend laterally out of each lateral side of the anvil mounting portion 2010 to be received in a corresponding trunnion cradle 1316 formed in the upstanding walls 1315 of the proximal end portion 1312 of the elongate channel 1310. The anvil trunnions 2012 can be pivotally retained in their corresponding trunnion cradle 1316 by the channel cap or anvil retainer 1290. The channel cap or anvil retainer 1290 may include a pair of attachment lugs that are configured to be retainingly received within corresponding lug grooves or notches formed in the upstanding walls 1315 of the proximal end portion 1312 of the elongate channel 1310. See FIG. 41.

Still referring to FIG. 41, in at least one arrangement, the distal closure member or end effector closure tube 3050 may employ two axially offset, proximal and distal positive jaw opening features 3060 and 3062. The positive jaw opening features 3060, 3062 may be configured to interact with corresponding relieved areas and stepped portions formed on the anvil mounting portion 2010 as described in further detail in U.S. patent application Ser. No. 15/635,631, now U.S. Pat. No. 10,639,037. Other jaw opening arrangements may be employed.

Figure 42:
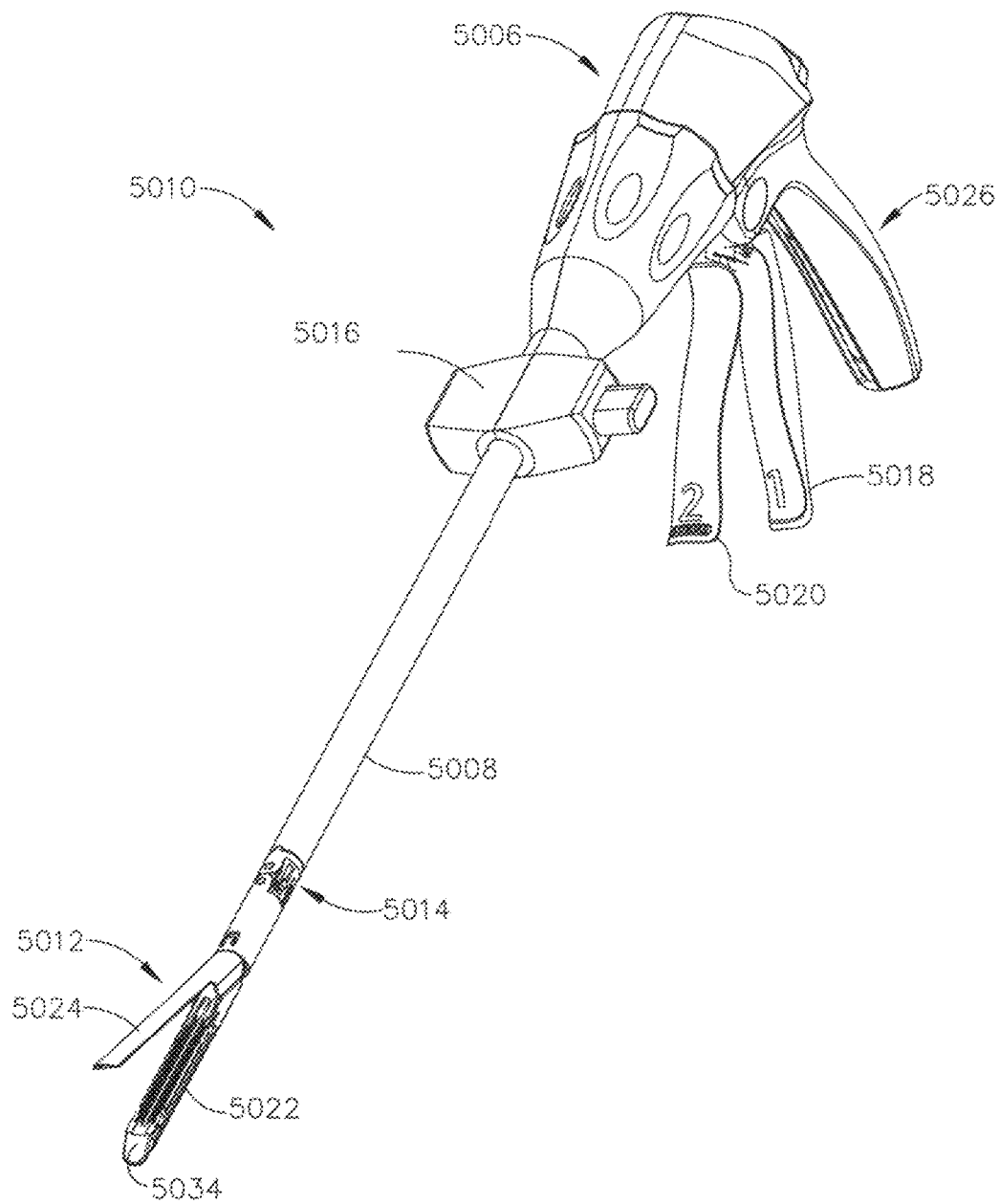
FIG. 42 is a perspective view of another powered surgical stapling system.

FIG. 42 is a perspective view of another powered surgical stapling system. FIG. 42 depicts a previous surgical cutting and fastening instrument 5010 that is configured to generate rotary drive motions for operating a surgical end effector 5012. The endoscopic surgical instrument 5010 may comprise a handle 5006, a shaft 5008, and an articulating surgical end effector 5012 pivotally connected to the shaft 5008 at an articulation pivot 5014. An articulation control 5016 may be provided adjacent to the handle 5006 to effect rotation of the end effector 5012 about the articulation pivot 5014. It will be appreciated that various embodiments may include a non-pivoting end effector, and therefore may not have an articulation pivot 5014 or articulation control 5016.

The handle 5006 of the instrument 5010 may include a closure trigger 5018 and a firing trigger 5020 for actuating the end effector 5012. It will be appreciated that instruments having end effectors directed to different surgical tasks may have different numbers or types of triggers or other suitable controls for operating the end effector 5012. In one embodiment, a clinician or operator of the instrument 5010 may articulate the end effector 5012 relative to the shaft 5008 by utilizing the articulation control 5016, as described in more detail in pending U.S. Pat. No. 7,670,334, entitled "SURGICAL INSTRUMENT HAVING AN ARTICULATING END EFFECTOR," which is hereby incorporated herein by reference in its entirety. The end effector 5012 may include in this example, among other things, a staple channel 5022 and a pivotally translatable clamping member, such as an anvil 5024, which can be maintained at a spacing that assures effective stapling and severing of tissue clamped in the end effector 5012. The handle 5006 may include a pistol grip 5026 toward which the closure trigger 5018 is pivotally drawn by the clinician to cause clamping or closing of the anvil 5024 towards the staple channel 5022 of the end effector 5012 to thereby clamp tissue positioned between the anvil 5024 and channel 5022.

Figure 46:
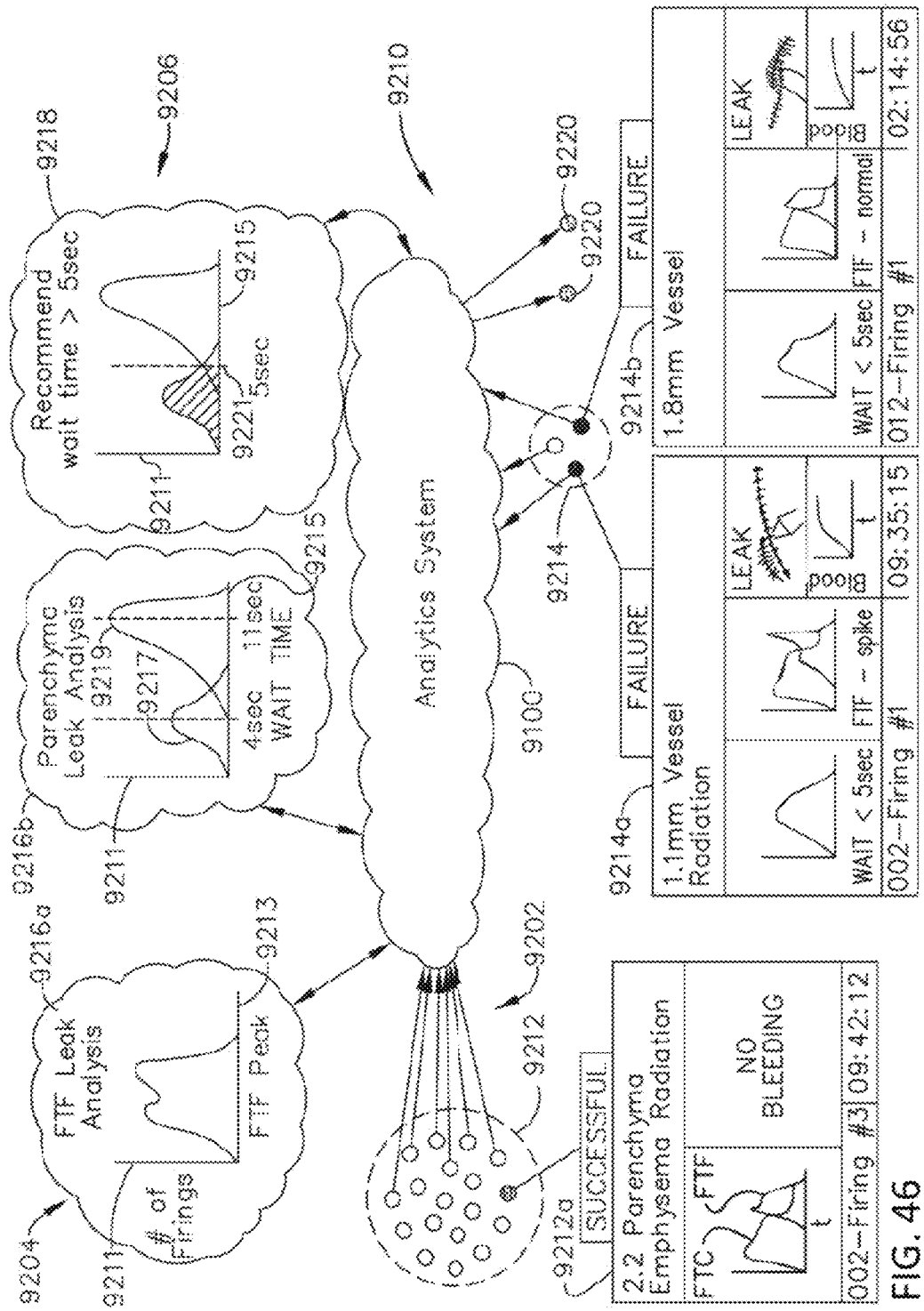
FIG. 46 is a diagram of an illustrative analytics system updating a surgical instrument control program, in accordance with at least one aspect of the present disclosure.

An example of parameters that may be gathered and communicated (e.g., as use instructions, recommendations, and/or other information) in one or more operating modes of a multi-mode surgical instrument is presented in FIG. 46. A variety of parameters that may be gathered and communicated (e.g., as use instructions, recommendations, and/or other information) in one or more operating modes of a multi-mode surgical instrument are disclosed in U.S. patent application Ser. No. 16/209,416, entitled, "METHOD OF HUB COMMUNICATION, PROCESSING, DISPLAY, AND CLOUD ANALYTICS," filed on Dec. 4, 2018, now U.S. Patent Application Publication No. 2019/0206562, which is hereby incorporated herein by reference in its entirety.

FIG. 46 illustrates a diagram of an illustrative analytics system 9100 updating a surgical instrument control program, in accordance with at least one aspect of the present disclosure. In one exemplification, a surgical hub 9000 or network of surgical hubs 9000 can be communicably coupled to an analytics system 9100. The analytics system 9100 can be configured to filter and analyze modular device 9050 data associated with surgical procedural outcome data to determine whether adjustments need to be made to the control programs of the modular devices 9050. The analytics system 9100 can then push updates to the modular devices 9050 through the surgical hubs 9000, as necessary. In the depicted exemplification, the analytics system 9100 comprises a cloud computing architecture. The modular device 9050 perioperative data received by the surgical 9000 hubs from their paired modular devices 9050 can include, for example, force to fire (e.g., the force required to advance a cutting member of a surgical stapling instrument through a tissue), force to close (i.e., the force required to clamp the jaws of a surgical stapling instrument on a tissue), the power algorithm (i.e., change in power over time of electrosurgical or ultrasonic instruments in response to the internal states of the instrument and/or tissue conditions), tissue properties (e.g., impedance, thickness, stiffness, etc.), tissue gap (i.e., the thickness of the tissue), and closure rate (i.e., the rate at which the jaws of the instrument clamped shut). It should be noted that the modular device 9050 data that is transmitted to the analytics system 9100 is not limited to a single type of data and can include multiple different data types paired with procedural outcome data. The procedural outcome data for a surgical procedure (or step thereof) can include, for example, whether there was bleeding at the surgical site, whether there was air or fluid leakage at the surgical site, and whether the staples of a particular staple line were formed properly. The procedural outcome data can further include or be associated with a positive or negative outcome, as determined by the surgical hub 9000 or the analytics system 9100, for example. The modular device 9050 data and the procedural outcome data corresponding to the modular device 9050 perioperative data can be paired together or otherwise associated with each other when they are uploaded to the analytics system 9100 so that the analytics system 9100 is able to recognize trends in procedural outcomes based on the underlying data of the modular devices 9050 that produced each particular outcome. In other words, the analytics system 9100 can aggregate the modular device 9050 data and the procedural outcome data to search for trends or patterns in the underlying device modular data 9050 that can indicate adjustments that can be made to the modular devices' 9050 control programs.

In the depicted exemplification, the analytics system 9100 may receive 9202 modular device 9050 data and procedural outcome data. When transmitted to the analytics system 9100, the procedural outcome data can be associated or paired with the modular device 9050 data corresponding to the operation of the modular device 9050 that caused the particular procedural outcome. The modular device 9050 perioperative data and corresponding procedural outcome data can be referred to as a data pair. The data is depicted as including a first group 9212 of data associated with successful procedural outcomes and a second group 9214 of data associated with negative procedural outcomes. For this particular exemplification, a subset of the data 9212, 9214 received 9202 by the analytics system 9100 is highlighted to further elucidate the concepts discussed herein.

For a first data pair 9212a, the modular device 9050 data can include the force to close (FTC) over time, the force to fire (FTF) over time, the tissue type (parenchyma), the tissue conditions (the tissue is from a patient suffering from emphysema and had been subject to radiation), what number firing this was for the instrument (third), an anonymized time stamp (to protect patient confidentiality while still allowing the analytics system to calculate elapsed time between firings and other such metrics), and an anonymized patient identifier (002). The procedural outcome data can include data indicating that there was no bleeding, which corresponds to a successful outcome (i.e., a successful firing of the surgical stapling instrument). For a second data pair 9212b, the modular device 9050 data can include the wait time prior the instrument being fired (which corresponds to the first firing of the instrument), the FTC over time, the FTF over time (which indicates that there was a force spike near the end of the firing stroke), the tissue type (1.1 mm vessel), the tissue conditions (the tissue had been subject to radiation), what number firing this was for the instrument (first), an anonymized time stamp, and an anonymized patient identifier (002). The procedural outcome data includes data indicating that there was a leak, which corresponds to a negative outcome (i.e., a failed firing of the surgical stapling instrument). For a third data pair 9212c, the modular device 9050 data may include the wait time prior the instrument being fired (which corresponds to the first firing of the instrument), the FTC over time, the FTF over time, the tissue type (1.8 mm vessel), the tissue conditions (no notable conditions), what number firing this was for the instrument (first), an anonymized time stamp, and an anonymized patient identifier (012). The procedural outcome data may include data indicating that there was a leak, which corresponds to a negative outcome (i.e., a failed firing of the surgical stapling instrument). It should be noted again that this data is intended solely for illustrative purposes to assist in the understanding of the concepts discussed herein and should not be interpreted to limit the data that is received and/or analyzed by the analytics system 9100 to generate control program updates.

When the analytics system 9100 receives 9202 perioperative data from the communicably connected surgical hubs 9000, the analytics system 9100 proceeds to aggregate and/or store the data according to the procedure type (or a step thereof) associated with the data, the type of the modular device 9050 that generated the data, and other such categories. By collating the data accordingly, the analytics system 9100 can analyze the data set to identify correlations between particular ways of controlling each particular type of modular device 9050 and positive or negative procedural outcomes. Based upon whether a particular manner of controlling a modular device 9050 can correlate to positive or negative procedural outcomes, the analytics system 9100 can determine 9204 whether the control program for the type of modular device 9050 should be updated.

For this particular exemplification, the analytics system 9100 can perform a first analysis 9216a of the data set by analyzing the peak FTF 9213 (i.e., the maximum FTF for each particular firing of a surgical stapling instrument) relative to the number of firings 9211 for each peak FTF value. In this exemplary case, the analytics system 9100 can determine that there is no particular correlation between the peak FTF 9213 and the occurrence of positive or negative outcomes for the particular data set. In other words, there are not distinct distributions for the peak FTF 9213 for positive and negative outcomes. As there is no particular correlation between peak FTF 9213 and positive or negative outcomes, the analytics system 9100 would thus determine that a control program update to address this variable is not necessary. Further, the analytics system 9100 can perform a second analysis 9216b of the data set by analyzing the wait time 9215 prior to the instrument being fired relative to the number of firings 9211. For this particular analysis 9216b, the analytics system 9100 can determine that there is a distinct negative outcome distribution 9217 and a positive outcome distribution 9219. In this exemplary case, the negative outcome distribution 9217 has a mean of 4 seconds and the positive outcome distribution has a mean of 11 seconds. Thus, the analytics system 9100 can determine that there is a correlation between the wait time 9215 and the type of outcome for this surgical procedure step. Namely, the negative outcome distribution 9217 can indicate that there is a relatively large rate of negative outcomes for wait times of 4 seconds or less. Based on this analysis 9216b demonstrating that there can be a large divergence between the negative outcome distribution 9217 and the positive outcome distribution 9219, the analytics system 9100 can then determine 9204 that a control program update should be generated 9208.

Once the analytics system 9100 analyzes the data set and determines 9204 that an adjustment to the control program of the particular module device 9050 that is the subject of the data set would improve the performance of the modular device 9050, the analytics system 9100 can then generate 9208 a control program update accordingly. In this exemplary case, the analytics system 9100 can determine based on the analysis 9216b of the data set that a control program update 9218 recommending a wait time of more than 5 seconds would prevent 90% of the distribution of the negative outcomes with a 95% confidence interval. Alternatively, the analytics system 9100 can determine based on the analysis 9216b of the data set that a control program update 9218 recommending a wait time of more than 5 seconds would result in the rate of positive outcomes being greater than the rate of negative outcomes. The analytics system 9100 could thus determine that the particular type of surgical instrument should wait more than 5 seconds before being fired under the particular tissue conditions so that negative outcomes are less common than positive outcomes. Based on either or both of these constraints for generating 9208 a control program update that the analytics system 9100 determines are satisfied by the analysis 9216b, the analytics system 9100 can generate 9208 a control program update 9218 for the surgical instrument that causes the surgical instrument, under the given circumstances, to either impose a 5 second or longer wait time before the particular surgical instrument can be fired or causes the surgical instrument to display a warning or recommendation to the user that indicates to the user that the user should wait at least 5 seconds before firing the instrument. Various other constraints can be utilized by the analytics system 9100 in determining whether to generate 9208 a control program update, such as whether a control program update would reduce the rate of negative outcomes by a certain percentage or whether a control program update maximizes the rate of positive outcomes.

After the control program update 9218 is generated 9208, the analytics system 9100 then can transmit 9210 the control program update 9218 for the appropriate type of modular devices 9050 to the surgical hubs 9000. In one exemplification, when a modular device 9050 that corresponds to the control program update 9218 is next connected to a surgical hub 9000 that has downloaded the control program update 9218, the modular device 9050 then automatically downloads the update 9218. In another exemplification, the surgical hub 9000 controls the modular device 9050 according to the control program update 9218, rather than the control program update 9218 being transmitted directly to the modular device 9050 itself.

In one aspect, the surgical system 9060 can be configured to push down verification of software parameters and updates if modular devices 9050 are detected to be out of date in the surgical hub 9000 data stream. In one exemplification, the analytics system 9000 can be configured to transmit a generated control program update for a particular type of modular device 9050 to a surgical hub 9000. In one aspect, each time a modular device 9050 connects to a surgical hub 9000, the modular device 9050 determines whether there is an updated version of its control program on or otherwise accessible via the surgical hub 9000. If the surgical hub 9000 does have an updated control program (or the updated control program is otherwise available from the analytics system 9100) for the particular type of modular device 9050, then the modular device 9050 downloads the control program update therefrom.

In one exemplification, any data set being transmitted to the analytics systems 9100 includes a unique ID for the surgical hub 9000 and the current version of its control program or operating system. In one exemplification, any data set being sent to the analytics systems 9100 can include a unique ID for the modular device 9050 and the current version of its control program or operating system. The unique ID of the surgical hub 9000 and/or modular device 9050 being associated with the uploaded data can allow the analytics system 9100 to determine whether the data corresponds to the most recent version of the control program. The analytics system 9100 could, for example, elect to discount (or ignore) data generated by a modular device 9050 or surgical hub 9000 being controlled by an out of date control program and/or cause the updated version of the control program to be pushed to the modular device 9050 or surgical hub 9000.

In one exemplification, the operating versions of the modular devices 9050 the surgical hub 9000 has updated control software for could also be included in a surgical hub 9000 status data block that is transmitted to the analytics system 9100 on a periodic basis. If the analytics system 9100 identifies that the operating versions of the control programs of the surgical hub 9100 and/or any of the connectable modular devices 9050 are out of date, the analytics system 9100 could push the most recent revision of the relevant control program to the surgical hub 9000.

In one exemplification, the surgical hub 9000 and/or modular devices 9050 can be configured to automatically download any software updates. In another exemplification, the surgical hub 9000 and/or modular devices 9050 can be configured to provide a prompt for the user to ask at the next setup step (e.g., between surgical procedures) if the user wants to update the out of date control program(s). In another exemplification, the surgical hub 9000 could be programmable by the user to never allow updates or only allow updates of the modular devices 9050 and not the surgical hub 9000 itself.

Figure 47:
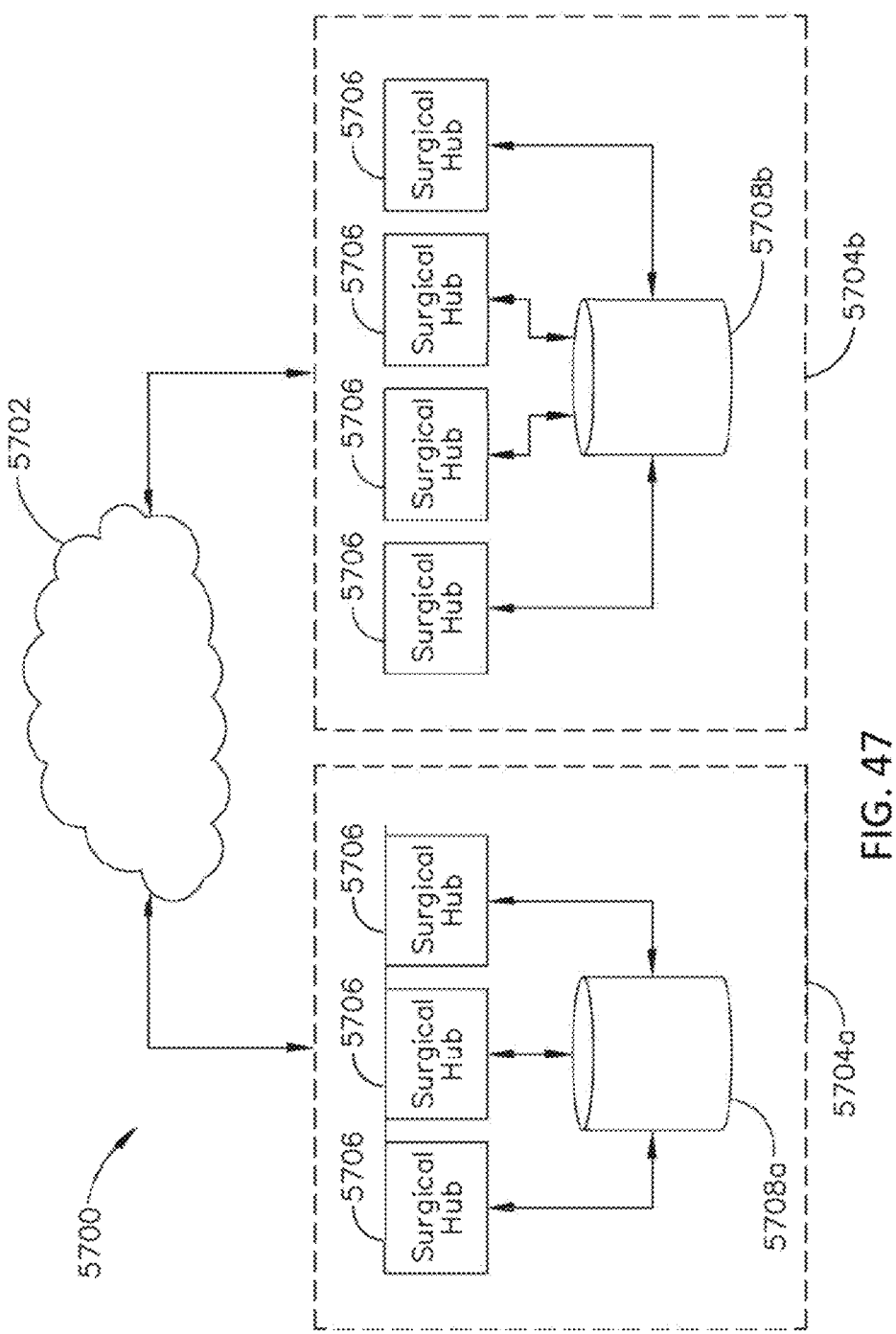
FIG. 47 is a block diagram of a computer-implemented interactive surgical system, in accordance with at least one aspect of the present disclosure.

An example of cloud aggregation of data from hubs is presented in FIG. 47. FIG. 47 illustrates a block diagram of a computer-implemented interactive surgical system 5700, in accordance with at least one aspect of the present disclosure. The system 5700 can include a number of surgical hubs 5706 that, as described above, are able to detect and track data related to surgical procedures that the surgical hubs 5706 (and the modular devices paired to the surgical hubs 5706) can be utilized in connection with. In one exemplification, the surgical hubs 5706 can be connected to form local networks such that the data being tracked by the surgical hubs 5706 is aggregated together across the network. The networks of surgical hubs 5706 can be associated with a medical facility, for example. The data aggregated from the network of surgical hubs 5706 can be analyzed to provide reports on data trends or recommendations. For example, the surgical hubs 5706 of a first medical facility 5704a can be communicably connected to a first local database 5708a and the surgical hubs 5706 of a second medical facility 5704b can be communicably connected to a second local database 5708b. The network of surgical hubs 5706 associated with the first medical facility 5704a can be distinct from the network of surgical hubs 5706 associated with the second medical facility 5704*b*, such that the aggregated data from each network of surgical hubs 5706 corresponds to each medical facility 5704*a*, 5704*b* individually. A surgical hub 5706 or another computer terminal communicably connected to the database 5708*a*, 5708*b* can be configured to provide reports or recommendations based on the aggregated data associated with the respective medical facility 5704*a*, 5704*b*. In this exemplification, the data tracked by the surgical hubs 5706 can be utilized to, for example, report whether a particular incidence of a surgical procedure deviated from the average in-network time to complete the particular procedure type.

In another exemplification, each surgical hub 5706 can be configured to upload the tracked data to the cloud 5702, which then processes and aggregates the tracked data across multiple surgical hubs 5706, networks of surgical hubs 5706, and/or medical facilities 5704*a*, 5704*b* that are connected to the cloud 5702. Each surgical hub 5706 can then be utilized to provide reports or recommendations based on the aggregated data. In this exemplification, the data tracked by the surgical hubs 5706 can be utilized to, for example, report whether a particular incidence of a surgical procedure deviated from the average global time to complete the particular procedure type.

In another exemplification, each surgical hub 5706 can further be configured to access the cloud 5702 to compare locally tracked data to global data aggregated from all of the surgical hubs 5706 that are communicably connected to the cloud 5702. Each surgical hub 5706 can be configured to provide reports or recommendations based on the comparison between the tracked local data relative to local (i.e., in-network) or global norms. In this exemplification, the data tracked by the surgical hubs 5706 can be utilized to, for example, report whether a particular incidence of a surgical procedure deviated from either the average in-network time or the average global time to complete the particular procedure type.

In one exemplification, each surgical hub 5706 or another computer system local to the surgical hub 5706 can be configured to locally aggregate the data tracked by the surgical hubs 5706, store the tracked data, and generate reports and/or recommendations according to the tracked data in response to queries. In cases where the surgical hub 5706 is connected to a medical facility network (which may include additional surgical hubs 5706), the surgical hub 5706 can be configured to compare the tracked data with the bulk medical facility data. The bulk medical facility data can include EMR data and aggregated data from the local network of surgical hubs 5706. In another exemplification, the cloud 5702 can be configured to aggregate the data tracked by the surgical hubs 5706, store the tracked data, and generate reports and/or recommendations according to the tracked data in response to queries.

Each surgical hub 5706 can provide reports regarding trends in the data and/or provide recommendations on improving the efficiency or effectiveness of the surgical procedures being performed. In various exemplifications, the data trends and recommendations can be based on data tracked by the surgical hub 5706 itself, data tracked across a local medical facility network containing multiple surgical hubs 5706, or data tracked across a number of surgical hubs 5706 communicably connected to a cloud 5702. The recommendations provided by the surgical hub 5706 can describe, for example, particular surgical instruments or product mixes to utilize for particular surgical procedures based on correlations between the surgical instruments/product mixes and patient outcomes and procedural efficiency. The reports provided by the surgical hub 5706 can describe, for example, whether a particular surgical procedure was performed efficiently relative to local or global norms, whether a particular type of surgical procedure being performed at the medical facility is being performed efficiently relative to global norms, and the average time taken to complete a particular surgical procedure or step of a surgical procedure for a particular surgical team.

For example, the surgical hub 5706 can be utilized to perform studies of performance by instrument type or cartridge type for various procedures. For example, the surgical hub 5706 can be utilized to perform studies on the performance of individual surgeons. For example, the surgical hub 5706 can be utilized to perform studies on the effectiveness of different surgical procedures according to patients' characteristics or disease states. Examples of data aggregation and analysis are described in detail in U.S. patent application Ser. No. 15/940,668, entitled "AGGREGATION AND REPORTING OF SURGICAL HUB DATA," filed on Mar. 29, 2018, now U.S. Patent Application Publication No. 2019/0201115, which is hereby incorporated herein by reference in its entirety.

In one exemplification, each surgical hub 5706 can be configured to determine when operating theater events occur (e.g., via a situational awareness system) and then track the length of time spent on each event. An operating theater event can be an event that a surgical hub 5706 can detect or infer the occurrence of. An operating theater event can include, for example, a particular surgical procedure, a step or portion of a surgical procedure, or downtime between surgical procedures. The operating theater events can be categorized according to an event type, such as a type of surgical procedure being performed, so that the data from individual procedures can be aggregated together to form searchable data sets.

The data tracked by the surgical hubs 5706 may be parsed to provide increasingly detailed metrics related to surgical procedures or the use of the surgical hub 5706 for an example data set. In one exemplification, the surgical hub 5706 can be configured to determine whether a surgical procedure is being performed and then track both the length of time spent between procedures (e.g., downtime) and the time spent on the procedures themselves. The surgical hub 5706 can further be configured to determine and track the time spent on each of the individual steps taken by the medical personnel (e.g., surgeons, nurses, orderlies) either between or during the surgical procedures. The surgical hub can determine when surgical procedures or different steps of surgical procedures are being performed via a situational awareness system, which is described in further detail herein. Aggregation (e.g., cloud aggregation) of data (e.g., from hubs) is further described in U.S. patent application Ser. No. 16/209,416, now U.S. Patent Application Publication No. 20190206562.

A surgical instrument (e.g., a powered intelligent surgical stapler) may have a means for displaying instrument functional data to a surgical user. Data displayed may be based on, for example, the intercommunication capabilities of the instrument (e.g., the surgical stapler), its accessories or consumables (e.g., cartridge(s)), and the display system. Data communicated from an accessory or consumable (e.g., a cartridge) to a user through the instrument may be or may include one or more static cartridge functional aspects, or the accessory or consumable (e.g., cartridge) data may be interactively combined with other data (e.g., instrument actuator or configuration data) to provide a broader understanding (e.g., a more complete or a full context) of instrument status.

Combined data may (e.g., additionally) be aggregated, for example, to determine tissue data or functional data from system interactions with a surgical site. Some or all (e.g., aggregated) data may be transferred to remote servers or storage. A user may be allowed to review, aggregate, or use stored data to provide insights for future uses of an instrument (e.g., a stapler). Capabilities such as instrument capabilities, features and/or user interactions allowed (e.g., and/or restricted) by a system (e.g., a control system of an instrument) may be based on, for example, system capacity parameters (e.g., a connectivity capability); system condition parameters (e.g., bandwidth, interference, conductivity, current load level); system authorization parameters (e.g., parameters indicating compatibility, authorized (e.g., purchased) mode/tier level of operation, authenticity); and/or control parameters provided to an instrument by a hub or external remote server (e.g., external control parameters), such as software version, revision or update level, subscription level, interconnectivity with an external/outside system, region of use, user input(s), or (e.g., secure) communication with an external database system).

An instrument may be subject to operating mode (e.g., tiered) control, which may be controlled by a hub. In some examples, a surgical hub may control instrument authentication, mode of operation and communication. Information about surgical hub coordination and control is provided in U.S. patent application Ser. No. 15/940,656, entitled "SURGICAL HUB COORDINATION OF CONTROL AND COMMUNICATION OF OPERATING ROOM DEVICES," filed on Mar. 29, 2018, now U.S. Patent Application Publication No. 2019/0201141, which is hereby incorporated herein by reference in its entirety.

An instrument may initialize and may or may not be upgraded operationally, for example, based on mode/tier control. A surgical instrument may be initialized, for example, upon initial or subsequent power on or wake up. For example, a surgical instrument may wake up (e.g., be turned on, powered up), and be initialized, e.g., by pairing with a surgical hub. A surgical instrument may initialize, for example, in an initial mode of operation (e.g., a default or entry-level mode). For example, a surgical instrument (e.g., upon being initialized) may send initialization mode (e.g., mode 1 or tier 1) information to a hub. The surgical instrument may receive an operation mode indication from the hub, which may be the same or different than an initialization mode. The instrument may (e.g., depending on the operation mode) receive (e.g., from a hub) operational parameters, instructions to download additional software, instructions to activate one or more functions, etc. Tiered operation (e.g., tiered access) for an instrument (e.g., an endocutter) may be controlled, for example, by a surgical hub. For example, a surgical instrument may receive an indication to download a software upgrade, e.g., to change operation from an initialization tier to another (e.g., higher or lower) tier. In an example, a surgical instrument may receive an indication to downgrade a mode/tier, for example, by disabling a functionality associated with a tier (e.g., an unauthorized or unsupported tier).

A surgical device may include communication capabilities, which may be wireless. For example, an instrument may have a Bluetooth communication array (e.g., to communicate with a hub). A wireless connection may be established between an instrument and a hub, for example, during instrument initialization. An instrument may provide information describing the instrument to a hub, such as one or more of a serial number, model number, and so on. An instrument may be configured with the ability to receive information (e.g., during initialization and/or during operation). Communication bandwidth may vary among operational modes. For example, an instrument may have limited bandwidth during initialization (e.g., to download basic information). An instrument may be capable of and/or configurable for higher bandwidth communication following initialization and/or if elevated to another mode/tier of operation. A hub may provide an instrument with improved firmware and/or software (e.g., communication software) to allow/support high bandwidth high data transfers (e.g., for real time data transfer), for example, if the improved communication software is not preloaded in the device at the time of initialization. An upgrade may involve, for example, downloading and installing firmware (e.g., BIOS) and/or software. Data aggregation capability, use of internal memory, and/or other features may also vary with modes of operation.

A processor in a surgical instrument may determine whether to allow or restrict bi-directional communication. An initialized mode of communication may be treated differently than an operational mode of communication. For example, a first mode of operation may include unidirectional communication (e.g., from an instrument to a hub), a second mode of operation may include bi-directional communication, and a third mode of operation may include interactive communication (e.g., with a local hub or other remote network portal).

Figure 43:
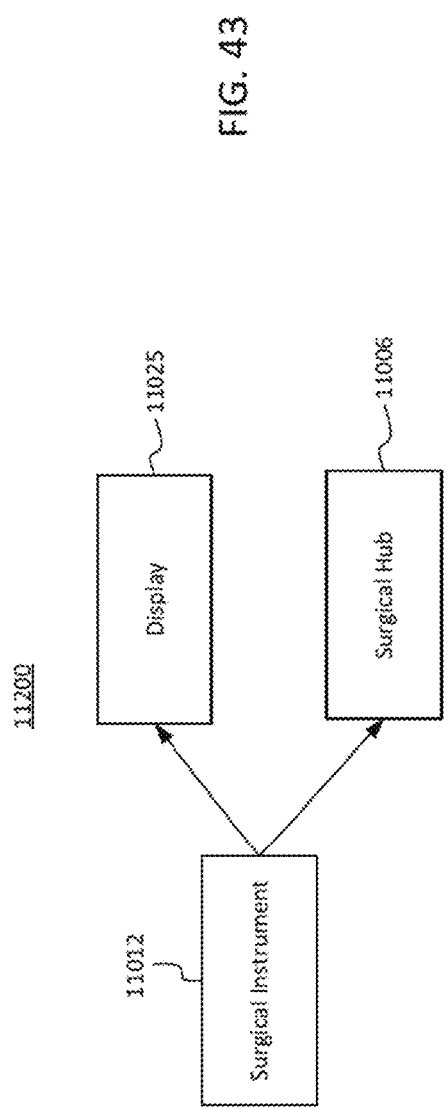
FIG. 43 illustrates an example surgical instrument operation mode.
Figure 44:
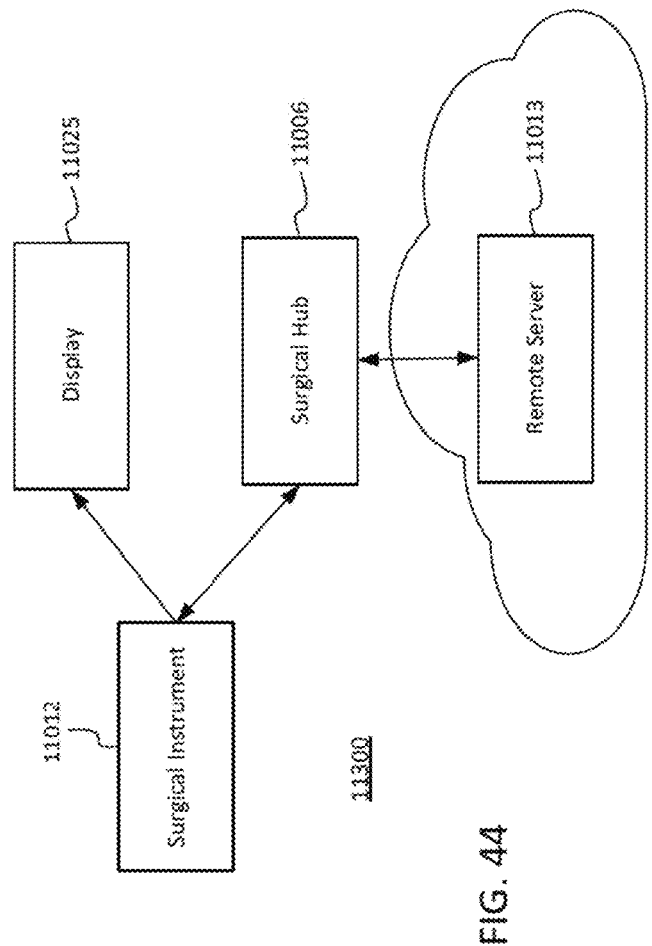
FIG. 44 illustrates an example surgical instrument operation mode.
Figure 45:
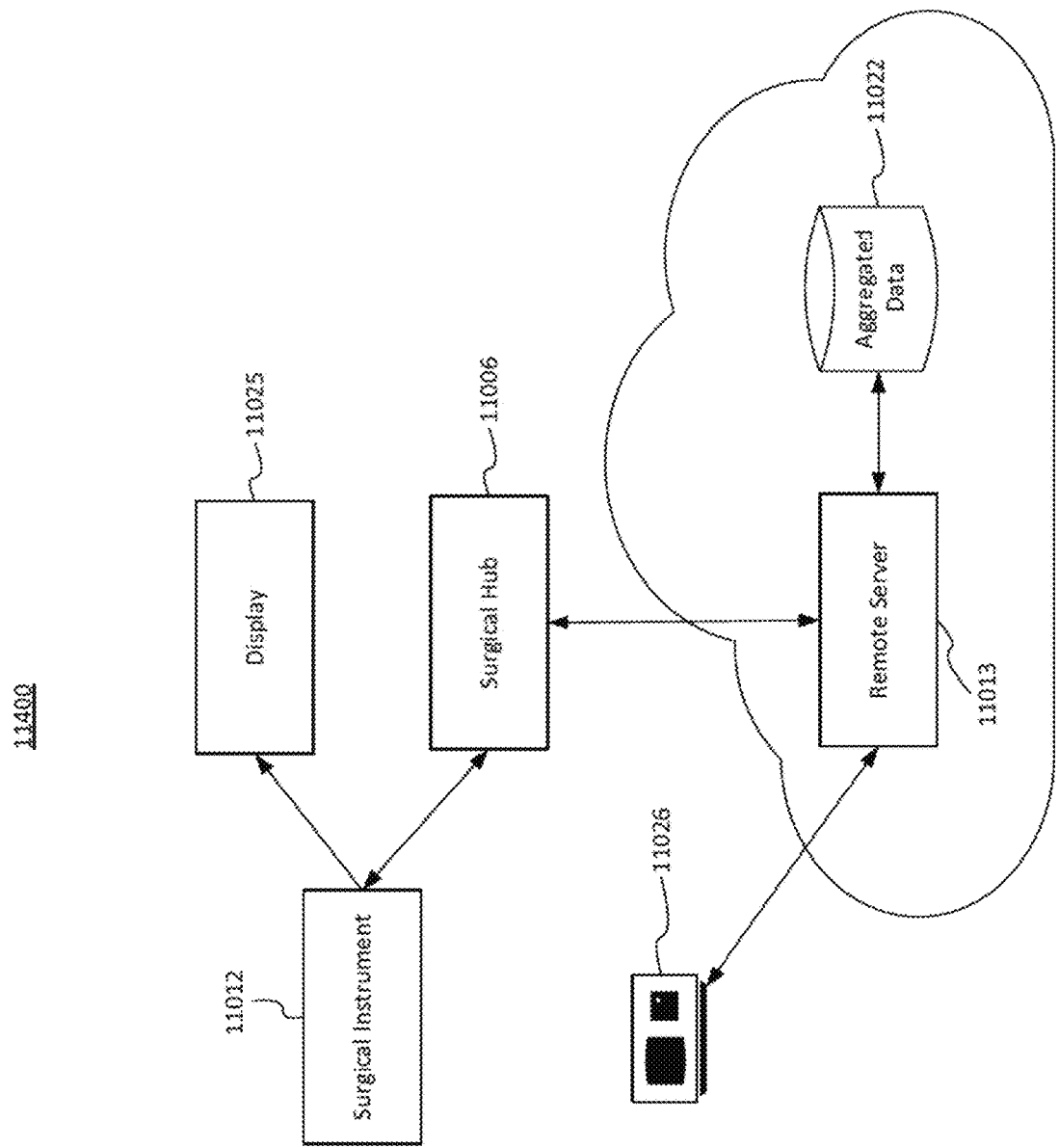
FIG. 45 illustrates an example surgical instrument operation mode.

FIGS. 43-45 show examples of three modes (e.g., tiers) of operation of a surgical instrument. Other examples may implement more or fewer tiers/modes with the same or different operational characteristics. Various levels/modes/tiers of instrument operation may vary the availability, access, level of use, level of interaction and/or support for one or more features available through an instrument, such as sensors, communications, displays, storage, analyses, feedback, recommendations or advice, and so on. In examples, an instrument processor may be configured to determine an operation mode, for example, based on an instrument operation control parameter (e.g., one or more of a system capacity parameter, a system condition parameter, a system authorization parameter, a tiered communication mode indication received from a hub, and/or a tiered communication mode indication received from a remote server).

FIG. 43 illustrates an example surgical instrument operation mode. FIG. 43 shows an example of a first mode of operation (e.g., tier I). Surgical instrument 11012 may, in an example of a first mode of operation, engage in unidirectional communication with surgical hub 11006 and provide information for display to display 11025. A processor in surgical instrument 11012, such as a surgical stapler, may obtain cartridge information (e.g., identification and/or authentication information), cartridge authentication information, status information (e.g., firing status information), error information, and so on. Cartridge information may include, for example, cartridge identification information (e.g., color, type, length, serial number, etc.), and/or cartridge authentication information (e.g., verified origin, lot information, etc.). Status information may include an instrument status (e.g., ready, fired, connected, etc.). Error information may include instrument or accessory (e.g., cartridge) errors (e.g., unable to read cartridge parameter, etc.). The surgical instrument 11012, such as a surgical stapler, may send the cartridge identification information, cartridge authentication information, status information, error information, and/or other information, for example, to surgical hub 11006 and/or to display 11025 (e.g., for display to a user). Information may be sent, for example, via a (e.g., wireless) transmitter (e.g., Bluetooth).

In an example, first mode (e.g., tier I) information may indicate a powered endocutter was fired with a cartridge of a particular color, and the cartridge may be associated with a serial number. Such information may be used to annotate a procedure, for example, to describe how the powered endocutter was used. For example, an instrument processor may be configured to obtain staple cartridge information and instrument status information from an end effector (e.g., for removably storing a surgical staple cartridge). The instrument processor may send the cartridge information and the instrument status information to the surgical hub.

FIG. 44 illustrates an example surgical instrument operation mode. FIG. 44 shows an example of a second mode of operation (e.g., tier II). Surgical instrument 11012 may, in an example of a second mode of operation, engage in bidirectional communication with surgical hub 11006 and provide information to display 11025 (e.g., for display to a user). Surgical hub 11006 may communicate with remote server 11013. A second mode of operation may build on (e.g., add capabilities or functionality to) first mode operation.

Examples of bi-directional communication may include, for example, sensed information from the end effector (e.g., sensed parameter(s), such as tissue thickness), sensed information from the handle (e.g., motor function, force to fire/close, etc.), usage information (e.g., time from clamp to fire, characterization of user controlled firing, etc.), prioritization of information to display, location to display information, compiled recommendations from database analysis, etc. Information may be communicated, for example, locally to/from (e.g., within) an operating room (OR) and/or to/from one or more systems outside the OR (e.g., cloud-based storage, etc.).

Figure 48:
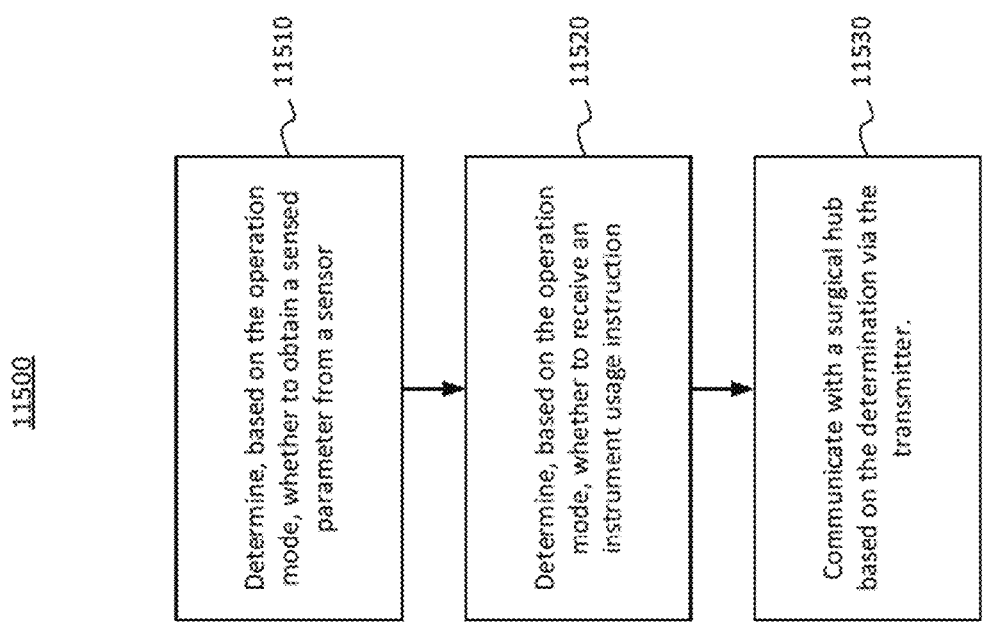
FIG. 48 illustrates an example flow for operating in accordance with surgical instrument operation mode(s).

FIG. 48 illustrates an example flow for operating in accordance with surgical instrument operation mode(s). In an example, a surgical instrument may include a processor, a transmitter and at least one sensor configured to provide a sensor signal (e.g., according to a physiological parameter of a tissue). The processor may be configured to make one or more determinations and/or take one or more actions based on an instrument operation mode.

At 11510, a determination may be made, based on the operation mode, whether to obtain a sensed parameter from a sensor. For example, a processor (e.g., in a surgical instrument) may determine (e.g., based on an instrument operation mode), whether to obtain (e.g., and/or send) a sensed parameter associated with a sensor signal from a sensor.

One or more sensors may sense and provide (e.g., in sensor signals) information, for example, from one or more portions (e.g., components or subcomponents) of a surgical instrument (e.g., a handle, an end effector, a knife, and/or a clamp). For example, a multitude of sensors are shown (e.g., in FIG. 40) and described in a surgical instrument comprising an adaptive control system in U.S. patent application Ser. No. 16/361,793, entitled "SURGICAL INSTRUMENT COMPRISING AN ADAPTIVE CONTROL SYSTEM," filed Mar. 22, 2019, now U.S. Patent Application Publication No. 20190314015, which is hereby incorporated herein by reference in its entirety. Sensed information from the handle may include, for example, a motor function, a force to fire/close, etc.

A sensor may be configured to sense and provide a sensor signal according to a physiological parameter of a tissue. For example, a surgical instrument may have a tissue thickness sensing module with a sensor that generates a sensor signal (e.g., tissue thickness signal) according to a physiological parameter of a tissue (e.g., tissue thickness), e.g., as shown and described with respect to FIGS. 7-15 in U.S. Pat. No. 9,345,481 and U.S. patent application Ser. No. 13/800,067, now U.S. Patent Application Publication No. 2014/0263552. In an example, a surgical instrument (e.g., an endocutter or surgical stapler) may include a tissue thickness sensing module, which may be located, for example, adjacent to the distal end of a staple cartridge. A tissue thickness sensing module may comprise a sensor and a controller. A sensor may be configured to generate a sensor signal, for example, a tissue thickness signal indicative of a thickness of the tissue (e.g., for tissue located between the anvil and the staple cartridge of an end effector portion of a surgical instrument). A controller may be in signal communication with the sensor. The controller may comprise a means for identifying the staple cartridge type of the staple cartridge. The staple cartridge type and the thickness of the tissue may be used, for example, to determine if the thickness of the tissue located between the anvil and the staple cartridge is within the optimal tissue thickness range of the staple cartridge.

In examples, a display or analysis (e.g., at a hub or remote server) may (e.g., interactively) combine sensed information with other information. For example, cartridge data may be interactively combined with instrument actuator or configuration data, e.g., to provide a broader understating of the (e.g., full) instrument status. Cartridge data can correspond to the size or type of staple being fired by the instrument, for example. Different types of staples may be utilized for different types of tissues. Usage information (e.g., time from clamp to fire, characterization of user-controlled firing, etc.) may be displayed and/or processed, for example, in combination with sensed information and/or other information.

At 11520, a determination may be made, based on the operation mode, whether to receive information (e.g., instrument usage instruction, operational information, and/or recommendations). For example, a processor (e.g., in a surgical instrument) may determine (e.g., based on an instrument operation mode), whether to receive information (e.g., from hub 11006 or remote server 11013 via surgical hub 11006).

Information received may include, for example, identification of the tissue to be operated on or that is being operated on (e.g., based on instrument or component position tracking information). See, for example, FIG. 40 and accompanying discussion in U.S. patent application Ser. No. 16/361,793, now U.S. Patent Application Publication No. 2019/0314015, which shows multiple sensors that may be used in a tracking system. A tracking procedure performed by the tracking system may be performed at a hub (e.g., surgical hub 11006). A processor in the instrument may receive position information from a tracking procedure at the hub.

Information received may include, for example, recommended usage information (e.g., time from clamp to fire, characterization of user-controlled firing, etc.). Information received may include, for example, force-to-fire, wait time/period, speed, time from clamp to fire, etc. Information received may include, for example, information for display and/or information indicating whether to display on one or more displays (e.g., a display on the handle of an instrument, a display associated with a hub or other display system), prioritization of information to display, location (e.g., on one or more display screens) in which to display information, etc. Information received may include instructions determined based on, for example, sensed information, a disease state of the issue, previous firings of a surgical instrument or device (e.g., an endocutter) and associated sensed information, etc. Information received may include, for example, a cartridge selection sequence/order.

Information received may include a recommendation to the surgeon, if another available stapler, another available energy device, and/or another stapler component (e.g., staple cartridge, shaft, etc. available for use with the selected stapler/device) is more optimal or optional. Information received may include a warning that a safety issue exists with the selected cartridge, or stapler/device. Examples of recommendations based on safety systems are described in detail in U.S. patent application Ser. No. 16/024,075, entitled "SAFETY SYSTEMS FOR SMART POWERED SURGICAL STAPLING," filed on Jun. 29, 2018, now U.S. Patent Application Publication No. 2019/0201146, which is hereby incorporated herein by reference in its entirety.

Information received may include, for example, situation awareness information. The recommendation may be indicated with an elevated priority level based on an anticipated surgical act and the input from the situationally-aware surgical hub For example, organ issue (e.g., stomach, lung, and so on) may be identified based on sensed information. A determination may be made based on sensed information, such as texture and/or compressibility (e.g., stomach tissue is very thick and very incompressible while lung tissue is very thick and very compressible). A clamping operation recommendation (e.g., speed and timing) and a firing operation recommendation (e.g., speed and timing, such as a wait period) may be determined, for example, based on tissue identification.

Examples of recommendations based on situation awareness are presented with respect to FIGS. 9 and 10. FIG. 9 is a diagram of an example situationally aware surgical system. FIG. 10 illustrates an example timeline of an illustrative surgical procedure and the inferences that the surgical hub can make from the data detected at each step in the surgical procedure. Other examples of recommendations based on situation awareness are disclosed in U.S. patent application Ser. No. 16/182,246, entitled "ADJUSTMENTS BASED ON AIRBORNE PARTICLE PROPERTIES," filed on Nov. 6, 2018, now U.S. Patent Application Publication No. 2019/0204201, which is hereby incorporated herein by reference in its entirety.

At 11530, communication may occur (e.g., via an instrument transmitter) with a surgical hub based on the determination at 11510 or 11520. Communications involving a surgical instrument (e.g., in second mode/tier operation) may include sending and/or receiving information (e.g., as shown by example in FIG. 44) using, respectively, a transmitter and/or a receiver. In examples, an instrument processor may be configured to obtain and send a sensed parameter to a surgical hub, for example, based on a determination that the instrument operation mode supports obtaining the sensed parameter. In examples, an instrument processor may be configured to receive an instrument usage instruction from the surgical hub via a receiver, for example, based on a determination that the instrument operation mode supports receiving the instrument usage instruction. The instrument processor may send the received instrument usage instruction to a display. In examples, an instrument processor may be configured to receive cartridge information from an end effector. The instrument processor may determine, based on the instrument operation mode, whether to combine the cartridge information with an instrument usage parameter (e.g., a time from clamp to fire and/or a characterization of a user-controlled firing). The instrument processor may, based on a determination that the instrument operation mode supports this capability, send the instrument usage parameter with the cartridge information to the surgical hub (e.g., via the transmitter).

FIG. 45 illustrates an example surgical instrument operation mode. FIG. 45 shows an example of a third mode of operation (e.g., tier III). Surgical instrument 11012 may, in an example of a third mode of operation, engage in bidirectional communication with surgical hub 11006 and provide information to display 11025 (e.g., for display to a user). Surgical hub 11006 may communicate with remote server 11013. Remote server 11013 may communicate with storage 11022 storing aggregated data. Remote server 11013 may communicate with a user portal 11026.

A third mode of operation may build on (e.g., add capabilities or functionality to) first and second modes of operation described herein. In some examples, a third mode of operation may add cloud storage of instrument usage, user accessibility, data aggregation, analyses and recommendations. For example, an instrument processor may be configured to determine (e.g., based on a mode of operation) whether to send information (e.g., instrument accessory information, such as cartridge data) that may be interactively combined (e.g., by a remote/cloud server) with instrument actuator or configuration data (e.g., for aggregation). Information that may be stored and aggregated (e.g., with instrument usage information) may include, for example, one or more of the following doctor identification information, type of surgery, patent information, or disease state. An instrument processor may be configured to send information to a hub and/or (e.g., directly) to a remote server.

An instrument processor may be configured to determine (e.g., based on a mode of operation) whether to receive a recommendation (e.g., an instrument usage recommendation and/or an accessory selection recommendation) based on stored information (e.g., aggregated historic/typical instrument usage information). For example, a recommendation may be recommended instrument usage information (e.g., stapler cartridge selection) generated based on aggregated historical instrument usage data. For example, a recommendation may be a stapler cartridge selection recommendation generated based on aggregated cartridge usage data associated with a procedural step (e.g., of using an instrument).

Historical information stored, aggregated, analyzed and used for recommendations may include, for example, information about previous procedures, such as procedure types, tissues, tissue conditions, accessory (e.g., cartridge) types selected and order of use in surgical instrument (e.g., surgical stapler), and so on. In various examples, historical information may include one or more of the following: compiled recommendations from database analysis (e.g., based on aggregated data); surgeon identification information (e.g., Dr. X); procedure information (e.g., bariatric procedure type); surgeon's usage information (e.g., trend, prediction, typical use), cartridge selection sequence/order; and/or display utilization (e.g., on an instrument handle or on a hub display/display system).

A remote server may aggregate data from multiple surgeries and users (e.g., surgeons). A remote server may send aggregated data and/or usage recommendations to a surgical instrument (e.g., directly or via a hub). A remote server may allow a user to review, aggregate, or use stored data to provide insights for future uses of an instrument (e.g., a surgical stapler).

A third mode/tier of instrument operation may provide a user (e.g., a surgeon) access to historical data (e.g., their own data). A surgeon may change a procedure over time (e.g., change cartridge selection of type(s), combination and sequence). A cartridge may be color coded, for example, to indicate staple heights (e.g., gray, white, blue, green, gold, or gold, green and black). Different staple heights may be used to staple tissue, for example, based on one or more variables, such as a type of tissue, a state of tissue, and/or a gap between tissue.

Cartridge selection and usage information associated with a surgeon may be stored for future review. Cartridge selection and usage information associated with a surgeon may be aggregated (e.g., over time). Surgical procedure information may be correlated with post-operative data, such as post-operative leaks, secondary complications and/or reoperation information.

Data analytics may be retrieved and viewed, for example, at a user portal 11026. Information about data collection, data aggregation, surgical data analytics, and remote (e.g., cloud) server access to data and recommendations are disclosed in U.S. patent application Ser. No. 15/940,679, entitled "CLOUD-BASED MEDICAL ANALYTICS FOR LINKING OF LOCAL USAGE TRENDS WITH THE RESOURCE ACQUISITION BEHAVIORS OF LARGER DATA SET," filed on Mar. 29, 2018, now U.S. Patent Application Publication No. 2019/0201144, which is hereby incorporated herein by reference in its entirety.

Remote (e.g., cloud) server 11013 may include an input/output interface configured for accessing data from a plurality of medical hub communication devices (e.g., including surgical hub 11006). A medical hub may be communicatively coupled to at least one surgical instrument (e.g., surgical instrument 11012). Remote server 11013 may include a processor configured to receive instrument usage information associated with a medical procedure performed by a user (e.g., a surgeon). The remote server processor may be configured to aggregate the received instrument usage information with historic usage information associated with the user. The processor may be configured to send the aggregated instruction usage information, for example, to a data analytics server, to a hub (e.g., surgical hub 11006), etc.

A remote server processor (e.g., in remote server 11013) may be configured to correlate received instrument usage information to an outcome of a medical procedure and/or to an instrument operation status during the medical procedure. The remote server processor may be configured to send the correlated information, for example, to a hub (e.g., surgical hub 11006 for display to a user before, during and/or after a medical procedure using surgical instrument 11012). A remote server may send correlated information, for example, as a reference before, during a medical procedure, and/or as a post-operative review following a medical procedure, etc.

A remote server processor (e.g., in remote server 11013) may be configured to determine a recommended instrument usage information associated with an upcoming (e.g., or ongoing) medical procedure based on the correlated information. The remote server processor may be configured to send the recommended instrument usage information, for example, to a hub (e.g., surgical hub 11006 for display to a user before or during a medical procedure using surgical instrument 11012).

In one general aspect, a powered surgical end-effector is provided. The powered surgical end-effector comprises a controllable jaw configured to operate on a tissue; an updatable memory having stored therein a default actuation algorithm; and a processor. The processor is configured to: operate in a first mode at a first time, wherein in the first mode the processor is configured to operate an aspect of the controllable jaw according to the default actuation algorithm; and receive data at a second time, after the first time, that causes the processor to operate in a second mode, wherein in the second mode the processor is configured to operate an aspect of the controllable jaw according to an alternative actuation algorithm.

In another general aspect, a powered surgical end-effector is provided. The powered surgical end-effector comprises: a controllable jaw configured to operate on a tissue; an updatable memory having stored therein a default actuation algorithm; and a processor. The processor is configured to determine whether to operate in a first mode or a second mode, wherein in the first mode the processor is configured to operate an aspect of the jaw according to the default actuation algorithm, and wherein in the second mode the processor is configured to operate an aspect of the jaw according to an alternative actuation algorithm.

In yet another general aspect, a surgical hub is provided. The surgical hub comprises: a transmitter and a receiver configured to establish a communication pathway between the surgical hub and a powered surgical end-effector; and a processor. The processor is configured to: determine whether communication is available with the powered surgical end-effector that is configured to operate in a first mode or in a second mode, wherein in the first mode, the powered surgical end-effector operates an aspect of a controllable jaw according to a default actuation algorithm stored in the updatable memory of the powered surgical end-effector; receive data from related to the powered surgical end-effector via the receiver; determine whether the surgical end-effector should operate in the first mode or the second mode based on the received data; and based on the determination, send updated data that causes the powered surgical end-effector to operate in the second mode, wherein in the second mode, the powered surgical end-effector operates the aspect of the controllable jaw according to an alternative actuation algorithm.

Examples herein describes a powered surgical end-effector that may include a controllable jaw configured to operate on a tissue, an updatable memory having stored therein a default actuation algorithm, and a processor. The processor may be configured to operate in a first mode at a first time, wherein in the first mode the processor may be configured to operate an aspect of the controllable jaw according to the default actuation algorithm. The processor may receive data at a second time, after the first time, that may cause the processor to operate in a second mode, wherein in the second mode the processor may be configured to operate an aspect of the controllable jaw according to an alternative actuation algorithm.

FIGS. 49-52 depict a motor-driven surgical instrument 150010 for cutting and fastening that may or may not be reused. In the illustrated examples, the surgical instrument 150010 includes a housing 150012 that comprises a handle assembly 150014 that is configured to be grasped, manipulated, and actuated by the clinician. The housing 150012 is configured for operable attachment to an interchangeable shaft assembly 150200 that has an end effector 150300 operably coupled thereto that is configured to perform one or more surgical tasks or procedures. In accordance with the present disclosure, various forms of interchangeable shaft assemblies may be effectively employed in connection with robotically controlled surgical systems. The term "housing" may encompass a housing or similar portion of a robotic system that houses or otherwise operably supports at least one drive system configured to generate and apply at least one control motion that could be used to actuate interchangeable shaft assemblies. The term "frame" may refer to a portion of a handheld surgical instrument. The term "frame" also may represent a portion of a robotically controlled surgical instrument and/or a portion of the robotic system that may be used to operably control a surgical instrument. Interchangeable shaft assemblies may be employed with various robotic systems, instruments, components, and methods disclosed in U.S. Pat. No. 9,072,535, titled SURGICAL STAPLING INSTRUMENTS WITH ROTATABLE STAPLE DEPLOYMENT ARRANGEMENTS, which is herein incorporated by reference in its entirety.

Figure 49:
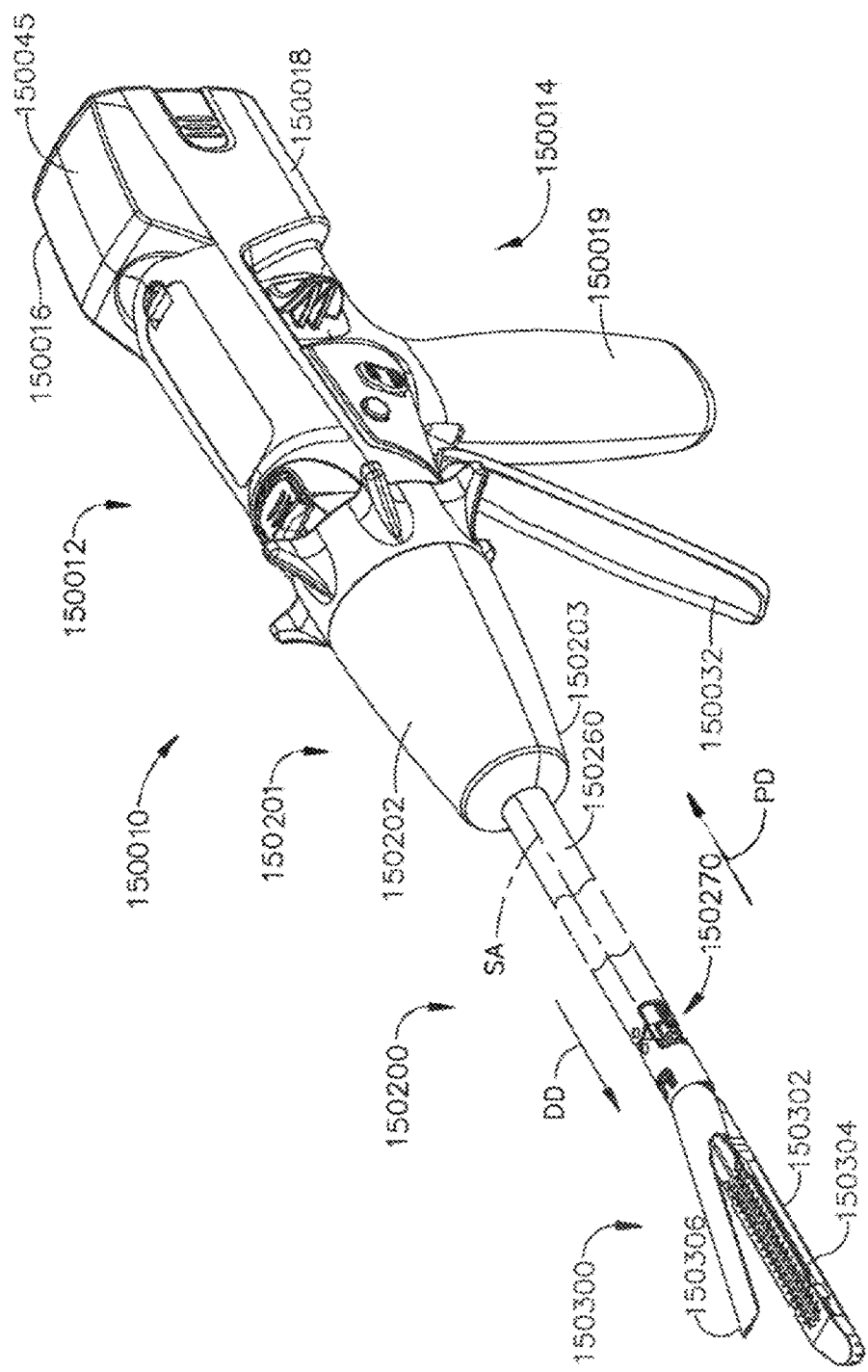
FIG. 49 is a perspective view of a surgical instrument that has an interchangeable shaft assembly operably coupled thereto, in accordance with at least one aspect of this disclosure.

FIG. 49 is a perspective view of a surgical instrument 150010 that has an interchangeable shaft assembly 150200 operably coupled thereto, in accordance with at least one aspect of this disclosure. The housing 150012 includes an end effector 150300 that comprises a surgical cutting and fastening device configured to operably support a surgical staple cartridge 150304 therein. The housing 150012 may be configured for use in connection with interchangeable shaft assemblies that include end effectors that are adapted to support different sizes and types of staple cartridges, have different shaft lengths, sizes, and types. The housing 150012 may be employed with a variety of interchangeable shaft assemblies, including assemblies configured to apply other motions and forms of energy such as, radio frequency (RF) energy, ultrasonic energy, and/or motion to end effector arrangements adapted for use in connection with various surgical applications and procedures. The end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

The handle assembly 150014 may comprise a pair of interconnectable handle housing segments 150016, 150018 interconnected by screws, snap features, adhesive, etc. The handle housing segments 150016, 150018 cooperate to form a pistol grip portion 150019 that can be gripped and manipulated by the clinician. The handle assembly 150014 operably supports a plurality of drive systems configured to generate and apply control motions to corresponding portions of the interchangeable shaft assembly that is operably attached thereto. A display may be provided below a cover 150045.

Figure 50:
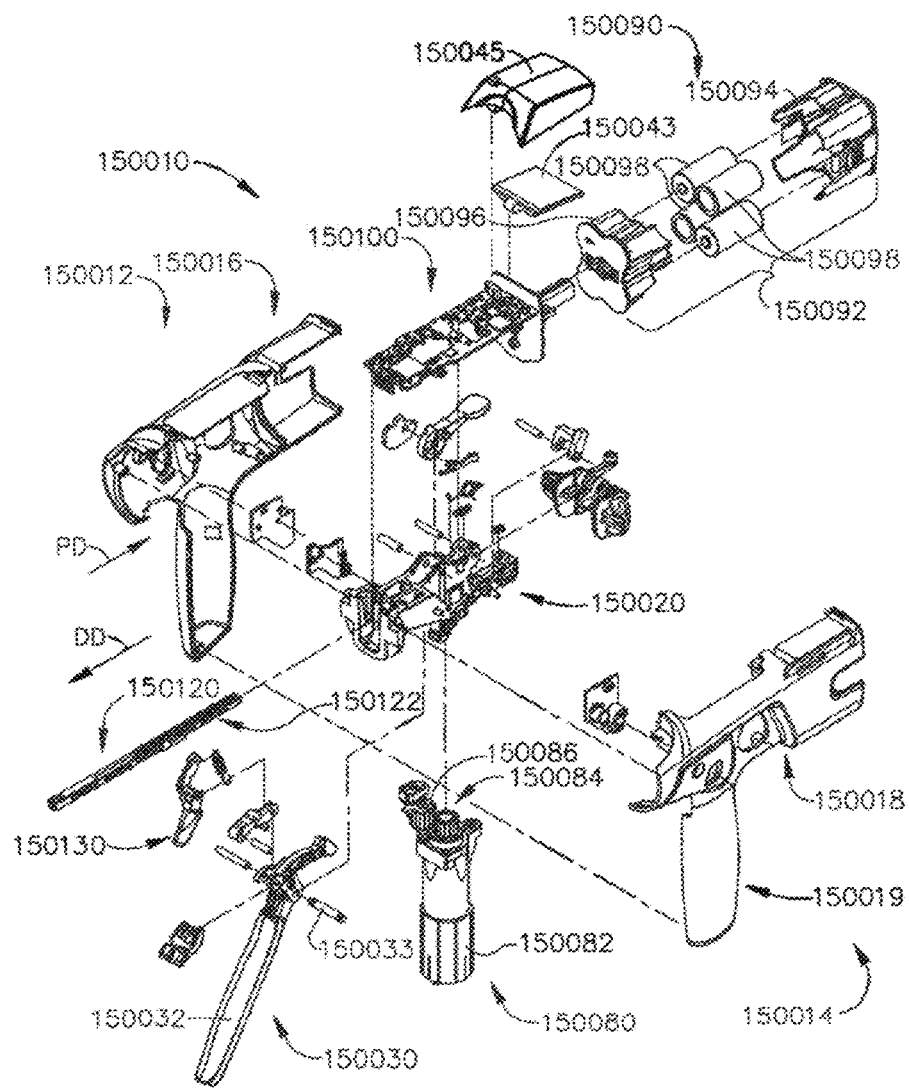
FIG. 50 is an exploded assembly view of a portion of the surgical instrument of FIG. 49, in accordance with at least one aspect of this disclosure.

FIG. 50 is an exploded assembly view of a portion of the surgical instrument 150010 of FIG. 49, in accordance with at least one aspect of this disclosure. The handle assembly 150014 may include a frame 150020 that operably supports a plurality of drive systems. The frame 150020 can operably support a "first" or closure drive system 150030, which can apply closing and opening motions to the interchangeable shaft assembly 150200. The closure drive system 150030 may include an actuator such as a closure trigger 150032 pivotally supported by the frame 150020. The closure trigger 150032 is pivotally coupled to the handle assembly 150014 by a pivot pin 150033 to enable the closure trigger 150032 to be manipulated by a clinician. When the clinician grips the pistol grip portion 150019 of the handle assembly 150014, the closure trigger 150032 can pivot from a starting or "unactuated" position to an "actuated" position and more particularly to a fully compressed or fully actuated position.

The handle assembly 150014 and the frame 150020 may operably support a firing drive system 150080 configured to apply firing motions to corresponding portions of the interchangeable shaft assembly attached thereto. The firing drive system 150080 may employ an electric motor 150082 located in the pistol grip portion 150019 of the handle assembly 150014. The electric motor 150082 may be a DC brushed motor having a maximum rotational speed of approximately 25,000 RPM, for example. In other arrangements, the motor may include a brushless motor, a cordless motor, a synchronous motor, a stepper motor, or any other suitable electric motor. The electric motor 150082 may be powered by a power source 150090 that may comprise a removable power pack 150092. The removable power pack 150092 may comprise a proximal housing portion 150094 configured to attach to a distal housing portion 150096. The proximal housing portion 150094 and the distal housing portion 150096 are configured to operably support a plurality of batteries 150098 therein. Batteries 150098 may each comprise, for example, a Lithium Ion (LI) or other suitable battery. The distal housing portion 150096 is configured for removable operable attachment to a control circuit board 150100, which is operably coupled to the electric motor 150082. Several batteries 150098 connected in series may power the surgical instrument 150010. The power source 150090 may be replaceable and/or rechargeable. A display 150043, which is located below the cover 150045, is electrically coupled to the control circuit board 150100. The cover 150045 may be removed to expose the display 150043.

The electric motor 150082 can include a rotatable shaft (not shown) that operably interfaces with a gear reducer assembly 150084 mounted in meshing engagement with a set, or rack, of drive teeth 150122 on a longitudinally movable drive member 150120. The longitudinally movable drive member 150120 has a rack of drive teeth 150122 formed thereon for meshing engagement with a corresponding drive gear 150086 of the gear reducer assembly 150084. In use, a voltage polarity provided by the power source 150090 can operate the electric motor 150082 in a clockwise direction wherein the voltage polarity applied to the electric motor by the battery can be reversed in order to operate the electric motor 150082 in a counter-clockwise direction. When the electric motor 150082 is rotated in one direction, the longitudinally movable drive member 150120 will be axially driven in the distal direction "DD." When the electric motor 150082 is driven in the opposite rotary direction, the longitudinally movable drive member 150120 will be axially driven in a proximal direction "PD." The handle assembly 150014 can include a switch that can be configured to reverse the polarity applied to the electric motor 150082 by the power source 150090. The handle assembly 150014 may include a sensor configured to detect the position of the longitudinally movable drive member 150120 and/or the direction in which the longitudinally movable drive member 150120 is being moved.

Actuation of the electric motor 150082 can be controlled by a firing trigger 150130 that is pivotally sup-ported on the handle assembly 150014. The firing trigger 150130 may be pivoted between an unactuated position and an actuated position.

Turning back to FIG. 49, the interchangeable shaft assembly 150200 includes an end effector 150300 comprising an elongated channel 150302 configured to operably support a surgical staple cartridge 150304 therein. The end effector 150300 may include an anvil 150306 that is pivot-ally supported relative to the elongated channel 150302. The interchangeable shaft assembly 150200 may include an articulation joint 150270. Construction and operation of the end effector 150300 and the articulation joint 150270 are set forth in U.S. Patent Application Publication No. 2014/0263541, titled ARTICULATABLE SURGICAL INSTRUMENT COMPRISING AN ARTICULATION LOCK, which is herein incorporated by reference in its entirety. The interchangeable shaft assembly 150200 may include a proximal housing or nozzle 150201 comprised of nozzle portions 150202, 150203. The interchangeable shaft assembly 150200 may include a closure tube 150260 extending along a shaft axis SA that can be utilized to close and/or open the anvil 150306 of the end effector 150300. Turning back to FIG. 49, the closure tube 150260 is translated distally (direction "DD") to close the anvil 150306, for example, in response to the actuation of the closure trigger 150032 in the manner described in the aforementioned reference U.S. Patent Application Publication No. 2014/0263541. The anvil 150306 is opened by proximally translating the closure tube 150260. In the anvil open position, the closure tube 150260 is moved to its proximal position.

Figure 51:
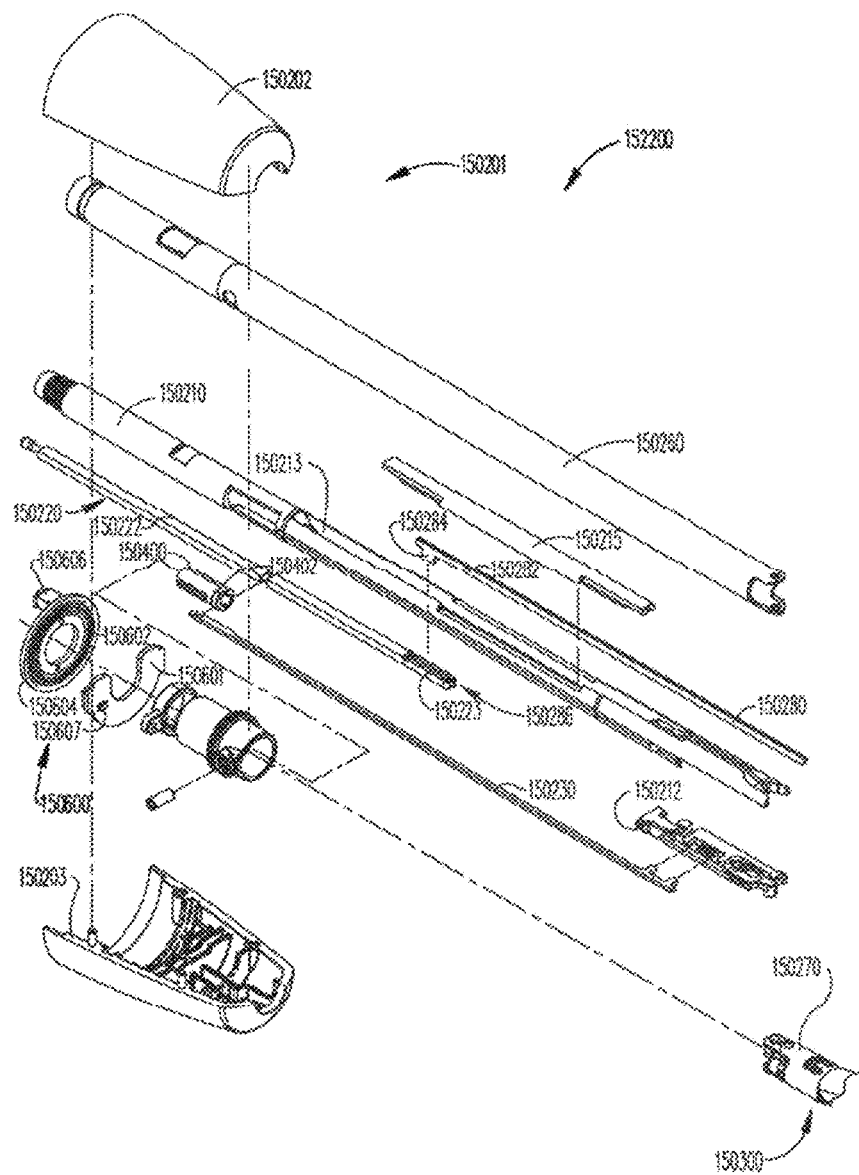
FIG. 51 is an exploded assembly view of portions of the interchangeable shaft assembly, in accordance with at least one aspect of this disclosure.

FIG. 51 is another exploded assembly view of portions of the interchangeable shaft assembly 150200, in accordance with at least one aspect of this disclosure. The interchangeable shaft assembly 150200 may include a firing member 150220 supported for axial travel within the spine 150210. The firing member 150220 includes an intermediate firing shaft 150222 configured to attach to a distal cutting portion or knife bar 150280. The firing member 150220 may be referred to as a "second shaft" or a "second shaft assembly". The intermediate firing shaft 150222 may include a longitudinal slot 150223 in a distal end configured to receive a tab 150284 on the proximal end 150282 of the knife bar 150280. The longitudinal slot 150223 and the proximal end 150282 may be configured to permit relative movement there between and can comprise a slip joint 150286. The slip joint 150286 can permit the intermediate firing shaft 150222 of the firing member 150220 to articulate the end effector 150300 about the articulation joint 150270 without moving, or at least substantially moving, the knife bar 150280. Once the end effector 150300 has been suitably oriented, the intermediate firing shaft 150222 can be advanced distally until a proximal sidewall of the longitudinal slot 150223 contacts the tab 150284 to advance the knife bar 150280 and fire the staple cartridge positioned within the channel 150302. The spine 150210 has an elongated opening or window 150213 therein to facilitate assembly and insertion of the intermediate firing shaft 150222 into the spine 150210. Once the intermediate firing shaft 150222 has been inserted therein, a top frame segment 150215 may be engaged with the shaft frame 150212 to enclose the intermediate firing shaft 150222 and knife bar 150280 therein. Operation of the firing member 150220 may be found in U.S. Patent Application Publication No. 2014/0263541. A spine 150210 can be configured to slidably support a firing member 150220 and the closure tube 150260 that extends around the spine 150210. The spine 150210 may slidably support an articulation driver 150230.

The interchangeable shaft assembly 150200 can include a clutch assembly 150400 configured to selectively and releasably couple the articulation driver 150230 to the firing member 150220. The clutch assembly 150400 includes a lock collar, or lock sleeve 150402, positioned around the firing member 150220 wherein the lock sleeve 150402 can be rotated between an engaged position in which the lock sleeve 150402 couples the articulation driver 150230 to the firing member 150220 and a disengaged position in which the articulation driver 150230 is not operably coupled to the firing member 150220. When the lock sleeve 150402 is in the engaged position, distal movement of the firing member 150220 can move the articulation driver 150230 distally and, correspondingly, proximal movement of the firing member 150220 can move the articulation driver 150230 proximally. When the lock sleeve 150402 is in the disengaged position, movement of the firing member 150220 is not transmitted to the articulation driver 150230 and, as a result, the firing member 150220 can move independently of the articulation driver 150230. The nozzle 150201 may be employed to operably engage and disengage the articulation drive system with the firing drive system in the various manners described in U.S. Patent Application Publication No. 2014/0263541.

The interchangeable shaft assembly 150200 can comprise a slip ring assembly 150600 which can be configured to conduct electrical power to and/or from the end effector 150300 and/or communicate signals to and/or from the end effector 150300, for example. The slip ring assembly 150600 can comprise a proximal connector flange 150604 and a distal connector flange 150601 positioned within a slot defined in the nozzle portions 150202, 150203. The proximal connector flange 150604 can comprise a first face and the distal connector flange 150601 can comprise a second face positioned adjacent to and movable relative to the first face. The distal connector flange 150601 can rotate relative to the proximal connector flange 150604 about the shaft axis SA-SA. The proximal connector flange 150604 can comprise a plurality of concentric, or at least substantially concentric, conductors 150602 defined in the first face thereof. A connector 150607 can be mounted on the proximal side of the distal connector flange 150601 and may have a plurality of contacts wherein each contact corresponds to and is in electrical contact with one of the conductors 150602. Such an arrangement permits relative rotation between the proximal connector flange 150604 and the distal connector flange 150601 while maintaining electrical contact there between. The proximal connector flange 150604 can include an electrical connector 150606 that can place the conductors 150602 in signal communication with a shaft circuit board, for example. In at least one instance, a wiring harness comprising a plurality of conductors can extend between the electrical connector 150606 and the shaft circuit board. The electrical connector 150606 may extend proximally through a connector opening defined in the chassis mounting flange. U.S. Patent Application Publication No. 2014/0263551, titled STAPLE CARTRIDGE TISSUE THICKNESS SENSOR SYSTEM, is incorporated herein by reference in its entirety. U.S. Patent Application Publication No. 2014/0263552, titled STAPLE CARTRIDGE TISSUE THICKNESS SENSOR SYSTEM, is incorporated by reference in its entirety. Further details regarding slip ring assembly 150600 may be found in U.S. Patent Application Publication No. 2014/0263541.

The interchangeable shaft assembly 150200 can include a proximal portion fixably mounted to the handle assembly 150014 and a distal portion that is rotatable about a longitudinal axis. The rotatable distal shaft portion can be rotated relative to the proximal portion about the slip ring assembly 150600. The distal connector flange 150601 of the slip ring assembly 150600 can be positioned within the rotatable distal shaft portion.

Figure 52:
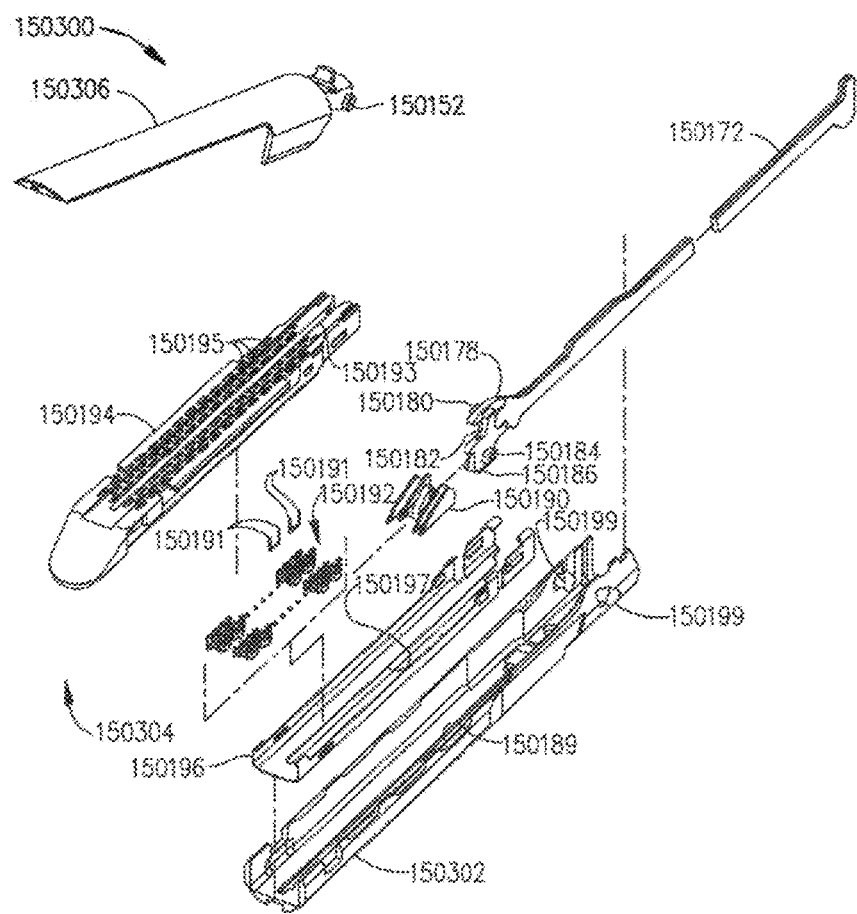
FIG. 52 is an exploded view of an end effector of the surgical instrument of FIG. 49, in accordance with at least one aspect of this disclosure.

FIG. 52 is an exploded view of one aspect of an end effector 150300 of the surgical instrument 150010 of FIG. 49, in accordance with at least one aspect of this disclosure. The end effector 150300 may include the anvil 150306 and the surgical staple cartridge 150304. The anvil 150306 may be coupled to an elongated channel 150302. Apertures 150199 can be defined in the elongated channel 150302 to receive pins 150152 extending from the anvil 150306 to allow the anvil 150306 to pivot from an open position to a closed position relative to the elongated channel 150302 and surgical staple cartridge 150304. A firing bar 150172 is configured to longitudinally translate into the end effector 150300. The firing bar 150172 may be constructed from one solid section, or may include a laminate material comprising a stack of steel plates. The firing bar 150172 comprises an I-beam 150178 and a cutting edge 150182 at a distal end thereof. A distally projecting end of the firing bar 150172 can be attached to the I-beam 150178 to assist in spacing the anvil 150306 from a surgical staple cartridge 150304 positioned in the elongated channel 150302 when the anvil 150306 is in a closed position. The I-beam 150178 may include a sharpened cutting edge 150182 to sever tissue as the I-beam 150178 is advanced distally by the firing bar 150172. In operation, the I-beam 150178 may, or fire, the surgical staple cartridge 150304. The surgical staple cartridge 150304 can include a molded cartridge body 150194 that holds a plurality of staples 150191 resting upon staple drivers 150192 within respective upwardly open staple cavities 150195. A wedge sled 150190 is driven distally by the I-beam 150178, sliding upon a cartridge tray 150196 of the surgical staple cartridge 150304. The wedge sled 150190 upwardly cams the staple drivers 150192 to force out the staples 150191 into deforming contact with the anvil 150306 while the cutting edge 150182 of the I-beam 150178 severs clamped tissue.

The I-beam 150178 can include upper pins 150180 that engage the anvil 150306 during firing. The I-beam 150178 may include middle pins 150184 and a bottom foot 150186 to engage portions of the cartridge body 150194, cartridge tray 150196, and elongated channel 150302. When a surgical staple cartridge 150304 is positioned within the elongated channel 150302, a slot 150193 defined in the cartridge body 150194 can be aligned with a longitudinal slot 150197 defined in the cartridge tray 150196 and a slot 150189 defined in the elongated channel 150302. In use, the I-beam 150178 can slide through the aligned longitudinal slots 150193, 150197, and 150189 wherein the bottom foot 150186 of the I-beam 150178 can engage a groove running along the bottom surface of elongated channel 150302 along the length of slot 150189, the middle pins 150184 can engage the top surfaces of cartridge tray 150196 along the length of longitudinal slot 150197, and the upper pins 150180 can engage the anvil 150306. The I-beam 150178 can space, or limit the relative movement between, the anvil 150306 and the surgical staple cartridge 150304 as the firing bar 150172 is advanced distally to fire the staples from the surgical staple cartridge 150304 and/or incise the tissue captured between the anvil 150306 and the surgical staple cartridge 150304. The firing bar 150172 and the I-beam 150178 can be retracted proximally allowing the anvil 150306 to be opened to release the two stapled and severed tissue portions.

Figure 53A:
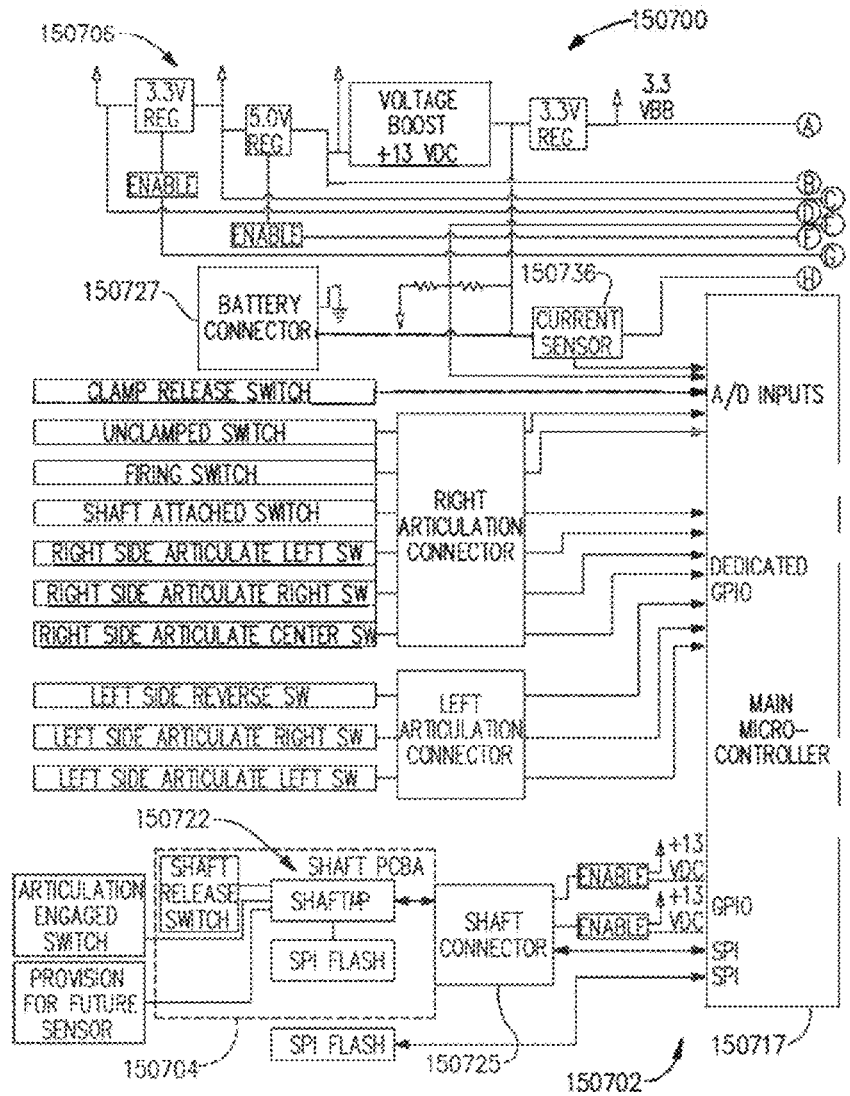
FIG. 53A is a block diagram of a control circuit of the surgical instrument of FIG. 49 spanning two drawing sheets, in accordance with at least one aspect of this disclosure.
Figure 53B:
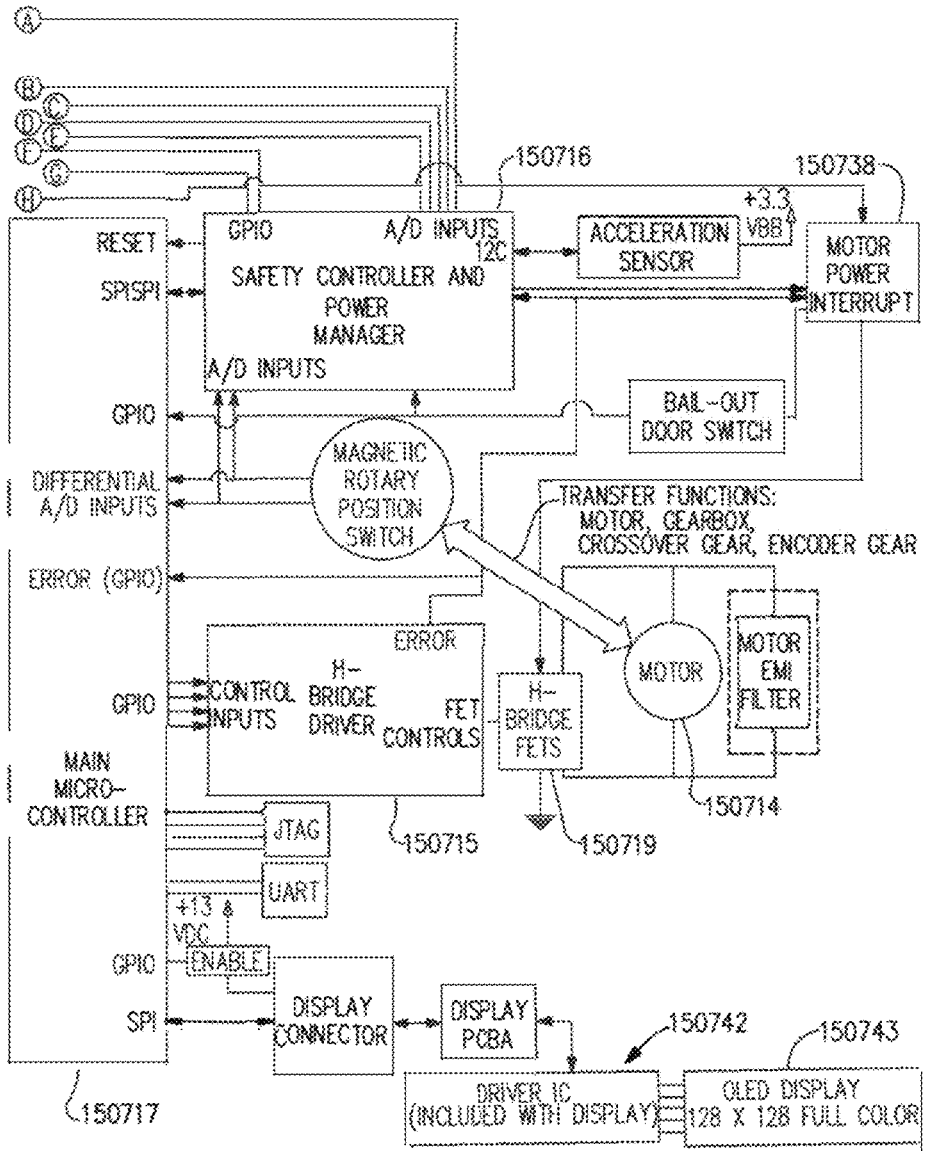
FIG. 53B is a block diagram of a control circuit of the surgical instrument of FIG. 49 spanning two drawing sheets, in accordance with at least one aspect of this disclosure.

FIGS. 53A and 53B is a block diagram of a control circuit 150700 of the surgical instrument 150010 of FIG. 49. spanning two drawing sheets, in accordance with at least one aspect of this disclosure. Referring primarily to FIGS. 53A and 53B, a handle assembly 150702 may include a motor 150714 which can be controlled by a motor driver 150715 and can be employed by the firing system of the surgical instrument 150010. In various forms, the motor 150714 may be a DC brushed driving motor having a maximum rotational speed of approximately 25,000 RPM. In other arrangements, the motor 150714 may include a brushless motor, a cordless motor, a synchronous motor, a stepper motor, or any other suitable electric motor. The motor driver 150715 may comprise an H-Bridge driver comprising field effect transistors (FETs) 150719, for example. The motor 150714 can be powered by the power assembly 150706 releasably mounted to the handle assembly 150200 for supplying control power to the surgical instrument 150010. The power assembly 150706 may comprise a battery which may include a number of battery cells connected in series that can be used as the power source to power the surgical instrument 150010. In certain circumstances, the battery cells of the power assembly 150706 may be replaceable and/or rechargeable. In at least one example, the battery cells can be Lithium-Ion batteries which can be separably couplable to the power assembly 150706.

The shaft assembly 150704 may include a shaft assembly controller 150722 which can communicate with a safety controller and power management controller 150716 through an interface while the shaft assembly 150704 and the power assembly 150706 are coupled to the handle assembly 150702. For example, the interface may comprise a first interface portion 150725 which may include one or more electric connectors for coupling engagement with corresponding shaft assembly electric connectors and a second interface portion 150727 which may include one or more electric connectors for coupling engagement with corresponding power assembly electric connectors to permit electrical communication between the shaft assembly controller 150722 and the power management controller 150716 while the shaft assembly 150704 and the power assembly 150706 are coupled to the handle assembly 150702. One or more communication signals can be transmitted through the interface to communicate one or more of the power requirements of the attached interchangeable shaft assembly 150704 to the power management controller 150716. In response, the power management controller may modulate the power output of the battery of the power assembly 150706, as described below in greater detail, in accordance with the power requirements of the attached shaft assembly 150704. The connectors may comprise switches which can be activated after mechanical coupling engagement of the handle assembly 150702 to the shaft assembly 150704 and/or to the power assembly 150706 to allow electrical communication between the shaft assembly controller 150722 and the power management controller 150716.

The interface can facilitate transmission of the one or more communication signals between the power management controller 150716 and the shaft assembly controller 150722 by routing such communication signals through a main controller 150717 residing in the handle assembly 150702, for example. In other circumstances, the interface can facilitate a direct line of communication between the power management controller 150716 and the shaft assembly controller 150722 through the handle assembly 150702 while the shaft assembly 150704 and the power assembly 150706 are coupled to the handle assembly 150702.

The main controller 150717 may be any single core or multicore processor such as those known under the trade name ARM Cortex by Texas Instruments. In one aspect, the main controller 150717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with Stellaris Ware® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 150706 may include a power management circuit which may comprise the power management controller 150716, a power modulator 150738, and a current sense circuit 150736. The power management circuit can be configured to modulate power output of the battery based on the power requirements of the shaft assembly 150704 while the shaft assembly 150704 and the power assembly 150706 are coupled to the handle assembly 150702. The power management controller 150716 can be programmed to control the power modulator 150738 of the power output of the power assembly 150706 and the current sense circuit 150736 can be employed to monitor power output of the power assembly 150706 to provide feedback to the power management controller 150716 about the power output of the battery so that the power management controller 150716 may adjust the power output of the power assembly 150706 to maintain a desired output. The power management controller 150716 and/or the shaft assembly controller 150722 each may comprise one or more processors and/or memory units which may store a number of software modules.

The surgical instrument 150010 (FIGS. 49-52) may comprise an output device 150742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 150742 may comprise a display 150743 which may be included in the handle assembly 150702. The shaft assembly controller 150722 and/or the power management controller 150716 can provide feedback to a user of the surgical instrument 150010 through the output device 150742. The interface can be configured to connect the shaft assembly controller 150722 and/or the power management controller 150716 to the output device 150742. The output device 150742 can instead be integrated with the power assembly 150706. In such circumstances, communication between the output device 150742 and the shaft assembly controller 150722 may be accomplished through the interface while the shaft assembly 150704 is coupled to the handle assembly 150702. The control circuit 150700 comprises circuit segments configured to control operations of the powered surgical instrument 150010. A safety controller segment (Segment 1) comprises a safety controller and the main controller 150717 segment (Segment 2). The safety controller and/or the main controller 150717 are configured to interact with one or more additional circuit segments such as an acceleration segment, a display segment, a shaft segment, an encoder segment, a motor segment, and a power segment. Each of the circuit segments may be coupled to the safety controller and/or the main controller 150717. The main controller 150717 is also coupled to a flash memory. The main controller 150717 also comprises a serial communication interface. The main controller 150717 comprises a plurality of inputs coupled to, for example, one or more circuit segments, a battery, and/or a plurality of switches.

The segmented circuit may be implemented by any suitable circuit, such as, for example, a printed circuit board assembly (PCBA) within the powered surgical instrument 150010. It should be understood that the term processor as used herein includes any microprocessor, processors, controller, controllers, or other basic computing device that incorporates the functions of a computer's central processing unit (CPU) on an integrated circuit or at most a few integrated circuits. The main controller 150717 is a multipurpose, programmable device that accepts digital data as input, processes it according to instructions stored in its memory, and provides results as output. It is an example of sequential digital logic, as it has internal memory. The control circuit 150700 can be configured to implement one or more of the processes described herein.

The acceleration segment (Segment 3) comprises an accelerometer. The accelerometer is configured to detect movement or acceleration of the powered surgical instrument 150010. Input from the accelerometer may be used to transition to and from a sleep mode, identify an orientation of the powered surgical instrument, and/or identify when the surgical instrument has been dropped. In some examples, the acceleration segment is coupled to the safety controller and/or the main controller 150717.

The display segment (Segment 4) comprises a display connector coupled to the main controller 150717. The display connector couples the main controller 150717 to a display through one or more integrated circuit drivers of the display. The integrated circuit drivers of the display may be integrated with the display and/or may be located separately from the display. The display may comprise any suitable display, such as, for example, an organic light emitting diode (OLED) display, a liquid-crystal display (LCD), and/or any other suitable display. In some examples, the display segment is coupled to the safety controller.

The shaft segment (Segment 5) comprises controls for an interchangeable shaft assembly coupled to the surgical instrument 150010 and/or one or more controls for an end effector 150300 coupled to the interchangeable shaft assembly 150200. The shaft segment comprises a shaft connector configured to couple the main controller 150717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 150200 and/or the shaft PCBA. The shaft PCBA may be coupled to the interchangeable shaft assembly 150200 and/or integral with the surgical instrument 150010. In some examples, the shaft segment comprises a second shaft EEPROM. The second shaft EEPROM comprises a plurality of algorithms, routines, parameters, and/or other data corresponding to one or more shaft assemblies 150200 and/or end effectors 150300 that may be interfaced with the powered surgical instrument 150010.

The position encoder segment (Segment 6) comprises one or more magnetic angle rotary position encoders. The one or more magnetic angle rotary position encoders are configured to identify the rotational position of the motor 150714, an interchangeable shaft assembly, and/or an end effector 150300 of a surgical instrument. In some examples, the magnetic angle rotary position encoders may be coupled to the safety controller and/or the main controller 150717.

The motor circuit segment (Segment 7) comprises a motor 150714 configured to control movements of a powered surgical instrument. The motor 150714 is coupled to the main microcontroller processor 150717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 150717 and/or the safety controller. In some examples, the motor 150714 is coupled to a motor electro-magnetic interference (EMI) filter.

The motor controller controls a first motor flag and a second motor flag to indicate the status and position of the motor 150714 to the main controller 150717. The main controller 150717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 150717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 150717. The switches may be configured to control operations of a surgical instrument, of the segmented circuit, and/or indicate a status of the surgical instrument. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly and/or an end effector. A left side reverse switch and a right side reverse switch are coupled to the main controller 150717. The left side switches comprising the left side articulation left switch, the left side articulation right switch, the left side articulation center switch, and the left side reverse switch are coupled to the main controller 150717 by a left flex connector. The right side switches comprising the right side articulation left switch, the right side articulation right switch, the right side articulation center switch, and the right side reverse switch are coupled to the main controller 150717 by a right flex connector. A firing switch, a clamp release switch, and a shaft engaged switch are coupled to the main controller 150717.

Any suitable mechanical, electromechanical, or solid state switches may be employed to implement the plurality of switches, in any combination. For example, the switches may be limit switches operated by the motion of components associated with a surgical instrument or the presence of an object. Such switches may be employed to control various functions associated with the surgical instrument. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-PET, metal-oxide semiconductor-PET (MOSFET), bipolar, and the like). Other switches may include wireless switches, ultra-sonic switches, accelerometers, inertial sensors, among others.

Figure 54:
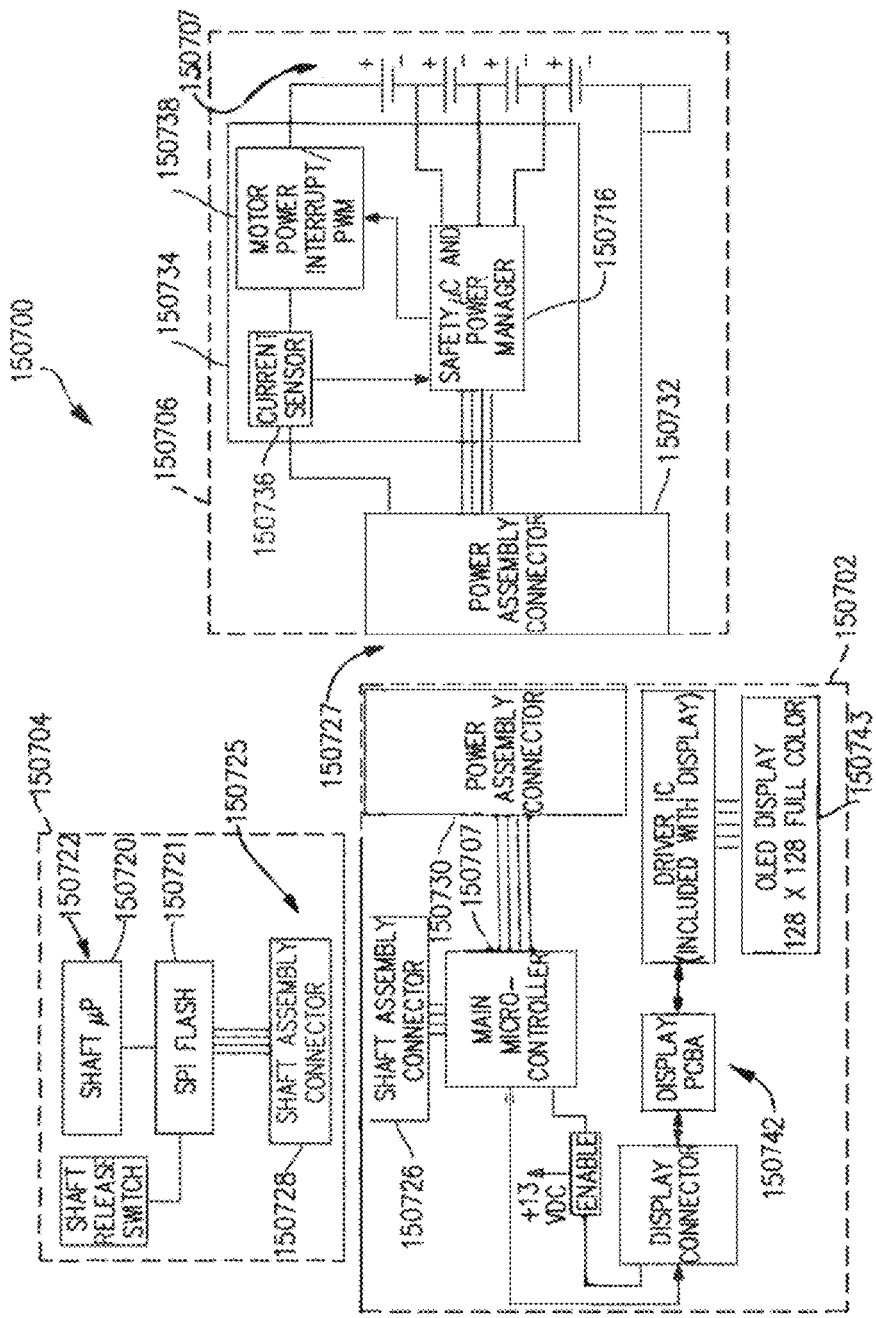
FIG. 54 is a block diagram of the control circuit of the surgical instrument of FIG. 49 illustrating interfaces between the handle assembly, the power assembly, and the handle assembly and the interchangeable shaft assembly, in accordance with at least one aspect of this disclosure.

FIG. 54 is another block diagram of the control circuit 150700 of a surgical instrument illustrating interfaces between the handle assembly 150702 and the power assembly 150706 and between the handle assembly 150702 and the interchangeable shaft assembly 150704, in accordance with at least one aspect of this disclosure. The handle assembly 150702 may comprise a main controller 150717, a shaft assembly connector 150726 and a power assembly connector 150730. The power assembly 150706 may include a power assembly connector 150732, a power management circuit 150734 that may comprise the power management controller 150716, a power modulator 150738, and a current sense circuit 150736. The shaft assembly connectors 150730, 150732 form an interface 150727. The power management circuit 150734 can be configured to modulate power output of the battery 150707 based on the power requirements of the interchangeable shaft assembly 150704 while the interchangeable shaft assembly 150704 and the power assembly 150706 are coupled to the handle assembly 150702. The power management controller 150716 can be programmed to control the power modulator 150738 of the power output of the power assembly 150706 and the current sense circuit 150736 can be employed to monitor power output of the power assembly 150706 to provide feedback to the power management controller 150716 about the power output of the battery 150707 so that the power management controller 150716 may adjust the power output of the power assembly 150706 to maintain a desired output. The shaft assembly 150704 comprises a shaft processor 150720 coupled to a non-volatile memory 150721 and shaft assembly connector 150728 to electrically couple the shaft assembly 150704 to the handle assembly 150702. The shaft assembly connectors 150726, 150728 form interface 150725. The main controller 150717, the shaft processor 150720, and/or the power management controller 150716 can be configured to implement one or more of the processes described herein.

The surgical instrument may comprise an output device 150742 to a sensory feedback to a user. Such devices may comprise visual feedback devices (e.g., an LCD display screen, LED indicators), audio feedback devices (e.g., a speaker, a buzzer), or tactile feedback devices (e.g., haptic actuators). In certain circumstances, the output device 150742 may comprise a display 150743 that may be included in the handle assembly 150702. The shaft assembly controller 150722 and/or the power management controller 150716 can provide feedback to a user of the surgical instrument 150010 through the output device 150742. The interface 150727 can be configured to connect the shaft assembly controller 150722 and/or the power management controller 150716 to the output device 150742. The output device 150742 can be integrated with the power assembly 150706. Communication between the output device 150742 and the shaft assembly controller 150722 may be accomplished through the interface 150725 while the interchangeable shaft assembly 150704 is coupled to the handle assembly 150702. Having described a control circuit for controlling the operation of a surgical instrument, the disclosure now turns to various configurations of a surgical instrument and the control circuit 150700.

Figure 55:
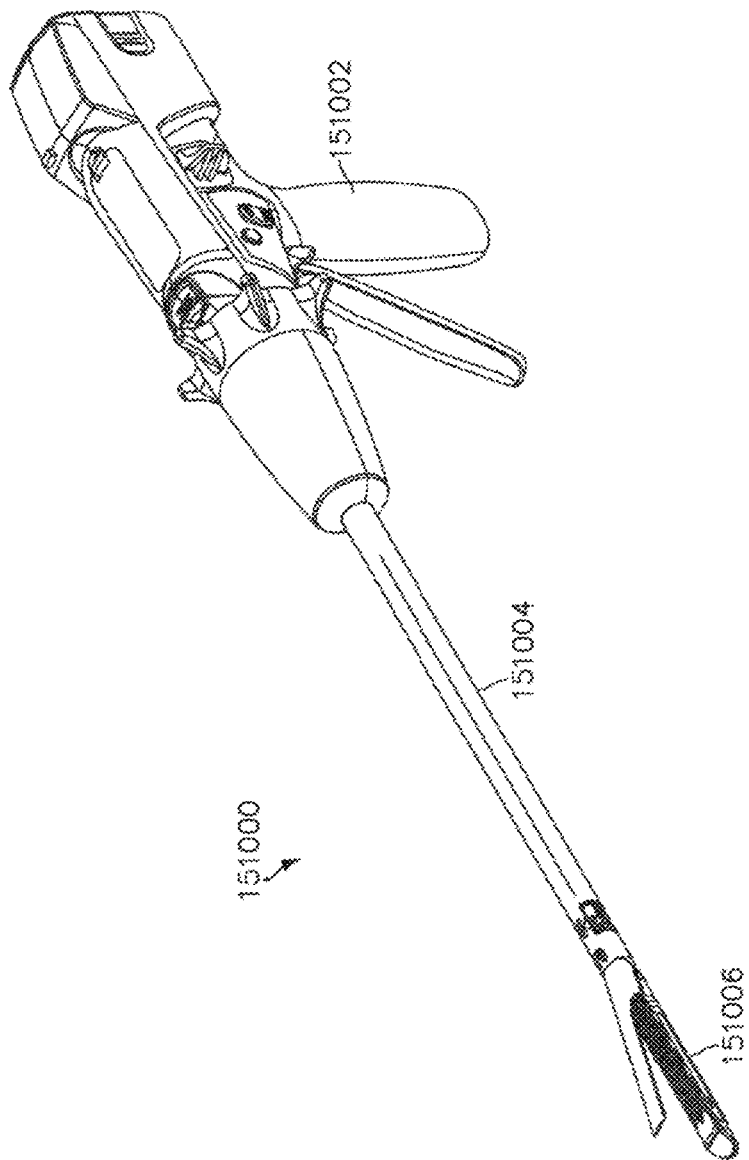
FIG. 55 depicts an example medical device that can include one or more aspects of the present disclosure.
Figure 56:
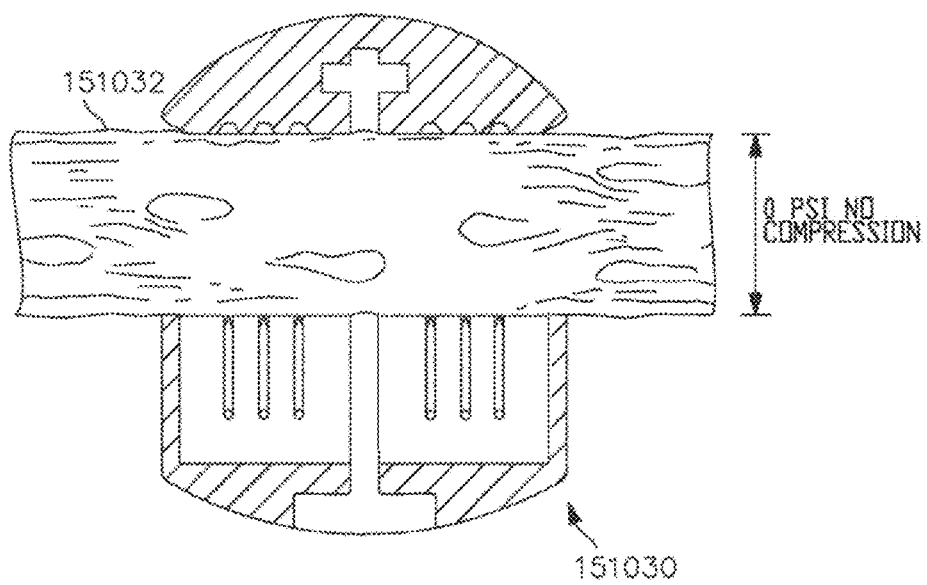
FIG. 56 depicts an example end-effector of a medical device surrounding tissue in accordance with one or more aspects of the present disclosure.
Figure 57:
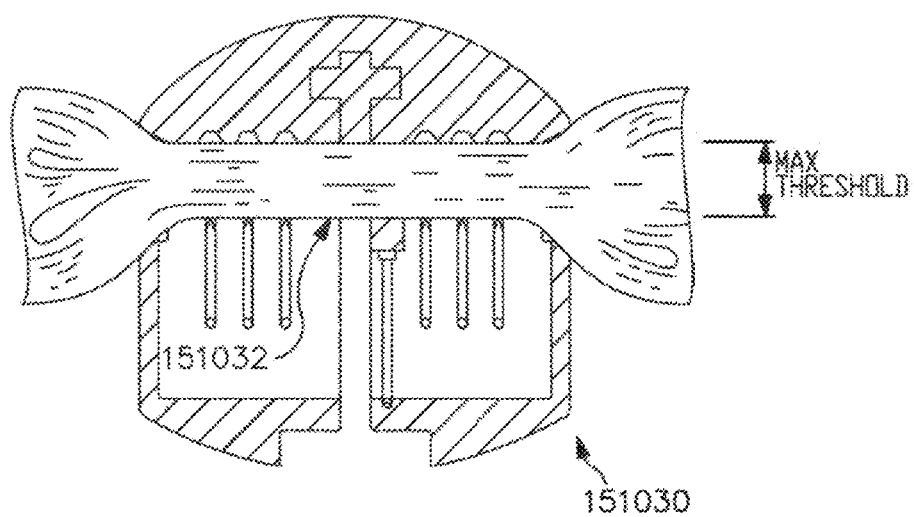
FIG. 57 depicts an example end-effector of a medical device compressing tissue in accordance with one or more aspects of the present disclosure.
Figure 58:
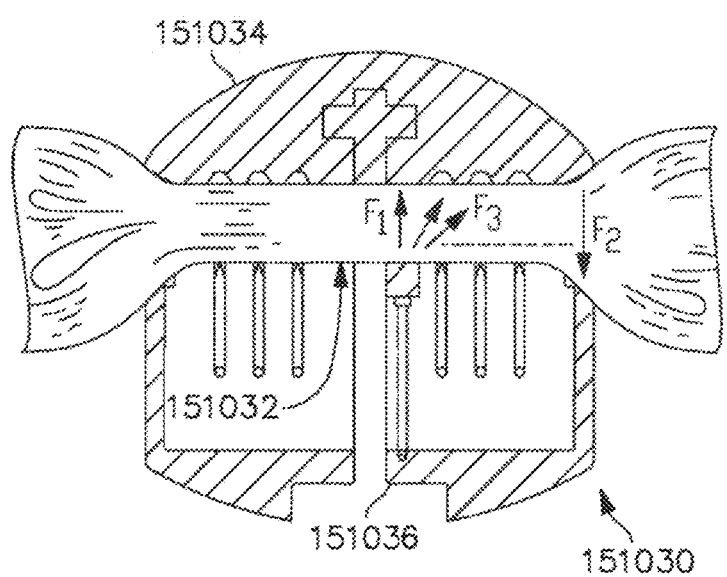
FIG. 58 depicts example forces exerted by an end-effector of a medical device compressing tissue in accordance with one or more aspects of the present disclosure.
Figure 59:
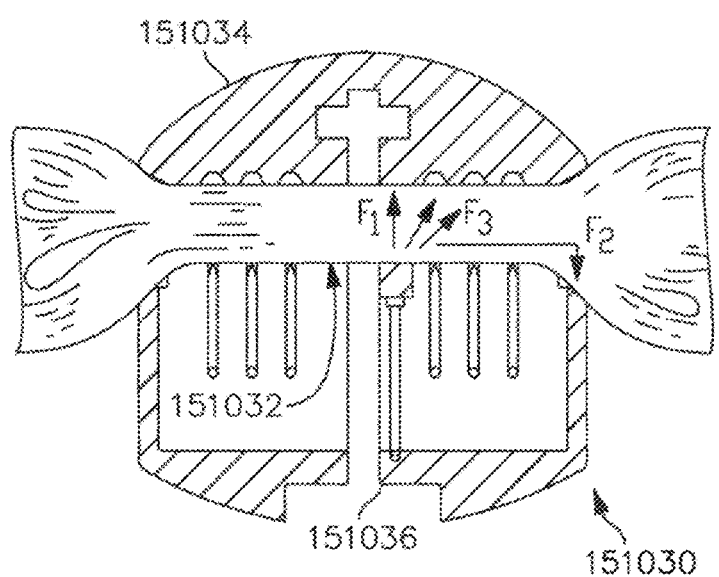
FIG. 59 also depicts example forces exerted by an end-effector of a medical device compressing tissue in accordance with one or more aspects of the present disclosure.

Referring to FIG. 55, a surgical stapler 151000 may include a handle component 151002, a shaft component 151004, and an end-effector component 151006. The surgical stapler 151000 is similarly constructed and equipped as the motor-driven surgical cutting and fastening instrument 150010 described in connection with FIG. 49. Accordingly, for conciseness and clarity the details of operation and construction will not be repeated here. The end-effector 151006 may be used to compress, cut, or staple tissue. Referring now to FIG. 56, an end-effector 151030 may be positioned by a physician to surround tissue 151032 prior to compression, cutting, or stapling. As shown in FIG. 56, no compression may be applied to the tissue while preparing to use the end-effector. Referring now to FIG. 57, by engaging the handle (e.g., handle 151002) of the surgical stapler, the physician may use the end-effector 151030 to compress the tissue 151032. In one aspect, the tissue 151032 may be compressed to its maximum threshold, as shown in FIG. 57. Referring to FIG. 58, various forces may be applied to the tissue 151032 by the end-effector 151030. For example, vertical forces F1 and F2 may be applied by the anvil 151034 and the channel frame 151036 of the end-effector 151030 as tissue 151032 is compressed between the two. Referring now to FIG. 59, various diagonal and/or lateral forces also may be applied to the tissue 151032 when compressed by the end-effector 151030. For example, force F3 may be applied. For the purposes of operating a medical device such as surgical stapler 151000, it may be desirable to sense or calculate the various forms of compression being applied to the tissue by the end-effector. For example, knowledge of vertical or lateral compression may allow the end-effector to more precisely or accurately apply a staple operation or may inform the operator of the surgical stapler such that the surgical stapler can be used more properly or safely.

The compression through tissue 151032 may be determined from an impedance of tissue 151032. At various levels of compression, the impedance Z of tissue 151032 may increase or decrease. By applying a voltage V and a current I to the tissue 151032, the impedance Z of the tissue 151032 may be determined at various levels of compression. For example, impedance Z may be calculated by dividing the applied voltage V by the current I.

Figure 60:
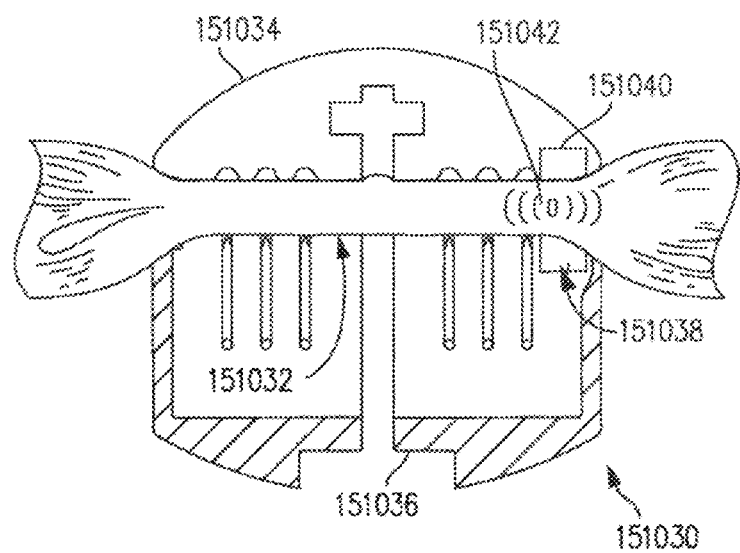
FIG. 60 depicts an example tissue compression sensor system in accordance with one or more aspects of the present disclosure.

Referring now to FIG. 60, in one aspect, an RF electrode 151038 may be positioned on the end-effector 151030 (e.g., on a staple cartridge, knife, or channel frame of the end-effector 151030). Further, an electrical contact 151040 may be positioned on the anvil 151034 of the end-effector 151030. In one aspect, the electrical contact may be positioned on the channel frame of the end-effector. As the tissue 151032 is compressed between the anvil 151034 and, for example, the channel frame 151036 of the end-effector 151030, an impedance Z of the tissue 151032 changes. The vertical tissue compression 151042 caused by the end-effector 151030 may be measured as a function of the impedance Z of the tissue 151032.

Figure 61:
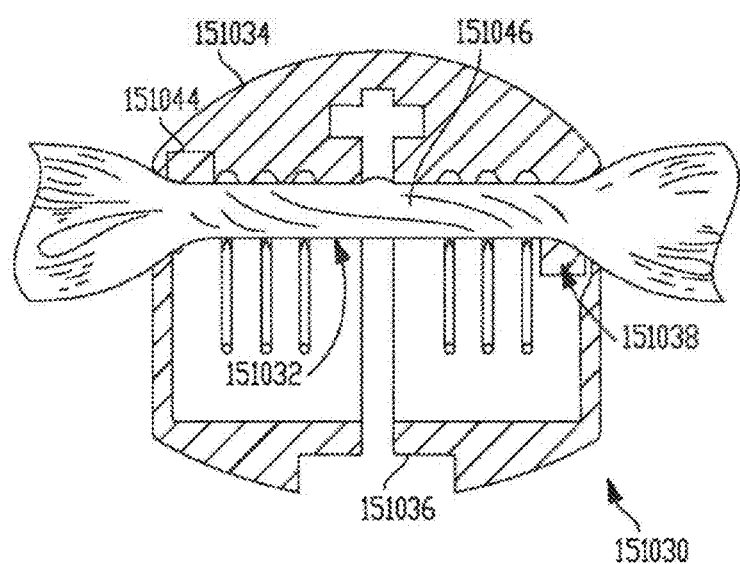
FIG. 61 also depicts an example tissue compression sensor system in accordance with one or more aspects of the present disclosure.

Referring now to FIG. 61, in one aspect, an electrical contact 151044 may be positioned on an opposite end of the anvil 151034 of the end-effector 151030 as the RF electrode 151038 is positioned. As the tissue 151032 is compressed between the anvil 151034 and, for example, the channel frame 151036 of the end-effector 151030, an impedance Z of the tissue 151032 changes. The lateral tissue compression 151046 caused by the end-effector 151030 may be measured as a function of the impedance Z of the tissue 151032.

Figure 62:
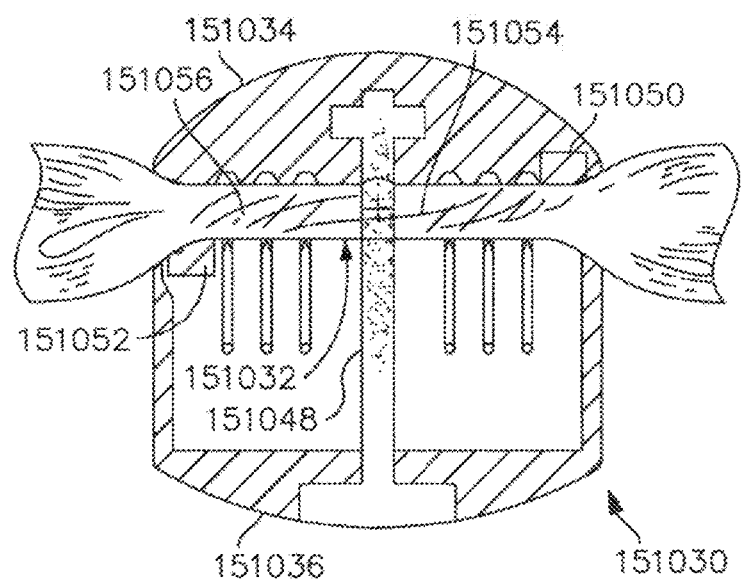
FIG. 62 also depicts an example tissue compression sensor system in accordance with one or more aspects of the present disclosure.

Referring now to FIG. 62, in one aspect, electrical contact 151050 may be positioned on the anvil 151034 and electrical contact 151052 may be positioned on an opposite end of the end-effector 151030 at channel frame 151036. RF electrode 151048 may be positioned laterally to the central to the end-effector 151030. As the tissue 151032 is compressed between the anvil 151034 and, for example, the channel frame 151036 of the end-effector 151030, an impedance Z of the tissue 151032 changes. The lateral compression or angular compressions 151054 and 151056 on either side of the RF electrode 151048 may be caused by the end-effector 151030 and may be measured as a function of different impedances Z of the tissue 151032, based on the relative positioning of the RF electrode 151048 and electrical contacts 151050 and 151052.

Figure 63:
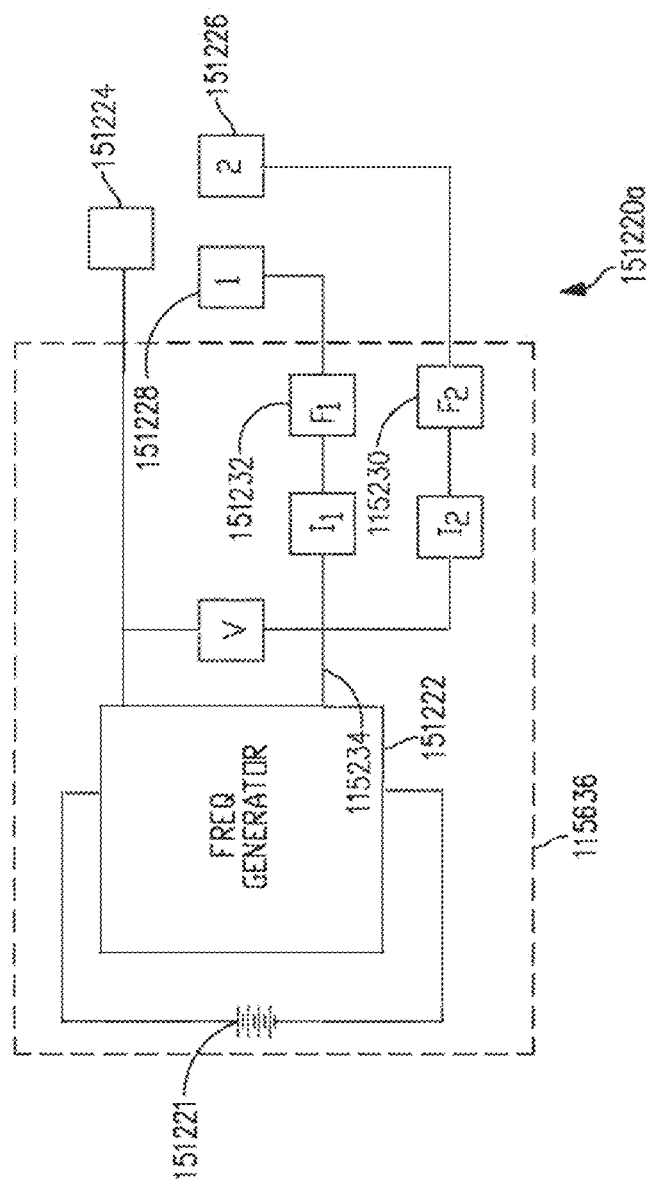
FIG. 63 is an example circuit diagram in accordance with one or more aspects of the present disclosure.

Referring now to FIG. 63, a frequency generator 151222 may receive power or current from a power source 151221 and may supply one or more RF signals to one or more RF electrodes 151224. As discussed above, the one or more RF electrodes may be positioned at various locations or components on an end-effector or surgical stapler, such as a staple cartridge or channel frame. One or more electrical contacts, such as electrical contacts 151226 or 151228 may be positioned on a channel frame or an anvil of an end-effector. Further, one or more filters, such as filters 151230 or 151232 may be communicatively coupled to the electrical contacts 151226 or 151228. The filters 151230 and 151232 may filter one or more RF signals supplied by the frequency generator 151222 before joining a single return path 151234. A voltage V and a current I associated with the one or more RF signals may be used to calculate an impedance Z associated with a tissue that may be compressed and/or communicatively coupled between the one or more RF electrodes 151224 and the electrical contacts 151226 or 151228.

Referring still to FIG. 63, various components of the tissue compression sensor system described herein may be located in a handle 151236 of a surgical stapler. For example, as shown in circuit diagram 151220$a$, frequency generator 151222 may be located in the handle 151236 and receives power from power source 151221. Also, current I1 and current I2 may be measured on a return path corresponding to electrical contacts 151228 and 151226. Using a voltage V applied between the supply and return paths, impedances Z1 and Z2 may be calculated. Z1 may correspond to an impedance of a tissue compressed and/or communicatively coupled between one or more of RF electrodes 151224 and electrical contact 151228. Further, Z2 may correspond to an impedance of a tissue compressed and/or communicatively coupled between one or more of RF electrodes 151224 and electrical contact 151226. Applying the formulas Z1=V/I1 and Z2=V/I2, impedances Z1 and Z2 corresponding to different compression levels of a tissue compressed by an end-effector may be calculated.

Figure 64:
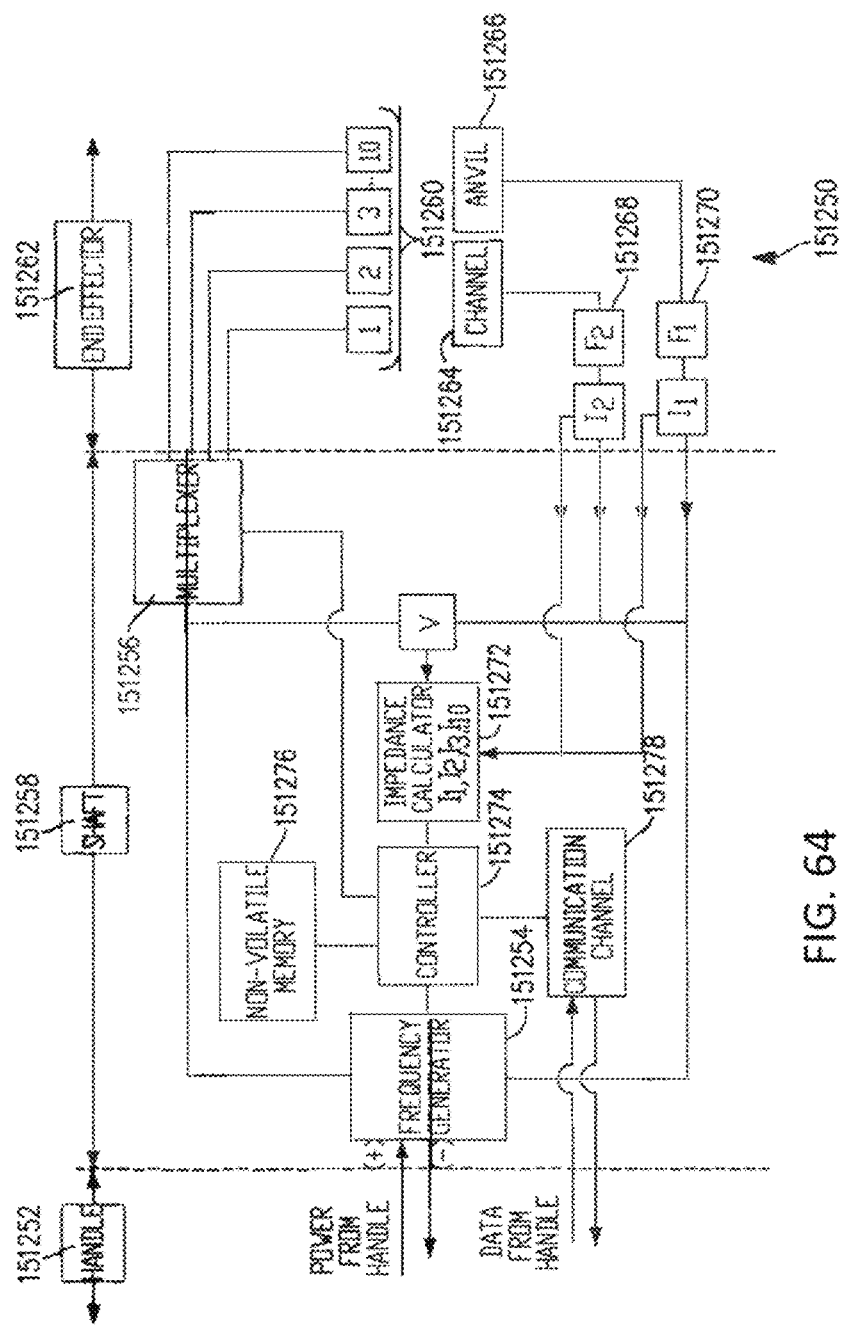
FIG. 64 is also an example circuit diagram in accordance with one or more aspects of the present disclosure.

Referring now to FIG. 64, one or more aspects of the present disclosure are described in circuit diagram 151250. In an implementation, a power source at a handle 151252 of a surgical stapler may provide power to a frequency generator 151254. The frequency generator 151254 may generate one or more RF signals. The one or more RF signals may be multiplexed or overlaid at a multiplexer 151256, which may be in a shaft 151258 of the surgical stapler. In this way, two or more RF signals may be overlaid (or, e.g., nested or modulated together) and transmitted to the end-effector. The one or more RF signals may energize one or more RF electrodes 151260 at an end-effector 151262 (e.g., positioned in a staple cartridge) of the surgical stapler. A tissue (not shown) may be compressed and/or communicatively coupled between the one or more of RF electrodes 151260 and one or more electrical contacts. For example, the tissue may be compressed and/or communicatively coupled between the one or more RF electrodes 151260 and the electrical contact 151264 positioned in a channel frame of the end-effector 151262 or the electrical contact 151266 positioned in an anvil of the end-effector 151262. A filter 151268 may be communicatively coupled to the electrical contact 151264 and a filter 151270 may be communicatively coupled to the electrical contact 151266.

A voltage V and a current I associated with the one or more RF signals may be used to calculate an impedance Z associated with a tissue that may be compressed between the staple cartridge (and communicatively coupled to one or more RF electrodes 151260) and the channel frame or anvil (and communicatively coupled to one or more of electrical contacts 151264 or 151266).

In one aspect, various components of the tissue compression sensor system described herein may be located in a shaft 151258 of the surgical stapler. For example, as shown in circuit diagram 151250 (and in addition to the frequency generator 151254), an impedance calculator 151272, a controller 151274, a non-volatile memory 151276, and a communication channel 151278 may be located in the shaft 151258. In one example, the frequency generator 151254, impedance calculator 151272, controller 151274, non-volatile memory 151276, and communication channel 151278 may be positioned on a circuit board in the shaft 151258.

The two or more RF signals may be returned on a common path via the electrical contacts. Further, the two or more RF signals may be filtered prior to the joining of the RF signals on the common path to differentiate separate tissue impedances represented by the two or more RF signals. Current I1 and current I2 may be measured on a return path corresponding to electrical contacts 151264 and 151266. Using a voltage V applied between the supply and return paths, impedances Z1 and Z2 may be calculated. Z1 may correspond to an impedance of a tissue compressed and/or communicatively coupled between one or more of RF electrodes 151260 and electrical contact 151264. Further, Z2 may correspond to an impedance of the tissue compressed and/or communicatively coupled between one or more of RF electrodes 151260 and electrical contact 151266. Applying the formulas Z1=V/I1 and Z2=V/I2, impedances Z1 and Z2 corresponding to different compressions of a tissue compressed by an end-effector 151262 may be calculated. In example, the impedances Z1 and Z2 may be calculated by the impedance calculator 151272. The impedances Z1 and Z2 may be used to calculate various compression levels of the tissue.

Figure 65:
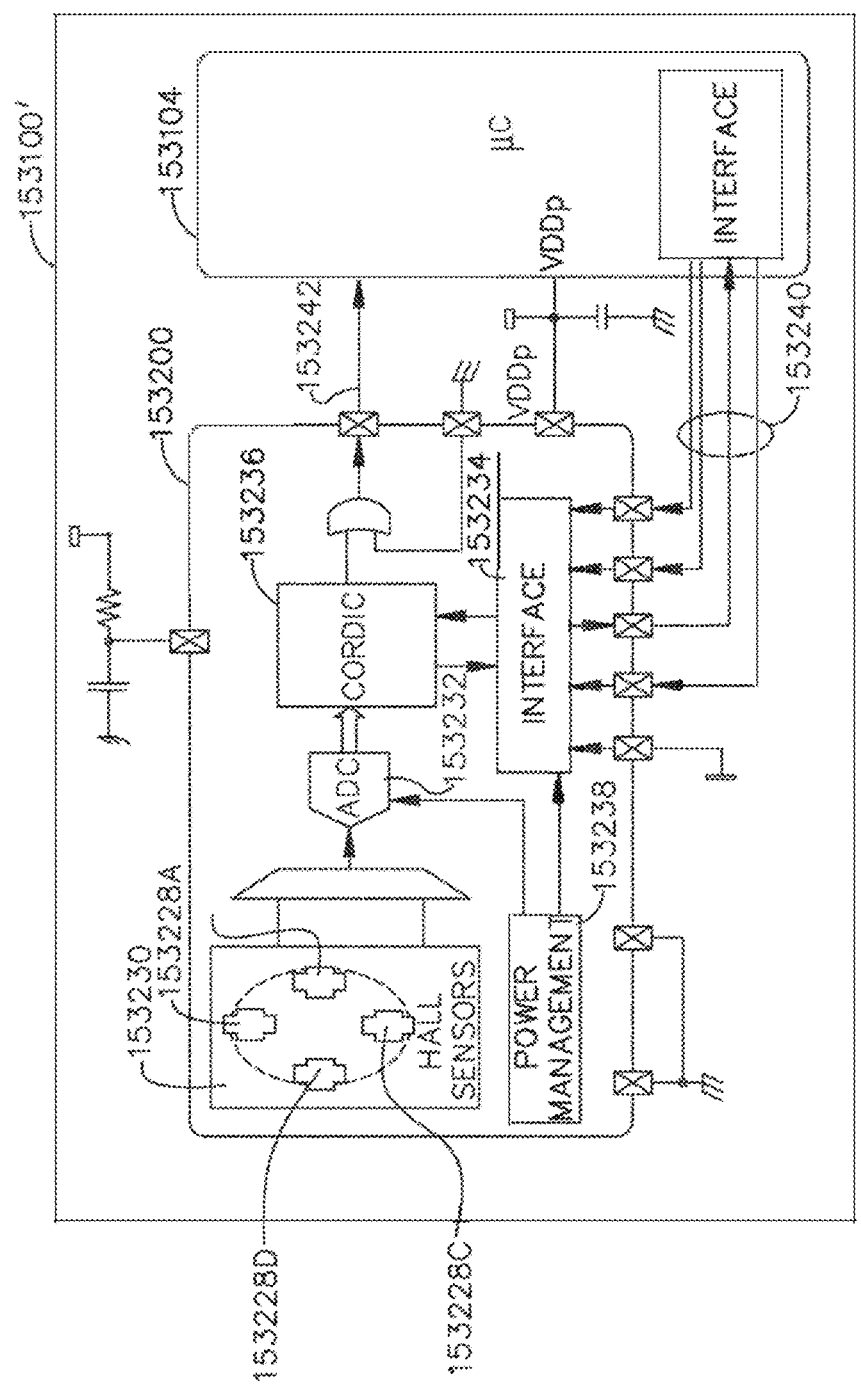
FIG. 65 is a diagram of a position sensor comprising a magnetic rotary absolute positioning system, in accordance with at least one aspect of this disclosure.

FIG. 65 is a diagram of a position sensor 153200 for an absolute positioning system 153100' comprising a magnetic rotary absolute positioning system, in accordance with at least one aspect of this disclosure. The absolute positioning system 153100' is similar in many respects to the absolute positioning system 153100. The position sensor 153200 may be implemented as an AS5055EQFT single chip magnetic rotary position sensor available from Austria Microsystems, AG. The position sensor 153200 is interfaced with the controller 153110 to provide the absolute positioning system 153100'. The position sensor 153200 is a low voltage and low-power component and includes four Hall-effect elements 153228A, 153228B, 153228C, 153228D in an area 153230 of the position sensor 153200 that is located above a magnet positioned on a rotating element associated with a displacement member such as, for example, a knife drive gear and/or a closure drive gear such that the displacement of a firing member and/or a closure member can be precisely tracked. A high-resolution ADC 153232 and a smart power management controller 153238 are also provided on the chip. A CORDIC processor 153236 (for Coordinate Rotation Digital Computer), also known as the digit-by-digit method and Voider's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface 153234 to the controller 153110. The position sensor 153200 provides 12 or 14 bits of resolution. The position sensor 153200 may be an AS5055 chip provided in a small QFN 16-pin 4×4×0.85 mm package.

The Hall-effect elements 153228A, 153228B, 153228C, 153228D are located directly above the rotating magnet. The Hall-effect is a well-known effect and for expediency will not be described in detail herein, however, generally, the Hall-effect produces a voltage difference (the Hall voltage) across an electrical conductor transverse to an electric current in the conductor and a magnetic field perpendicular to the current. A Hall coefficient is defined as the ratio of the induced electric field to the product of the current density and the applied magnetic field. It is a characteristic of the material from which the conductor is made, since its value depends on the type, number, and properties of the charge carriers that constitute the current. In the AS5055 position sensor 153200, the Hall-effect elements 153228A, 153228B, 153228C, 153228D are capable producing a voltage signal that is indicative of the absolute position of the magnet in terms of the angle over a single revolution of the magnet. This value of the angle, which is unique position signal, is calculated by the CORDIC processor 153236 is stored onboard the AS5055 position sensor 153200 in a register or memory. The value of the angle that is indicative of the position of the magnet over one revolution is provided to the controller 153110 in a variety of techniques, e.g., upon power up or upon request by the controller 153110.

The AS5055 position sensor 153200 requires only a few external components to operate when connected to the controller 153110. Six wires are needed for a simple application using a single power supply: two wires for power and four wires 153240 for the SPI interface 153234 with the controller 153110. A seventh connection can be added in order to send an interrupt to the controller 153110 to inform that a new valid angle can be read. Upon power-up, the AS5055 position sensor 153200 performs a full power-up sequence including one angle measurement. The completion of this cycle is indicated as an INT output 153242, and the angle value is stored in an internal register. Once this output is set, the AS5055 position sensor 153200 suspends to sleep mode. The controller 153110 can respond to the INT request at the INT output 153242 by reading the angle value from the AS5055 position sensor 153200 over the SPI interface 153234. Once the angle value is read by the controller 153110, the INT output 153242 is cleared again. Sending a "read angle" command by the SPI interface 153234 by the controller 153110 to the position sensor 153200 also automatically powers up the chip and starts another angle measurement. As soon as the controller 153110 has completed reading of the angle value, the INT output 153242 is cleared and a new result is stored in the angle register. The completion of the angle measurement is again indicated by setting the INT output 153242 and a corresponding flag in the status register.

Due to the measurement principle of the AS5055 position sensor 153200, only a single angle measurement is performed in very short time (~600 μs) after each power-up sequence. As soon as the measurement of one angle is completed, the AS5055 position sensor 153200 suspends to power-down state. An on-chip filtering of the angle value by digital averaging is not implemented, as this would require more than one angle measurement and, consequently, a longer power-up time that is not desired in low-power applications. The angle jitter can be reduced by averaging of several angle samples in the controller 153110. For example, an averaging of four samples reduces the jitter by 6 dB (50%).

Figure 66:
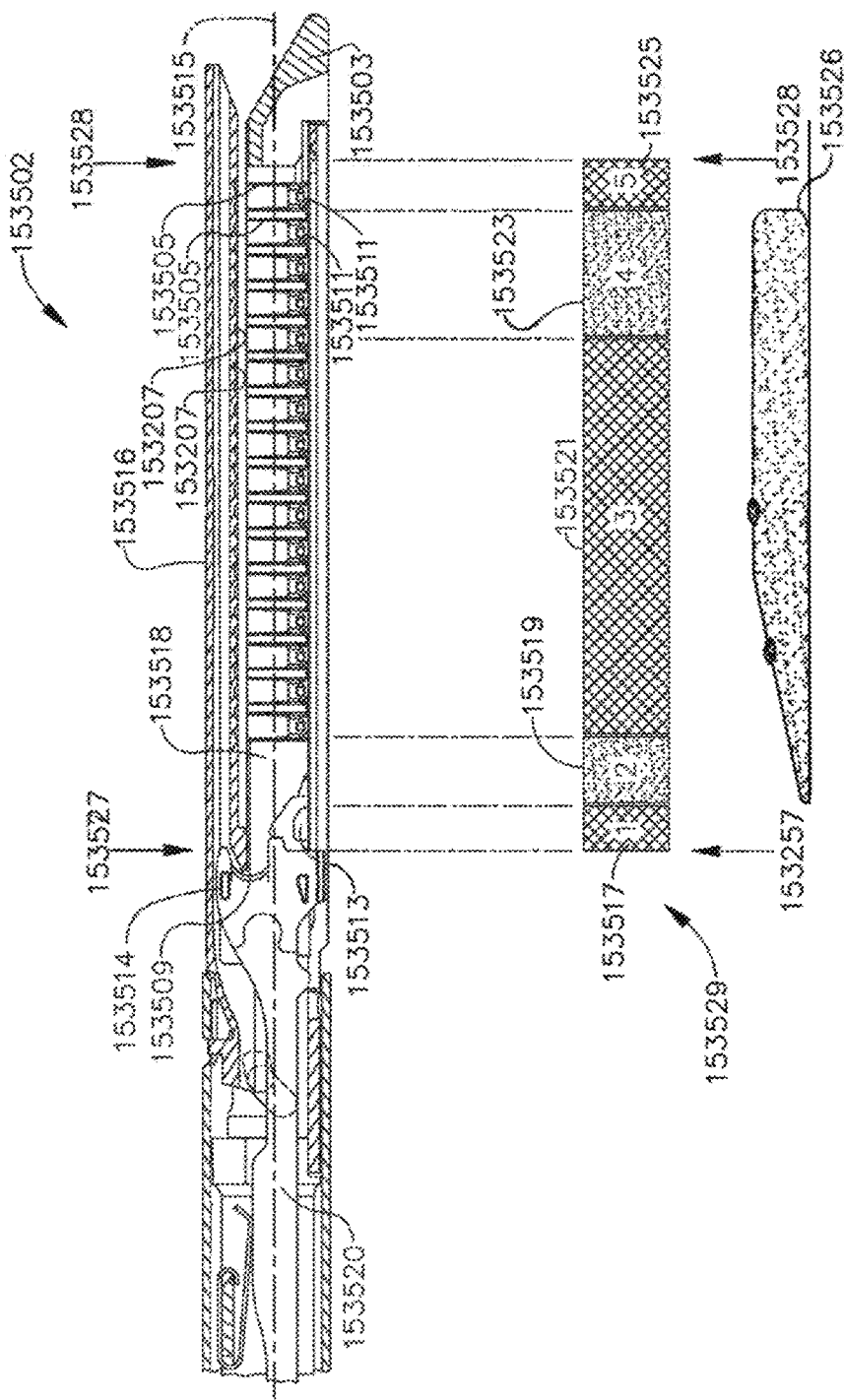
FIG. 66 is a section view of an end effector of a surgical instrument showing a firing member stroke relative to tissue grasped with the end effector, in accordance with at least one aspect of this disclosure.

FIG. 66 is a section view of an end effector 153502 showing an I-beam 153514 firing stroke relative to tissue 153526 grasped within the end effector 153502, in accordance with at least one aspect of this disclosure. The end effector 153502 is configured to operate with any of the surgical instruments or systems in accordance with the present disclosure. The end effector 153502 comprises an anvil 153516 and an elongated channel 153503 with a staple cartridge 153518 positioned in the elongated channel 153503. A firing bar 153520 is translatable distally and proximally along a longitudinal axis 153515 of the end effector 153502. When the end effector 153502 is not articulated, the end effector 153502 is in line with the shaft of the instrument. An I-beam 153514 comprising a cutting edge 153509 is illustrated at a distal portion of the firing bar 153520. A wedge sled 153513 is positioned in the staple cartridge 153518. As the I-beam 153514 translates distally, the cutting edge 153509 contacts and may cut tissue 153526 positioned between the anvil 153516 and the staple cartridge 153518. Also, the I-beam 153514 contacts the wedge sled 153513 and pushes it distally, causing the wedge sled 153513 to contact staple drivers 153511. The staple drivers 153511 may be driven up into staples 153505, causing the staples 153505 to advance through tissue and into pockets 153507 defined in the anvil 153516, which shape the staples 153505.

An example I-beam 153514 firing stroke is illustrated by a chart 153529 aligned with the end effector 153502. Example tissue 153526 is also shown aligned with the end effector 153502. The firing member stroke may comprise a stroke begin position 153527 and a stroke end position 153528. During an I-beam 153514 firing stroke, the I-beam 153514 may be advanced distally from the stroke begin position 153527 to the stroke end position 153528. The I-beam 153514 is shown at one example location of a stroke begin position 153527. The I-beam 153514 firing member stroke chart 153529 illustrates five firing member stroke regions 153517, 153519, 153521, 153523, 153525. In a first firing stroke region 153517, the I-beam 153514 may begin to advance distally. In the first firing stroke region 153517, the I-beam 153514 may contact the wedge sled 153513 and begin to move it distally. While in the first region, however, the cutting edge 153509 may not contact tissue and the wedge sled 153513 may not contact a staple driver 153511. After static friction is overcome, the force to drive the I-beam 153514 in the first region 153517 may be substantially constant.

In the second firing member stroke region 153519, the cutting edge 153509 may begin to contact and cut tissue 153526. Also, the wedge sled 153513 may begin to contact staple drivers 153511 to drive staples 153505. Force to drive the I-beam 153514 may begin to ramp up. As shown, tissue encountered initially may be compressed and/or thinner because of the way that the anvil 153516 pivots relative to the staple cartridge 153518. In the third firing member stroke region 153521, the cutting edge 153509 may continuously contact and cut tissue 153526 and the wedge sled 153513 may repeatedly contact staple drivers 153511. Force to drive the I-beam 153514 may plateau in the third region 153521.

By the fourth firing stroke region 153523, force to drive the I-beam 153514 may begin to decline. For example, tissue in the portion of the end effector 153502 corresponding to the fourth firing region 153523 may be less compressed than tissue closer to the pivot point of the anvil 153516, requiring less force to cut. Also, the cutting edge 153509 and wedge sled 153513 may reach the end of the tissue 153526 while in the fourth region 153523. When the I-beam 153514 reaches the fifth region 153525, the tissue 153526 may be completely severed. The wedge sled 153513 may contact one or more staple drivers 153511 at or near the end of the tissue. Force to advance the I-beam 153514 through the fifth region 153525 may be reduced and, in some examples, may be similar to the force to drive the I-beam 153514 in the first region 153517. At the conclusion of the firing member stroke, the I-beam 153514 may reach the stroke end position 153528.

As discussed above, the electric motor 153120 positioned within a master controller of the surgical instrument and can be utilized to advance and/or retract the firing system of the shaft assembly, including the I-beam 153514, relative to the end effector 153502 of the shaft assembly in order to staple and/or incise tissue captured within the end effector 153502. The I-beam 153514 may be advanced or retracted at a desired speed, or within a range of desired speeds. The controller 153110 may be configured to control the speed of the I-beam 153514. The controller 153110 may be configured to predict the speed of the I-beam 153514 based on various parameters of the power supplied to the electric motor 153120, such as voltage and/or current, for example, and/or other operating parameters of the electric motor 153120 or external influences. The controller 153110 may be configured to predict the current speed of the I-beam 153514 based on the previous values of the current and/or voltage supplied to the electric motor 153120, and/or previous states of the system like velocity, acceleration, and/or position. The controller 153110 may be configured to sense the speed of the I-beam 153514 utilizing the absolute positioning sensor system described herein. The controller can be configured to compare the predicted speed of the I-beam 153514 and the sensed speed of the I-beam 153514 to determine whether the power to the electric motor 153120 should be increased in order to increase the speed of the I-beam 153514 and/or decreased in order to decrease the speed of the I-beam 153514.

Force acting on the I-beam 153514 may be determined using various techniques. The I-beam 153514 force may be determined by measuring the motor 153120 current, where the motor 153120 current is based on the load experienced by the I-beam 153514 as it advances distally. The I-beam 153514 force may be determined by positioning a strain gauge on the drive member, the firing member, I-beam 153514, the firing bar, and/or on a proximal end of the cutting edge 153509. The I-beam 153514 force may be determined by monitoring the actual position of the I-beam 153514 moving at an expected velocity based on the current set velocity of the motor 153120 after a predetermined elapsed period T1 and comparing the actual position of the I-beam 153514 relative to the expected position of the I-beam 153514 based on the current set velocity of the motor 153120 at the end of the period T1. Thus, if the actual position of the I-beam 153514 is less than the expected position of the I-beam 153514, the force on the I-beam 153514 is greater than a nominal force. Conversely, if the actual position of the I-beam 153514 is greater than the expected position of the I-beam 153514, the force on the I-beam 153514 is less than the nominal force. The difference between the actual and expected positions of the I-beam 153514 is proportional to the deviation of the force on the I-beam 153514 from the nominal force.

Figure 67:
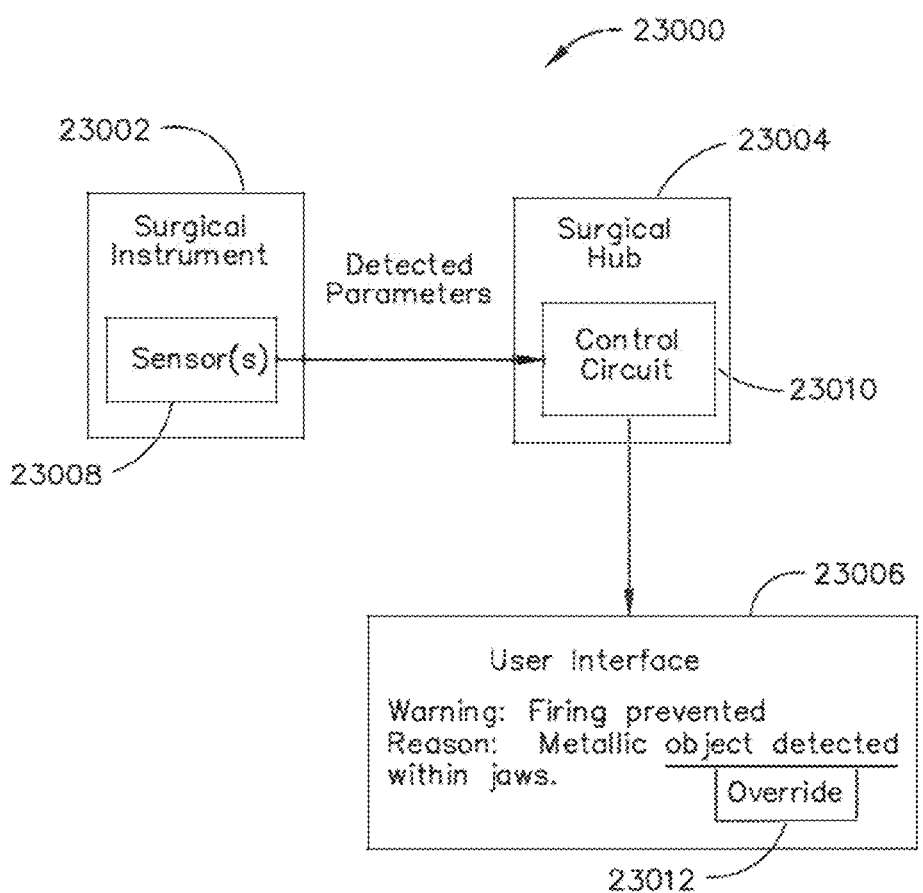
FIG. 67 illustrates a block diagram of a surgical system configured to control a surgical function, in accordance with at least one aspect of the present disclosure.

Various aspects of the present disclosure are directed to improved safety systems capable of adapting, controlling, and/or tuning internal drive operations of a surgical instrument in response to tissue parameters detected via one or more than one sensor of the surgical instrument. In accordance with at least one aspect, a force detected, via one or more than one sensor, at the jaws of an end effector may be of a magnitude that prohibits one or more than one subsequent/further functionality of the end effector from being performed. According to another aspect, a metallic object may be detected, via one or more than one sensor, as within the jaws of the end effector that prohibits one or more than one subsequent/further functionality of the end effector from being performed. FIG. 67 illustrates a surgical system 23000 comprising a surgical instrument 23002, a surgical hub 23004, and a user interface 23006. In such an aspect, the surgical instrument 23002 may comprise one or more than one sensor 23008 and parameters detected by the one or more than one sensor 23008 of the surgical instrument 23002 may be transmitted/communicated (e.g., wirelessly) to a control circuit 23010 of the surgical hub 23004. Further, in such an aspect, the surgical hub 23004 may be configured to determine whether a surgical function (e.g., dissect, clamp, coagulate, staple, cut, rotate, articulate, etc.) associated with a component (e.g., end effector, shaft, etc.) of the surgical instrument 23002 may be performed safely based on the parameters detected by the one or more than one sensor 23008 of the surgical instrument 23002. Notably, in such an aspect, the surgical hub 23004 may be configured to transmit/communicate a result(s) (i.e., a warning associated with the surgical function, a reason the surgical function is prevented, etc.) associated with that determination to the user interface 23006. Further, according to various aspects, various user interfaces disclosed herein may comprise a selectable user interface feature (e.g., override element 23012) to proceed with the surgical function despite any warnings and/or reasons supporting prevention. Notably, in such aspects, such a user interface feature (e.g., override element 23012) may not be displayed (e.g., performing the surgical function may endanger the patient).

Figure 68:
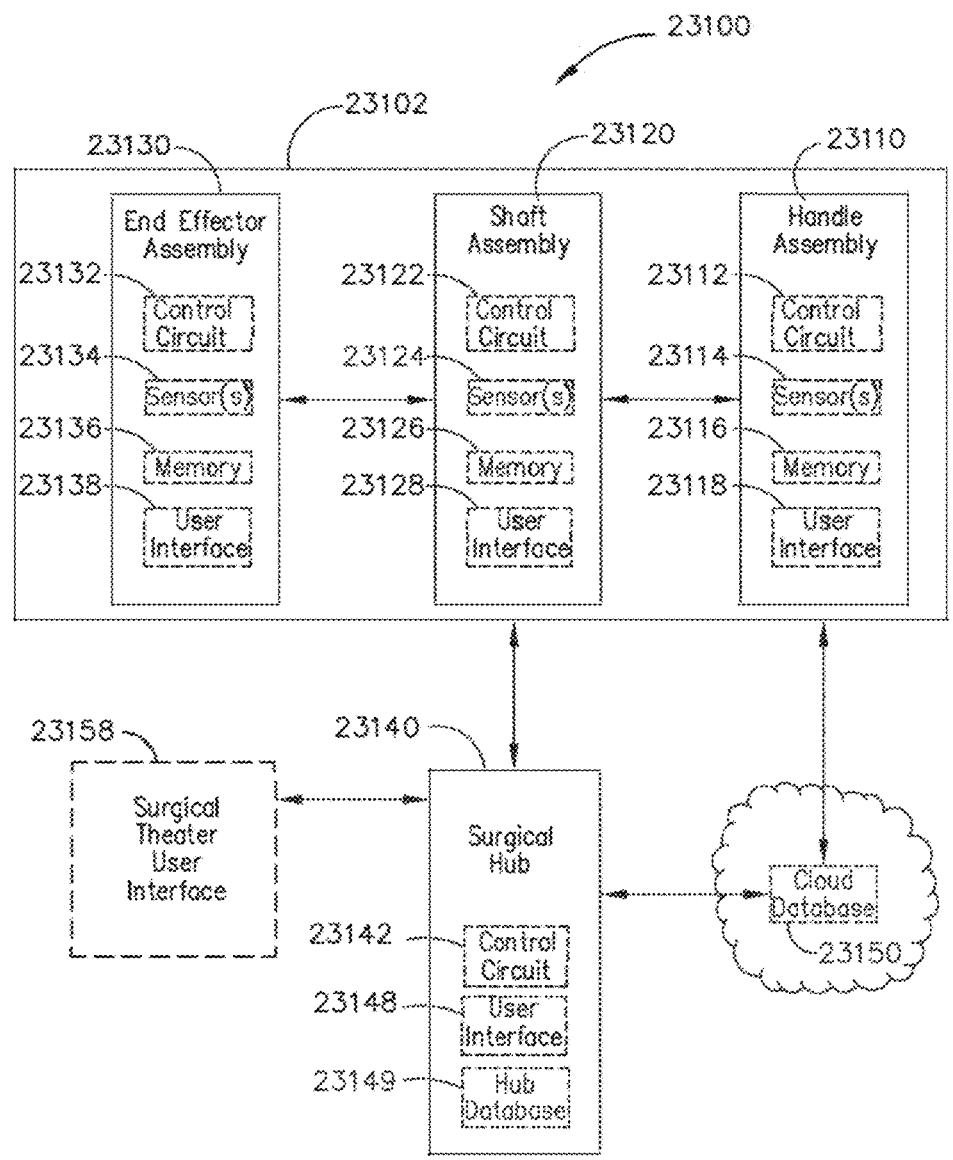
FIG. 68 illustrates a block diagram of a situationally aware surgical system configured to control a surgical function, in accordance with at least one aspect of the present disclosure.

Referring to FIG. 68, according to various aspects of the present disclosure, a surgical system 23100 may comprise a control circuit (23112, 23122, 23132 and/or 23142, e.g., in phantom to show optional location(s)), a user interface (23118, 23128, 23138, 23148 and/or 23158, e.g., in phantom to show optional locations), and a surgical instrument 23102 including, for example, a handle assembly 23110, a shaft assembly 23120, and an end effector assembly 23130. In such aspects, the control circuit may be integrated into one or more than one component (e.g., the handle assembly 23110, the shaft assembly 23120, and/or the end effector assembly 23130, etc.) of the surgical instrument 23102 (e.g., 23112, 23122, and/or 23132) and/or integrated into a surgical hub 23140 (e.g., 23142) paired (e.g., wirelessly) with the surgical instrument 23102. Notably, according to various aspects, the surgical instrument 23102 and/or the surgical hub 23140 may be a situationally aware surgical instrument and/or a situationally aware surgical hub. Situational awareness refers to the ability of a surgical system, e.g., 23100, to determine or infer information related to a surgical procedure from data received from databases (e.g., historical data associated with a surgical procedure, e.g., 23149 and/or 23150) and/or surgical instruments (e.g., sensor data during a surgical procedure). For example, the determined or inferred information can include the type of procedure being undertaken, the type of tissue being operated on, the body cavity that is the subject of the procedure, etc. Based on such contextual information related to the surgical procedure, the surgical system 23102 can, for example, control a paired surgical instrument 23102 or a component thereof (e.g., 23110, 23120, and/or 23130) and/or provide contextualized information or suggestions to a surgeon throughout the course of the surgical procedure (e.g., via user interface 23118, 23128, 23138, 23148 and/or 23158). Additional details regarding situational awareness can be found, for example, above under the heading "Situational Awareness."

Also in FIG. 68, according to one aspect, a situationally aware surgical hub 23140 is paired (e.g., wirelessly) with a surgical instrument 23102 being utilized to perform a surgical procedure. In such an aspect, the surgical instrument 23102 may comprise an end effector assembly 23130, including a first jaw, a second jaw pivotably coupled to the first jaw, and a sensor 23134 configured to detect a parameter associated with a function (e.g., dissect, clamp, coagulate, cut, staple, etc.) of the end effector assembly 23130 and to transmit the detected parameter to a control circuit 23142 of the surgical hub 23140.

Further, in such an aspect, the surgical instrument 23102 may further comprise a shaft assembly 23120 including a sensor 23124 configured to detect a parameter associated with a function (e.g., rotation, articulation, etc.) of the shaft assembly 23120 and to transmit the detected parameter to the control circuit 23142 of the surgical hub 23140. Notably, it should be appreciated that a sensor, as referenced herein and in other disclosed aspects, may comprise a plurality of sensors configured to detect a plurality of parameters associated with a plurality of end effector assembly and/or shaft assembly functions. As such, further, in such an aspect, the surgical hub control circuit 23142 may be configured to receive detected parameters (e.g., sensor data) from such sensors 23134 and/or 23124 throughout the course of the surgical procedure.

A detected parameter can be received each time an associated end effector assembly 23130 function (e.g., dissection, clamping, coagulation, cutting, stapling, etc.) and/or an associated shaft assembly 23120 function (e.g., rotating, articulating, etc.) is performed. The surgical hub control circuit 23142 may be further configured to receive data from an internal database (e.g., a surgical hub database 23149) and/or an external database (e.g., from a cloud database 23150) throughout the course of the surgical procedure. According to various aspects, the data received from the internal and/or external databases may comprise procedural data (e.g., steps to perform the surgical procedure) and/or historical data (e.g., data indicating expected parameters based on historical data associated with the surgical procedure).

In various aspects, the procedural data may comprise current/recognized standard-of-care procedures for the surgical procedure and the historical data may comprise preferred/ideal parameters and/or preferred/ideal parameter ranges based on historical data associated with the surgical procedure (e.g., system-defined constraints). Based on the received data (e.g., sensor data, internal and/or external data, etc.), the surgical hub control circuit 23142 may be configured to continually derive inferences (e.g., contextual information) about the ongoing surgical procedure. Namely, the situationally aware surgical hub may be configured to, for example, record data pertaining to the surgical procedure for generating reports, verify the steps being taken by the surgeon to perform the surgical procedure, provide data or prompts (e.g., via a user interface associated with the surgical hub and/or the surgical instrument, e.g., 23148, 23158, 23118, 23128, and/or 23138) that may be pertinent for a particular procedural step, control a surgical instrument function, etc. According to various aspects, the situationally aware surgical hub 23140 may (e.g., after an initial surgical function of the end effector assembly 23130 or the shaft assembly 23120 is performed) infer a next surgical function to be performed based on procedural data received from an internal database 23149 and/or an external database 23150.

Further, in such an aspect, the situationally aware surgical hub 23140 may evaluate detected parameters (e.g., received from sensors 23134 and/or 23124 in response to the initial surgical function) based on historical data received from the internal database 23149 and/or the external database 23150 (e.g., preferred/ideal parameters). Here, if the detected parameters do not exceed the preferred/ideal parameters and/or are within respective preferred/ideal parameter ranges, the situationally aware surgical hub 23140 may permit the next surgical function to be performed and/or not prevent/control the next surgical function from being performed. Alternatively, if the detected parameters do exceed the preferred/ideal parameters and/or are not within respective preferred/ideal parameter ranges, the situationally aware surgical hub 23140 may proactively prevent the next surgical function from being performed.

According to another aspect of the present disclosure, the situationally aware surgical hub 23140 may receive a communication (e.g., from a component, e.g., 23130 and/or 23120, of the surgical instrument 23102) that a particular surgical function is being attempted/requested/actuated. In such an aspect, the situationally aware surgical hub 23140 may compare that particular surgical function to an inferred next surgical function to ensure that current/recognized standard-of-care procedures are being adhered to. If so, the situationally aware surgical hub 23140 may then evaluate detected parameters (e.g., as described) before permitting that particular surgical function to proceed (as described). If not, the situationally aware surgical hub 23140 may prevent that particular surgical function from being performed or prevent that particular surgical function from being performed until an override is received (e.g., via a user interface 23, 158, 23148, 23138, 23128 and/or 23118, see, e.g., FIG. 67, selectable user interface element 23012). In such an aspect, if the override is received, the situationally aware surgical hub 23140 may then evaluate detected parameters before permitting that particular surgical function to proceed (as described).

Referring again to FIG. 68, according to another aspect, a situationally aware surgical instrument 23102 may be utilized to perform a surgical procedure. In such an aspect, the surgical instrument 23102 may comprise a handle assembly 23110, a shaft assembly 23120, and an end effector assembly 23130. The end effector assembly 23130 may include a first jaw, a second jaw pivotably coupled to the first jaw, and a sensor 23134 configured to detect a parameter associated with a function (e.g., dissect, clamp, coagulate, cut, staple, etc.) of the end effector assembly 23130 and to transmit the detected parameter to a control circuit (23112, 23122, 23132 and/or 23142, e.g., in phantom to show optional location(s)).

For example, in such an aspect, the detected parameter may be transmitted to a control circuit 23132 of the end effector assembly 23130. Here, the end effector assembly control circuit 23132 may be configured to receive detected parameters (e.g., sensor data) from the sensor 23134 throughout the course of the surgical procedure. A detected parameter can be received each time an associated end effector assembly 23130 function (e.g., dissection, clamping, coagulation, cutting, stapling, etc.) is performed.

The end effector assembly 23130 may be further configured to receive data from an internal database (e.g., end effector memory 23136) and/or an external database (e.g., from a cloud database 23150 via a surgical hub 23140, from a surgical hub database 23149, etc.) throughout the course of the surgical procedure. According to various aspects, the data received from the internal and/or external databases may comprise staple cartridge data (e.g., sizes and/or types of staples associated with a staple cartridge positioned in the end effector assembly) and/or historical data (e.g., data indicating expected tissues and/or types of tissues to be stapled with those sizes and/or types of staples based on historical data). In various aspects, the received data may comprise preferred/ideal parameters and/or preferred/ideal parameter ranges associated with those sizes and/or types of staples or those expected tissues and/or tissue types, based on historical data (e.g., system-defined constraints). Based on the received data (e.g., sensor data, internal and/or external data, etc.), the end effector control circuit 23132 may be configured to continually derive inferences (e.g., contextual information) about the ongoing surgical procedure. Notably, according to an alternative aspect, the sensor 23134 of the end effector assembly 23130 may transmit the detected parameter to a control circuit (e.g., 23112 and/or 23122) associated with another surgical instrument 23102 component, for example, the handle assembly 23110 and/or the shaft assembly 23120. In such an aspect, that other surgical instrument component control circuit (e.g., 23112 and/or 23122) may be similarly configured to perform the various aspects of the end effector control circuit 23132 as described above. Furthermore, according to various aspects, the shaft assembly 23120 of the surgical instrument 23102 may include a sensor 23124 configured to detect a parameter associated with a function (e.g., rotation, articulation, etc.) of the shaft assembly 23120 and to transmit the detected parameter to a control circuit (e.g., 23112) similarly configured to perform the various aspects of the end effector control circuit 23132 as described above. In end, the situationally aware surgical instrument 23102 may be configured to, for example, alert its user of a discrepancy (e.g., via a user interface 23138 of the end effector assembly 23130, via a user interface (e.g., 23128 and/or 23118) of another surgical instrument 23102 component, for example, the shaft assembly 23120 and/or the handle assembly 23110, and/or via a user interface 23148 and/or 23158 associated with a surgical hub 23140 coupled to the surgical instrument 23102). For example, the discrepancy may include that a detected parameter exceeds a preferred/ideal parameter and/or a preferred/ideal parameter range associated with those sizes and/or types of staples or those expected tissues and/or tissue types. As a further example, the situationally aware surgical instrument 23102 may be configured to control a surgical instrument 23102 function based on the discrepancy. In accordance with at least one aspect, the situationally aware surgical instrument 23102 may prevent a surgical function based on a discrepancy.

Figure 69:
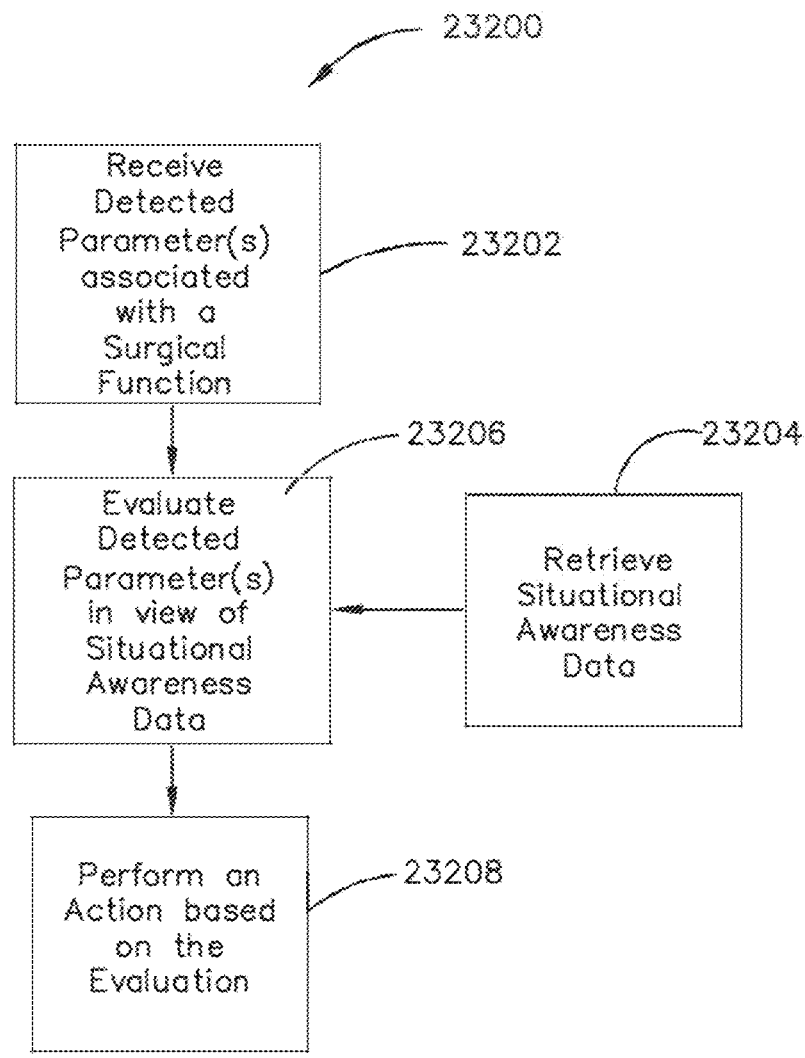
FIG. 69 is a logic flow diagram depicting a situational awareness-based algorithm for controlling a surgical function, in accordance with at least one aspect of the present disclosure.

As highlighted herein, various aspects of the present disclosure pertain to a surgical instrument performing a function (e.g., clamping), detecting a parameter associated with that function, using situational awareness aspects to assess, via a control circuit, whether that detected parameter is below or exceeds a predefined parameter (e.g., considered ideal/preferred) or is below or exceeds a predefined range (e.g., considered normal) for that parameter, and performing an action (i.e., stop a function(s), alert the user, inform the user of possible causes, etc.) in response to the detected parameter being outside the predefined parameter and/or predefined parameter/range. For example, FIG. 69 illustrates an algorithm 23200 to implement such aspects wherein a control circuit receives a detected parameter(s) associated with a surgical function performed by a surgical instrument 23202 and retrieves situational awareness data from an internal and/or external database 23204. The control circuit then evaluates the detected parameter(s) in view of the situational awareness data 23206 and performs an action based on the evaluation 23208.

According to various aspects of the present disclosure, a force detected (e.g., via one or more than one sensor) at the jaws of an end effector assembly may be of a magnitude that prohibits one or more than one subsequent/further functionality of the end effector assembly from being performed. In such an aspect, the sensor may be a strain gauge coupled to the end effector wherein the strain gauge is configured to measure the magnitude/amplitude of strain on a jaw(s) of the end effector, which is indicative of closure forces being applied to the jaw(s). Further, in such an aspect, sensor may be a load sensor configured to measure a closure force applied to the jaws by a closure drive system. Yet further, in such an aspect, sensor may be a current sensor configured to measure a current drawn by the motor, which correlates to a closure force applied to the jaws.

Figure 70:
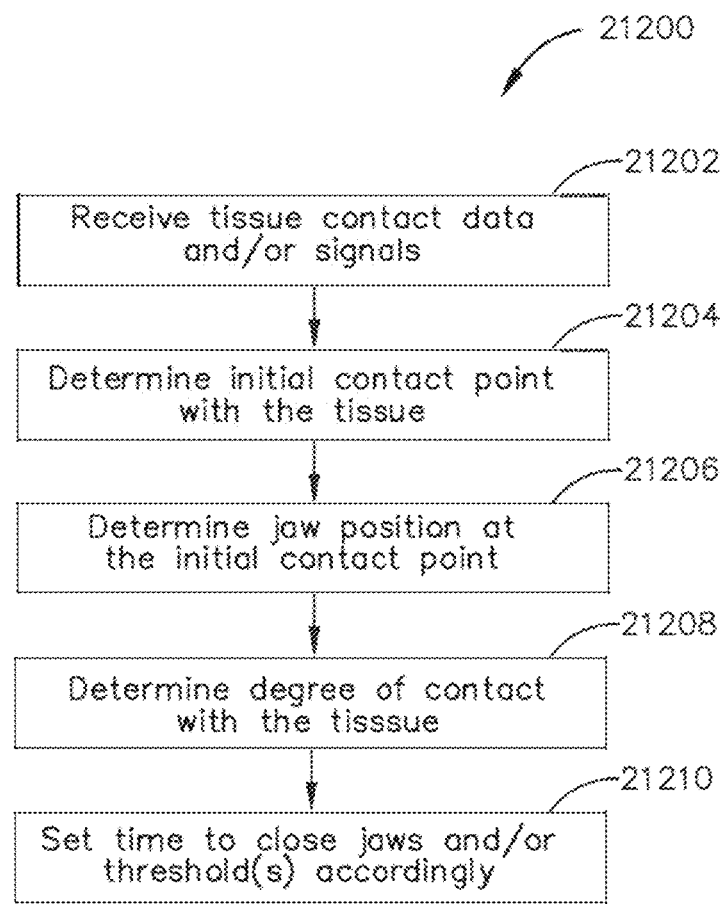
FIG. 70 illustrates a logic flow diagram of a process for controlling a surgical instrument according to the physiological type of the clamped tissue, in accordance with at least one aspect of the present disclosure.

FIG. 70 illustrates a logic flow diagram of a process 21200 for controlling a surgical instrument according to the physiological type of the clamped tissue, in accordance with at least one aspect of the present disclosure. The illustrated process can be executed by, for example, the control circuit 21002 of the surgical instrument 21000. Accordingly, the control circuit 21002 executing the illustrated process 21200 receives 21202 tissue contact data and/or signals from the sensor(s) 21004. The received 21202 tissue contact data and/or signals indicate whether tissue is contacting at least one of the sensors 21004. Accordingly, the control circuit 21002 can determine 21204 the initial point of contact between the end effector 21008 and the tissue being clamped In one aspect, the control circuit 21002 determines 21204 when the initial tissue contact occurs by detecting when at least one of the sensors 21004 disposed on each of the jaws detects tissue contact thereagainst.

Accordingly, the control circuit 21002 determines 21206 the position of the jaws at the initial tissue contact point. In one aspect, the control circuit 21002 is communicably coupled to a Hall effect sensor disposed on one of the jaws of the end effector 21008 that is configured to detect the relative position of a corresponding magnetic element disposed on the opposing jaw. The control circuit 21002 can thus determine 21206 the position of the jaws according to the sensed distance or gap therebetween. In another aspect, the control circuit 21002 is communicably coupled to a position sensor that is configured to detect the absolute or relative position of a closure tube that is configured to close the jaws as the closure tube is driven from a first or proximal position to a second or distal position. The control circuit 21002 can thus determine 21206 the position of the jaws according to the sensed position of the closure tube. In yet another aspect, the control circuit 21002 is communicably coupled to an angle sensor, such as a TLE5012B 360° angle sensor from Infineon Technologies, that is configured to detect the angle at which at least one of the jaws is oriented. The control circuit 21002 can thus determine 21206 the position of the jaws according to the sensed angle at which the jaw(s) are oriented.

Accordingly, the control circuit 21002 determines 21208 the degree of contact between the grasped tissue and the tissue-contacting surface(s) of the jaws. The degree of tissue contact can correspond to the number or ratio of the sensors 21004 that have detected the presence (or absence) of tissue. In one aspect, the control circuit 21002 can determine the degree of tissue contact according to the ratio of the sensor(s) 21004 that have detected the presence of tissue to the sensor(s) 21004 that have not detected the presence of tissue.

Accordingly, the control circuit 21002 sets 21210 control parameters for the motor 21006 according to the determined 21206 position of the jaws and the determined 21208 degree of tissue contact. The motor control parameters can include, for example, the time to close the jaws and/or closure threshold(s). In one aspect, the control circuit 21002 can be configured to perform a runtime calculation and/or access a memory (e.g., a lookup table) to retrieve the motor control parameters (e.g., the jaw closure rate and closure threshold) associated with the particular position of the jaws and the particular degree of tissue contact sensed via the various sensors. In various aspects, the control circuit 21002 can control the motor 21006 to adjust the jaw closure time by, for example, adjusting the rate at which the jaws are transitioned from the open position to the closed position, adjusting the length of time that the jaws are paused after the initial clamping of the tissue (i.e., the tissue creep wait time), and/or adjusting the stabilization threshold that ends the clamping phase. In various aspects, the closure threshold(s) can include, for example, the maximum allowable FTC the end effector 21008 or rate of change for the FTC (i.e., llFTC) at which the control circuit 21002 stops the motor 21006 driving the closure of the jaws or takes other actions, as discussed above under the heading "Compression Rate to Determine Tissue Integrity." The control circuit 21002 can then control the motor 21206 according to the motor control parameters set 21210 by the process 21200.

The position of the jaws and the degree of contact with the tissue at the initial point of contact with the tissue corresponds to the thickness or geometry of the tissue being grasped, which in turn corresponds to the physiological type of the tissue. Thus, the control circuit 21002 can be configured to differentiate between tissue types and then set 21210 the control parameters for the motor 21006 accordingly. For example, the control circuit 21002 can be configured to determine whether parenchyma or vessel tissue has been grasped by the end effector 21008 and then set 21210 motor control parameters that are appropriate for the detected tissue type.

In some aspects, jaw closure rate can be selected for each tissue type to maintain the maximum FTC and/or llFTC under a particular closure threshold, which can likewise be selected for each tissue type. In one aspect, the control circuit 21002 can be configured to institute a mini-mum clamp rate so that the closure motion of the jaws is never permanently halted. In one aspect, the control circuit 21002 can be configured to control the maximum pause times to ensure that jaw closure progresses at least a default rate. In one aspect, the control circuit 21002 can be configured to halt the motor 21006 and/or provide feedback to the user when closure threshold(s) are exceeded or otherwise beached during user of the surgical instrument 21000.

It should be noted that although the steps of the particular example of the process 21200 in FIG. 70 are depicted as occurring in a particular order or sequence, such a depiction is solely for illustrative purposes and no particular sequence of the process 21200 is intended, unless a particular sequence of particular steps is explicitly necessary from the description hereabove. For example, in other aspects of the process 21200, the control circuit 21002 can determine 21208 the degree of tissue contact prior to determining 21206 the jaw position at the initial contact point.

Figure 71:
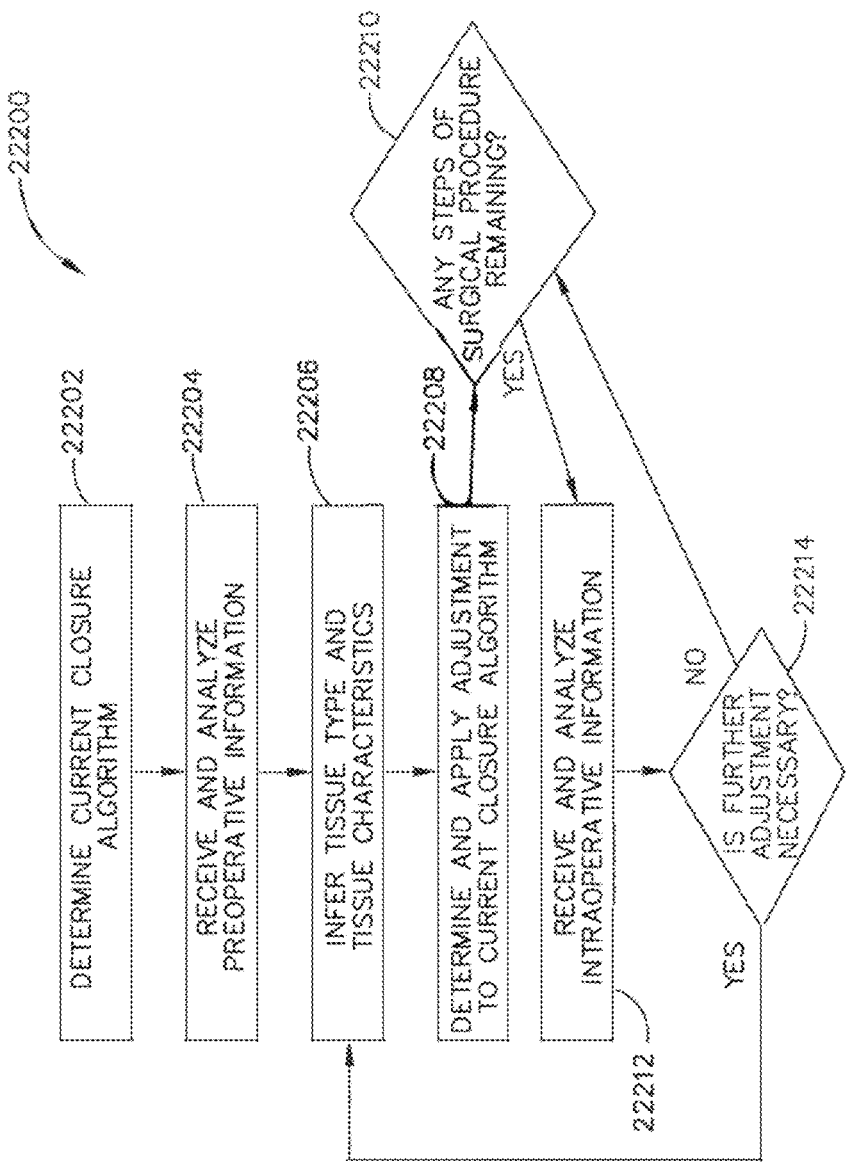
FIG. 71 is a logic flow diagram depicting a process of a control program or a logic configuration for adjusting a closure rate algorithm, in accordance with at least one aspect of the present disclosure.

FIG. 71 is a flow diagram 22200 of an aspect of adjusting a closure rate algorithm by the computer-implemented interactive surgical system 100, according to one aspect of the present disclosure. At step 22202, the current closure algorithm is determined. This may refer to determining the closure control program currently executed by the control circuit 500 of a surgical instrument 112. The current closure algorithm or control program may include a closure threshold function (e.g., closure threshold parameter) and applied closure force (FTC) function (e.g., closure rate of change parameter). The flow diagram 22200 proceeds next to step 22204, where preoperative information is received and analyzed. As discussed above, preoperative information may include initial tissue thickness based on tissue contact sensors 474, patient history including prior diagnoses and treatments (e.g., listed on a patient information EMR record stored in the hub or cloud), clinician history such as a surgeon's typical surgical routine, identified surgical instrument and associated materials, and identified current surgical procedure. This preoperative information can be used to determine, infer, or predict tissue type or tissue characteristics at step 22206.

For example, the undeformed initial tissue thickness as measured by tissue contact sensors 474 may be used to determine an initial closure algorithm. Preoperative information such as a patient history of lung issues might be used to determine that the current surgical procedure being performed is a thoracic procedure and the tissue type is a lung tissue. This preoperative information may further be used to determine an adjustment to the initial closure algorithm. Additionally or alternatively, an initial tissue stiffness measured via comparing a non-therapeutic (or quasi non-therapeutic) initial tissue compression measurement and a closure member position measurement (e.g., position of first and second jaws of end effector) could also be used in conjunction with the preoperative information. Ventilation preoperative information received from a ventilation device in the surgical theater could further be used to infer that the current procedure is thoracic. Other preoperative information could also be used to further predict the specific thoracic procedure being performed. For example, based on the patient EMR record in the cloud indicating that the patient has cancer, it could be inferred at step 22206 that the thoracic procedure is a pulmonary lobectomy to excise cancerous tissue in a lung lobe.

Moreover, the patient EMR record could further indicate that the patient history indicates the patient has previously undergone radiation treatments for the cancer. In this situation, it may be inferred or predicted that the irradiated lung tissue would be stiff, but also susceptible to the application of monopolar RF energy by the surgical instrument 112, for example. This would be one example of an inferred tissue characteristic. Also, the inference that a pulmonary lobectomy is being performed may also be used to determine that possible tissues for stapling by the surgical instrument 112 include blood vessels (PA/PV), bronchus, and parenchyma. At step 22208, adjustments to the current closure algorithm are determined based on the preoperative information and applied. As discussed above, the closure threshold and applied FTC may be adjusted based on the tissue type and tissue characteristics. For example, high tissue stiffness may necessitate a slower more conservative rate of change of applied FTC (e.g., as represented by FTC lines 22012, 22112) as well as a closure threshold that generally outputs a lower maximum threshold (e.g., as represented by FTCL2 22010 and llFTCL2 22110).

The maximum threshold may indicate the threshold at which the first and second jaw members 152002, 152004 are in a sufficient position for the surgical instrument 112 to fire staples. A relatively thicker tissue may correspond to a slower closure force rate of change and also a generally higher maximum closure threshold, for example. Also, tissue type or structure could be inferred based on the determined surgical procedure and clinician history for identifying other closure algorithm adjustments at step 22208. For example, the treating surgeon's clinician history may indicate a practice of treating blood vessels first. It could be inferred that the tissue type and structure is vascular lung tissue with high blood content (i.e., high vasculature). Based on this inferred tissue type and characteristic information, it could be determined that adjustment to a slower applied FTC rate of change would be beneficial. In sum, adjustments to the current closure algorithm are determined based on the inferred information and applied at step 22208. Accordingly, the current surgical operation may be performed with the surgical instrument 112 using the adjusted current closure algorithm.

The flow diagram 22200 then proceeds to decision operation 22210, at which it is determined whether any steps of the identified surgical procedure are remaining If there are no steps remaining (i.e., the answer to decision operation 22210 is no), the flow diagram 22200, in some aspects, terminates. However, if the answer to decision operation 22210 is yes, there are further steps of the surgical procedure remaining Therefore, the current state of the flow diagram 22200 is intraoperation. In this case, the flow diagram proceeds to step 22212, where intraoperative information may be received and analyzed. For example, intraoperative information could indicate that the tissue type treated during this step of the surgical procedure is parenchyma. In particular, it could be inferred that the tissue is parenchyma based on clinician history, for example. This inference could be made in conjunction with tissue contact sensor 474 measurements and load sensor 474 versus closure member position measurements. Moreover, clinician history may indicate that the treating surgeon routinely completes a lung fissure (a double-fold of visceral pleura that folds inward to sheath lung parenchyma) after dissection with a monopolar RF energy surgical instrument. In this situation, it may be inferred based on the previously completed monopolar RF dissection that the current step of the surgical procedure is lung parenchyma tissue.

Additionally, the surgical hub 106 may determine whether the surgical instrument 112 being used is an appropriate stapler for parenchyma firings, for example. The initial tissue contact sensor 474 measurements may indicate that the tissue is relatively thick, such as based on tissue contacting the length of the first and second jaw members 152002, 152004 when the end effector 702 is fully open (at the maximum jaw aperture), which may be consistent with parenchyma. Furthermore, the load sensor 474 versus dosure member position measurements as represented by a closure compared to jaw aperture curve may indicate relatively high tissue stiffness. This stiffness characteristic could be consistent with irradiated parenchyma, which is a prediction that could be confirmed by reference to patient EMR data in the cloud. In this way for example at step 22212, sensor signals and perioperative information could be used in conjunction.

Based on this received and analyzed intraoperative information, it may be determined at decision operation 22214, that further adjustment is necessary. On the other hand, if the answer is no at decision operation 22214, the flow diagram would proceed back to decision operation 22210. When the answer at decision operation 22214 is yes, tissue type and tissue characteristics are inferred such as determining parenchyma tissue structure and stiffness characteristics, similar to as described above at step 22206. Subsequently, adjustments to the currently applied closure algorithm can be determined and applied at step 22208. In particular, the inference that stiff and fragile parenchyma tissue is being treated could cause adjustment to a slower, more conservative rate of change of applied closure force.

Accordingly, the current closure algorithm may be adjusted to an algorithm that minimizes the closure threshold and rate of change. That is, the adjusted threshold may have a reduced maximum closure force threshold, a more gradual rate of change in closure force, a reduced rate of change of closure force threshold, or some combination or subcombination of the above. In situations in which the clinician inadvertently exceeds the closure threshold, a wait time can be instituted, for example. Exceeding the closure threshold may indicate that the tissue or material being compressed is too thick for firing staples, for example, so this wait time may be necessary.

Upon applying this modified closure algorithm to the parenchyma tissue at step 22208, the flow diagram again proceeds to decision operation 22210. Here, the answer may again be yes because there are remaining steps of the surgical procedure. For example, the lobectomy procedure may then proceed to a vessel stapling step Again, at step 22212, intraoperative information is received and analyzed. For example, the surgical hub could determine that the clinician has selected a vascular stapler surgical instrument. Also, an initial measurement from the tissue contact sensors 474 may indicate that tissue contact occurs almost immediately during closure. In addition, the tissue contact may be determined to encompass a small area of the vascular stapler 112 and is bounded on the distal side of the stapler 112. Load sensor 474 measurements may also indicate a compliant tissue structure. Further, it may be inferred that the tissue may have relatively low stiffness which may be consistent with a lung pulmonary vessel. Moreover, clinician history may indicate that the treating surgeon generally uses a vascular stapler 112 for blood vessels as the step subsequent to completing the lung fissure. Thus, intraoperative information, in conjunction with closure parameter sensor signals for example, may be used to infer tissue type and tissue characteristics. In particular, it can be predicted that vessel tissue is being treated based on the specific characteristics of the selected vascular stapler 112. The initial tissue contact and load sensor 474 measurements may confirm this initial prediction, for example.

Consequently, it can be determined at decision operation 22214 that further adjustment is necessary, which causes the flow diagram 22200 to proceed to step 22206. At step 22206, it may be inferred that the tissue is blood vessel tissue with relatively low tissue thickness and stiffness. Accordingly, the flow diagram 22200 proceeds to step 22208, where the previously applied conservative closure algorithm is adjusted to a normal closure algorithm. A normal closure algorithm may comprise a constant closure rate of change. Also, the closure threshold could be higher than the threshold used in the control algorithm for the parenchyma tissue. In other words, the normal closure algorithm may reach a higher maximum applied closure force and the closure rate of change may be faster than for parenchyma tissue. The surgical instrument can also inform the clinician of the adjustment to the normal closure algorithm via a suitable indicator, such as a light emitting diode (LED) indicator displaying a particular color. In another example, it could be determined at step 22206 that the patient has a complete lung fissure. Accordingly, there would not have been any staple firings of parenchyma tissue performed yet in the surgical procedure. In response to this determination, the surgical instrument may prompt the clinician for confirmation that this inference is correct, such as via a display of the surgical instrument. The clinician could then manually select an appropriate closure control algorithm for this step or stage of the surgical procedure. Additionally or alternatively, the surgical instrument 112 may default to a conservative closure algorithm because the inferences performed at step 22206 may not be definitive. In any case, the adjusted closure algorithm is applied at step 22208.

Continuing the description of the lung lobectomy procedure example, the flow diagram proceeds to decision operation 22210. At decision operation 22210, it may be determined that there are remaining steps of the surgical procedure. Accordingly, at step 22212, intraoperative information is received and analyzed. Based on intraoperative information, it may be inferred that the tissue type being treated is bronchus tissue. Furthermore, the initial tissue contact sensor 474 measurements could indicate that the tissue grasped between the end effector 702 contacts the first and second jaw members 152002, 152004 almost immediately during initial closure of the end effector 702 and that such contact corresponds to a small area of the stapling surgical instrument 112. Also, such contact is bounded on both sides of the jaw members 152002, 152004.

Consequently, it may be predicted that this tissue contact scenario corresponds to bronchus tissue. As dis-cussed above, these initial tissue contact sensor 474 measurements may be non-therapeutic or quasi non-therapeutic. Furthermore, the closure load sensor 474 measurements as represented by a closure compared to jaw aperture curve may indicate a stiff tissue structure that is consistent with bronchus tissue. The indication by the surgical procedure history that a vascular stapler 112 has already been used in the surgical procedure may also mean it is likely that parenchyma staple firings have already been performed and significant monopolar RF energy usage has occurred. This surgical procedure history considered in conjunction with clinician history, for example, may be used to predict that the surgeon is treating bronchus tissue. This prediction would be consistent with the surgeon's routine practice of stapling the bronchus as the last step in a lobectomy procedure. Based on analyzing this type of and other suitable intraoperative information at step 22212, it can be determined at decision operation 22214 that further adjustment is necessary. Because the answer to decision operation 22214 is yes, the flow diagram proceeds to step 22206 where it is inferred that the treated tissue is bronchus tissue with a normal tissue stiffness and thickness.

In one aspect, it may be easy to conclude that the treated tissue is bronchus tissue because the surgical instrument 112 is only configured for a specific tissue type. For example, the surgical instrument 112 may only be adaptable to fire staples that are used for bronchus. Conversely, the surgical instrument 112 might only be adaptable to fire staples that are used for parenchyma tissue. In that scenario, a warning might be generated by the surgical instrument 112 because the surgeon is attempting to treat bronchus tissue with staples exclusively used for parenchyma tissue. This warning could be an auditory, visual, or some other appropriate warning. In another example, a warning may be provided by a vascular stapler 112 if the vascular stapler 112 is selected for use with bronchus tissue. As discussed above, it may be determined based on perioperative information that the tissue being treated is bronchus tissue that the vascular stapler is contraindicated for. Similarly, other perioperative information such as closure loads and stapler cartridge selection may be used to provide warnings when surgical instruments 112 are used for tissue types or characteristics that they are not compatible with. As discussed above, inferences made using perioperative information may be made in conjunction with closure parameter sensor signals In all situations, safety checks may be implemented to ensure that the surgical instrument 112 being used is safe for the tissue being treated.

In accordance with the inferred tissue type and characteristics, at step 22208, an adjustment to the current closure algorithm is made. Although it may be determined that a constant closure rate is suitable, the closure rate may be adjusted to be faster or slower depending on the inferred tissue characteristics of the bronchus, for example. The closure threshold could be modified in the same or similar way. Moreover, the current closure algorithm may also be adjusted such that if and when the surgical instrument 112 exceeds the instantaneously applicable closure threshold, a longer wait time is automatically enabled or suggested. For example, this wait time for bronchus tissue may be longer than the wait time used for parenchyma tissue. As discussed above, the surgeon is informed of the selected adjustment to the closure algorithm via the LED indicators, for example. A clinician override to the longer wait time is also possible so that the surgeon may be permitted to fire the stapler surgical instrument 112 in appropriate circumstances. The flow diagram 22200 then proceeds to step 22212, where it may be determined that in one aspect, the flow diagram 22200 may be implemented by the control circuit. However, in other aspects, the flow diagram 22200 can be implemented by the surgical hub 106 or cloud 104. Additionally, although steps 22204 and 22212 are described in terms of preoperative information and intraoperative information respectively, they are not limited in this way. Specifically, perioperative information in general may be received and analyzed rather than specific preoperative or intraoperative information. As discussed above, perioperative information encompasses preoperative, intraoperative, and postoperative information. Moreover, sensor signals may be used in conjunction with perioperative information for contextual and inferential closure algorithm adjustments. no further steps of the surgical procedure remain.

Figure 72:
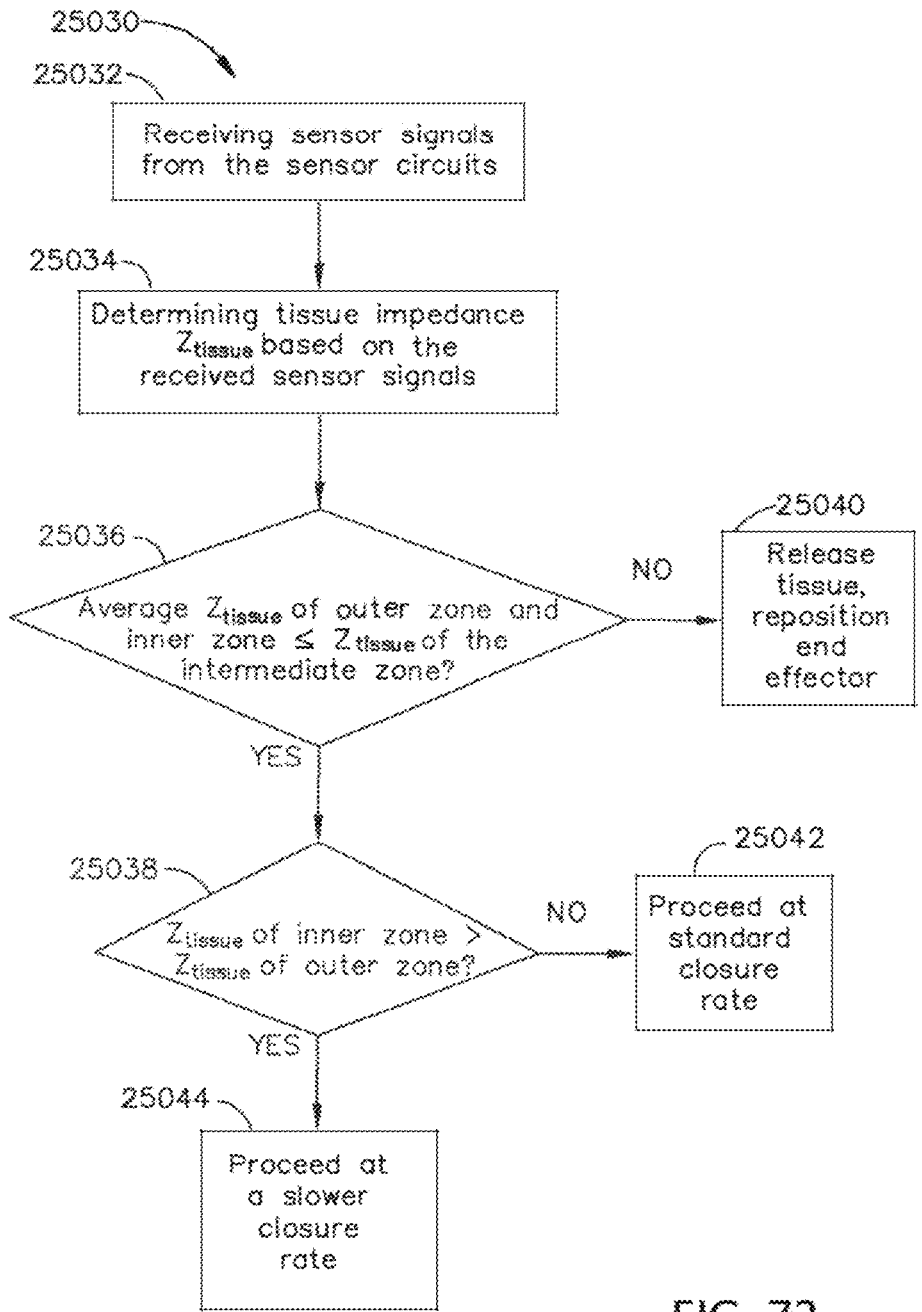
FIG. 72 illustrates a logic flow diagram of a process depicting a control program of a logic configuration for identifying irregularities in tissue distribution within an end effector of a surgical instrument, in accordance with at least one aspect of the present disclosure.

FIG. 72 illustrates a logic flow diagram of a process 25030 depicting a control program or a logic controller for identifying irregularities in tissue distribution within an end effector 25002 of a surgical instrument, in accordance with at least one aspect of the present disclosure. In one aspect, the process 25030 is executed by a control circuit. In another aspect, the process 25030 can be executed by a combinational logic circuit. In yet another aspect, the process 25030 can be executed by a sequential logic circuit.

The process 25030 includes receiving 25032 senor signals from sensor circuits of a sensing circuit assembly 25471 corresponding to predetermined zones (e.g. Zone 1, Zone 2, and Zone 3) within the end effector 25002, determining 25034 tissue impedance Z tissue of tissue portions at such zones based on the received sensor signals.

Figure 73:
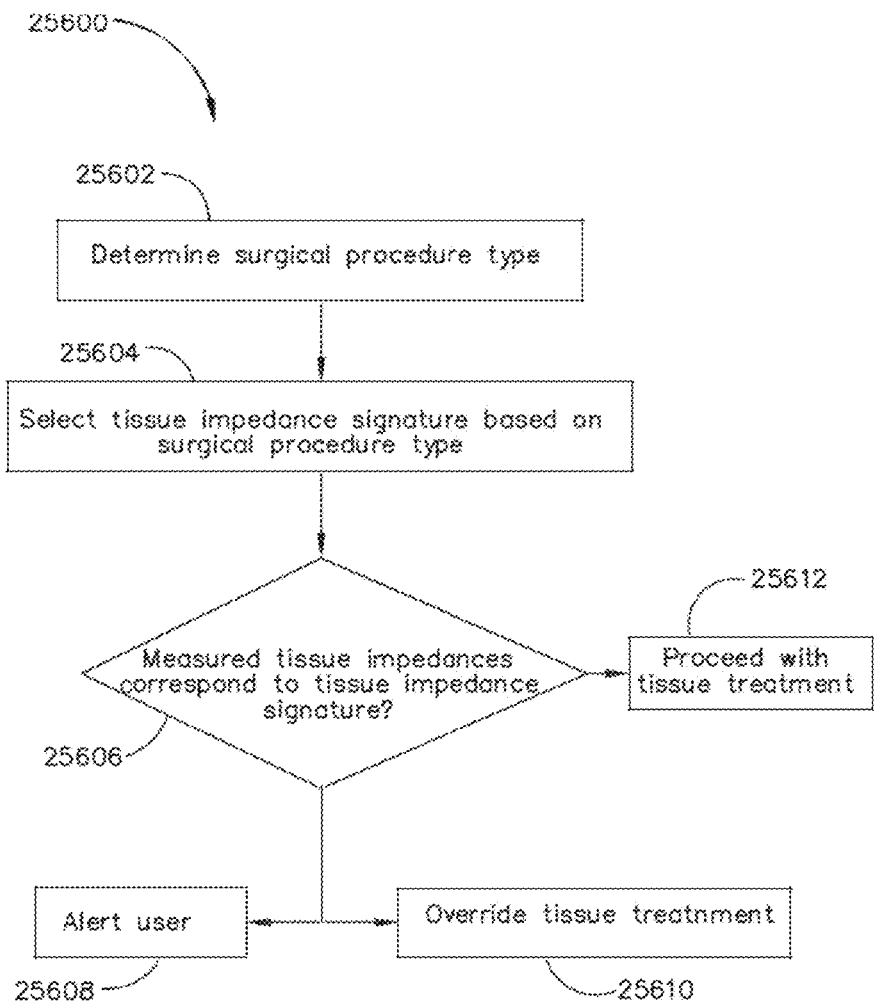
FIG. 73 illustrates a logic flow diagram of a process depicting a control program or a logic configuration for properly positioning a previously stapled tissue within an end effector, in accordance with at least one aspect of the present disclosure.

FIG. 73 illustrates a logic flow diagram of a process 25600 depicting a control program or a logic configuration for properly positioning a previously-stapled tissue within an end effector (e.g. end effectors 25500, 25510) of a surgical stapler. In one aspect, the process 25600 is executed by a control circuit. In another aspect, the process 25600 is executed by a combinational logic circuit. In yet another aspect, the process 25600 is executed by a sequential logic circuit.

For illustrative purposes, the following description depicts the process 25600 as being executable by a control circuit that includes a controller 461, which includes a processor 461. A memory 468 stores program instructions, which are executable by the processor 461 to perform the process 25600.

The process 25600 determines 25602 the type of surgical procedure being performed by the surgical stapler. The surgical procedure type can be determined using various techniques described under the heading "Situational Awareness". The processor 25600 then selects 25604, based on the determined surgical procedure type, a tissue impedance signature for a properly positioned previously-stapled tissue. As described above, a properly positioned previously stapled tissue in a J-pouch procedure, for example, comprises a different tissue impedance signature than in an End-To-End Anastomosis procedure, for example.

The process 25600 then determines 25606 whether measured tissue impedances in the predetermined zones correspond to the selected tissue impedance signature. If not, the processor 461 may alert 25608 the user and/or override 25610 the tissue treatment. In one aspect, the processor 461 may alert 25608 the user through the display 473. In addition, the processor 461 may override 25610 the tissue treatment by preventing the end effector from completing its firing, which can be accomplished by causing the motor driver to stop the motor, for example.

If, however, the measured tissue impedances in the predetermined zones correspond to the selected tissue impedance signature, the processor 461 permits the end effector to proceed 25612 with the tissue treatment.

Figure 74:
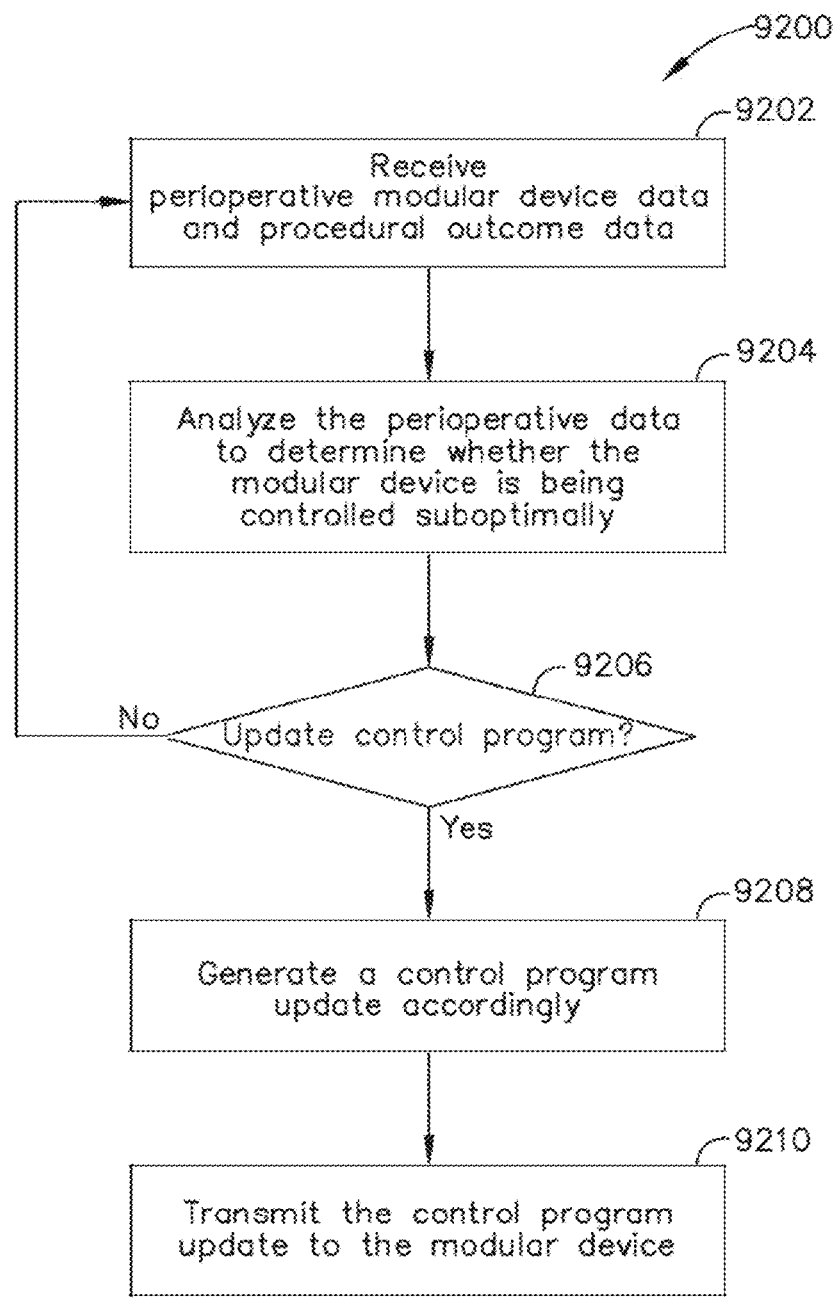
FIG. 74 illustrates a logic flow diagram of a process for updating the control program of a modular device, in accordance with at least one aspect of the present disclosure.

FIG. 74 illustrates a logic flow diagram of a process 9200 for updating the control program of a modular device 9050, in accordance with at least one aspect of the present disclosure. The process 9200 can be executed by, for example, one or more processors of the analytics servers 9070 of the analytics system 9100. In one exemplification, the analytics system 9100 can be a cloud computing system. For economy, the following description of the process 9200 will be described as being executed by the analytics system 9100; however, it should be understood that the analytics system 9100 includes processor(s) and/or control circuit(s) that are executing the describe steps of the process 9200.

The analytics system 9100 receives 9202 modular device 9050 perioperative data and surgical procedural outcome data from one or more of the surgical hubs 9000 that are communicably connected to the analytics system 9100. The perioperative data includes preoperative data, intraoperative data, and/or postoperative data detected by a modular device 9050 in association with a given surgical procedure. For modular devices 9050 or particular functions of modular devices 9050 that are manually controlled, the perioperative data indicates the manner in which a surgical staff member operated the modular devices 9050. For modular devices 9050 or particular functions of modular devices 9050 that are controlled by the modular devices' control programs, the perioperative data indicates the manner in which the control programs operated the modular devices 9050. The manner in which the modular devices 9050 function under particular sets of conditions (either due to manual control or control by the modular devices' 9050 control programs) can be referred to as the "operational behavior" exhibited by the modular device 9050. The modular device 9050 perioperative data includes data regarding the state of the modular device 9050 (e.g., the force to fire or force to close for a surgical stapling and cutting instrument or the power output for an electrosurgical or ultrasonic instrument), tissue data measured by the modular device 9050 (e.g., impedance, thickness, or stiffness), and other data that can be detected by a modular device 9050. The perioperative data indicates the manner in which the modular devices 9050 were programmed to operate or were manually controlled during the course of a surgical procedure because it indicates how the modular devices 9050 functioned in response to various detected conditions.

The surgical procedural outcome data includes data pertaining to an overall outcome of a surgical procedure (e.g., whether there was a complication during the surgical procedure) or data pertaining to an outcome of a specific step within a surgical procedure (e.g., whether a particular staple line bled or leaked). The procedural outcome data can, for example, be directly detected by the modular devices 9050 and/or surgical hub 9000 (e.g., a medical imaging device can visualize or detect bleeding), determined or inferred by a situational awareness system of the surgical hub 9000 as described in U.S. Patent Publication No. 2019/0201140 A1 by the surgical hub 9000 or the analytics system 9100. The procedural outcome data can include whether each outcome represented by the data was a positive or negative result. Whether each outcome was positive or negative can be determined by the modular devices 9050 themselves and included in the perioperative data transmitted to the surgical hubs 9000 or determined or inferred by the surgical hubs 9000 from the received perioperative data. For example, the procedural outcome data for a staple line that bled could include that the bleeding represented a negative outcome. Similarly, the procedural outcome data for a staple line that did not bleed could include that the lack of bleeding represented a positive outcome. In another exemplification, the analytics system 9100 can be configured to determine whether a procedural outcome is a positive or negative outcome based upon the received procedural outcome data. In some exemplifications, correlating the modular device 9050 data to positive or negative procedural outcomes allows the analytics system 9100 to determine whether a control program update should be generated 9208.

Upon the analytics system 9100 receiving 9202 the data, the analytics system 9100 analyzes the modular device 9050 and procedural outcome data to determine 9204 whether the modular devices 9050 are being utilized suboptimally in connection with the particular procedure or the particular step of the procedure. A modular device 9050 can be controlled suboptimally if the particular manner in which the modular device 9050 is being controlled is repeatedly causing an error or if an alternative manner of controlling the modular device 9050 is superior under the same conditions. The analytics system 9100 can thus determine whether a modular device 9050 is being controlled suboptimally (either manually or by its control program) by comparing the rate of positive and/or negative outcomes produced by the modular device 9050 relative to set thresholds or the performance of other modular devices 9050 of the same type.

For example, the analytics system 9100 can determine whether a type of modular device 9050 is being operated suboptimally if the rate of negative procedural outcomes produced by the modular device 9050 under a particular set of conditions in association with a particular operational behavior exceeds an average or threshold level. As a specific example, the analytics system 9100 can analyze 9204 whether a control program for a surgical stapling instrument that dictates a particular force to fire (or ranges of forces to fire) is suboptimal for a particular tissue thickness and tissue type. If the analytics system 9100 determines that the instrument generates an abnormally high rate of leaky staple lines when fired at the particular force (e.g., causing the staples to be malformed, not fully penetrate the tissue, or tear the tissue) relative to an average or threshold staple line leakage rate, then the analytics system 9100 can determine that the control program for the surgical stapling instrument is performing suboptimally given the tissue conditions.

As another example, the analytics system 9100 can determine whether a type of modular device 9050 is being operated suboptimally if the rate of positive outcomes produced by an alternative manner of control under a particular set of conditions in association with a particular operational behavior exceeds the rate of positive outcomes generated by the analyzed manner of control under the same conditions. In other words, if one subpopulation of the type of modular device 9050 exhibits a first operational behavior under a certain set of conditions and a second subpopulation of the same type of modular device 9050 exhibits a second operational behavior under the same set of conditions, then the analytics system 9100 can determine whether to update the control programs of the modular devices 9050 according to whether the first or second operational behavior is more highly correlated to a positive procedural outcome. As a specific example, the analytics system 9100 can analyze 9204 whether a control program for an RF electrosurgical or ultrasonic instrument that dictates a particular energy level is suboptimal for a particular tissue type and environmental conditions. If the analytics system 9100 determines that a first energy level given a set of tissue conditions and environmental conditions (e.g., the instrument being located in a liquid-filled environment, as in an arthroscopic procedure) produces a lower rate of hemostasis than a second energy level, then the analytics system 9100 can determine that the control program for the electrosurgical or ultrasonic instrument dictating the first energy level is performing suboptimally for the given tissue and environmental conditions.

After analyzing 9204 the data, the analytics system 9100 determines 9206 whether to update the control program. If the analytics system 9100 determines that the modular device 9050 is not being controlled suboptimally, then the process 9200 continues along the NO branch and the analytics system 9100 continues analyzing 9204 received 9202 data, as described above. If the analytics system 9100 determines that the modular device 9050 is being controlling suboptimally, then the process 9200 continues along the YES branch and the analytics system 9100 generates 9208 a control program update. The generated 9208 control program update includes, for example, a new version of the control program for the particular type of modular device 9050 to overwrite the prior version or a patch that partially overwrites or supplements the prior version.

The type of control program update that is generated 9208 by the analytics system 9100 depends upon the particular suboptimal behavior exhibited by the modular device 9050 that is identified by the analytics system 9100. For example, if the analytics system 9100 determines that a particular force to fire a surgical stapling instrument results in an increased rate of leaking staple lines, then the analytics system 9100 can generate 9208 a control program update that adjusts the force to fire from a first value to a second value that corresponds to a higher rate of non-leaking staple lines or a lower rate of leaking staple lines. As another example, if the analytics system 9100 determines that a particular energy level for an electrosurgical or ultrasonic instrument produces a low rate of hemostasis when the instrument is used in a liquid-filled environment (e.g., due to the energy dissipating effects of the liquid), then the analytics system 9100 can generated 9208 a control program update that adjusts the energy level of the instrument when it is utilized in surgical procedures where the instrument will be immersed in liquid.

The type of control program update that is generated 9208 by the analytics system 9100 also depends upon whether the suboptimal behavior exhibited by the modular device 9050 is caused by manual control or control by the control program of the modular device 9050. If the suboptimal behavior is caused by manual control, the control program update can be configured to provide warnings, recommendations, or feedback to the users based upon the manner in which they are operating the modular devices 9050. Alternatively, the control program update can change the manually controlled operation of the modular device 9050 to an operation that is controlled by the control program of the modular device 9050. The control program update may or may not permit the user to override the control program's control of the particular function. In one exemplification, if the analytics system 9100 determines 9204 that surgeons are manually setting an RF electrosurgical instrument to a suboptimal energy level for a particular tissue type or procedure type, then the analytics system 9100 can generate 9208 a control program update that provides an alert (e.g., on the surgical hub 9000 or the RF electrosurgical instrument itself) recommending that the energy level be changed. In another exemplification, the generated 9208 control program update can automatically set the energy level to a default or recommended level given the particular detected circumstances, which could then be changed as desired by the medical facility staff. In yet another exemplification, the generated 9208 control program update can automatically set the energy level to a set level determined by the analytics system 9100 and not permit the medical facility staff to change the energy level. If the suboptimal behavior is caused by the control program of the modular device 9050, then the control program update can alter how the control program functions under the particular set of circumstances that the control program is performing suboptimally under.

Once the control program update has been generated 9208 by the analytics system 9100, the analytics system 9100 then transmits 9210 or pushes the control program update to all of the modular devices 9050 of the relevant type that are connected to the analytics system 9100. The modular devices 9050 can be connected to the analytics system 9100 through the surgical hubs 900, for example. In one exemplification, the surgical hubs 9000 are configured to download the control program updates for the various types of modular devices 9050 from the analytics system 9100 each time an update is generated 9208 thereby. When the modular devices 9050 subsequently connect to or pair with a surgical hub 9000, the modular devices 9050 then automatically download any control program updates therefrom. In one exemplification, the analytics system 9100 can thereafter continue receiving 9202 and analyzing 9204 data from the modular devices 9050, as described above.

Figure 75:
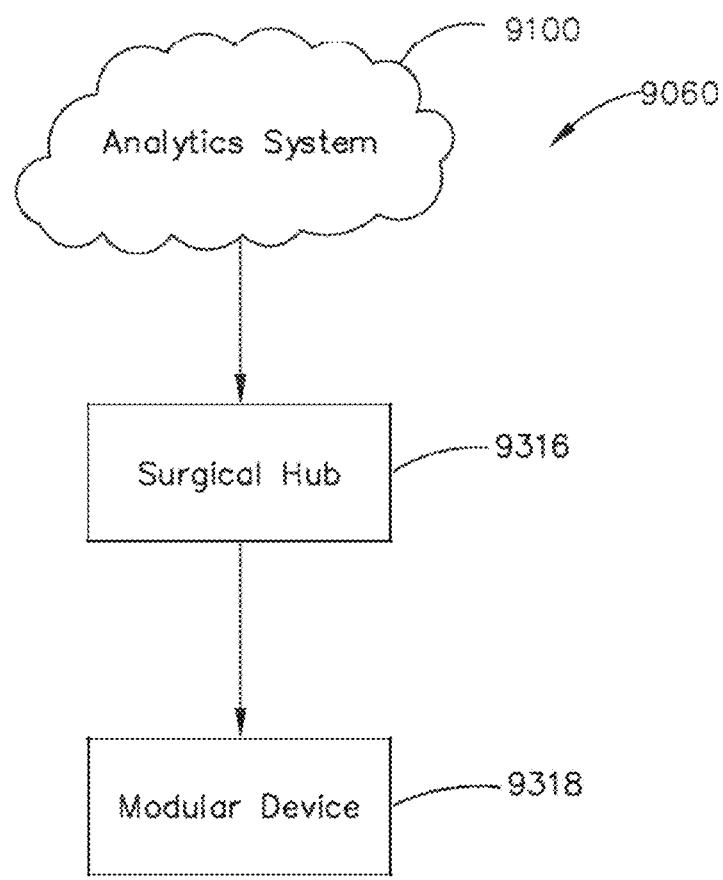
FIG. 75 illustrates a diagram of an analytics system pushing an update to a modular device through a surgical hub, in accordance with at least one aspect of the present disclosure.

In one aspect, the surgical system 9060 is configured to push down verification of software parameters and updates if modular devices 9050 are detected to be out of date in the surgical hub 9000 data stream. FIG. 75 illustrates a diagram of an analytics system 9100 pushing an update to a modular device 9050 through a surgical hub 9000, in accordance with at least one aspect of the present disclosure. In one exemplification, the analytics system 9000 is configured to transmit a generated control program update for a particular type of modular device 9050 to a surgical hub 9000. In one aspect, each time a modular device 9050 connects to a surgical hub 9000, the modular device 9050 determines whether there is an updated version of its control program on or otherwise accessible via the surgical hub 9000. If the surgical hub 9000 does have an updated control program (or the updated control program is otherwise avail-able from the analytics system 9100) for the particular type of modular device 9050, then the modular device 9050 downloads the control program update therefrom.

In one exemplification, any data set being transmitted to the analytics systems 9100 includes a unique ID for the surgical hub 9000 and the current version of its control program or operating system. In one exemplification, any data set being sent to the analytics systems 9100 includes a unique ID for the modular device 9050 and the current version of its control program or operating system. The unique ID of the surgical hub 9000 and/or modular device 9050 being associated with the uploaded data allows the analytics system 9100 to determine whether the data corresponds to the most recent version of the control program. The analytics system 9100 could, for example, elect to discount (or ignore) data generated by a modular device 9050 or surgical hub 9000 being controlled by an out of date control program and/or cause the updated version of the control program to be pushed to the modular device 9050 or surgical hub 9000.

In one exemplification, the operating versions of all modular devices 9050 the surgical hub 9000 has updated control software for could also be included in a surgical hub 9000 status data block that is transmitted to the analytics system 9100 on a periodic basis. If the analytics system 9100 identifies that the operating versions of the control programs of the surgical hub 9100 and/or any of the connectable modular devices 9050 are out of date, the analytics system 9100 could push the most recent revision of the relevant control program to the surgical hub 9000.

In one exemplification, the surgical hub 9000 and/or modular devices 9050 can be configured to automatically download any software updates. In another exemplification, the surgical hub 9000 and/or modular devices 9050 can be configured to provide a prompt for the user to ask at the next setup step (e.g., between surgical procedures) if the user wants to update the out of date control program(s). In another exemplification, the surgical hub 9000 could be programmable by the user to never allow updates or only allow updates of the modular devices 9050 and not the surgical hub 9000 itself.

Figure 76:
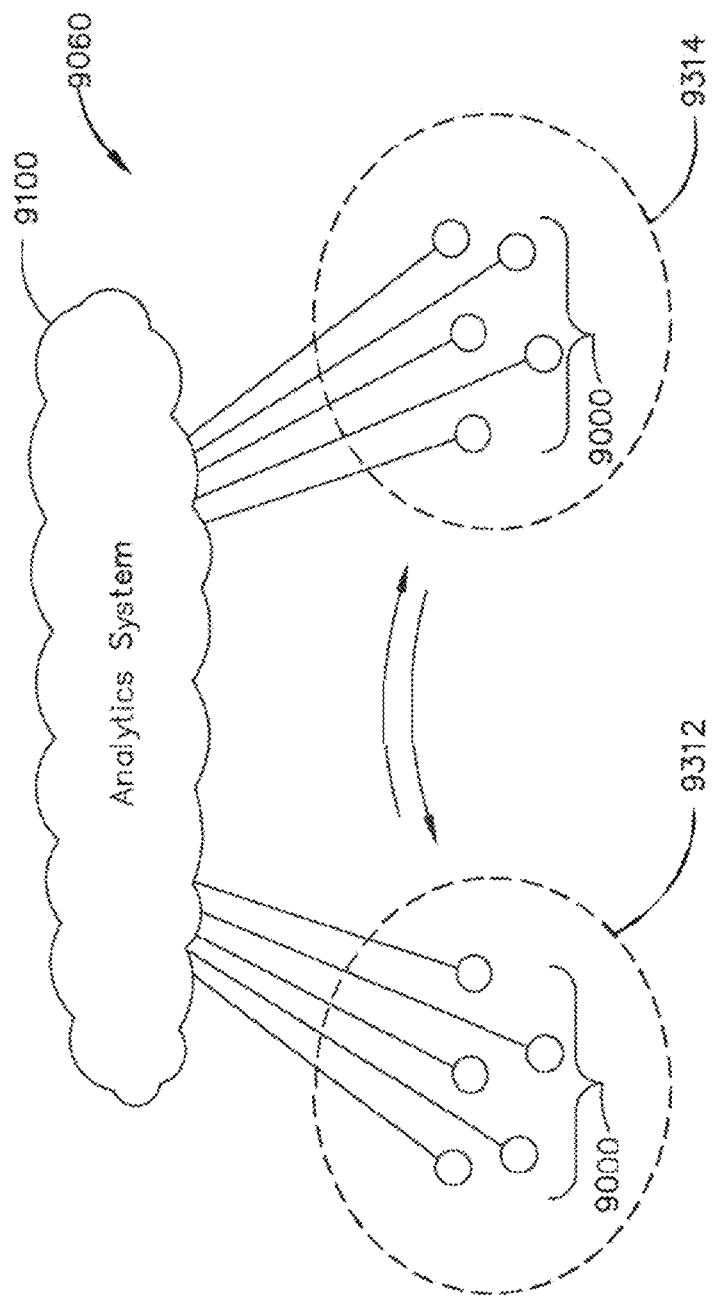
FIG. 76 illustrates a diagram of a computer-implemented interactive surgical system that is configured to adaptively generate control program updates for surgical hubs, in accordance with at least one aspect of the present disclosure.

FIG. 76 illustrates a diagram of a computer-implemented adaptive surgical system 9060 that is configured to adaptively generate control program updates for surgical hubs 9000, in accordance with at least one aspect of the present disclosure. The surgical system 9060 includes several surgical hubs 9000 that are communicably coupled to the analytics system 9100. Subpopulations of surgical hubs 9000 (each of which can include individual surgical hubs 9000 or groups of surgical hubs 9000) within the overall population connected to the analytics system 9100 can exhibit different operational behaviors during the course of a surgical procedure. The differences in operational behavior between groups of surgical hubs 9000 within the population can result from the surgical hubs 9000 running different versions of their control program, by the surgical hubs' 9000 control programs being customized or programmed differently by local surgical staff, or by the local surgical staff manually controlling the surgical hubs 9000 differently. In the depicted example, the population of surgical hubs 9000 includes a first subpopulation 9312 that is exhibiting a first operational behavior and a second subpopulation 9314 that is exhibiting a second operational behavior for a particular task. Although the surgical hubs 9000 are divided into a pair of subpopulations 9312, 9314 in this particular example, there is no practical limit to the number of different behaviors exhibited within the population of surgical hubs 9000. The tasks that the surgical hubs 9000 can be executing include, for example, controlling a surgical instrument or analyzing a dataset in a particular manner.

The surgical hubs 9000 can be configured to transmit perioperative data pertaining to the operational behavior of the surgical hubs 9000 to the analytics system 9100. The perioperative data can include preoperative data, intraoperative data, and postoperative data. The preoperative data can include, for example, patient-specific information, such as demographics, health history, preexisting conditions, preoperative workup, medication history (i.e., medications currently and previously taken), genetic data (e.g., SNPs or gene expression data), EMR data, advanced imaging data (e.g., MRI, CT, or PET), metabolomics, and microbiome. Various additional types of patient-specific information that can be utilized by the analytics system 9100 are described by U.S. Pat. No. 9,250,172, U.S. patent application Ser. No. 13/631,095, U.S. patent application Ser. No. 13/828,809, and U.S. Pat. No. 8,476,227, each of which is incorporated by reference herein to the extent that they describe patient specific information. The preoperative data can also include, for example, operating theater-specific information, such as geographic information, hospital location, operating theater location, operative staff performing the surgical procedure, the responsible surgeon, the number and type of modular devices 9050 and/or other surgical equipment that could potentially be used in the particular surgical procedure, the number and type of modular devices 9050 and/or other surgical equipment that are anticipated to be used in the particular surgical procedure, patient identification information, and the type of procedure being performed.

The intraoperative data can include, for example, modular device 9050 utilization (e.g., the number of firings by a surgical stapling instrument, the number of firings by an RF electrosurgical instrument or an ultrasonic instrument, or the number and types of stapler cartridges utilized), operating parameter data of the modular devices 9050 (e.g., the FTF curve for a surgical stapling instrument, a FTC curve for a surgical stapling instrument, the energy output of a generator, the internal pressure or pressure differential of a smoke evacuator), unexpected modular device 9050 utilization (i.e., the detection of the utilization of a modular device that is nonstandard for the procedure type), adjunctive therapies administered to the patient, and utilization of equipment other than the modular devices 9050 (e.g., sealants to address leaks). The intraoperative data can also include, for example, detectable misuse of a modular device 9050 and detectable off-label use of a modular device 9050.

The postoperative data can include, for example, a flag if the patient does not leave the operating theater and/or is sent for nonstandard postoperative care (e.g., a patient undergoing a routine bariatric procedure is sent to the ICU after the procedure), a postoperative patient evaluation relating to the surgical procedure (e.g., data relating to a spirometric performance after a thoracic surgery or data relating to a staple line leakage after bowel or bariatric procedures), data related to postoperative complications (e.g., transfusions or air leaks), or the patient's length of stay in the medical facility after the procedure. Because hospitals are increasingly being graded on readmission rates, complication rates, average length of stay, and other such surgical quality metrics, the postoperative data sources can be monitored by the analytics system 9100 either alone or in combination with surgical procedural outcome data (discussed below) to assess and institute updates to the controls programs of the surgical hubs 9000 and/or modular devices 9050.

In some exemplifications, the intraoperative and/or postoperative data can further include data pertaining to the outcome of each surgical procedure or a step of the surgical procedure. The surgical procedural outcome data can include whether a particular procedure or a particular step of a procedure had a positive or negative outcome. In some exemplifications, the surgical procedural outcome data can include procedure step and/or time stamped images of modular device 9050 performance, a flag indicating whether a modular device 9050 functioned properly, notes from the medical facility staff, or a flag for poor, suboptimal, or unacceptable modular device 9050 performance. The surgical procedural outcome data can, for example, be directly detected by the modular devices 9050 and/or surgical hub 9000 (e.g., a medical imaging device can visualize or detect bleeding), determined or inferred by a situational awareness system of the surgical hub 9000 as described in U.S. Patent Publication No. 2019/0201140 A1 by the surgical hub 9000 or the analytics system 9100. In some exemplifications, perioperative data including a flag indicating that a modular device 9050 failed or otherwise performed poorly during the course of a surgical procedure can be prioritized for communication to and/or analysis by the analytics system 9100.

In one exemplification, the perioperative data can be assembled on a procedure-by-procedure basis and uploaded by the surgical hubs 9000 to the analytics system 9100 for analysis thereby. The perioperative data indicates the manner in which the surgical hubs 9000 were programmed to operate or were manually controlled in association with a surgical procedure (i.e., the operational behavior of the surgical hubs 9000) because it indicates what actions the surgical hub 9000 took in response to various detected conditions, how the surgical hubs 9000 controlled the modular devices 9050, and what inferences the situationally aware surgical hubs 9000 derived from the received data. The analytics system 9100 can be configured to analyze the various types and combinations of preoperative, intraoperative, and post-operative data to determine whether a control program update should be generated and then push the update to the overall population or one or more sub-populations of surgical hubs 9000, as necessary.

Figure 77:
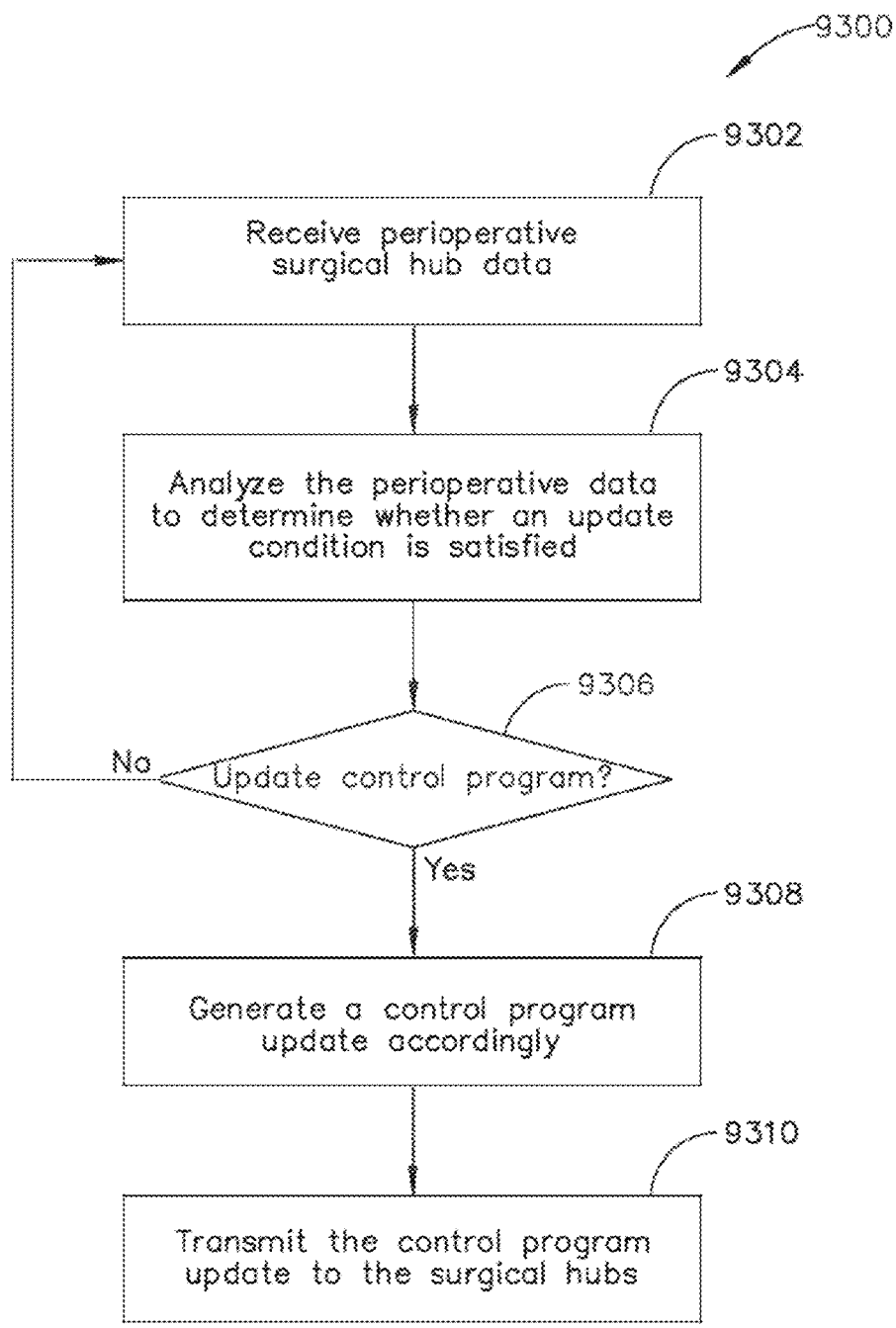
FIG. 77 illustrates a logic flow diagram of a process for updating the control program of a surgical hub, in accordance with at least one aspect of the present disclosure.

FIG. 77 illustrates a logic flow diagram of a process 9300 for updating the control program of a surgical hub 9000, in accordance with at least one aspect of the present disclosure. The process 9200 can be executed by, for example, one or more processors of the analytics servers 9070 of the analytics system 9100. In one exemplification, the analytics system 9100 can be a cloud computing system. For economy, the following description of the process 9300 will be described as being executed by the analytics system 9100; however, it should be understood that the analytics system 9100 includes processor(s) and/or control circuit(s) that are executing the describe steps of the process 9300.

The analytics system 9100 executing the process 9300 receives 9302 perioperative data from the surgical hubs 9000 that are communicably connected to the analytics system 9100. The perioperative data indicates the manner in which the surgical hubs 9000 are programmed to operate by their control programs or are controlled by the surgical staff during a surgical procedure. In some aspects, the perioperative data can include or being transmitted to the analytics system 9100 in association with surgical procedural outcome data. The surgical procedural outcome data can include data pertaining to an overall outcome of a surgical procedure (e.g., whether there was a complication during the surgical procedure) or data pertaining to a specific step within a surgical procedure (e.g., whether a particular staple line bled or leaked).

After an analytics system 9100 executing the process 9300 has received 9302 the perioperative data, the analytics system 9100 then analyzes 9304 the data to determine whether an update condition has been satisfied. In one exemplification, the update condition includes whether a threshold number or percentage of surgical hubs 9000 within the population exhibit a particular operational behavior. For example, the analytics system 9100 can determine that a control program update should be generated to automatically active an energy generator at a particular step in a type of surgical procedure when a majority of the surgical hubs 9000 are utilized to active the energy generator at that procedural step. In another exemplification, the update condition includes whether the rate of positive procedural outcomes (or lack of negative procedural outcomes) correlated to a particular operational behavior exceeds a threshold value (e.g., an average rate of positive procedural outcomes for a procedure step). For example, the analytics system 9100 can determine that a control program update should be generated to recommend that the energy generator be set at a particular energy level when the associated rate of hemostasis (i.e., lack of bleeding) at that energy level for the particular tissue type exceeds a threshold rate. In another exemplification, the update condition includes whether the rate of positive procedural outcomes (or lack of negative procedural outcomes) for a particular operational behavior is higher than the rate of positive procedural outcomes (or a lack of negative procedural outcomes) for related operational behaviors. In other words, if one subpopulation of surgical hubs 9000 exhibits a first operational behavior under a certain set of conditions and a second subpopulation of surgical hubs 9000 exhibits a second operational behavior under the same set of conditions, then the analytics system 9100 can determine whether to update the control programs of the surgical hubs 9000 according to whether the first or second operational behavior is more highly correlated to a positive procedural outcome. In another exemplification, the analytics system 9100 analyzes 9304 the data to determine whether multiple update conditions have been satisfied.

If an update condition has not been satisfied, the process 9300 continues along the NO branch and the analytics system 9100 continues receiving 9302 and analyzing 9304 perioperative data from the surgical hubs 9000 to monitor for the occurrence of an update condition. If an update condition has been satisfied, the process 9300 continues along the YES branch and the analytics system 9100 proceeds to generate 9308 a control program update. The nature of the generated 9308 control program update corresponds to the particular operational behavior of the surgical hub 9000 that is identified by the analytics system 9100 as triggering the update condition. In other words, the control program update adds, removes, or otherwise alters functions performed by the surgical hub 9000 so that the surgical hub operates differently under the conditions that gave rise to the identified operational behavior.

Furthermore, the type of control program update also depends upon whether the identified operational behavior results from manual control or control by the control program of the surgical hub 9000. If the identified operational behavior results from manual control, the control program update can be configured to provide warnings, recommendations, or feedback to the users based upon the manner in which they are operating the surgical hub 9000. For example, if the analytics system 9100 determines that taking a particular action or utilizing a particular instrument for a step in a surgical procedure improves outcomes, then the analytics system 9100 can generate 9308 a control program update that provides a prompt or warning to the surgical staff when the surgical hub 9000 determines that the designated step of the surgical procedure is occurring or will subsequently occur. Alternatively, the control program update can change one or more functions of the surgical hub 9000 from being manually controllable to being controlled by the control program of the surgical hub 9000. For example, if the analytics system 9100 determines that a display of the visualization system is set to a particular view by the surgical staff in a predominant number of surgical procedures at a particular step, the analytics system 9100 can generate a control program update that causes the surgical hub 9000 to automatically change the display to that view under those conditions. If the identified operational behavior results from the control program of the surgical hub 9000, then the control program update can alter how the control program functions under the set of circumstances that cause the identified operational behavior. For example, if the analytics system 9100 determines that a particular energy level for an RF electrosurgical or ultrasonic instrument correlates to poor or negative outcomes under a certain set of conditions, then the analytics system 9100 can generate 9308 a control program update that causes the surgical hub 9000 to adjust the energy level of the connected instrument to a different value when the set of conditions is detected (e.g., when the surgical hub 9000 determines that an arthroscopic procedure is being performed).

The analytics system 9100 then transmits 9310 the control program update to the overall population of surgical hubs 9000 or the subpopulation(s) of surgical hubs 9000 that are performing the operational behavior that is identified by the analytics system 9100 as triggering the update condition. In one exemplification, the surgical hubs 9000 are configured to download the control program updates from the analytics system 9100 each time an update is generated 9308 thereby. In one exemplification, the analytics system 9100 can thereafter continue the process 9300 of analyzing 9304 the data received 9302 from the surgical hubs 9000, as described above.

Figure 79:
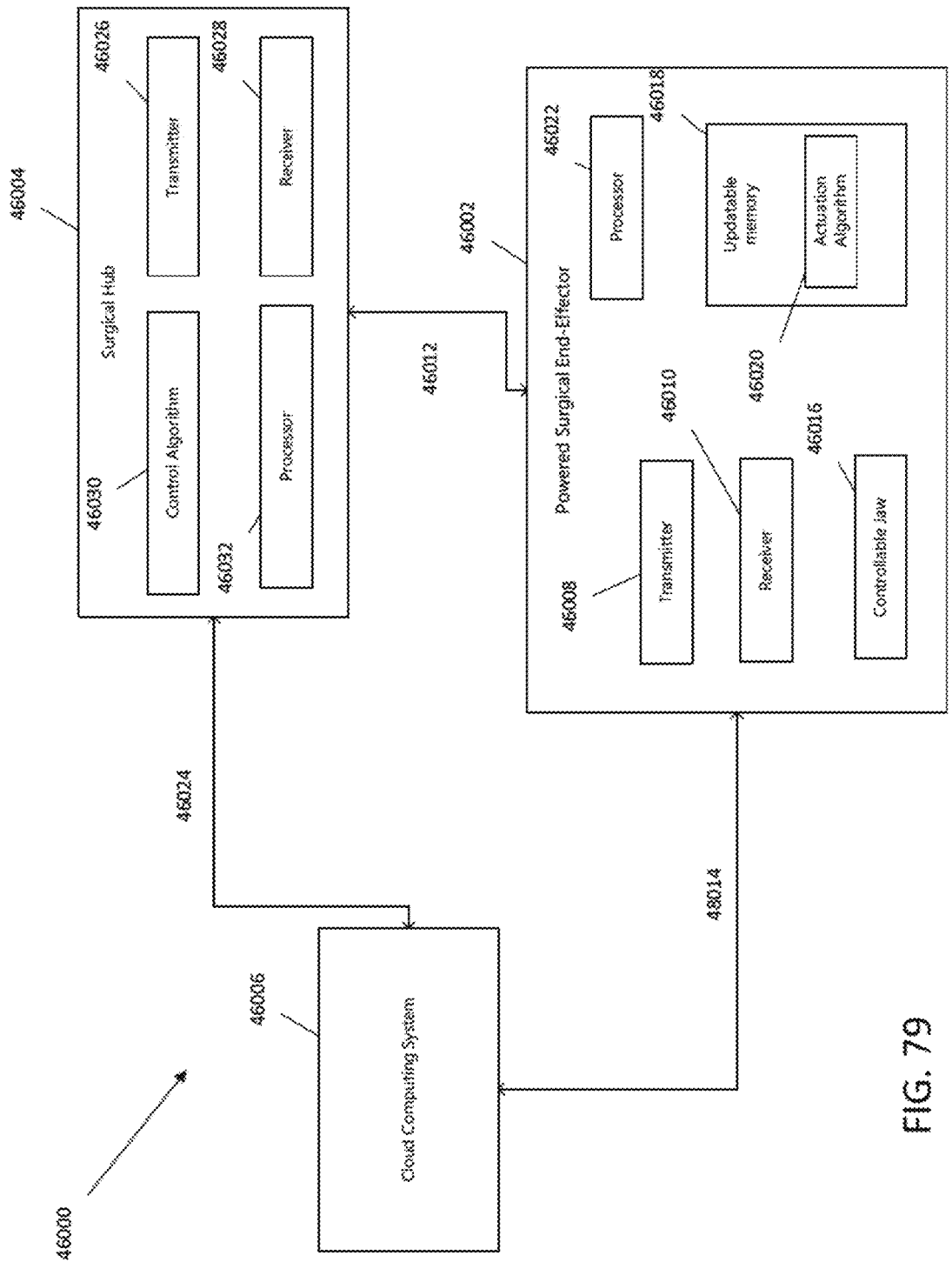
FIG. 79 illustrates a logic flow diagram of a process for updating the data analysis algorithm of a control program of a surgical hub, in accordance with at least one aspect of the present disclosure.

FIG. 79 illustrates a representative implementation of the process 9300 depicted in FIG. 77. FIG. 79 illustrates a logic flow diagram of a process 9400 for updating the data analysis algorithm of a control program of a surgical hub 9000, in accordance with at least one aspect of the present disclosure. As with the process 9300 depicted in FIG. 77, the process 9400 illustrated in FIG. 79 can, in one exemplification, be executed by the analytics system 9100. In one exemplification of the adaptive surgical system 9060 depicted in FIG. 76, the first surgical hub subpopulation 9312 is utilizing a first data analysis algorithm and the second surgical hub subpopulation 9314 is utilizing a second data analysis algorithm. For example, the first surgical hub subpopulation 9312 can be utilizing a normal continuous probability distribution to analyze a particular dataset, whereas the second surgical hub subpopulation 9314 can be utilizing a bimodal distribution for analyzing the particular dataset. In this exemplification, the analytics system 9100 receives 9402, 9404 the perioperative data from the first and second surgical hub subpopulations 9312, 9314 corresponding to the respective data analysis algorithms. The analytics system 9100 then analyzes 9406 the perioperative datasets to determine whether one of the perioperative datasets satisfies one or more update conditions. The update conditions can include, for example, a particular analysis method being utilized by a threshold percentage (e.g., 75%) of the surgical hubs 9000 in the overall population and a particular analysis method being correlated to positive surgical procedural outcomes in a threshold percentage (e.g., 50%) of cases.

In this exemplification, the analytics system 9100 determines 9408 whether one of the data analysis algorithms utilized by the first and second surgical hub subpopulations 9312, 9314 satisfies both of the update conditions. If the update conditions are not satisfied, then the process 9400 proceeds along the NO branch and the analytics system 9100 continues receiving 9402, 9404 and analyzing 9406 perioperative data from the first and second surgical hub subpopulations 9312, 9314. If the update conditions are satisfied, the process 9400 proceeds along the YES branch and the analytics system 9100 generates 9412 a control program update according to which of the data analysis algorithms the analysis 9406 determined satisfied the update conditions. In this exemplification, the control program update would include causing the surgical hub 9000 to utilize the data analysis algorithm that satisfied the update conditions when performing the corresponding analysis type. The analytics system 9100 then transmits 9414 the generated 9412 control program update to the population of surgical hubs 9000. In one exemplification, the control program update is transmitted 9414 to the entire population of surgical hubs 9000. In another exemplification, the control program update is transmitted 9414 to the subpopulation of surgical hubs 9000 that did not utilize the data analysis algorithm that satisfied the update conditions. In other words, if the analytics system 9100 analyzes 9406 the perioperative data and determines 9408 that the second (bimodal) data analysis method satisfies the update conditions, then the generated 9412 control program update is transmitted 9414 to the first subpopulation of surgical hubs 9000 in this exemplification. Furthermore, the control program update can either force the updated surgical hubs 9000 to utilize the second (bimodal) data analysis algorithm when analyzing the particular dataset or cause the updated surgical hubs 9000 to provide a warning or recommend to the user that the second (bimodal) data analysis algorithm be used under the given conditions (allowing the user to choose whether to follow the recommendation).

This technique improves the performance of the surgical hubs 9000 by updating their control programs generated from data aggregated across the entire network of surgical hubs 9000. In effect, each surgical hub 9000 can be adjusted according to shared or learned knowledge across the surgical hub 9000 network. This technique also allows the analytics system 9100 to determine when unexpected devices (e.g., modular devices 9050) are utilized during the course of a surgical procedure by providing the analytics system 9100 with knowledge of the devices being utilized in each type of surgical procedure across the entire surgical hub 9000 network.

Figure 80:
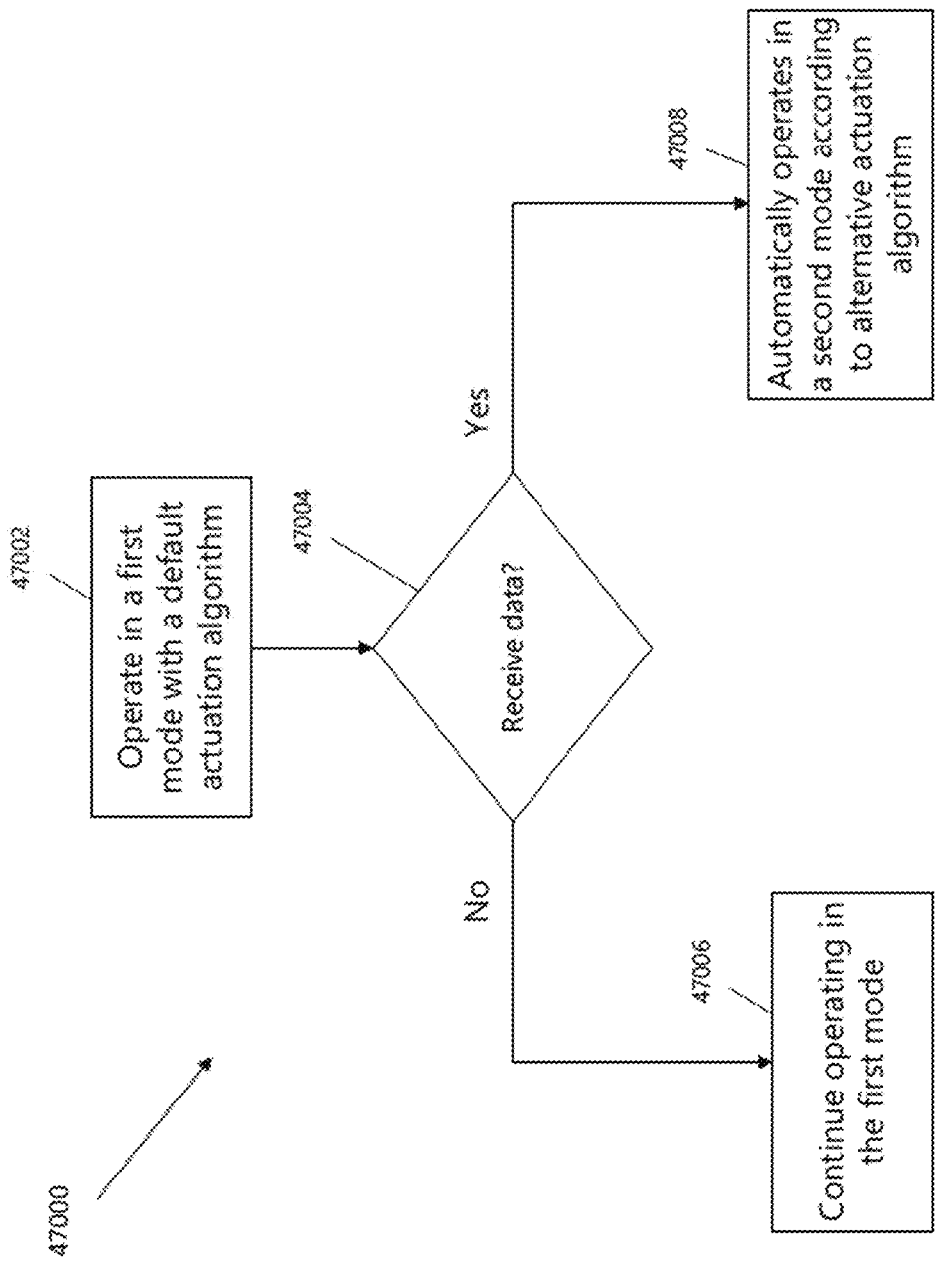
FIG. 80 illustrates a system for communication between a surgical instrument, a surgical hub, and a cloud computing system, in accordance with at least one aspect of the present disclosure.

FIG. 80 illustrates a system 46000 for communication between a powered surgical end-effector 46002, a surgical hub 46004, and a cloud computing system 46006, in accordance with at least one aspect of the present disclosure. The powered surgical end-effector 46002 may include a transmitter 46008 and a receiver 46010 that may be configured to establish communication pathways 46012 and 46014 between at least one external device. For example, the communication pathway 46012 may be between the powered surgical end-effector 46002 and the surgical hub 46004 and the communication pathway 46014 may be between the powered surgical end-effector 46002 and the cloud-computing system 46006. The powered-surgical end-effector 46002 may include a controllable jaw 46016 that may be configured to operate on a tissue. The controllable jaw 46016 may include a first jaw and a second jaw. The tissue to be operated on may be positioned between the first and second jaws and may be clamped by the first and second jaws closing together. The powered surgical end-effector 46002 may include an updatable memory 46018 that may have stored data including a default actuation algorithm 46020. The powered surgical end-effector 46002 may include a processor 46022 that may be configured to operate the default actuation algorithm 46020. The default actuation algorithm 46020 may be configured to operate an aspect of the controllable jaw 46016. The processor 46022 may update the default actuation algorithm 46020. The default actuation algorithm 46020 may perform a set of operations based on input data received about the controllable jaw 46016. The default actuation algorithm 46020 may transmit the input data into output signals. For example, the input data received about an aspect of the controllable jaw 46020 may relate to a clamp pressure, a hold time, and/or a fire speed of the controllable jaw 46020. For example, the input data received may relate to procedure information, properties of the tissue, and/or to supplementary measurements. For example, the supplementary measurements may be determined through situational awareness, as described above. For example, the supplementary measurements may also be determined by hospital inputs and/or by user inputs. The default control algorithm 46020 may include algorithms described above, such as the algorithm 23200 (FIG. 69), the closure algorithms (FIG. 71), and the data analysis algorithms (FIG. 79).

The surgical hub 46004 may include a transmitter 46026 and a receiver 46028. The transmitter 46026 and/or the receiver 46028 may be configured to establish the communication pathways between the surgical hub 46004 and at least one external device. For example, the communication pathway 46012 may be between the surgical hub 46004 and the surgical end-effector 46002. A communication pathway 46024 may be between the surgical hub 46004 and the cloud-computing system 46006. The surgical hub 46004 may include data that includes a control algorithm 46030. The surgical hub 46004 may include a processor 46032 that is configured to receive and interpret data.

Figure 78:
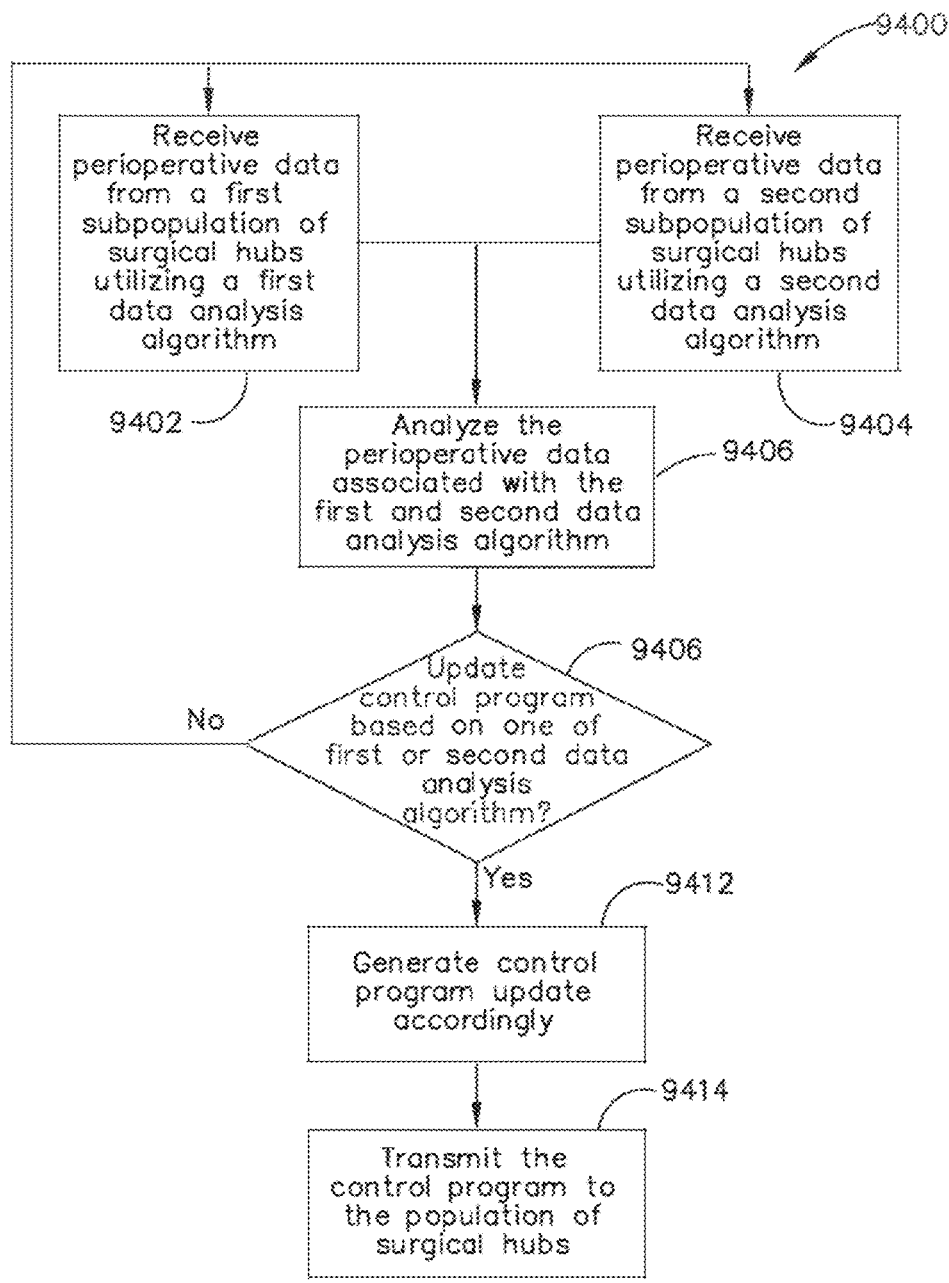
Figure 81:
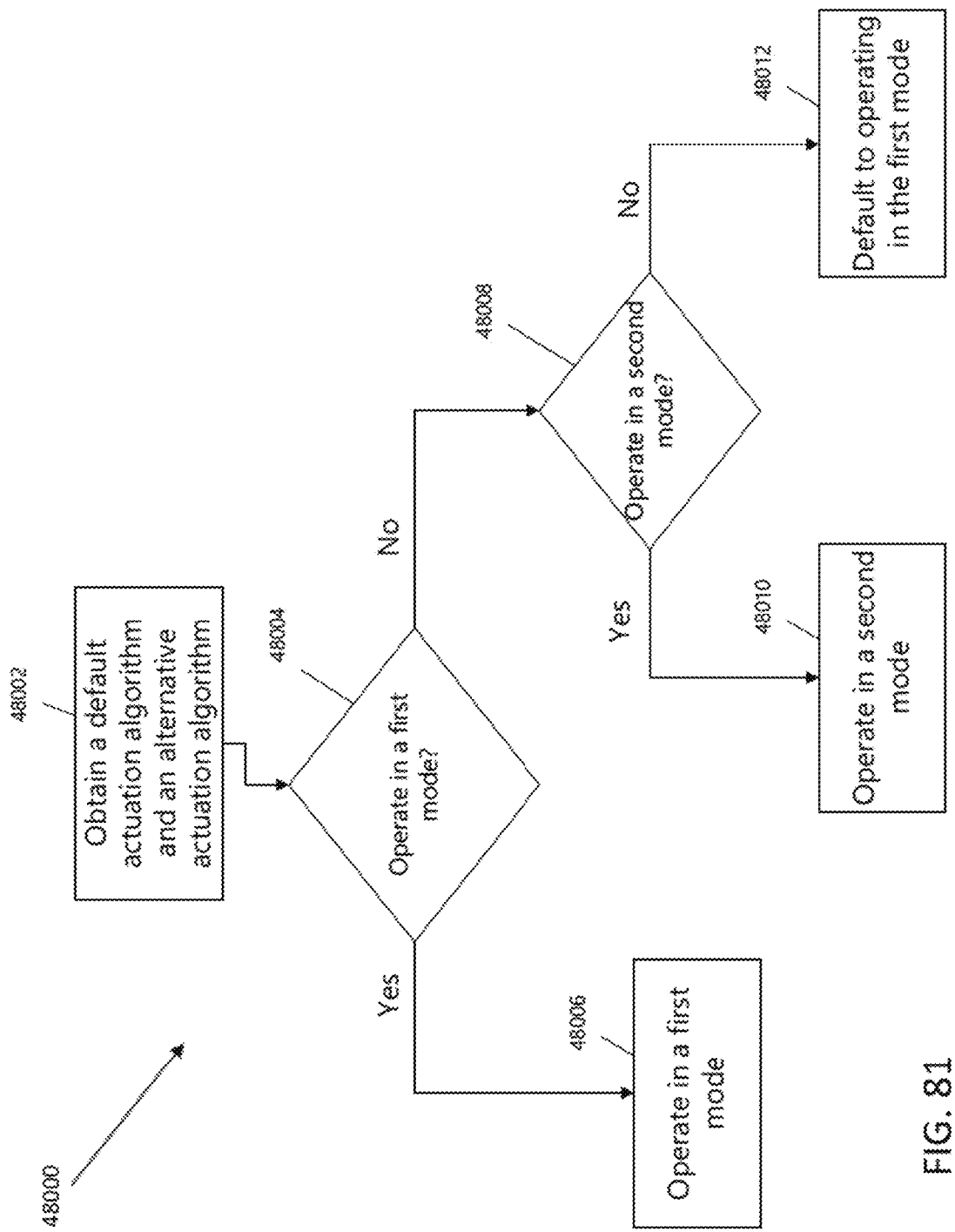
FIG. 81 illustrates another logic flow diagram of a process for updating an algorithm of a surgical instrument, in accordance with at least one aspect of the present disclosure.

FIG. 81 illustrates a logic flow diagram of a process 47000 for updating the algorithm of a surgical instrument, in accordance with at least one aspect of the present disclosure. At 47002, the process 47000 may configure the powered surgical end-effector 46002 to operate in a first mode and at a first time. The first mode may be configured to operate an aspect of the controllable jaw 46016 according to the default actuation algorithm 46020 stored in the updatable memory 46018 of the powered surgical end-effector 46002. At 47004, the process 47000 may determine whether the powered surgical end-effector 46002 receives data at a second time after the first time. If no, at 47006, the process 47000 may continue to operate in the first mode. If yes, at 47008, the received data may automatically cause the powered surgical end-effector 46002 to change from operating in a first mode to operating in a second mode. The received data may be received from an external source via the receiver 46010 of the powered surgical end-effector 46004. For example, external source can be the surgical hub 46004 and/or the cloud computing system 46006. The received data may relate to procedure information, properties of the tissue, and/or to supplementary measurements. For example, the supplementary measurements may be determined through situational awareness, as described above. For example, the supplementary measurements may also be determined by hospital inputs and/or by user inputs. The second mode may be configured to operate an aspect of the controllable jaw 46016 according to an alternative actuation algorithm. The aspect of the controllable jaw 46016 that may be updated may relate to clamp pressure, a hold time, and/or a fire speed of the aspect of the controllable jaw 46016, for example. The actuation algorithm may be updated from the default actuation algorithm 46020 to the alternative actuation algorithm using the process 9300 described above in FIGS. 77-78 for updating the control algorithm.

FIG. 81 illustrates a logic flow diagram of a process 48000 for updating the algorithm of a surgical instrument, in accordance with at least one aspect of the present disclosure. At 48002, the powered surgical end-effector 46002 is configured to obtain the default actuation algorithm 46020 and the alternative actuation algorithm. The default actuation algorithm 46020 may be correspond to data stored in the updatable memory 46018 of the powered surgical end-effector 46002. The default actuation algorithm 46020 may cause the powered surgical end-effector 46002 to operate an aspect of the controllable jaw 46016 according to a first mode. The default actuation algorithm 46020 and the alternative actuation algorithm may be obtained as described above in FIGS. 75-77. Some examples of the aspects of the controllable jaw 46016 may be a clamp pressure, a hold time, and/or a fire speed of the aspect of the controllable jaw 46016, for example. The alternative actuation algorithm may correspond to data received from an external source. For example, the external source may be the surgical hub 46004 and/or the cloud computing system 46006. The alternative actuation algorithm may cause the powered surgical end-effector 46002 to operate an aspect of the controllable jaw according to a second mode. At 48004, the powered surgical end-effector 46002 determines whether or not it should operate according to the first mode, which may act as a default mode. The determination may be based on procedure information, properties of the tissue, and/or to supplementary measurements. For example, the supplementary measurements may be determined through situational awareness, as described above. For example, the supplementary measurements may also be determined by hospital inputs and/or by user inputs. If yes at 48004, at 48006, the powered surgical end-effector 46002 may operate in the first mode. At 48008, the powered surgical end-effector 46002 determines whether or not it should operate according to the second mode, which may act as an alternative mode. The determination may be based on procedure information, properties of the tissue, and/or to supplementary measurements. For example, the supplementary measurements may be determined through situational awareness, as described above. For example, the supplementary measurements may also be determined by hospital inputs and/or by user inputs. If yes to 48008, at 48010, the powered surgical end-effector 46002 may change from operating in the first mode to operating in the second mode according to the alternative actuation algorithm. The actuation algorithm may be updated from the default actuation algorithm 46020 to the alternative actuation algorithm using the process 9300 described above in FIGS. 77-78 for updating the control algorithm. If no to 48008, at 48012, the powered surgical end-effector 46002 may continue operating in the first mode, which may the default mode.

Figure 82:
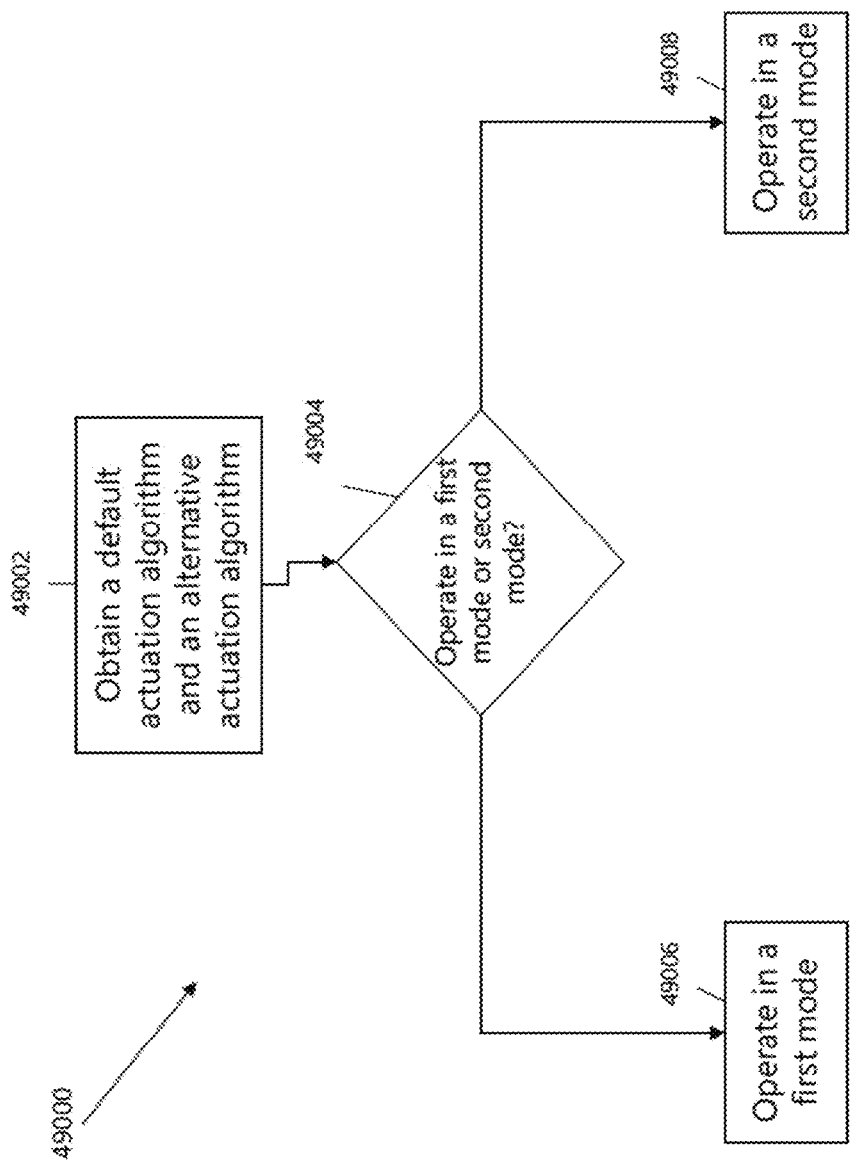
FIG. 82 illustrates another logic flow diagram of a process for updating an algorithm of a surgical instrument, in accordance with at least one aspect of the present disclosure.

FIG. 82 illustrates a logic flow diagram of a process 49000 for updating the algorithm of a surgical instrument, in accordance with at least one aspect of the present disclosure. At 49002, the powered surgical end-effector 46002 is configured to obtain a default actuation algorithm and an alternative actuation algorithm. The default actuation algorithm may be correspond to data stored in the updatable memory 46018 of the powered surgical end-effector 46002. The default actuation algorithm may cause the powered surgical end-effector 46002 to operate an aspect of the controllable jaw 46016 according to a first mode. Some examples of the aspects of the controllable jaw 46016 may be a clamp pressure, a hold time, and/or a fire speed of the aspect of the controllable jaw 46016, for example. The alternative actuation algorithm may correspond to data received from an external source. For example, the external source can be the surgical hub 46004 and/or the cloud computing system 46006. The alternative actuation algorithm may cause the powered surgical end-effector 46002 to operate an aspect of the controllable jaw 46016 according to a second mode. At 49004, the powered surgical end-effector 46002 determines whether it should operate in the first mode or operate in the second mode. The determination may be based on data received regarding procedure information, properties of the tissue, and/or to supplementary measurements. For example, the supplementary measurements may be determined through situational awareness, as described above. For example, the supplementary measurements may also be determined by hospital inputs and/or by user inputs. At 49006, the powered surgical end-effector 46002 may operate in the first mode if it determines it should operate in the first mode at 49004. At 49008, the powered surgical end-effector 46002 may operate in the second mode according to the alternative actuation algorithm if it determines it should operate in the second mode at 49004. The actuation algorithm may be updated from the default actuation algorithm 46020 to the alternative actuation algorithm using the process 9300 described above in FIGS. 77-78 for updating the control algorithm.

Figure 83:
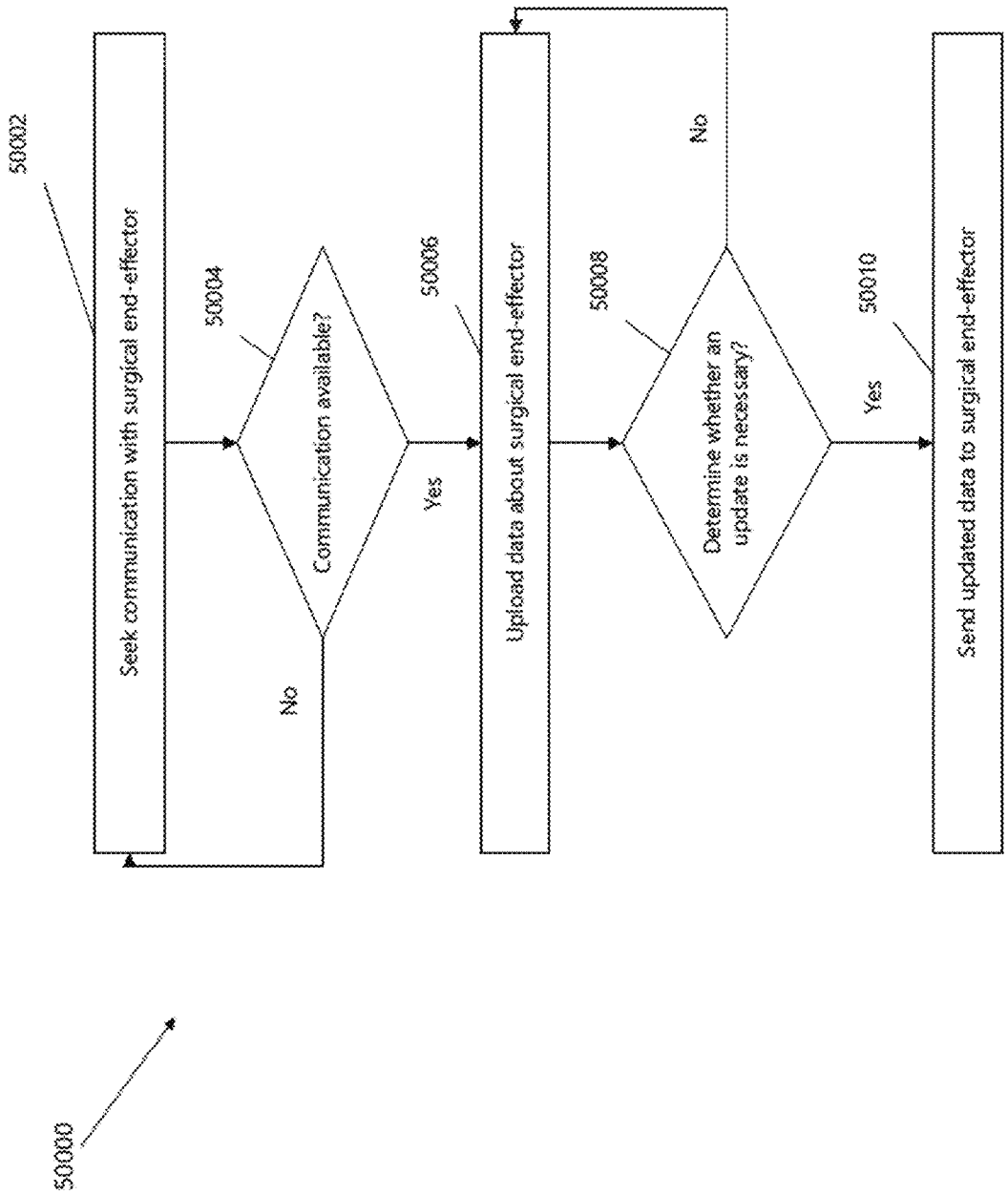
FIG. 83 illustrates a logic flow diagram of a process for a surgical hub updating an algorithm of a surgical instrument, in accordance with at least one aspect of the present disclosure.

FIG. 83 illustrates a logic flow diagram of a process 50000 for a surgical hub updating an algorithm of a surgical instrument, in accordance with at least one aspect of the present disclosure. At 50002, the surgical hub 46004 may seek communication with the powered surgical end-effector 46002. The surgical hub 46004 may seek communication by sending a communication request to the powered surgical end-effector 46002. At 50004, the surgical hub 46004 may determine whether communication is available with the powered surgical end-effector 46002 that may be configured to operate in a first mode or in a second mode. The determination whether communication is available may be determined by an available processing capacity, a memory, a bandwidth, a software revision, and/or a subscription level, for example. If communication is not available, the process 50000 may go back to 50002 and the surgical hub 46004 may seek communication with the powered surgical end-effector 46002. If communication is available, at 50006, the surgical hub 46004 may receive data from the powered surgical end-effector 46002 via the receiver 46028 and then upload the received data. At 50008, the surgical hub 46004 may determine whether the surgical end-effector 46002 should operate in the first mode or the second mode based on the received data. The determination may be based on received data. The received data may be based on procedure information, properties of the tissue, and/or to supplementary measurements. For example, the supplementary measurements may be determined through situational awareness, as described above. For example, the supplementary measurements may also be determined by hospital inputs and/or by user inputs. If the surgical hub 46004 determines it should operate in a first mode, the process 50000 may go back to 50006 and receive updated data from the powered surgical end-effector 46002 at the later time via the receiver 46028 and then upload the updated received data. If the surgical hub 46004 determines it should operate in a second mode, then at 50010, based on the determination, the surgical hub 46004 may send updated data that causes the powered surgical end-effector 46002 to operate in the second mode. In the second mode, the powered surgical end-effector 46002 may operate the aspect of the controllable jaw 46016 according to an alternative actuation algorithm. The actuation algorithm may be updated from the default actuation algorithm 46020 to the alternative actuation algorithm using the process 9300 described above in FIGS. 77-78 for updating the control algorithm.

In one aspect, the surgical hub 46004 can be connected to or paired with a variety of surgical devices, such as surgical instruments, generators, smoke evacuators, and/or displays. Through their connections to these surgical devices, the surgical hub 46004 may receive an array of perioperative data from these paired surgical devices while the devices are in use during a surgical procedure. The data can provide feed-back to the surgical staff members in real time during the surgical procedure. The real-time feedback can include a graphical notification and/or recommendation displayed on a display, audio feedback emitted by the surgical hub 46004 and/or the powered surgical end-effector 46002. The updated data may update algorithms of the powered surgical end-effector 46002 based on use in real time and adjust the algorithms with each action. For example, impedance within the powered surgical end-effector 46002 can indicate what the tissue properties are for specific patients, based on received information the powered surgical end-effector 46002 communicates to the surgical hub 46004. The surgical hub 46004 may then alert the powered surgical end-effector 46002 that an algorithm update is coming and update aspects of the controllable jaw 46016 in real time based on the tissue properties. Examples of aspects of the controllable jaw 46016 may be clamp pressure, hold time, and/or fire speed.

In another example, the surgical hub 46004 can provide postoperative feedback to the surgical staff members. The postoperative feedback can include graphical overlays or notifications displayed on the captured video of the procedure that can be reviewed by the surgical staff for learning purposes, a post-surgery report indicating times or/or particular surgical steps where the surgical staff deviated from the baselines. Any visually identifiable physical characteristic (or combination of physical characteristics) can be utilized as the basis for suggesting improvements in the technique exhibited by the surgical staff.

Disclosed herein are techniques for controlling the communication capabilities between a surgical instrument and a removable component. A surgical instrument may be configured to determine parameters associated with one or more of the surgical instruments and the removable component. The surgical instrument may process values of parameters associated with, for example, the owner or operator of the device, hardware comprised in the surgical instrument and/or component, software comprised in the surgical instrument and/or component, and/or a purchase or subscription level associated with the surgical instrument and/or component.

The surgical instrument may determine, based upon the considered parameters, a communication capability between the surgical instrument and the component. For example, a surgical instrument may determine the type and degree of communication between the surgical instrument and a component based on a parameter indicating a purchase or subscription level associated with the surgical instrument or attached component. If a surgical instrument, such as a surgical stapler, or a removable component, such as a surgical staple cartridge, attached to the surgical instrument is associated with a low subscription level, the surgical stapler may determine that the surgical instrument may provide one-way static communication from the surgical component to the surgical instrument. If the surgical instrument or component is associated with a higher subscription level, the surgical instrument may determine that the surgical instrument may provide real-time two-way communication between the surgical instrument and the component.

A surgical instrument may determine the communication capability between the surgical instrument and component based on parameters relating to the hardware and/or software comprised in the surgical instrument and/or component. If a component attached to a surgical instrument is configured with outdated software, the surgical instrument may determine that the communication capability with the component may comprise one-way static communication from the component to the surgical instrument. If the component attached to the surgical instrument is configured with recently updated software, the surgical instrument may determine that the communication capability with the component may comprise two-way real-time communication.

The surgical instrument may communicate with the removable component consistent with the determined communication capability. If the surgical instrument determined the communication capability comprised one-way communication with the removable component, the surgical instrument performs one-way communication with the component. If the surgical instrument determined the communication comprised real-time two-way communication with the removable component, the surgical instrument performs real-time two-way communication.

A surgical instrument may control communication capabilities between the surgical instrument and a removable component. The surgical instrument may determine parameters associated with the surgical instrument and the removable component. Based on the parameters, the surgical instrument determines a level or tier of communication between the surgical instrument and the removable component. The surgical instrument may determine to configure one or more of the following levels: one-way static communication with the component; two-way communication with the component; real-time two-way communication with the component; and communication with a surgical hub.

Figure 84:
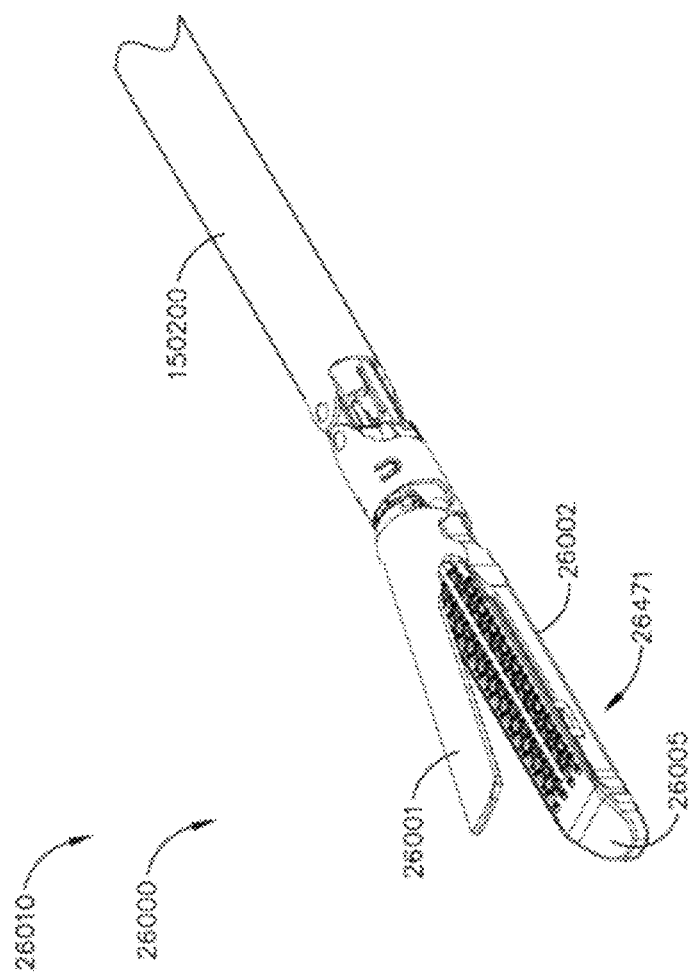
FIG. 84 illustrates an end effector of an example surgical instrument.
Figure 85:
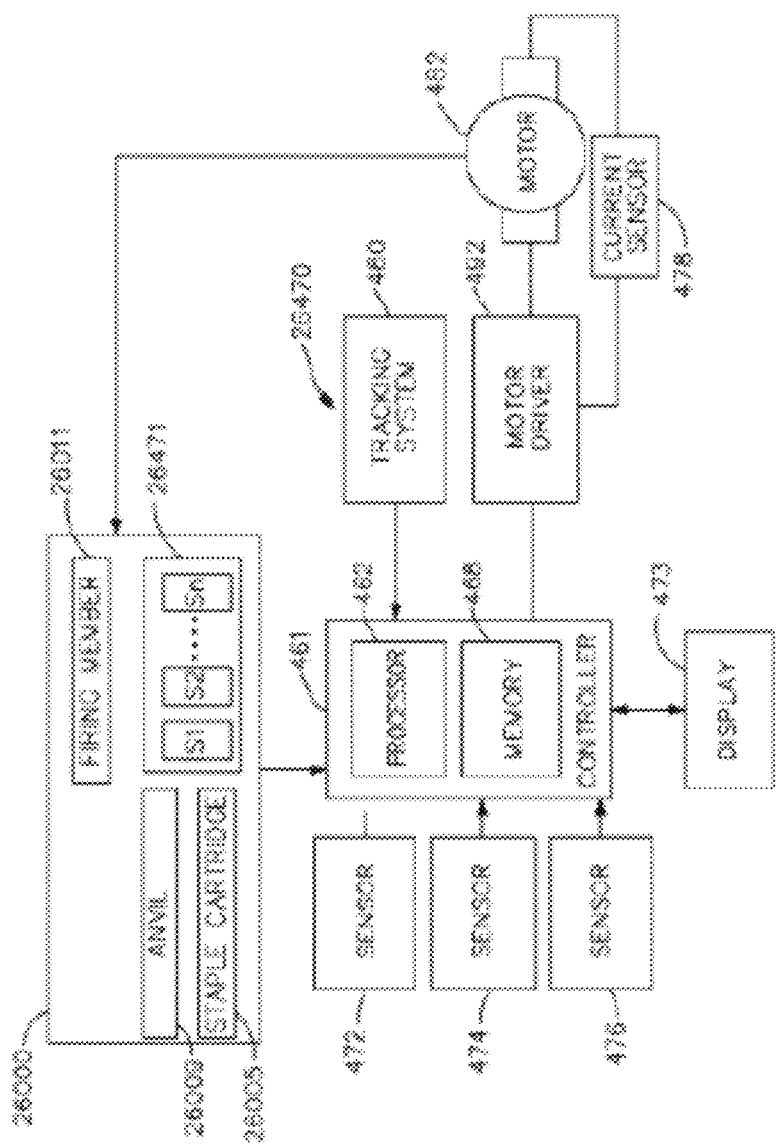
FIG. 85 illustrates a control system of an example surgical instrument.

The end effector 26000, as illustrated in FIGS. 84 and 85, includes a sensor array 26471 configured to generate or provide sensor signals indicative of a physiological parameter of the tissue that represents proximity of the end effector to cancerous tissue. FIG. 85 illustrates a control system 26470 including a control circuit coupled to the sensor array 26471. The control system 26470 is configured to assess proximity of the end effector 26000 to cancerous tissue based on the sensor signals of the sensor array 26471.

In one aspect, the physiological parameter is glucose level within the tissue. A low glucose level indicates a close proximity of the end effector to cancerous tissue.

Figure 86:
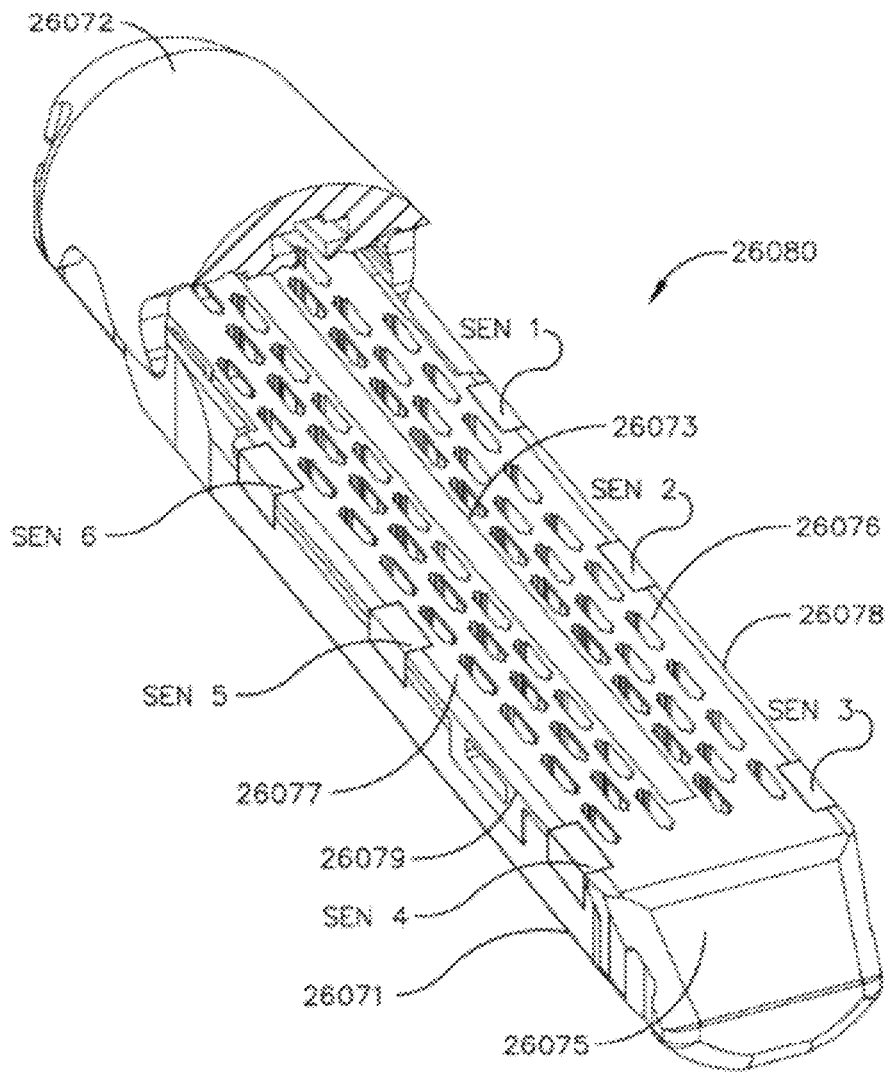
FIG. 86 illustrates a partial view of an end effector of an example surgical instrument.

In another aspect, the physiological parameter is a pH level. A low pH level indicates a close proximity of the end effector to cancerous tissue In various aspects, as illustrated in FIG. 86, an end effector 26070 may be equipped with a sensor array 26080 that includes six sensors ($Sen_1$-$Sen_6$): two proximal sensors ($Sen_1$ and $Sen_6$), two medial sensors ($Sen_2$ and $Sen_5$), and two distal sensors ($Sen_3$ and $Sen_4$). The added sensors allow the microcontroller 461, among other things, to more accurately predict the position of the end effector 26070 with respect to cancerous tissue.

The end effector 26070 is similar in many respects to the end effectors 26000, 26050. For example, the end effector 26070 includes a first jaw 26071 and a second jaw 26072. At least one of the first jaw 26071 and the second jaw 26072 is movable relative to the other to grasp tissue therebetween.

Further to the above, the end effector 26070 includes an anvil defined in the second jaw 26072 and a staple cartridge 26075 defined in the first jaw 26071. To treat tissue grasped by the end effector 26070, staples are deployed from the staple cartridge 26075 into the grasped tissue, and are deformed by the anvil. To cut the tissue, a transection member is moved relative to an elongated slot that defines a transection path 26073 for the transection member. The transection path 26073 defines two opposite sides 26076, 26077 of the end effector 26070.

Further to the above, the sensor array 26080 is similar in many respects to the sensor array 26471. For example, the sensor array 26080 can also be coupled to the microcontroller 461. The sensor array 26080 includes six sensors ($Sen_1$-$Sen_6$) configured to provide the microcontroller 461 with sensor signals according to a physiological parameter of the tissue that indicates proximity of the end effector 26070 to cancerous tissue. In other examples, the sensor array 26080, like the sensor array 26471, may include more or less than six sensors.

The sensors of the sensor array 26080 are spaced apart and arranged on outer edges 26078, 26079 of the staple cartridge 26075. In the example of FIG. 86, $Sen_1$, $Sen_2$, and $Sen_3$ are arranged on the side 26076 while $Sen_4$, $Sen_5$, and $Sen_6$ are arranged on the side 26077. In other words, the transection path 26052 extends between the sensors of the sensor array 26080.

In various examples, the differential between the sensor signals and the mean of the signals can give insight into tumor proximity. If a signal indicates a sensor is on a tumor, the differential between that sensor and the other sensors will give insight if the tumor is along one side (not transected) or across the transection path (transected). If the differential between the signals and mean is small but the mean is high, the entire end effector is on the tumor.

Cartridge Sensor Assemblies

Typical sensor assemblies utilized in surgical instruments are only able to passively detect tissue and physical environmental conditions, which can limit the amount, type, and detail of the data that they are able to detect. Aspects of the present disclosure present a solution, wherein the cartridges for use with the surgical instruments include active sensors that can be utilized to dynamically evaluate the tissue by stimulating or perturbing the tissue during the course of a surgical procedure and then detecting the corresponding response in the tissue. By applying a stimulus to the tissue through an active sensor incorporated with the cartridge, the surgical instrument can sense additional or different information than could have been detected using passive sensors.

Figure 87:
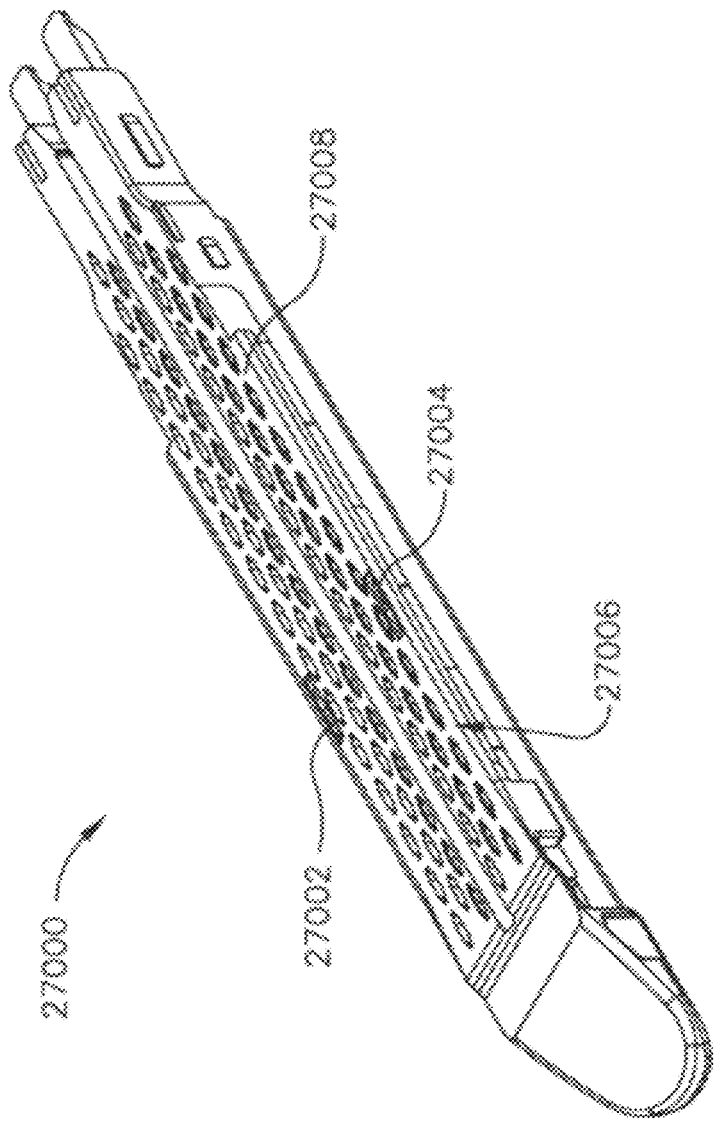
FIG. 87 illustrates a perspective view of an example staple cartridge including an active element and a sensor.

FIG. 87 illustrates a perspective view of a staple cartridge 27000 including an active sensor 27006, in accordance with at least one aspect of the present disclosure. The staple cartridge 27000 can be received within an end effector 150300 of a surgical instrument 150010, such as the surgical instrument 150010 described with respect to FIG. 49. In one aspect, the staple cartridge 27006 includes an active sensor 27006, which in turn includes an active element 27002 and a sensor 27004. The active sensor 27006 is configured to actively perturb or stimulate its environment, via the active element 27002, and then measure the corresponding environmental response, via the sensor 27004. The active sensor 27006 differs from passive sensors, which are configured to passively measure their environment.

The active element 27002 is configured to provide a stimulus to a tissue clamped by the end effector 150300 in which the staple cartridge 27000 is inserted (i.e., a tissue positioned or secured between the cartridge deck 27008 and the anvil 150306 of the end effector 150300). The sensor 27004 is configured to sense a tissue parameter associated with the perturbation or stimulus applied to the tissue and thereby determine the change in the tissue parameter resulting from the stimulus. In one aspect, the active element 27002 and the sensor 27004 are incorporated together or otherwise associated with each other to form an active sensor 27006 as single integral unit. In another aspect, the active element 27002 and the sensor 27004 are positioned separately from each other on or in the cartridge or otherwise disassociated with each other to form an active sensor 27006 as a distributed unit.

Figure 88:
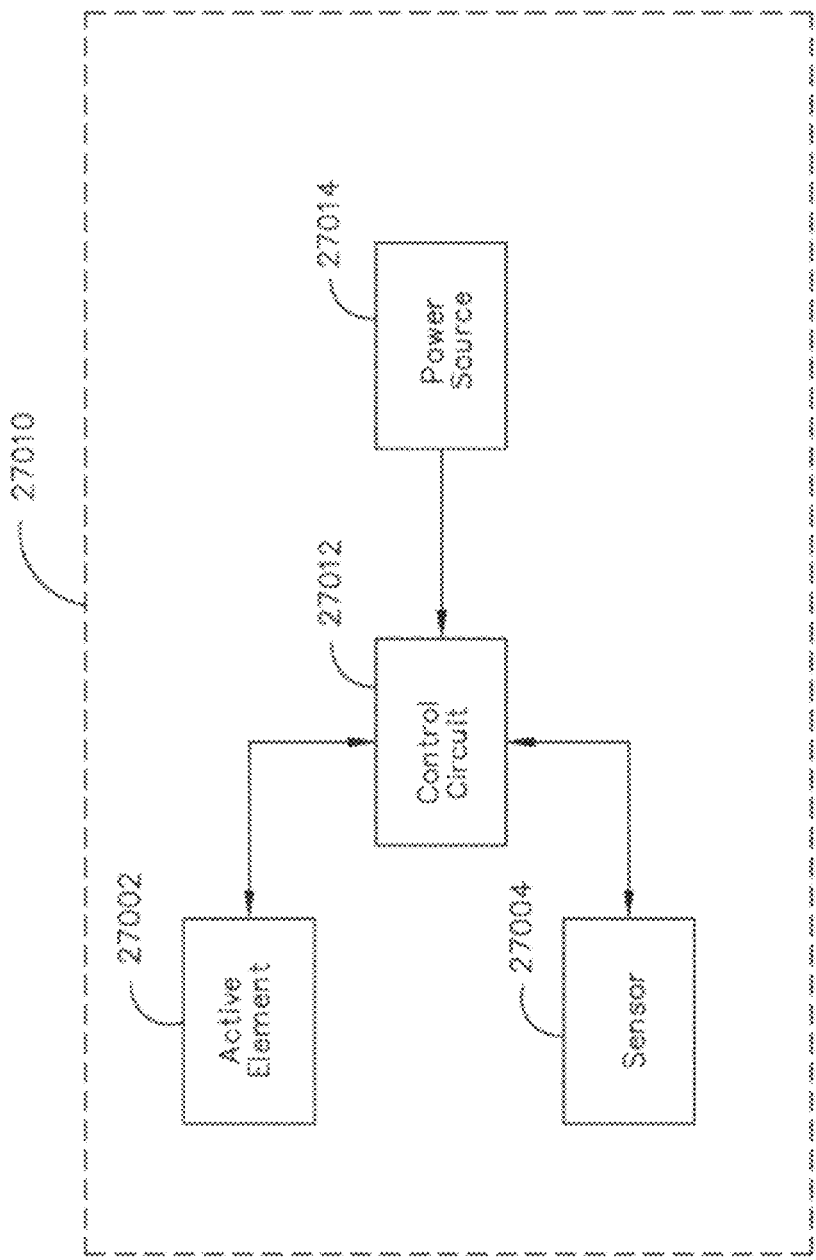
FIG. 88 illustrates a block diagram of an example active sensor assembly.

FIG. 88 illustrates a block diagram of a circuit 27010, in accordance with at least one aspect of the present disclosure. In one aspect, the cartridge 27000 includes a circuit 27010, which includes an active element 27002, a sensor 27004, a control circuit 27012 that is communicably connected to each of the active element 27002 and the sensor 27004, and a power source 27014 that is connected to the control circuit 27012 for supplying power thereto. The circuit 27010 and/or control circuit 27012 can include, for example, hardwired circuitry, programmable circuitry, state machine circuitry, firmware that stores instructions executed by programmable circuitry, and any combination thereof. In one aspect, the control circuit 27012 can be configured to activate the active element 27002, cause the active element 27002 to discharge or supply the stimulus to a tissue clamped by the end effector, or otherwise control the state of the active element 27002. The control circuit 27014 can be configured to activate the sensor 27004, receive data or an electrical signal indicative of a tissue property from the sensor 27004, or otherwise control the sensor 27004. In various aspects, either or both of the active element 27002 and the sensor 27004 can be exposed or positioned on the deck 27008 of the cartridge 27000 to contact a tissue positioned against the cartridge deck 27008, such as is illustrated in FIG. 87. In one aspect, the circuit 27010 illustrated in FIG. 88 can be embodied as a flex circuit. In one aspect, the circuit 27010 is a separate circuit from a cartridge circuit and/or a channel circuit, such as the cartridge circuit and channel circuit disclosed in U.S. patent application Ser. No. 15/636,096, filed Jun. 28, 2017, titled SURGICAL SYSTEM COUPLABLE WITH STAPLE CARTRIDGE AND RADIO FREQUENCY CARTRIDGE, AND METHOD OF USING SAME, which is hereby incorporated by reference herein in its entirety. In such aspects, the circuit 27010 may or may not be communicably coupled to the cartridge circuit and/or channel circuit. In another aspect, the circuit 27010 is integrated into the cartridge circuit and/or channel circuit.

In one aspect, the active element 27002 comprises a heating element and the sensor 27004 comprises a temperature sensor (e.g., a temperature measuring array). In this aspect, the active element 27002 is configured to provide a stimulus (perturbation) in the form of heat or thermal energy to a tissue grasped by the end effector 150300 and/or positioned against the cartridge deck 27008. Further, the sensor 27004 is configured to sense the physiologic response of the tissue to which the thermal energy from the active element 27002 is applied. The control circuit 27012 can thus be configured to evaluate the physiologic response of the tissue via data and/or signals received from the sensor 27004.

In one aspect, the active element 27002 is configured to apply thermal energy to a predetermined or localized area of a tissue grasped by the end effector 150300 and/or positioned against the cartridge deck 27008. For example, the heating element can comprise a heat sink (e.g., constructed from aluminum and/or copper) that is configured to convert electrical energy (e.g., from the power source 27014) into heat to apply thermal energy to a predetermined or localized area of a tissue adjacent or localized to the heat sink. In another aspect, the active element 27002 is configured to apply thermal energy across the entirety of or a larger portion of the surface of the cartridge deck 27008. For example, the heating element can comprise a flexible heating grid built into one or more of the layers of the cartridge circuit. In such aspects, the heating grid can be configured to enable the entirety or a large portion of the cartridge 27000 to emit thermal energy. Alternatively or additionally, the heating grid can be configured such that various regions of the heating grid can be activated to produce thermal energy. In this example, the heating grid can likewise be utilized to apply thermal energy at localized or predefined heating areas with a specified amount of thermal energy output to apply to a tissue.

Applying thermal energy to a tissue can be utilized to derive a variety of physiological information regarding the tissue. For example, the rate at which the temperature of a tissue rises is a function of its water content. Accordingly, applying thermal energy to a tissue can be utilized to determine the overall water content of the tissue by sensing the rate at which the temperature of the tissue increases in response to applied thermal energy. The water content of a tissue in turn corresponds to, for example, the tissue type. Further, applying thermal energy to different portions of a tissue can be utilized to determine the location(s) of high or low water content tissue by comparing the rates at which the temperatures of the different portions of the tissue increase in response to applied thermal energy.

In one aspect, the active element 27002 comprises a pressure-applying element and the sensor 27004 comprises a tissue compression sensor. The pressure-applying element can include, for example, a magnetic or electroactive polymer that, when energized, is configured to deform in shape and thereby apply a local pressure to a specific area of tissue situated thereagainst. The pressure-applying element can be disposed on, for example, the cartridge deck 27008 such that the pressure-applying element contacts and applies pressure to a tissue situated thereagainst. The tissue compression sensor can include, for example, an impedance sensor configured to measure an impedance of the tissue. As the impedance of the tissue can correspond to the thickness of the tissue (i.e., tissue compression), monitoring the time rate change of the tissue impedance can be utilized to monitor the change in the viscoelastic properties of the tissue over time in response to the pressure stimulus. Such viscoelastic properties of the tissue can include, for example, tissue creep and stability. The tissue compression sensor can also include, for example, a force sensor (e.g., a load cell or force-sensitive resistor) configured to sense a force or pressure exerted on the tissue or a gap sensor (e.g., a Hall effect sensor) configured to sense the gap or distance between the jaws (e.g., the anvil 150306 and/or channel 150302 of the surgical instrument 150010 depicted in FIG. 49) of the end effector 150300, which in turn corresponds to the degree to which a tissue grasped by the end effector 150300 is being compressed.

The magnetic or electroactive polymers can be configured to deform in a predetermined manner according to the manner in which they are manufactured. In one aspect, the control circuit 27012 can be configured to receive measurements from the sensor 27004 regarding the tissue compression while the added pressure is applied to determine accelerated creep aspects of the tissue. In one aspect, the control circuit 27012 can be configured to receive measurements from the sensor 27004 regarding the tissue pressure after the added pressure is relieved to evaluate the tissue recovery characteristics of the tissue.

Applying pressure to a tissue can be utilized to derive a variety of physiological information regarding the tissue. For example, the viscoelastic properties exhibited by a tissue correspond to its tissue type. In other words, different types of tissue each exhibit consistent viscoelastic properties. Accordingly, applying a pressure to a tissue can be utilized to determine the viscoelastic properties of a tissue by sensing the rate at which the tissue compresses, the rate at which the tissue returns to its prior shape when the pressure is removed, and other viscoelastic properties. Additional details regarding monitoring the viscoelastic properties of tissue can be found in U.S. Patent Publication No. 2016/0256156, filed Sep. 14, 2015, titled TIME DEPENDENT EVALUATION OF SENSOR DATA TO DETERMINE STABILITY, CREEP, AND VISCOELASTIC ELEMENTS OF MEASURES, which is hereby incorporated by reference herein in its entirety.

Surgical instrument cartridges may have multiple and/or duplicative means for storing or relaying data (i.e., data elements) associated with the cartridge. The data associated with the cartridge can include, for example, the cartridge type, characteristics of the cartridge, and whether the cartridge has been fired previously. Data redundancy is beneficial in avoiding total data loss if there is an error with one of the data elements or one of the data elements is destroyed. However, if one of the data elements incorrectly stores data, fails to store data, or has an error in transmitting the data, then an unresolvable conflict between the data elements may be created. When the surgical instrument or another system attempts to retrieve the data from the cartridge, the data conflict may cause errors in the surgical instrument or other system retrieving the data. Aspects of the present disclosure present a solution, wherein the surgical instruments are configured to resolve conflicts between data storage elements by prioritizing one of the data elements over the other data elements. In that way, the prioritized data element will supersede the other data elements, avoiding conflicts in attempting to select the proper cartridge data for use by the control circuit of the surgical instrument or another system.

Figure 89:
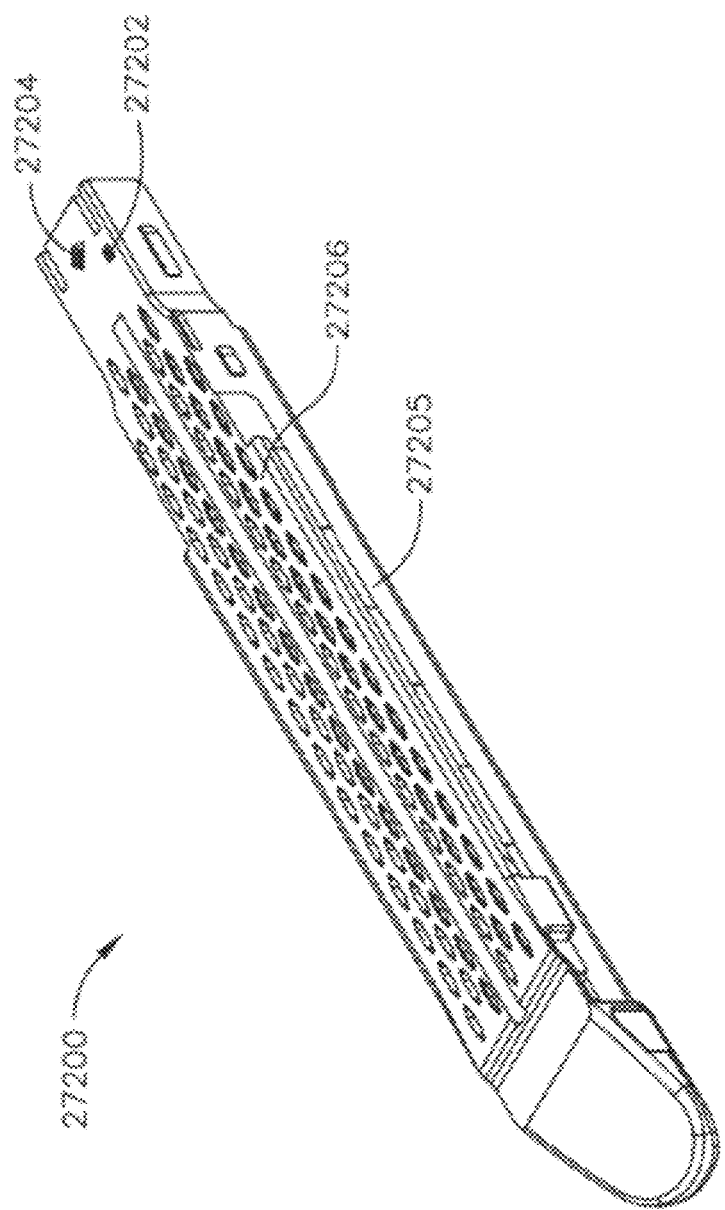
FIG. 89 illustrates a perspective view of an example cartridge including a pair of data elements.

FIG. 89 illustrates a perspective view of a cartridge 27200 including a pair of data elements, in accordance with at least one aspect of the present disclosure. In one aspect, the data elements include features, characteristics, and/or devices that are associated with the cartridge 27200 and are capable of storing, representing, and/or relaying data associated with the cartridge. The data elements can include, for example, a data storage element 27202 that is configured to store data related to the cartridge and a data-representative feature 27204 that is configured to represent data related to the cartridge. In some aspects, the data elements can be broadly characterized as automatic identification and data capture (AIDC) technologies. Although the cartridge depicted in FIG. 89 includes two data elements, in alternative aspects the cartridge can include one or more than two data elements in various combinations of data storage elements and data-representative features of the cartridge. Further, it should be noted that although the cartridge 27200 is depicted as a staple cartridge, the cartridge 27200 also includes RF cartridges and any other such cartridges.

In various aspects, the data-representative feature 27204 can include, for example, a physically or visually identifiable feature or structure that is associated with or disposed on the cartridge 27200. In one such aspect, the data-representative feature 27204 can include the material that the cartridge body 27205 is constructed from and/or the thickness of the cartridge body 27205. The cartridge body 27205 material and/or thickness can be different for the various cartridge types in order to create keyed resistance ranges for each cartridge type, which can then be detected by a sensor 27224 (FIG. 90) associated with the end effector 150300 of the surgical instrument 150302. The sensor 27224 for detecting the cartridge body 27205 material and/or thickness can be disposed in the channel 150302 of the end effector 150300 for example. In such aspects, the end effector 150300 could be electrically insulated.

In another such aspect, the data-representative feature 27204 can include a layer of material or a structure disposed on the cartridge deck 27206 (e.g., at the proximal end of cartridge deck 27206) that is configured to influence the initial phase of clamping force. For example, in FIG. 89 the data-representative feature 27204 includes a structure that extends generally orthogonally from the proximal end of the cartridge deck 27206 such that the anvil 150306 of the end effector 150300 would contact the structure as the anvil 150306 is clamped shut. The force as the anvil 150306 contacts the data-representative feature 27204 can then be detected by a control circuit 27222 (FIG. 90) via, e.g., a current sensor detecting the motor current (which corresponds to the force exerted by the anvil 150306 as the anvil 150306 is driven closed by a motor). The material and/or geometry of the data-representative feature(s) 27204 disposed on the cartridge deck 27206 can be customized for each of the various cartridge types to yield different detectable responses in the force to close (FTC) the anvil 150306. A control circuit 27222 coupled to a sensor capable of detecting the data-representative feature 27204 can thus determine the cartridge type according to the degree or level of the maximum FTC, the characteristics of the FTC response, and other such characteristics of the FTC detected over time. For example, a first cartridge type can include a data-representative feature 27204 that is constructed from a stiff material and a second cartridge type can include a data-representative feature 27204 that is constructed from a flexible material. According to the type of FTC response detected by the control circuit 27222, the control circuit 27222 can thus determine whether the anvil 150306 is making contact with a stiff or flexible structure as the anvil 150306 is closed and thereby determine whether the cartridge 27200 is the first cartridge type or the second cartridge type, respectively.

In various aspects, the data storage element 27202 can, for example, be associated with or disposed on the cartridge 27200 and be configured to transmit data stored by the data storage element 27202 via a wired or wireless connection. In one aspect, the data storage element 27202 comprises a RFID micro-transponder or RFID chip including a digital signature. In another such aspect, the data storage elements comprise a battery-assisted passive RFID tag. A battery-assisted passive RFD tag can exhibit improved range and signal length as compared to RFID micro-transponders and/or RFID chips. In this aspect, the RFID tag can include a writable section that could be used to store data associated with the cartridge 27200, such as whether the cartridge 27200 has been fired. Data can be written to the writable section of the cartridge 27200 via a circuit, such as a control circuit of the cartridge 27200 or the surgical instrument. The writable section could then be read subsequently by a sensor of the surgical instrument so that the surgical instrument can determine, for example, that the cartridge 27200 should not be re-fired.

In aspects wherein the data storage element 27202 includes an RFID tag utilizing ultra high-frequencies and higher frequencies, the RFID tag may be more than one radio wavelength away from the reader (sensor) of the surgical instrument. Therefore, simply transmitting the RF signal may not be sufficient to communicate the data from the RFID tag. In these aspects, the RFID tag can be configured to backscatter a signal. The active RFID tags may contain transmitters and receivers that are functionally separated and the RFID tags need not respond on a frequency related to the reader's interrogation signal.

In another aspect, the data storage element 27202 can include a one-wire chip configured to store identification data. The data storage element 27202 can be configured to transmit or provide the stored identification data to the surgical instrument, either upon the cartridge 27200 being inserted in the end effector or in response to receiving a query from the surgical instrument. In such aspects, the one-wire chip can include a writable section that could be used to store data associated with the cartridge 27200, such as whether the cartridge 27200 has been fired. In another such aspect, the data storage elements comprise an integrated circuit (IC) executing a particular communication protocol, such as an I-squared-C (i.e., I-two-C), SPI, or other multi-master, multi-slave, packet-switched, single-ended, serial computer bus. Various additional details regarding wired electrical connections between the cartridge 27200 and the surgical instrument can be found in U.S. patent application Ser. No. 15/636,096, filed Jun. 28, 2017, titled SURGICAL SYSTEM COUPLABLE WITH STAPLE CARTRIDGE AND RADIO FREQUENCY CARTRIDGE, AND METHOD OF USING SAME, which is hereby incorporated by reference herein in its entirety.

Although FIG. 89 depicts a cartridge 27200 including a single data-representative feature 27204 and a single data storage element 27202, it should be noted that different aspects of the cartridge 27200 can include various combinations of the aforementioned data elements. In other words, various aspects of the cartridge 27200 can include combinations of multiple data-representative features 27204, multiple data storage elements 27202, different types of data storage elements 27202 and/or data-representative features 27204, and so on.

The data storage element 27202 can store or represent a variety of data pertaining to the cartridge 27200, including, for example, data identifying the cartridge type and data identifying characteristics of the cartridge (e.g., the cartridge size). In one aspect, the data storage element 27202 can be configured to store an Electronic Product Code (EPC). In aspects wherein the data storage element is an RFID tag, the EPC can be written into the tag by an RFID printer and can contain, for example, a 96-bit string of data. The string of data can include, for example, a header (e.g., of eight bits) identifying the version of the protocol; an organization number (e.g., of 28 bits) that identifies the organization that manages the data for this tag (which can be assigned by the EPC Global consortium); an object class (e.g., of 24 bits) identifying the kind of product; and a unique serial number (e.g., of 36 bits) for a particular tag. The object class and unique serial number fields can be set by the organization that issued the tag. Similarly to a URL, the EPC number can be used as a key into a global database to uniquely identify a particular product.

Figure 90:
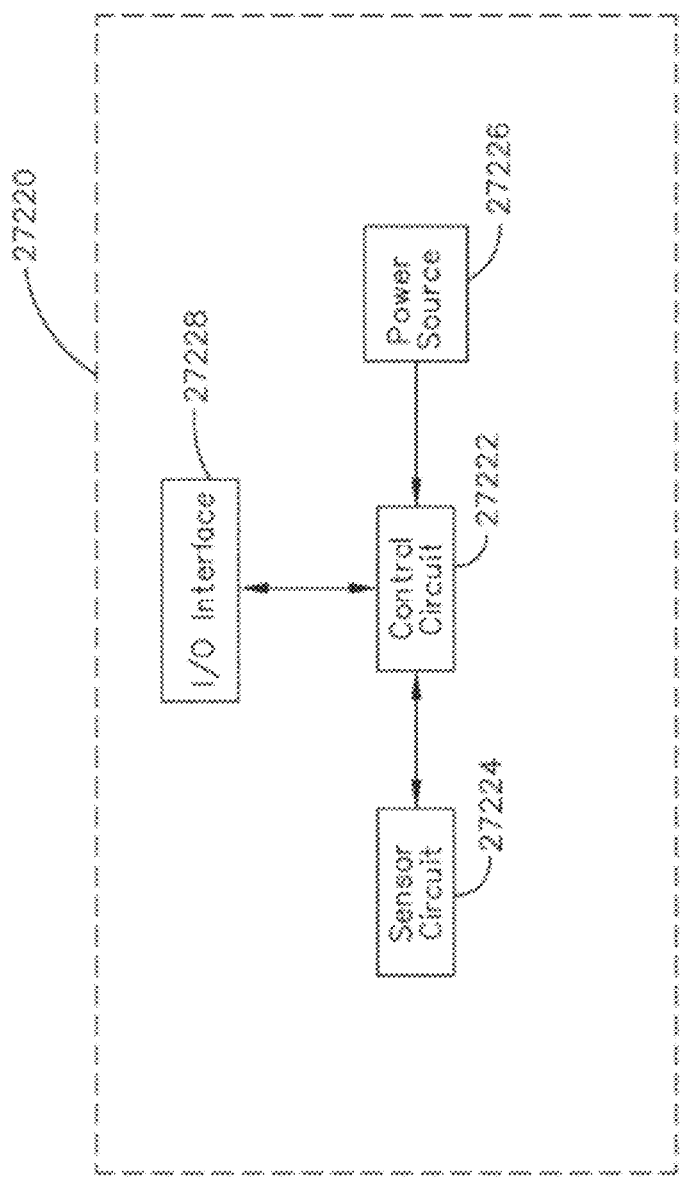
FIG. 90 illustrates a block diagram of an example sensor assembly for detecting and/or receiving data from data elements associated with a cartridge.

FIG. 90 illustrates a block diagram of a sensor assembly 27220 for detecting and/or receiving data from data elements associated with a cartridge 27200, in accordance with at least one aspect of the present disclosure. In the following description of the sensor assembly 27220, reference should also be made to FIG. 89. The sensor assembly 27220 can be included in or communicably coupled with a surgical instrument that is configured to receive a cartridge 27200. In one aspect, the sensor assembly 27220 includes a control circuit 27222 communicably connected to a sensor 27224 configured to detect a data-representative feature 27204 representing cartridge data and an I/O interface 27228 that is configured to receive data from a data storage element 27202 storing cartridge data. In one aspect, the sensor assembly 27220 be a component of or integrated with a circuit disposed in the channel 150302 (FIG. 49) of the end effector 150300, such as the channel circuit disclosed in U.S. patent application Ser. No. 15/636,096. In another aspect, the sensor assembly 27220 be a distinct or separate from the channel circuit, such as the channel circuit disclosed in U.S. patent application Ser. No. 15/636,096. The control circuit 27222 is further connected to a power source to draw power therefrom. The sensor 27224 can include any type of sensor that is able to identify a particular physical or visual feature identifying the cartridge 27200. In one aspect, the sensor 27224 can include a current sensor that is configured to detect the current drawn by a motor during at least the initial or clamping portion of the firing member stroke, thereby allowing the control circuit 27222 to determine the FTC and thereby determine whether the anvil 150306 of the end effector 150300 is encountering a physical feature disposed on the cartridge 27200 identifying the cartridge type, as described above. In another aspect, the sensor 27224 can include an optical sensor configured to detect an icon, color, bar code, or other marking or series of markings disposed on the cartridge 27200 that identify the cartridge type. In one aspect, the I/O interface 27228 can include bus wires (e.g., cartridge and channel electrical contacts disclosed in U.S. patent application Ser. No. 15/636,096) configured to electrically connect to a data storage element 27202 storing data to receive the data stored thereon utilizing a wired communication protocol (e.g., I-squared-C). In another aspect, the I/O interface 27228 can include a wireless transmitter configured to wirelessly connect to a data storage element 27202 storing data to receive the data stored thereon utilizing a wireless communication protocol (e.g., Bluetooth).

Other aspects of the sensor assembly 27220 can include various combinations of sensors 27224 configured to detect data-representative features 27204 and I/O interfaces 27228 configured to receive data from data storage elements 27202 associated with a cartridge 2700, including multiple sensors 27224 (of the same or different types), multiple I/O interfaces 27228 (of the same or different types), no I/O interfaces 27228, no sensors 27224, and all combinations thereof. The particular combination of sensors 27224 and/or I/O interfaces 27228 included in the sensor assembly 27220 to detect data associated with the cartridge 27200 corresponds to the combination of data elements utilized by the cartridge 27200 to store cartridge data.

A surgical instrument may be adapted to communicate with components that interface with the surgical instrument. For example, a surgical instrument, which may be a surgical stapler, may be configured to communicate with a surgical staple cartridge that is removably attached to the surgical stapler. A surgical instrument may be configured to control the communication capability or capacity between the surgical instrument and the components attached to it. The surgical instrument may provide different levels or tiers of communication between the surgical instrument and the components. For example, a surgical stapler may configure communication with an attached surgical staple cartridge to allow for one or more of the following communication tiers: one-way static communication with the surgical staple cartridge; two-way communication with the surgical staple cartridge; real-time two-way communication with the surgical staple cartridge; and communication with a surgical hub or other computing system.

A surgical instrument may be configured to determine the communication capability including a type or degree of communication to provide depending upon parameters or data associated with the instrument, the component attached to the device, the operator of the device, the owner of the device, or other relevant element. For example, a surgical instrument may determine the type and degree of communication between the surgical instrument and a component based on a parameter indicating a purchase or subscription level associated with the surgical instrument or attached component. If a surgical stapler or a surgical staple cartridge attached to the surgical stapler is associated with a low purchase or subscription level, the surgical stapler may determine that the surgical stapler may provide one-way static communication from the surgical staple cartridge to the surgical stapler. If the surgical stapler or surgical staple cartridge is associated with a higher purchase or subscription level, the surgical stapler may determine that the surgical stapler may provide real-time two-way communication between the surgical stapler and the surgical staple cartridge.

A surgical instrument may determine the communication capability between the surgical instrument and component based on parameters of the surgical instrument and/or component. If a surgical staple cartridge attached to a surgical stapler is configured with relatively outdated software, the surgical stapler may determine that the communication capability with the surgical staple cartridge may comprise one-way communication of static data from the surgical staple cartridge to the surgical stapler. If the surgical staple cartridge attached to the surgical stapler is configured with relatively recent software, the surgical stapler may determine that the communication capability with the surgical stapler cartridge may comprise two-way real-time communication.

Figures 91A, 91B:
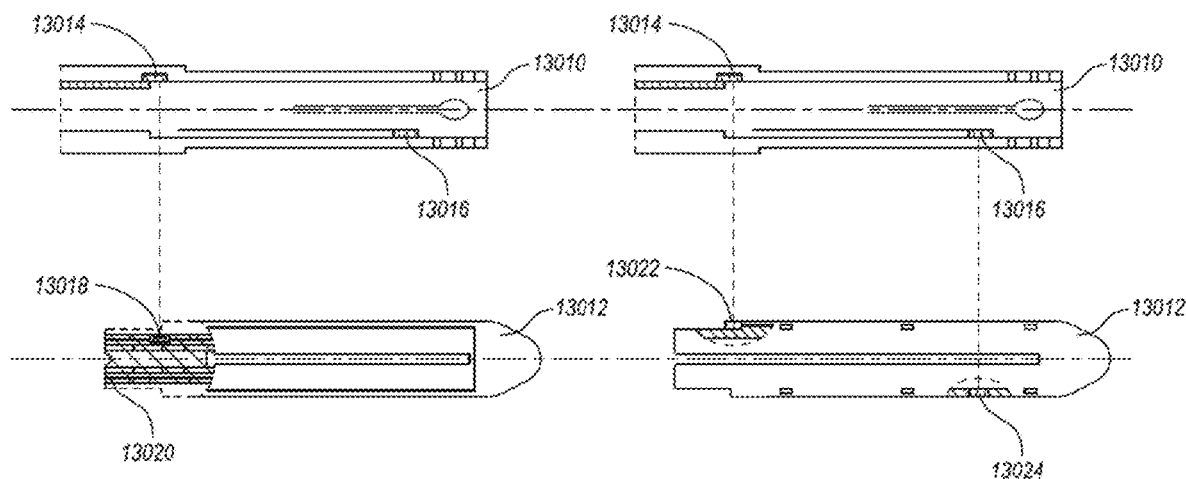
FIG. 91A illustrates an example surgical staple cartridge.
FIG. 91B illustrates an example surgical staple cartridge.

Communication between a surgical instrument and a component engaged with the surgical instrument may be performed using, for example, sensing arrays and communication devices. A surgical instrument and the corresponding component may comprise sensing arrays and communications devices that are positioned so as to communicatively couple the component and surgical instrument. FIG. 91A depicts an example coupling between a surgical stapler's elongated channel 13010 and a surgical staple cartridge 13012 that is coupled with the surgical stapler. As shown, the elongated channel 13010 may comprise a first sensing array 13014 positioned along a first side of the channel and at a proximal end of the elongated channel 13010. The elongated channel 13010 may further comprise a second sensing array 13016 longitudinally displaced from the first sensing array 13014 and positioned along an opposite side of the elongated channel 13010 and proximate a distal end of the elongated channel 13010. The sensing arrays 13014 and 13016 may be configured to sense data communicated by corresponding communication devices comprised in the surgical staple cartridge 13012. The sensing arrays 13014 and 13016 may be further configured to communicate data and power to corresponding communication devices in the surgical staple cartridge 13012.

The surgical staple cartridge 13012 may comprise one or more communication devices such as, for example, a Radio Frequency Identification chip (RFID) 13018. The RFID chip 13018 may be positioned in a sled 13020 comprised in the surgical staple cartridge 13012. In the example depicted in FIG. 91A, the RFID chip 13018 may be located in an initial home position and may align with the first sensing array 13014 comprised in the elongated channel 13010 of the surgical stapler. In an example, the RFID chip may be configured to communicate data identifying the surgical stapler cartridge 13012 along with data identifying a status of the cartridge. In the example of FIG. 91A, the second communication array 13016 may not align with or correspond to a communication device in the surgical stapler cartridge 13012.

FIG. 91B depicts an example communication and power coupling between a surgical stapler's elongated channel 13010 and a surgical stapler 13012. As shown, the elongated channel 13010 comprises the first array 13014 and second array 13016 positioned longitudinally along the elongated channel 13010. Surgical stapler cartridge 13012 may comprise a first array 13022 positioned in the proximal end of the cartridge and a second array 13024 positioned near a distal end of the cartridge. When surgical staple cartridge 13012 is interfaced with the elongated channel 150302 of the surgical stapler, the first sensing array 13022 may align with and communicate with array 13014. The second sensing array 13024 may align with and communicate with array 13016. Data may be communicated between the surgical stapler and the surgical staple cartridge 13012 using the aligned arrays. For example, data relating to measurements such as tissue measurements that are gathered by other sensors in the surgical staple cartridge 13012 may be communicated by arrays 13022 and 13024. Likewise, power may be communicated from the surgical stapler and arrays 13014 and 13016 to arrays 13022 and 13024. The power may be used by the surgical staple cartridge 13012 to operate sensors the collect data regarding tissue that is operated on by the surgical staple cartridge 13012. This data may be communicated by arrays 13022 and 13023 to arrays 13014 and 13016.

Figure 92:
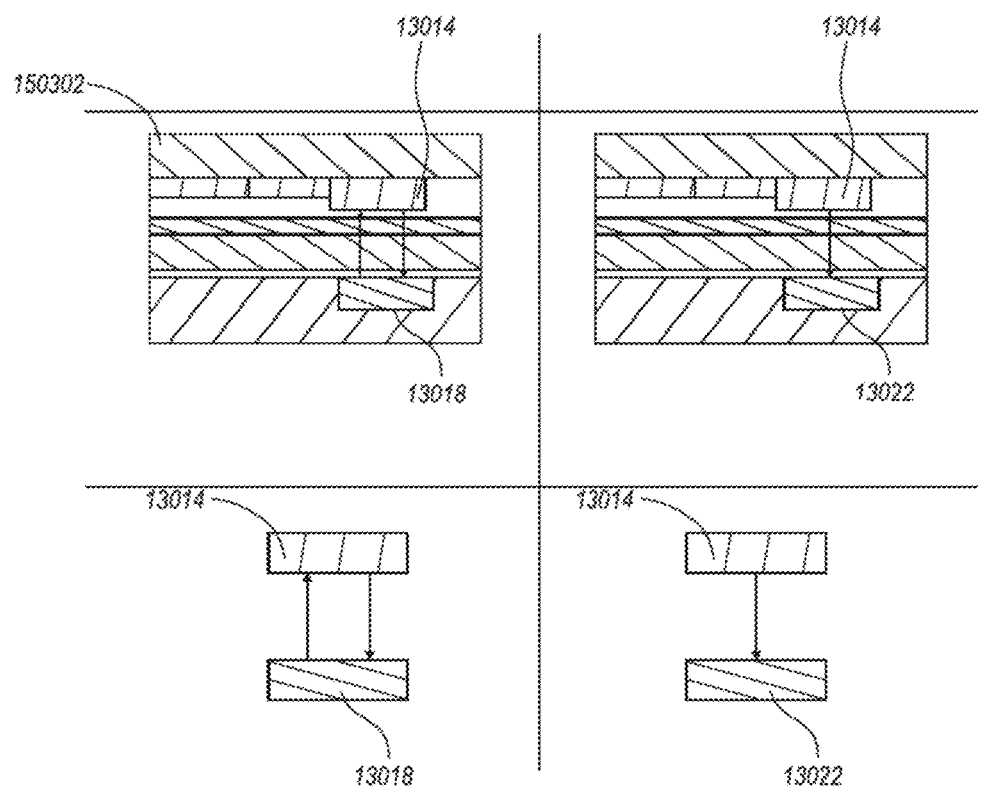
FIG. 92 illustrates example power and data communication.

FIG. 92 provides isolated views of communications between arrays in a surgical staple and surgical staple cartridge. As shown, in a first example illustrated on the left of the figure, a sensing array 13012 comprised in an elongated channel 150302 aligns with a communication device, which may be an RFID chip 13018, in the surgical staple cartridge 13012. In an example, both data and power may be communicated between the sensing array 13014 and RFID chip 13018. Data may be communicated to and from the RFID chop 13018 and power may be communicated from the array 13014 to the RFID chop 13018. In a second example illustrated on the right portion of FIG. 92, the sensing array 13014 is illustrated communicating power to a corresponding array 13022 in the surgical staple cartridge 13012. In this second example, power may be communicated while data may not.

A surgical instrument may be configured to control the amount and type of communication that may take place between the surgical instrument and a component attached to the surgical instrument. In a first example or tier, a surgical stapler instrument may control the communication between the stapler and a surgical staple cartridge attached thereto so as to allow for one-way communication from the surgical staple cartridge to the surgical stapler. The surgical stapler may communicate data identifying the cartridge and/or data providing status regarding the cartridge. In a second example or tier, a surgical stapler may control the communication between the stapler and a surgical staple cartridge attached thereto to provide for communication of static measurements taken by sensors comprised in the surgical staple cartridge to the surgical stapler. The communications may identify the cartridge and the position of tissue that is being operated on by the surgical staple cartridge. In a third example or tier, a surgical stapler may control the communication between the stapler and a surgical staple cartridge attached thereto to provide continuous communication of data between the staple cartridge and the surgical staple. A surgical staple cartridge may comprise sensors that continuously detect and measure tissue features such as compression in multiple areas or zones and provide continuous measurements to the surgical stapler over time. The surgical stapler may control the surgical staple cartridge to continuously receive such measurements in real time.

Figure 93:
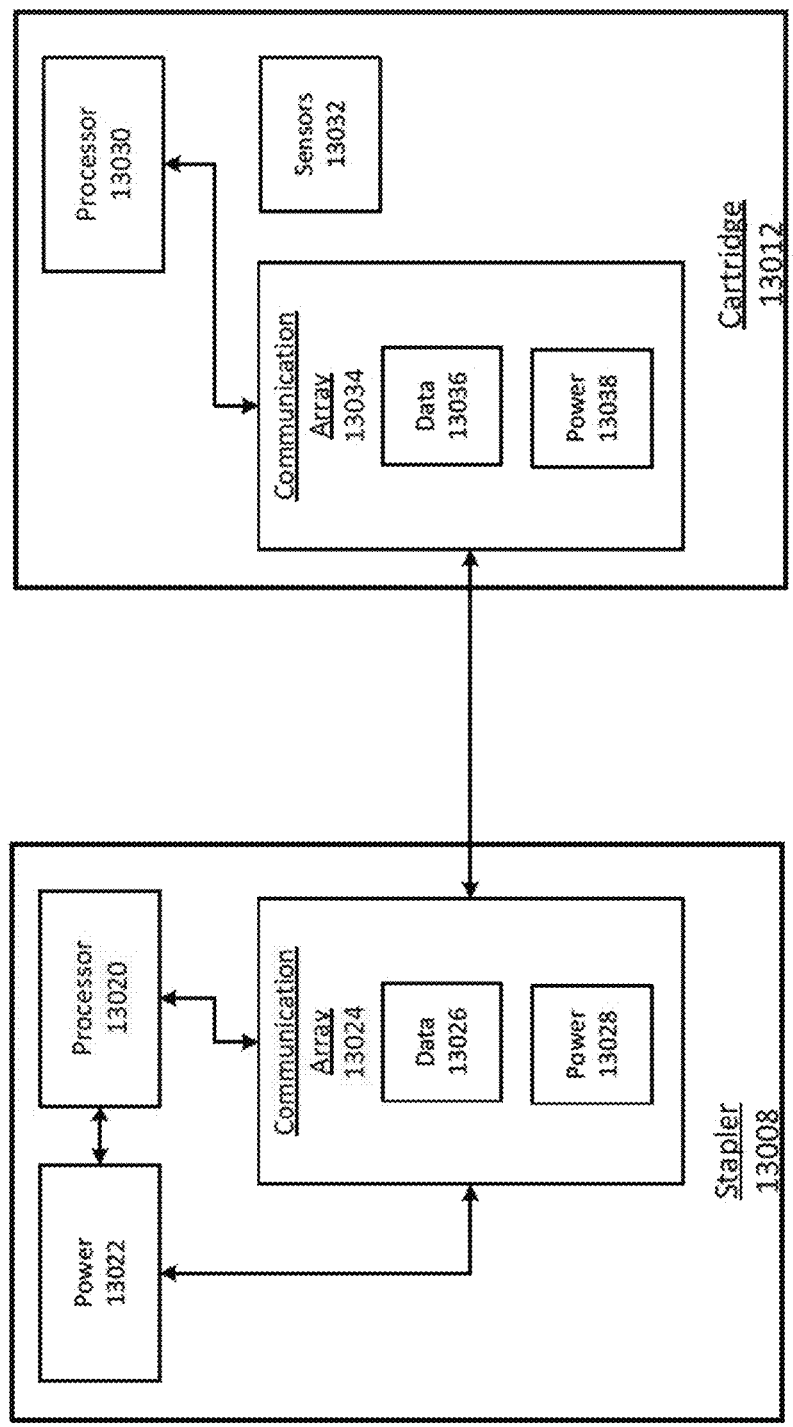
FIG. 93 illustrates an example block diagram depicting components of an example surgical stapler and an example staple cartridge.

FIG. 93 depicts functional components of an example surgical stapler 13008 and staple cartridge 13012. As shown, the surgical stapler 13008 may comprise a processor 13020, a power source 13022, and a communication array 13024. The processor 13020 may be programmed with executable instructions for performing functions attendant to operation of the surgical stapler 13008 including determining communication capability of the surgical stapler 13008 relative to the surgical staple cartridge 13012. The processor 13020 may control the receipt and transmission of data and power to the surgical staple cartridge 13012. The communications array 13024 may comprise one or more data communication arrays 13026 and/or power communication arrays 13028. The processor 13008 may be programmed to control the data communication arrays 13026 and power communication arrays 13028 and thereby control communicating data and power between the surgical stapler 13008 and the staple cartridge 13012. The processor 13020 may control power source 13022 and communication of power via power communications arrays 13028 to the surgical staple cartridge 13012.

The surgical staple cartridge 13012 may comprise a processor 13030, sensors 13032, and a communication array 13034. The processor 13020 may be programmed with executable instructions for performing functions attendant to operation of the surgical staple cartridge 13012 including communication of data and receiving power from the surgical stapler 13008. The processor 13030 may control sensors 13032 to measure and gather data relating to tissue operated on by the surgical staple cartridge 13012 and surgical stapler 13008. The sensors 13032 may be configured to, and may be controlled by processor 13030 to measure and collect data relating to tissue compression. The sensors 13032 may collect data in multiple areas or zones and communicate the data in real time. The communications array 13034 may comprise one or more data communication arrays 13036 and/or power communication arrays 13038. The processor 13030 may be programmed to control the data communication arrays 13036 and power communication arrays 13038 and thereby control communicating data and power between the surgical stapler 13008 and the staple cartridge 13012. The processor 13020 may control sensors 13032 and data communication array 13036 to communicate measurement data to the surgical stapler 13008. The processor may control power communication array 13038 to receive power from surgical stapler 13008.

The surgical stapler 13008 may be programmed to control a communication capability between the surgical staple cartridge 13012 and the surgical stapler 13008. The surgical stapler 13008 may be programmed to determine the type and amount of data and power that may be communicated with the surgical stapler 13008 by a connected component such as surgical staple cartridge 13012. The surgical stapler 13008 may also be programmed to determine the type and amount of data that may be communicated with a separate computing system such as, for example, a surgical hub 106 as described above. The surgical stapler 13008 may control, for example, which of the following communication capabilities or capacities are implemented: one-way communication from the surgical staple cartridge 13012 to the surgical stapler 13008; two-way communication between the surgical staple cartridge 13012 and the surgical stapler 13008; real-time two-way communication relating to measured data; communication of power from the surgical stapler to the surgical staple cartridge 13012; and communication by the surgical stapler 13008 with a separate server system such as, for example, a surgical hub 106.

The surgical stapler 13008 may determine a communication capability based on the value of one or more parameters associated with at least one of the surgical stapler 13008 or the surgical staple cartridge 13012. The surgical stapler 13008 may process values of parameters associated with, for example, the owner or operator of the device, hardware comprised in the surgical stapler 13008 and/or surgical staple cartridge 13012, software comprised in the surgical stapler 13008 and/or surgical staple cartridge 13012, and/or a purchase or subscription level associated with the surgical stapler 13008 and/or surgical staple cartridge 13012. The surgical stapler 13008 may determine a communication capability based on the values of one or more of environmental parameters, interference, system capabilities, or system control parameters. System control parameters may comprise one or more of a software level, a software revision, software authenticity, purchase level, or subscription level. Depending on the value of these or other parameters, the surgical stapler 13008 may determine to implement a particular communication capability including the type of data and manner of communication between the surgical stapler 13008 and the surgical staple cartridge 13012 and/or with a surgical hub 106. For example, a surgical stapler 13008 may determine, based on a parameter indicating the surgical stapler 13008 or the surgical stapler cartridge 13012 is associated with an entry level purchase or subscription, that the communication capability between the surgical stapler 13008 and the staple cartridge 13012 may allow for one-way communication of static data from the surgical staple cartridge 13012 to the surgical stapler 13008. A surgical stapler 13008 may determine, based on a parameter indicating the surgical stapler 13008 or the surgical stapler cartridge 13012 is associated with a medium level purchase or subscription, that the communication capability between the surgical stapler 13008 and the staple cartridge 13012 may allow for two-way communication of data between the surgical staple cartridge 13012 and the surgical stapler 13008. A surgical stapler 13008 may determine, based on a parameter indicating the surgical stapler 13008 or the surgical stapler cartridge 13012 is associated with a relatively high level purchase or subscription, that the communication capability between the surgical stapler 13008 and the staple cartridge 13012 may allow for real-time two-way (e.g., bi-directional) communication of data between the surgical staple cartridge 13012 and the surgical stapler 13008. The surgical stapler 13008 may determine, based on a parameter indicating the surgical stapler 13008 or the surgical staple cartridge 13012 is associated with a higher level purchase or subscription, that the communication capability may comprise two-way communication between the surgical stapler 13008 and the surgical staple cartridge 13012 as well as communication with a server such as the hub server 106. The surgical stapler 13008 may determine based on a parameter associated with a sensing capacity of the surgical staple cartridge 13012 to communicate power from the surgical stapler 13008 to the surgical staple cartridge 13012.

The surgical stapler 13008 may determine the communication capability between the surgical stapler 13008 and the surgical staple cartridge 13012 based on parameters relating to the hardware and/or software comprised in the surgical stapler 13008 and/or surgical staple cartridge 13012. For example, if the surgical staple cartridge 13012 is configured with outdated software, the surgical stapler 13008 may determine that the communication capability with the surgical staple cartridge 13012 may comprise one-way communication of static data from the surgical staple cartridge 13012 to the surgical instrument. If the surgical staple cartridge 13012 is configured with the recently updated software, the surgical stapler 13008 may determine that the communication capability with the surgical staple cartridge 13012 may comprise two-way communication. If the surgical staple cartridge 13012 comprises tissue sensing arrays, the surgical stapler 13008 may determine that the communication capability with the surgical staple cartridge 13012 may comprise real-time data communication with the cartridge, communicating power to the cartridge, and communicating data from the surgical stapler 13008 to a third device such as, for example a surgical hub 106.

Figure 94:
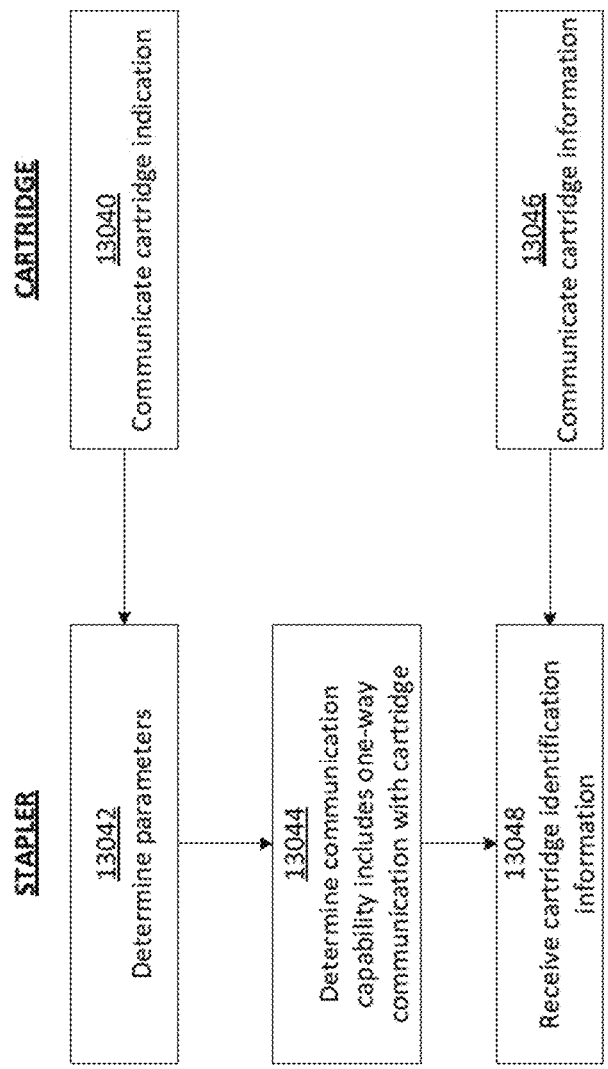
FIG. 94 illustrates example processing for determining communication capabilities.

The surgical stapler 13008 may determine that the communication capability may be a first tier and may comprise one-way data communication from the staple cartridge to the surgical stapler. FIG. 94 depicts a flow diagram for processing associated with a selection of one-way communication capability. As shown, at 13040, a surgical staple cartridge 13012 may be coupled to a surgical stapler 13008 and may communicate an indication that it has coupled. The surgical staple cartridge 13012 may determine that it is physically coupled to the surgical staple cartridge 13012 and, in response, may communicate the indication that it has coupled.

At 13042, the surgical stapler 13008 may determine the value of parameters relevant to determining communication capability. For example, the surgical stapler 13008 may determine values for one or more of: environmental parameters, interference, system capabilities, or system control parameters. System control parameters may comprise one or more of a software level, a software revision, software authenticity, purchase level, or subscription level. The surgical stapler 13008 may determine the operating capacity of the surgical stapler and/or staple cartridge, the current software version operating on the stapler and/or cartridge, and/or the level of purchased or subscribed service associated with the stapler and/or cartridge.

At 13044, the surgical stapler 13008 may determine, based on the determined parameters, the communication capability for interfacing with the surgical staple cartridge 13012 and any additional system. The surgical stapler 13008 may determine, based on a parameter value indicating the surgical stapler 13008 or the surgical staple cartridge 13012 is associated with an entry level purchase or subscription, that the communication capability between the surgical stapler 13008 and the staple cartridge 13012 may allow for one-way communication of static data from the surgical staple cartridge 13012 to the surgical stapler 13008. The surgical stapler 13008 may determine based on a parameter value indicating the surgical stapler 13008 or the surgical staple cartridge 13012 is configured with a non-current software version that the communication capability may allow for one-way communication of static data from the surgical staple cartridge 13012 to the surgical stapler 13008.

At 13046, the surgical staple cartridge 13012 may communicate data to the surgical stapler 13008. The surgical staple cartridge 13012 may employ a data communications array 13036 to communicate data from the surgical staple cartridge 13012 to a data communications array 13026 in the surgical stapler 13008. The data communicated by the surgical staple cartridge 13012 may comprise data relating to the features and characteristics of the staple cartridge 13012. The data communicated by the surgical staple cartridge 13012 and received by the surgical stapler 13008 at block 13048, may comprise one or more of a serial number associated with the staple cartridge, a color associated with the staple cartridge, a length associated with the staple cartridge, or a status associated with the staple cartridge. Where the surgical staple cartridge 13012 comprise a RFID chip as discussed above in connection with FIG. 91A, the data may be transmitted by the RFID chip and received at a communications array 13024 comprised in the surgical stapler 13008.

Figure 95:
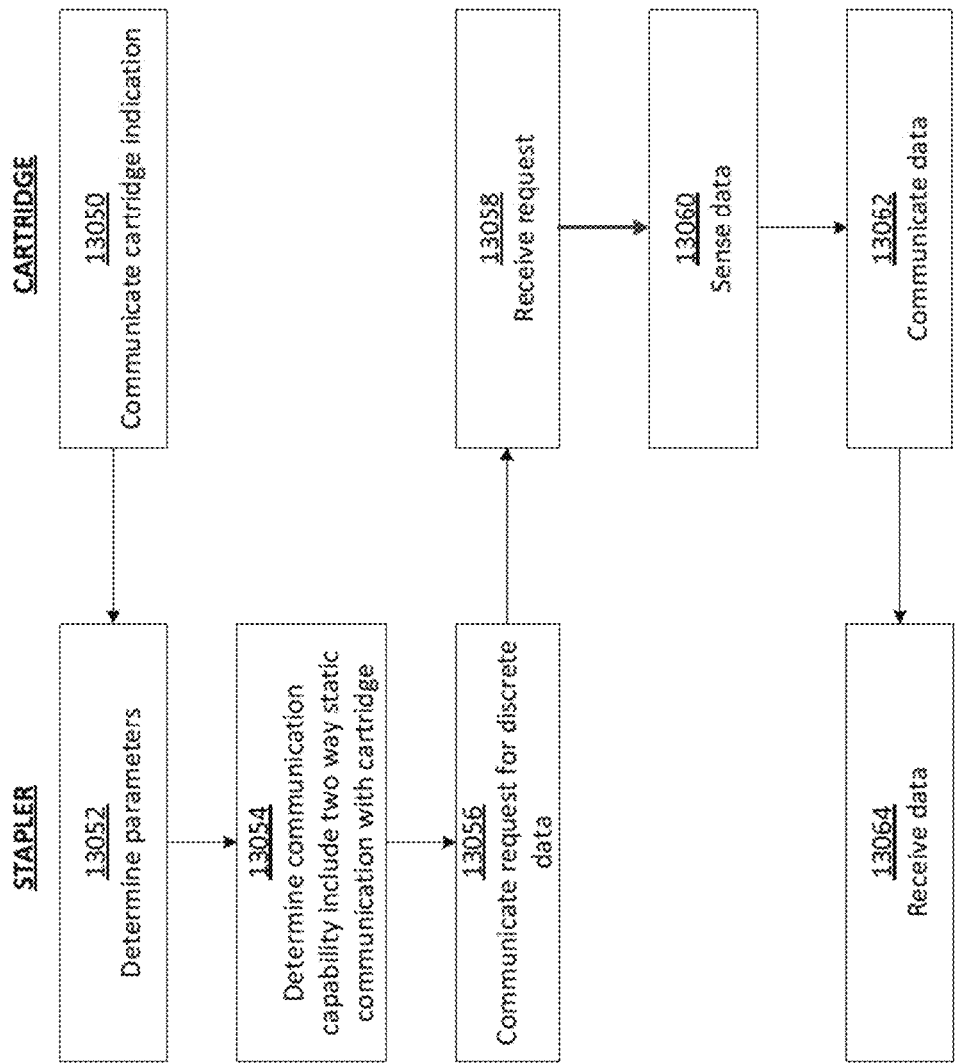
FIG. 95 illustrates example processing for determining communication capabilities.

The surgical stapler 13008 may determine that the communication capability or capacity may be a second tier comprising two-way data communication of static or discrete data readings from the staple cartridge to the surgical stapler. FIG. 95 depicts a flow diagram for processing associated with a selection of two-way data communication of static data as a communication capability. As shown, at 13050, a surgical staple cartridge 13012 may be coupled to a surgical stapler 13008 and may communicate an indication that it has coupled. The surgical staple cartridge 13012 may determine that it is physically coupled to the surgical staple cartridge 13012 and, in response, may communicate the indication that it has coupled.

At 13052, the surgical stapler 13008 may determine parameters relevant to determining communication capability. For example, the surgical stapler 13008 may determine values for one or more of: environmental parameters, interference, system capabilities, or system control parameters relating to the surgical stapler 13008 and/or the surgical stale cartridge 13012. System parameters for the surgical stapler 13008 may comprise, for example, a wiring harness compatibility with the staple cartridge, a software communication level associated with the surgical stapler, and/or a power supply capability associated with the surgical stapler. System parameters for the surgical cartridge may comprise, for example, an antenna array, a power requirement, presence of a local power accumulator, a memory location, and/or a local signal processing capability System control parameters may comprise one or more of a software level, a software revision, software authenticity, purchase level, or subscription level. The surgical stapler 13008 may determine the operating capacity of the surgical stapler and/or staple cartridge, the current software version operating on the stapler and/or cartridge, and/or the level of purchased or subscribed service associated with the stapler and/or cartridge.

At 13054, the surgical stapler 13008 may determine, based on the determined parameter values, the communication capability for interfacing with the surgical staple cartridge 13012 and/or other system. For example, the surgical stapler 13008 may determine, based on a parameter indicating the surgical stapler 13008 or the surgical stapler cartridge 13012 is associated with a medium level purchase or subscription, that the communication capability between the surgical stapler 13008 and the staple cartridge 13012 may allow for two-way communication of discrete data readings between the surgical staple cartridge 13012 and the surgical stapler 13008. The surgical stapler 13008 may determine based on a parameter value indicating the surgical stapler 13008 or the surgical staple cartridge 13012 is configured with a current software version and/or has hardware compatible with two-way communication that the communication capability may allow for two-way communication of static data from the surgical staple cartridge 13012 to the surgical stapler 13008.

At 13056, having determined the communication capability, the surgical stapler 13008 may communicate a request for data to the surgical staple cartridge 13012. The request may specify a request for discrete data readings. The request may specify to provide data items gathered by sensors comprised in the surgical staple cartridge 13012. The surgical stapler 13008 may employ a data communications array 13026 to communicate the request to the surgical staple cartridge 13012.

At 13058, the surgical staple cartridge 13012 may receive the request. The request may be received by the surgical staple cartridge 13012 using data communication array 13036. In response to the request, at block 13060, the surgical staple cartridge 13012 senses data relevant to the request. For example, the surgical staple cartridge 13012 may employ sensors to gather data relating to tissue presently being operated on by the surgical staple cartridge 13012 and surgical stapler 13008. The sensor readings may identify which portions of the surgical staple cartridge 13012 are engaged with tissue. The data may indicate a location of the tissue in relation to the surgical staple cartridge 13012. The sensor readings may identify pressure readings regarding the amount of pressure applied to tissue and the location of the pressure readings. The sensor readings may comprise data relating to tissue impedance, tissue location, tissue thickness, and/or tissue viscoelasticity.

At 13062, the surgical staple cartridge 13012 may communicate data readings to the surgical stapler 13008. The communicated data may comprise data items corresponding to the sensor readings made by the surgical staple cartridge 13012. The data items may correspond to readings made at discrete points in time. The data items may comprise data associated with tissue location relative to the surgical staple cartridge 13012 and/or the surgical stapler 13008. The tissue location data may be a static tissue location. The surgical staple cartridge 13012 may employ a data communications array 13036 to communicate data from the surgical staple cartridge 13012 to a data communications array 13026 in the surgical stapler 13008.

At 13064, the surgical stapler 13008 may receive the transmitted data. The surgical stapler 13008 may then use the received data in its operation. For example, the surgical stapler 13008 may use tissue readings and tissue compression data in a display for the operator. The surgical stapler 13008 may process the data to determine whether the surgical stapler is properly situated relative to tissue to perform a stapling operation.

Figure 96:
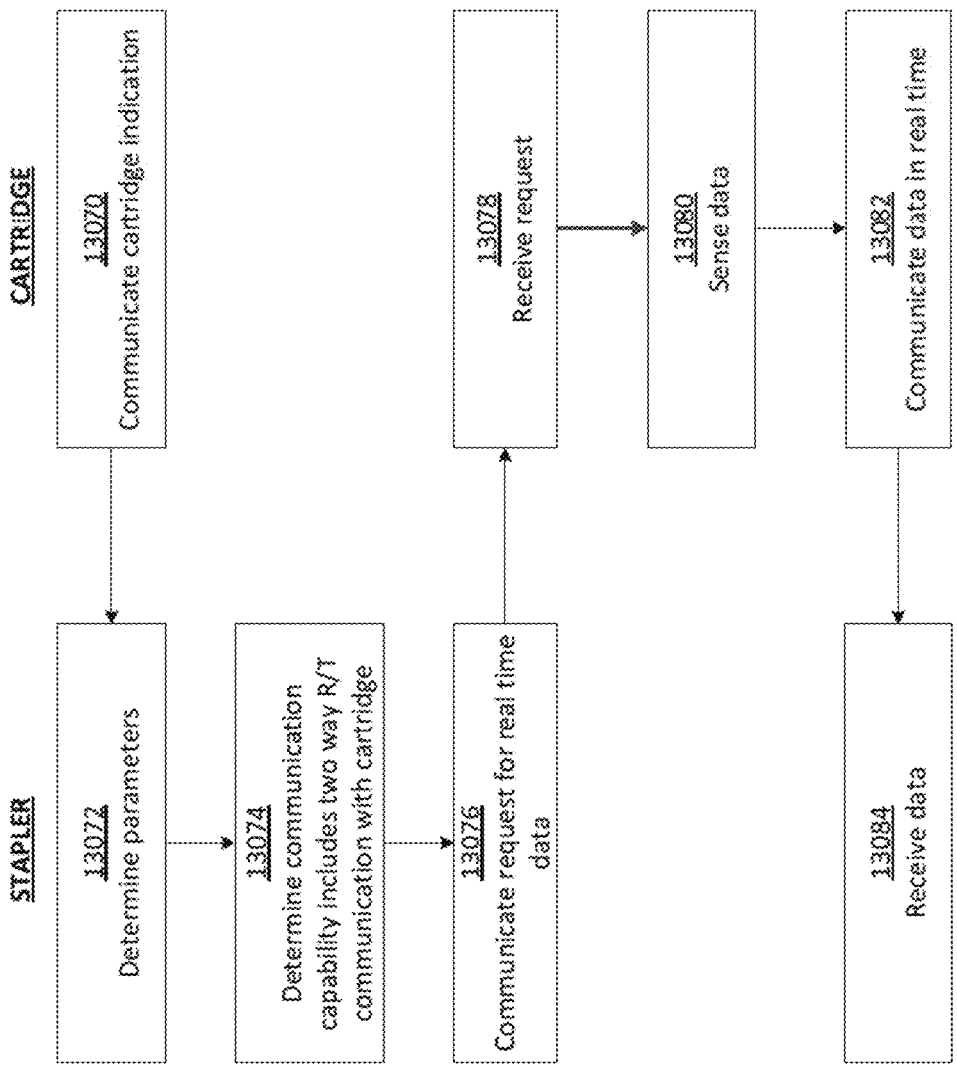
FIG. 96 illustrates example processing for determining communication capabilities.

The surgical stapler 13008 may determine that the communication capacity or capability may be a third tier comprising two-way data communication relating to real-time data readings from the staple cartridge to the surgical stapler. FIG. 96 depicts a flow diagram for processing associated with a selection of two-way data communication of real-time data as a communication capability. As shown, at 13070, a surgical staple cartridge 13012 may be coupled to a surgical stapler 13008 and may communicate an indication that it has coupled. The surgical staple cartridge 13012 may determine that it is physically coupled to the surgical staple cartridge 13012 and, in response, may communicate the indication that it has coupled.

At 13072, the surgical stapler 13008 may determine parameters relevant to determining communication capability. For example, the surgical stapler 13008 may determine values for one or more of: environmental parameters, interference, system capabilities, or system control parameters relating to the surgical stapler 13008 and/or the surgical stale cartridge 13012. System parameters for the surgical stapler 13008 may comprise, for example, a wiring harness compatibility with the staple cartridge, a software communication level associated with the surgical stapler, and/or a power supply capability associated with the surgical stapler. System parameters for the surgical cartridge may comprise, for example, an antenna array, a power requirement, presence of a local power accumulator, a memory location, and/or a local signal processing capability. System control parameters may comprise one or more of a software level, a software revision, software authenticity, purchase level, or subscription level. The surgical stapler 13008 may determine the operating capacity of the surgical stapler and/or staple cartridge, the current software version operating on the stapler and/or cartridge, and/or the level of purchased or subscribed service associated with the stapler and/or cartridge.

At 13074, the surgical stapler 13008 may determine, based on the determined parameters, the communication capability for interfacing with the surgical staple cartridge 13012 and/or other system such as a surgical hub 106. The surgical stapler 13008 may determine, based on a parameter indicating the surgical stapler 13008 or the surgical stapler cartridge 13012 is associated with a relatively high level purchase or subscription, that the communication capability between the surgical stapler 13008 and the staple cartridge 13012 may allow for real-time two-way (e.g., bi-directional) communication of data between the surgical staple cartridge 13012 and the surgical stapler 13008. The surgical stapler 13008 may determine based on a parameter value indicating the surgical stapler 13008 or the surgical staple cartridge 13012 is configured with a current software version that the communication capability may allow for two-way communication and communication in real time of data collected from sensors in the surgical staple cartridge 13012.

At 13076, having determined the communication capability, the surgical stapler 13008 may communicate a request for data to the surgical staple cartridge 13012. The request may specify a request for two-way communication relating to real-time data readings. The surgical stapler 13008 may employ a data communications array 13026 to communicate the request to the surgical staple cartridge 13012.

At 13078, the surgical staple cartridge 13012 may receive the request. The request may be received by the surgical staple cartridge 13012 using data communication array 13036. In response to the request, at block 13080, the surgical staple cartridge 13012 may sense data relevant to the request. For example, the surgical staple cartridge 13012 may employ sensors 13032 to gather data relating to tissue presently being operated on by the surgical staple cartridge 13012 and surgical stapler 13008. The sensor readings may identify which portions of the surgical staple cartridge 13012 are engaged with tissue. The data may indicate a location of the tissue in relation to the surgical staple cartridge 13012. The sensor readings may identify pressure readings regarding the amount of pressure applied to tissue and the location of the pressure readings. The sensor readings may comprise data relating to tissue impedance, tissue location, tissue thickness, and/or tissue viscoelasticity.

At 13082, the surgical staple cartridge 13012 may communicate data readings to the surgical stapler 13008. The communicated data may comprise data items corresponding to the sensor readings made by the surgical staple cartridge 13012. The data items may correspond to continuous readings made in real time. The data items may correspond to sensor readings relating to tissue made across time. The surgical staple cartridge 13012 may employ a data communications array 13036 to communicate data from the surgical staple cartridge 13012 to a data communications array 13026 in the surgical stapler 13008. The communications may be made continuously in real time to reflect real time measurements made by sensors in the surgical staple cartridge 13012.

At 13084, the surgical stapler 13008 may receive the transmitted data. The data may be received in real time and continuously. The surgical stapler 13008 may then use the received data in its operation. For example, the surgical stapler 13008 may use tissue readings and tissue compression data in a display to the operator and/or to determine whether the surgical stapler is properly situated to perform a stapling operation. The surgical stapler 13008 may use the received data to determine characteristics of tissue being operated on by the surgical stapler 13008 and surgical staple cartridge 13012. The surgical stapler 13008 may use the received data to determine characteristics relating to tissue type, organ type, and/or tissue stiffness.

The surgical stapler 13008 may continuously monitor the characteristics of the tissue operated on by the surgical stapler 13008. The surgical stapler 13008 may compare the monitored characteristics to one or more threshold values. If the surgical stapler 13008 determines a threshold has been met, the surgical stapler may determine to perform a function such as, for example, perform a mechanical or electrical operation. For example, if the received data relates to a tissue thickness, and the thickness satisfies a threshold for stapling, the surgical stapler 13008 may indicate to the operator that a stapling operation is permitted.

Figure 97:
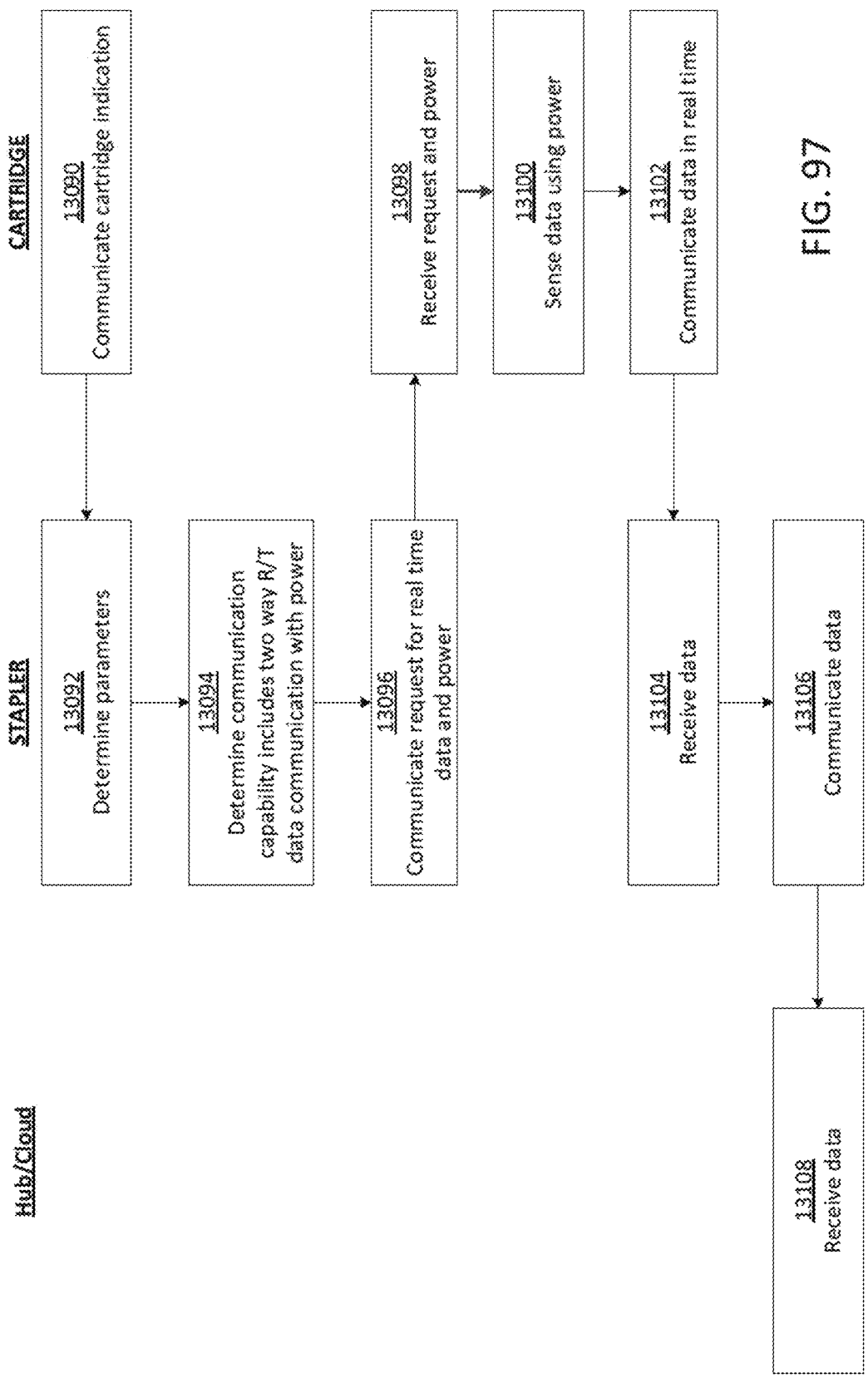
FIG. 97 illustrates example processing for determining communication capabilities.

The surgical stapler 13008 may determine that the communication capability or capacity may be a tier comprising two-way data communication relating to real-time data readings from the surgical staple cartridge 13012 to the surgical stapler 13008, power communication from the surgical stapler 13008 to the surgical staple cartridge 13012, and data communication to an external system such as a surgical hub 106. FIG. 97 depicts a flow diagram for processing associated with a selection of communication capability comprising two-way data communication of real-time data, power communication, and communication with an external system. As shown, at 13090, a surgical staple cartridge 13012 may be coupled to a surgical stapler 13008 and may communicate an indication that it has coupled. The surgical staple cartridge 13012 may determine that it is physically coupled to the surgical staple cartridge 13012 and, in response, may communicate the indication that it has coupled.

At 13092, the surgical stapler 13008 may determine parameters relevant to determining communication capability. For example, the surgical stapler 13008 may determine values for one or more of: environmental parameters, interference, system capabilities, or system control parameters relating to the surgical stapler 13008 and/or the surgical stale cartridge 13012. System parameters for the surgical stapler 13008 may comprise, for example, a wiring harness compatibility with the staple cartridge, a software communication level associated with the surgical stapler, and/or a power supply capability associated with the surgical stapler. System parameters for the surgical cartridge may comprise, for example, an antenna array, a power requirement, presence of a local power accumulator, a memory location, and/or a local signal processing capability System control parameters may comprise one or more of a software level, a software revision, software authenticity, purchase level, or subscription level. The surgical stapler 13008 may determine the operating capacity of the surgical stapler and/or staple cartridge, the current software version operating on the stapler and/or cartridge, and/or the level of purchased or subscribed service associated with the stapler and/or cartridge.

At 13094, the surgical stapler 13008 may determine, based on the determined parameters, the communication capability for interfacing with the surgical staple cartridge 13012 and an external system. The surgical stapler 13008 may determine, based on a parameter indicating the surgical stapler 13008 or the surgical staple cartridge 13012 is associated with a higher level purchase or subscription, that the communication capability may comprise two-way communication between the surgical stapler 13008 and the surgical staple cartridge 13012 as well as communication with a server such as hub server. The surgical stapler 13008 may also determine based on a parameter associated with sensors comprised in the surgical staple cartridge 13012 to communicate power from the surgical stapler 13008 to the surgical staple cartridge 13012.

At 13096, having determined the communication capability, the surgical stapler 13008 may communicate a request for data to the surgical staple cartridge 13012. The request may specify a request for two-way communication relating to real-time data readings. The surgical stapler 13008 may employ a data communications array 13026 to communicate the request to the surgical staple cartridge 13012. The surgical stapler 13008 may also communicate power to the surgical staple cartridge 13012. The surgical stapler 13008 may employ a power communication array 13028 to communicate the power. The surgical staple cartridge 13012 may use the received power to operate sensors for collecting data.

At 13098, the surgical staple cartridge 13012 receives the request for data and the power. The request may be received by the surgical staple cartridge 13012 using data communication array 13036. The power may be received at power communication array 13038.

In response to the request, at 13100, the surgical staple cartridge 13012 may sense data relevant to the request. For example, the surgical staple cartridge 13012 may employ sensors 13032 to gather data relating to tissue presently being operated on by the surgical staple cartridge 13012. The sensor readings may identify which portions of the surgical staple cartridge 13012 are engaged with tissue. The data may indicate a location of the tissue in relation to the surgical staple cartridge 13012. The sensor readings may identify pressure readings regarding the amount of pressure applied to tissue and the location of the pressure readings. The surgical staple cartridge 13012 may employ the received power to fulfill the request. The surgical staple cartridge 13012 may employ the received power to operate sensors that are used to collect the requested data.

At 13102, the surgical staple cartridge 13012 communicates data readings to the surgical stapler 13008. The communicated data may comprise data items corresponding to the sensor readings made by the surgical staple cartridge 13012. The data items may correspond to continuous readings made in real time. The surgical staple cartridge 13012 may employ a data communications array 13036 to communicate data from the surgical staple cartridge 13012 to a data communications array 13026 in the surgical stapler 13008. The communications may be made continuously in real time to reflect real time measurements made by sensors in the surgical staple cartridge 13012.

At 13104, the surgical stapler 13008 receives the transmitted data. The data may be received in real time and continuously. The surgical stapler 13008 may use the received data in its operation. For example, the surgical stapler 13008 may display tissue readings and tissue compression data and/or determine whether the surgical stapler is properly situated to perform a stapling operation. The surgical stapler 13008 may use the received data to determine characteristics of tissue being operated on by the surgical stapler 13008 and surgical staple cartridge 13012. The surgical stapler 13008 may use the received data to determine characteristics relating to tissue type, organ type, and/or tissue stiffness. The surgical stapler 13008 may employ artificial intelligence processing in determining aspects of the tissue from the received data or to otherwise process the received data.

The surgical stapler 13008 may continuously monitor the characteristics of the tissue operated on by the surgical stapler 13008. The surgical stapler 13008 may compare the monitored characteristics to one or more threshold values. If the surgical stapler 13008 determines a threshold has been met, the surgical stapler may determine to perform a function such as, for example, perform a mechanical or electrical operation. For example, if the received data relates to a tissue thickness, and the thickness satisfies a threshold for stapling, the surgical stapler 13008 may indicate to the operator that a stapling operation is permitted.

At 13106, the surgical stapler 13008 may communicate data received from the surgical staple cartridge 13012 or derived from the received data to an external system such as, for example a surgical hub 106. For example, the surgical stapler 13008 may communicate data relating to tissue measurements to the surgical hub 106 for further analysis.

At 13108, the surgical hub 106 may receive the data. The surgical hub 106 may store and process the data. For example, the surgical hub 106 may determine, based on the received data, to respond to the surgical stapler 13080 with instructions for further processing along with data to be used in performing the instructions.

Accordingly, systems and techniques are disclosed for controlling the communication capabilities between a surgical instrument such as, for example, a surgical stapler and a removeable component such as, for example, staple cartridge. A surgical instrument may determine one or more parameters associated with the surgical instrument and the removable component. The surgical instrument may determine the type and degree of communication that may take place between the surgical instrument and the removable component based on the one or more parameters.

The combination of a programmable or smart Endocutter with a smart or intelligent cartridge may establish communications in multiple different manners. Each of these levels or tiers of communication interconnection may be dependent on a number of smart stapler aspects (e.g., wiring harness compatibility with needs of the cartridge, software communication level of the instrument, communication array capabilities for signal processing, power supply capabilities, subscription level, etc.) as well as a number of cartridge capabilities (e.g., antenna array, power requirements, presence of a local power accumulator or memory location, and local signal processing, such as described, for example, in U.S. Pat. No. 10,695,081 titled "Time Dependent Evaluation of Sensor Data to Determine Stability, Creep, and Viscoelastic Elements or Measures," the contents of which are hereby incorporated by reference in their entirety). The systems may connect in one of several tiered manners which may control the capabilities of the cartridge that the instrument may employ. By way of example, the level of subscription an institution has purchased may be used to determine a level of software and interconnection with a local hub system that the instrument may employ. An operator of an instrument may have the option of disabling the function if the function is unlikely to provide a benefit for the planned surgical procedure which may allow the device to perform in its base or tier 1 level of functionality. Depending on the cost structure of the software, this may allow the operator to pull the desired hardware to increase operating room efficiency while allowing the surgeon to use the functions needed to complete the case.

Systems and techniques are disclosed herein for adaptive control of surgical instrument functions. A surgical instrument may be configured to communicate with an external system such as, for example, a surgical hub. The surgical instrument may receive from the surgical hub an indication of one or more functions that are to be adaptively controlled by the surgical instrument. For example, a surgical stapler instrument may receive an indication to adaptively control a display of tissue compression. The surgical instrument may determine values for parameters associated with the identified function and adapt the control of the identified function based upon the determined parameters. A surgical stapler may receive an indication from the surgical hub to provide an adaptable representation of an operating range for tissue compression. In response to receiving the indication, the surgical stapler may determine one or more parameters associated with the surgical stapler. For example, the surgical stapler may determine parameters relating to the size of an anvil head of an end effector. The surgical stapler may modify the adaptable representation of the operating range for tissue compression based on the value of the parameters. For example, if the size of the anvil head is relatively small, the surgical stapler may modify the width of a band comprised in the adaptable representation of the operating range for tissue compression.

This Summary is provided to introduce a selection of concepts in a simplified form that are further described herein in the Detailed Description. This Summary is not intended to identify key features or essential features of the claimed subject matter, nor is it intended to be used to limit the scope of the claimed subject matter. Other features are described herein.

A surgical instrument receives an indication to provide adaptive control of surgical instrument functions. The indication may indicate to provide adaptable staple height operating range, to control motors associated with tissue compression, and/or to operate using the operational parameters associated with previous surgical procedures. The surgical instrument may determine values for parameters associated with the identified function and adapt the control of the identified function based upon the determined parameters. The surgical instrument may adapt a display of staple height operating range based on parameters indicating a size of an anvil head. The surgical instrument may control motors associated with tissue compression based on parameters indicating force applied in the instrument. The surgical instrument may operate according to operational parameters identified by a surgical hub.

Figure 98:
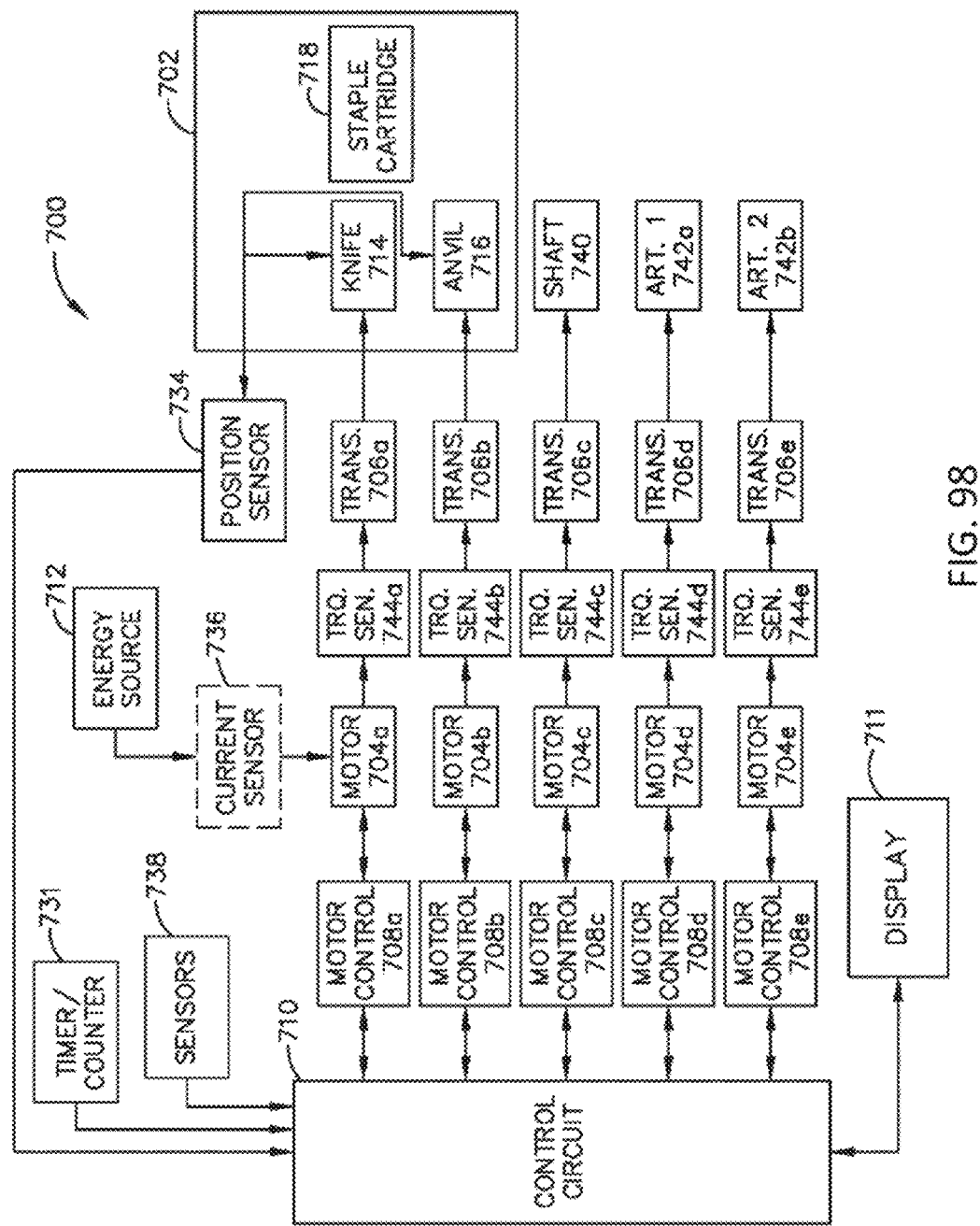
FIG. 98 is a schematic diagram of a surgical instrument configured to operate a surgical tool described herein, in accordance with at least one aspect of the present disclosure.

FIG. 98 is a schematic diagram of a surgical instrument 700 configured to operate a surgical tool described herein according to one aspect of this disclosure. The surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members. In one aspect, the surgical instrument 700 is representative of a hand held surgical instrument. In another aspect, the surgical instrument 700 is representative of a robotic surgical instrument. In other aspects, the surgical instrument 700 is representative of a combination of a hand held and robotic surgical instrument. In various aspects, the surgical stapler 700 may be representative of a linear stapler or a circular stapler.

In one aspect, the surgical instrument 700 comprises a control circuit 710 configured to control an anvil 716 and a knife 714 (or cutting element including a sharp cutting edge) portion of an end effector 702, a removable staple cartridge 718, a shaft 740, and one or more articulation members 742 *a*, 742 *b* via a plurality of motors 704 *a*-704 *e*. A position sensor 734 may be configured to provide position feedback of the knife 714 to the control circuit 710. Other sensors 738 may be configured to provide feedback to the control circuit 710. A timer/counter 731 provides timing and counting information to the control circuit 710. An energy source 712 may be provided to operate the motors 704 *a*-704 *e*, and a current sensor 736 provides motor current feedback to the control circuit 710. The motors 704 a-704 e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the knife 714 as determined by the position sensor 734 with the output of the timer/counter 731 such that the control circuit 710 can determine the position of the knife 714 at a specific time (t) relative to a starting position or the time (t) when the knife 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742 a, 742 b.

In one aspect, the control circuit 710 may generate motor set point signals. The motor set point signals may be provided to various motor controllers 708 a-708 e. The motor controllers 708 a-708 e may comprise one or more circuits configured to provide motor drive signals to the motors 704 a-704 e to drive the motors 704 a-704 e as described herein. In some examples, the motors 704 a-704 e may be brushed DC electric motors. For example, the velocity of the motors 704 a-704 e may be proportional to the respective motor drive signals. In some examples, the motors 704 a-704 e may be brushless DC electric motors, and the respective motor drive signals may comprise a PWM signal provided to one or more stator windings of the motors 704 a-704 e. Also, in some examples, the motor controllers 708 a-708 e may be omitted and the control circuit 710 may generate the motor drive signals directly.

In one aspect, the control circuit 710 may initially operate each of the motors 704 a-704 e in an open-loop configuration for a first open-loop portion of a stroke of the displacement member. Based on the response of the surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704 a-704 e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704 a-704 e based on translation data describing a position of the displacement member in a closed-loop manner to translate the displacement member at a constant velocity.

In one aspect, the motors 704 a-704 e may receive power from an energy source 712. The energy source 712 may be a DC power supply driven by a main alternating current power source, a battery, a super capacitor, or any other suitable energy source. The motors 704 a-704 e may be mechanically coupled to individual movable mechanical elements such as the knife 714, anvil 716, shaft 740, articulation 742 a, and articulation 742 b via respective transmissions 706 a-706 e. The transmissions 706 a-706 e may include one or more gears or other linkage components to couple the motors 704 a-704 e to movable mechanical elements. A position sensor 734 may sense a position of the knife 714. The position sensor 734 may be or include any type of sensor that is capable of generating position data that indicate a position of the knife 714. In some examples, the position sensor 734 may include an encoder configured to provide a series of pulses to the control circuit 710 as the knife 714 translates distally and proximally. The control circuit 710 may track the pulses to determine the position of the knife 714. Other suitable position sensors may be used, including, for example, a proximity sensor. Other types of position sensors may provide other signals indicating motion of the knife 714. Also, in some examples, the position sensor 734 may be omitted. Where any of the motors 704 a-704 e is a stepper motor, the control circuit 710 may track the position of the knife 714 by aggregating the number and direction of steps that the motor 704 has been instructed to execute. The position sensor 734 may be located in the end effector 702 or at any other portion of the instrument. The outputs of each of the motors 704 a-704 e include a torque sensor 744 a-744 e to sense force and have an encoder to sense rotation of the drive shaft.

In one aspect, the control circuit 710 is configured to drive a firing member such as the knife 714 portion of the end effector 702. The control circuit 710 provides a motor set point to a motor control 708 a, which provides a drive signal to the motor 704 a. The output shaft of the motor 704 a is coupled to a torque sensor 744 a. The torque sensor 744 a is coupled to a transmission 706 a which is coupled to the knife 714. The transmission 706 a comprises movable mechanical elements such as rotating elements and a firing member to control the movement of the knife 714 distally and proximally along a longitudinal axis of the end effector 702. In one aspect, the motor 704 a may be coupled to the knife gear assembly, which includes a knife gear reduction set that includes a first knife drive gear and a second knife drive gear. A torque sensor 744 a provides a firing force feedback signal to the control circuit 710. The firing force signal represents the force required to fire or displace the knife 714. A position sensor 734 may be configured to provide the position of the knife 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708 a. In response to the firing signal, the motor 704 a may drive the firing member distally along the longitudinal axis of the end effector 702 from a proximal stroke start position to a stroke end position distal to the stroke start position. As the firing member translates distally, a knife 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708 b, which provides a drive signal to the motor 704 b. The output shaft of the motor 704 b is coupled to a torque sensor 744 b. The torque sensor 744 b is coupled to a transmission 706 b which is coupled to the anvil 716. The transmission 706 b comprises movable mechanical elements such as rotating elements and a closure member to control the movement of the anvil 716 from the open and closed positions. In one aspect, the motor 704 b is coupled to a closure gear assembly, which includes a closure reduction gear set that is supported in meshing engagement with the closure spur gear. The torque sensor 744 b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708 b. In response to the closure signal, the motor 704 b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708 c, which provides a drive signal to the motor 704 c. The output shaft of the motor 704 c is coupled to a torque sensor 744 c. The torque sensor 744 c is coupled to a transmission 706 c which is coupled to the shaft 740. The transmission 706 c comprises movable mechanical elements such as rotating elements to control the rotation of the shaft 740 clockwise or counterclockwise up to and over 360°. In one aspect, the motor 704 c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744 c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In a circular stapler implementation, the transmission 706 c element is coupled to the trocar to advance or retract the trocar. In one aspect, the shaft 740 is part of a closure system that comprises a trocar 201904 and a trocar actuator 201906 as discussed in more detail with reference to FIGS. 101A-101C hereinbelow. Accordingly, the control circuit 710 controls the motor control circuit 708 c to control the motor 704 c to advance or retract the trocar. A torque sensor 744 c is provided to measure the torque applied by the shaft of the motor 704 c to the transmission components 706 c employed in advancing and retracting the trocar. The position sensor 734 may include a variety of sensors to track the position of the trocar, the anvil 716, or the knife 714, or any combination thereof. Other sensors 738 may be employed to measure a variety of parameters including position or velocity of the trocar, the anvil 716, or the knife 714, or any combination thereof. The torque sensor 744 c, the position sensor 734, and the sensors 738 are coupled to the control circuit 710 as inputs to various processes for controlling the operation of the surgical instrument 700 in a desired manner.

In one aspect, the control circuit 710 is configured to articulate the end effector 702. The control circuit 710 provides a motor set point to a motor control 708 d, which provides a drive signal to the motor 704 d. The output shaft of the motor 704 d is coupled to a torque sensor 744 d. The torque sensor 744 d is coupled to a transmission 706 d which is coupled to an articulation member 742 a. The transmission 706 d comprises movable mechanical elements such as articulation elements to control the articulation of the end effector 702 ±65°. In one aspect, the motor 704 d is coupled to an articulation nut, which is rotatably journaled on the proximal end portion of the distal spine portion and is rotatably driven thereon by an articulation gear assembly. The torque sensor 744 d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742 a, 742 b. These articulation members 742 a, 742 b are driven by separate disks on the robot interface (the rack) which are driven by the two motors 708 d, 708 e. When the separate firing motor 704 a is provided, each of articulation links 742 a, 742 b can be antagonistically driven with respect to the other link in order to provide a resistive holding motion and a load to the head when it is not moving and to provide an articulation motion as the head is articulated. The articulation members 742 a, 742 b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704 a-704 e may comprise a brushed DC motor with a gearbox and mechanical links to a firing member, closure member, or articulation member. Another example includes electric motors 704 a-704 e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704 a-704 e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744 a-744 e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704 a-704 e. The force required to advance any of the movable mechanical elements such as the knife 714 corresponds to the current drawn by one of the motors 704 a-704 e. The force is converted to a digital signal and provided to the control circuit 710. The control circuit 710 can be configured to simulate the response of the actual system of the instrument in the software of the controller. A displacement member can be actuated to move a knife 714 in the end effector 702 at or near a target velocity. The surgical instrument 700 can include a feedback controller, which can be one of any feedback controllers, including, but not limited to a PID, a state feedback, a linear-quadratic (LQR), and/or an adaptive controller, for example. The surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

The surgical instrument 700 may comprise wired or wireless communication circuits to communicate with the modular communication hub as shown in FIGS. 1-6 and 9-13. The surgical instrument 700 may be the motorized circular stapling instrument 201800 (FIG. 100), 201000 (FIGS. 103-104).

Figure 99:
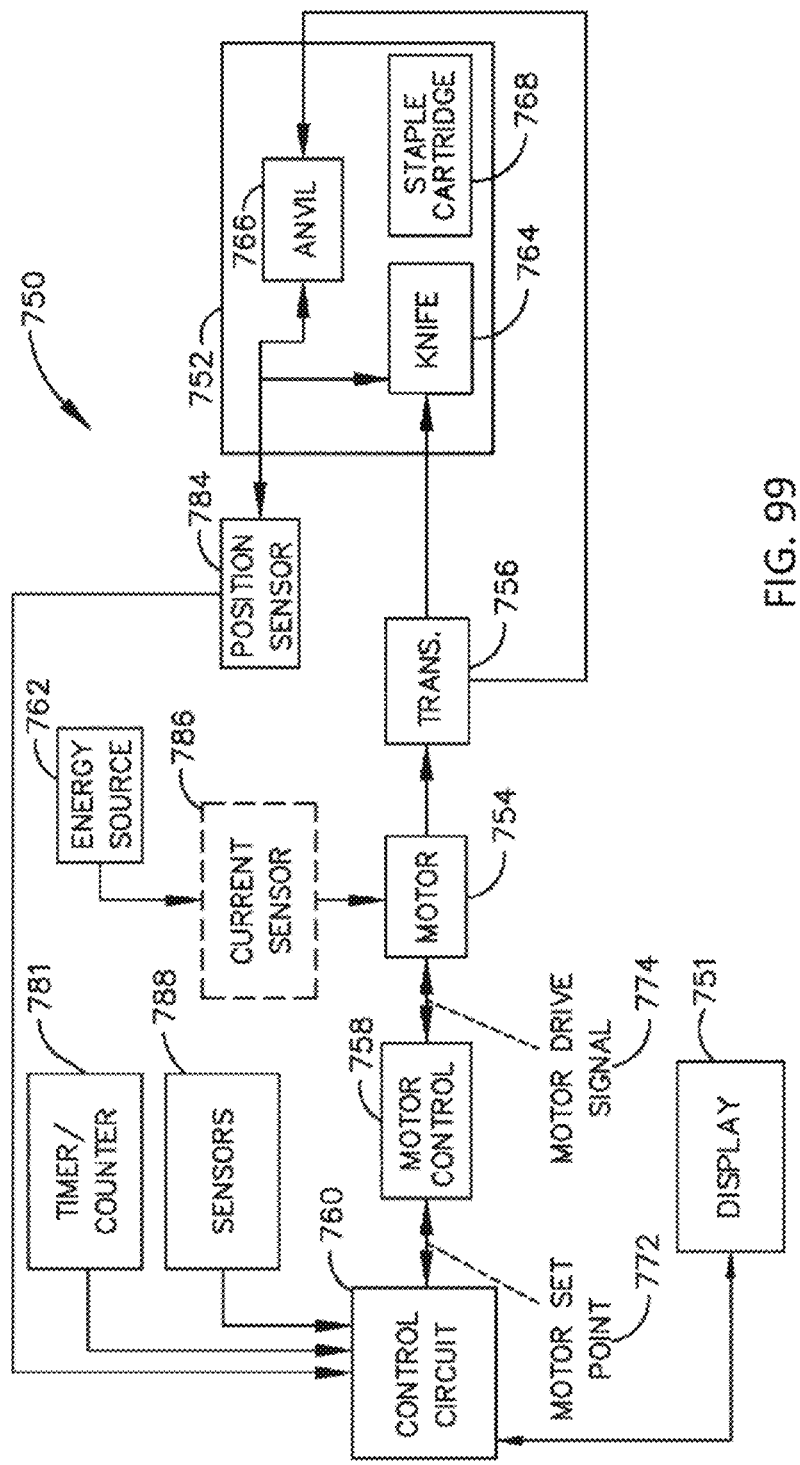
FIG. 99 illustrates a block diagram of a surgical instrument configured to control various functions, in accordance with at least one aspect of the present disclosure.

FIG. 99 illustrates a block diagram of a surgical instrument 750 configured to control various functions, according to one aspect of this disclosure. In one aspect, the surgical instrument 750 is programmed to control the distal translation of a displacement member such as the knife 764, or other suitable cutting element. The surgical instrument 750 comprises an end effector 752 that may comprise an anvil 766, a knife 764 (including a sharp cutting edge), and a removable staple cartridge 768.

The position, movement, displacement, and/or translation of a linear displacement member, such as the knife 764, can be measured by an absolute positioning system, sensor arrangement, and position sensor 784. Because the knife 764 is coupled to a longitudinally movable drive member, the position of the knife 764 can be determined by measuring the position of the longitudinally movable drive member employing the position sensor 784. Accordingly, in the following description, the position, displacement, and/or translation of the knife 764 can be achieved by the position sensor 784 as described herein. A control circuit 760 may be programmed to control the translation of the displacement member, such as the knife 764. The control circuit 760, in some examples, may comprise one or more microcontrollers, microprocessors, or other suitable processors for executing instructions that cause the processor or processors to control the displacement member, e.g., the knife 764, in the manner described. In one aspect, a timer/counter 781 provides an output signal, such as the elapsed time or a digital count, to the control circuit 760 to correlate the position of the knife 764 as determined by the position sensor 784 with the output of the timer/counter 781 such that the control circuit 760 can determine the position of the knife 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the knife 764 via a transmission 756. The transmission 756 may include one or more gears or other linkage components to couple the motor 754 to the knife 764. In one aspect, the transmission is coupled to a trocar actuator of a circular stapler to advance or retract the trocar. A position sensor 784 may sense a position of the knife 764, the trocar, or the anvil 766, or a combination thereof. The position sensor 784 may be or include any type of sensor that is capable of generating position data that indicate a position of the knife 764. In some examples, the position sensor 784 may include an encoder configured to provide a series of pulses to the control circuit 760 as the knife 764 translates distally and proximally. The control circuit 760 may track the pulses to determine the position of the knife 764. Other suitable position sensors may be used, including, for example, a proximity sensor. Other types of position sensors may provide other signals indicating motion of the knife 764. Also, in some examples, the position sensor 784 may be omitted. Where the motor 754 is a stepper motor, the control circuit 760 may track the position of the knife 764 by aggregating the number and direction of steps that the motor 754 has been instructed to execute. The position sensor 784 may be located in the end effector 752 or at any other portion of the instrument.

In a circular stapler implementation, the transmission 756 element may be coupled to the trocar to advance or retract the trocar, to the knife 764 to advance or retract the knife 764, or the anvil 766 to advance or retract the anvil 766. These functions may be implemented with a single motor using suitable clutching mechanism or may be implemented using separate motors as shown with reference to FIG. 98, for example. In one aspect, the transmission 756 is part of a closure system that comprises a trocar 201904 and a trocar actuator 201906 as discussed in more detail with reference to FIGS. 101A-101C hereinbelow. Accordingly, the control circuit 760 controls the motor control circuit 758 to control the motor 754 to advance or retract the trocar. Similarly, the motor 754 may be configured to advance or retract the knife 764 and advance or retract the anvil 766. A torque sensor may be provided to measure the torque applied by the shaft of the motor 754 to the transmission components 756 employed in advancing and retracting the trocar, the knife 764, or the anvil 766, or combinations thereof. The position sensor 784 may include a variety of sensors to track the position of the trocar, the knife 764, or the anvil 766, or any combination thereof. Other sensors 788 may be employed to measure a variety of parameters including position or velocity of the trocar, the knife 764, or the anvil 766, or any combination thereof. The torque sensor, the position sensor 784, and the sensors 788 are coupled to the control circuit 760 as inputs to various processes for controlling the operation of the surgical instrument 750 in a desired manner.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors. In one aspect, the sensors 788 may be configured to determine the position of a trocar of a circular stapler.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the knife 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a knife 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or knife 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, a knife 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the knife 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

The surgical instrument 750 may comprise wired or wireless communication circuits to communicate with the modular communication hub as shown in FIGS. 1-6 and 9-13. The surgical instrument 750 may be the motorized circular stapling instrument 201800 (FIG. 100), 201000 (FIGS. 103-104).

Figure 100:
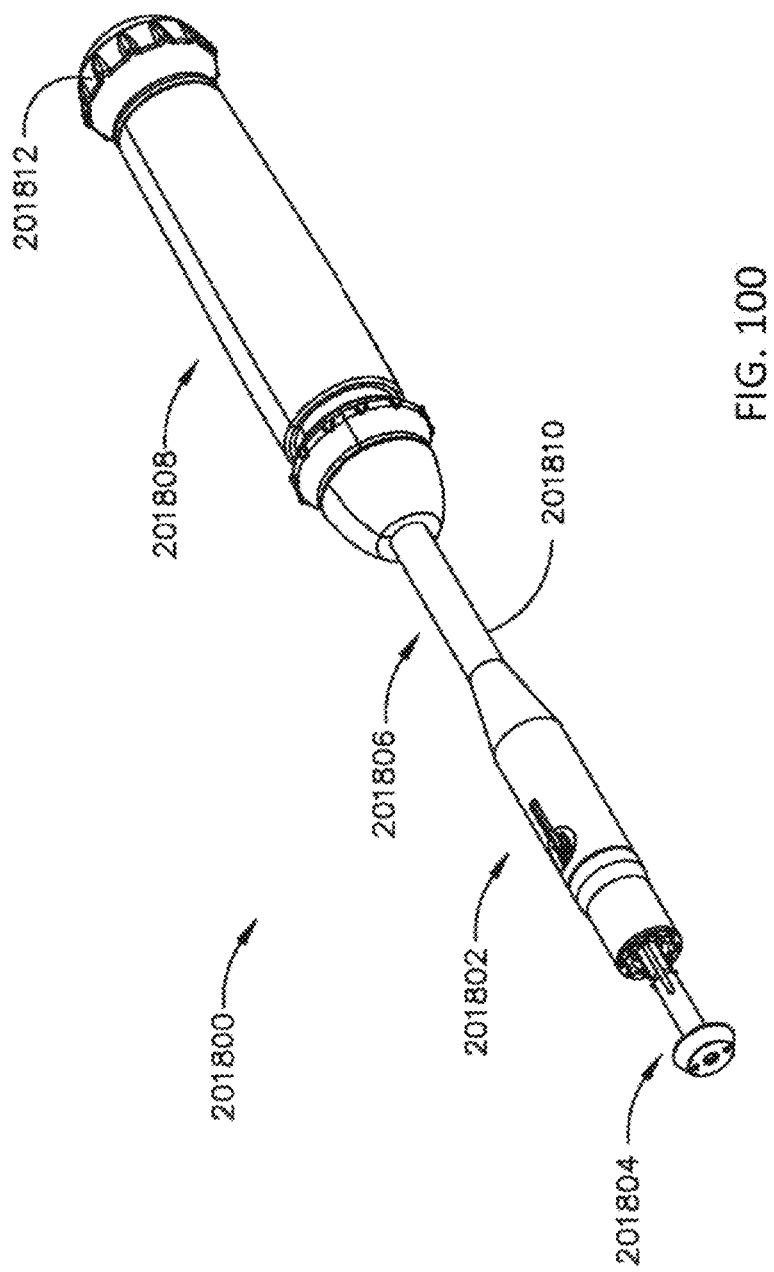
FIG. 100 depicts a perspective view of a circular stapling surgical instrument, in accordance with at least one aspect of the present disclosure.

FIG. 100 shows an example motorized circular stapling instrument 201800. The Instrument 201800 of this example comprises a stapling head assembly 201802, an anvil 201804, a shaft assembly 201806, a handle assembly 201808, and a rotation knob 201812. The stapling head assembly 201802 selectively couples with the anvil 201804. The stapling head assembly 201802 is operable to clamp tissue between staple pockets and staple forming pockets of the anvil 201804. The stapling head assembly 201802 comprises a cylindrical knife that is operable to sever tissue captured between stapling head assembly 201802 and the anvil 201804. The stapling head assembly 201802 drives staples through the tissue captured between stapling head assembly 201802 and the anvil 201804. The stapling instrument 201800 may be used to create a secure anastomosis (e.g., an end-to-end anastomosis) within a gastro-intestinal tract of a patient or elsewhere. An outer tubular member 201810 is coupled to the actuator handle assembly 201808. The outer tubular member 201810 provides a mechanical ground between the stapling head assembly 201802 and the handle assembly 201808.

The stapling head assembly 201802 is operable to clamp tissue, sever tissue, and staple tissue all in response to a single rotary input communicated via the shaft assembly 201806. Accordingly, actuation inputs translated linearly through shaft assembly 201806 are not required for the stapling head assembly 201802, though the stapling head assembly 201802 may comprise a translating clutch feature. By way of example only, at least part of stapling head assembly 201802 may be configured in accordance with at least some of the teachings of U.S. patent application Ser. No. 13/716,318, entitled "Motor Driven Rotary Input Circular Stapler with Modular End Effector," filed on Dec. 17, 2012, and published as U.S. Pat. Pub. No. 2014/0166728 on Jun. 19, 2014, the disclosure of which is incorporated by reference herein. Other suitable configurations for the stapling head assembly 201802 will be apparent to those of ordinary skill in the art in view of the teachings herein.

The shaft assembly 201806 couples the handle assembly 201808 with the stapling head assembly 201802. The shaft assembly 201806 comprises a single actuation feature, rotary driver actuator. Additional details about the handle assembly 201808 and the rotary driver actuator are disclosed in U.S. patent application Ser. No. 16/182,229, titled ADJUSTMENT OF STAPLE HEIGHT OF AT LEAST ONE ROW OF STAPLES BASED ON THE SENSED TISSUE THICKNESS OR FORCE IN CLOSING, filed Nov. 6, 2018, which is herein incorporated by reference in its entirety.

Figure 101A:
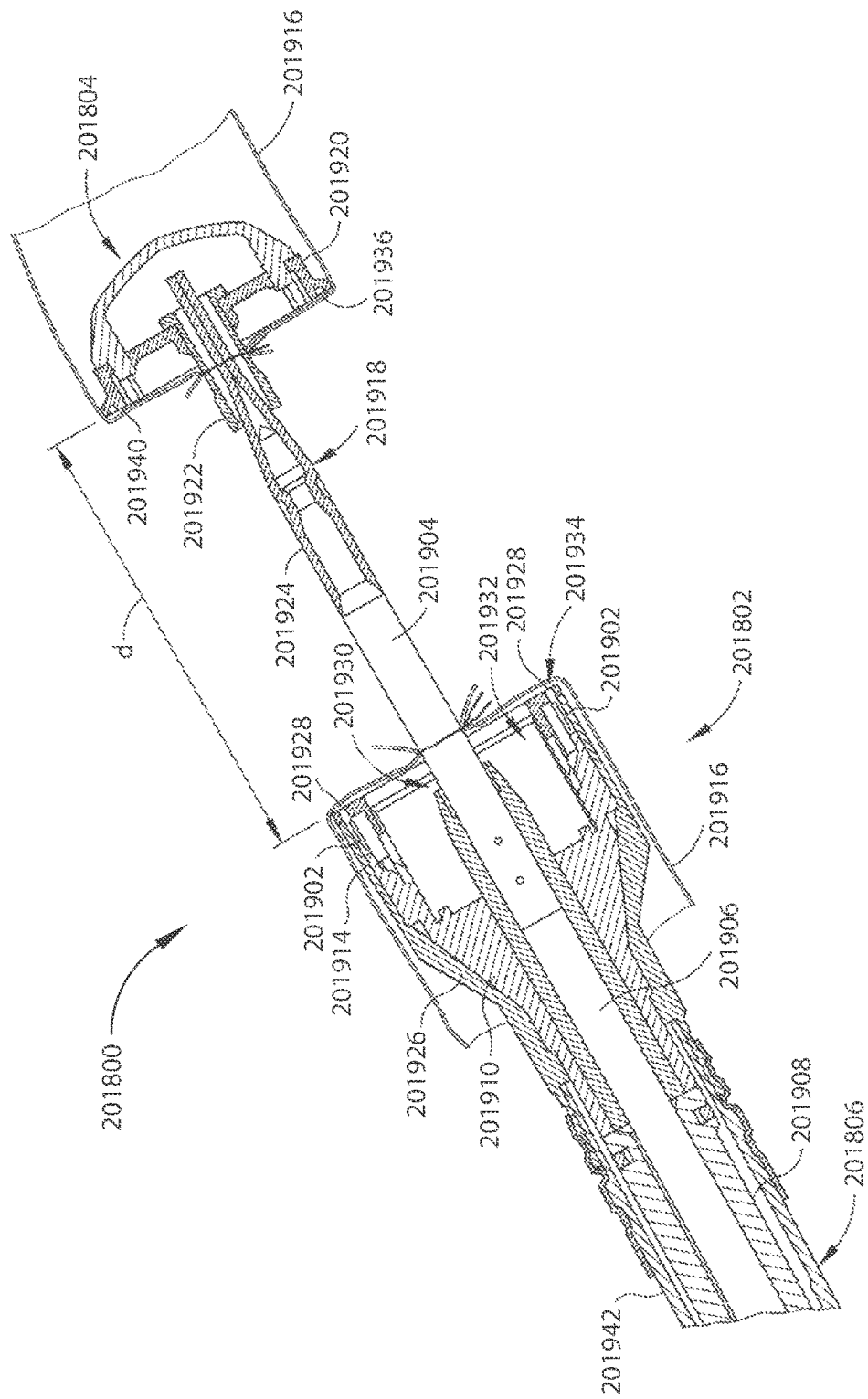
FIG. 101A depicts an enlarged longitudinal cross-section view of a stapling head assembly of the instrument of FIG. 100 showing an anvil in an open position, in accordance with at least one aspect of the present disclosure.
Figure 101B:
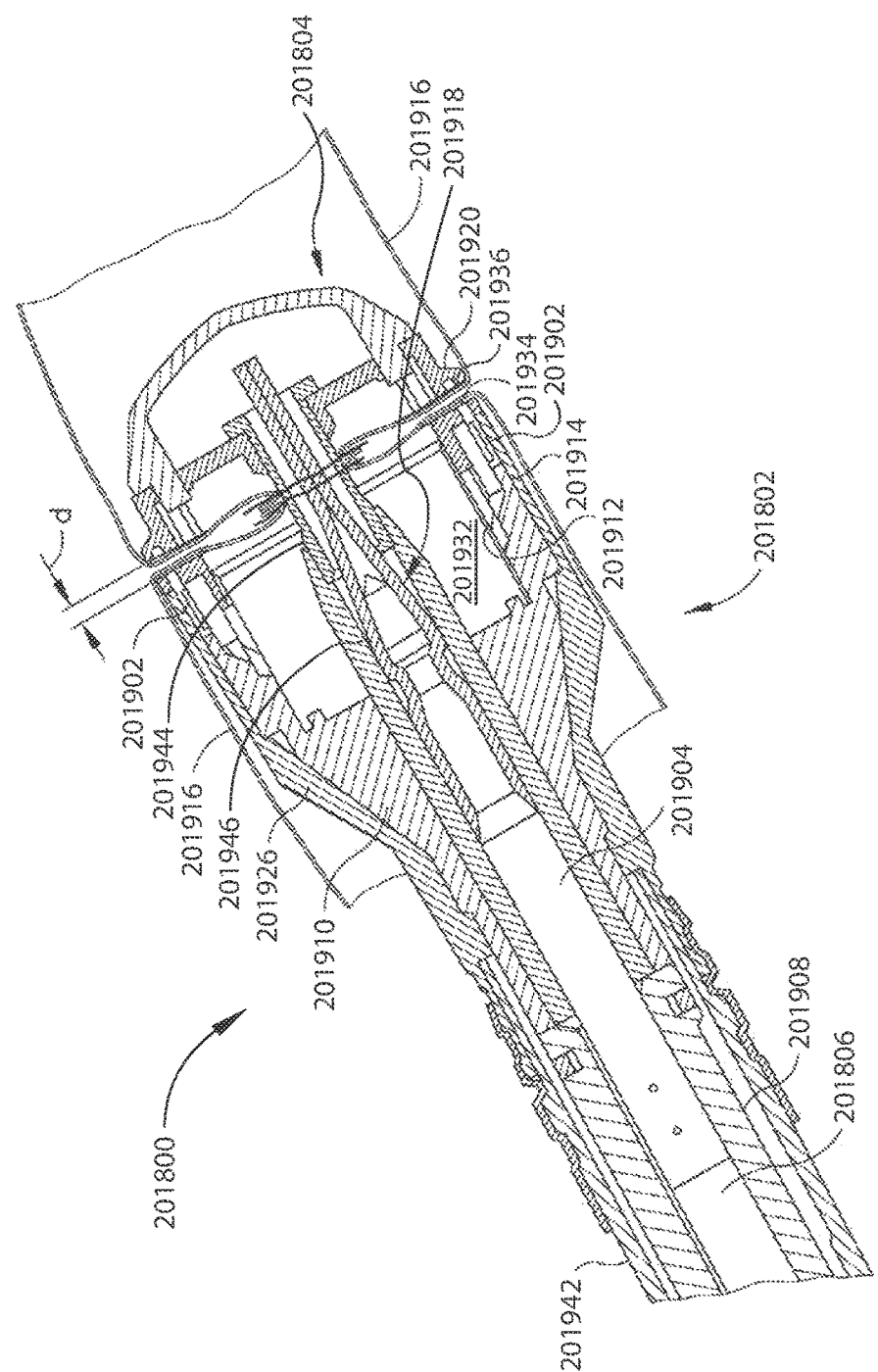
FIG. 101B depicts an enlarged longitudinal cross-sectional view of the stapling head assembly of the instrument of FIG. 100 showing the anvil in a closed position, in accordance with at least one aspect of the present disclosure.
Figure 101C:
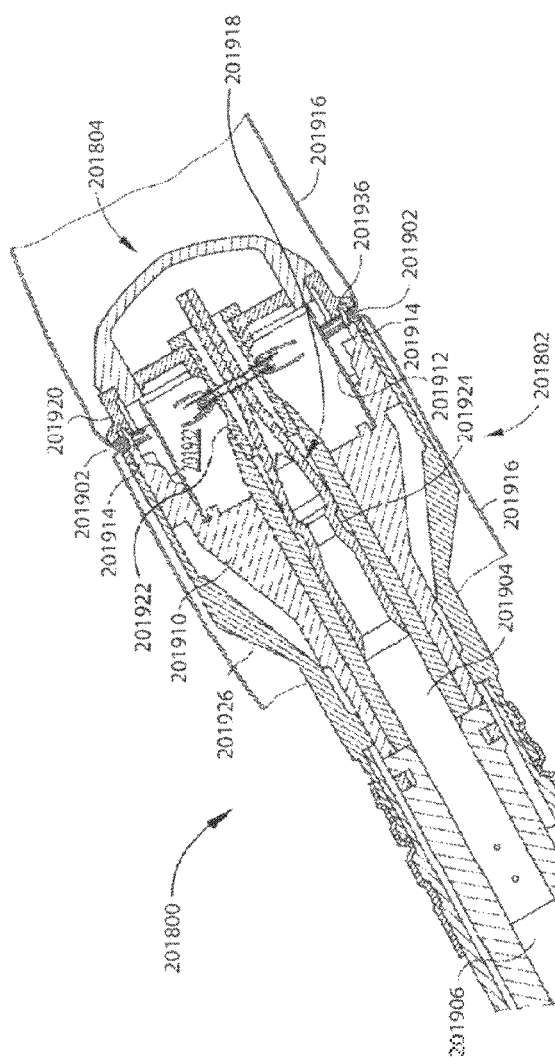
FIG. 101C depicts an enlarged longitudinal cross-sectional view of the stapling head assembly of the instrument of FIG. 100 showing a staple driver and blade in a fired position, in accordance with at least one aspect of the present disclosure.

Referring now to FIGS. 101A-101C, in the present example, instrument 201800 comprises a closure system and a firing system. The closure system comprises a trocar 201904, a trocar actuator 201906, and a rotating knob 201812 (FIG. 100). As previously discussed, the rotation knob 201812 may be coupled to a motor to rotate the rotation knob 201812 in a clockwise or counterclockwise direction. An anvil 201804 may be coupled to a distal end of trocar 201904. Rotating knob 201812 is operable to longitudinally translate trocar 201904 relative to stapling head assembly 201802, thereby translating anvil 201804 when anvil 201804 is coupled to trocar 201904, to clamp tissue between anvil 201804 and stapling head assembly 201804. The firing system comprises a trigger, a trigger actuation assembly, a driver actuator 201908, and a staple driver 201910. Staple driver 201910 includes a cutting element, such as a knife 201912, configured to sever tissue when staple driver 201910 is actuated longitudinally. In addition, staples 201902 are positioned distal to a plurality of staple driving members 201914 of staple driver 201910 such that staple driver 201910 also drives staples 201902 distally when staple driver 201910 is actuated longitudinally. Thus, when staple driver 201910 is actuated via driver actuator 201908, knife 201912 members 201914 substantially simultaneously sever tissue 201916 and drive staples 201902 distally relative to stapling head assembly 201802 into tissue. The components and functionalities of the closure system and firing system will now be described in greater detail.

As shown in FIGS. 101A-101C, anvil 201804 is selectively coupleable to instrument 201800 to provide a surface against which staples 201902 may be bent to staple material contained between stapling head assembly 201802 and anvil 201804. Anvil 201804 of the present example is selectively coupleable to a trocar or pointed rod 201904 that extends distally relative to stapling head assembly 201802. Referring to FIGS. 101A-101C, anvil 201804 is selectively coupleable via the coupling of a proximal shaft 201918 of anvil 201904 to a distal tip of trocar 201904. Anvil 201804 comprises a generally circular anvil head 201920 and a proximal shaft 201918 extending proximally from anvil head 201920. In the example shown, proximal shaft 201918 comprises a tubular member 201922 having resiliently biased retaining clips 201924 to selectively couple anvil 201804 to trocar 201904, though this is merely optional, and it should be understood that other retention features for coupling anvil 201804 to trocar 201904 may be used as well. For example, C-clips, clamps, threading, pins, adhesives, etc. may be employed to couple anvil 201804 to trocar 201904. In addition, while anvil 201804 is described as selectively coupleable to trocar 201904, in some versions proximal shaft 201918 may include a one-way coupling feature such that anvil 201804 cannot be removed from trocar 201904 once anvil 201804 is attached. By way of example one-way features include barbs, one way snaps, collets, collars, tabs, bands, etc. Of course still other configurations for coupling anvil 201804 to trocar 201904 will be apparent to one of ordinary skill in the art in view of the teachings herein. For instance, trocar 201904 may instead be a hollow shaft and proximal shaft 201918 may comprise a sharpened rod that is insertable into the hollow shaft.

Anvil head 201920 of the present example comprises a plurality of staple forming pockets 201936 formed in a proximal face 201940 of anvil head 201920. Accordingly, when anvil 201804 is in the closed position and staples 201902 are driven out of stapling head assembly 201802 into staple forming pockets 201936, as shown in FIG. 101C, legs 201938 of staples 201902 are bent to form completed staples.

With anvil 201804 as a separate component, it should be understood that anvil 201804 may be inserted and secured to a portion of tissue 201916 prior to being coupled to stapling head assembly 201802. By way of example only, anvil 201804 may be inserted into and secured to a first tubular portion of tissue 201916 while instrument 201800 is inserted into and secured to a second tubular portion of tissue 201916. For instance, the first tubular portion of tissue 201916 may be sutured to or about a portion of anvil 201804, and the second tubular portion of tissue 201916 may be sutured to or about trocar 201904.

As shown in FIG. 101A, anvil 201804 is then coupled to trocar 201904. Trocar 201904 of the present example is shown in a distal most actuated position. Such an extended position for trocar 201904 may provide a larger area to which tissue 201916 may be coupled prior to attachment of anvil 201804. In addition, the extended position of trocar 20190400 may also provide for easier attachment of anvil 201804 to trocar 201904. Trocar 201904 further includes a tapered distal tip. Such a tip may be capable of piercing through tissue and/or aiding the insertion of anvil 201804 on to trocar 201904, though the tapered distal tip is merely optional. For instance, in other versions trocar 201904 may have a blunt tip. In addition, or in the alternative, trocar 201904 may include a magnetic portion (not shown) which may attract anvil 201804 towards trocar 201904. Of course still further configurations and arrangements for anvil 201804 and trocar 201904 will be apparent to one of ordinary skill in the art in view of the teachings herein.

When anvil 201804 is coupled to trocar 201904, the distance between a proximal face of the anvil 201804 and a distal face of stapling head assembly 201802 defines a gap distance d. Trocar 201904 of the present example is translatable longitudinally relative to stapling head assembly 201802 via an adjusting knob 201812 (FIG. 100) located at a proximal end of actuator handle assembly 201808 (FIG. 100), as will be described in greater detail below. Accordingly, when anvil 201804 is coupled to trocar 201904, rotation of adjusting knob 201812 enlarges or reduces gap distance d by actuating anvil 201804 relative to stapling head assembly 201802. For instance, as shown sequentially in FIGS. 101A-101B, anvil 201804 is shown actuating proximally relative to actuator handle assembly 201808 from an initial, open position to a closed position, thereby reducing the gap distance d and the distance between the two portions of tissue 201916 to be joined. Once the gap distance d is brought within a predetermined range, stapling head assembly 201802 may be fired, as shown in FIG. 101C, to staple and sever tissue 201916 between anvil 201804 and stapling head assembly 201802. Stapling head assembly 201802 is operable to staple and sever tissue 201916 by a trigger of actuator handle assembly 201808, as will be described in greater detail below.

Still referring to FIGS. 101A-101C, a user sutures a portion of tissue 201916 about tubular member 201944 such that anvil head 201920 is located within a portion of the tissue 201916 to be stapled. When tissue 201916 is attached to anvil 201804, retaining clips 201924 and a portion of tubular member 201922 protrude out from tissue 201916 such that the user may couple anvil 201804 to trocar 201904. With tissue 201916 coupled to trocar 201904 and/or another portion of stapling head assembly 201802, the user attaches anvil 201804 to trocar 201904 and actuates anvil 201804 proximally towards stapling head assembly 201802 to reduce the gap distance d. Once instrument 201800 is within the operating range, the user then staples together the ends of tissue 201916, thereby forming a substantially contiguous tubular portion of tissue 201916.

Figure 102:
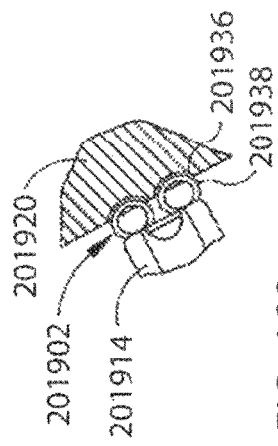
FIG. 102 depicts an enlarged partial cross-sectional view of a staple formed against the anvil, in accordance with at least one aspect of the present disclosure.

Stapling head assembly 201802 of the present example is coupled to a distal end of shaft assembly 201806 and comprises a tubular casing 201926 housing a slidable staple driver 201910 and a plurality of staples 201902 contained within staple pockets 201928. Shaft assembly 201806 of the present example comprises an outer tubular member 201942 and a driver actuator 201908. Staples 201902 and staple pockets 201928 are disposed in a circular array about tubular casing 201926. In the present example, staples 201902 and staple pockets 201928 are disposed in a pair of concentric annular rows of staples 201902 and staple pockets 201928. Staple driver 201910 is operable to actuate longitudinally within tubular casing 201926 in response to rotation of actuator handle assembly 201808 (FIG. 100). As shown in FIGS. 101A-101C, staple driver 201910 comprises a flared cylindrical member having a trocar opening 201930, a central recess 201932, and a plurality of members 201914 disposed circumferentially about central recess 201932 and extending distally relative to shaft assembly 201806. Each member 201914 is configured to contact and engage a corresponding staple 201902 of the plurality of staples 201902 within staple pockets 201928. Accordingly, when staple driver 201910 is actuated distally relative to actuator handle assembly 201808, each member 201914 drives a corresponding staple 201902 out of its staple pocket 201928 through a staple aperture 201934 formed in a distal end of tubular casing 201926. Because each member 201914 extends from staple driver 201910, the plurality of staples 201902 is driven out of stapling head assembly 201802 at substantially the same time. When anvil 201804 is in the closed position, staples 201902 are driven into staple forming pockets 201936 to bend legs 201938 of the staples 201902, thereby stapling the material located between anvil 201804 and stapling head assembly 201808. FIG. 102 depicts by way of example staple 201902 driven by a member 201914 into a staple forming pocket 201928 of anvil 201804 to bend legs 201938.

The motorized circular stapling instruments 201800, 201000 described herein with reference to FIGS. 100-103 may be controlled using any of the control circuits described in connection with FIGS. 7-8 and 16-17. For example, the control system 470 described with reference to FIG. 7. Further, the motorized circular stapling instrument 201800 may be employed in a hub and cloud environment as described in connection with FIGS. 1-6 and 9-13.

FIG. 103 is a partial cutaway view of a powered circular stapling device 201000 comprising a circular stapling head assembly 201002 and an anvil 201004, in accordance with at least one aspect of the present disclosure. The powered circular stapling device 20100 is shown clamping a first portion of tissue 201006 and a second portion of tissue 201008 between the anvil 201004 and the circular stapling head assembly 201002. Compression of the tissue 201006, 201008 between the anvil 201004 and the circular stapling head assembly 201002 is measured with a sensor 201018, such as a strain gauge, for example. The circular stapling head assembly 201002 also includes a knife 201019 that can be advanced at different rates to cut through tissue 201006, 201008 clamped between the anvil 201004 and the circular stapling head assembly 201002 after the inner and outer rows of staples 201010, 201014 are fired and formed against corresponding staple forming pockets 201011, 201015 of the anvil 201004.

FIG. 104 is a partial top view of the circular stapling head assembly 201002 shown in FIG. 103 showing a first row of staples 201010 (inner staples) and a second row of staples 201014 (outer staples), in accordance with at least one aspect of the present disclosure. The inner row of staples 201010 and the second row of staples 201014 are independently actuatable by first and second staple drivers 201012, 201016.

With reference now to FIGS. 103 and 104, once the tissue 201006, 201008 is clamped between the anvil 201004 and the circular stapling head assembly 201002, a first gap δ1 is set for the inner row of staples 201010 and a second gap δ2 is set for the outer row of staples 201014. As the tissue compression is increased or the tissue gap δ1, δ2 is decreased, and the nominal staple height for the center of a window is adjusted. The first staple driver 201012 drives the inner row of staples 201010 through the tissue 201006, 201008 and the inner row of staples 201010 are formed against the anvil 201004. Subsequently, the second staple driver 201016 independently drives the outer row of staples 201010 through the tissue 201006, 201008 and the outer row of staples 201014 are formed against the anvil 201004.

Figure 105:
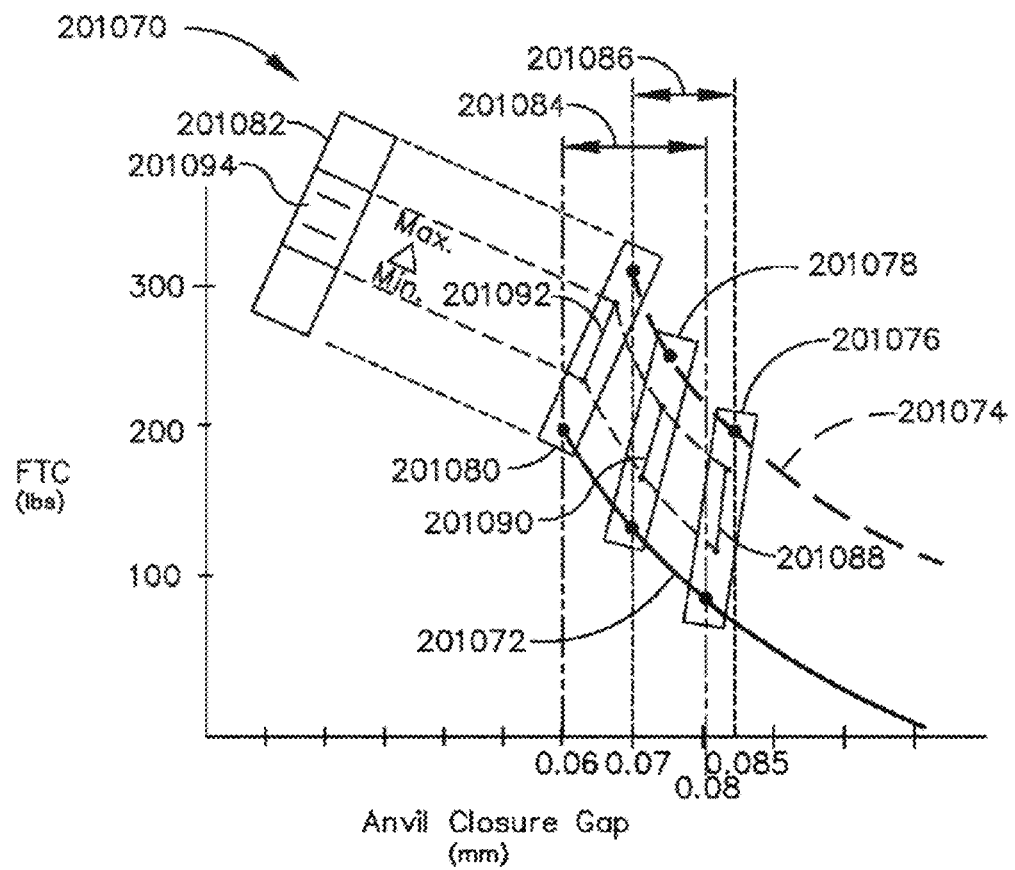
FIG. 105 is a graphical representation of viable staple firing range as indicated by usable staple height windows based on the tissue gap, closure force (FTC), or tissue creep stabilization sensed by the device or combinations thereof, in accordance with at least one aspect of the present disclosure.

The independently actuatable staple rows 201010, 201014 may be formed based on the FTC clamped by the anvil 201004 on the tissue 201006, 201008 or the tissue gap δ1, δ2 between the anvil 201004 clamp and the circular stapling head assembly 201002. Adjustment of the staple height of at least one row of staples based on the sensed tissue thickness or FTC focuses on the adjustment of a selection window based on tissue 201006, 201008 thickness/load in closing. In other aspects, the user adjustable range of selectable staple heights may be varied based on the tissue loading detected during an anvil 201004 retraction operation. As the tissue compression (e.g., FTC) is increased or the tissue gap δ1, δ2 is decreased the nominal staple height for the center of the window may be adjusted as described herein with reference to FIG. 105. In other aspects, the adjustment of the window range of acceptable staples is displayed as the compression is increased or the tissue gap decreased. In other aspects, once the tissue compression is completed then stabilization of the tissue, can further adjust the acceptable range based on the rate of tissue creep and time waited.

Figure 106:
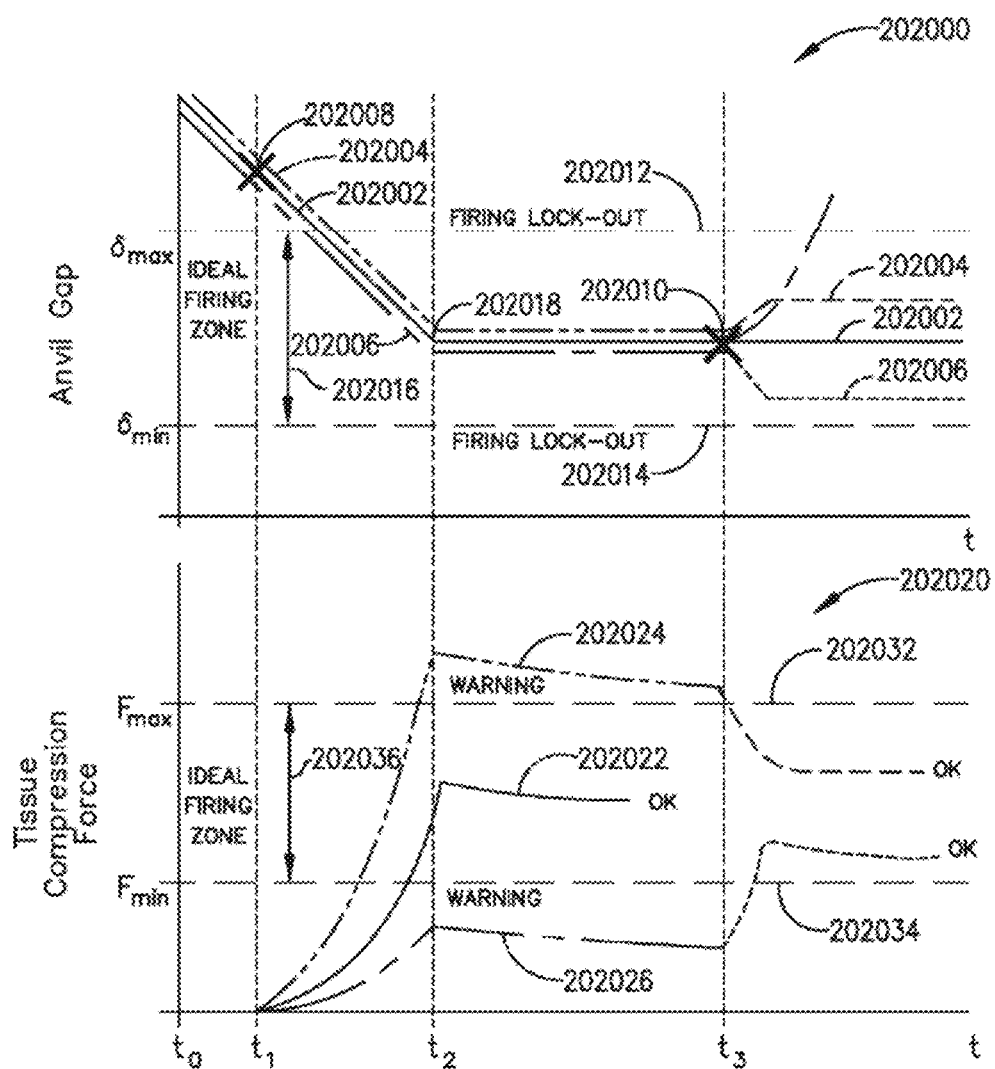
FIG. 106 is a graphical representation of a first pair of graphs depicting anvil gap and tissue compression force verse time for illustrative firings of a stapling instrument, in accordance with at least one aspect of the present disclosure.

FIG. 106 is a graphical representation of a first pair of graphs 202000, 202020 depicting anvil gap and tissue compression force F verse time for illustrative firings of a stapling instrument, in accordance with at least one aspect of the present disclosure. The tissue compression force F also may be expressed as force to close (FTC). The top graph 202000 depicts three separate anvil gap curves 202002, 202004, 202006 representative of anvil gap closure over time at three separate tissue compression forces, as shown in the bottom graph 202020, where anvil gap δ is shown along the vertical axis and time is shown along the horizontal axis. The anvil gap curves 202002, 202004, 202006 represent anvil closure of a powered circular stapling device 202080 (FIG. 108) as a function of time t for tissue of variable stiffness, constant thickness, and constant anvil gap δ, until adjustment(s) of the anvil gap δ are made by a control algorithm. A control algorithm implemented by any of the control circuits described herein with reference to FIGS. 7-8 and 98-99 can be configured to adjust the anvil gap according to the sensed tissue compression force F compared to one or more different thresholds. Additional details about the control circuits are disclosed in U.S. patent application Ser. No. 16/182,229, titled ADJUSTMENT OF STAPLE HEIGHT OF AT LEAST ONE ROW OF STAPLES BASED ON THE SENSED TISSUE THICKNESS OR FORCE IN CLOSING, filed Nov. 6, 2018, which is herein incorporated by reference in its entirety.

Figure 108:
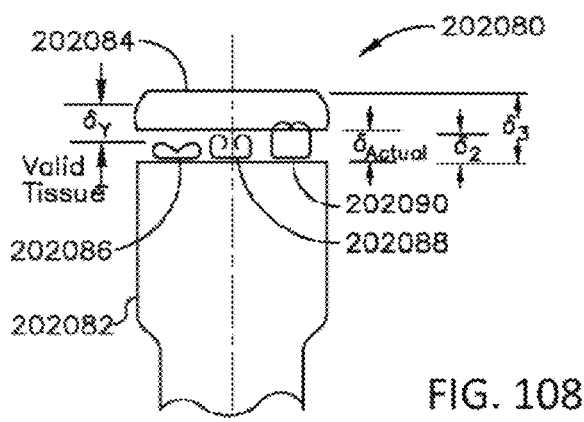
FIG. 108 is a schematic diagram of a powered circular stapling device illustrating valid tissue gap, actual gap, normal range gap, and out of range gap, in accordance with at least one aspect of the present disclosure.

Turning now briefly to FIG. 108, there is shown a schematic diagram of a powered circular stapling device 202080 illustrating valid tissue gap δy, actual gap δactual, normal range gap δ2, and out of range gap δ3, in accordance with at least one aspect of the present disclosure. The powered circular stapling device 202080 includes a circular stapler 202082 and an anvil 202084, which is retracted from an open position to a closed position to clamp tissue between the anvil 201084 and the stapler 202082. Once the anvil 202084 is fully clamped on the tissue, there will be a gap δ defined between the anvil 202084 and the stapler 202082. When the circular stapler 202082 is fired (e.g., actuated), the staple formation is dependent upon the tissue gap δ. As shown in FIG. 108, for a normal range gap δ2, the staples 202088 are well formed. When the gap δ is too small, the staples 202086 are too tightly formed and when the gap δ is too large, the staples 202090 are too loosely formed.

Turning back now to FIG. 106, with reference to the top and bottom graphs 202000, 202020 and FIG. 108, at time t0 the anvil 201084 is initially open beyond the maximum anvil gap δmax before the anvil 201084 reaches the initial tissue contact point 202008 at time t1. As shown, due to constant tissue thickness, t1 is a common tissue contact point for tissue having variable tissue stiffness. At time t1, the anvil gap δ is still outside of the ideal firing zone 202016 shown between a maximum anvil gap δmax defining a upper firing lockout threshold 202012, and a minimum anvil gap δmin 202014, defining a lower firing lockout threshold 202014. From the initial tissue contact point 202008 at time t1 as the anvil 201084 continues to close the tissue compression force F starts to increase. The tissue compression force F will vary as a function of the biomechanical properties of tissue in terms of stiffness. As indicated in the bottom graph 202020, tissue of normal stiffness is represented by a first tissue compression force curve 202022, tissue of high stiffness is represented by a second tissue compression force curve 202024, and tissue of low stiffness is represented by a third tissue compression force curve 202026.

As the anvil 201084 continues to close between the maximum anvil gap δmax and the minimum anvil gap the anvil gap δmin, reaches a point of constant anvil gap 202018 at time t2. As shown in the lower graph 202020, at time t2 the tissue compression force F for tissue of normal stiffness represented by the first tissue compression force curve 202022 is within the ideal firing zone 202036, which is defined between a maximum compression force Fmax, defining an upper warning threshold 202032, and a minimum compression force Fmin, defining a lower warning threshold 202034. At time t2, the tissue compression force F for tissue of high stiffness represented by the second tissue compression force curve 202024 is above the upper warning threshold 202032 outside the ideal firing zone 202036 and the tissue compression force for tissue of low stiffness represented by the third tissue compression force curve 202026 is below the lower warning threshold 202034 outside the ideal firing zone 202036.

From time t2 to time t3, the anvil 201084 is maintained at a constant gap δ, as shown in the upper graph 202000, by the three anvil gap curves 202002, 202004, 202006. This period of constant gap δ, allows for tissue creep, as shown in the lower graph 202020, during which the average tissue compression force F slowly drops as shown by the three tissue compression force curves 202022, 202024, 202026. Tissue creep is a phase that is entered after tissue is grasped and the average tissue compression force F reaches a predetermined threshold and the closure motion of the anvil 201084 such that the anvil 201084 and the stapler 202082 hold the tissue therebetween for a predetermined time before initiating the firing phase in which the staples and knife are deployed. During the tissue creep phase the average tissue compression force F drops over the time period between t2 and t3. Tissue, in part because it is composed of solid and liquid material, tends to elongate when compressed. One way to account for this property is "tissue creep." When tissue is compressed, a certain amount of tissue creep can occur.

Affording the compressed tissue an adequate amount of time under certain circumstances to accomplish tissue creep can therefore produce benefits. One benefit can be adequate staple formation. This can contribute to a consistent staple line. Accordingly, a certain time can be given to enable tissue creep prior to firing.

With reference now also to FIG. 99, after a period where the anvil gap δ is maintained constant to allow for tissue creep, at time t3, prior to deploying the staples, the control circuit 760 at point 202010 determines whether a possible adjustment of the anvil 766 relative to the staple cartridge 764 (anvil 201804 and stapler 202084 in FIG. 108) is necessary. Accordingly, the control circuit 760 determines if the tissue compression force F is between the ideal firing zone 202036, above the maximum compression force Fmax threshold 202032, or below the minimum compression force Fmin threshold 202034 and makes any necessary adjustments to the anvil gap δ. If the tissue compression force F is between the ideal firing zone 202036, the control circuit 760 deploys the staples in the staple cartridge 768 and deploys the knife 764.

If the tissue compression force F is above the maximum compression force Fmax threshold 202032, the control circuit 760 is configured to register a warning that the compression force is too tight and to adjust the anvil gap δ, increase the wait time before firing, lower the firing speed, or enable a firing lockout, or any combination thereof. The control circuit 760 can adjust the anvil gap δ by advancing the anvil 766 distally, e.g. away, from the staple cartridge 768 (anvil 201804 and stapler 202084 in FIG. 108) to increase the anvil gap δ as shown by the segment of the anvil gap curve 2002004 beyond time t3. As shown by the segment of the tissue compression force curve 202024 beyond time t3, after the control circuit 760 increases the anvil gap δ, the tissue compression force F decreases into the ideal firing zone 202036.

If the tissue compression force F is below the minimum compression force Fmin threshold 202034, the control circuit 760 is configured to register a warning that the compression force is too loose and to adjust the anvil gap δ, proceed with caution, or enable a firing lockout, or any combination thereof. The control circuit 760 is configured to adjust the anvil gap δ by retracting the anvil 766 proximally, e.g. toward, the staple cartridge 768 (anvil 201804 and stapler 202084 in FIG. 108) to decrease the anvil gap δ as shown by the segment of the anvil gap curve 2002006 beyond time t3, As shown by the segment of the tissue compression force curve 202026 beyond time t3, after decreasing the anvil gap δ, the tissue compression force F increases into the ideal firing zone 202036.

Figure 107:
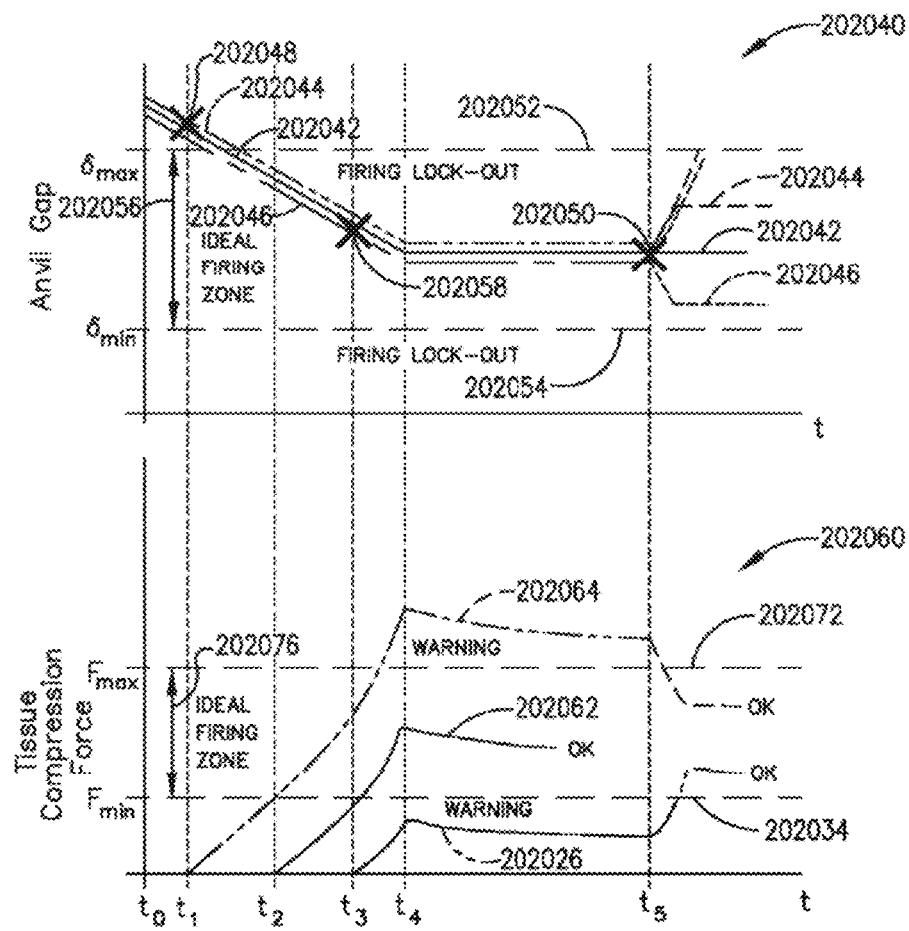
FIG. 107 is a graphical representation of a second pair of graphs depicting anvil gap and tissue compression force verse time for illustrative firings of a stapling instrument, in accordance with at least one aspect of the present disclosure.

Turning now to FIG. 107, there is shown a graphical representation of a second pair of graphs 202040, 202060 depicting anvil gap and tissue compression force F verse time for illustrative firings of a stapling instrument, in accordance with at least one aspect of the present disclosure. The top graph 202040 depicts three separate anvil gap curves 202042, 202046, 202046 representative of anvil gap closure over time at three separate tissue thicknesses, where anvil gap δ is shown along the vertical axis and time is shown along the horizontal axis. The anvil gap curves 202042, 202044, 202046 represent anvil closure of a powered circular stapling device 202080 (FIG. 108) as a function of time t for tissue of variable thickness, constant stiffness, and constant anvil gap δ, until adjustment(s) of the anvil gap δ are made by a control algorithm. A control algorithm implemented by any of the control circuits described herein with reference to FIGS. 7-8 and 98-99 can be configured to adjust the anvil gap according to the sensed tissue compression force F compared to one or more different thresholds.

With reference now to the top and bottom graphs 202040, 202060 and FIG. 108, at time t0 the anvil 201084 is initially open beyond the maximum anvil gap δmax before the anvil 201084 reaches a first tissue contact point 202048 for tissue of high thickness at time t1, where the tissue compression force curve 202064 for tissue of high thickness starts to increase. At time t1, the anvil gap δ is still outside of the ideal firing zone 202056 shown between a maximum anvil gap δ max, defining a upper firing lockout threshold 202052, and a minimum anvil gap δ min, defining a lower firing lockout threshold 202054. As shown, due to constant tissue stiffness and variable tissue thickness, the anvil 201084 contacts the tissue at different times. For example, time t1 is a first tissue contact point 202048 for tissue having high tissue thickness, time t2 is a second tissue contact point for tissue of normal thickness, and time t3 is a third tissue contact point 202058 for tissue of low thickness.

The first tissue compression force curve 202062 represents the compression force for tissue of normal thickness and starts to increase at time t2 when tissue of normal thickness initially contacts the anvil 201804. The second tissue compression force curve 202064 represents tissue of high thickness and starts to increase at time t1 when tissue of high thickness initially contacts the anvil 201804. The third tissue compression force curve 202066 represents tissue of low thickness and starts to increase at time t3 when tissue of low thickness initially contacts the anvil 201804. At the second and third tissue contact points at times t2 and t3, for tissue of normal and low thickness, the anvil gap δ is within the ideal firing zone 202056, 202076. The tissue compression force F will vary as a function of the biomechanical properties of tissue thickness. As indicated in the bottom graph 202040, tissue of normal thickness is represented by a first tissue compression force curve 202042, tissue of high thickness is represented by a second tissue compression force curve 202044, and tissue of low stiffness is represented by a third tissue compression force curve 202066. From the initial tissue contact points at times t1, t2, t3 as the anvil 201084 continues to close, the tissue compression forces for each curve 202062, 202064, 2020066 start to increase until time t4 where the anvil gap reaches a predetermined value and remains constant between t4 and t5 until the stapler 202082 is ready to fire.

As the anvil 201084 continues to close between the maximum anvil gap δ max and the minimum anvil gap δ min, the anvil gap δ reaches a point of constant anvil gap at time t4. As shown in the lower graph 202060, at time t4 the tissue compression force F for tissue of normal thickness represented by the first tissue compression force curve 202062 is within the ideal firing zone 202076, which is defined between a maximum compression force Fmax, defining an upper warning threshold 202072, and a minimum compression force Fmin, defining a lower warning threshold 202074. At time t4 the tissue compression force F for tissue of high thickness represented by the second tissue compression force curve 202064 is above the upper warning threshold 202072 outside the ideal firing zone 202076 and the tissue compression force F for tissue of low thickness represented by the third tissue compression force curve 202066 is below the lower warning threshold 202074 outside the ideal firing zone 202076.

From time t4 to time t5, the anvil 201084 is maintained at a constant gap δ, as shown in the upper graph 202040, by the three anvil gap curves 202042, 202044, 202046. This period of constant gap δ, allows for tissue creep, as shown in the lower graph 202060, during which the average tissue compression force F slowly drops as shown by the three tissue compression force curves 202062, 202064, 202066. Tissue creep is a phase that is entered after tissue is grasped and the average tissue compression force F reaches a predetermined threshold and the closure motion of the anvil 201084 such that the anvil 201084 and the stapler 202082 hold the tissue therebetween for a predetermined time before initiating the firing phase in which the staples and knife are deployed. During the tissue creep phase the average tissue compression force F drops over the time period between t2 and t3. Tissue, in part because it is composed of solid and liquid material, tends to elongate when compressed. One way to account for this property is "tissue creep." When tissue is compressed, a certain amount of tissue creep can occur. Affording the compressed tissue an adequate amount of time under certain circumstances to accomplish tissue creep can therefore produce benefits. One benefit can be adequate staple formation. This can contribute to a consistent staple line. Accordingly, a certain time can be given to enable tissue creep prior to firing.

With reference now also to FIG. 99, after a period where the anvil gap δ is maintained constant to allow for tissue creep, at time t5, prior to deploying the staples, the control circuit 760 at point 202050 determines whether a possible adjustment of the anvil 766 relative to the staple cartridge 764 (anvil 201804 and stapler 202084 in FIG. 108) is necessary. Accordingly, the control circuit 760 determines if the tissue compression force F is between the ideal firing zone 202076, above the maximum compression force Fmax threshold 202072, or below the minimum compression force Fmin threshold 202074 and makes any necessary adjustments to the anvil gap δ. If the tissue compression force F is between the ideal firing zone 202076, the control circuit 760 deploys the staples in the staple cartridge 768 and deploys the knife 764.

If the tissue compression force F is above the maximum compression force Fmax threshold 202072, the control circuit 760 is configured to register a warning that the compression force is too tight and to adjust the anvil gap δ, increase the wait time before firing, lower the firing speed, or enable a firing lockout, or any combination thereof. The control circuit 760 can adjust the anvil gap δ by advancing the anvil 766 distally, e.g. away, from the staple cartridge 768 (anvil 201804 and stapler 202084 in FIG. 108) to increase the anvil gap δ as shown by the segment of the anvil gap curve 2002044 beyond time t5. As shown by the segment of the tissue compression force curve 202064 beyond time t5, after the control circuit 760 increases the anvil gap δ, the tissue compression force F decreases into the ideal firing zone 202076.

If the tissue compression force F is below the minimum compression force Fmin threshold 202074, the control circuit 760 is configured to register a warning that the compression force is too loose and can adjust the anvil gap δ, proceed with caution, or enable a firing lockout, or any combination thereof. The control circuit 760 is configured to adjust the anvil gap δ by retracting the anvil 766 proximally, e.g. toward, the staple cartridge 768 (anvil 201804 and stapler 202084 in FIG. 108) to decrease the anvil gap δ as shown by the segment of the anvil gap curve 202046 beyond time t5. As shown by the segment of the tissue compression force curve 202066 beyond time t5, after decreasing the anvil gap δ, the tissue compression force F increases into the ideal firing zone 202076.

With reference to FIGS. 106-107, in one aspect, the anvil gap δ may be determined by the controller 620 based on readings from the closure motor 603 as described with reference to FIG. 8, for example. In one aspect, the anvil gap δ may be determined by the control circuit 710 based on readings from the position sensor 734 coupled to the anvil 716 as described with reference to FIG. 98, for example. In one aspect, the anvil gap δ may be determined by the control circuit 760 based on readings from the position sensor 784 coupled to the anvil 766 as described with reference to FIG. 99, for example.

With reference to FIGS. 106-107, in one aspect, the tissue compression force F may be determined by the controller 620 based on readings from the closure motor 603 as described with reference to FIG. 8. For example, the tissue compression force F may be determined based on the current draw of the motor where higher current draw while closing the anvil is related to higher tissue compression force. In one aspect, the tissue compression force F may be determined by the control circuit 710 based on readings from sensors 738, such as strain gauges, coupled to the anvil 716 or the staple cartridge 718 as described with reference to FIG. 98, for example. In one aspect, the tissue compression force F may be determined by the control circuit 760 based on readings from the sensors 788, such as strain gauges, coupled to the anvil 766 as described with reference to FIGS. 99, for example.

Figure 109:
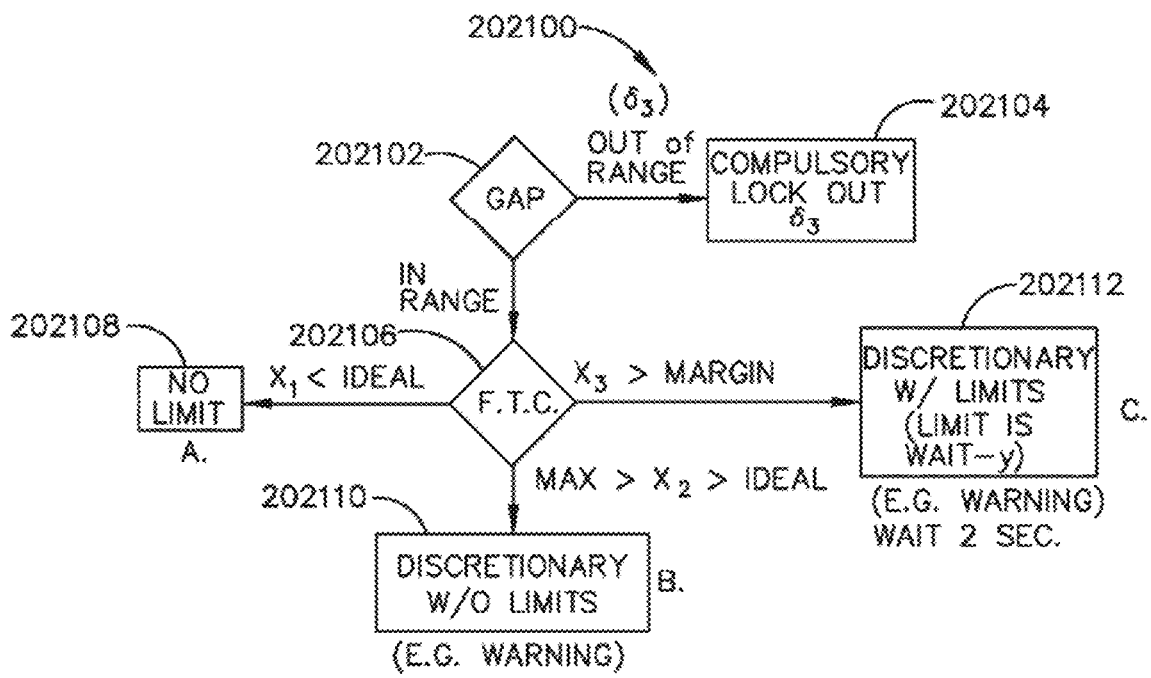
FIG. 109 is a logic flow diagram of a process depicting a control program or a logic configuration to provide discretionary or compulsory lockouts according to sensed parameters compared to thresholds, in accordance with at least one aspect of the present disclosure.

FIG. 109 is a logic flow diagram of a process 202100 depicting a control program or a logic configuration to provide discretionary or compulsory lockouts according to sensed parameters compared to thresholds, in accordance with at least one aspect of the present disclosure. As depicted in FIG. 109, according to a comparison of the measured anvil gap relative to one or more thresholds and the measured tissue compression force F (otherwise referred to as FTC) relative to one or more thresholds, a control algorithm can allow the instrument to be fired (e.g., actuated) without limitations, implement a discretionary lockout (e.g., provide a warning to the user), or implement a compulsory lockout of the instrument.

Accordingly, with reference to FIGS. 99, 108, and 109, the process 202100 will be described with reference to FIGS. 99-107. The control circuit 760 implements the algorithm to execute the process 202100 where the anvil 766 in FIG. 99 is shown as anvil 202084 in FIG. 108 and the staple cartridge 768 in FIG. 99 is shown as the stapler 202082 in FIG. 108. Additional details regarding the configuration and operation of a powered circular stapling device 202080 are described herein with reference to FIGS. 100-102. Turning back to the process 202100, the control circuit 760 determines the anvil gap δ as described in connection with FIGS. 106 and 107 based on readings from the position sensor 784 coupled to the anvil 766. When the anvil gap δ is δ3>δMax, the anvil gap is out of range and the control circuit 760 engages a compulsory lockout 202104. When the anvil gap δ is δMaX>δ2>δMin, the anvil gap δ is in range and the control circuit 760 determines 202106 the tissue compression force F (FTC) as described with reference to FIG. 111. As described above, the tissue compression force may be determined by the control circuit 760 based on readings from strain gauge sensors 788 coupled to the anvil 766 or the staple cartridge 768. Alternatively, tissue compression force may be determined based current draw by the motor 754.

Figure 111:
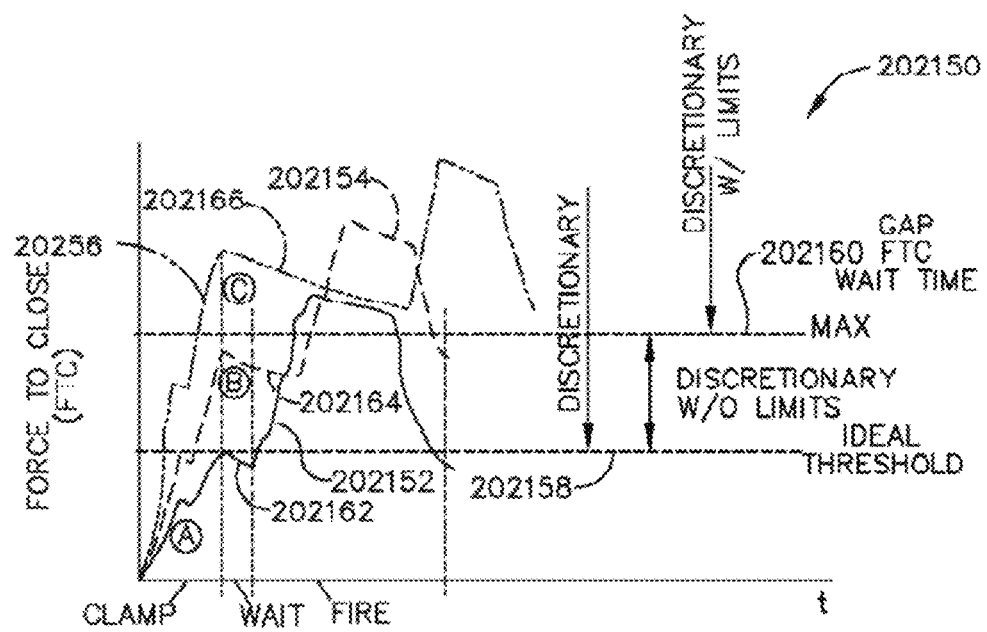
FIG. 111 is a graphical representation of three force to close (FTC) curves verse time, in accordance with at least one aspect of the present disclosure.

With reference now to FIGS. 109 and 111, when the FTC is less than an ideal FTC threshold (X1<Ideal FTC), zone A in FIG. 111, the control circuit 760 executes 202108 a no limits electronic lockout. When the FTC is between a maximum FTC threshold and the ideal FTC threshold (Max>X2>Ideal), zone B in FIG. 111, the control circuit 760 executes 202110 discretionary electronic lockouts without limits. In one aspect, under this condition, the control circuit 760 issues a warning in the form of a message or alert (audio, visual, tactile, etc.). When the FTC is greater than a maximum FTC threshold (X3>Margin), zone C in FIG. 111, the control circuit executes 202112 discretionary electronic lockouts with limits. Under this condition, the control circuit 760 issues a warning in the form of a message or alert (audio, visual, tactile, etc.) and applies a wait period before firing. In various aspects, the powered circular stapling device 202080 includes adjustable electronic lockouts as described herein, which can either prevent the actuation of the 202082 stapler or adjust the function of the powered circular stapling device 202080 based on a sensed condition and a secondary measure.

In one aspect, powered circular stapling device 202080 control algorithm described herein as the process 202100 can be configured to initiate discretionary and compulsory lockouts based on marginal and required conditions for the powered circular stapling device 202080 to operate. In one aspect, the process 202100 for the powered circular stapling device 202080 can be configured to implement both compulsory and discretionary lockouts based on sensed parameters within the system. A discretionary lockout pauses the automatic execution of a sequential operation, but can be overridden by the user input, for example. A compulsory lockout prevents the next sequential step, causing the user to back up a step of operation and resolve the lockout condition which induced the lockout, for example. In one aspect, both compulsory and discretionary lockouts can have both upper and lower bounded thresholds. Accordingly, the powered circular stapling device 202080 can comprise a combination of discretionary and compulsory lockouts.

In one aspect, powered circular stapling device 202080 control algorithm described herein as the process 202100 can be configured to adjust electronic lockouts that can either prevent the actuation of a system or adjust its function based on the sensed condition and a secondary measure. The sensed condition may be FTC, anvil displacement, gap δ, formation of staples and the secondary measure can include the severity of failure, a user input, or predefined comparison lookup table, for example.

In one aspect, the reaction of compulsory electronic lockouts is to prohibit the powered circular stapling device 202080 function until the situation is resolved. Conversely, the reaction to a discretionary lockout can be more subtle. For example, discretionary lockout could include a warning indication, an alert requiring user consent to proceed, a change in the rate or force of an actuation or wait time, or a prohibition of certain functions being performed until the situation is resolved or stabilized. In operation, compulsory conditions for the powered circular stapling device 202080 can include, for example, having the anvil 202084 fully seated before clamping or the stapler cartridge being loaded with staples before firing. Viable conditions for the powered circular stapling device 202080 can include, for example, being within the acceptable staple height for a given tissue thickness or a minimum tissue compression. Further, different conditions could have both discretionary and compulsory level thresholds on the same parameter, e.g., power level within the battery pack.

In one aspect, the powered circular stapling device 202080 can be configured to implement various control mechanisms to prevent or adjust the function of the powered circular stapling device 202080 based on the lockout type. In one aspect, compulsory lockouts could be solely electronic, mechanical interlocks, or a combination of the two. In various aspects having two lockouts, the lockouts could be redundant or optionally used based on the settings of the device. In one aspect, discretionary lockouts can be electronic lockouts so that they can be adjustable based on sensed parameters. For example, the discretionary lockouts could be a mechanical interlock that is electronically disabled or they could be a solely electronic lockout.

Figure 110:
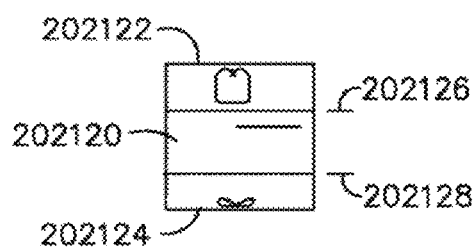
FIG. 110 is a diagram illustrating a range of tissue gaps and resulting staple forms, in accordance with at least one aspect of the present disclosure.

FIG. 110 is a diagram illustrating the anvil gap ranges and corresponding staple formation, in accordance with at least one aspect of the present disclosure. When the anvil gap 202120 is between an upper limit 202126 and a lower limit 202128, the staple formation is proper and within an acceptable range of staple heights for a given range of tissue thickness or minimum tissue compression force. When the anvil gap 202122 is greater than the upper limit 202126, the staple formation is loose. When the anvil gap 202124 is less than the lower limit 202128, the staple formation is tight.

FIG. 111 is a graphical representation 202150 of three force to close (FTC) curves 202152, 202154, 202156 verse time, in accordance with at least one aspect of the present disclosure. The FTC curves 202152, 202154, 202156 are divided into three phases: clamp, wait, and fire. The clamp phase has a common starting point, which means that the tissue has a common thickness and variable tissue stiffness as described in detail in FIG. 106. At the end of the clamp phase, there is a wait period before starting the fire phase to account for tissue creep.

The first FTC curve 202152 corresponds to tissue having a low tissue stiffness. During the clamping phase, the FTC curve 202152 exhibits a rise in tissue compression force that peaks below the ideal FTC threshold 202158 in zone A. At the end of the clamp phase, the powered circular stapling device 202080 (FIG. 108) waits a user controlled period 202162 before initiating the firing phase to account for tissue creep.

The second FTC curve 202154 corresponds to tissue having a normal tissue stiffness. During the clamping phase, the FTC curve 202154 exhibits a rise in tissue compression force that peaks between the ideal FTC threshold 202158 and the maximum FTC threshold 202160 in zone B. At the end of the clamp phase, the powered circular stapling device 202080 (FIG. 108) waits a user controlled period 202164 before initiating the firing phase to account for tissue creep.

The third FTC curve 202154 corresponds to tissue having a high tissue stiffness. During the clamping phase, the FTC curve 202156 exhibits a rise in tissue compression force that peaks above the maximum FTC threshold 202160 in zone C. At the end of the clamp phase, the powered circular stapling device 202080 (FIG. 108) controls a wait period 202166 before initiating the firing phase to account for tissue creep.

Figure 112:
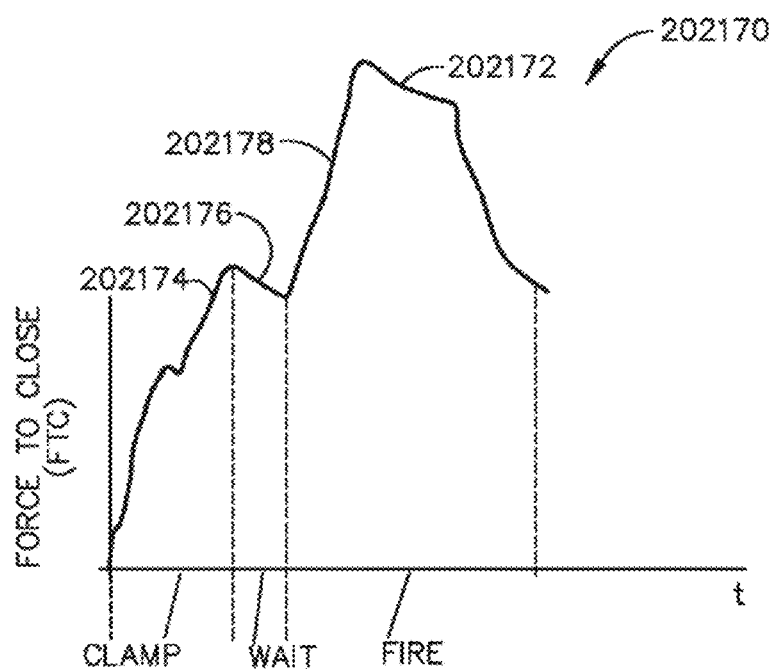
FIG. 112 is a detail graphical representation of a force to close (FTC) curve verse time, in accordance with at least one aspect of the present disclosure.

FIG. 112 is a detail graphical representation 202170 of a FTC curve 202172 verse time, in accordance with at least one aspect of the present disclosure. As shown, the PIC curve 202172 is divided over three phases: a clamp phase, a wait phase, and a fire phase. During the clamp phase, the FTC curve 202172 exhibits and increase in tissue compression force as indicated by the clamp phase segment 202174. After the clamp phase, there is a wait period 202176 before initiating the fire phase. The wait period 202176 may be either user controlled or device controlled depending on the value of the tissue compression force relative to ideal and maximum compression force thresholds. During the fire phase, the tissue compression force increases as shown by FTC curve segment 202178 and then drops.

Figure 113:
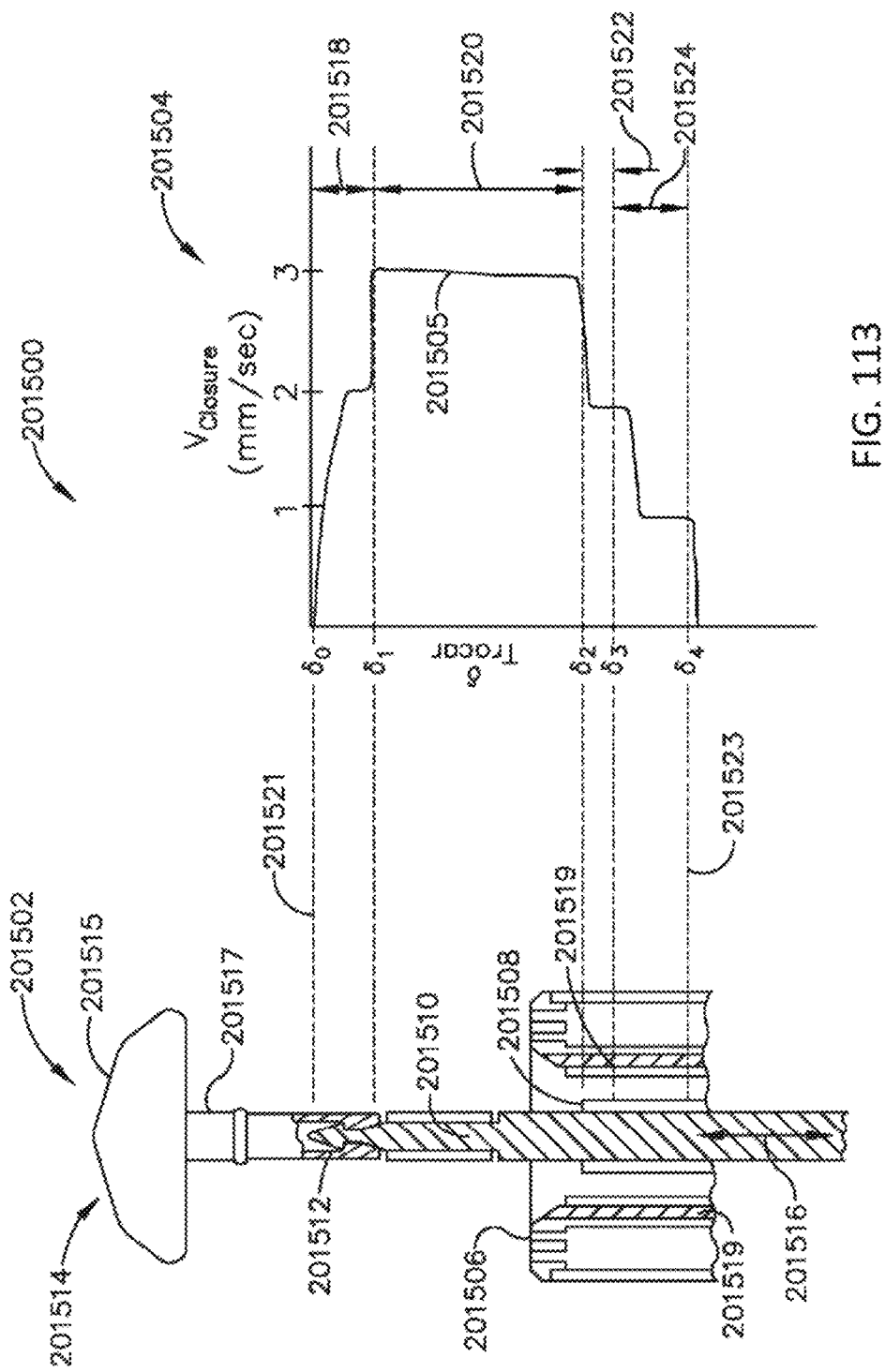
FIG. 113 is a diagram of graph and associated powered stapling device illustrating anvil closure rate adjustment at certain key points along a trocars retraction stroke, in accordance with at least one aspect of the present disclosure.

In various aspects, the closure rate or direction of a circular stapler, or a combination thereof, can be adjusted based on the sensed attachment, relative to the fully attached state, of the anvil. In one aspect, the present disclosure provides a digitally enabled circular stapler algorithm for determining the variation the closure rate of the anvil at key locations of the trocar to ensure proper seating of the anvil on the trocar. FIG. 113 is a diagram 201500 of a powered stapling device 201502 and a graph 201504 illustrating the closure rate adjustment of an anvil 201514 portion of the powered stapling device 201502 at certain key points along the retraction stroke of a trocar 201510, in accordance with at least one aspect of the present disclosure. The powered stapling device 201502 is similar to the motorized circular stapling instrument 201800 described herein with reference to FIGS. 18-20, may be controlled using any of the control circuits described in connection with FIGS. 7-8 and 98-99, and may be employed in a hub and cloud environment as described in connection with FIGS. 1-6 and 9-13. The anvil 201514 includes an anvil head 201515 and an anvil shank 201517. The trocar 201510 can be advanced and retracted in the direction indicated by arrow 201516. In one aspect, the closure rate of the anvil 210514 can be adjusted at certain key points along the retraction stroke of the trocar 201510 to improve the final seating of the anvil 201514 on the trocar 201510 if the trocar 201510 is marginally attached but not fully attached to the anvil 201514.

The powered stapling device 201502, shown on the left side of FIG. 113, includes a circular stapling head assembly 201506 with a seating collar 201508 that receives the trocar 201510 therethrough. The trocar 201510 engages the anvil 201514 via a locking feature 201512. The trocar 210510 is movable, e.g., advanced and retracted, in the directions indicated by arrow 201516. A cutting element, such as a knife 201519, severs tissue when the circular stapling head assembly 201506 is driven towards the anvil 201514. In one aspect, the closure rate of the anvil 201514 can be adjusted at certain key points along the retraction stroke of the anvil 201510 in order to, for example, improve the final seating of the anvil 201514 on the trocar 201510 if the trocar 210510 is marginally attached but not fully attached to the anvil 201514. Accordingly, the closure rate of the anvil 201514 can be varied at key locations to ensure proper seating. The position or displacement of the trocar 210510 as it is advanced or retracted by a trocar actuator coupled to a motor may be detected by a plurality of proximity sensors disposed along the displacement path of the trocar 210510. In some aspects, the position or displacement of the trocar 210510 may be tracked using the tracking system 480 (FIG. 7) or the position sensors 734, 784 (FIGS. 98-99).

On the right side of FIG. 113, the graph 201504 illustrates the closure rate of the anvil 201514 as a function of the position of the trocar 201510 at certain key points, labeled as "δ Trocar" along the vertical axis and "Vclosure mm/sec" along the horizontal axis, in accordance with at least one aspect of the present disclosure. An anvil 201514 closure rate velocity profile curve 201505 is plotted as a function of the position of the trocar 201510. The closure rate of the anvil 201514 can be slow at a first zone 201518 to ensure proper attachment of the trocar 210510 to the anvil 201514, faster at a second zone 201520 during closure, slower again at a third zone 201522 to verify attachment, and then even slower at a fourth zone 201524 during application of a high closure load.

The anvil 201514 closure rate adjustment at certain key points along the trocars 201510 retraction stroke improves the final seating of the anvil 201514 on the trocar 201510 if it marginally attached but not fully attached. At trocar 201510 position δ0 the anvil 201514 is in a fully open position 201521 and at trocar 201510 position δ4 the anvil 201514 is in a fully closed position 201523. Between the trocar 201510 fully open position 201521 δ0 and fully closed position δ4 the closure rate of the anvil 201514 is adjusted based on the position of the trocar 201510. For example, at the first zone 201518, as the trocar 201510 moves from the fully opened position 201521 δ0 to a first trocar 201510 position δ1, the closure rate of the anvil 201514 is slow (between 0-2 mm/sec) to ensure proper attachment of the anvil 201514 to the trocar 201510. At the second zone 201520, when the trocar 201510 moves from δ1 to δ2, the anvil 201514 is closed at a constant quick closure rate (3 mm/sec). When the trocar 201510 moves from δ2 to δ3 position, in the third zone 201522, the closure rate of the anvil 201514 is slowed to verify full attachment of the anvil 201514 to the trocar 201510. Finally, when the trocar 201510 moves from δ3 to δ4 position, in the fourth zone 201524, the closure rate of the anvil 201514 is slowed once again during high closure loads.

Figure 114:
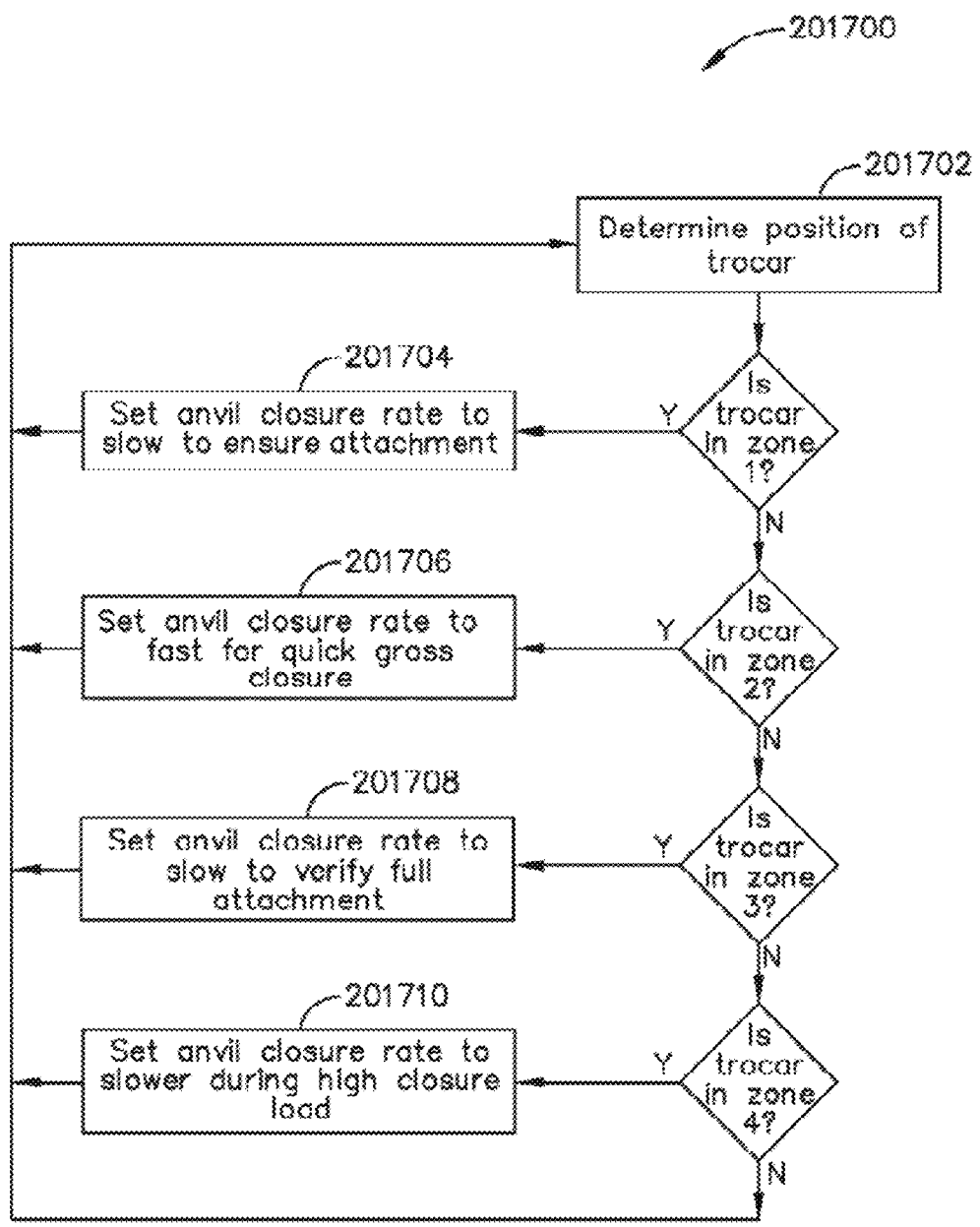
FIG. 114 is a logic flow diagram of a process depicting a control program or a logic configuration to adjust a closure rate of the anvil portion of the powered stapling device at certain key points along the retraction stroke of a trocar, in accordance with at least one aspect of the present disclosure.

FIG. 114 is a logic flow diagram of a process 201700 depicting a control program or a logic configuration to adjust a closure rate of the anvil 201514 portion of the powered stapling device 201502 at certain key points along the retraction stroke of a trocar 201510, in accordance with at least one aspect of the present disclosure. This process 201700 may be implemented with any of the control circuits described with reference to FIGS. 7-8 and 98-99. This process 201700 may be implemented in a hub or cloud computing environment described with reference to FIGS. 1-6 and 9-13, for example.

In particular, the process 201700 depicted in FIG. 114 will now be described with reference to the control circuit 760 of FIG. 99. The control circuit 760 determines 201702 the position of the trocar 201510 based on information received from position sensor 784. Alternatively, the position of the trocar 201510 may be determined based on information received from the sensors 788 or the timer/counter 781 circuit or a combination thereof. Based on the position of the trocar 201510, the control circuit 760 controls the closure rate of the anvil 201514 (Vclosure mm/sec) as a function of the position of the trocar 201510 at certain key points, in accordance with at least one aspect of the present disclosure. Accordingly, when the position of the trocar 201510 is located in a first zone 201518, where the anvil 201514 is attached to the trocar 201510, the process 201700 continues along the yes (Y) branch and the control circuit 760 sets 201704 the closure rate of the anvil 201514 to slow to ensure proper attachment of the trocar 210510 to the anvil 201514. Otherwise the process 201700 continues along the no (N) branch. When the position of the trocar 201510 is located in a second zone 201520, referred to as a quick gross closure zone, the process 201700 continues along the yes (Y) branch and the control circuit 760 sets 201706 the closure rate of the anvil 201514 to fast to rapidly close the anvil 201514. Otherwise the process 201700 continues along the no (N) branch. When the position of the trocar 201510 is located in a third zone 201522, referred to as a verification zone, the process continues along the yes (Y) branch and the control circuit 760 sets 201708 the closure rate of the anvil 201514 to slow to verify full attachment of the anvil 201514 to the trocar 201510. Otherwise the process 201700 continues along the no (N) branch. When the position of the trocar 201510 is located in a fourth zone 201524, referred to as a high closure load zone, the process 201700 continues along the yes (Y) branch and the control circuit 760 sets 201710 the closure rate of the anvil 201514 to a slower rate than in the previous verification zone 201522 during the application of a high closure load. Once the anvil 201514 is fully closed trocar 201510 to capture tissue therebetween, the control circuit 760 actuates the knife 201519 to sever the tissue.

Figure 115:
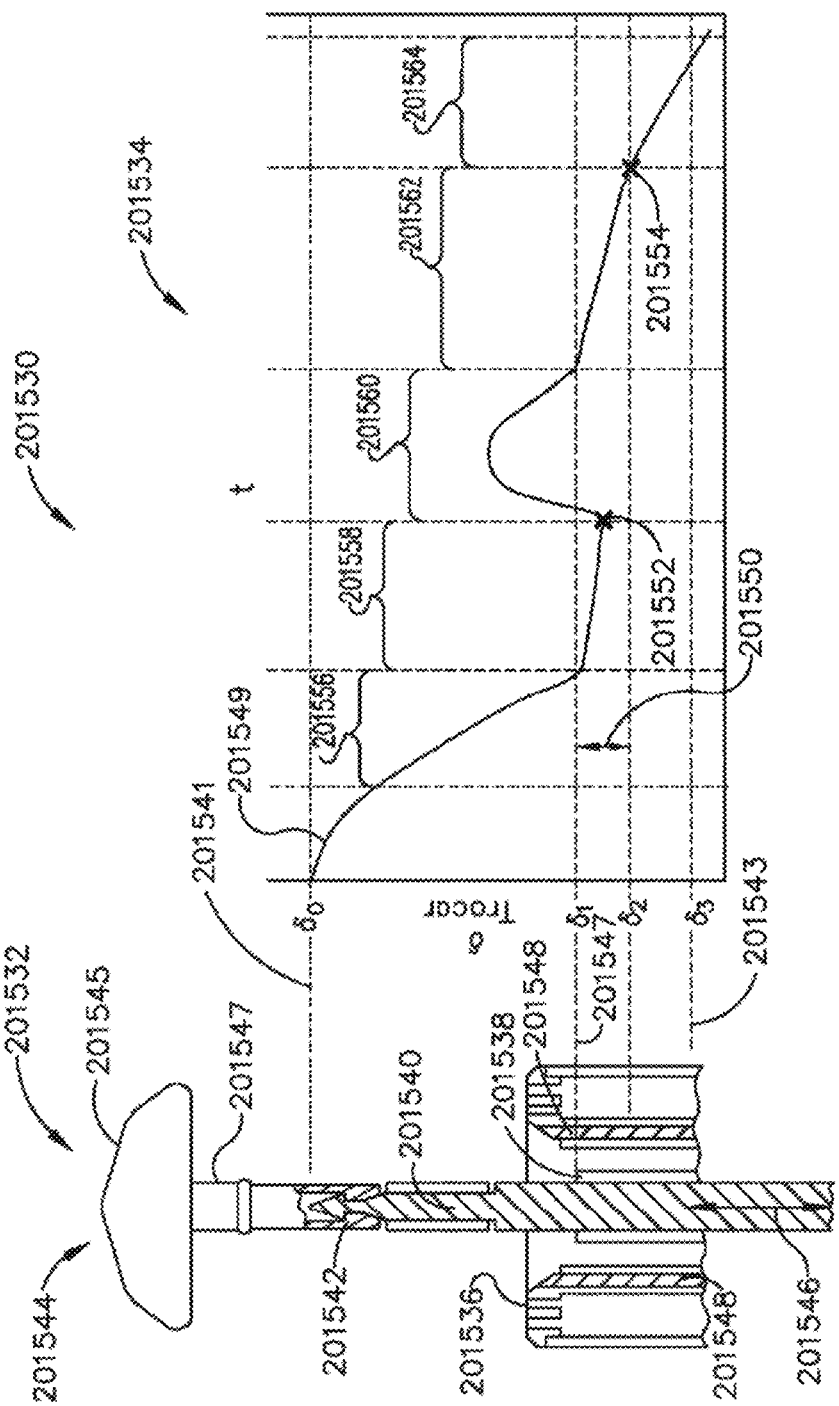
FIG. 115 is a diagram of graph and associated power stapling device diagram illustrating trocar position over time, in accordance with at least one aspect of the present disclosure.

In one aspect, the present disclosure provides a digitally enabled circular stapler adaptive algorithm for determining multi-directional seating motions on the trocar to drive the anvil into proper seating. FIG. 115 is a diagram 201530 of a powered stapling device 201532 and a graph 201534 illustrating detection of closure rates of the trocar 201540 and the anvil 201544, in accordance with at least one aspect of the present disclosure. The powered stapling device 201532 is similar to the motorized circular stapling instrument 201800 described herein with reference to FIGS. 100-103, may be controlled using any of the control circuits described in connection with FIGS. 7-8 and 98-99, and may be employed in a hub and cloud environment as described in connection with FIGS. 1-6 and 9-13. The anvil 201544 includes an anvil head 201545 and an anvil shank 201547. The trocar 201540 can be advanced and retracted in the direction indicated by arrow 201546. In one aspect, if the anvil shank 201547 is detected pulling loose from the trocar 201540, the powered stapling device 210530 could stop retraction or reverse and advance towards an open position 201541 until the instability of the anvil 201544 seating is resolved. If the anvil 201544 is pulled fully off, the powered stapling device 210530 could fully open 201541 indicating to the user to try re-attaching the anvil shank 201547 to the trocar 201540.

The powered stapling device 201532, shown on the left side of FIG. 115, includes a circular stapling head assembly 201536 with a seating collar 201538 that receives the trocar 201540 therethrough. The trocar 201540 engages the anvil 201544 via a locking feature 201542. The trocar 210540 is movable, e.g., advanced and retracted, in the directions indicated by arrow 201546. A cutting element, such as a knife 201548, severs tissue when the circular stapling head assembly 201536 is driven towards the anvil 201544.

In one aspect, the closure rates of the trocar 201540 and the anvil 201544 can be detected and any discrepancy between the closure rates of the two components could generate an automatic extension of the trocar 201540 and then retraction of the trocar 201540 in order to fully seat the anvil 201544 on the trocar 201540. In one aspect, any discrepancy between the closure rates of the trocar 201540 and the anvil 201544 may be provided to a control circuit or processor to operate a motor coupled to the trocar 201540 to generate an automatic extension of the trocar 201540 and then re-retraction in order to fully seat the anvil 201544 on the trocar 201540. If the anvil shank 201547 is detected pulling loose from the trocar 201540 the smart powered stapling device 201532 could stop retraction or even reverse and advance towards open until the instability of seating the anvil 201544 is resolved. If the anvil 201544 were pulled fully off it could even fully open indicating to the user to try re-attaching the anvil shank 201547 to the trocar 201540. As shown FIG. 115, the control algorithm can be configured to extend the trocar 201540 back towards the open position 201541 to reset the anvil 201544 if an anvil 201544 detachment is sensed, prior to then re-verifying attachment of the anvil 201544 and proceeding as normal upon confirming that the anvil 201544 is attached.

Accordingly, the system can be configured for multi-directional seating motions on the trocar 201540 to drive the anvil 201544 into proper seating. For example, if the anvil shank 201547 is detected as pulling loose from the trocar 201540, the smart powered stapling device 201530 could be configured to stop retraction or even reverse and advance towards open until the instability of seating the anvil 201544 is resolved. If the anvil 201544 were pulled fully off, the smart powered stapling device 201532 could even be configured to fully open, indicating to the user to try reattaching the anvil shank 201547 to the trocar 201540.

On the right side of FIG. 115, the graph 201534 illustrates the position of the trocar 201510 as a function of time at certain key points, labeled as "δ Trocar" along the vertical axis and "t" along the horizontal axis, in accordance with at least one aspect of the present disclosure. A trocar 201540 position profile curve 201549 is plotted as a function of time (t). With reference to the trocar 201540 position profile curve 201549, the trocar 201540 moves from a fully open position 201541 towards a fully closed position 201543 over a first period 201556 at a quick closure rate. During a second period 201558, the trocar 201540 moves into the verification zone 201547 where the anvil locking feature 201542 engages the seating collar 201538, at a slow rate to verify that the anvil locking feature 201542 has properly engaged the seating collar 201538. In the illustrated example, an anvil 201544 detached initiation is sensed at time 201552. Upon sensing that the anvil 201544 is detached, the trocar 201540 is advanced towards an open position and back over a third period 201560. The trocar 201540 then moves slowly during a fourth period 201562 until it is confirmed or verified that the anvil 201544 is attached to the trocar 201540 at time 201554. Thereafter, the trocar 201540 moves towards the closed position 201543 very slowly during a fifth period 201564 under high tissue load before the knife 201548 is advanced to sever the tissue captured between the anvil 201544 and the circular stapling head assembly 201536.

Figure 116:
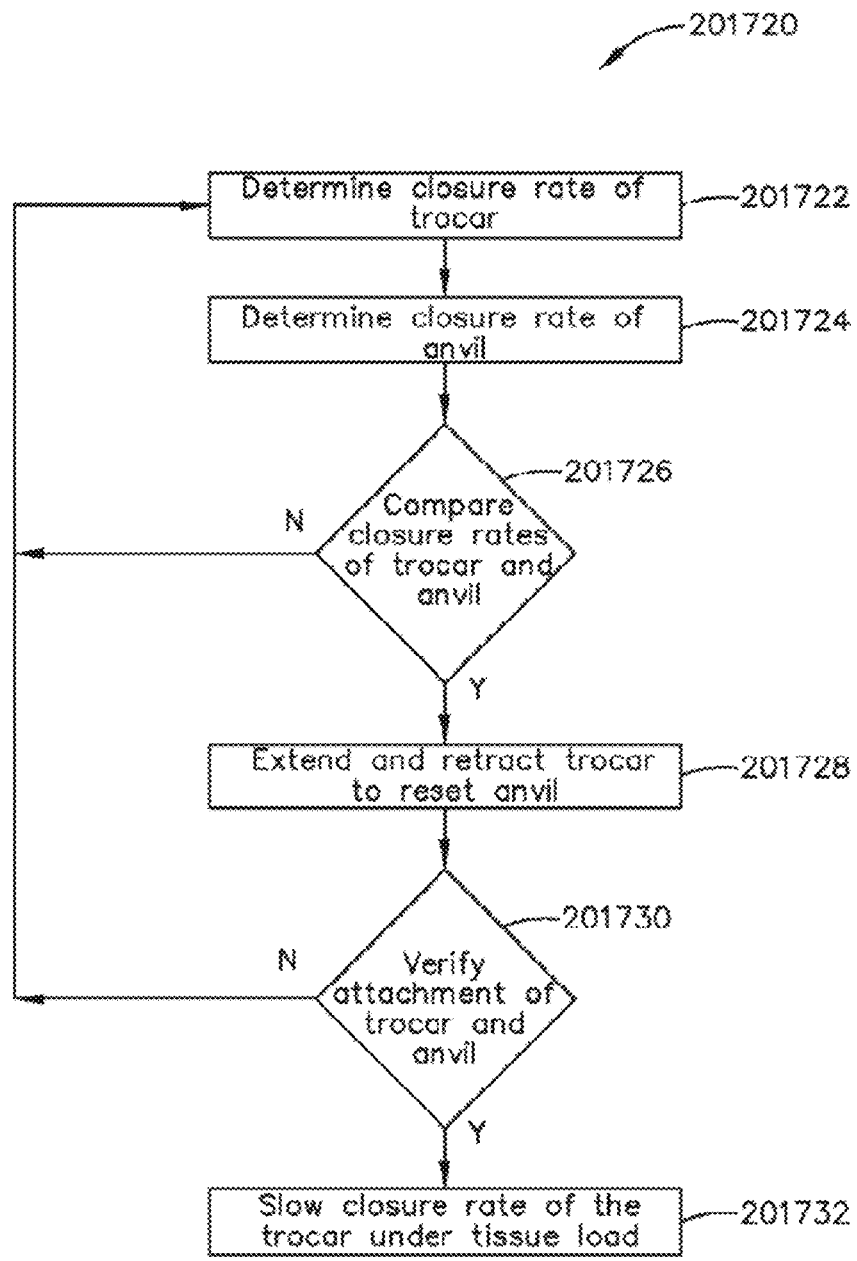
FIG. 116 is a logic flow diagram of a process depicting a control program or a logic configuration to detect multi-directional seating motions on the trocar to drive the anvil into proper seating, in accordance with at least one aspect of the present disclosure.

FIG. 116 is a logic flow diagram of a process 201720 depicting a control program or a logic configuration to detect multi-directional seating motions on the trocar 201540 to drive the anvil 201544 into proper seating, in accordance with at least one aspect of the present disclosure. This process 201720 may be implemented with any of the control circuits described herein with reference to FIGS. 7-8 and 98-99. This process 201720 may be implemented in a hub or cloud computing environment described with reference to FIGS. 1-6 and 9-13, for example.

In particular, the process 201720 depicted in FIG. 116 will now be described with reference to the control circuit 760 of FIG. 99. The control circuit 760 determines 201722 the closure rate of the trocar 201540 based on information received from position sensor 784. The control circuit 760 then determines 201724 the closure rate of the anvil 201544 based on information received from position sensor 784. Alternatively, the closure rate of the trocar 201540 or the anvil 201544 may be determined based on information received from the sensors 788 or the timer/counter 781 circuit or a combination thereof. The control circuit 760 compares 207126 the closure rates of the trocar 201540 and the anvil 201544. When there is no discrepancy between the closure rates of the trocar 201540 and the anvil 201544, the process 201720 continues along the no (N) branch and loops until there is a discrepancy between the closure rates of the trocar 201540 and the anvil 201544. When there is a discrepancy between the closure rates of the trocar 201540 and the anvil 201544, the process 201720 continues along the yes (Y) branch and the control circuit 760 extends and retracts 207128 the trocar 201540 to reset the anvil 201544. Subsequently, the process 201720 verifies 201130 the attachment of the trocar 201540 and anvil 201544. If the attachment is verified, the process 201720 continues along the yes (Y) branch and the control circuit 760 slows 207132 the closure rate of the trocar 201540 under tissue load. If the attachment is not verified, the process 201720 continues along the no (N) branch and loops until the attachment of the trocar 201540 to the anvil 201544 is verified. Once the anvil 201544 is fully closed on the trocar 201540 to capture tissue therebetween, the control circuit 760 actuates the knife 201548 to sever the tissue.

In various aspects, the knife speed of a circular stapler and end points can be adjusted based on the sensed toughness or thickness of the tissue between the anvil and cartridge. Accordingly, the circular stapler control algorithm can be configured to detect the tissue gap and force-to-fire to adjust the knife stroke and speed. In one aspect, the present disclosure provides a digitally enabled circular stapler adaptive algorithm for detecting tissue gap and force-to-fire to adjust knife stroke and knife speed, in accordance with at least one aspect of the present disclosure.

Figure 117:
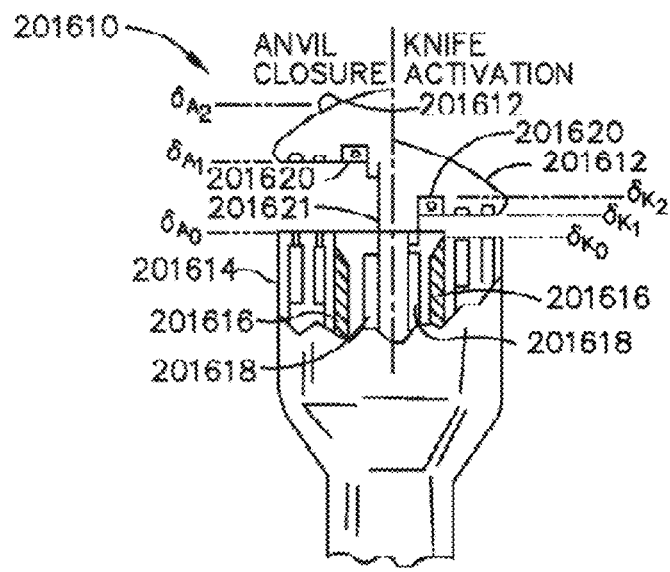
Figure 118:
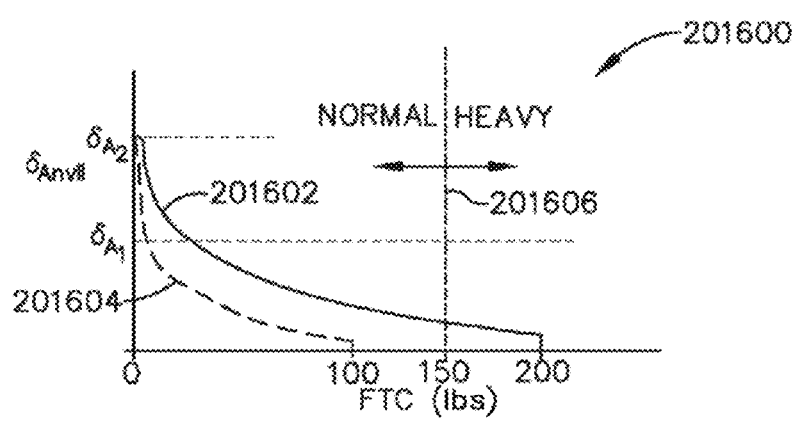
Figure 119:
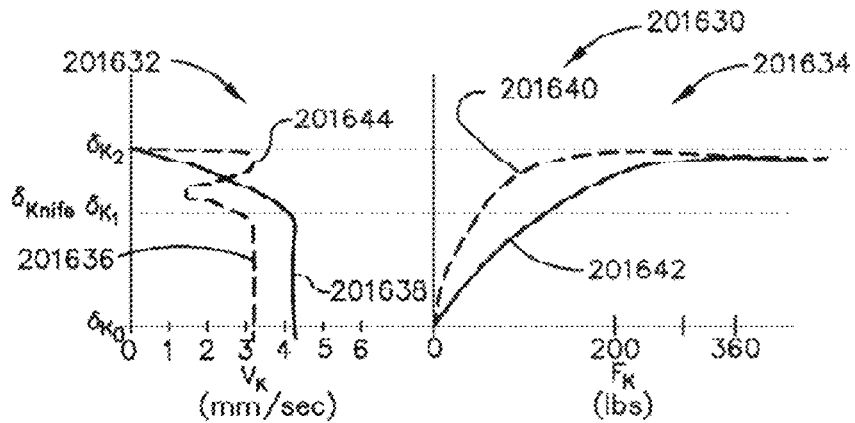

Generally, FIGS. 117-119 represent a circular powered stapling device 201610 and a series of graphs depicting force-to-close (FTC) a clamp relative to the position of the anvil 201612 (δAnvil) and knife 201616 velocity (VK) and knife 201616 force (FK) relative to the position of the knife 201616 (δKnife), in accordance with at least one aspect of the present disclosure. Using sensed data at different points along length of the shank 201621, a control algorithm can generate a map of tissue gap or reaction force vector of the anvil 201612, monitoring for a high or low side when compressed on tissue. When firing, the system measures forces acting on a compression element 201620 comprising a force sensor and adjusts to act evenly along the force vector of the shank to provide even and complete cutting.

In particular, FIG. 117 is a partial schematic diagram of a circular powered stapling device 201610 showing anvil 201612 closure on the left side and knife 201616 actuation on the right side, in accordance to at least one aspect of the present disclosure. The circular powered stapling device 201610 comprises an anvil 201612 that is movable from a fully open position δA2 to a fully closed position δA0. An intermediate position δA1 represents the point at which the anvil 201612 contacts tissue located between the anvil 201612 and the circular stapler 201614. One or more position sensors located along the length of the anvil shank 201621 monitor the position of the anvil 201612. In one aspect, the position sensor may be located within the seating collar 201618. The compression element 201620 may comprise a force sensor, such as a strain gauge for example, to monitor the force applied to the tissue and to detect the point of initial contact of the anvil 201612 with the tissue, shown as intermediate position δA1. The position sensor and the force sensor interface with any of the control circuits described herein with reference to FIGS. 7-8 and 98-99, for example, which implement the circular stapler control algorithm. The circular powered stapling device 201610 also comprises a movable cutting element such as a knife 201616 that is movable from a fully retracted position δA0 to a fully extended position δA2 to achieve a complete tissue cut. The intermediate position δA1 of the knife 201616 represents the point at which the knife 201616 contacts with the compression element 201620 comprising a strain gauge or other contact or proximity sensor.

The power stapling device 201610 includes motors, sensors, and control circuits as described herein in connection with FIGS. 7-8 and 98-102. The motors are controlled by the control circuits to move the anvil 201612 and the knife 201616. One or more position sensors located on the power stapling device 201610 provide the position of the anvil 201612 and the knife 201616 to the control circuit. Additional sensors such as force sensors 201620 also provide tissue contact and force acting on the anvil 201612 and the knife 201616 to the control circuit. The control circuit employs the position of the anvil 201612, the position of the knife 201616, initial tissue contact, or force acting of the anvil 201612 or knife 201616 to implement the circular stapler control algorithm described hereinbelow in connection with FIG. 120.

FIG. 118 is a graphical representation 201600 of anvil 201612 displacement (δAnvil) along the vertical axis as a function of force-to-close (FTC) a clamp along the horizontal axis, in accordance with at least one aspect of the present disclosure. The vertical line represents a FTC threshold 201606 that indicates tissue toughness. The left side of the FTC threshold 201606 represents tissue having normal toughness and the right side of the FTC threshold 201606 represents tissue having heavy toughness. As the anvil 201612 is retracted from the fully open position δA2 to the intermediate position δA1, where the anvil 201612 initially contacts tissue, the FTC is substantially low (~0). As the anvil 201612 continues closing past this point towards the circular stapler 201614 to the fully retracted position δA0 minus the compressed tissue thickness, the FTC is nonlinear. Each tissue type from normal to heavy toughness will produce a different FTC curve. For example, the first FTC curve 201604, shown in broken line, spans from ~0 to ~100 lbs., where the maximum FTC is below the FTC threshold 201606. The second FTC curve 201602, shown in solid line, spans from ~0 to ~200 lbs., where the maximum FTC exceeds the FTC threshold 201606. As previously discussed, the FTC is measured by force sensors located in the compression element 201620 and coupled to the control circuit.

FIG. 119 is a graphical representation 201630 of knife 201616 displacement (δKnife) along the vertical axis as a function of knife 201616 velocity (VK mm/sec) along the horizontal axis on the left and also as a function of knife 201616 force (FK lbs) along the horizontal axis on the right, in accordance with at least one aspect of the present disclosure. On the left is a graphical representation 201632 of knife 201616 displacement (δKnife) along the vertical axis as a function of knife 201616 velocity (VK mm/sec) along the horizontal axis. On the right is a graphical representation 201634 of knife 201616 displacement (δKnife) along the vertical axis as a function of knife 201616 force (FK lbs) along the horizontal axis. The curves in dashed line 201638, 20142 in each of the graphical representations 201632, 201634 represent tissue of normal toughness whereas the curves in solid line 201636, 201640 represent tissue of heavy toughness.

Turning to the graphical representation 201632 on the left, for normal tissue toughness, as shown by the normal tissue knife velocity profile 201638, the initial velocity of the knife 201616 for normal tissue toughness starts at a first velocity, e.g., just over 4 mm/sec, at the initial knife position δK0. The knife 201616 continues at that velocity until it reaches knife position δK1 where the knife 201616 contacts tissue and slows the velocity of the knife 201616 as it cuts through the tissue until the knife 201616 reaches knife position δK2 indicating a complete cut and the control circuit stops the motor and hence stops the knife 201616. Turning to the graphical representation 201634 on the right, for normal tissue toughness, as shown by the normal tissue knife force curve 201642, the force acting on the knife 201616 is 0 lbs. at the initial knife position δK0 and varies nonlinearly until the knife 201616 reaches knife position δK2 until the cut is complete.

Turning to the graphical representation 201632 on the left, for heavy tissue toughness, as shown by the heavy tissue knife velocity profile 201636, the initial velocity of the knife 201616 for heavy tissue toughness starts at a second velocity, e.g., just over 3 mm/sec, which is lower relative to the first velocity, at the initial knife position δK0, which is less than the initial velocity for normal tissue toughness. The knife 201616 continues at that velocity until it reaches knife position δK1 where the knife 201616 contacts tissue. At this point the velocity of the knife 201616 starts to slow down nonlinearly as it cuts through the tissue for a short displacement of the knife 201616. The control circuit detects that the knife 201616 contacted tissue and in response increases the velocity of the motor to increase the velocity of the knife 201616, e.g., to the initial velocity until the knife 201616, until the knife 201616 reaches position δ indicating a complete cut and the control circuit stops the motor and hence stops the knife 201616. This is shown as velocity spike 201644 to improve cutting of tissue of heavy toughness. Turning to the graphical representation 201634 on the right, for heavy tissue toughness, as shown by the heavy tissue knife force curve 201640, the force acting on the knife 201616 is 0 lbs. at the initial knife position δK0 and varies nonlinearly until the knife 201616 reaches knife position δK2 and the cut is complete. A comparison of the normal and heavy tissue knife force curves 201640, 201642 shows that, with lower velocity and adding the velocity spike 201644 shortly after tissue contact with the knife 201616, the knife 201616 experiences a lower force when cutting tissue of heavy toughness than it experiences when cutting tissue of normal toughness.

Figure 120:
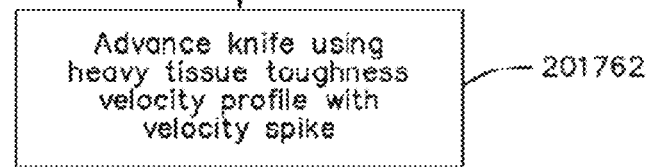

FIG. 120 is a logic flow diagram of a process 201720 depicting a control program or a logic configuration to detect the tissue gap and force-to-fire to adjust the knife stroke and speed, in accordance with at least one aspect of the present disclosure. This process 201750 may be implemented with any of the control circuits described with reference to FIGS. 7-8 and 98-99. This process 201750 may be implemented in a hub or cloud computing environment described with reference to FIGS. 1-6 and 9-13, for example.

In particular, the process 201750 depicted in FIG. 120 will now be described with reference to the control circuit 760 of FIG. 99 and the circular powered stapling device 201610 shown in FIGS. 117-119. The control circuit 760 monitors 201752 the displacement of the anvil 201612 based on position feedback received from the position sensor 784. As previously discussed, in one aspect, the position sensor 784 may be embedded in the shank 201612 of the anvil 201612. As the anvil 201612 is displaced, the control circuit 760 monitors 201754 contact of the anvil 201612 with tissue positioned between the anvil 201612 and the circular stapler 201614. In one aspect, tissue contact may be provided by a force sensor embedded in the compression element 201620. The force sensor is represented as the sensors 788 element of the surgical instrument 790 shown in FIG. 99. The force sensor 788 is employed to monitor 201756 the force-to-close (FTC) a clamp, which is the closing force of the anvil 201612 onto the tissue positioned between the anvil 201612 and the circular stapler 201614. The control circuit 760 compares 201758 the FTC to a predetermined threshold. When the FTC is below the predetermined threshold, the control circuit 760 sets the velocity of the motor 754 to advance 201760 the knife 201616 using a normal tissue toughness velocity profile 201638 as shown in FIG. 119. When the FTC is above the predetermined threshold, the control circuit 760 sets the velocity of the motor 754 to advance 201762 the knife 201616 using a heavy tissue toughness velocity profile 201636 with a velocity spike 201644 as shown in FIG. 119.

Figure 121:
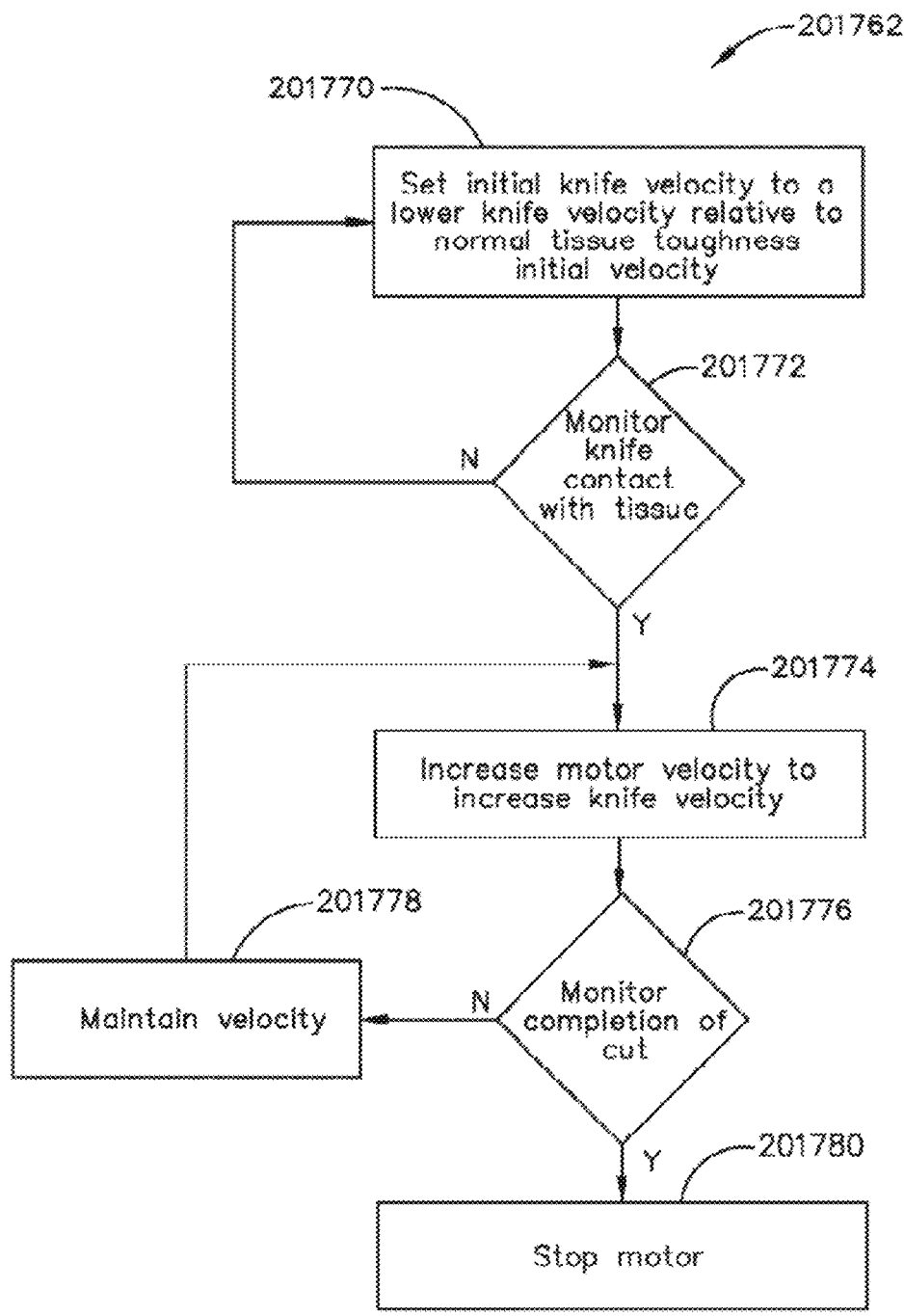

FIG. 121 is a logic flow diagram of a process 201762 depicting a control program or a logic configuration to advance 201762 the knife 201616 under a heavy tissue toughness velocity profile 201636 with a velocity spike 201644 as shown in FIG. 119, in accordance with at least one aspect of the present disclosure. This process 201762 may be implemented with any of the control circuits described with reference to FIGS. 7-8 and 98-99. This process 201750 may be implemented in a hub or cloud computing environment described with reference to FIGS. 1-6 and 9-13, for example.

In particular, the process 201762 depicted in FIG. 121 will now be described with reference to the control circuit 760 of FIG. 99 and the circular powered stapling device 201610 shown in FIGS. 117-119. When heavy tissue toughness is detected, the control circuit 760 sets 201770 the initial velocity of the knife 201616 a lower knife velocity relative to the knife velocity used for cutting normal tissue toughness. In one aspect, a slower knife velocity in heavy tissue toughness conditions promotes a better cut. The control circuit 760 monitors 201772 when the knife 201616 contacts the tissue. As previously discussed, tissue contact may be detected by a force sensor embedded in the compression element 201620. As shown in FIG. 119, when the knife 201616 contacts tissue the knife 201616 naturally slows down. Accordingly, once the control circuit 760 detects that the knife 201616 has contacted tissue, the tissue contact is detected, the control circuit 760 increases 201774 the velocity of the motor 754 to increase the velocity of the knife 201616 cutting through the tissue. The control circuit 760 monitors 201776 the completion of the cut and maintains 201778 the velocity of the motor 740 until completion of the cut is detected and then stops 201780 the motor 740.

Referring now to FIGS. 122-126, not only the amount and location of the tissue can affect the stapling outcome but also the nature, type, or state of the tissue. For example, irregular tissue distribution also manifests in situations that involve stapling previously stapled tissue such as, for example, in End-To End anastomosis procedures. Poor positioning and distribution of the previously stapled tissue within the end effector of a staple cartridge may cause the previously fired staple lines to be concentrated in one zone over another within the end effector, which negatively affects the outcome of such procedures.

Aspects of the present disclosure present a surgical stapling instrument that includes an end effector configured to staple tissue clamped between a first jaw and a second jaw of the end effector. In one aspect, positioning and orientation of previously stapled tissue within the end effector is determined by measuring and comparing tissue impedance at a number of predetermined zones within the end effector. In various aspects, tissue impedance measurements can also be utilized to identify overlapped layers of tissue and their position within an end effector.

Figure 122:
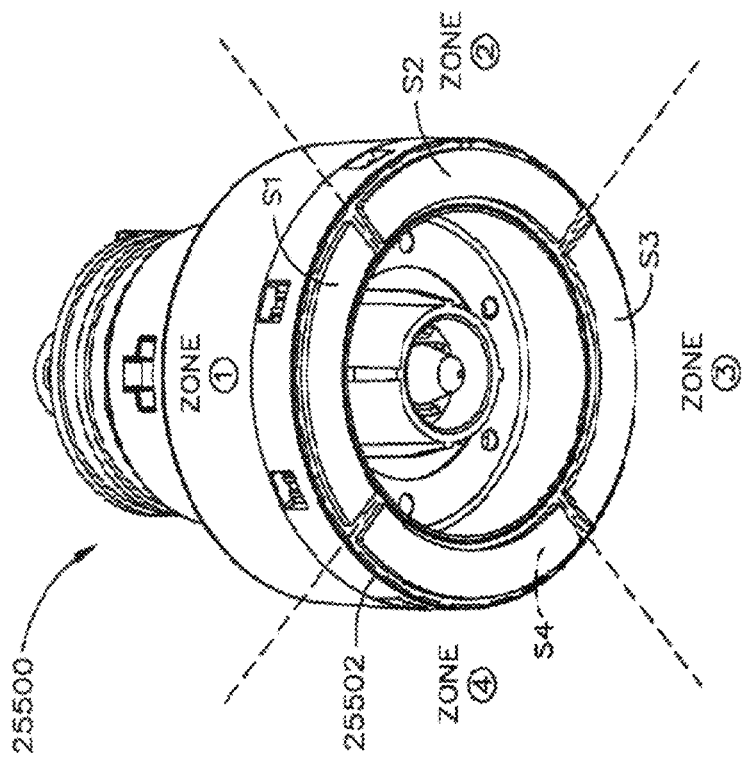
Figure 124:
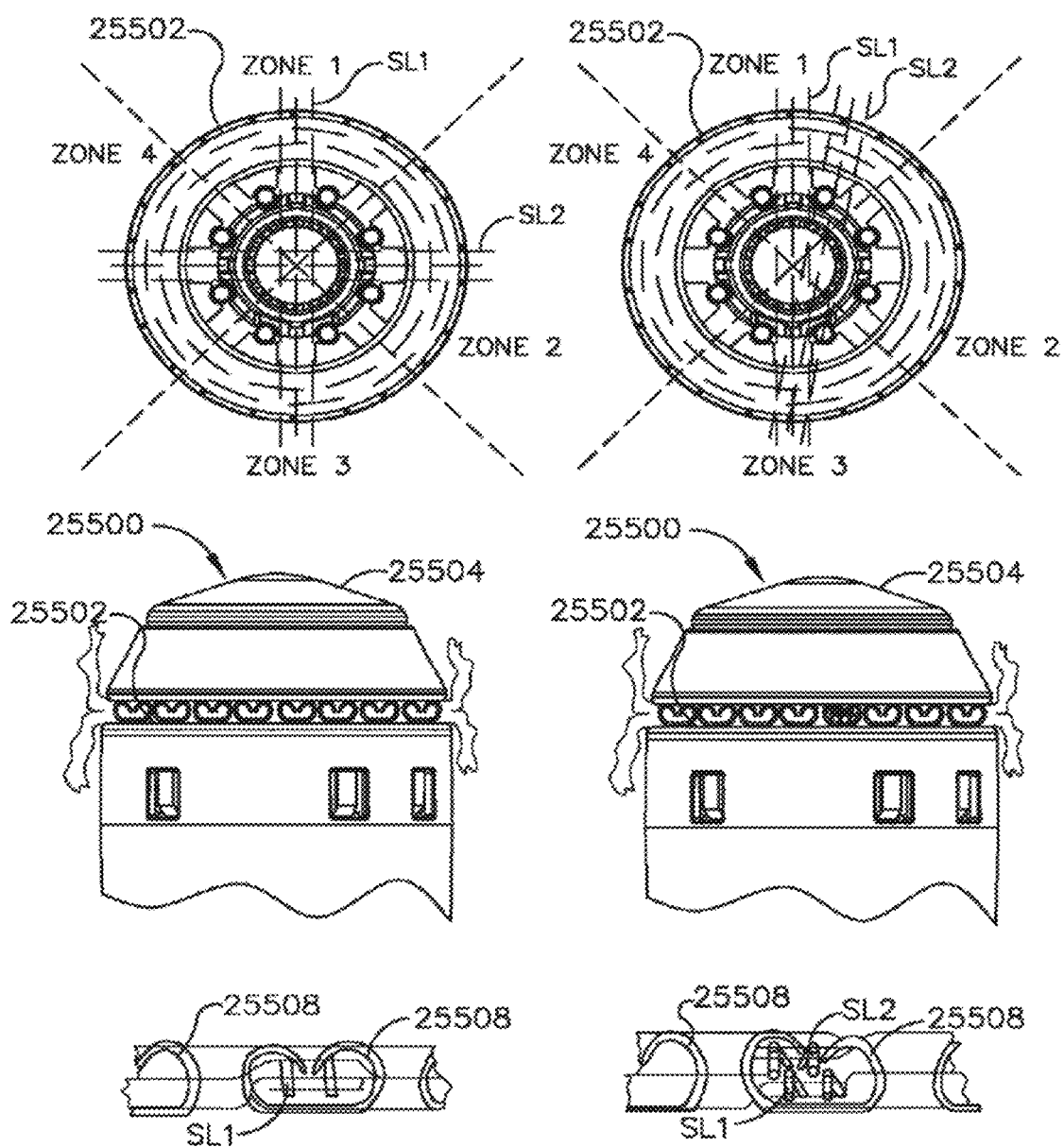

FIGS. 122, 124 illustrate an end effector 25500 of a circular stapler that includes a staple cartridge 25502 and an anvil 25504 configured to grasp tissue therebetween. The anvil 25504 and staple cavities 25505 of the staple cartridge 25502 are removed from FIG. 122 to highlight other features of the end effector 25500. The staple cartridge 25502 includes four predetermined zones (Zone 1, Zone 2, Zone 3, Zone 4) defined by sensing circuits (S1, S2, S3, S4), in accordance with the present disclosure.

Figure 123:
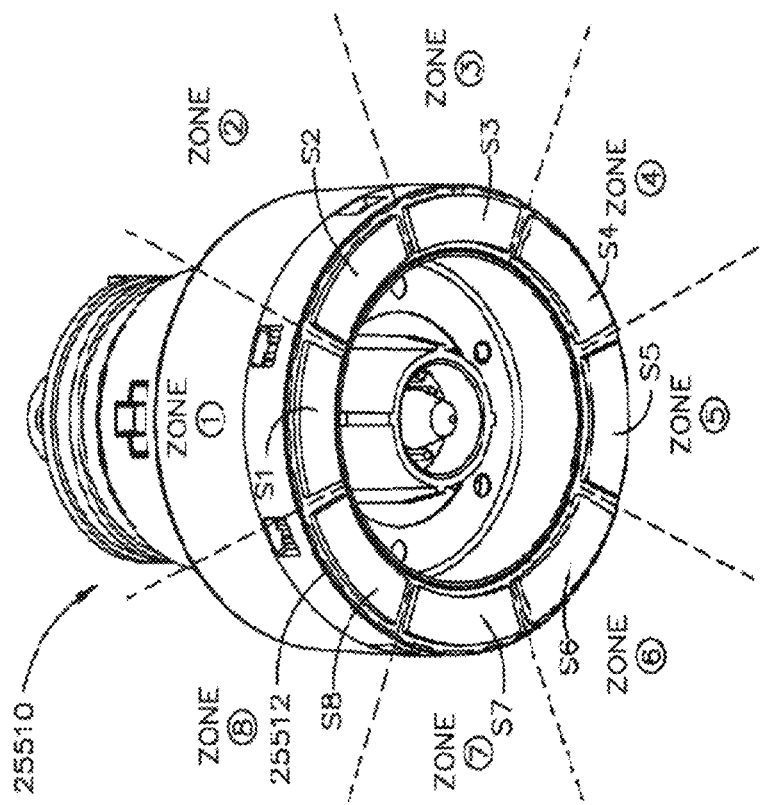

FIG. 123 illustrates another end effector 25510 of a circular stapler that includes staple cartridge 25512 and an anvil configured to grasp tissue therebetween. The anvil and staple cavities of the staple cartridge 25512 are removed to highlight other features of the end effector 25510. The staple cartridge 25512 includes eight predetermined zones (Zone 1-Zone 8) defined by sensing circuits (S1-S8), in accordance with the present disclosure. The zones defined in each of the circular staplers of FIGS. 122 and 123 are equal, or at least substantially equal, in size, and are arranged circumferentially around a longitudinal axis extending longitudinally through shafts of the circular staplers.

As described above, a previously stapled tissue is a tissue that includes staples that were previously deployed into the tissue. Circular staplers are often utilized in stapling previously stapled tissue to other previously stapled tissue (e.g. End-To-End Anastomosis procedures), as illustrated in FIG. 124.

The presence of the staples in tissue affects the tissue impedance as the staples usually have different conductivity than tissue. The present disclosure presents various tools and techniques for monitoring and comparing tissue impedances at the predetermined zones of an end effector (e.g. end effectors 25500, 25510) of a circular stapler to determine an optimal positioning and orientation of a previously-stapled tissue with respect to the end effector.

The examples on the left sides of FIG. 124 demonstrate properly positioned and oriented previously-stapled tissue with respect to predetermined zones of a circular stapler. The previously-stapled tissue properly extends through the center of the staple cartridge 25502, and only once intersects a predetermined zone. The bottom left side of FIG. 124 demonstrate staples 25508 of the staple cartridge 25502 deployed into properly positioned and oriented previously-stapled tissue.

The examples on the right sides of FIG. 124 demonstrate poorly positioned and oriented previously-stapled tissue. The previously-stapled tissue is off center or overlaps at one or more predetermined zones. The bottom right side of FIG. 124 demonstrate staples 25508 of the staple cartridge 25502 deployed into poorly positioned and oriented previously-stapled tissue.

As used in connection with FIGS. 122-126 a staple line may include multiple rows of staggered staples and typically includes two or three rows of staggered staples, without limitation. In the examples of FIG. 124, a circular stapler of FIG. 122 is utilized to staple two tissues that include previously deployed staple lines SL1, SL2. In the example to the left of FIG. 124, which represents properly positioned and orientated staple lines SL1, SL2, each of Zone 1 through Zone 4 receives a discrete portion of one of the staple lines SL1, SL2. The first staple line SL1 extends across Zone 2 and Zone 4, while the second staple line SL2, which intersects the first staple line SL1 at a central point, extends across Zone 1 and Zone 3. Accordingly, the measured impedances in the four zones will be equal, or at least substantially equal, to one another, and will be less than the impedance of an unstapled tissue.

On the contrary, in the example to the right of FIG. 124, which represents improperly positioned and orientated staple lines SL1, SL2, the staple lines SL1, SL2 overlap, or extend substantially on top of one another, across Zone 1 and Zone 3 yielding lower impedance measurements in zone 1 and Zone 3 as compared to Zone 2 and Zone 4.

Figure 125:
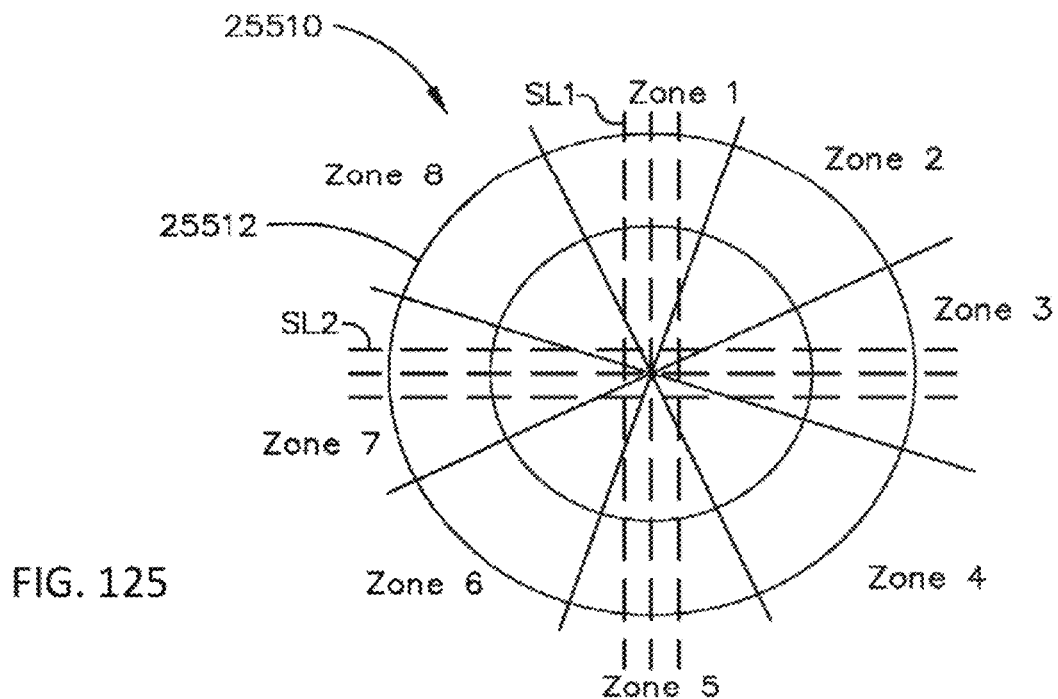
Figure 126:
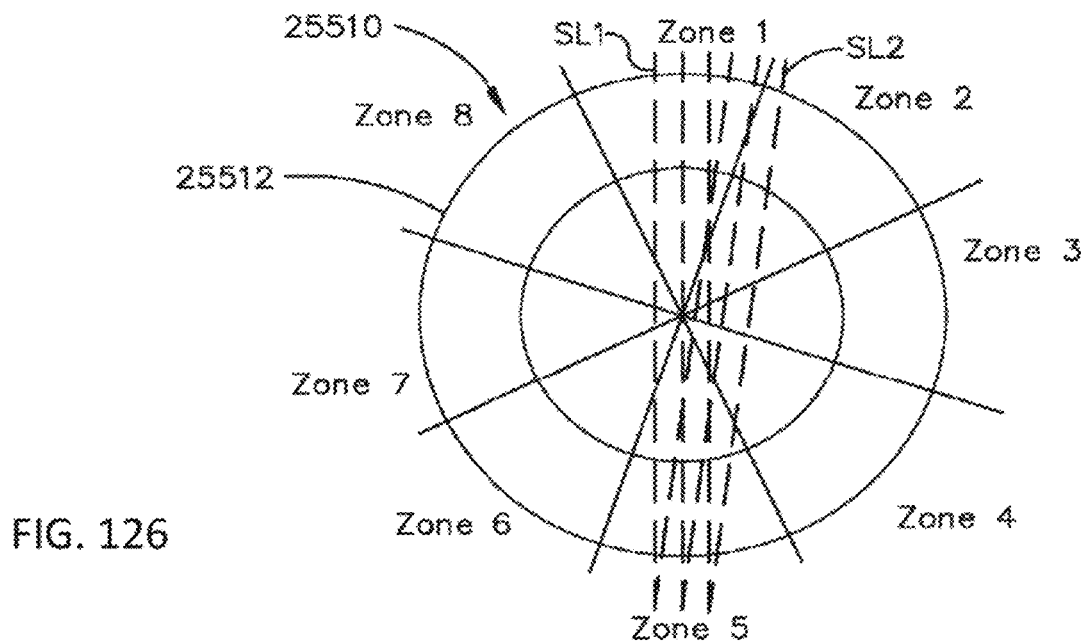

FIGS. 125 and 126 illustrate staple lines SL1, SL2 in an End-To-End anastomosis procedure performed by an end effector 25510 of a circular stapler that includes eight predetermined zones (zone 1: Zone 8) defined by eight sensing circuits S1-S8, as described above. The anvil of the end effector 25510 and staple cavities of the staple cartridge 25512 are removed from FIGS. 125 and 126 to highlight other features of the end effector 25510.

Figure 128:
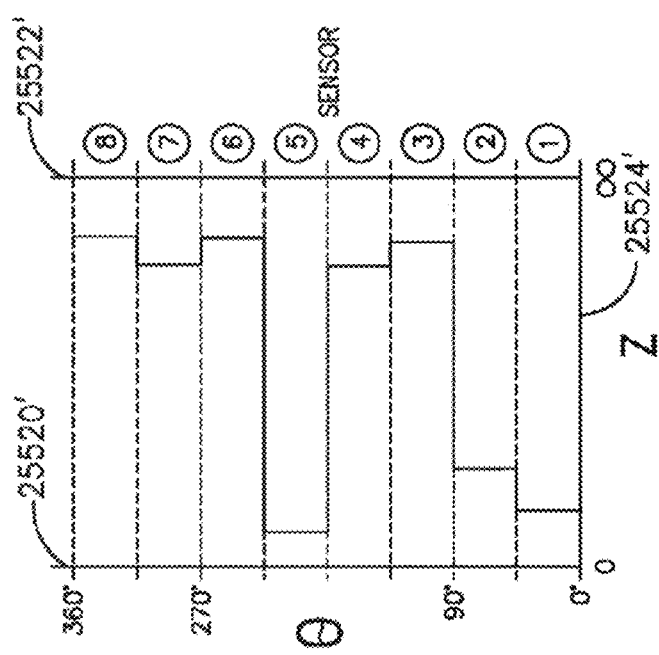
Figure 127:
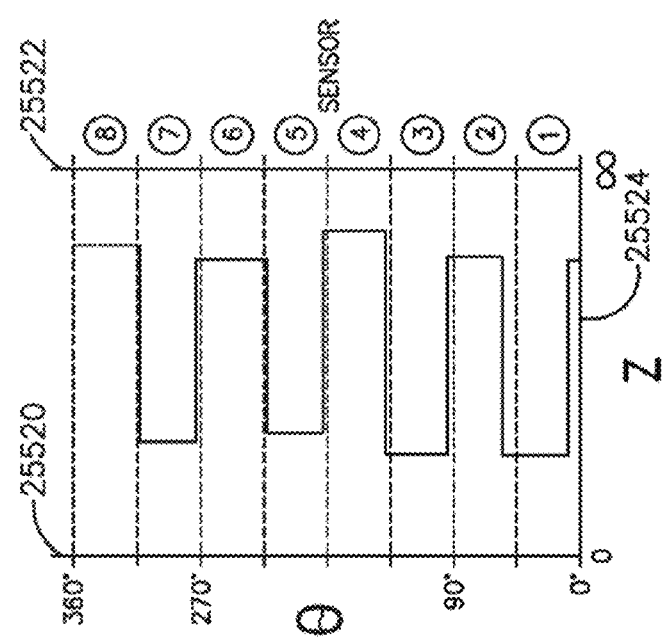

FIGS. 127 and 128 illustrate measured tissue impedances based on sensor signals from the sensing circuits S1-S8. The individual measurements define tissue impedance signatures. Vertical axes 25520, 25520' represent an angle of orientation (θ), while vertical axes 25522, 25522' list corresponding predetermined zones (Zone 1: Zone 8). Tissue impedance (Z) is depicted on horizontal axes 25524, 25524'.

In the example of FIGS. 125 and 127 the impedance measurements represent properly positioned and orientated staple lines SL1, SL2. As illustrated in FIG. 125, the staple lines SL1, SL2 extend through Zone 1, Zone 3, Zone 5, and Zone 7, and only overlap at a central point of the staple cartridge 25512. Since the previously-stapled tissue is evenly distributed among Zone 1, Zone 3, Zone 5, and Zone 7, tissue impedance measurements at such zones are the same, or at least substantially the same, in magnitude, and are significantly less than tissue impedance measurements at Zone 2, Zone 4, Zone 6, and Zone 8, which did not receive previously-stapled tissue.

Conversely, in the example of FIGS. 126, 128, the impedance measurements represent improperly positioned and orientated staple lines SL1, SL2. The staple lines SL1, SL2 overlap on top of one another extending only through Zone 1 and Zone 5. Accordingly, tissue impedance measurements at Zone 1 and Zone 5 are significantly lower in magnitude than the remaining zones, which did not receive previously-stapled tissue.

FIG. 129 illustrates is a logic flow diagram of a process 206520 depicting a control program or a logic configuration for selecting operational modes of a surgical hub 5104, in a surgical procedure, depending on a determined progress status of the surgical procedure. The process 2065520 can be performed by any suitable control circuit such as, for example, a control circuit of a surgical hub 5104. Data can be received 206522 from at least one data source, and may include patient data 206532 from a patient monitoring device, surgical staff data 206534 from a surgical staff detection device, modular device data 206536 from one or more modular devices and/or hospital data 206538 from a hospital database. The received 206522 data is processed by the surgical hub 5104 to determine a progress status of the surgical procedure. Additional details regarding determine whether surgery is process are disclosed in U.S. patent application Ser. No. 16/209,465, titled Method for adaptive control schemes for surgical network control and interaction, filed Dec. 4, 2018, which is herein incorporated by reference in its entirety.

As illustrated in FIG. 129, the received 206522 data can be utilized by the surgical hub 5104 to determine 206523 whether the surgical procedure is underway. If not, the surgical hub 5104 activates or selects a previous procedure/network interaction mode 206524. If, however, the surgical hub 5104 determines 206523 that the surgical procedure is underway, it further determines 206525 whether surgery is in progress. If not, the surgical hub 5104 activates or selects an interactive/configurable control mode 206526. If, however, the surgical hub 5104 determines 206525 that the surgery is in progress, the surgical hub 5104 activates or selects an instrument display control & procedural display mode 206528

The mode 206524 is more restrictive than the mode 206526, and the mode 206526 is more restrictive than the mode 206528. This arrangement is designed to take into consideration a user error in the form of inadvertent commands, for example. Before the surgical procedure starts, the mode 206524 only permits access to previous procedure data, and a limited interaction with a cloud-based system 104, 204, for example. During the preoperative steps, but before surgery is begun, the mode 206526 provides a less restrictive interface that permits a user to access and/or configure various parameters and/or controls without being able to use or activate such controls. In the least restrictive mode 206528, which is only available during surgery, the user is allowed to use or activate controls of certain modular devices depending on the surgical step being performed.

Surgical hubs may receive data determinative of a situational parameter of surgical procedure and in response adjust response to sensed parameter based on determined situational parameter. In at least one example, as illustrated in FIG. 130, the sensed parameter can be detecting 206552 a security threat. In other examples, the sensed parameter can be detecting 206554 a surgeon. In other examples, the sensed parameter can be detecting 20559 an instrument fault such as, for example, a modular device.

Further to the above, responding to a detected 206552 security threat depends on whether surgery is progress, which can be determined 206525, as described above in connection with FIG. 129. If it is determined 206525 that surgery is in progress, an isolated operation mode 206553 can be activated. If surgery is not in progress, the current security level can escalated 206551 to a higher security level, and an appropriate reaction or response can be taken to address the detected 206552 security threat. Additional details regarding determine whether surgery is process are disclosed in U.S. patent application Ser. No. 16/209,465, titled Method for adaptive control schemes for surgical network control and interaction, filed Dec. 4, 2018.

In various examples, the isolated operation mode 206553 comprises interrupting communications with external systems such as, for example, the cloud-based system 104, 204. In certain examples, the communications interruption excludes local communications within an operating room such as, for example, instrument-to-instrument communications, instrument-to-surgical hub 106, 206 communications, and/or remote controller-to-instrument communications.

Referring still to FIG. 130, responding to a detected 206554 surgeon depends on whether the surgical procedure is underway, which can be determined 206523, as described above in connection with FIG. 129. If it is determined 206523 that a surgical procedure is underway, linked instruments can be set 206557 to pre-defined parameters based on previous use configurations for the detected 206554 surgeon, for example. If, however, a surgical procedure is not underway, previous captured data and/or previous surgeries data can be called up 206555, for example. Additional details regarding determine whether surgical procedure is underway is process are disclosed in U.S. patent application Ser. No. 16/209,465, titled Method for adaptive control schemes for surgical network control and interaction, filed Dec. 4, 2018, which is herein incorporated by reference in its entirety Referring still to FIG. 130, responding to a detected 206556 instrument fault depends on whether the surgical procedure is underway, and further depends on whether surgery is in progress which can be determined 206523, 206525, as described above in connection with FIG. 129. An instrument can be, for example, a modular device. If it is determined 206523 that a surgical procedure is underway, and it is further determined 206525 that surgery is in progress, a limp mode can be activated 206565 for the instrument. If, however, a surgical procedure is not underway, a lockout of the surgical instrument can be engaged 206561 to prevent the surgical instrument from being used. Furthermore, if it is determined 206523 that a surgical procedure is underway, but surgery is not in progress, an alert or warning can be issued 206563 by the surgical hub 5104 to the surgical staff, for example, advising options.

FIG. 131 depicts a GUI displaying a series of menus comprising selectable options to aid a clinician in operating a particular surgical instrument, such as the instrument 208100 (shown in FIG. 132), for example. In the illustrated example, a first series of displays 208010 depict multiple selectable menu options where, in this instance, a specific surgeon is selected, a specific instrument is selected, and a specific function is selected. In such an instance, a specific surgeon can be selected so that a control circuit, such as the control circuit 208103, for example, may load particular settings, such as learned adaptive limits, for example, for that particular surgeon. A specific instrument, such as the instrument 208100, for example, can be selected so as to allow the control circuit to load a specific control program to operate that instrument. This may include a specific adaptive-limiting program corresponding to a specific instrument and a specific surgeon. All of the selected options can be taken into account by the control circuit so as to load the correct control program(s) and/or settings for operating the desired device. In the illustrated example, the firing function of STAPLER 2 for Dr. Jones has been selected. These options may be automatically sensed by the control circuit and, in at least one instance, are not selected. For example, the information may already be delivered to the control circuit in a package corresponding to the particular procedure by a surgical hub (e.g. 102, 202), for example. In another instance, a surgeon may wear an identifier chip that a component of the control circuit can sense, a surgical robot, such as the surgical robot 110, for example, to which the instrument is attached may be able to automatically identify what instrument is attached to the operating arm of the robot 110, and/or the firing setting of the particular instrument may be identified by the robot based on an indirect input from the surgeon on a surgical robot control interface, for example.

Still referring to FIG. 131, two displays 208020 are depicted showing selectable, in at least one instance, options for Dr. Jones for the firing function of STAPLER 2. As can be seen in these displays 208020, firing time and clamp force are displayed and can be related to the overall firing speed of the instrument, such as the instrument 208100, for example. In this instance, Dr. Jones may have limited experience. Such experience can be known by the control circuit, such as the control circuit 208103, for example, based on information stored about Dr. Jones. In such an instance, the range of permitted values for the firing speed, whether they be selectable learned limits and/or selectable direct function parameters, may be larger than a range of permitted values allowed for an experienced surgeon. For example, a display 208030 is illustrated where Dr. Smith, a more experienced surgeon than Dr. Smith, is provided tighter default settings. This may occur due to the amount of repetitions a surgeon has with a particular instrument, such as the instrument 208100, for example. In at least one instance, a permitted value range indicating safer operation of a particular instrument may be provided to a surgeon with less experience where more a permitted value range indicating riskier operation of a particular instrument may be provided to a surgeon with more experience.

FIG. 132 depicts a surgical instrument 208100 comprising a user interface 208101 and a control circuit 208103 con-figured to receive inputs from at the user interface 208101. The surgical instrument 208100 further comprises a motor driver 208105, a motor 208107 configured to be driven by the motor driver 208105 and controlled by the control circuit 208103, and an end effector 208109 comprising a firing member 208111 configured to be driven by the motor 208107. In at least one instance, various components of the surgical instrument 208100 may be substituted for an energy-based surgical instrument such as, for example, an ultrasonic surgical instrument. The control circuits described herein, such as the control circuit 208103, are configured to control any suitable end effector function, or parameter, powered by any suitable device. In at least one instance, the user interface 208101 comprises computer-based inputs rather than human-based inputs. For example, such computer-based inputs may originate from a surgical hub (e.g. 102, 202), for example. The surgical instrument 208100 can be employed with any of the systems, devices, and/or control circuits described herein. Various systems, devices, and/or control circuits described herein can be used for treating surgical patients. In the illustrated example, a surgical stapler can utilize a firing member, such as the firing member 208111, to cut the tissue of a patient and/or drive staples through tissue to fasten tissue during a surgical procedure. In such an instance, it can be advantageous to provide a control circuit capable of providing improved operation of the firing member. Any of the control circuits herein may provide such an advantage. In at least one instance, the firing member 208111 includes a firing assembly extending between the motor 208107 and the staples, for example, configured to be ejected by a sled. In at least one instance, the firing member 208111 includes one or more components of a firing assembly extending between the motor 208107 and the staples, for example, configured to be ejected by a sled.

FIGS. 133 and 134 illustrate a technique 4000 for interacting with a patient Electronic Medical Record (EMR) database 4002, according to one aspect of the present disclosure. In one aspect, the present disclosure provides a method of embedding a key 4004 within the EMR database 4002 located within the hospital or medical facility. A data barrier 4006 is provided to preserve patient data privacy and allows the reintegration of stripped and isolated data pairs, as described hereinbelow, from the surgical hub 106, 206 or the cloud 104, 204, to be reassembled. A schematic diagram of the surgical hub 206 is described generally in FIGS. 1-6 and 9-13. Therefore, in the description of FIG. 133, the reader is guided to FIGS. 1-6 and 9-13 for any implementation details of the surgical hub 206 that may be omitted here for conciseness and clarity of disclosure. Returning to FIG. 133, the method allows the users full access to all the data collected during a surgical procedure and patient information stored in the form of electronic medical records 4012. As shown in FIG. 134, the reassembled data can be displayed on a monitor 4010 coupled to the surgical hub 206 or secondary monitors but is not permanently stored on any surgical hub storage device 248. The reassembled data is temporarily stored in a storage device 248 located either in the surgical hub 206 or the cloud 204 and is deleted at the end of its use and overwritten to insure it cannot be recovered. The key 4004 in the EMR database 4002 is used to reintegrate anonymized hub data back into full integrated patient electronic medical records 4012 data.

As shown in FIG. 133, the EMR database 4002 is located within the hospital data barrier 4006. The EMR database 4002 may be configured for storing, retrieving, and managing associative arrays, or other data structures known today as a dictionary or hash. Dictionaries contain a collection of objects, or records, which in turn have many different fields within them, each containing data. The patient electronic medical records 4012 may be stored and retrieved using a key 4004 that uniquely identifies the patient electronic medical record 4012, and is used to quickly find the data within the EMR database 4002. The key-value EMR database 4002 system treats the data as a single opaque collection which may have different fields for every record.

Information from the EMR database 4002 may be transmitted to the surgical hub 206 and the patient electronic medical records 4012 data is redacted and stripped before it is sent to an analytics system based either on the hub 206 or the cloud 204. An anonymous data file 4016 is created by redacting personal patient data and stripping relevant patient data 4018 from the patient electronic medical record 4012. As used herein, the redaction process includes deleting or removing personal patient information from the patient electronic medical record 4012 to create a redacted record that includes only anonymous patient data. A redacted record is a record from which sensitive patient information has been expunged. Un-redacted data may be deleted 4019. The relevant patient data 4018 may be referred to herein as stripped/extracted data 4018. The relevant patient data 4018 is used by the surgical hub 206 or cloud 204 processing engines for analytic purposes and may be stored on the storage device 248 of the surgical hub 206 or may be stored on the cloud 204 based analytics system storage device 205. The surgical hub anonymous data file 4016 can be rebuilt using a key 4004 stored in the EMR database 4002 to reintegrate the surgical hub anonymous data file 4016 back into a fully integrated patient electronic medical record 4012. The relevant patient data 4018 that is used in analytic processes may include information such as the patient's diagnoses of emphysema, pre-operative treatment (e.g., chemotherapy, radiation, blood thinner, blood pressure medication, etc.), typical blood pressures, or any data that alone cannot be used to ascertain the identity of the patient. Data 4020 to be redacted includes personal information removed from the patient electronic medical record 4012, may include age, employer, body mass index (BMI), or any data that can be used to ascertain the identity of the patient. The surgical hub 206 creates a unique anonymous procedure ID number (e.g., 380i4z), for example. Within the EMR database 4002 located in the hospital data barrier 4006, the surgical hub 206 can reunite the data in the anonymous data file 4016 stored on the surgical hub 206 storage device 248 with the data in the patient electronic medical record 4012 stored on the EMR database 4002 for surgeon review. The surgical hub 206 displays the combined patient electronic medical record 4012 on a display or monitor 4010 coupled to the surgical hub 206. Ultimately, un-redacted data is deleted 4019 from the surgical hub 206 storage 248.

Creation of a Hospital Data Barrier, Inside which the Data from Hubs can be Compared Using Non-Anonymized Data and Outside of which the Data has to be Stripped In one aspect, the present disclosure provides a surgical hub 206 as described in FIGS. 5 and 6, for example, where the surgical hub 206 comprises a processor 244; and a memory 249 coupled to the processor 244. The memory 249 stores instructions executable by the processor 244 to interrogate a surgical instrument 235, retrieve a first data set from the surgical instrument 235, interrogate a medical imaging device 238, retrieve a second data set from the medical imaging device 238, associate the first and second data sets by a key, and transmit the associated first and second data sets to a remote network, e.g., the cloud 204, outside of the surgical hub 206. The surgical instrument 235 is a first source of patient data and the first data set is associated with a surgical procedure. The medical imaging device 238 is a second source of patient data and the second data set is associated with an outcome of the surgical procedure. The first and second data records are uniquely identified by the key.

In another aspect, the surgical hub 206 provides a memory 249 storing instructions executable by the processor 244 to retrieve the first data set using the key, anonymize the first data set, retrieve the second data set using the key, anonymize the second data set, pair the anonymized first and second data sets, and determine success rate of surgical procedures grouped by the surgical procedure based on the anonymized paired first and second data sets.

In another aspect, the surgical hub 206 provides a memory 249 storing instructions executable by the processor 244 to retrieve the anonymized first data set, retrieve the anonymized second data set, and reintegrate the anonymized first and second data sets using the key.

In another aspect, the first and second data sets define first and second data payloads in respective first and second data packets.

In various aspects, the present disclosure provides a control circuit to associate the first and second data sets by a key as described above. In various aspects, the present disclosure provides a non-transitory computer readable medium storing computer readable instructions which, when executed, causes a machine to associate the first and second data sets by a key as described above.

During a surgical procedure it would be desirable to monitor data associated with the surgical procedure to enable configuration and operation of instruments used during the procedure to improve surgical outcomes. The technical challenge is to retrieve the data in a manner that maintains the anonymity of the patient to maintain privacy of the data associated with the patient. The data may be used for conglomeration with other data without individualizing the data.

One solution provides a surgical hub 206 to interrogate an electronic medical records database 4002 for patient electronic medical records 4012 data, strip out desirable or relevant patient data 4018 from the patient electronic medical record 4012, and redact any personal information that could be used to identify the patient. The redaction technique removes any information that could be used to correlate the stripped relevant patient data 4018 to a specific patient, surgery, or time. The surgical hub 206 and the instruments 235 coupled to the surgical hub 206 can then be configured and operated based on the stripped relevant patient data 4018.

As disclosed in connection with FIG. 133, extracting (or stripping) relevant patient data 4018 from a patient electronic medical record 4012 while redacting any information that can be used to correlate the patient with the surgery or a scheduled time of the surgery enables the relevant patient data 4018 to be anonymized. The anonymous data file 4016 can then be sent to the cloud 204 for aggregation, processing, and manipulation. The anonymous data file 4016 can be used to configure the surgical instrument 235, or any of the modules shown in FIGS. 5 and 6 or the surgical hub 206 during the surgery based on the extracted anonymous data file 4016.

In one aspect, a hospital data barrier 4006 is created such that inside the data barrier 4006 data from various surgical hubs 206 can be compared using non-anonymized un-redacted data and outside the data barrier 4006 data from various surgical hubs 206 are stripped to maintain anonymity and protect the privacy of the patient and the surgeon. Additional details regarding this aspect are disclosed in U.S. patent application Ser. No. 16/209,385, titled Method of hub communication, processing, storage and display, filed Dec. 4, 2018, which is herein incorporated by reference in its entirety.

In one aspect, the data from a surgical hub 206 can be exchanged between surgical hubs 206 (e.g., hub-to-hub, switch-to-switch, or router-to-router) to provide in-hospital analysis and display of the data. FIG. 1 shows an example of multiple hubs 106 in communication which each other and with the cloud 104. Additional details regarding this aspect are disclosed in U.S. patent application Ser. No. 16/209,385, titled Method of hub communication, processing, storage and display, filed Dec. 4, 2018.

In another aspect, an artificial time measure is substituted for a real time clock for all information stored internally within an instrument 235, a robot located in a robot hub 222, a surgical hub 206, and/or hospital computer equipment. The anonymized data, which may include anonymized patient and surgeon data, is transmitted to the server 213 in the cloud 204 and it is stored in the cloud storage device 205 coupled to the server 213. The substitution of an artificial real time clock enables anonymizing the patient data and surgeon data while maintaining data continuity. In one aspect, the instrument 235, robot hub 222, surgical hub 206, and/or the cloud 204 are configured to obscure patient identification (ID) while maintaining data Within the surgical hub 206, a local decipher key 4004 allows information retrieved from the surgical hub 206 itself to reinstate the real-time information from the anonymized data set located in the anonymous data file 4016. The data stored on the hub 206 or the cloud 204, however, cannot be reinstated to real-time information from the anonymized data set in the anonymous data file 4016. The key 4004 is held locally in the surgical hub 206 computer/storage device 248 in an encrypted format. The surgical hub 206 network processor ID is part of the decryption mechanism such that if the key 4004 and data is removed, the anonymized data set in the anonymous data file 4016 cannot be restored without being on the original surgical hub 206 computer/storage device 248.

FIG. 47 illustrates a block diagram of a computer-implemented interactive surgical system 5700, in accordance with at least one aspect of the present disclosure. The system 5700 includes a number of surgical hubs 5706 that, as described above, are able to detect and track data related to surgical procedures that the surgical hubs 5706 (and the modular devices paired to the surgical hubs 5706) are utilized in connection with. In one exemplification, the surgical hubs 5706 are connected to form local networks such that the data being tracked by the surgical hubs 5706 is aggregated together across the network. The networks of surgical hubs 5706 can be associated with a medical facility, for example. The data aggregated from the network of surgical hubs 5706 can be analyzed to provide reports on data trends or recommendations. For example, the surgical hubs 5706 of a first medical facility 5704 a are communicably connected to a first local database 5708 a and the surgical hubs 5706 of a second medical facility 5704 b are communicably connected to a second local database 5708 b. The network of surgical hubs 5706 associated with the first medical facility 5704 a can be distinct from the network of surgical hubs 5706 associated with the second medical facility 5704 b, such that the aggregated data from each network of surgical hubs 5706 corresponds to each medical facility 5704 a, 5704 b individually. A surgical hub 5706 or another computer terminal communicably connected to the database 5708 a, 5708 b can be configured to provide reports or recommendations based on the aggregated data associated with the respective medical facility 5704 a, 5704 b. In this exemplification, the data tracked by the surgical hubs 5706 can be utilized to, for example, report whether a particular incidence of a surgical procedure deviated from the average in-network time to complete the particular procedure type.

In another exemplification, each surgical hub 5706 is configured to upload the tracked data to the cloud 5702, which then processes and aggregates the tracked data across multiple surgical hubs 5706, networks of surgical hubs 5706, and/or medical facilities 5704 a, 5704 b that are connected to the cloud 5702. Each surgical hub 5706 can then be utilized to provide reports or recommendations based on the aggregated data. In this exemplification, the data tracked by the surgical hubs 5706 can be utilized to, for example, report whether a particular incidence of a surgical procedure deviated from the average global time to complete the particular procedure type.

In another exemplification, each surgical hub 5706 can further be configured to access the cloud 5702 to compare locally tracked data to global data aggregated from all of the surgical hubs 5706 that are communicably connected to the cloud 5702. Each surgical hub 5706 can be configured to provide reports or recommendations based on the comparison between the tracked local data relative to local (i.e., in-network) or global norms. In this exemplification, the data tracked by the surgical hubs 5706 can be utilized to, for example, report whether a particular incidence of a surgical procedure deviated from either the average in-network time or the average global time to complete the particular procedure type.

In one exemplification, each surgical hub 5706 or another computer system local to the surgical hub 5706 is configured to locally aggregate the data tracked by the surgical hubs 5706, store the tracked data, and generate reports and/or recommendations according to the tracked data in response to queries. In cases where the surgical hub 5706 is connected to a medical facility network (which may include additional surgical hubs 5706), the surgical hub 5706 can be configured to compare the tracked data with the bulk medical facility data. The bulk medical facility data can include EMR data and aggregated data from the local network of surgical hubs 5706. In another exemplification, the cloud 5702 is configured to aggregate the data tracked by the surgical hubs 5706, store the tracked data, and generate reports and/or recommendations according to the tracked data in response to queries.

Each surgical hub 5706 can provide reports regarding trends in the data and/or provide recommendations on improving the efficiency or effectiveness of the surgical procedures being performed. In various exemplifications, the data trends and recommendations can be based on data tracked by the surgical hub 5706 itself, data tracked across a local medical facility network containing multiple surgical hubs 5706, or data tracked across a number of surgical hubs 5706 communicably connected to a cloud 5702. The recommendations provided by the surgical hub 5706 can describe, for example, particular surgical instruments or product mixes to utilize for particular surgical procedures based on correlations between the surgical instruments/product mixes and patient outcomes and procedural efficiency. The reports provided by the surgical hub 5706 can describe, for example, whether a particular surgical procedure was performed efficiently relative to local or global norms, whether a particular type of surgical procedure being performed at the medical facility is being performed efficiently relative to global norms, and the average time taken to complete a particular surgical procedure or step of a surgical procedure for a particular surgical team.

In one exemplification, each surgical hub 5706 is configured to determine when operating theater events occur (e.g., via a situational awareness system) and then track the length of time spent on each event. An operating theater event is an event that a surgical hub 5706 can detect or infer the occurrence of. An operating theater event can include, for example, a particular surgical procedure, a step or portion of a surgical procedure, or downtime between surgical procedures. The operating theater events can be categorized according to an event type, such as a type of surgical procedure being performed, so that the data from individual procedures can be aggregated together to form searchable data sets. In one exemplification, the surgical hub 5706 is configured to determine whether a surgical procedure is being performed and then track both the length of time spent between procedures (i.e., downtime) and the time spent on the procedures themselves. The surgical hub 5706 can further be configured to determine and track the time spent on each of the individual steps taken by the medical personnel (e.g., surgeons, nurses, orderlies) either between or during the surgical procedures. The surgical hub can determine when surgical procedures or different steps of surgical procedures are being performed via a situational awareness system, which is described in further detail above. Additional details regarding this aspect are disclosed in U.S. patent application Ser. No. 16/209,385, titled Method of hub communication, processing, storage and display, filed Dec. 4, 2018.

FIG. 46 illustrates a diagram of an illustrative analytics system 9100 updating a surgical instrument control program, in accordance with at least one aspect of the present disclosure. In one exemplification, a surgical hub 9000 or network of surgical hubs 9000 is communicably coupled to an analytics system 9100, as illustrated above in FIG. 13. The analytics system 9100 is configured to filter and analyze modular device 9050 data associated with surgical procedural outcome data to determine whether adjustments need to be made to the control programs of the modular devices 9050. The analytics system 9100 can then push updates to the modular devices 9050 through the surgical hubs 9000, as necessary. In the depicted exemplification, the analytics system 9100 comprises a cloud computing architecture. The modular device 9050 perioperative data received by the surgical 9000 hubs from their paired modular devices 9050 can include, for example, force to fire (i.e., the force required to advance a cutting member of a surgical stapling instrument through a tissue), force to close (i.e., the force required to clamp the jaws of a surgical stapling instrument on a tissue), the power algorithm (i.e., change in power over time of electrosurgical or ultrasonic instruments in response to the internal states of the instrument and/or tissue conditions), tissue properties (e.g., impedance, thickness, stiffness, etc.), tissue gap (i.e., the thickness of the tissue), and closure rate (i.e., the rate at which the jaws of the instrument clamped shut). It should be noted that the modular device 9050 data that is transmitted to the analytics system 9100 is not limited to a single type of data and can include multiple different data types paired with procedural outcome data. The procedural outcome data for a surgical procedure (or step thereof) can include, for example, whether there was bleeding at the surgical site, whether there was air or fluid leakage at the surgical site, and whether the staples of a particular staple line were formed properly. The procedural outcome data can further include or be associated with a positive or negative outcome, as determined by the surgical hub 9000 or the analytics system 9100, for example. The modular device 9050 data and the procedural outcome data corresponding to the modular device 9050 perioperative data can be paired together or otherwise associated with each other when they are uploaded to the analytics system 9100 so that the analytics system 9100 is able to recognize trends in procedural outcomes based on the underlying data of the modular devices 9050 that produced each particular outcome. In other words, the analytics system 9100 can aggregate the modular device 9050 data and the procedural outcome data to search for trends or patterns in the underlying device modular data 9050 that can indicate adjustments that can be made to the modular devices' 9050 control In the depicted exemplification, the analytics system 9100 executing the process 9200 described in connection with FIG. 13 is receiving 9202 modular device 9050 data and procedural outcome data. When transmitted to the analytics system 9100, the procedural outcome data can be associated or paired with the modular device 9050 data corresponding to the operation of the modular device 9050 that caused the particular procedural outcome. The modular device 9050 perioperative data and corresponding procedural outcome data can be referred to as a data pair. The data is depicted as including a first group 9212 of data associated with successful procedural outcomes and a second group 9214 of data associated with negative procedural outcomes. For this particular exemplification, a subset of the data 9212, 9214 received 9202 by the analytics system 9100 is highlighted to further elucidate the concepts discussed herein.

For a first data pair 9212 a, the modular device 9050 data includes the force to close (FTC) over time, the force to fire (FTF) over time, the tissue type (parenchyma), the tissue conditions (the tissue is from a patient suffering from emphysema and had been subject to radiation), what number firing this was for the instrument (third), an anonymized time stamp (to protect patient confidentiality while still allowing the analytics system to calculate elapsed time between firings and other such metrics), and an anonymized patient identifier (002). The procedural outcome data includes data indicating that there was no bleeding, which corresponds to a successful outcome (i.e., a successful firing of the surgical stapling instrument). For a second data pair 9212 b, the modular device 9050 data includes the wait time prior the instrument being fired (which corresponds to the first firing of the instrument), the FTC over time, the FTF over time (which indicates that there was a force spike near the end of the firing stroke), the tissue type (1.1 mm vessel), the tissue conditions (the tissue had been subject to radiation), what number firing this was for the instrument (first), an anonymized time stamp, and an anonymized patient identifier (002). The procedural outcome data includes data indicating that there was a leak, which corresponds to a negative outcome (i.e., a failed firing of the surgical stapling instrument). For a third data pair 9212 c, the modular device 9050 data includes the wait time prior the instrument being fired (which corresponds to the first firing of the instrument), the FTC over time, the FTF over time, the tissue type (1.8 mm vessel), the tissue conditions (no notable conditions), what number firing this was for the instrument (first), an anonymized time stamp, and an anonymized patient identifier (012). The procedural outcome data includes data indicating that there was a leak, which corresponds to a negative outcome (i.e., a failed firing of the surgical stapling instrument). It should be noted again that this data is intended solely for illustrative purposes to assist in the understanding of the concepts discussed herein and should not be interpreted to limit the data that is received and/or analyzed by the analytics system 9100 to generate control program updates.

When the analytics system 9100 receives 9202 perioperative data from the communicably connected surgical hubs 9000, the analytics system 9100 proceeds to aggregate and/or store the data according to the procedure type (or a step thereof) associated with the data, the type of the modular device 9050 that generated the data, and other such categories. By collating the data accordingly, the analytics system 9100 can analyze the data set to identify correlations between particular ways of controlling each particular type of modular device 9050 and positive or negative procedural outcomes. Based upon whether a particular manner of controlling a modular device 9050 correlates to positive or negative procedural outcomes, the analytics system 9100 can determine 9204 whether the control program for the type of modular device 9050 should be updated.

For this particular exemplification, the analytics system 9100 performs a first analysis 9216 of the data set by analyzing the peak FTF 9213 (i.e., the maximum FTF for each particular firing of a surgical stapling instrument) relative to the number of firings 9211 for each peak FTF value. In this exemplary case, the analytics system 9100 can determine that there is no particular correlation between the peak FTF 9213 and the occurrence of positive or negative outcomes for the particular data set. In other words, there are not distinct distributions for the peak FTF 9213 for positive and negative outcomes. As there is no particular correlation between peak FTF 9213 and positive or negative outcomes, the analytics system 9100 would thus determine that a control program update to address this variable is not necessary. Further, the analytics system 9100 performs a second analysis 9216 *b* of the data set by analyzing the wait time 9215 prior to the instrument being fired relative to the number of firings 9211. For this particular analysis 9216 *b*, the analytics system 9100 can determine that there is a distinct negative outcome distribution 9217 and a positive outcome distribution 9219. In this exemplary case, the negative outcome distribution 9217 has a mean of 4 seconds and the positive outcome distribution has a mean of 11 seconds. Thus, the analytics system 9100 can determine that there is a correlation between the wait time 9215 and the type of outcome for this surgical procedure step. Namely, the negative outcome distribution 9217 indicates that there is a relatively large rate of negative outcomes for wait times of 4 seconds or less. Based on this analysis 9216 *b* demonstrating that there is a large divergence between the negative outcome distribution 9217 and the positive outcome distribution 9219, the analytics system 9100 can then determine 9204 that a control program update should be generated 9208.

Once the analytics system 9100 analyzes the data set and determines 9204 that an adjustment to the control program of the particular module device 9050 that is the subject of the data set would improve the performance of the modular device 9050, the analytics system 9100 then generates 9208 a control program update accordingly. In this exemplary case, the analytics system 9100 can determine based on the analysis 9216 *b* of the data set that a control program update 9218 recommending a wait time of more than 5 seconds would prevent 90% of the distribution of the negative outcomes with a 95% confidence interval. Alternatively, the analytics system 9100 can determine based on the analysis 9216 *b* of the data set that a control program update 9218 recommending a wait time of more than 5 seconds would result in the rate of positive outcomes being greater than the rate of negative outcomes. The analytics system 9100 could thus determine that the particular type of surgical instrument should wait more than 5 seconds before being fired under the particular tissue conditions so that negative outcomes are less common than positive outcomes. Based on either or both of these constraints for generating 9208 a control program update that the analytics system 9100 determines are satisfied by the analysis 9216 *b*, the analytics system 9100 can generate 9208 *a* control program update 9218 for the surgical instrument that causes the surgical instrument, under the given circumstances, to either impose a 5 second or longer wait time before the particular surgical instrument can be fired or causes the surgical instrument to display a warning or recommendation to the user that indicates to the user that the user should wait at least 5 seconds before firing the instrument. Various other constraints can be utilized by the analytics system 9100 in determining whether to generate 9208 *a* control program update, such as whether a control program update would reduce the rate of negative outcomes by a certain percentage or whether a control program update maximizes the rate of positive outcomes.

After the control program update 9218 is generated 9208, the analytics system 9100 then transmits 9210 the control program update 9218 for the appropriate type of modular devices 9050 to the surgical hubs 9000. In one exemplification, when a modular device 9050 that corresponds to the control program update 9218 is next connected to a surgical hub 9000 that has downloaded the control program update 9218, the modular device 9050 then automatically downloads the update 9218. In another exemplification, the surgical hub 9000 controls the modular device 9050 according to the control program update 9218, rather than the control program update 9218 being transmitted directly to the modular device 9050 itself.

FIGS. 135-136 depict an example surgical circular stapling instrument 216010 that can be adapted to include an RFID system and a control system thereof, in accordance with at least one aspect of the present disclosure. The stapling instrument 216010 may be used to provide an end-to-end anastomosis between two sections of an anatomical lumen such as a portion of a patient's digestive tract. Instrument 216010 of this example comprises a housing assembly 216100, a shaft assembly 216200, a stapling head assembly 216300, and an anvil 216400. Housing assembly 216100 comprises a casing 216110 defining an obliquely oriented pistol grip 216112. Although the housing assembly 216100 is depicted in the form of a handle, this is not limiting. In various instances, the housing assembly 216100 can be a component of a robotic system, for example.

Housing assembly 216100 further includes a window 216114 that permits viewing of a movable indicator needle. In some versions, a series of hash marks, colored regions, and/or other fixed indicators are positioned adjacent to window 216114 in order to provide a visual context for indicator needle, thereby facilitating operator evaluation of the position of needle within window 216114. The movement of the indicator needle corresponds to a closing motion of the anvil 216400 relative to the stapling head assembly 216300. The hash marks, colored regions, and/or other fixed indicators can define an optimal anvil closure zone for firing the instrument 216010. Accordingly, when the indicator needle is in the optimal anvil closure zone, the user may fire the instrument 216010. Various suitable alternative features and configurations for housing assembly 216100 will be apparent to those of ordinary skill in the art in view of the teachings herein.

Instrument 216010 of the present example further includes a power source which can be in the form of a battery pack 216120. Battery pack 216120 is operable to provide electrical power to a motor 216160 (shown in FIG. 137) in pistol grip 216112. In various aspects, battery pack 216120 is removable from housing assembly 216100. In particular, as shown in FIGS. 135-136, battery pack 216120 may be inserted into a socket 216116 defined by casing 216110. Once battery pack 216120 is fully inserted in socket 216116, latches 216122 of battery pack 216120 may resiliently engage interior features of casing 216110 to provide a snap fit. To remove battery pack 216120, the operator may press latches 216122 inwardly to disengage latches 216122 from the interior features of casing 216110 then pull battery pack 216120 proximally from socket 216116. It should be understood that battery pack 216120 and housing assembly 216100 may have complementary electrical contacts, pins and sockets, and/or other features that provide paths for electrical communication from battery pack 216120 to electrically powered components in housing assembly 216100 when battery pack 216120 is inserted in socket 216116. It should also be understood that, in some versions, battery pack 216120 is unitarily incorporated within housing assembly 216100 such that battery back 216120 cannot be removed from housing assembly 216100.

Shaft assembly 216200 extends distally from housing assembly 216100 and includes a preformed bend. In some versions, the preformed bend is configured to facilitate positioning of stapling head assembly 216300 within a patient's colon. Various suitable bend angles or radii that may be used will be apparent to those of ordinary skill in the art in view of the teachings herein. In some other versions, shaft assembly 216200 is straight, such that shaft assembly 216200 lacks a preformed bend. Various exemplary components that may be incorporated into shaft assembly 216200 will be described in greater detail below.

Stapling head assembly 216300 is located at the distal end of shaft assembly 216200. As shown in FIGS. 135-136, anvil 216400 is configured to removably couple with shaft assembly 216200, adjacent to stapling head assembly 216300. Anvil 216400 and stapling head assembly 216300 are configured to cooperate to manipulate tissue in three ways, including clamping the tissue, cutting the tissue, and stapling the tissue. A knob 216130 at the proximal end of housing assembly 216100 is rotatable relative to casing 216110 to provide precise clamping of the tissue between anvil 216400 and stapling head assembly 216300. When a safety trigger 216140 of housing assembly 216100 is pivoted away from a firing trigger 216150 of housing assembly 216100, firing trigger 216150 may be actuated to thereby provide cutting and stapling of the tissue.

In the following discussion of anvil 216400, the terms "distal" and "proximal" and variations thereof will be used with reference to the orientation of anvil 216400 when anvil 216400 is coupled with shaft assembly 216200 of instrument 216010. Thus, proximal features of anvil 216400 will be closer to the operator of instrument 216010; while distal features of anvil 216400 will be further from the operator of instrument 216010.

FIG. 137 illustrates a logic diagram of a control system 221211 of a surgical instrument or tool in accordance with one or more aspects of the present disclosure. The control system 221211 includes a control circuit 221210 that can be integrated with the RFID scanner 221202 or can be coupled to, but positioned separately from, the RFID scanner 221202 in the housing assembly 216100, for example. The control circuit 221210 can be configured to receive input from the RFID scanner 221202 indicative of the information about a staple cartridge located on stapling head assembly 216300 that is stored in the RFID tag 221203 and/or information about the anvil 221200 that is stored in the RFID tag 221201.

In various examples, the RFID tag 221203 stores identification information of the staple cartridge and the RFID tag 221201 stores identification information of the anvil 221200. In such examples, the control circuit 221210 receives input from the RFID scanner 221202 indicative of the identification information of the staple cartridge and verifies the identity of the staple cartridge based on the input. Further, the control circuit 221210 receives input from RFID scanner 221202 indicative of the identification information of the anvil 221200 and verifies the identity of the anvil 221200 based on the input.

In at least one example, the control circuit 221210 includes a microcontroller 221213 that has a processor 221214 and a storage medium such as, for example, a memory 221212. The memory 221212 stores program instructions for performing various processes such as, for example, identity verification. The program instructions, when executed by the processor 221214, cause the processor 221214 to verify the identity of the staple cartridge and the identity of the anvil 221200 by comparing the identification information received from the RFID tags 221201, 221203 to identification information stored in the memory 221212 in the form of an identity database or table, for example.

In at least one example, the control circuit 221210 can be configured to check compatibility of the anvil 221200 with staple cartridge of the stapling head assembly 216300 based on input from the RFID scanner 221202. The processor 221214 can, for example, check the identity information of the anvil 221200 and the staple cartridge against a compatibility database or table stored in memory 221212.

In various examples, the memory 221212 comprises a local memory of the instrument 216010. In other examples, identity databases or tables and/or compatibility databases or tables can be downloaded from a remote server. In various aspects, the instrument 216010 may transmit the information received from RFID tags 221201, 221203 to a remote server that stores the databases or tables for performing the identity and/or compatibility checks remotely.

Referring to FIG. 137, motors 216160, 221160 are coupled to motor drivers 216161 and 221161, respectively, which are configured to control the operation of the motors 216160 and 221160 including the flow of electrical energy from a power source (e.g. battery pack 216120) to the motors 216160 and 221160. In various examples, the processor 221214 is coupled to the motors 216160, 221160 through the motor drivers 216161, 221161. In various forms, the motor 216160 and/or the motor 221160 may be a brushed direct current (DC) motor with a gearbox and mechanical links to effect a tissue treatment by a surgical end effector. In one aspect, motor drivers 216161, 221161 may be in the form of an A3941 available from Allegro Microsystems, Inc. Other motor drivers may be readily substituted for use with the control system 221211.

In various forms, the motors 216160, 221160 may be a brushed DC driving motor having a maximum rotational speed of approximately 25,000 RPM. In other arrangements, the motors 216160, 221160 may include a brushless motor, a cordless motor, a synchronous motor, a stepper motor, or any other suitable electric motor. The motor driver 216161, 221161 may comprise an H-bridge driver comprising field-effect transistors (FETs), for example. The motors 216160, 221160 can be powered by a power source. The power source may comprise a battery which may include a number of battery cells connected in series that can be used as the power source to power the surgical instrument or tool. In certain circumstances, the battery cells of the power source may be replaceable and/or rechargeable. In at least one example, the battery cells can be lithium-ion batteries which can be couplable to and separable from the power source.

In various aspects, a motor driver in accordance with the present disclosure may be a full-bridge controller for use with external N-channel power metal-oxide semiconductor field-effect transistors (MOSFETs) specifically designed for inductive loads, such as brush DC motors. The motor driver may comprise a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system comprising an absolute positioning system.

In various aspects, one or more of the motors of the present disclosure can include a rotatable shaft that operably interfaces with a gear assembly that is mounted in meshing engagement with a set, or rack, of drive teeth on a displacement member of a firing drive assembly 221163 or a closure drive assembly 216163, for example. A sensor element may be operably coupled to a gear assembly such that a single revolution of the position sensor element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable a closure member, firing member, firing bar, I-beam, or combinations thereof.

In certain examples, as illustrated in FIG. 137, transition of the anvil 216400 to a closed configuration with the stapling head assembly 216300 is driven by the motor 221160. In such examples, the control circuit 221210 permits the motor 221160 to drive closure of the anvil 216400 if proper orientation, full seating, and/or proper identity of the anvil 216400 is detected by the control circuit 221210 based on input from the RFID scanner 221202 and/or RFID scanner 221204, as described above. Accordingly, a detected failure at establishing one or more of proper orientation, full seating, and/or proper identity of the anvil 216400 causes the control circuit 221210 to prevent the motor 221160 from starting and/or completing closure of the anvil 216400.

In certain examples, the control circuit 221210 permits the motor 216160 to drive staple firing and advancement of the cylindrical knife member if staple cartridge-anvil compatibility is confirmed based on the information stored in the RFID tags 221201, 221203 as reported by RFID scanners 221202. Conversely, the control circuit 221210 is configured to prevent the motor 216160 from driving staple firing and advancement of the cylindrical knife member if the staple cartridge-anvil compatibility cannot be established based on the information stored in the RFID tags 221201, 221203 as reported by RFID scanners 221202.

In various examples, antennas of one or more of the RFID tags 221201, 221203 and the RFID scanner 221202 may be supplemented with booster antennas that are engaged upon connection. In various examples, the antennas of active RFID tags on the surgical instrument 216010 such as, for example, the RFID tag 221201 and RFID tag 221203 can be cut during normal operation of the surgical instrument 216010 in planned manner. The lost signals from such RFID tags can signify completion of a surgical task.

In various aspects, an RFID tag can be positioned along the pathway of the cylindrical knife member. The RFID tag may transmit a signal through its antenna to the RFID scanner 221202, for example. When the antenna is severed by the knife member, the signal is lost. The signal loss can confirm advancement of the knife member.

In one example, the RFID tag is positioned on a breakable washer of the anvil 216400. In such example, the breakable washer is broken by the knife member toward the end of a full distal range of motion of the knife member. The knife member cuts the antenna of the RFID tag while breaking the breakable washer. When the antenna is severed, the signal transmitted from the RFID tag to the RFID scanner 221202, for example, is lost. The RFID scanner 221202 can be coupled to the control circuit 221210, and can report the signal loss to the control circuit 221210. The signal loss is interpreted by the control circuit 221210 to indicate completion of a firing sequence of the surgical instrument 216010.

In various aspects, as described above greater detail, a surgical instrument such as, for example, the instrument 216010 includes an anvil 216400 movable toward a stapling head assembly 216300 to capture tissue therebetween in a closed configuration. The tissue is then stapled and cut in a firing sequence of the surgical instrument 216010. The instrument 216010 further includes an RFID tag such as, for example, the RFID tag 221201 and an RFID scanner such as, for example, the RFID scanner 221202 that is configured to read and/or write to the RFID tag 221201. The RFID tag 221201 and the RFID scanner 221202 define an RFID system that can be employed by a control circuit 221210 to determine a characteristic of the tissue based on the RF signal backscatter from the tissue.

The positions of the RFID tag 221201 and the RFID scanner 221202 with respect to the tissue grasped between the anvil 216400 and the stapling head assembly 216300 can be selected for optimal measurements of the RF signal backscatter. In at least one example, the RFID tag 221201 and the RFID scanner 221202 can be positioned on opposite sides of the tissue.

The RF signal from the backscatter data can be gathered and correlated with known tissue characteristics to permit tissue analysis. In various aspects, the spectral characteristics of the backscatter data can be analyzed to determine various characteristics of the tissue. In at least one example, the backscatter data is employed to identify boundary features within the tissue. In at least one example, the backscatter data can be used to assess thickness of the tissue grasped between the anvil 216400 and the stapling head assembly 216300.

Applicant discloses systems and techniques for adaptive control of surgical instrument functions. A surgical instrument may be configured to communicate with an external system such as, for example, a surgical hub. The surgical hub may generate, and the surgical instrument may receive, an indication of one or more functions to be adaptively controlled by the surgical instrument. For example, a surgical stapler instrument may receive an indication to adaptively control a display of staple height operating range and/or to adaptively control motorized features of the surgical instrument. The surgical instrument may determine values for parameters associated with the identified function and adapt the control of the identified function based upon the determined parameters. The surgical instrument may modify its operation of the one or more controlled functions based upon the parameters. The surgical instrument may communicate additional information such as additional parameter values to the external system and may receive further input regarding continued control of the indicated one or more functions.

FIG. 138 depicts a flow chart of example processing for adaptive control of surgical instrument functions. As shown, at 225010, a surgical instrument may establish communication with an external system such as, for example, a surgical hub system. The surgical instrument may communicate parameters associated with the surgical instrument to the surgical hub. For example, the surgical instrument may communicate an indication of hardware comprised in the device, software operating on the device, and/or any other relevant information relating to the surgical instrument and its use.

The surgical hub system may use the identity of the surgical instrument and the one or more parameter values received from the surgical instrument to determine one or more functions that the surgical instrument may control during its processing. For example, if the parameters indicate the surgical instrument is a surgical circular stapler with an interchangeable end effector, the surgical hub system may determine that the surgical instrument should provide adaptive control of the staple height operating range. If the parameters indicate the surgical instrument is a surgical circular stapler of a type that has been used in previous surgical procedures for which the surgical hub system has relevant operating or operational parameters, the surgical hub system may determine that the surgical instrument should provide control of its system using operational parameters derived from prior surgical procedures.

At 225020, the surgical hub system transmits, and the surgical instrument receives, an indication to provide one or more controlled functions from the surgical hub system. The indication may be communicated in any suitable manner including, for example, as parameters. The indication may indicate to the surgical instrument to provide, for example, an adaptive staple height operating range, adaptive control of motorized tissue compression, and/or device control using operational parameters associated with previous surgical procedures.

At 225030, the surgical instrument may determine one or more parameters associated with the one or more controlled functions that were indicated in the communication from the surgical hub system. For example, if the surgical instrument has received an indication to provide an adaptive staple height operating range, the surgical instrument may determine parameters relating to the size of an anvil head associated with an end effector of the surgical instrument. If the surgical instrument has received an indication to provide adaptable control of a motor associated with force applied by a tissue compression anvil, the surgical instrument may monitor for an indication that a force to insert a staple is being applied. If the surgical instrument has received an indication to use operational parameters from previously completed surgical procedures, the surgical instrument may determine operational parameters from previous procedures by requesting and receiving the operational parameters from the surgical hub system.

At 225040, the surgical instrument may provide the one or more controlled functions indicated in the communication from the surgical hub based upon the determine parameters. For example, the surgical instrument may provide an adaptable staple height operating range based upon the parameters indicating a size of the anvil head of an end effector. If the anvil head is relatively small or large, the staple height operating range may be modified from a default representation. If the surgical instrument has received an indication to provide control of motors adapted for tissue compression, upon receiving data indicating a staple is being or is about to be inserted, the surgical instrument may control the motor to increase force applied to provide compression at the appropriate time and for the appropriate duration. If the surgical instrument has received an indication to provide control based upon operational parameters associated with previously completed surgical procedures, the surgical instrument may use the received operational parameters to perform its operations.

At 225050, the surgical instrument may continue to communicate with the surgical hub system as needed to provide additional parameters and information regarding its status and operation to the surgical hub and to receive additional instructions and data for performing controlled operations from the surgical hub.

A surgical instrument may receive an indication from the surgical hub to provide an adaptable stable height operating range. FIG. 139 depicts an example motorized circular stapling instrument 210100. The example motorized circular stapling instrument 210100 may include structure may be adapted to perform functions as described in connection with instrument 201800 appearing in FIG. 100 and in connection with instrument 216010 appearing in FIG. 135. The circular stapling instrument 210100 may include a shaft assembly 210150, a handle assembly 210170, and a rotation knob 210180. The shaft assembly 210150, handle assembly 210170, and rotation knob 210180 may operate as described in connection with 201806, 201808, and 201812, respectively, in connection with the instrument 201800. The shaft assembly 210150, handle assembly 210170, and rotation knob 210180 may operate as described in connection with 216200, 216100, and 216130, respectively, in the instrument 216010.

The shaft assembly 210150 may be configured to be attached to and operate with one or more end effectors. The end effectors may include end effectors of different configurations. For example, the end effectors may be configured with different sizes, different shapes, different functionality, and the like. The end effectors may be configured for different tissue types and/or for different conditions of a particular tissue type, for example.

The end effector may include an anvil, such as 201804 or 216400. The end effector may include a head assembly 201802. The shaft assembly 210150 may be configured to operate with head assemblies of different sizes. For example, the shaft assembly 210150 may be configured to operate with a small-sized anvil 210110A. The shaft assembly 210150 may be configured to operate with a small-sized stapling head assembly 210130A. The shaft assembly 210150 may be configured to operate with a medium-sized (e.g., the standard size) anvil 210110B. The shaft assembly 210150 may be configured to operate with a medium-sized (e.g., the standard size) stapling head assembly 210130B. The shaft assembly 210150 may be configured to operate with a large-sized anvil 210110C. The shaft assembly 210150 may be configured to operate with a large-sized stapling head assembly 210130C.

Each stapling head assembly 210130A-C may include a respective data storage element 210120A-C. For example, stapling head assembly 210130B may include data storage element 210120B. The data storage element 210130B may be configured to store data and to transmit the stored data. The data may be transmitted via a wired and/or wireless connection. The data storage element 210120B may store data and/or information pertaining to the respective anvil 210110B and/or the stapling head assembly 210130B. The data may comprise data identifying the type of the stapling head assembly (e.g., motorized circular stapler head assembly), characteristics of the anvil 210110B (e.g., the anvil head's size, such as the diameter), the status of the stapling head assembly (e.g., whether staples have been fired), and/or the like.

The data storage element 210120B may include any device, system, and/or subsystem suitable for storing and/or providing stored data. For example, the data storage element 210120B may comprise an RFID micro-transponder and/or an RFID chip including a digital signature. The data storage element 210120B may include a battery-assisted passive RFID tag. A battery-assisted passive RFD tag may exhibit improved range and signal length (e.g., as compared to RFID micro-transponders and/or RFID chips). The data storage element 210120B may include a writable section that may be used to store data described herein. The data may be written to the writable section via a control circuit of the instrument 210100 such as is described in connection with FIGS. 7-8 and 98-99. The writable section may be read by a sensor of instrument 210100. For example, when a staple is fired, the instrument 210100 may write data indicative of the fired staple event to the writeable section. The instrument 210100 (or another instrument, for example) may subsequently read the data indicative of the fired staple event from the writeable section. This data writing and reading may enable the instrument 210100 to inform the user and/or other related systems of the staple firing history.

The stapling head assemblies 210130A and 210130C may include data storage elements 210120A and 210120C, respectively. The data storage elements 210120A and 210120C may function and be implemented as described with reference to the data storage element 210120B.

The stapling head assemblies 210130A, 210130B, and 210130C may each include a respective staple cartridge. A staple cartridge may include predetermined zones. The predetermined zones may be defined by sensing circuits. The predetermined zones may, via the sensing circuits, enable measurement of tissue impedance. The stapling head assemblies may include a stapling head assembly such as is illustrated in FIG. 122 or FIG. 123. As illustrated in FIG. 123, the staple cartridge 25512 may comprise eight predetermined zones (Zone 1-Zone 8) defined by sensing circuits ($S_1$-$S_8$). The zones defined in the circular staplers of FIGS. 122 and 41 may be equal, or at least substantially equal, in size, and may be arranged circumferentially around a longitudinal axis extending longitudinally through shafts of the circular staplers. FIG. 127 illustrates an example where tissue impedance measurements on the staple cartridge 25512 are substantially similar in magnitude, in Zone 1, Zone 3, Zone 5, and Zone 7, which may have received previously-stapled tissue. Significantly higher tissue impedance measurements on the staple cartridge 25512 may be substantially uniform in magnitude in Zone 2, Zone 4, Zone 6, and Zone 8, which may not have received previously-stapled tissue. FIG. 128 illustrates tissue impedance measurements unevenly distributed among the zones.

The handle assembly 210170 may include a motor as described with reference to instrument 201800. The handle assembly 210170 may include a plurality of motors as described in FIGS. 8, 98, 99, and 137. For example, the handle assembly 210170 may include at least a separately controlled anvil closure motor (e.g., closure motor 603 shown in FIG. 8 and motor 216160 shown in FIG. 137) and a separately controlled firing motor (e.g., firing motor 602 shown in FIG. 8 and motor 221160 shown in FIG. 137).

The handle assembly 210170 may comprise a graphical representation of an adaptable staple height operating range 210160, which also may be referred to as a representation of an operating range for tissue compression. The adaptable staple height operating range 210160 may operate similar to window 216114 as described in connection with FIGS. 135-136. The graphical representation may include variable staple height windows (such as, for example, those described with reference to variable staple height windows 201076, 201078, 201080, 201082 in FIG. 23). The graphical representation may include variable staple firing ranges (such as, for example, those described with reference to staple firing ranges 201088, 201090, 201092 in FIG. 105). The adaptable staple height operating range 210160 may be adapted based on one or more parameters sensed by the instrument 210100. The adaptable staple height operating range 210160 may be adapted based on one or more previously used parameter configurations.

The adaptable staple height operating range 210160 may operate as described in connection with FIGS. 140-143. FIG. 140 illustrates an example representation of an adaptable staple height operating range displayed as it might appear on an example motorized circular stapling instrument 210100. A control circuit may enable the adaptable staple height operating range 210160. The adaptable staple height operating range 210160 may be adapted according to a mode, such as a stroke control mode, a load control mode, and/or a previous-configuration control mode, for example. The adaptable staple height operating range 210160 may be adapted according to a mode in a tiered system of operation modes. Mode selection (e.g., whether the instrument 210100 operates in a stroke control mode, a load control mode, or a previous-configuration control mode) may be determined by a system parameter that the instrument 210100 receives from an external system. For example, the instrument 210100 may be linked (e.g., paired) with a surgical hub in an operating room and may receive configuration information from the surgical hub. An indication which may be, for example, a system parameter, may be transmitted from the surgical hub to the instrument 210100. The system parameter may indicate to the instrument 210100 to operate in a particular control mode. The instrument 210100 may determine to operate in one of the stroke control mode, load control mode, or a previous-configuration control mode based on the received system parameter. The system parameter may be a setting associated with one or more of the following: a medical professional (e.g., a surgeon); a particular patient and/or class of patients; a medical facility or an institution; a subscription level and/or purchased software tier; or the like.

FIG. 141 is a flow diagram depicting example processing for providing an adaptable staple height operating range while the motorized circular stapling instrument operates in a stroke control operation mode. At 211010, a surgical circular stapler 211000, which may an instrument 210100, may receive an indication, which may comprise a system parameter, to provide an adaptable staple height operating range (illustrated at 210160 in FIG. 139 and at 210160A-C in FIG. 140) while operating in a stroke control mode. The stroke control mode may refer to adapting the adaptable staple height operating range 210160 at least based on the stroke position of the anvil and the anvil head size during, for example, tissue clamping. For example, when a medium-sized anvil head 210110B with a medium-sized diameter ($D_{medium}$) is selected to operate with the surgical circular stapler 211000, at 211012, the surgical circular stapler's control circuitry may determine the $D_{medium}$ diameter size from the value stored in the data storage element 210120B (as shown in FIG. 139).

At 211014, the surgical circular stapler may use the determined size of the anvil head, e.g., medium, to determine that a standard adaptable staple height operating range 210160B should be presented. The standard adaptable staple height operating range 210160B may include a standard viable (e.g., workable) staple height range represented by a standard yellow zone y and a standard viable staple firing range represented by a green zone g. As shown in FIG. 140, the yellow zone represents a first laterally extending band and the green zone represents a second laterally extending band positioned within the first laterally extending band.

When the large-sized anvil head 210110C with a large-sized diameter ($D_{large}$) is selected to operate with the surgical circular stapler 211000, at 211012, the surgical circular stapler's 211000 control circuit may determine the $D_{large}$ diameter size from the value stored in data storage element 210120C (shown in FIG. 139). At 211014, the surgical circular stapler may use the determined size of the anvil head, i.e., large, to determine that an adaptable staple height operating range 210160C should be presented. Referring to FIG. 140, the adaptable staple height operating range 210160C may include a viable staple height range represented by a yellow zone $y_2$ and a viable staple firing range represented by a green zone $g_2$. A viable staple height range may be referred to as an adaptable viable staple height range. A viable staple firing range may be referred to as an adaptable viable staple firing range and/or adaptable staple firing range. The tissue 210540C being clamped on by the anvil head 210110C may have the same tissue thickness $G_{standard}$ as the tissue 210540B clamped by the anvil head 210110B. The surgical circular stapler 211000 may determine the adaptable staple height operating range 210160C by shifting up the standard yellow zone y and the standard green zone g to be yellow zone $y_2$ and the green zone $g_2$, respectively. As compared with the standard yellow, the laterally extending band representing the yellow zone, y2, may be compressed or narrower. As compared with the standard green zone, the laterally extending band representing green zone, $g_2$, may be shifted upwards. The shift may be due to $D_{large}$ being larger than $D_{medium}$ and result from the same anvil closure force effecting a higher staple height when clamping with a large anvil head. Such an effect may be due to a large anvil head size with a larger clamping surface area requiring a larger anvil closure force to effect the same staple height. The surgical circular stapler 211000 may determine the adaptable staple height operating range 210160C by determining a narrower $y_2$ and a narrower green zone $g_2$ than the standard yellow zone y and the standard green zone g, respectively. Such adaptation may be caused by a higher staple height being effected when clamping with a large anvil head given the same clamping force. The unavailable lower staple height range renders the yellow zone and the green zone narrower.

When the small-sized anvil head 210110A with a small-sized diameter ($D_{small}$) is selected to operate with the surgical circular stapler 211000, at 211012, the surgical circular stapler's 211000 control circuit may determine the $D_{small}$ diameter size from the value stored in data storage element 210120A (shown in FIG. 139). At 211014, the surgical circular stapler may determine an adaptable staple height operating range 210160A. The adaptable staple height operating range 210160A may include a viable staple height range represented by a yellow zone $y_1$ and a viable staple firing range represented by a green zone $g_1$. The tissue 210540C being clamped by the anvil head 210110C may have a thinner tissue thickness $G_{thin}$ (corresponding to a longer anvil stroke relative to the fully open stroke position) of the tissue 210540A as compared to the tissue thickness $G_{standard}$ (corresponding to a shorter anvil stroke relative to the fully open stroke position) of the tissue 210540B clamped by the anvil head 210110B. The surgical circular stapler 211000 may determine the adaptable staple height operating range 210160A by shifting down the standard yellow zone y and the standard green zone g to be yellow zone $y_1$ and the green zone $g_1$, respectively. As compared with the standard yellow, the laterally extending band representing the yellow zone, y, may be shifted downward. As compared with the standard green zone, the laterally extending band representing green zone, g1, may be wider. The surgical circular stapler 211000 may determine the adaptable staple height operating range 210160A by determining a wider green zone $g_1$ than the standard green zone g. Such adaptation may be due to $D_{small}$ being smaller than $D_{medium}$ because the same anvil closure force may effect a lower staple height when clamping with a smaller anvil head. Such an effect may be due to a smaller anvil head size with a smaller clamping surface area requiring a smaller anvil closure force to effect the same staple height. Such adaptation may also be due to the thinner tissue thickness $G_{thin}$ of the tissue 210540A than the tissue thickness $G_{standard}$ of the tissue 210540B being clamped on by the anvil head 210110B which corresponds to a smaller anvil gap at the beginning of tissue clamping.

At 211016, the surgical circular stapler may display the adaptable staple height operating range.

FIG. 142 depicts a flow diagram of example processing for providing an adaptable staple height operating range while the motorized circular stapling instrument operates in a load control operation mode. At 211510, the surgical circular stapler may receive an indication, which may be a system parameter, to provide an adaptable staple height operating range (illustrated at 210160 in FIG. 139 and at 210160A-C in FIG. 140) in a load control mode. The load control mode may refer to adapting the adaptable staple height operating range 210160 based on a force-to-close (FTC) (e.g., sensed motor load as a proxy for FTC) during tissue clamping and tissue creep/wait phase, in addition to the anvil head size and the stroke position of the anvil.

During tissue clamping, when the small-sized anvil head 210110A with a small-sized diameter ($D_{small}$) is selected to operate with the surgical circular stapler 211000, at 211512, the surgical circular stapler's 211000 control circuit may determine the FTC in addition to determining the $D_{small}$ parameter and sensing the tissue thickness $G_{thin}$ upon the anvil head 210110A's initial contact with the tissue 210540A as described at 211012 in connection with FIG. 141. At 211514, the surgical circular stapler 211000 may determine an adaptable staple height operating range and, at 211516, may display the adaptable staple height operating range. Such adaptable staple height operating range may be a further adaptation from that described at 211014 with reference to FIG. 141. For example, given a same tissue thickness, the determined FTC during tissue clamping may vary depending on variable tissue stiffness as described between times $t_1$ and $t_2$ in the Tissue Compression Force v. Time function graph in FIG. 106 herein. In the example of the tissue compression force curve 202026 that corresponds to tissue of low stiffness, because a lower FTC is sensed, the yellow zone and the green zone of the adaptable staple height operating range may shift further down as compared to tissue of normal stiffness. In the example of the tissue compression force curve 202024 that corresponds to tissue of high stiffness, because a higher FTC is sensed, the yellow zone and the green zone of the adaptable staple height operating range may shift up as compared tissue of normal stiffness.

At 211014, given a same anvil gap, the determined FTC during tissue creep/wait phase may vary depending on variable tissue stiffness as described between $t_2$ and $t_3$ in the Tissue Compression Force v. Time function graph in FIG. 106 herein. If the example tissue compression force curves 202022, 202024, 202026 were to be applied, because a decreased FTC is sensed, the yellow zone and the green zone of the adaptable staple height operating range may shift further down during tissue creep/wait phase as compared to the yellow zone and the green zone as determined during tissue clamping.

A surgical instrument may receive an indication from the surgical hub to provide adaptive motor control. FIG. 144 is a diagram illustrating various aspects of an example motorized circular stapling instrument operating using adaptive motor control in a load control operation mode. FIG. 144 illustrates that the surgical circular stapler 211000, such as the instrument 210100, may be used in a surgical procedure to maintain a constant anvil gap during staple firing/tissue cutting by dynamically adapting the anvil closure motor's (described in FIG. 139) output to the firing motor's (as described in FIG. 139) output. Such adaptation may counter a force generated by the firing motor with a force in the opposite direction generated by the anvil closure motor. Both forces may be applied on the anvil to maintain a constant anvil gap. Graph 212510 depicts sensed motor load for the anvil closure motor (e.g., FTC) and sensed motor load for the firing motor (e.g., force to fire (FTF) or force to advance knife (FAK)) versus time. Graph 211512 depicts sensed anvil gap versus time. Graph 211514 depicts sensed tissue stretching versus time. Graph 211516 depicts motor output (e.g., power, current, and/or torque) of the anvil closure motor and the firing motor versus time.

FIG. 145 depicts a flow diagram of an example motorized circular stapling instrument operating using adaptive motor control in a load control operation mode. At 213010, a surgical circular stapler 211000, such as the instrument 210100, may receive an indication to provide motor control. For example, the surgical circular stapler may receive a system parameter for setting load control mode.

At 213012, the surgical circular stapler 211000 may monitor a first motor associated with force applied by an anvil to compress tissue (e.g., the anvil closure motor described herein). In the example surgical processing described in connection with FIG. 144, at t0 (e.g., when the anvil senses an initial contact with the tissue), the surgical circular stapler's 211000 control circuit may start monitoring the stroke position of the anvil by, for example, sensing the anvil gap as illustrated in graph 212512. The control circuit may also start monitoring the motor load for the anvil closure motor as illustrated in graph 212510. As the anvil gap decreases, the control circuit may cause the anvil closure motor to start generating a constant output ("first anvil closure motor output") to effect motorized tissue clamping as illustrated in graph 212516. Consequently, the control circuit may start sensing an increasing motor load (e.g., FTC) for the anvil closure motor as illustrated in graph 212510. In such manner, the surgical circular stapler 211000 may monitor the anvil closure motor's motor load.

Referring to FIG. 144, at t1, the surgical circular stapler's 211000 control circuit may sense the anvil gap has stopped decreasing and remains constant, and in response may cause the anvil closure motor to stop generating the first anvil closure motor output to end motorized tissue clamping and allow tissue creep/wait phase to start as illustrated in graph 212516. As the control circuit continues to monitor the anvil closure motor's motor load, the control circuit may sense a decreasing motor load (e.g., FTC) and then sense a constant motor load (e.g., FTC) as tissue stabilization is reached at t2 as illustrated in graph 212510. In such manner, the surgical circular stapler 211000 further monitors the anvil closure motor's motor load. Between t0 and t2, graph 212514 illustrates tissue stretch increasing at the end of tissue clamping, reaching a maximum at time t1, decreasing as tissue creep starts, and becoming constant at t2.

At 213014 in FIG. 145, the surgical circular stapler 211000 may monitor a second motor associated with application of force to insert a surgical staple (e.g. the firing motor described herein). In the example surgical procedure depicted in FIG. 144, at t2, the surgical circular stapler's 211000 control circuit may cause the firing motor to start generating a constant output ("first firing motor output") upon, for example, an instrument operator (e.g., a surgeon) triggering staple firing as illustrated in graph 212516. In response, the control circuit may start monitoring the motor load for the firing motor as illustrated in graph 212510, in addition to monitoring the constant motor load for the anvil closure motor starting at t2. In such manner, the surgical circular stapler 211000 monitors the firing motor's motor load.

At 213016 in FIG. 145, the surgical circular stapler 211000 may identify an indication associated with application of a force to insert a surgical staple into tissue compressed by the anvil. For example, continuing with the timeline illustrated in FIG. 144, at t2, as the surgical circular stapler's 211000 control circuit starts monitoring the motor load for the firing motor, the control circuit may start sensing an increasing motor load (e.g., FTF) for the firing motor as illustrated in graph 212510 resulting from the first firing motor output. In such manner, the surgical circular stapler 211000 may identify an indication associated with application of a force for staple firing. Graph 212514 illustrates the tissue stretch increasing starting at $t_2$ as the motor load (e.g., FTF) for the firing motor increases.

At 213018 in FIG. 145, the surgical circular stapler 211000 may determine, in response to identifying the indication associated with application of force to insert a surgical staple, to control the first motor to cause the anvil to apply force to the tissue. Continuing with the timeline illustrated in FIG. 144, at t3, the surgical circular stapler's 211000 control circuit senses an increasing motor load (e.g., FTF) for the firing motor. In response, the control circuit may generate a constant output ("second anvil closure motor output"). The second anvil closure motor output may effect a force for anvil closure in order to counter the increasing tissue stretching described at 213016 and thereby maintain a constant anvil gap. The surgical circular stapler 211000 controls the anvil closure motor to apply a force for anvil closure in response to identifying an indication of application of a force for staple firing.

As a further example of processing at 213016 and 213018, in FIG. 145, and continuing with the timeline illustrated in FIG. 144, at t4, the instrument's 210100 advancing knife may make the initial contact with the breakable washer (as described in connection with FIG. 137). Upon sensing the initial contact, the surgical circular stapler's 211000 control circuit may cause the anvil closure motor to generate a higher constant output ("third anvil closure motor output") than the second anvil closure motor output. The third anvil closure motor output may effect a higher force for anvil closure for a brief period to counter the anticipated additional force spike to be applied on the anvil as the knife pushes and cuts through the breakable washer as illustrated in graph 212516. The period may end at t5 when the breakable washer is cut. The surgical circular stapler 211000 thereby further controls the anvil closure motor to apply a force for anvil closure in response to identifying an indication of application of a force for staple firing (i.e., the force for cutting through the breakable washer).

In FIG. 144, an increased motor load spike sensed, $F_w$, that corresponds to the force applied by the knife as it cuts through the breakable washer and the countering anvil closure force effected by the anvil closure motor are depicted in graph 212510. This is yet another example of FIG. 145's steps 213012 and 213014 for monitoring the motor for anvil closure and the motor for staple firing, respectively. In graph 212514 between t4 and t5, an increased tissue stretching is depicted as another effect of the force applied by the knife cutting through the breakable washer. As illustrated with a dotted line in FIG. 144, between t4 and t5, graph 212512 depicts a potential increased anvil gap that may be caused by the force applied by the knife cutting through breakable washer had the third anvil closure motor output not been generated. In such manner, a constant anvil gap may be maintained as the knife pushes and cuts through the breakable washer.

Between t5 and t6, illustrated in graph 21516, is another generated anvil closure motor output ("fourth anvil closure motor output") for a very brief period to effect a force for anvil opening. Such force may be used to counter the force the knife applies on the breakable washer in the anvil closing direction as the knife retracts to its seated position after having cut through the breakable washer.

Between t6 and t7, a period is depicted before the anvil gap increases upon an instrument operator initiating an anvil stroke to open the anvil. At t7, as the surgical circular stapler's 211000 control circuit senses an increasing anvil gap, the control circuit causes the anvil closure motor to generate another constant output ("fifth anvil closure motor output") to effect motorized anvil opening.

FIGS. 146-148 depict flow diagrams for processing associated with three sub-modes in a tiered system of operation modes under which the instrument 210100 operates in the load control mode. FIG. 146 illustrates the instrument 210100 operating under a sub-mode, e.g., the default sub-mode, where the motor load for the anvil closure motor (e.g., current drawn by the motor as a proxy for FTC) may be statically measured to ensure the instrument 210100 satisfies a predetermined criteria for staple firing ("static measurement sub-mode"). FIG. 147 illustrates the instrument 210100 operating under a sub-mode where sensor readings may be repeatedly measured to ensure the instrument 210100 satisfies a predetermined criteria for staple firing ("repeated sensor measurement sub-mode"). FIG. 148 illustrates the instrument 210100 operating under a sub-mode, which is the previous-configuration control mode described above with reference to FIGS. 140-0143, where the predetermined criteria described in FIGS. 146 and 147 may be preconfigured with previously used configurations which may be stored in an external system, such as a surgical hub. Mode selection for such sub-modes may be determined by a system parameter as described above.

Referring to FIG. 146, in the example of load control mode's static measurement sub-mode, at 213510, the surgical circular stapler 211000, which may be the instrument 210100, may receive an indication to provide motor control that includes motorized control of anvil closure and motorized control of surgical stapler firing. For example, the system parameter for setting the surgical circular stapler 211000 to operate in load control mode described herein may, by default, serve as such indication.

At 213512, the surgical circular stapler 211000 may determine, based on an indication associated with the first motor, that a force applied by the anvil to compress the tissue satisfies a predetermined threshold. For example, an indication associated with the motor associated with force applied by an anvil to compress tissue may be a motor load for the surgical circular stapler's 211000 anvil closure motor. The motor load may be sensed at the end of the tissue creep/wait phase. The sensed motor load may be a tissue compression force (also referred to as FTC) with a magnitude that is within a predetermined range, such as the tissue compression force curve 202022 between t2 and t3 (i.e., a tissue creep/wait phase) that lies within a range from $F_{min}$ to $F_{max}$, i.e., ideal firing zone 202036, as illustrated in FIG. 106. The tissue compression force curve 202062 between t4 and t5 (i.e., a tissue creep/wait phase) that lies within a range from $F_{min}$ to $F_{max}$ illustrated in FIG. 107 may be another such example.

At 213514, the surgical circular stapler 211000 may determine to apply the force to insert the surgical staple into the tissue compressed by the anvil after determining a force applied by the anvil to compress the tissue satisfies a predetermined threshold. For example, the surgical circular stapler's 211000 control circuit may be configured, similar to the control circuit 760 described in FIG. 106, to deploy the staples in the staple cartridge upon the surgical circular stapler's 211000 control circuit determining the tissue compression force F is within an ideal firing zone, such as the ideal firing zone 202036 in FIG. 106.

FIG. 147 illustrates the load control mode's repeated sensor measurement sub-mode. At 214010, the surgical circular stapler 211000 may receive an indication to provide motor control that includes motorized control based on sensor readings. A system parameter described herein for setting the surgical circular stapler 211000 to operate in load control mode's repeated sensor measurement sub-mode may serve as such indication.

At 214012, the surgical circular stapler 211000 may receive sensor readings associated with pressure applied to the tissue. For example, as described in FIG. 139 the surgical circular stapler's 211000 control circuit may receive tissue impedance measurements from predetermined zones on the staple cartridge as illustrated in FIGS. 122-123.

At 214014, the surgical circular stapler 211000 may determine the sensor readings indicating pressure applied to the tissue is applied substantially uniformly. For example, as described in connection with FIG. 139, the surgical circular stapler's 211000 control circuit may determine that tissue impedance measurements are substantially uniform as illustrated in FIG. 127. This determination may be based on a predetermined threshold that defines how much each predetermined zone's tissue impedance measurement may deviate from other zones and still be considered uniform. The surgical circular stapler's 211000 control circuit may be configured to perform tissue impedance measurements repeatedly (e.g., once per a pre-determined number of seconds) to determine the tissue impedance measurements are substantially uniform over a period of time, such as during tissue creep, including when tissue stabilization is reached.

At 214016, the surgical circular stapler 211000 may determine, based on the sensor readings indicating pressure applied to the tissue is applied substantially uniformly, to apply the force to insert the surgical staple into the tissue. For example, after the surgical circular stapler's 211000 control circuit determines the tissue impedance measurements are substantially uniform in the staple cartridge's predetermined zones as illustrated in FIG. 127 when tissue stabilization is reached, the surgical circular stapler's 211000 control circuit may deploy the staples in the staple cartridge when, for example, sensed motor load for the anvil closure motor (such as tissue compression F illustrated in FIG. 106) is also within an ideal firing zone as illustrated in FIG. 106.

A surgical instrument may receive an indication from the surgical hub to provide control using operating or operational parameters associated with previously performed procedures. FIG. 149 is a functional flow diagram associated with an example previous-configuration control mode. The previous-configuration control mode may include processes and functionality as described herein with reference to FIGS. 140-143 and with reference to FIGS. 144-148.

Referring to FIG. 149, at 215020, a surgical hub 215005, which may be, for example, a surgical hub as described in connection with FIGS. 1-6 and 9-13, may maintain a data store of relevant data including operational parameters for a surgical instrument such as a surgical circular stapler 211000. The operational parameters may comprise "previous operational parameters" or "previous operating parameters" which may be parameters associated with previously performed surgical procedures. As described in connection with FIGS. 47 and 134, operational parameters that a surgical hub may receive from surgical instruments and store locally may comprise, for example, force-to-close (FTC) curve versus time (FTC curve), force-to-fire (FTF) curve versus time (FTF curve), anvil closure rate, tissue properties (e.g., impedance, thickness, stiffness, etc.), as well as others.

The operational parameters that may be relevant to the operation of a surgical circular stapler 2111000 and may be provided to a stapler by a surgical hub, may vary depending upon the operational mode of the stapler. For example, operational parameters used in stroke control mode surgical procedures may include, for example, the following: stroke control mode indicator, anvil head size, tissue thickness, viable staple height range, viable staple firing range, and wait time before staple firing phase. Operational parameters used in load control mode in an example surgical procedure may include, for example, the following: load control mode indicator, anvil head size, tissue thickness, viable staple height range, viable staple firing range, and wait time before staple firing phase. Operational parameters used in previous-configuration control mode in an example surgical procedure may include, for example, the following previous-configuration control mode indicator, anvil head size, tissue thickness, tissue stiffness, viable staple height range, viable staple firing range, and wait time before staple firing phase.

The combination of parameters used for a procedure and which might be provided by a surgical hub to a surgical instrument may vary. For example, the combination of operational parameters used in the load control mode in an example surgical procedure may include, for example, the following: load control mode indicator, anvil head size, tissue thickness, tissue stiffness, viable staple height range, viable staple firing range, maximum FTC and minimum FTC allowed for staple firing, FTC curve, FTF curve, anvil closure motor output curve (e.g., graph 212516 shown in FIG. 144), firing motor output curve (e.g., graph 212516 shown in FIG. 144). In another example, the combination of operational parameters used in the load control mode in an example surgical procedure may include, for example, the following: load control mode indicator, repeated sensor measurement sub-mode indicator, anvil head size, tissue thickness, tissue stiffness, frequency of repeated measurement, tissue impedance for each predetermined zone on staple cartridge upon staple firing, viable staple height range, viable staple firing range, maximum FTC and minimum FTC allowed for staple firing, FTC curve, FTF curve, anvil closure motor output curve (e.g., graph 212516 shown in FIG. 144), firing motor output curve (e.g., graph 212516 shown in FIG. 144). In another example, the combination of operational parameters used in the load control mode in an example surgical procedure may include: previous-configuration control mode indicator, anvil head size, tissue thickness, tissue stiffness, sensor zone's tissue impedance uniformity deviation threshold, frequency of repeated sensor measurement, viable staple height range, viable staple firing range, maximum FTC and minimum FTC allowed for staple firing, FTC curve, FTF curve, anvil closure motor output curve (e.g., graph 212516 shown in FIG. 144), firing motor output curve (e.g., graph 212516 shown in FIG. 144).

Previous operational parameters for a surgical procedure may be stored along with a procedural outcome associated with a step of the procedure or the overall procedure. As described in in connection with FIG. 46, an example outcome may be whether there was bleeding at the surgical site. Another example may be whether the staples of a particular staple line were formed properly for the staple firing step of the procedure. As described in FIG. 46, procedural outcome may be further analyzed to be associated with a positive or negative outcome and such analyzed procedural outcome may be stored along with previous operational parameters.

Previous operational parameters for a surgical procedure may be stored along with an instrument operator identifier and/or patient parameters. As described in FIG. 76, for example, a responsible surgeon may be stored. As described in connection with FIG. 133, the patient parameters may be from patient records from an Electronic Medical Record database (EMR) and, after an anonymization process, may be stored in a surgical hub, such as the surgical hub 215005. Examples of patient parameters may include: the patient's diagnoses of emphysema, pre-operative treatment (e.g., chemotherapy, radiation, blood thinner, blood pressure medication, etc.), typical blood pressures, and etc.

Previous operational parameters may be operational parameter aggregate data based on multiple previous surgical procedures. As described in FIG. 47, for example, previous operational parameters from multiple previous surgical procedures may be aggregated locally at a surgical hub (e.g., the surgical hub 215005), aggregated across a network of surgical hubs (e.g., surgical hubs like the surgical hub 215005) associated with a medical facility, or aggregated globally at the cloud 5702. An example aggregate data may be operational parameter averages of surgical procedures with the same procedure type, similar patient parameters, and similar operational parameters (e.g., tissue properties) such as, for example, wait time (before staple firing phase) average at a surgical hub locally, at a medical facility, and globally at the cloud 5702. Another example aggregate data may further aggregate the above operational parameter averages based on procedural outcomes, such as the wait time average at a medical facility only for procedures with no malformed staples or generally with a positive outcome.

Referring to FIG. 149, as shown on the left side of the figure, the surgical circular stapler 211000 that is linked with the surgical hub 211005 may receive an indication to configure the surgical circular stapler based on operational parameters associated with previously performed surgical procedures. Such indication may be the system parameter as described in FIG. 143 to set the surgical circular stapler 211000 to operate in previous-configuration control mode. The surgical circular stapler 211000 and the surgical hub 211005 may be linked in an operating room in preparation for a planned surgical procedure.

At 215012, the surgical circular stapler 211000 may communicate to a linked surgical hub, such as the surgical hub 211005, characteristics associated with the surgical circular stapler 211000. For example, the surgical circular stapler 211000 may be operating with an end effector with an anvil, such as 210110B (shown in FIG. 139), and a staple heading assembly, such as 210130B (shown in FIG. 139). In such example, the surgical circular stapler 211000 may transmit a previous-configuration control mode indicator and an indication of medium anvil head size to the surgical hub 211005.

At 215022, the surgical hub 211005 may receive characteristics associated with a planned surgical procedure. Continuing with the example at 215012, the surgical hub 211005 may receive a previous-configuration control mode indicator and medium anvil head size transmitted from the surgical circular stapler 211000.

At 215024, the surgical hub 211005 may retrieve from the data store operational parameters corresponding to the received characteristics from the surgical circular stapler 211000. At 215022, the surgical hub 211005 may retrieve from the datastore the operational parameters used in the last surgical procedure performed by the instrument operator (e.g., the responsible surgeon for the planned surgical procedure) where a surgical circular stapler was used, the surgical circular stapler operation mode was a load control mode, and the anvil head size was medium. In such example, the retrieved operational parameters may include: a load control mode indicator, a medium anvil head size, normal tissue thickness, normal tissue stiffness, viable staple height range, viable staple firing range, a maximum FTC and a minimum FTC allowed for staple firing, a FTC curve, a FTF curve, an anvil closure motor output curve, a firing motor output curve.

At 215026, the surgical hub 211005 may send the retrieved operational parameters at 212024 to the surgical circular stapler 211000 for use in configuring the surgical circular stapler 211000 to perform the planned surgical procedure. In response, at 215014, the surgical circular stapler 211000 may receive from the surgical hub 211005 the retrieved operational parameters at 212024.

At 215016, the surgical circular stapler 211000 may be preconfigured using the received operational parameters at 215014 as the default operational parameters. Given the received operational parameters at 215014, the surgical circular stapler 211000 may be preconfigured to operate with the received viable staple height range, viable staple firing range, a maximum FTC and a minimum FTC allowed for staple firing, a FTC curve, a FTF curve, an anvil closure motor output curve, a firing motor output curve, when the tissue to be operated in the planned surgical procedure has the matching tissue properties, that is, a tissue with normal thickness and normal stiffness.

FIG. 150 is a flow chart corresponding to another example process for a surgical circular stapler 211000 to be configured to operate a previous-configuration control mode as described herein with reference to FIGS. 140-143 and 144-148.

At 215520, the surgical hub 215005 may maintain a data store of operational parameters that are associated with previously performed surgical procedures, as described at 215020 in FIG. 149.

At 215510, the surgical circular stapler 211000 may receive an indication to configure the surgical circular stapler based on operational parameters associated with previously performed surgical procedures as described at 211005 in FIG. 149.

At 215522, the surgical hub 215005 may receive a query specifying characteristics associated with surgical procedures. For example, the instrument operator as described in FIG. 149 may initiate a query on the surgical hub 215005 against the data store with the same characteristics received from the surgical circular stapler 211000 to retrieve operational parameters used in surgical procedures previously performed by the instrument operator as described at 215022 in FIG. 149. The instrument operator may initiate the query using a graphical user interface (GUI) located on the surgical hub 215005. FIG. 131 provides an example GUI that may be located on a surgical hub that may provide the ability for an instrument operator to interact with the surgical hub.

The instrument operator may initiate a query to obtain aggregated operational parameters to preconfigure the surgical circular stapler 211000. An example of aggregated operational parameters may be a medical facility (where surgical hub 215005 is located) average for viable staple height range and viable staple firing range for tissue with normal thickness where a surgical circular stapler with medium-sized anvil head size was used, the operation mode was a load control mode, and the procedural outcome was positive. At 215524, the surgical hub 215005 may retrieve from the data store matching operational parameters as described at 215024 in FIG. 149. At 215526, the surgical hub 215005 may send the retrieved operational parameters to the surgical circular stapler 211000, as described at 215026 in FIG. 149. At 215514, the surgical circular stapler 211000 may receive the retrieved operational parameters as described at 215014 in FIG. 149. At 215516, the surgical circular stapler 211000 may be preconfigured using the received operational parameters at 215514, as described at 215014 in FIG. 149. In such example, the surgical circular stapler 211000 may be preconfigured to operate with the received medical facility average for viable staple height range and viable staple firing range among other operational parameters.

FIG. 143 depicts processing for preconfiguring the surgical circular stapler 211000 to provide an adaptable representation of an operating range for tissue compression using previous operational parameters retrieved from the surgical hub 215005 based on an instrument operator's query against the surgical hub's 215005 data store, at 212022, 212024, 212026, and 212018, as described in FIG. 150. After preconfiguring the surgical circular stapler 211000, it may be operated in effectively the load control mode at 212012, 212014, and 212016 as described in FIG. 142.

FIG. 148 depicts processing for preconfiguring the surgical circular stapler 211000 to provide motorized control in the load control mode with previous operational parameters retrieved from the surgical hub 215005 based on an instrument operator's query against the surgical hub's 215005 data store, at 214522, 214524, 214526, and 214512, as described in FIG. 150. After being preconfigured, the surgical circular stapler 211000 may be operated in both the "static measurement" sub-mode and "repeated sensor measurement" sub-mode under the local control mode as described in FIG. 146 and FIG. 147, respectively, at 214514, 214516, 214517, 214518, and 214519.

Accordingly, systems and techniques for adaptive control of surgical instrument functions have been disclosed. A surgical instrument may be configured to communicate with an external system such as, for example, a surgical hub. The surgical hub may generate, and the surgical instrument may receive, an indication of one or more functions to be adaptively controlled by the surgical instrument. For example, a surgical stapler instrument may receive an indication to adaptively control a display of staple height operating range and/or to adaptively control motorized features of the surgical instrument. The surgical instrument may determine values for parameters associated with the identified function and adapt the control of the identified function based upon the determined parameters. The surgical instrument may modify its operation of the one or more controlled functions based upon the parameters. The surgical instrument may communicate additional information such as additional parameter values to the external system and may receive further input regarding continued control of the indicated one or more functions.

A surgical system may include tiered-access features. The surgical system may be used to analyze at least a portion of a surgical field. Based on a control parameter, the system may scale up or down various capabilities, such as visualization processing, endocutter communication, endocutter algorithm updates, smart cartridge connectivity, smart motor control for circular stapler, smart energy control, cloud analytics, hub connectivity control, and/or hub visualization and control interactions. The control parameter may include system aspects such as processing capability or bandwidth for example and/or the identification of an appropriate service tier.

In one general aspect, a powered surgical end-effector is provided. The powered surgical end-effector comprises a controllable jaw configured to operate on a tissue; an updatable memory having stored therein a default actuation algorithm; and a processor. The processor is configured to: operate in a first mode at a first time, wherein in the first mode the processor is configured to operate an aspect of the controllable jaw according to the default actuation algorithm; and receive data at a second time, after the first time, that causes the processor to operate in a second mode, wherein in the second mode the processor is configured to operate an aspect of the controllable jaw according to an alternative actuation algorithm.

In another general aspect, a powered surgical end-effector is provided. The powered surgical end-effector comprises: a controllable jaw configured to operate on a tissue; an updatable memory having stored therein a default actuation algorithm; and a processor. The processor is configured to determine whether to operate in a first mode or a second mode, wherein in the first mode the processor is configured to operate an aspect of the jaw according to the default actuation algorithm, and wherein in the second mode the processor is configured to operate an aspect of the jaw according to an alternative actuation algorithm.

In yet another general aspect, a surgical hub is provided. The surgical hub comprises: a transmitter and a receiver configured to establish a communication pathway between the surgical hub and a powered surgical end-effector; and a processor. The processor is configured to: determine whether communication is available with the powered surgical end-effector that is configured to operate in a first mode or in a second mode, wherein in the first mode, the powered surgical end-effector operates an aspect of a controllable jaw according to a default actuation algorithm stored in the updatable memory of the powered surgical end-effector; receive data from related to the powered surgical end-effector via the receiver; determine whether the surgical end-effector should operate in the first mode or the second mode based on the received data; and based on the determination, send updated data that causes the powered surgical end-effector to operate in the second mode, wherein in the second mode, the powered surgical end-effector operates the aspect of the controllable jaw according to an alternative actuation algorithm.

Examples herein describe a surgical instrument that deliver a first energy and a second energy configured to seal the tissue. The first energy may be operated by a first energy algorithm and second energy may be operated by a second energy algorithm. The surgical instrument may include an updatable memory that may store a default control algorithm that may control both the first energy algorithm and the second energy algorithm simultaneously. The surgical instrument may include a processor that may be configured to operate in a first mode at a first time, wherein in the first mode the processor may be configured to operate according to the default control algorithm. The processor may receive data at a second time that may cause the processor to operate in a second mode, wherein in the second mode the processor may be configured to operate according to an alternative control algorithm.

FIG. 151 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, or one or more articulation members, or combinations thereof. The surgical instrument 700 comprises a control circuit 710 configured to control motor-driven firing members, closure members, shaft members, or one or more articulation members, or combinations thereof.

In one aspect, the robotic surgical instrument 700 comprises a control circuit 710 configured to control a clamp arm 716 and a closure member 714 portion of an end effector 702, an ultrasonic blade 718 coupled to an ultrasonic transducer 719 excited by an ultrasonic generator 721, a shaft 740, and one or more articulation members 742a, 742b via a plurality of motors 704a-704e. A position sensor 734 may be configured to provide position feedback of the closure member 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the closure member 714 as determined by the position sensor 734 with the output of the timer/counter 731 such that the control circuit 710 can determine the position of the closure member 714 at a specific time (t) relative to a starting position or the time (t) when the closure member 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the clamp arm 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the closure member 714, clamp arm 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the closure member 714. The position sensor 734 may be or include any type of sensor that is capable of generating position data that indicate a position of the closure member 714. In some examples, the position sensor 734 may include an encoder configured to provide a series of pulses to the control circuit 710 as the closure member 714 translates distally and proximally. The control circuit 710 may track the pulses to determine the position of the closure member 714. Other suitable position sensors may be used, including, for example, a proximity sensor. Other types of position sensors may provide other signals indicating motion of the closure member 714. Also, in some examples, the position sensor 734 may be omitted. Where any of the motors 704a-704e is a stepper motor, the control circuit 710 may track the position of the closure member 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the closure member 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the closure member 714. The transmission 706a comprises movable mechanical elements such as rotating elements and a firing member to control the movement of the closure member 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the closure member 714. A position sensor 734 may be configured to provide the position of the closure member 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708*a*. In response to the firing signal, the motor 704*a* may drive the firing member distally along the longitudinal axis of the end effector 702 from a proximal stroke start position to a stroke end position distal to the stroke start position. As the closure member 714 translates distally, the clamp arm 716 closes towards the ultrasonic blade 718.

In one aspect, the control circuit 710 is configured to drive a closure member such as the clamp arm 716 portion of the end effector 702. The control circuit 710 provides a motor set point to a motor control 708*b*, which provides a drive signal to the motor 704*b*. The output shaft of the motor 704*b* is coupled to a torque sensor 744*b*. The torque sensor 744*b* is coupled to a transmission 706*b* which is coupled to the clamp arm 716. The transmission 706*b* comprises movable mechanical elements such as rotating elements and a closure member to control the movement of the clamp arm 716 from the open and closed positions. In one aspect, the motor 704*b* is coupled to a closure gear assembly, which includes a closure reduction gear set that is supported in meshing engagement with the closure spur gear. The torque sensor 744*b* provides a closure force feedback signal to the control circuit 710. The closure force feedback signal represents the closure force applied to the clamp arm 716. The position sensor 734 may be configured to provide the position of the closure member as a feedback signal to the control circuit 710. Additional sensors 738 in the end effector 702 may provide the closure force feedback signal to the control circuit 710. The pivotable clamp arm 716 is positioned opposite the ultrasonic blade 718. When ready to use, the control circuit 710 may provide a closure signal to the motor control 708*b*. In response to the closure signal, the motor 704*b* advances a closure member to grasp tissue between the clamp arm 716 and the ultrasonic blade 718.

In one aspect, the control circuit 710 is configured to rotate a shaft member such as the shaft 740 to rotate the end effector 702. The control circuit 710 provides a motor set point to a motor control 708*c*, which provides a drive signal to the motor 704*c*. The output shaft of the motor 704*c* is coupled to a torque sensor 744*c*. The torque sensor 744*c* is coupled to a transmission 706*c* which is coupled to the shaft 740. The transmission 706*c* comprises movable mechanical elements such as rotating elements to control the rotation of the shaft 740 clockwise or counterclockwise up to and over 360°. In one aspect, the motor 704*c* is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744*c* provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 7 40 to the control circuit 710.

In one aspect, the control circuit 710 is configured to articulate the end effector 702. The control circuit 710 provides a motor set point to a motor control 708*d*, which provides a drive signal to the motor 704*d*. The output shaft of the motor 704*d* is coupled to a torque sensor 744*d*. The torque sensor 744*d* is coupled to a transmission 706*d* which is coupled to an articulation member 742*a*. The transmission 706*d* comprises movable mechanical elements such as articulation elements to control the articulation of the end effector 702±65°. In one aspect, the motor 704*d* is coupled to an articulation nut, which is rotatably journaled on the proximal end portion of the distal spine portion and is rotatably driven thereon by an articulation gear assembly. The torque sensor 744*d* provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742*a*, 742*b*. These articulation members 742*a*, 742*b* are driven by separate disks on the robot interface (the rack) which are driven by the two motors 708*d*, 708*e*. When the separate firing motor 704*a* is provided, each of articulation links 742*a*, 742*b* can be antagonistically driven with respect to the other link in order to provide a resistive holding motion and a load to the head when it is not moving and to provide an articulation motion as the head is articulated. The articulation members 742*a*, 742*b* attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704*a*-704*e* may comprise a brushed DC motor with a gearbox and mechanical links to a firing member, closure member, or articulation member. Another example includes electric motors 704*a*-704*e* that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704*a*-704*e*. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Voider's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the clamp arm 716 to determine tissue location using segmented electrodes.

The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the ultrasonic blade 718 has tissue on it, and (4) the load and position on both articulation rods.

In one aspect, the one or more sensors 738 may comprise a strain gauge, such as a micro-strain gauge, configured to measure the magnitude of the strain in the clamp arm 716 during a clamped condition. The strain gauge provides an electrical signal whose amplitude varies with the magnitude of the strain. The sensors 738 may comprise a pressure sensor configured to detect a pressure generated by the presence of compressed tissue between the clamp arm 716 and the ultrasonic blade 718. The sensors 738 may be configured to detect impedance of a tissue section located between the clamp arm 716 and the ultrasonic blade 718 that is indicative of the thickness and/or fullness of tissue located there between.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the clamp arm 716 by the closure drive system. For example, one or more sensors 738 can be at an interaction point between the closure tube and the clamp arm 716 to detect the closure forces applied by the closure tube to the clamp arm 716. The forces exerted on the clamp arm 716 can be representative of the tissue compression experienced by the tissue section captured between the clamp arm 716 and the ultrasonic blade 718. The one or more sensors 738 can be positioned at various interaction points along the closure drive system to detect the closure forces applied to the clamp arm 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the clamp arm 716.

In one aspect, a current sensor 736 can be employed to measure the current drawn by each of the motors 704a-704e. The force required to advance any of the movable mechanical elements such as the closure member 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move the closure member 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

FIG. 152 illustrates a schematic diagram of a surgical instrument 750 configured to control the distal translation of a displacement member according to one aspect of this disclosure. In one aspect, the surgical instrument 750 is programmed to control the distal translation of a displacement member such as the closure member 764. The surgical instrument 750 comprises an end effector 752 that may comprise a clamp arm 766, a closure member 764, and an ultrasonic blade 768 coupled to an ultrasonic transducer 769 driven by an ultrasonic generator 771.

The position, movement, displacement, and/or translation of a linear displacement member, such as the closure member 764, can be measured by an absolute positioning system, sensor arrangement, and position sensor 784. Because the closure member 764 is coupled to a longitudinally movable drive member, the position of the closure member 764 can be determined by measuring the position of the longitudinally movable drive member employing the position sensor 784. Accordingly, in the following description, the position, displacement, and/or translation of the closure member 764 can be achieved by the position sensor 784 as described herein. A control circuit 760 may be programmed to control the translation of the displacement member, such as the closure member 764. The control circuit 760, in some examples, may comprise one or more microcontrollers, microprocessors, or other suitable processors for executing instructions that cause the processor or processors to control the displacement member, e.g., the closure member 764, in the manner described. In one aspect, a timer/counter 781 provides an output signal, such as the elapsed time or a digital count, to the control circuit 760 to correlate the position of the closure member 764 as determined by the position sensor 784 with the output of the timer/counter 781 such that the control circuit 760 can determine the position of the closure member 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the closure member 764 via a transmission 756. The transmission 756 may include one or more gears or other linkage components to couple the motor 754 to the closure member 764. A position sensor 784 may sense a position of the closure member 764. The position sensor 784 may be or include any type of sensor that is capable of generating position data that indicate a position of the closure member 764. In some examples, the position sensor 784 may include an encoder configured to provide a series of pulses to the control circuit 760 as the closure member 764 translates distally and proximally. The control circuit 760 may track the pulses to determine the position of the closure member 764. Other suitable position sensors may be used, including, for example, a proximity sensor. Other types of position sensors may provide other signals indicating motion of the closure member 764. Also, in some examples, the position sensor 784 may be omitted. Where the motor 754 is a stepper motor, the control circuit 760 may track the position of the closure member 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the clamp arm 766 during a clamped condition. The strain gauge provides an electrical signal whose amplitude varies with the magnitude of the strain. The sensors 788 may comprise a pressure sensor configured to detect a pressure generated by the presence of compressed tissue between the clamp arm 766 and the ultrasonic blade 768. The sensors 788 may be configured to detect impedance of a tissue section located between the clamp arm 766 and the ultrasonic blade 768 that is indicative of the thickness and/or fullness of tissue located therebetween.

The sensors 788 may be is configured to measure forces exerted on the clamp arm 766 by a closure drive system. For example, one or more sensors 788 can be at an interaction point between a closure tube and the clamp arm 766 to detect the closure forces applied by a closure tube to the clamp arm 766. The forces exerted on the clamp arm 766 can be representative of the tissue compression experienced by the tissue section captured between the clamp arm 766 and the ultrasonic blade 768. The one or more sensors 788 can be positioned at various interaction points along the closure drive system to detect the closure forces applied to the clamp arm 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the clamp arm 766.

A current sensor 786 can be employed to measure the current drawn by the motor 754. The force required to advance the closure member 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a closure member 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or closure member 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical sealing and cutting implements. For example, a motor 754 may drive a displacement member distally and proximally along a longitudinal axis of the end effector 752. The end effector 752 may comprise a pivotable clamp arm 766 and, when configured for use, an ultrasonic blade 768 positioned opposite the clamp arm 766. A clinician may grasp tissue between the clamp arm 766 and the ultrasonic blade 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, the closure member 764 with a cutting element positioned at a distal end, may cut the tissue between the ultrasonic blade 768 and the clamp arm 766.

In various examples, the surgical instrument 750 may comprise a control circuit 760 programmed to control the distal translation of the displacement member, such as the closure member 764, for example, based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the displacement member. Different control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

FIG. 153 is a schematic diagram of a surgical instrument 790 configured to control various functions according to one aspect of this disclosure. In one aspect, the surgical instrument 790 is programmed to control distal translation of a displacement member such as the closure member 764. The surgical instrument 790 comprises an end effector 792 that may comprise a clamp arm 766, a closure member 764, and an ultrasonic blade 768 which may be interchanged with or work in conjunction with one or more RF electrodes 796 (shown in dashed line). The ultrasonic blade 768 is coupled to an ultrasonic transducer 769 driven by an ultrasonic generator 771.

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

N In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Voider's algorithm, that is provided to implement a simple and efficient algorithm to calculate hyperbolic and trigonometric functions that require only addition, subtraction, bitshift, and table lookup operations.

In some examples, the position sensor 784 may be omitted. Where the motor 754 is a stepper motor, the control circuit 760 may track the position of the closure member 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

An RF energy source 794 is coupled to the end effector 792 and is applied to the RF electrode 796 when the RF electrode 796 is provided in the end effector 792 in place of the ultrasonic blade 768 or to work in conjunction with the ultrasonic blade 768. For example, the ultrasonic blade is made of electrically conductive metal and may be employed as the return path for electrosurgical RF current. The control circuit 760 controls the delivery of the RF energy to the RF electrode 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

FIG. 154 is a system 800 configured to execute adaptive ultrasonic blade control algorithms in a surgical data network comprising a modular communication hub, in accordance with at least one aspect of the present disclosure. In one aspect, the generator module 240 is configured to execute the adaptive ultrasonic blade control algorithm(s) 802. In another aspect, the device/instrument 235 is configured to execute the adaptive ultrasonic blade control algorithm(s) 804. In another aspect, both the generator module 240 and the device/instrument 235 are configured to execute the adaptive ultrasonic blade control algorithms 802,804.

The generator module 240 may comprise a patient isolated stage in communication with a non-isolated stage via a power transformer. A secondary winding of the power transformer is contained in the isolated stage and may comprise a tapped configuration (e.g., a center-tapped or a non-center-tapped configuration) to define drive signal outputs for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, the drive signal outputs may output an ultrasonic drive signal (e.g., a 420V root-mean-square (RMS) drive signal) to an ultrasonic surgical instrument 241, and the drive signal outputs may output an RF electrosurgical drive signal (e.g., a 100V RMS drive signal) to an RF electrosurgical instrument 241.

FIG. 155 illustrates an example of a generator 900, which is one form of a generator configured to couple to an ultrasonic instrument and further configured to execute adaptive ultrasonic blade control algorithms in a surgical data network comprising a modular communication hub as shown in FIG. 154. The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGY n terminals may be provided, where n is a positive integer greater than 1. It also will be appreciated that up to "n" return paths RETURN may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY$_1$/RETURN or the second voltage sensing circuit 924 coupled across the terminals labeled ENERGY$_2$/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultra-sonic energy and the second energy modality ENERGY 2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 156 shows a single return path RETURN may be provided for two or more energy modalities, in other aspects, multiple return paths RETURN may be provided for each energy modality ENERGY. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 155, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY' and RETURN as shown in FIG. 155. In one example, a connection of RF bipolar electrodes to the generator 900 output would be preferably located between the output labeled ENERGY$_2$ and RETURN. In the case of monopolar output, the preferred connections would be active electrode (e.g., pencil or other probe) to the ENERGY$_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to W-Fi (IEEE 802.11 family), (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions-all on a single substrate. A SoC integrates a microcontroller (or microprocessor) with advanced peripherals like graphics processing unit (GPU), W-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAMI, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with Stellaris Ware® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include modules that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

FIG. 156 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 156 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1134*a*, 1134*b*, 1134*c* to energize and drive the ultrasonic blade 1128 or other function. The toggle buttons 1134*a*, 1134*b*, 1134*c* can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124. The end effector 1124 comprises electrodes in clamp arms 1142*a*, 1142*b* and return through an electrical conductor portion of the shaft 1127. The electrodes are coupled to and energized by a bipolar energy source within the generator 1100. The handpiece 1107 comprises a trigger 1145 to operate the clamp arms 1142*a*, 1142*b* and an energy button 1135 to actuate an energy switch to energize the electrodes in the end effector 1124.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 1137*a*, 1137*b*, 1137*c* to energize and drive the ultrasonic blade 1149 or other function. The toggle buttons 1137*a*, 1137*b*, 1137*c* can be configured to energize the ultrasonic transducer 1120 with the generator 1100 and energize the ultrasonic blade 1149 with a bipolar energy source also contained within the generator 1100.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 157 the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator 1100. The generator 1100 also may comprise one or more output devices 1112. Further aspects of generators for digitally generating electrical signal waveforms and surgical instruments are described in US patent publication US-2017-0086914-A1, which is herein incorporated by reference in its entirety.

In one aspect, a surgical hub 106 can be embodied as a modular energy system 2000, which is illustrated in connection with FIGS. 157-163. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). The modular energy system 2000 can also include a variety of different components or accessories that are also connectable to or otherwise associable with the modules 2001. In another aspect, the modular energy system 2000 can be a distinct system from a surgical hub 106. In such aspects, the modular energy system 2000 can be communicably couplable to a surgical hub 206 for transmitting and/or receiving data therebetween.

The modular energy system 2000 can be assembled from a variety of different modules 2001, some examples of which are illustrated in FIG. 157. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004 can be configured to generate one or multiple energy modalities for driving electrosurgical and/or ultrasonic surgical instruments connected thereto, such as is described above in connection with the generator 900 illustrated in FIG. 156. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electro surgical and ultrasonic energy generators) and supports software-driven algorithms for customized tissue effects. Still further, the surgical system architecture reduces the capital footprint by combining multiple technologies critical for surgery into a single system.

Referring now to FIG. 158A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 163. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 162. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon. Referring still to FIG. 158A, the energy module 2004 can include a port assembly 2012 including a number of different ports configured to deliver different energy modalities to corresponding surgical instruments that are connectable thereto. In the particular aspect illustrated in FIGS. 159-165, the port assembly 2012 includes a bipolar port 2014, a first monopolar port 2016a, a second monopolar port 2018b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 158A and 158B illustrate a first illustrative configuration of the modular energy system 2000 including a header module 2002 (including a display screen 2006) and an energy module 2004 connected together. Such a configuration can be suitable for laparoscopic and open surgical procedures, for example.

FIG. 159A illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 159B illustrates a third illustrative configuration that is similar to the second configuration, except that the header module 2002 lacks a display screen 2006. This configuration can be suitable for robotic surgical applications or mobile display applications, as noted above.

FIG. 160 illustrates a fourth illustrative configuration of the modular energy system 2000 including a header module 2002 (including a display screen 2006), a first energy module 2004a, a second energy module 2004b, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

FIG. 161 illustrates a fifth illustrative configuration of the modular energy system 2000 including a header module 2002 (including a display screen 2006), a first energy module 2004a, a second energy module 2004b, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 158-162 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 162. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems.

Referring now to FIG. 163, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 163, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056a corresponding to the bipolar port 2014, a second widget 2056b corresponding to the first monopolar port 2016a, a third widget 2056c corresponding to the second monopolar port 2016b, and a fourth widget 2056d corresponding to the combination energy port 2020. Each of these widgets 2056a-d provides data related to its corresponding port of the port assembly 2012 and controls for controlling the modes and other features of the energy modality delivered by the energy module 2004 through the respective port of the port assembly 2012. For example, the widgets 2056a-d can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the activation of each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

FIG. 164 is a block diagram of a stand-alone hub configuration of a modular energy system 3000, in accordance with at least one aspect of the present disclosure and FIG. 165 is a block diagram of a hub configuration of a modular energy system 3000 integrated with a surgical control system 3010, in accordance with at least one aspect of the present disclosure. As depicted in FIGS. 166 and 167, the modular energy system 3000 can be either utilized as stand-alone units or integrated with a surgical control system 3010 that controls and/or receives data from one or more surgical hub units. In the examples illustrated in FIGS. 164 and 165, the integrated header/VI module 3002 of the modular energy system 3000 includes a header module and a UI module integrated together as a singular module. In other aspects, the header module and the UI module can be provided as separate components that are communicatively coupled though a data bus 3008.

As illustrated in FIG. 164, an example of a standalone modular energy system 3000 includes an integrated header module/user interface (UI) module 3002 coupled to an energy module 3004. Power and data are transmitted between the integrated header/VI module 3002 and the energy module 3004 through a power interface 3006 and a data interface 3008. For example, the integrated header/VI module 3002 can transmit various commands to the energy module 3004 through the data interface 3008. Such commands can be based on user inputs from the UI. As a further example, power may be transmitted to the energy module 3004 through the power interface 3006.

In FIG. 165, a surgical hub configuration includes a modular energy system 3000 integrated with a control system 3010 and an interface system 3022 for managing, among other things, data and power transmission to and/or from the modular energy system 3000. The modular energy system depicted in FIG. 167 includes an integrated header module/VI module 3002, a first energy module 3004, and a second energy module 3012. In one example, a data transmission pathway is established between the system control unit 3024 of the control system 3010 and the second energy module 3012 through the first energy module 3004 and the header/VI module 3002 through a data interface 3008. In addition, a power pathway extends between the integrated header/VI module 3002 and the second energy module 3012 through the first energy module 3004 through a power interface 3006. In other words, in one aspect, the first energy module 3004 is configured to function as a power and data interface between the second energy module 3012 and the integrated header/VI module 3002 through the power interface 3006 and the data interface 3008. This arrangement allows the modular energy system 3000 to expand by seamlessly connecting additional energy modules to energy modules 3004, 3012 that are already connected to the integrated header/VI module 3002 without the need for dedicated power and energy interfaces within the integrated header/VI module 3002.

The system control unit 3024, which may be referred to herein as a control circuit, control logic, micro-processor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

As described in more detail hereinbelow, the energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

FIGS. 166-168 are block diagrams of various modular energy systems connected together to form a hub, in accordance with at least one aspect of the present disclosure. FIGS. 166-168 depict various diagrams (e.g., circuit or control diagrams) of hub modules. The modular energy system 3000 includes multiple energy modules 3004 (FIG. 167), 3012 (FIG. 168), a header module 3150 (FIG. 168), a UI module 3030 (FIG. 166), and a communications module 3032 (FIG. 166), in accordance with at least one aspect of the present disclosure. The UI module 3030 includes a touch screen 3046 displaying various relevant information and various user controls for controlling one or more parameters of the modular energy system 3000. The UI module 3030 is attached to the top header module 3150, but is separately housed so that it can be manipulated independently of the header module 3150. For example, the UI module 3030 can be picked up by a user and/or reattached to the header module 3150. Additionally, or alternatively, the UI module 3030 can be slightly moved relative to the header module 3150 to adjust its position and/or orientation. For example, the UI module 3030 can be tilted and/or rotated relative to the header module 3150.

In some aspects, the various hub modules can include light piping around the physical ports to communicate instrument status and also connect on-screen elements to corresponding instruments. Light piping is one example of an illumination technique that may be employed to alert a user to a status of a surgical instrument attached/connected to a physical port. In one aspect, illuminating a physical port with a particular light directs a user to connect a surgical instrument to the physical port. In another example, illuminating a physical port with a particular light alerts a user to an error related an existing connection with a surgical instrument.

Turning to FIG. 166, there is shown a block diagram of a user interface (UI) module 3030 coupled to a communications module 3032 via a pass-through hub connector 3034, in accordance with at least one aspect of the present disclosure. The UI module 3030 is provided as a separate component from a header module 3150 (shown in FIG. 168) and may be communicatively coupled to the header module 3150 via a communications module 3032, for example. In one aspect, the UI module 3030 can include a UI processor 3040 that is configured to represent declarative visualizations and behaviors received from other connected modules, as well as perform other centralized UI functionality, such as system configuration (e.g., language selection, module associations, etc.). The UI processor 3040 can be, for example, a processor or system on module (SOM) running a framework such as Qt, .NET WPF, Web server, or similar.

In the illustrated example, the UI module 3030 includes a touchscreen 3046, a liquid crystal display 3048 (LCD), and audio output 3052 (e.g., speaker, buzzer). The UI processor 3040 is configured to receive touchscreen inputs from a touch controller 3044 coupled between the touch screen 3046 and the UI processor 3040. The UI processor 3040 is configured to output visual information to the LCD display 3048 and to output audio information the audio output 3052 via an audio amplifier 3050. The UI processor 3040 is configured to interface to the communications module 3032 via a switch 3042 coupled to the pass-through hub connector 3034 to receive, process, and forward data from the source device to the destination device and control data communication therebetween. DC power is supplied to the UI module 3030 via DC/DC converter modules 3054. The DC power is passed through the pass-through hub connector 3034 to the communications module 3032 through the power bus 3006. Data is passed through the pass-through hub connector 3034 to the communications module 3032 through the data bus 3008. Switches 3042, 3056 receive, process, and forward data from the source device to the destination device.

Continuing with FIG. 168, the communications module 3032, as well as various surgical hubs and/or surgical systems can include a gateway 3058 that is configured to shuttle select traffic (i.e., data) between two disparate networks (e.g., an internal network and/or a hospital network) that are running different protocols. The communications module 3032 includes a first pass-through hub connector 3036 to couple the communications module 3032 to other modules. In the illustrated example, the communications module 3032 is coupled to the UI module 3030. The communications module 3032 is configured to couple to other modules (e.g., energy modules) via a second pass-through hub connector 3038 to couple the communications module 3032 to other modules via a switch 3056 disposed between the first and second pass-through hub connectors 3036, 3038 to receive, process, and forward data from the source device to the destination device and control data communication therebetween. The switch 3056 also is coupled to a gateway 3058 to communicate information between external communications ports and the UI module 3030 and other connected modules. The gateway 3058 may be coupled to various communications modules such as, for example, an Ethernet module 3060 to communicate to a hospital or other local network, a universal serial bus (USB) module 3062, a WiFi module 3064, and a Bluetooth module 3066, among others. The communications modules may be physical boards located within the communications module 3032 or may be a port to couple to remote communications boards.

In some aspects, all of the modules (i.e., detachable hardware) are controlled by a single UI module 3030 that is disposed on or integral to a header module. FIG. 168 shows a stand alone header module 3150 to which the UI module 3030 can be attached. FIGS. 164, 165, and 169 show an integrated header/VI Module 3002. Returning now to FIG. 166, in various aspects, by consolidating all of the modules into a single, responsive UI module 3002, the system provides a simpler way to control and monitor multiple pieces of equipment at once. This approach drastically reduces footprint and complexity in an operating room (OR).

Turning to FIG. 167, there is shown a block diagram of an energy module 3004, in accordance with at least one aspect of the present disclosure. The communications module 3032 (FIG. 166) is coupled to the energy module 3004 via the second pass-through hub connector 3038 of the communications module 3032 and a first pass-through hub connector 3074 of the energy module 3004. The energy module 3004 may be coupled to other modules, such as a second energy module 3012 shown in FIG. 168, via a second pass-through hub connector 3078. Turning back to FIG. 167, a switch 3076 disposed between the first and second pass-through hub connectors 3074, 3078 receives, processes, and forwards data from the source device to the destination device and controls data communication therebetween. Data is received and transmitted through the data bus 3008. The energy module 3032 includes a controller 3082 to control various communications and processing functions of the energy module 3004.

DC power is received and transmitted by the energy module 3004 through the power bus 3006. The power bus 3006 is coupled to DC/DC converter modules 3138 to supply power to adjustable regulators 3084, 3107 and isolated DC/DC converter ports 3096, 3112, 3132.

In one aspect, the energy module 3004 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of an advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog-to-digital converter 3102 (A/D). Also coupled to the controller 3082 through the advanced energy receptacle 3100 is the isolated DC/DC converter port 3096, which receives DC power from the power bus 3006, and a medium bandwidth data port 3098.

In one aspect, the energy module 3004 can include a wideband RF power amplifier 3108, which in one aspect may be a linear class H amplifier that is capable of generating arbitrary waveforms and drive RF loads at a range of output frequencies. The wideband RF power amplifier 3108 is fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the wideband RF amplifier 3086 via a DAC 3122. The output of the wideband RF power amplifier 3108 can be fed through RF selection relays 3124. The RF selection relays 3124 are configured to receive and selectively transmit the output signal of the wideband RF power amplifier 3108 to various other components of the energy module 3004. In one aspect, the output signal of the wideband RF power amplifier 3108 can be fed through RF selection relays 3124 to an RF power transformer 3110, which is coupled to an RF output portion of a bipolar RF energy receptacle 3118. Bipolar RF voltage (V) and current (I) feedback (FB) signals, which may be employed to compute RF impedance, are fed back to the controller 3082 via an RF VI FB transformer 3114 through an input portion of the bipolar RF energy receptacle 3118. The RF voltage and current feedback signals are routed back to the controller 3082 through an A/D 3120. Also coupled to the controller 3082 through the bipolar RF energy receptacle 3118 is the isolated DC/DC converter port 3112, which receives DC power from the power bus 3006, and a low bandwidth data port 3116.

As described above, in one aspect, the energy module 3004 can include RF selection relays 3124 driven by the controller 3082 (e.g., FPGA) at rated coil current for actuation and can also be set to a lower hold-current via pulse-width modulation (P to limit steady-state power dissipation. Switching of the RF selection relays 3124 is achieved with force guided (safety) relays and the status of the contact state is sensed by the controller 3082 as a mitigation for any single fault conditions. In one aspect, the RF selection relays 3124 are configured to be in a first state, where an output RF signal received from an RF source, such as the wideband RF power amplifier 3108, is transmitted to a first component of the energy module 3004, such as the RF power transformer 3110 of the bipolar energy receptacle 3118. In a second aspect, the RF selection relays 3124 are configured to be in a second state, where an output RF signal received from an RF source, such as the wideband RF power amplifier 3108, is transmitted to a second component, such as an RF power transformer 3128 of a monopolar energy receptacle 3136, described in more detail below. In a general aspect, the RF selection relays 3124 are configured to be driven by the controller 3082 to switch between a plurality of states, such as the first state and the second state, to transmit the output RF signal received from the RF power amplifier 3108 between different energy receptacles of the energy module 3004.

As described above, the output of the wideband RF power amplifier 3108 can also fed through the RF selection relays 3124 to the wideband RF power transformer 3128 of the RF monopolar receptacle 3136. Monopolar RF voltage (V) and current (I) feedback (FB) signals, which may be employed to compute RF impedance, are fed back to the controller 3082 via an RF VI FB transformer 3130 through an input portion of the monopolar RF energy receptacle 3136. The RF voltage and current feedback signals are routed back to the controller 3082 through an A/D 3126. Also coupled to the controller 3082 through the monopolar RF energy receptacle 3136 is the isolated DC/DC converter port 3132, which receives DC power from the power bus 3006, and a low bandwidth data port 3134.

The output of the wideband RF power amplifier 3108 can also fed through the RF selection relays 3124 to the wideband RF power transformer 3090 of the advanced energy receptacle 3100. RF voltage (V) and current (I) feedback (FB) signals, which may be employed to compute RF impedance, are fed back to the controller 3082 via an RF VI FB transformer 3094 through an input portion of the advanced energy receptacle 3100. The RF voltage and current feedback signals are routed back to the controller 3082 through an A/D 3104.

FIG. 168 is a block diagram of a second energy module 3012 coupled to a header module 3150, in accordance with at least one aspect of the present disclosure. The first energy module 3004 shown in FIG. 167 is coupled to the second energy module 3012 shown in FIG. 170 by coupling the second pass-through hub connector 3078 of the first energy module 3004 to a first pass-through hub connector 3074 of the second energy module 3012. In one aspect, the second energy module 3012 can a similar energy module to the first energy module 3004, as is illustrated in FIG. 168. In another aspect, the second energy module 2012 can be a different energy module compared to the first energy module, such as an energy module illustrated in FIG. 170, described in more detail. The addition of the second energy module 3012 to the first energy module 3004 adds functionality to the modular energy system 3000.

The second energy module 3012 is coupled to the header module 3150 by connecting the pass-through hub connector 3078 to the pass-through hub connector 3152 of the header module 3150. In one aspect, the header module 3150 can include a header processor 3158 that is configured to manage a power button function 3166, software upgrades through the upgrade VSB module 3162, system time management, and gateway to external networks (i.e., hospital or the cloud) via an Ethernet module 3164 that may be running different protocols. Data is received by the header module 3150 through the pass-through hub connector 3152. The header processor 3158 also is coupled to a switch 3160 to receive, process, and forward data from the source device to the destination device and control data communication therebetween. The header processor 3158 also is coupled to an OTS power supply 3156 coupled to a mains power entry module 3154.

FIG. 169 is a block diagram of a header/user inter-face (VI) module 3002 for a hub, such as the header module depicted in FIG. 166, in accordance with at least one aspect of the present disclosure. The header/VI module 3002 includes a header power module 3172, a header wireless module 3174, a header VSB module 3176, a header audio/screen module 3178, a header network module 3180 (e.g., Ethernet), a backplane connector 3182, a header standby processor module 3184, and a header footswitch module 3186. These functional modules interact to provide the header/VI 3002 functionality. A header/VI controller 3170 controls each of the functional modules and the communication therebetween including safety critical control logic modules 3230, 3232 coupled between the header/VI controller 3170 and an isolated communications module 3234 coupled to the header footswitch module 3186. A security co-processor 3188 is coupled to the header/UI controller 3170.

The header power module 3172 includes a mains power entry module 3190 coupled to an OTS power supply unit 3192 (PSU). Low voltage direct current (e.g., 5V) standby power is supplied to the header/UI module 3002 and other modules through a low voltage power bus 3198 from the OTS PSU 3192. High voltage direct current (e.g., 60V) is supplied to the header/UI module 3002 through a high voltage bus 3200 from the OTS PSU 3192. The high voltage DC supplies DC/DC converter modules 3196 as well as isolated DC/DC converter modules 3236. A standby processor 3204 of the header/standby module 3184 provides a PSU/enable signal 3202 to the OTS PSU 3192.

The header wireless module 3174 includes a WiFi module 3212 and a Bluetooth module 3214. Both the WiFi module 3212 and the Bluetooth module 3214 are coupled to the header/VI controller 3170. The Bluetooth module 3214 is used to connect devices without using cables and the Wi-Fi module 3212 provides high-speed access to networks such as the Internet and can be employed to create a wireless network that can link multiple devices such as, for examples, multiple energy modules or other modules and surgical instruments, among other devices located in the operating room. Bluetooth is a wireless technology standard that is used to exchange data over short distances, such as, less than 30 feet.

The header USB module 3176 includes a USB port 3216 coupled to the header/VI controller 3170. The USB module 3176 provides a standard cable connection interface for modules and other electronics devices over short-distance digital data communications. The USB module 3176 allows modules comprising USB devices to be connected to each other with and transfer digital data over USB cables.

The header audio/screen module 3178 includes a touchscreen 3220 coupled to a touch controller 3218. The touch controller 3218 is coupled to the header/UI controller 3170 to read inputs from the touchscreen 3220. The header/UI controller 3170 drives an LCD display 3224 through a display/port video output signal 3222. The header/UI controller 3170 is coupled to an audio amplifier 3226 to drive one or more speakers 3228.

In one aspect, the header/UI module 3002 provides a touchscreen 3220 user interface configured to control modules connected to one control or header module 3002 in a modular energy system 3000. The touchscreen 3220 can be used to maintain a single point of access for the user to adjust all modules connected within the modular energy system 3000. Additional hardware modules (e.g., a smoke evacuation module) can appear at the bottom of the user interface LCD display 3224 when they become connected to the header/UI module 3002, and can disappear from the user interface LCD display 3224 when they are disconnected from the header/VI module 3002.

Further, the user touchscreen 3220 can provide access to the settings of modules attached to the modular energy system 3000. Further, the user interface LCD display 3224 arrangement can be configured to change according to the number and types of modules that are connected to the header/UI module 3002. For example, a first user interface can be displayed on the LCD display 3224 for a first application where one energy module and one smoke evacuation module are connected to the header/UI module 3002, and a second user interface can be displayed on the LCD display 3224 for a second application where two energy modules are connected to the header/UI module 3002. Further, the user interface can alter its display on the LCD display 3224 as modules are connected and disconnected from the modular energy system 3000.

In one aspect, the header/UI module 3002 provides a user interface LCD display 3224 configured to display on the LCD display coloring corresponds to the port lighting. In one aspect, the coloring of the instrument panel and the LED light around its corresponding port will be the same or otherwise correspond with each other. Each color can, for example, convey a unique meaning. This way, the user will be able to quickly assess which instrument the indication is referring to and the nature of the indication. Further, indications regarding an instrument can be represented by the changing of color of the LED light lined around its corresponding port and the coloring of its module. Still further, the message on screen and hardware/software port alignment can also serve to convey that an action must be taken on the hardware, not on the interface. In various aspects, all other instruments can be used while alerts are occurring on other instruments. This allows the user to be able to quickly assess which instrument the indication is referring to and the nature of the indication.

In one aspect, the header/UI module 3002 provides a user interface screen configured to display on the LCD display 3224 to present procedure options to a user. In one aspect, the user interface can be configured to present the user with a series of options (which can be arranged, e.g., from broad to specific). After each selection is made, the modular energy system 3000 presents the next level until all selections are complete. These settings could be managed locally and transferred via a secondary means (such as a USB thumb drive). Alternatively, the settings could be managed via a portal and automatically distributed to all connected systems in the hospital.

The procedure options can include, for example, a list of factory preset options categorized by specialty, procedure, and type of procedure. Upon completing a user selection, the header module can be configured to set any connected instruments to factory-preset settings for that specific procedure. The procedure options can also include, for example, a list of surgeons, then subsequently, the specialty, procedure, and type. Once a user completes a selection, the system may suggest the surgeon's preferred instruments and set those instrument's settings according to the surgeon's preference (i.e., a profile associated with each surgeon storing the surgeon's preferences).

In one aspect, the header/UI module 3002 provides a user interface screen configured to display on the LCD display 3224 critical instrument settings. In one aspect, each instrument panel displayed on the LCD display 3224 of the user interface corresponds, in placement and content, to the instruments plugged into the modular energy system 3000. When a user taps on a panel, it can expand to reveal additional settings and options for that specific instrument and the rest of the screen can, for example, darken or otherwise be deemphasized.

In one aspect, the header/UI module 3002 provides an instrument settings panel of the user interface configured to comprise/display controls that are unique to an instrument and allow the user to increase or decrease the intensity of its output, toggle certain functions, pair it with system accessories like a footswitch connected to header footswitch module 3186, access advanced instrument settings, and find additional information about the instrument. In one aspect, the user can tap/select an "Advanced Settings" control to expand the advanced settings drawer displayed on the user interface LCD display 3224. In one aspect, the user can then tap/select an icon at the top right-hand corner of the instrument settings panel or tap anywhere outside of the panel and the panel will scale back down to its original state. In these aspects, the user interface is configured to display on the LCD display 3224 only the most critical instrument settings, such as power level and power mode, on the ready/home screen for each instrument panel. This is to maximize the size and readability of the system from a distance. In some aspects, the panels and the settings within can be scaled proportionally to the number of instruments connected to the system to further improve readability. As more instruments are connected, the panels scale to accommodate a greater amount of information.

The header network module 3180 includes a plurality of network interfaces 3264, 3266, 3268 (e.g., Ethernet) to network the header/UI module 3002 to other modules of the modular energy system 3000. In the illustrated example, one network interface 3264 may be a 3rd party network interface, another network interface 3266 may be a hospital network interface, and yet another network interface 3268 may be located on the backplane network interface connector 3182.

The header standby processor module 3184 includes a standby processor 3204 coupled to an On/Off switch 3210. The standby processor 3204 conducts an electrical continuity test by checking to see if electrical current flows in a continuity loop 3206. The continuity test is performed by placing a small voltage across the continuity loop 3206. A serial bus 3208 couples the standby processor 3204 to the backplane connector 3182.

The header footswitch module 3186 includes a controller 3240 coupled to a plurality of analog footswitch ports 3254, 3256, 3258 through a plurality of corresponding presence/ID and switch state modules 3242, 3244, 3246, respectively. The controller 3240 also is coupled to an accessory port 3260 via a presence/ID and switch state module 3248 and a transceiver module 3250. The accessory port 3260 is powered by an accessory power module 3252. The controller 3240 is coupled to header/UI controller 3170 via an isolated communication module 3234 and first and second safety critical control modules 3230, 3232. The header footswitch module 3186 also includes DC/DC converter modules 3238.

In one aspect, the header/UI module 3002 provides a user interface screen configured to display on the LCD display 3224 for controlling a footswitch connected to any one of the analog footswitch ports 3254, 3256, 3258. In some aspects, when the user plugs in a non hand-activated instrument into any one of the analog footswitch ports 3254, 3256, 3258, the instrument panel appears with a warning icon next to the footswitch icon. The instrument settings can be, for example, greyed out, as the instrument cannot be activated without a footswitch.

When the user plugs in a footswitch into any one of the analog footswitch ports 3254, 3256, 3258, a pop-up appears indicating that a footswitch has been assigned to that instrument. The footswitch icon indicates that a footswitch has been plugged in and assigned to the instrument. The user can then tap/select on that icon to assign, reassign, unassign, or otherwise change the settings associated with that footswitch. In these aspects, the system is configured to automatically assign footswitches to non hand-activated instruments using logic, which can further assign single or double-pedal footswitches to the appropriate instrument. If the user wants to assign/reassign footswitches manually there are two flows that can be utilized.

In one aspect, the header/UI module 3002 provides a global footswitch button. Once the user taps on the global footswitch icon (located in the upper right of the user interface LCD display 3224), the footswitch assignment overlay appears and the contents in the instrument modules dim. A (e.g., photo-realistic) representation of each attached footswitch (dual or single-pedal) appears on the bottom if unassigned to an instrument or on the corresponding instrument panel. Accordingly, the user can drag and drop these illustrations into, and out of, the boxed icons in the footswitch assignment overlay to assign, unassign, and reassign footswitches to their respective instruments.

In one aspect, the header/UI module 3002 provides a user interface screen displayed on the LCD display 3224 indicating footswitch auto-assignment, in accordance with at least one aspect of the present disclosure. As discussed above, the modular energy system 3000 can be configured to auto-assign a footswitch to an instrument that does not have hand activation. In some aspects, the header/UI module 3002 can be configured to correlate the colors displayed on the user interface LCD display 3224 to the lights on the modules themselves as means of tracking physical ports with user interface elements.

In one aspect, the header/UI module 3002 may be configured to depict various applications of the user inter-face with differing number of modules connected to the modular energy system 3000. In various aspects, the overall layout or proportion of the user interface elements displayed on the LCD display 3224 can be based on the number and type of instruments plugged into the header/UI module 3002. These scalable graphics can provide the means to utilize more of the screen for better visualization.

In one aspect, the header/UI module 3002 may be configured to depict a user interface screen on the LCD display 3224 to indicate which ports of the modules connected to the modular energy system 3000 are active. In some aspects, the header/UI module 3002 can be configured to illustrate active versus inactive ports by highlighting active ports and dimming inactive ports. In one aspect, ports can be represented with color when active (e.g., monopolar tissue cut with yellow, monopolar tissue coagulation with blue, bipolar tissue cut with blue, advanced energy tissue cut with warm white, and so on). Further, the displayed color will match the color of the light piping around the ports. The coloring can further indicate that the user cannot change settings of other instruments while an instrument is active. As another example, the header/UI module 3002 can be configured to depict the bipolar, monopolar, and ultrasonic ports of a first energy module as active and the monopolar ports of a second energy module as likewise active.

In one aspect, the header/VI module 3002 can be configured to depict a user interface screen on the LCD display 3224 to display a global settings menu. In one aspect, the header/VI module 3002 can be configured to display a menu on the LCD display 3224 to control global settings across any modules connected to the modular energy system 3000. The global settings menu can be, for example, always displayed in a consistent location (e.g., always available in upper right hand corner of main screen).

In one aspect, the header/VI module 3002 can be configured to depict a user interface screen on the LCD display 3224 configured to prevent changing of settings while a surgical instrument is in use. In one example, the header/VI module 3002 can be configured to prevent settings from being changed via a displayed menu when a connected instrument is active. The user interface screen can include, for example, an area (e.g., the upper left hand corner) that is reserved for indicating instrument activation while a settings menu is open. In one aspect, a user has opened the bipolar settings while monopolar coagulation is active. In one aspect, the settings menu could then be used once the activation is complete. In one aspect, the header/VI module 3002 can be is configured to never overlay any menus or other information over the dedicated area for indicating critical instrument information in order to maintain display of critical information.

In one aspect, the header/VI module 3002 can be configured to depict a user interface screen on the LCD display 3224 configured to display instrument errors. In one aspect, instrument error warnings may be displayed on the instrument panel itself, allowing user to continue to use other instruments while a nurse troubleshoots the error. This allows users to continue the surgery without the need to stop the surgery to debug the instrument.

In one aspect, the header/VI module 3002 can be configured to depict a user interface screen on the LCD display 3224 to display different modes or settings available for various instruments. In various aspects, the header/VI module 3002 can be configured to display settings menus that are appropriate for the type or application of surgical instrument (s) connected to the stack/hub. Each settings menu can provide options for different power levels, energy delivery profiles, and so on that are appropriate for the particular instrument type. In one aspect, the header/VI module 3002 can be configured to display different modes available for bipolar, monopolar cut, and monopolar coagulation applications.

In one aspect, the header/VI module 3002 can be configured to depict a user interface screen on the LCD display 3224 to display pre-selected settings. In one aspect, the header/VI module 3002 can be configured to receive selections for the instrument/device settings before plugging in instruments so that the modular energy system 3000 is ready before the patient enters the operating room. In one aspect, the user can simply click a port and then change the settings for that port. In the depicted aspect, the selected port appears as faded to indicate settings are set, but no instrument is plugged into that port.

FIG. 170 is a block diagram of an energy module 3270 for a hub, such as the energy module depicted in FIGS. 164, 165, 167, and 168, in accordance with at least one aspect of the present disclosure. The energy module 3270 is configured to couple to a header module, header/VI module, and other energy modules via the first and second pass-through hub connectors 3272, 3276. A switch 3076 disposed between the first and second pass-through hub connectors 3272, 3276 receives, processes, and forwards data from the source device to the destination device and controls data communication therebetween. Data is received and transmitted through the data bus 3008. The energy module 3270 includes a controller 3082 to control various communications and processing functions of the energy module 3270.

DC power is received and transmitted by the energy module 3270 through the power bus 3006. The power bus 3006 is coupled to the DC/DC converter modules 3138 to supply power to adjustable regulators 3084, 3107 and isolated DC/DC converter ports 3096, 3112, 3132.

In one aspect, the energy module 3270 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of the advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog multiplexer 3280 and a dual analog-to-digital converter 3278 (AID). In one aspect, the dual AID 3278 has a sampling rate of 80 MSPS. Also coupled to the controller 3082 through the advanced energy receptacle 3100 is the isolated DC/DC converter port 3096, which receives DC power from the power bus 3006, and a medium bandwidth data port 3098.

In one aspect, the energy module 3270 can include a plurality of wideband RF power amplifiers 3108, 3286, 3288, among others, which in one aspect, each of the wideband RF power amplifiers 3108, 3286, 3288 may be linear class H amplifiers capable of generating arbitrary waveforms and drive RF loads at a range of output frequencies. Each of the wideband RF power amplifiers 3108, 3286, 3288 are fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the first wideband RF power amplifier 3108 via a DAC 3122.

Unlike the energy modules 3004, 3012 shown and described in FIGS. 169 and 170, the energy module 3270 does not include RF selection relays configured to receive an RF output signal from the adjustable buck regulator 3107. In addition, unlike the energy modules 3004, 3012 shown and described in FIGS. 169 and 170, the energy module 3270 includes a plurality of wideband RF power amplifiers 3108, 3286, 3288 instead of a single RF power amplifier. In one aspect, the adjustable buck regulator 3107 can switch between a plurality of states, in which the adjustable buck regulator 3107 outputs an output RF signal to one of the plurality of wideband RF power amplifiers 3108, 3286, 3288 connected thereto. The controller 3082 is configured to switch the adjustable buck regulator 3107 between the plurality of states. In a first state, the controller drives the adjustable buck regulator 3107 to output an RF energy signal to the first wideband RF power amplifier 3108. In a second state, the controller drives the adjustable buck regulator 3107 to output an RF energy signal to the second wideband RF power amplifier 3286. In a third state, the controller drives the adjustable buck regulator 3107 to output an RF energy signal to the third wideband RF power amplifier 3288.

The output of the first wideband RF power amplifier 3108 can be fed to an RF power transformer 3090, which is coupled to an RF output portion of an advanced energy receptacle 3100. RF voltage (V) and current (I) feedback (FB) signals, which may be employed to compute RF impedance, are fed back to the controller 3082 via RF VI FB transformers 3094 through an input portion of the advanced energy receptacle 3100. The RF voltage and current feedback signals are routed back to the controller 3082 through the RF VI FB transformers 3094, which are coupled to an analog multiplexer 3284 and a dual AID 3282 coupled to the controller 3082. In one aspect, the dual AID 3282 has a sampling rate of 80 MSPS.

The output of the second RF wideband power amplifier 3286 is fed through an RF power transformer 3128 of the RF monopolar receptacle 3136. Monopolar RF voltage (V) and current (I) feedback (FB) signals, which may be employed to compute RF impedance, are fed back to the controller 3082 via RF VI FB transformers 3130 through an input portion of the monopolar RF energy receptacle 3136. The RF voltage and current feedback signals are routed back to the controller 3082 through the analog multiplexer 3284 and the dual AID 3282. Also coupled to the controller 3082 through the monopolar RF energy receptacle 3136 is the isolated DC/DC converter port 3132, which receives DC power from the power bus 3006, and a low bandwidth data port 3134.

The output of the third RF wideband power amplifier 3288 is fed through an RF power transformer 3110 of a bipolar RF receptacle 3118. Bipolar RF voltage (V) and current (I) feedback (FB) signals, which may be employed to compute RF impedance, are fed back to the controller 3082 via RF VI FB transformers 3114 through an input portion of the bipolar RF energy receptacle 3118. The RF voltage and current feedback signals are routed back to the controller 3082 through the analog multiplexer 3280 and the dual AID 3278. Also coupled to the controller 3082 through the bipolar RF energy receptacle 3118 is the isolated DC/DC converter port 3112, which receives DC power from the power bus 3006, and a low bandwidth data port 3116.

A contact monitor 3290 is coupled to an NE receptacle 3292. Power is fed to the NE receptacle 3292 from the monopolar receptacle 3136.

In one aspect, with reference to FIGS. 164-170, the modular energy system 3000 can be configured to detect instrument presence in a receptacle 3100, 3118, 3136 via a photo-interrupter, magnetic sensor, or other non-contact sensor integrated into the receptacle 3100, 3118, 3136. This approach prevents the necessity of allocating a dedicated presence pin on the MTD connector to a single purpose and instead allows multipurpose functionality for MTD signal pins 6-9 while continuously monitoring instrument presence.

In one aspect, with reference to FIGS. 164-170, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 164-170, the modules of the modular energy system 3000 can include a multi-function circuit block which can: (i) read presence resistor values via AID and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled and set to a high impedance state.

In one aspect, with reference to FIGS. 164-170, the modules of the modular energy system 3000 can include an amplifier pulse/stimulation/auxiliary DC amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

FIG. 171 illustrates a system 36000 for communication between a surgical instrument 36002, a surgical hub 36024, and a cloud computing system 36036, in accordance with at least one aspect of the present disclosure. The surgical instrument 36002 may be a powered surgical end-effector. For example, the surgical instrument 36002 may refer to the surgical instrument 6502 (FIG. 14) and/or the surgical instruments 1104, 1106, 1108 (FIG. 156). The surgical instrument 36002 may include a generator 36003. For example, the generator 36003 may refer to generator 900 described above in FIGS. 155-156. The generator 36003 may provide power in the form of one or more energy modalities described herein, such as ultrasonic, bipolar or monopolar RF, irreversible and/or reversible electroporation, and/or microwave energy, among others, for example, to the surgical instrument 36002 depending on the type of treatment of tissue being performed. The surgical instrument 36002 may include a transmission 36004 and a receiver 36006. The transmission 36004 and the receiver 36006 may be configured to establish communication pathways 36008 and 36010 between at least one external device. For example, the communication pathway 36008 may be between the surgical instrument 36002 and the surgical hub 36004 and the communication pathway 36010 may be between the surgical instrument 36002 and the cloud computing system 36036. The surgical instrument 36002 may include a controllable jaw 36012 that may be configured to operate on a tissue. The controllable jaw 36012 may include a first jaw and a second jaw. The tissue to be operated on may be positioned between the first and second jaws and may be clamped by the first and second jaws closing together. The surgical instrument 36002 may include an updatable memory 36016 that may have stored data including a control algorithm 36018, which may be a default control algorithm. The surgical instrument 36002 may include a processor 36014 that may be configured to operate the control algorithm 36018. The surgical instrument 36002 includes a first electrode 36020 that delivers a first energy and a second electrode 36022 that delivers a second energy. The first energy may be controlled by a first energy algorithm 36038 and a second energy may be controlled by a second energy algorithm 36040. The control algorithm 36018 may be configured to control the first energy algorithm 36038 and the second energy algorithm 36040. In examples, the surgical instrument 36002 may use at least two energy modalities in any suitable combination. In examples, the surgical instrument 36002 may use at least two energy modalities in a sequential manner. The generator 36003 may deliver power to the first electrode 36020 and the second electrode 36022, such as ultrasonic, bipolar or monopolar RF, irreversible and/or reversible electroporation, and/or microwave energy, as described above.

The surgical hub 36024 may include a transmitter 36026 and a receiver 36028 that may be configured to establish communication pathways 36008 and 36030 between the surgical hub 36024 and at least one external device. For example, the communication pathway 36008 may be between the surgical hub 36024 and the surgical instrument 36002. The communication pathway 36030 may be between the surgical hub 36004 and the cloud-computing system 36036. The surgical hub 36004 may include data that includes a control algorithm 36034. The surgical hub 36024 may include a processor 36032 that is configured to receive and interpret data, including the control algorithm 36034.

The cloud computing system 36036 may constitute a cloud-based analytics system and may including one or more networked computing resources. The cloud computing system 36036 may be communicatively coupled to the surgical hub 36004 via the communication pathway 36030. The cloud computing system 36036 may be communicatively coupled to the surgical instrument 36002 via the communication pathway 36010. The cloud computing system 36036 may quickly and efficiently identify data based on specific criteria. In some situations, the cloud computing system 36036 may aggregate data determined from multiple surgical sites. The cloud computing system 36036 may handle the aggregated data by data sorting, prioritizing, and other types of data handling based on specific criteria or thresholds.

FIG. 172 illustrates a logic flow diagram of a process 37000 for updating the algorithm of a surgical instrument, in accordance with at least one aspect of the present disclosure. At 37002, the process 37000 may configure the surgical instrument 36002 to operate in a first mode. For example, the first mode may operate at a first time. The first mode may be configured to operate via the control algorithm 36018 stored in the updatable memory 36016. When operating in the first mode, the control algorithm 36018 is operating according to a default control algorithm. The default control algorithm 36018 may control both the first energy operated by the first energy algorithm 36038 and the second energy operated by the second energy algorithm 36040 simultaneously. At 37004, the process 37000 may determine whether the surgical instrument 36002 may receive data at a second time after the first time, for example. If no, at 37006, the process 37000 may continue to operate in a first mode according to the default control algorithm. If yes, at 37008, the received data may automatically cause the surgical instrument 36002 to change from operating in a first mode to operating in a second mode. The second mode may be configured to operate according to an alternative control algorithm that may be configured to update the control of both the first energy algorithm 36038 and the second energy algorithm simultaneously 36040. The modification of the control algorithm 36018 from a default control algorithm to an alternative control algorithm may be controlled by the generator 36003 as described above, and/or by the surgical hub 36004. In examples, aspects of the control algorithm 36018 may be adjusted and/or updated during operation, for example. In examples, the control algorithm 36018 may be updated while the device is in service. In examples, the control algorithm 36018 may be updated during a maintenance window.

The received data may be received from an external source via the receiver 36006 of the surgical instrument 36002. For example, external source can be the surgical hub 36004 and/or the cloud computing system 36036. In examples, the received data can relate to control parameters such as the combined power draw, temperature, pressure applied, and/or tissue parameters. Properties of the tissue can be related to the tissue type or the tissue impedance, for example. Methods to help identify tissue type can use situational awareness, as discussed above. The surgical instrument 36002 may apply energy to the tissue according to an algorithm. The algorithm may modulate the energy modality, the power, and/or other aspects of operation as the tissue proceeds through coagulation and/or cutting. For example, a situational awareness system or method may identify a tissue type to be addressed. The situational awareness system or method may be used, in part, to select and/or to modify parameter of an algorithms. Such selection and/or modification may be used to optimize direct results and/or patient outcomes. For example, such a selection and/or modification may provide improved direct results and/or patient outcomes compared with that provided by a generalized algorithms (e.g., an algorithm that is generalized to be suitable for a wide range of tissue types).

In examples, the received data can relate to measures of forces by the surgical instrument 36002. The forces can direct/indirect measures of forces. In examples, the received data can relate to supplementary information obtained through situational awareness, hospital inputs, and/or user inputs. In examples, the control of the use of each of the energy modalities may be based on and/or influenced by various parameters, measurements, rules, procedures, inputs, algorithms, and the like. In examples, energy modalities may be changed and/or blended to maximize sealing and/or dissection. In examples, energy modalities may be changed and/or blended to minimize residual heat in the surgical instrument 36002. In examples, In examples, the surgical instrument 36002 can include the upgradeable element 3014 described above in FIG. 15B. The upgradeable element 3014 may act update the operational mode of the control algorithm 36018 of the surgical instrument 36002 based on the aggregated data received. In examples, the surgical instrument 36002 may include a closure drive system as described in FIG. 151 above. Clamping pressure of the closure drive system may be applied to the tissue during the delivery of energy. The amount of clamping pressure may be controlled according to the control algorithm 36018.

FIG. 173 illustrates a logic flow diagram of a process 38000 for updating the algorithm of a surgical instrument, in accordance with at least one aspect of the present disclosure. At 38002, the surgical instrument 36002 is configured to obtain a default control algorithm and an alternative control algorithm. The default control algorithm may correspond to data stored in the updatable memory 36018 of the surgical instrument 36002. The default actuation algorithm may cause the surgical instrument 36002 to operate the first energy algorithm 36038 and the second energy algorithm 36040 according to a first mode. The alternative actuation algorithm may correspond to data received from an external source. For example, the external source can be the surgical hub 36004 and/or the cloud computing system 36036. The alternative actuation algorithm may cause the surgical instrument 36002 to operate the first energy algorithm 36038 and the second energy algorithm 36040 according to a second mode. At 38004, the surgical instrument 36002 determines whether or not it can operate according to the first mode, which may act as a default mode. The determination may be based on control parameters of the surgical instrument 36002 such as the combined power draw, temperature, pressure applied, and/or tissue parameters. Properties of the tissue can be related to the tissue type or the tissue impedance, for example. Methods to help identify tissue type can use situational awareness, as discussed above. In examples, the determination may be based on measures of forces by the surgical instrument 36002. The forces can direct/indirect measures of forces. In examples, the determination may be based on supplementary information obtained through situational awareness, hospital inputs, and/or user inputs. If it is determined the surgical instrument 36002 may operate in a first mode, at 38006, the surgical instrument 36002 may operate in the first mode. At 38008, the surgical instrument 36002 determines whether or not it can operate according to the second mode, which may act as an alternative mode. The determination may be based on control parameters of the surgical instrument 36002 such as the combined power draw, temperature, pressure applied, and/or tissue parameters. Properties of the tissue can be related to the tissue type or the tissue impedance, for example. Methods to help identify tissue type can use situational awareness, as discussed above. In examples, the determination may be based on measures of forces by the surgical instrument 36002. The forces can direct/indirect measures of forces. In examples, the determination may be based on supplementary information obtained through situational awareness, hospital inputs, and/or user inputs. If yes, at 38010, the surgical instrument 36002 may change from operating in the first mode to operating in the second mode. If yes, at 38012, the surgical instrument 36002 may continue operating in the first mode, which may the default mode, as mentioned above. In some examples, the surgical instrument 36002 can include the upgradeable element 3014 described above in FIG. 15B. The upgradeable element 3014 may act update the operational mode of the one or more control algorithms of the surgical instrument 36002 based on the aggregated data received.

FIG. 174 illustrates a logic flow diagram of a process 39000 for updating the algorithm of a surgical instrument, in accordance with at least one aspect of the present disclosure. At 39002, the surgical instrument 36002 is configured to obtain a default control algorithm and an alternative control algorithm. The default control algorithm may correspond to data stored in the updatable memory 36018 of the surgical instrument 36002. The default control algorithm may operate the first energy algorithm 36038 and the second energy algorithm 36040 according to a first mode. The alternative control algorithm may correspond to data received from an external source. For example, the external source can be the surgical hub 36004 and/or the cloud computing system 36036. The alternative control algorithm may cause the surgical instrument 36002 to operate the first energy algorithm 36038 and the second energy algorithm 36040 according to a second mode. At 39004, the surgical instrument 36002 determines whether it should operate in the first mode or operate in the second mode. The determination may be based on control parameters of the surgical instrument 36002 such as the combined power draw, temperature, pressure applied, and/or tissue parameters. Properties of the tissue can be related to the tissue type or the tissue impedance, for example. Methods to help identify tissue type can use situational awareness, as discussed above. In examples, the determination may be based on measures of forces by the surgical instrument 36002. The forces can direct/indirect measures of forces. In examples, the determination may be based on supplementary information obtained through situational awareness, hospital inputs, and/or user inputs. At 39006, the surgical instrument 36002 may operate in the first mode if it determines it should operate in the first mode at 39004. At 39008, the surgical instrument 36002 may operate in the second mode if it determines it should operate in the second mode at 39004. In some examples, the surgical instrument 36002 can include the upgradeable element 3014 described above in FIG. 15B. The upgradeable element 3014 may act update the operational mode of the one or more control algorithms of the surgical instrument 36002 based on the aggregated data received.

FIG. 175 illustrates a logic flow diagram of a process 40000 for a surgical hub updating an algorithm of a surgical instrument, in accordance with at least one aspect of the present disclosure. At 40002, the surgical hub 36004 may seek communication with the surgical instrument 36002. The surgical hub 36004 may seek communication by sending a communication request to the surgical instrument 36002. At 40004, the surgical hub 36004 may determine whether communication is available with the surgical instrument 36002 that may be configured to operate in a first mode or in a second mode. The determination whether communication is available may be determined by an available processing capacity, a memory, a bandwidth, a software revision, or a subscription level, for example. Such a subscription level may enable the control algorithm 36018 and/or other software to be updated. Such a subscription level may be based on the present availability of network connectivity, for example. The presence of network connectivity and/or interaction with the cloud computing system 36036 may provide the surgeon with the option to operate, in accordance with an algorithm provided by the cloud computing system 36036. If communication is not available, the process 40000 may go back to 40002 and the surgical hub 36004 may seek communication with the surgical instrument 36002. If communication is available, at 40006, the surgical hub 36004 may receive data from the surgical instrument 36002 via the receiver 36028 and then upload the received data. At 40008, the surgical hub 36004 may determine whether the surgical instrument 36002 should operate in the first mode or the second mode based on the received data. The determination may be based on control parameters of the surgical instrument 36002 such as the combined power draw, temperature, pressure applied, and/or tissue parameters. Properties of the tissue can be related to the tissue type or the tissue impedance, for example. Methods to help identify tissue type can use situational awareness, as discussed above. In examples, the determination may be based on measures of forces by the surgical instrument 36002. The forces can direct/indirect measures of forces. In examples, the determination may be based on supplementary information obtained through situational awareness, hospital inputs, and/or user inputs. If the surgical hub 36004 determines it should operate in a first mode, the process 40000 may go back to 40006 and receive updated data from the surgical instrument 36002 at the later time via the receiver 36028 and then upload the updated received data. If the surgical hub 36004 determines it should operate in a second mode, then at 40010, based on the determination, the surgical hub 36004 may send updated data that causes the surgical instrument 36002 to operate in the second mode. In the second mode, the surgical instrument 36002 may control the first energy algorithm 36038 and the second energy algorithm 36040 simultaneously according to an alternative control algorithm. In some examples, the surgical hub 36004 can include the upgradeable element 3014 described above in FIG. 15B. The upgradeable element 3014 may act update the operational mode of the one or more control algorithms of the surgical hub 36004 based on the aggregated data received.

FIG. 176 illustrates a logic flow diagram of a process 41000 for changing or blending energy modalities of a surgical instrument based on detected threshold parameters, in accordance with at least one aspect of the present disclosure. At 41002, the surgical instrument 36002 and/or surgical hub 36004 may detect multiple energy modalities within the surgical instrument 36002. The control of the each of each of the energy modalities may be based on certain parameters. For example, the parameters may be some measure to the tissue such as tissue impedance and/or the type of tissue. Methods to help identify tissue type can use situational awareness, as described above. For example, the parameters may be some measure related to the surgical instrument 36002. The measure can be direct or indirect measures of force. For example, the parameters may come from exterior sources, such as an EMR database, system parameters, and/or other instrumentation in the surgery.

At 41004, the surgical instrument 36002 and/or surgical hub 36004 may determine whether the parameters reach a threshold. At 41006, if the surgical instrument 36002 and/or surgical hub 36004 determines a threshold is reached, the surgical instrument 36002 may be changed to a different energy modulate. Reaching a certain threshold can trigger the surgical instrument 36002 to operate in different modes, such as the first mode and the second modes described above. The different modes can be associated with different control algorithms that may control the first energy algorithm 36038 and second energy algorithm 36040, which may control the first energy and second energy, respectively. For example, reaching a certain tissue threshold impedance can trigger in a change in mode. For example, different tissue types can trigger changes to the mode at different times, which can sometimes change automatically at certain times. For example, reaching a certain threshold force can trigger a change in the mode. The change in mode can change the first energy algorithm 36038 and the second energy algorithm 36040 such that the surgical instrument 36002 can automatically change to a different energy modulate to optimize sealing and dissection while maintaining residual heat in the surgical instrument 36002. The change in mode can change the power of the surgical instrument 36002 as it cuts the tissue. The change in mode can change the clamping pressure as it cuts the tissue. At 41008, if the surgical instrument 36002 and/or surgical hub 36004 determines a threshold is not reached, the surgical instrument 36002 may be changed to a different energy modulate.

In another aspect, the control algorithm 36018 of the surgical instrument 36002 may be updated based on the use of other surgical instruments within the surgical environment. The communication can be between the surgical instrument 36002 and the surgical hub 36004 or between the surgical instrument 36002 and one or more of the other surgical instruments within the surgical environment. Information could be monitored by the surgical hub 36004 or the surgical instrument 36002 and could adjust the control algorithm 36018 after each step in the surgical procedure. For example, the control algorithm 36018 may be updated after monitoring the blood pressure of the patient, after receiving image data from the surgical hub 36004, and/or based on the sensor feedback received through the surgical instrument 36004. Each of the surgical instruments could communicate with each other in real-time and adjust with each action.

In one general aspect, a surgical hub is provided. The surgical hub comprises a transmitter and a receiver configured to establish a communication pathway between the surgical hub and a cloud computing system; and a processor. The processor is configured is determine whether communication is available with the cloud computing system that is configured to aggregate data from multiple surgical devices; receive the aggregate data from the multiple surgical devices via the receiver; update one or more control algorithms based on the aggregated data received; and continue to communicate with the cloud computing system to receive additional updates, wherein the additional updates relate to updated aggregate data determined by the cloud computing system.

In another general aspect, a surgical instrument is provided. The surgical instrument comprises a transmitter and a receiver configured to establish a communication pathway between the surgical hub and a cloud computing system; and a processor. The processor is configured to: determine whether communication is available with the cloud computing system that is configured to aggregate data from multiple surgical devices; receive the aggregate data from the multiple surgical devices via the receiver; update one or more control algorithms based on the aggregated data received;

and continue to communicate with the cloud computing system to receive additional updates, wherein the additional updates relate to updated aggregate data determined by the cloud computing system.

In yet another general aspect, a surgical system is provided. The surgical system comprises a cloud computing system, a surgical hub, and a surgical instrument. The cloud computing system is configured to aggregate data from multiple surgical devices. The surgical hub comprises: a transmitter and a receiver configured to establish a communication pathway between the surgical hub and the cloud computing system and a processor. The processor is configured to: determine whether communication is available with the cloud computing system; receive the aggregate data from the multiple surgical devices via the receiver; update one or more surgical hub control algorithms based on the aggregated data received; and continue to communicate with the cloud computing system to receive additional updates, wherein the additional updates relate to updated aggregate data determined by the cloud computing system. The surgical instrument comprises a transmitter and a receiver configured to establish a communication pathway between the surgical hub and the cloud computing system and a processor. The process is configured to: determine whether communication is available with the cloud computing system and with the surgical hub; receive the aggregate data relating to the multiple surgical devices from the cloud computing system or the surgical hub via the receiver; update one or more surgical instrument control algorithms based on the aggregated data received; and continue to communicate with the cloud computing system and the surgical hub to receive additional updates, wherein the additional updates relate to updated aggregate data determined by the cloud computing system.

Examples here describe a surgical system that may include a cloud computing system, a surgical hub, and a surgical instrument. The cloud computing system may be configured to aggregate data from multiple surgical devices. The surgical hub may determine whether communication is available with the cloud computing system, may receive the aggregate data from the multiple surgical devices via the receiver, may update one or more surgical hub control algorithms based on the aggregated data received, and may continue to communicate with the cloud computing system to receive additional updates, wherein the additional updates relate to updated aggregate data determined by the cloud computing system. The surgical instrument may determine whether communication is available with the cloud computing system and with the surgical hub and may receive the aggregate data relating to the multiple surgical devices from the cloud computing system or the surgical hub via the receiver.

FIG. 177 illustrates a system 21000 for communication between a surgical instrument 21002, a surgical hub 21004, and a cloud computing system 21006, in accordance with at least one aspect of the present disclosure. The surgical instrument 21002 may include a transmitter 21008 and a receiver 21010. The transmitter 21008 and a receiver 21010 may be configured to establish communication pathways 21012 and 21014 between at least one external device. For example, the communication pathway 21012 may be between the surgical instrument 21002 and the surgical hub 21004. The communication pathway 21014 may be between the surgical instrument 21002 and the cloud-computing system 21006. The surgical instrument 21002 may include a control algorithm 21016. The control algorithm 21016 may be updated based on new data received. The surgical instrument 21002 may include a processor 21018. The processor 21018 may update the control algorithm 21016. The control algorithm 21016 may perform a set of operations based on control parameters in the form of input data. The control algorithm 21016 may transmit the input data into output signals. The input data may be aggregated by the cloud computing system 21006, as described above. For example, the input data may be related to setup, EMR information, procedure information, and/or product mix usage. In some examples, the aggregated data may be related to compiled steps-of-use and/or procedure planning. In some examples, the aggregated data may be used to determine trends in outcomes, usage, and/or products. In some examples, the aggregated data is used as an education and process improvement system. Although FIG. 177 shows the surgical instrument 21002, it may also include the surgical instrument 112 (FIG. 1), the surgical instrument 600 (FIG. 8), the surgical instrument 7012 (FIG. 11), and/or the surgical instrument 6502 (FIG. 14).

The surgical hub 21004 may include a transmitter 21026 and a receiver 21028 that may be configured to establish the communication pathways between the surgical hub 21004 and at least one external device. For example, the communication pathway 21012 may be between the surgical hub 21004 and the surgical instrument 21002 and a communication pathway 21024 may be between the surgical hub 21004 and the cloud-computing system 21006. The surgical hub 21004 may include a control algorithm 21030 that may be updated based on new data received. The surgical hub 21004 may include a processor 21032 that may update the control algorithm 21030. Although FIG. 177 shows the surgical hub 21004, it may also include the surgical hub 205 (FIG. 5), the surgical hub 206 (FIG. 6), the surgical hub 5104 (FIG. 9), the surgical hub 7006 (FIG. 11), and/or the surgical hub 9000 (FIG. 13).

The cloud computing system 21006 may constitute a cloud-based analytics system and may including one or more networked computing resources. The cloud computing system 21006 may be communicatively coupled to the surgical hub 21004 via the communication pathway 21024 and to the surgical instrument 21002 via the communication pathway 21014. The cloud computing system 21006 may quickly and efficiently identify data based on specific criteria. In some situations, the cloud computing system 21006 may aggregate data determined from multiple surgical sites. The cloud computing system 21006 may handle the aggregated data by data sorting, prioritizing, and other types of data handling based on specific criteria or thresholds. Although FIG. 177 shows the cloud computing system 21006, it may also include the analytics system 9100 described in FIG. 0.16.

FIG. 178 illustrates a logic flow diagram of a process 22000 for updating the control algorithm of the surgical hub 21004, in accordance with at least one aspect of the present disclosure. At 22002, the process 22000 may configure the surgical hub 21004 to seek communication with the cloud computing system 21006. The transmitter 21026 and the receiver 21028 may be configured to establish the communication pathway 21024 between the surgical hub 21004 and a cloud computing system 21006. For example, the transmitter 21026 of the surgical hub 21004 may send a communication request to the cloud computing system 21006. At 22004, the surgical hub 21004 may determine whether communication is available with the cloud computing system 21006. For example, the determination whether communication is available with the cloud computing system 21006 may be determined by system generation, software revision, system capabilities, types of interconnected devices, level of networking, data capacity, and/or power capacity. The cloud computing system 21006 may be configured to aggregate data from multiple surgical devices. If communication is not available, the surgical hub 21004 may be configured to operate in a default mode of operation if no communication is available with the cloud computing system and may seek communication with the cloud computing system 21006 at 22002 at a later time. If communication is available, at 22006, the surgical hub 21004 may receive the aggregate data from the cloud computing system 21006 via the receiver 21028. In some examples, the aggregated data may be related to setup, EMR information, procedure information, and/or product mix usage. In some examples, the aggregated data may be related to compiled steps-of-use and/or procedure planning. In some examples, the aggregated data may be used to determine trends in outcomes, usage, and/or products. In some examples, the aggregated data is used as an education and process improvement system. At 22008, the surgical hub 21004 may update one or more control algorithms based on the aggregated data received. At 22010, the surgical hub 21004 may determine whether additional updates are available from the cloud computing system 21006. If no additional updates are available, the surgical hub 21004 may seek communication with the cloud computing system 21006 at 22002, for example, at a later time. If additional updates are available, the surgical hub 21004, at 22012 may continue to communicate with the cloud computing system 21006 to receive additional updates, wherein the additional updates relate to updated aggregate data determined by the cloud computing system 21006. In some examples, the surgical hub 21004 can include the upgradeable element 3014 described above in FIG. 15B. The upgradeable element 3014 may act update the operational mode of the one or more control algorithms of the surgical hub 21004 based on the aggregated data received.

FIG. 179 illustrates a logic flow diagram of a process 23000 for updating the algorithm of the surgical instrument 21002, in accordance with at least one aspect of the present disclosure. At 23002, the process 23000 may configure the surgical instrument 21002 to seek communication with the cloud computing system 21006. The transmitter 21008 and the receiver 21010 may be configured to establish a communication pathway between the surgical instrument 21002 and a cloud computing system 21006. For example, the transmitter 21008 of the surgical instrument 21002 may send a communication request to the cloud computing system 21006. At 23004, the surgical instrument 21002 may determine whether communication is available with the cloud computing system 21006. For example, the determination whether communication is available with the cloud computing system 21006 may be determined by system generation, software revision, system capabilities, types of interconnected devices, level of networking, data capacity, and/or power capacity. The cloud computing system 21006 may be configured to aggregate data from multiple surgical devices. If communication is not available, the surgical instrument 21002 may be configured to operate in a default mode of operation if no communication is available with the cloud computing system and may seek communication with the cloud computing system 21006 at 23002, for example, at a later time. If communication is available, at 23006, the surgical instrument 21002 may receive the aggregate data from the cloud computing system 21006 via the receiver 21010. In some examples, the aggregated data may be related to setup, EMR information, procedure information, and/or product mix usage. In some examples, the aggregated data may be related to compiled steps-of-use and procedure planning. In some examples, the aggregated data may be used to determine trends in outcomes, usage, and/or products. In some examples, the aggregated data is used as an education and process improvement system. At 23008, the surgical instrument 21002 may update one or more control algorithms based on the aggregated data received. At 23010, the surgical instrument 21002 may determine whether additional updates are available from the cloud computing system 21006. If no additional updates are available, the surgical instrument 21002 may seek communication with the cloud computing system 21006 at 23002, for example, at a later time. If additional updates are available, the surgical instrument 21002, at 23012 may continue to communicate with the cloud computing system 21006 to receive additional updates, wherein the additional updates relate to updated aggregate data determined by the cloud computing system 21006. In some examples, the surgical instrument 21004 can include the upgradeable element 3014 described above in FIG. 15B. The upgradeable element 3014 may act update the operational mode of the one or more control algorithms of the surgical instrument 21002 based on the aggregated data received.

FIG. 180 illustrates a logic flow diagram of a process 24000 for updating a surgical system, in accordance with at least one aspect of the present disclosure. At 24002, the process 22000 may configure the surgical hub 21004 to seek communication with the cloud computing system 21006. The transmitter 21026 and the receiver 21028 may be configured to establish a communication pathway between the surgical hub 21004 and a cloud computing system 21006. For example, the transmitter 21026 of the surgical hub 21004 may send a communication request to the cloud computing system 21006. At 24004, the surgical hub 21004 may determine whether communication is available with the cloud computing system 21006. For example, the determination whether communication is available with the cloud computing system 21006 may be determined by system generation, software revision, system capabilities, types of interconnected devices, level of networking, data capacity, and/or power capacity. The cloud computing system 21006 may be configured to aggregate data from multiple surgical devices. If communication is not available, the surgical hub 21004 may be configured to operate in a default mode of operation if no communication is available with the cloud computing system and may seek communication with the cloud computing system 21006 at 24002, for example, at a later time. If communication is available, at 24006, the surgical hub 21004 may receive the aggregate data from the cloud computing system 21006 via the receiver 21028. In some examples, the aggregated data may be related to setup, EMR information, procedure information, and/or product mix usage. In some examples, the aggregated data may be related to compiled steps-of-use and procedure planning. In some examples, the aggregated data may be used to determine trends in outcomes, usage, and/or products. In some examples, the aggregated data is used as an education and process improvement system. At 24008, the surgical hub 21004 may update one or more control algorithms based on the aggregated data received. At 24010, the surgical hub 21004 may determine whether additional updates are available from the cloud computing system 21006. If no additional updates are available, the surgical hub 21004 may seek communication with the cloud computing system 21006 at 24002, for example, at a later time. If additional updates are available, the surgical hub 21004, at 24012 may continue to communicate with the cloud computing system 21006 to receive additional updates, wherein the additional updates relate to updated aggregate data determined by the cloud computing system 21006. In some examples, the surgical system can include the upgradeable element 3014 described above in FIG. 15B. The upgradeable element 3014 may act update the operational mode of the one or more control algorithms of the surgical hub 21004 and/or the surgical instrument 21002 based on the aggregated data received.

After the surgical 21004 receives additional updates, at 24014, the process 24000 may configure the surgical instrument 21002 to seek communication with the surgical hub 21004 and/or directly with the cloud computing system 21006. The transmitter 21008 and the receiver 21010 may be configured to establish communication pathway between the surgical instrument 21002 and the surgical hub 21004 and a communication pathway between the surgical instrument 21002 and the cloud computing system 21006. For example, the transmitter 21008 of the surgical instrument 21002 may send a communication request to the surgical hub 21004 and/or to the cloud computing system 21006. At 24016, the surgical instrument 21002 may determine whether communication is available with the surgical hub 21004 and/or with the cloud computing system 21006. For example, the determination whether communication is available with the surgical hub 21004 and/or with the cloud computing system 21006 may be determined by system generation, software revision, system capabilities, types of interconnected devices, level of networking, data capacity, and/or power capacity. The surgical hub 21004 may be configured to store aggregated data received from the cloud computing system 21006. The cloud computing system 21006 may be configured to aggregate data from multiple surgical devices. If communication is not available, the surgical instrument 21002 may be configured to operate in a default mode of operation if no communication is available with the surgical hub 21004 or with the cloud computing system 21006 and may seek communication with the surgical hub 21004 or with the cloud computing system 21006 at 23002, for example, at a later time. If communication is available, at 24018, the surgical instrument 21002 may receive the aggregate data from the surgical hub 21004 or directly from the cloud computing system 21006 via the receiver 21010. In some examples, the aggregated data may be related to setup, EMR information, procedure information, and/or product mix usage. In some examples, the aggregated data may be related to compiled steps-of-use and procedure planning. In some examples, the aggregated data may be used to determine trends in outcomes, usage, and/or products. In some examples, the aggregated data is used as an education and process improvement system. At 24020, the surgical instrument 21002 may update one or more control algorithms based on the aggregated data received. At 24022, the surgical instrument 21002 may determine whether additional updates are available from the surgical hub 21004 or directly from the cloud computing system 21006. If no additional updates are available, the surgical instrument 21002 may seek communication with the surgical hub 21004 or with the cloud computing system 21006 at 24002, for example, at a later time. If additional updates are available, the surgical instrument 21002, at 24024 may continue to communicate with the surgical hub 21004 and/or the cloud computing system 21006 to receive additional updates, wherein the additional updates relate to updated aggregate data determined by the cloud computing system 21006.

The cloud computing system 21006 may provide data monitoring with monthly/quarterly reports, utilize data collected at unique sites compared to any national/regional/local area. The cloud computing system 21006 may provide recommendations to either reduce risk, improve safety, reducing operating time, and/or improve reduce total product usage. In one aspect, the cloud computing system 21006 may provide inventory control methods. For example, the cloud computing device 21006 may provide guidance based on demographic, utilization, and/or procedure type to optimize inventory. For example, at the end of a surgery, the cloud computing system 21006 may report all devices and cartridges used so individual hospitals can know what has been used and needs ordering. In one aspect, the cloud computing system 21006 can track of all the items disposed in a location to ensure items are placed in their current places.

The cloud computing system 21006 may provide a service that monitors surgery and offers reconfiguration of room layout and resources that can reduce surgical time/room use. For example, the cloud computing system 21006 can be linked to a system/app that give an instant answer, such as a mobile device app, regarding questions on device, procedure, and training. For example, the cloud computing system 21006 can provide access databases and message boards that can allow users to ask questions and see questions asked by others and the responses to those questions. In one aspect, the cloud computing system 21006 may provide a service based on the data that could create specific training programs tailored for best practices, which can be location specific.

A surgical hub may be connected, wired or wireless, with various devices and servers in the operating room, in the medical facility and/or outside of the medical facility. The surgical hub may determine the hub connectivity mode based on a hub connectivity control parameter. The hub connectivity mode may be selected from multiple connectivity modes that may be preconfigured, dynamically updated, semi-dynamically updated, periodically updated, or preset. The hub connectivity modes may control inter-device connectivity within a network associated with a hospital, and/or communication with an external network associated with a different hospital, for example.

For example, the surgical hub may determine whether to disable obtaining instructional information based on the connectivity mode. Based on a determination that the current connectivity mode is a flow-through mode, the surgical hub may disable obtaining instructional information.

For example, the surgical hub may determine whether to provide instructional information to at least one smart surgical instrument based on the hub connectivity mode. On a condition that the hub connectivity mode does not support provisioning instructional information to surgical devices, provisioning instructional information to surgical devices may be disabled. On a condition that the hub connectivity mode supports provisioning instructional information to surgical devices, the surgical hub may determine to obtain and provide instructional information to surgical devices.

For example, the surgical hub may determine whether to retrieve aggregation analysis from the remote server based on the hub connectivity mode. Based on a determination that the current hub connectivity mode supports remote data aggregation and analysis, the surgical hub may generate an aggregation analysis request. The request may be generated based on the received surgical data and may be sent to a remote server. For example, the aggregation analysis request may indicate a request for recommendation on generator data associated with a particular step in a surgical procedure. In response, the surgical hub may receive an aggregation analysis response from the remote server. For example, the aggregation analysis response may include a recommendation and/or a report. The aggregation analysis response may include one or more of: an energy mode of the generator for a particular surgical procedure, a power output of the generator for a particular surgical procedure, and/or a duration of the power output of the generator for a particular surgical procedure. The aggregation analysis response may include instructional information as described herein. The surgical hub may generate and send instructional information to one or more surgical device(s) based on the received aggregation analysis response. Based on a determination that the current hub connectivity mode supports remote data aggregation analysis, the surgical hub may disable data aggregation analysis requests.

The hub connectivity control parameter(s) may include, but not limited to, systems capabilities such as hardware capability, firmware capability and/or software capability. The hub connectivity control parameter(s) may include a consumer-controlled parameter, such as a subscription level. For example, a medical facility may purchase a subscription to hub connectivity capabilities. Some subscription level(s) may provide the hub access to surgical data gathered from external systems, while others may limit the hub connectivity to internal devices.

In an example hub connectivity mode, the surgical hub may receive information from surgical instrument(s) and may send the received information to a remote server (such as a remote processing server and/or a remote database in the cloud).

In an example connectivity mode, the surgical hub may receive information from surgical instrument(s) and may send the received information to a remote server (such as a remote processing server and/or a remote database in the cloud). The surgical hub may receive information from surgical instrument(s), obtain instructional information based on the information received from the surgical instrument(s), and may send the instructional information to one or more surgical instrument(s).

In an example connectivity mode, the surgical hub may receive information from surgical instrument(s) and may send the received information to a remote server (such as a remote processing server and/or a remote database in the cloud). The surgical hub may receive information from surgical instrument(s), obtain instructional information based on the information received from the surgical instrument(s), and may send the instructional information to one or more surgical instrument(s). The surgical hub may record various surgical information and send surgical information to a remote server for archiving and/or analysis. The archived surgical information may be aggregated with information received from other surgical hub(s), and/or surgical information associated with other medical facilities. The aggregated information may be accessed to generate instructional information to one or more surgical instrument(s). In an example, the surgical communication hub may aggregate information, such as information received from smart surgical devices, information associated with multiple surgeries, surgical information and corresponding outcome associated with multiple patients. The aggregated information may be stored in a remote database. In an example, the surgical information may be aggregated at a remote server.

A surgical hub may obtain a hub connectivity mode based on a hub connectivity control parameter. For example, the hub connectivity mode may be selected from multiple connectivity modes that may be preconfigured, dynamically updated, semi-dynamically updated, periodically updated, or preset. The hub connectivity modes may control inter-device connectivity within a network associated with a hospital, and/or communication with an external network associated with a different hospital. The surgical hub may determine whether to provide instructional information to at least one smart surgical instrument based on the hub connectivity mode. On a condition that the hub connectivity mode does not support provisioning instructional information to surgical devices, provisioning instructional information to surgical devices may be disabled. On a condition that the hub connectivity mode supports provisioning instructional information to surgical devices, the surgical hub may determine to obtain and provide instructional information to surgical devices.

FIG. 181 shows an example flow for a hub operating under tiered communication modes. At 16104, one or more hub connectivity control parameters may be identified. At 16108, a hub connectivity mode may be determined based on the identified hub connectivity control parameter(s). For example, the surgical hub 7006 shown in FIG. 11 may determine the hub connectivity mode based on a hub connectivity control parameter. The hub connectivity mode may be selected from multiple connectivity modes that may be preconfigured, dynamically updated, semi-dynamically updated, periodically updated, or preset. The hub connectivity modes may control inter-device connectivity within a network associated with a hospital, and/or communication with an external network associated with a different hospital, for example.

The hub connectivity control parameter(s) may include, but not limited to, systems capabilities such as hardware capability, firmware capability and/or software capability. For example, if a surgical instrument lacks the hardware capability to provide indications of instructional information, the surgical hub may switch to a connectivity mode that may disable providing instructional information to the surgical instrument.

The hub connectivity control parameter(s) may include a consumer-controlled parameter, such as a subscription level. For example, a medical facility may purchase a subscription to hub connectivity capabilities. Some subscription level(s) may provide the hub access to surgical data gathered from external systems, while others may limit the hub connectivity to internal devices.

The hub connectivity control parameter(s) may include available data bandwidth, power capacity and usage, processor and memory utilization, and/or internal or attached systems.

The hub connectivity control parameter(s) may include an indication from a tiered system. The tiered system may scale the communication between the surgical hub 7006 and the device(s) 7012, the communication between the surgical hub 7006 and external server(s) 7013/7002 and/or the like, based on the available data bandwidth, power capacity and usage, processor and memory utilization, and/or internal or attached systems. The tiered system may determine max communication capabilities the surgical hub may operate under. For example, upon detecting the power capability associated with the operation room, associated with the surgical hub, and/or associated with a medical facility is below a threshold, the tiered system may scale down the surgical hub's connectivity capabilities. For example, upon detecting available data bandwidth is below a threshold, memory utilization is above a certain threshold, power usage is above a certain threshold, and/or other system conditions that may warrant scaling down the surgical hub's connectivity capabilities, the tiered system may limit or disable the communication between the surgical hub and the devices and/or the communication between the surgical hub and external server(s). For example, bi-directional connectivity mode (as shown in FIG. 180B) may be scaled down to flow-through connectivity mode (as shown in FIG. 180A). External communications (as shown in FIG. 180) may be disabled. In examples, the tiered system may be a module within the surgical hub or may be a system external to the surgical hub.

At 16110, the surgical hub may communicate with devices in the operating room, servers in the internal and/or external network(s) in accordance with the determined hub connectivity mode.

In an example hub connectivity mode, the surgical hub may receive information from surgical instrument(s) and may send the received information to a remote server (such as a remote processing server and/or a remote database in the cloud).

In an example connectivity mode, the surgical hub may receive information from surgical instrument(s) and may send the received information to a remote server (such as a remote processing server and/or a remote database in the cloud). The surgical hub may receive information from surgical instrument(s), obtain instructional information based on the information received from the surgical instrument(s), and may send the instructional information to one or more surgical instrument(s).

In an example connectivity mode, the surgical hub may receive information from surgical instrument(s) and may send the received information to a remote server (such as a remote processing server and/or a remote database in the cloud). The surgical hub may receive information from surgical instrument(s), obtain instructional information based on the information received from the surgical instrument(s), and may send the instructional information to one or more surgical instrument(s). The surgical hub may record various surgical information and send surgical information to a remote server for archiving and/or analysis. The archived surgical information may be aggregated with information received from other surgical hub(s), and/or surgical information associated with other medical facilities. The aggregated information may be accessed to generate instructional information to one or more surgical instrument(s). In an example, the surgical communication hub may aggregate information, such as information received from smart surgical devices, information associated with multiple surgeries, surgical information and corresponding outcome associated with multiple patients. The aggregated information may be stored in a remote database. In an example, the surgical information may be aggregated at a remote server.

FIGS. 180A-C illustrate example hub connectivity modes that a surgical hub, such as the surgical hub 7006 may operate under. As shown in FIGS. 180A-C, the surgical hub 15504 may communicate with the various devices 15506, remote server(s) in the cloud 15502 and/or devices, servers and databases in external networks 15508 in different connectivity modes.

For example, the surgical hub may determine to operate in a connectivity mode where surgical information may flow through the surgical hub to a remote server. As shown in FIG. 180A, the surgical hub 15504 may serve as a communication portal between the local devices/systems (e.g., surgical instruments and other equipment within the operating room) 15506 and the other connected systems 15502, including systems local or remote to the surgical hub. In this flow-through connectivity mode, the surgical hub 15504 may act as a communication bus between different devices and systems, enabling them to communicate via the surgical hub.

The surgical hub 15504 may receive surgical information data from one or more smart surgical devices 15506 in the operating room, for example, as described herein with reference to FIG. 13. As shown in FIG. 13, the surgical hub 9000 may receive surgical data associated with a surgical procedure being performed in the surgical operating room from the modular surgical device(s) 9050.

During a surgical procedure, surgical devices 9050 may track and record surgical data and variables (e.g., surgical parameters). The surgical parameters may include force-to-fire (FTF), force-to-close (FTC), firing progress, tissue gap, power level, impedance, tissue compression stability (creep), and/or the like.

The surgical devices 9050 may include an end effector including a staple cartridge. The captured surgical data may include snapshots taken via an endoscope of the surgical hub during a stapling portion of a surgical procedure. The surgical devices 9050 may include a temperature sensor. The captured surgical data may include least one temperature detected by the temperature sensor during a tissue sealing portion of a surgical procedure.

For example, when operating under flow-through connectivity mode, the surgical hub 15504 may disable interpretation, control or operation on the received information. The surgical hub 15504 may determine whether to disable obtaining instructional information based on the connectivity mode. Based on a determination that the current connectivity mode is a flow-through mode, the surgical hub 15504 may disable obtaining instructional information.

In an example hub connectivity mode, the surgical hub may generate instructional information based on the received surgical data.

FIG. 182A shows an example flow for operating under variable hub communication modes. As shown in FIG. 182A, at 16182, a hub connectivity mode may be determined based on the identified hub connectivity control parameter(s) as described herein. At 16184, whether the hub connectivity mode indicates the hub may provide instructional information to surgical devices may be determined. For example, the surgical hub 5104 as described with respect to FIG. 9 may determine whether to provide instructional information to at least one smart surgical device 5102 based on the hub connectivity mode. On a condition that the hub connectivity mode does not support provisioning instructional information to surgical devices, at 16188, provisioning instructional information to surgical devices may be disabled. On a condition that the hub connectivity mode supports provisioning instructional information to surgical devices, at 16186, the surgical hub may determine to obtain and provide instructional information to surgical devices.

The surgical hub may obtain instructional information to surgical devices based at least in part on surgical data received from one or more surgical devices. For example, based on a determination that the current hub connectivity mode is a bi-directional mode, the surgical hub may receive surgical data from a surgical device and may obtain a response to the surgical device based on the received surgical data. Based on a determination that the current hub connectivity mode is a bi-directional mode, the surgical hub may receive surgical data from a first device and may obtain an indication to a second device based on the surgical data received from the first device. The indication to the second device may include the surgical data received from the first device and/or other information.

FIG. 180B shows an example bi-directional mode. As shown, the surgical hub 15506 may receive surgical data from surgical device(s) 15506, and may send data, such as instructional information to device(s) 15506. The surgical hub 15506 may aggregate the surgical data received from surgical device(s) 15506 prior to sending to the remote server(s) in the cloud 15502.

In an example, the surgical data received by the surgical hub and sent to the remote server(s) may include a property of airborne particles in a fluid within a patient's abdominal cavity, such as a particle type, particle size, particle concentration, particle velocity, and/or particle direction. The instructional information that the surgical hub obtains based on the received surgical data may include, but not limited to, an adjustment to a surgical function, such as proportionately increasing the surgical function based on the property of airborne particles in the fluid, adding a supplemental surgical function to the surgical function, adjusting the power level provided to an energy device, adjusting the speed of a pump in a smoke evacuator, adjusting a flow path through the filtering system of the smoke evacuator, adjusting the operating room vent to increase ventilation therethrough, adjusting a degree of the activation of an actuator, and/or replacing the surgical function with an alternative surgical function.

In examples, the instructional information that the surgical hub obtains based on the received surgical data may include, but not limited to, prioritization information (e.g., display prioritization information), cartridge usage or selection recommendation, a warning message and/or surgical device usage instructions.

For example, when the current hub connectivity mode is a bi-directional mode, the surgical hub may determine to obtain and provide instructional information. An example bi-directional connectivity mode may enable situational awareness and controlling surgical device(s). The surgical hub may infer progression of the surgical procedure from the surgical data and may obtain instructional information based on the inferred progression of the surgical procedure. The surgical hub may assess a surgical activity performed by an end effector of the modular surgical device at the surgical site from the data extracted from the at least one image frame.

For example, as shown in FIG. 9, the surgical hub 5104 may receive perioperative data from the devices 5102 and other data sources (e.g., databases 5122 and patient monitoring devices 5124) that are communicably coupled to the surgical hub 5706. The surgical hub 5104 may determine whether an event has occurred based on the received data. The event can include, for example, a surgical procedure, a step or portion of a surgical procedure, or downtime between surgical procedures or steps of a surgical procedure. The surgical hub 5104 may track data associated with the particular event, such as the length of time of the event, the surgical instruments and/or other medical products utilized during the course of the event, and the medical personnel associated with the event. The surgical hub 5104 may determine event data via, for example, the situational awareness processes as described herein.

The surgical hub 5104 may provide the devices 5102 with instructional information such as, but not limited to, control adjustment information, prioritization information, warning, display instructions. For example, the surgical hub 5104 may receive surgical data that may include perioperative data detected by one or more smart surgical devices 5102 during a surgical procedure. The surgical hub 5104 may determine contextual information regarding the surgical procedure according to the perioperative data. The surgical hub may obtain control adjustments for one or more surgical devices 5102 based on the contextual information. The perioperative data include one or more parameter associated with the modular device and/or one or more parameter associated with a patient.

The instructional data information be provided to a surgical device with an associated priority. The instructional information that the surgical hub obtains based on the received surgical data may include recommendation to a clinician in an operating room. The recommendation may be provided to a surgical device with a priority that may be determined by the surgical hub. For example, an elevated priority level may be communicated with at least one of marking, emphasizing, highlighting, or flashing. For example, the surgical hub may determine a surgical state based on the received surgical data and may determine the priority level of the recommendation based on the surgical state. For example, the surgical hub 5104 may determine a surgical state based on the received surgical data. The surgical state may include, a step in a surgical procedure, identification of a suite of surgical devices currently in use in a surgical theater, a position of a portion of the surgical device, a position of a jaw of an end effector of the surgical device, a gross usage surgical step, and/or a precision usage surgical step.

The surgical hub may select one or more recommendations from multiple possible recommendations based on the surgical state. The priority level of the recommendation may be adjusted based on an anticipated surgical action. The anticipated surgical action may be determined based on the surgical state, and/or based on a position of a surgical device at a surgical site.

Situational awareness processes are described in greater detail in U.S. patent application Ser. No. 15/940,654, titled SURGICAL HUB SITUATIONAL AWARENESS, filed Mar. 29, 2018; U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Dec. 4, 2018; and U.S. patent application Ser. No. 16/182,246, titled ADJUSTMENTS BASED ON AIRBORNE PARTICLE PROPERTIES, filed Nov. 6, 2018; the disclosure of each is herein incorporated by reference in its entirety.

Surgical procedures are performed by different surgeons at different locations, some with much less experience than others. For a given surgical procedure, there may be many parameters that can be varied to attempt to realize a desired outcome. For example, for a given surgical procedure which utilizes energy supplied by a generator, the surgeon often relies on experience alone for determining which mode of energy to utilize, which level of output power to utilize, the duration of the application of the energy, etc., in order to attempt to realize the desired outcome. To increase the likelihood of realizing desired outcomes for different surgical procedures, a surgeon may be provided with best practice recommendations, which may be generated based on aggregated surgical data sets associated with multiple surgical procedures performed in multiple locations over time.

As shown in FIG. 182B, at 16202, a hub connectivity mode may be determined based on the identified hub connectivity control parameter(s) as described herein. At 16204, whether the determined hub connectivity mode supports data aggregation with external sources may be determined. For example, the hub may determine whether to send recorded surgical information associated with a procedure to a remote server for archiving and potential aggregation with data associated with external network(s) based on the hub connectivity mode. If the determined hub connectivity mode supports data aggregation with external sources, at 16206, the surgical hub may send recorded surgical information to a remote server. For example, the surgical hub may enable communication to external system(s) when operating in a certain connectivity mode. Based on a determination to send recorded surgical information to a remote server, surgical data may be sent to an external hub associated with an external network (e.g., a different medial facility, a different hospital, or the like).

FIG. 180C shows an example hub connectivity mode that supports data aggregation with external data sets. As shown, the surgical hub 15506 may receive surgical data from surgical device(s) 15506, and may send data, such as instructional information to device(s) 15506. The surgical hub 15504 may facilitate recording and archiving surgical data and may exchange surgical data and/or related analysis with an external network(s) 15508. Data from various hospitals or medical organizations 15508 can be aggregated. Surgical data, outcome, patient information can be compiled to determine instructional information, surgical recommendations, aggregation analysis, and/or the like. As shown, the surgical hub 15504 may retrieve aggregation analysis from remote server(s) or database(s) in the cloud 15502. The aggregation analysis may be used to generate instructional information for sending to surgical devices 15506.

As shown in FIG. 182B, the surgical hub may determine whether to disable communication to an external system based on the hub connectivity mode. If the determined hub connectivity mode does not support data aggregation with external sources, at 16208, sending recorded surgical information for aggregation with external sources may be disabled. For example, the surgical hub may disable communication to external system(s) when operating under certain connectivity modes, such as the flow-through connectivity mode and the bi-directional connectivity mode described herein.

Recording surgical data is described in greater detail in U.S. patent application Ser. No. 16/209,385, titled METHOD OF HUB COMMUNICATION, PROCESSING, STORAGE AND DISPLAY, filed Dec. 4, 2018, the disclosure of which is herein incorporated by reference in its entirety. The recorded surgical data may include surgical event data as described herein. Surgical event data, for example, recorded and/or aggregated surgical event data may be sent to a remote server for aggregation with surgical data from external networks and for further analysis.

Examples of aggregation (e.g., remote aggregation), requests and analysis are described in detail in U.S. patent application Ser. No. 15/940,668 titled AGGREGATION AND REPORTING OF SURGICAL HUB DATA; filed on Mar. 29, 2018, which is herein incorporated by reference in its entirety.

When operating in a connectivity mode that allows external communication, the surgical hub may request information from a remote server and/or external systems. As shown in FIG. 182C, at 16302, a hub connectivity mode may be determined based on the identified hub connectivity control parameter(s) as described herein. At 16304, the hub may determine whether to retrieve aggregation analysis from the remote server based on the hub connectivity mode. Based on a determination that the current hub connectivity mode supports remote data aggregation and analysis, at 16308, the surgical hub may generate an aggregation analysis request. The request may be generated based on the received surgical data and may be sent to a remote server at 16310. For example, the aggregation analysis request may indicate a request for recommendation on generator data associated with a particular step in a surgical procedure. In response, the surgical hub may receive an aggregation analysis response from the remote server at 16312.

For example, the aggregation analysis response may include a recommendation and/or a report. The aggregation analysis response may include one or more of: an energy mode of the generator for a particular surgical procedure, a power output of the generator for a particular surgical procedure, and/or a duration of the power output of the generator for a particular surgical procedure. The aggregation analysis response may include instructional information as described herein. At 16314, the surgical hub may generate and send instructional information to one or more surgical device(s) based on the received aggregation analysis response. As shown in FIG. 182C, based on a determination that the current hub connectivity mode supports remote data aggregation analysis, the surgical hub may disable data aggregation analysis requests at 16306.

FIG. 47 is a block diagram of a computer-implemented interactive surgical system 5700, in accordance with at least one aspect of the present disclosure. The system 5700 may include a number of surgical hubs 5706 that, as described herein, may detect and track data related to surgical procedures that the surgical hubs 5706 (and the modular devices paired to the surgical hubs 5706) are utilized in connection with. The surgical hubs 5706 may be connected to form local networks such that the data being tracked by the surgical hubs 5706 is aggregated together across the network. The networks of surgical hubs 5706 can be associated with a medical facility, for example. The data aggregated from the network of surgical hubs 5706 can be analyzed to provide reports on data trends or recommendations. For example, the surgical hubs 5706 of a first medical facility 5704a may be communicably connected to a first local database 5708a and the surgical hubs 5706 of a second medical facility 5704b are communicably connected to a second local database 5708b. The network of surgical hubs 5706 associated with the first medical facility 5704a can be distinct from the network of surgical hubs 5706 associated with the second medical facility 5704b, such that the aggregated data from networks of surgical hubs 5706 may correspond to medical facility 5704a, 5704b individually. A surgical hub 5706 or another computer terminal communicably connected to the database 5708a, 5708b can be configured to provide reports or recommendations based on the aggregated data associated with the respective medical facility 5704a, 5704b. The data tracked by the surgical hubs 5706 can be utilized to, for example, report whether a particular incidence of a surgical procedure deviated from the average in-network time to complete the particular procedure type.

The surgical hub 5706 may upload the tracked data to the cloud 5702, for processing and aggregating the tracked data across multiple surgical hubs 5706, networks of surgical hubs 5706, and/or medical facilities 5704a, 5704b that are connected to the cloud 5702. The surgical hub 5706 may provide reports or recommendations based on the aggregated data. The data tracked by the surgical hubs 5706 can be utilized to, for example, report whether a particular incidence of a surgical procedure deviated from the average global time to complete the particular procedure type.

The surgical hub 5706 can be configured to access the cloud 5702 to compare locally tracked data to global data aggregated from the surgical hubs 5706 that are communicably connected to the cloud 5702. The surgical hub 5706 may provide reports or recommendations based on the comparison between the tracked local data relative to local (e.g., in-network) or global norms. The data tracked by the surgical hubs 5706 can be utilized to, for example, report whether a particular incidence of a surgical procedure deviated from either the average in-network time or the average global time to complete the particular procedure type.

The surgical hub 5706 or a computer system local to the surgical hub 5706 may locally aggregate the data tracked by the surgical hubs 5706, store the tracked data, and generate reports and/or recommendations according to the tracked data in response to queries. In cases where the surgical hub 5706 is connected to a medical facility network (which may include additional surgical hubs 5706), the surgical hub 5706 may compare the tracked data with the bulk medical facility data. The bulk medical facility data can include EMR data and aggregated data from the local network of surgical hubs 5706. The cloud 5702 (e.g., a remote server in the cloud) may aggregate the data tracked by the surgical hubs 5706, store the tracked data, and generate reports and/or recommendations according to the tracked data in response to queries.

The surgical hub 5706 can provide reports regarding trends in the data and/or provide recommendations on improving the efficiency or effectiveness of the surgical procedures being performed. The data trends and recommendations can be based on data tracked by the surgical hub 5706 itself, data tracked across a local medical facility network containing multiple surgical hubs 5706, and/or data tracked across a number of surgical hubs 5706 communicably connected to a cloud 5702. The recommendations provided by the surgical hub 5706 can describe, for example, particular surgical instruments or product mixes to utilize for particular surgical procedures based on correlations between the surgical instruments/product mixes and patient outcomes and procedural efficiency. The reports provided by the surgical hub 5706 can describe, for example, whether a particular surgical procedure was performed efficiently relative to local or global norms, whether a particular type of surgical procedure being performed at the medical facility is being performed efficiently relative to global norms, and the average time taken to complete a particular surgical procedure or step of a surgical procedure for a particular surgical team.

The surgical hub 5706 may determine when operating theater events occur (e.g., via a situational awareness module/system) and track the length of time spent on each event. An operating theater event is an event that a surgical hub 5706 can detect or infer the occurrence of. An operating theater event can include, for example, a particular surgical procedure, a step or portion of a surgical procedure, or downtime between surgical procedures. The operating theater events can be categorized according to an event type, such as a type of surgical procedure being performed, so that the data from individual procedures can be aggregated together to form searchable data sets. The data tracked by the surgical hubs 5706 being parsed to provide metrics related to surgical procedures or the use of the surgical hub 5706.

The surgical hub 5706 may determine whether a surgical procedure is being performed and then track both the length of time spent between procedures (e.g., downtime) and the time spent on the procedures themselves. The surgical hub 5706 can determine and track the time spent on the individual steps taken by the medical personnel (e.g., surgeons, nurses, orderlies) either between or during the surgical procedures. The surgical hub may determine when surgical procedures or different steps of surgical procedures are being performed via a situational awareness module/system as described in herein.

Near-field-communication (NFC) cards may be used to automate supply chain. FIG. 183A illustrates an example surgical supply packaged with a radio frequency identification (RFID) NFC chip. As shown, surgical supply 16510 may include surgical devices, sutures, biosurgery supply, and/or the like. Medical personnel may scan the chip 16530 on the surgical supply 16510 prior to introduction to surgery. This may allow the supply chain for customers ordering and may provide full case device profiles, for example, via cloud 16520. NFC reader may be used to track inventory, for example, by adding an RFID card 16530 into devices or packaging.

A surgical hub may be configured to receive an image from a laparoscopic scope and surgical information from at least one surgical instrument. The surgical hub may be operatively connected to multiple displays such as a primary display and a secondary display. The surgical hub may generate visualization data for the primary display. The surgical hub may obtain a visualization control mode based on a visualization control parameter, and may determine whether to generate a different set of visualization data for a secondary display based on the visualization control mode. When the visualization control mode supports multiple display capabilities, the surgical hub may generate the visualization data specifically for the secondary display. When the visualization control mode does not support multiple display capabilities, the surgical hub may send the same the visualization data for display at the secondary display as the primary display. The visualization data may be generated by receiving data from multiple smart surgical devices, and combining the received data for displaying on both the primary and secondary displays.

For example, the surgical hub may receive an indication of changing the visualization control mode to an updated visualization control mode. The surgical hub may generate and send visualization data to the primary display and/or the secondary display in accordance with the updated visualization control mode. For example, based on updated visualization control mode, the surgical hub may generate and send visualization data for display to the primary display and a different set of visualization data for display to the secondary display. In an example visualization control mode that supports contactless control, the surgical hub may generate the visualization data based on a contactless control parameter such as user motions, user's head orientation relative to a monitor, user hand gesture(s), and/or user voice activation. In an example visualization control mode that supports augmented reality, the surgical hub may generate overlay information for overlaying on the primary display via the secondary display.

In various examples, the visualization control parameter may include one or more of available memory, available data bandwidth, heat generated by the surgical hub, heat generated by the secondary display, power capacity associated with the surgical hub, power capacity associated with an operating room, power capacity associated with a medical facility, a power usage, a balance of the power consumption to at least one attached system, processor utilization, and/or memory utilization. The visualization control parameter may include one or more of a subscription level associated with surgical display; a user preference associated with surgical display; a hardware capability associated with the surgical hub, the primary display and the secondary display; a software capability associated with the surgical hub, the primary display and the secondary display; or an indication from a tiered control system.

For example, the visualization control parameter(s) may include an indication from a tiered system. The tiered system may scale the display capabilities and interactive display control capabilities and/or the like, based on the available data bandwidth, power capacity and usage, processor and memory utilization, and/or internal or attached systems. The tiered system may determine max display and interactive display control capabilities the surgical hub may operate under.

A surgical hub may be configured to receive an image from a laparoscopic scope and surgical information from at least one surgical instrument. The surgical hub may be operatively connected to multiple displays such as a primary display and a secondary display. The surgical hub may generate visualization data for the primary display. The surgical hub may obtain a visualization control mode based on a visualization control parameter and may determine whether to generate a different set of visualization data for a secondary display based on the visualization control mode. When the visualization control mode supports multiple display capabilities, the surgical hub may generate the visualization data specifically for the secondary display. When the visualization control mode does not support multiple display capabilities, the surgical hub may send the same the visualization data for display at the secondary display as the primary display.

FIG. 183B illustrates an example primary display 6200 associate with the surgical hub 206 comprising a global display window 6202 and a local instrument display window 6204, according to one aspect of the present disclosure. With continued reference to FIGS. 1-11 to show interaction with an interactive surgical system 100 environment including a surgical hub 106, 206 and FIGS. 12-14 for surgical hub connected instruments together, the local instrument display 6204 behavior may be displayed when the instrument 235 senses the connectable presence of a global display window 6202 through the surgical hub 206. The global display window 6202 may show a field of view 6206 of a surgical site 6208, as viewed through a medical imaging device such as, for example, a laparoscope/endoscope 219 coupled to an imaging module 238, at the center of the surgical hub display 215, referred to herein also as a monitor, for example. The end effector 6218 portion of the connected instrument 235 may be shown in the field of view 6206 of the surgical site 6208 in the global display window 6202. The images shown on the display 237 located on an instrument 235 coupled to the surgical hub 206 is shown, or mirrored, on the local instrument display window 6204 located in the lower right corner of the monitor 6200 as shown in FIG. 183B, for example.

During operation, relevant instrument and information and menus may be displayed on the display 237 located on the instrument 235 until the instrument 235 senses a connection of the instrument 235 to the surgical hub 206 at which point all or some sub-set of the information presented on the instrument display 237 may be displayed (e.g., only) on the local instrument display window 6204 portion of the surgical hub display 6200 through the surgical hub 206. The information displayed on the local instrument display window 6204 may be mirrored on the display 237 located on the instrument 235 or may be no longer accessible on the instrument display 237 detonated screen. This technique frees up the instrument 235 to show different information or to show larger font information on the surgical hub display 6200.

The primary display 6200 may provide perioperative visualization of the surgical site 6208. Advanced imaging may identify and visually highlight 6222 critical structures such as the ureter 6220 (or nerves, etc.) and may track instrument proximity displays 6210 and shown on the left side of the display 6200. In the illustrated example, the instrument proximity displays 6210 may show instrument specific settings. For example, the top instrument proximity display 6212 may show settings for a monopolar instrument, the middle instrument proximity display 6214 may show settings for a bipolar instrument, and the bottom instrument proximity display 6212 may show settings for an ultrasonic instrument.

FIG. 184 illustrate an example primary display having a composite overhead views of an end-effector 6234 portion of a surgical stapler mapped using two or more imaging arrays or one array and time to provide multiple perspective views of the end-effector 6234 to enable the composite imaging of an overhead field of view. The techniques described herein may be applied to ultrasonic instruments, electrosurgical instruments, combination ultrasonic/electrosurgical instruments, and/or combination surgical stapler/electrosurgical instruments. Several techniques may be performed for overlaying or augmenting images and/or text from multiple image/text sources to present composite images on a display (e.g., a single display).

As shown in FIG. 184, a primary display 6200 of the surgical hub 206 may display a primary window 6230. The primary window 6230 may be located at the center of the screen shows a magnified or exploded narrow angle view of a surgical field of view 6232. The primary window 6230 located in the center of the screen shows a magnified or narrow angle view of an end-effector 6234 of the surgical stapler grasping a vessel 6236. The primary window 6230 may display knitted images to produce a composite image that enables visualization of structures adjacent to the surgical field of view 6232. A second window 6240 may be shown in the lower left corner of the primary display 6200. The second window 6240 displays a knitted image in a wide-angle view at standard focus of the image shown in the primary window 6230 in an overhead view. The overhead view provided in the second window 6240 can enable the viewer to easily see items that are out of the narrow field surgical field of view 6232 without moving the laparoscope, or other imaging device 239 coupled to the imaging module 238 of the surgical hub 206. A third window 6242 can be shown in the lower right corner of the primary display 6200 shows an icon 6244 representative of the staple cartridge of the end-effector 6234 (e.g., a staple cartridge in this instance) and additional information such as "4 Row" indicating the number of staple rows 6246 and "35 mm" indicating the distance 6248 traversed by the knife along the length of the staple cartridge. Below the third window 6242 is displayed an icon 6258 of a frame of the current state of a clamp stabilization sequence 6250 that indicates clamp stabilization.

In an example visualization control mode, display may be controlled by the user, for example, via motion tracking (e.g., head orientation relative to a monitor), hand gestures, voice activation and other means within the sterile field. User gestures may be determined based on a wearable device worn by a user such as smart watch and/or camera(s) in the OR. The user's head movement may be determined based on AR goggles and/or camera(s) in the OR.

FIG. 186 is a diagram of an illustrative OR setup that may enable display control via motion tracking, gesture tracking and/or voice activation. In various implementations, a surgical hub 211801 can be communicably connected to one or more cameras 211802, surgical instruments 211810, displays 211806, overheard lights 211808, and other surgical devices within the OR 211800 via a communications protocol (e.g., Bluetooth). The cameras 211802 can be oriented in order to capture images and/or video of the surgical staff members 211803 and/or surgical instruments 211810 (or other surgical devices) within the OR 211800 during the course of a surgical procedure. The captured image(s) can include static images or moving images (e.g., video). The images of the surgical staff members 211803 and/or surgical instruments 211810 can be captured at a variety of angles and magnifications, utilize different filters, and so on. For example, the cameras 211802 may be arranged within the OR 211800 so that they can collectively visualize each surgical staff member performing the procedure. Accordingly, the surgical hub 211801 can receive the captured image and/or video data from the cameras 211802 to visually analyze the surgical staff members 211803 and/or the surgical instruments 211810 during the surgical procedure. The image and/or video data can be processed utilizing a variety of machine vision, image processing, object recognition, and optical tracking techniques to track characteristics, properties, actions, and movements of the surgical staff members 211803 and/or the surgical instruments 211810.

FIG. 187 is a block diagram of a gesture recognition system 211500 that may be used to control display(s) in an example visualization control mode. The gesture recognition system 211500 includes a gesture recognition module 211504 that can be executed by a processor or control circuit of a computer system, such as the processor 244 of the surgical hub 206 illustrated in FIG. 10. Accordingly, the gesture recognition module 211504 can be embodied as a set of computer-executable instructions stored in a memory 249 that, when executed by the processor 244, cause the computer system (e.g., a surgical hub 211801) to perform the described steps.

The gesture recognition system 211500 may receive image or video data from the image recognition hardware/software (e.g., the cameras 211802), recognize various gestures 211804 that can be performed by the surgical staff members 211803 (e.g., determine 211604, 211624 whether a gesture is being performed in the processes 211600, 211620), and take a corresponding action or otherwise respond to the particular detected gesture 211804 (e.g., control 211606 a surgical device or save 211626 the data as metadata in the processes 211600, 211620). In an aspect, the gesture recognition module 211504 can include a feature extraction module 211506 and a gesture classification module 211508. The feature extract module 211506 may extract measurable, discriminative properties or characteristics (e.g., features) from the image/video data. The features can include edges (extracted via a Canny edge detector algorithm, for example), curvature, corners (extracted via a Harris & Stephens corner detector algorithm, for example), and so on. The gesture classification module 211508 may determine whether the extracted features correspond to a gesture from a gesture set. In an aspect, the gesture classification module 211508 can include a machine learning model (e.g., an artificial neural network or a support vector machine) that has been trained via supervised or unsupervised learning techniques to correlate a feature vector of the extracted features to one or more output gestures. In another aspect, the gesture classification module 211508 can include a Hu invariant moment-based algorithm or a k-curvature algorithm to classify gestures. In yet another aspect, the gesture classification module 211508 can include a template-matching algorithm programmed to match the featurized image/video data (or portions thereof) to templates corresponding to predefined gestures. Other aspects can include various combinations of the aforementioned techniques and other techniques for classifying gestures.

Upon recognizing a gesture via the gesture recognition module 211504, the gesture recognition system 211500 can take an action 211510 or make a response that corresponds to the identified gesture. For example, the action 211510 taken by the computer system includes controlling a surgical display within the OR.

The action 211510 taken by the computer system may include saving the gestures made by the surgical staff as metadata associated with or linked to the perioperative data generated by the surgical devices during the course of the surgical procedure. Such metadata can be useful in order to determine whether surgical staffs are manually controlling the surgical devices or controlling the surgical devices via gestures, which can in turn be correlated to performances of the surgical staff, procedure times, and other such metrics. In various other aspects, the computer system can both control one or more surgical devices and save the gesture data as metadata.

The gesture recognition system 211500 may utilize a magnetic sensing system for receiving non-contact input from users, in addition to or in lieu of cameras 211802 to visually identify gestures. In this aspect, the gesture recognition system 211500 can include, for example, a magnetic sensing array that can be positioned within the OR.

Gesture recognition is further described in U.S. patent application Ser. No. 16/182,269 titled IMAGE CAPTURING OF THE AREAS OUTSIDE THE ABDOMEN TO IMPROVE PLACEMENT AND CONTROL OF A SURGICAL DEVICE IN USE, filed Nov. 6, 2018, which is incorporated by reference herein in its entirety.

FIG. 205 shows a detailed example flow for a hub operation under tiered visualization control modes. The hub may obtain a visualization control mode at 17510. At 17511, the hub may generate and send data to the primary display(s) as described herein. At 17512, the hub, based on the visualization control mode, may determine whether to generate visualization data for the secondary display(s).

Some example visualization control mode(s) may support multi-display capabilities, while other example visualization control mode(s) may restrict visualization display to be on the primary display(s) or display the same content on both primary and secondary displays. If the visualization control mode supports multi-display capabilities, at 17513, the hub may generate the visualization data for the secondary display(s) and send the generated visualization data to the respective secondary display(s). If the visualization control mode does not support multi-display capabilities, at 17514, the hub may disable generating and sending of visualization data for the secondary displays and may continue sending the data to the primary displays.

FIG. 207 shows an example flow for a hub operating under a visualization control mode that supports multi-display capabilities. At 17601, the hub can obtain display control parameter(s) associated with a surgical procedure. The display control parameter may comprise at least one of: a user's orientation relative to at least one display, a progression of the surgical procedure, a surgical context, and/or the detection of an abnormality associated with the surgical procedure. For example, the display control parameter may be a voice command, a user input via an interactive display, the content type, the intended viewer of the display information, and/or content of information to be displayed.

The hub may determine, based on the display control parameter, different contents for different displays, at 17602. The hub may generate and send the display contents to their respective displays, at 17603.

For example, the display control parameter may be a user's orientation relative to a display. The surgical hub may determine the display content and/or format at one or more displays based on the orientation of the lead surgeons head (or user for which the information is valuable) relative to displays in the OR. The surgical hub may determine the display content and/or format at one or more displays based on user inputs, including user inputs either in or out of the OR. For example, the surgical hub may determine a display location, such as identifying a display, or identify a displaying window within a display, based on the intended viewer of the information and the viewer's relative positions to one or more displays (e.g., each display) in the OR. For example, the surgical hub may select a display closest to the intended viewer of the information. The surgical hub may determine to remove certain display content based on the intended viewer of the information and the viewer's relative positions to various displays in the OR.

In various aspects, controls for a surgical hub, surgical instruments, and other devices can be adjusted based on a screen in operation on a sterile field display. The controls of the surgical devices can be adjusted based on the displayed information. For example, a control that normally controls panning or adjusting the focus of a visualization device (e.g., a scope) can be configured to adjust magnification if a hyperspectral imaging overlay is active, for example. Hyperspectral imaging is further described in U.S. patent application Ser. No. 15/940,722, titled CHARACTERIZATION OF TISSUE IRREGULARITIES THROUGH THE USE OF MONO-CHROMATIC LIGHT REFRACTIVITY, filed Mar. 29, 2018, which is incorporated by reference herein in its entirety.

For example, the surgeon can control to change, focus, or control that data on the displays. This may enable the healthcare professional to more seamlessly see where they are relative to other imaging or even pre-surgery imaging mechanisms.

The on-handle controls for a surgical instrument in the field of view of a sterile field display can be adjusted by selections on the sterile field display. Moreover, the adjustments can be based on situational awareness in various instances. For example, the system can determine that a particular surgical device is being utilized and permit the functions of that surgical device to be controlled from a second device, such as a display screen within the sterile field.

In an example visualization control mode that supports cooperative display capabilities, multiple displays may be used to display differing aspects of the information or different types of information with relevance to the primary viewer of the display. Some or all of the displays can be controlled by another system that the main hub is only in communication with rather than in control of.

The multiple displays may include but not limited to a primary display on the hub, a visualization tower that may include at least one monitor, displays around the room, and/or tiny device displays.

In an example visualization control mode that supports cooperative display capabilities, the surgical hub may enable a healthcare professional to control a display outside of the sterile field via a display inside the sterile field. During a surgical procedure, the surgeon may not have a user interface device accessible for interactive input by the surgeon and display within the sterile field. Thus, the surgeon may not interface with the user interface device and the surgical hub from within the sterile field and cannot control other surgical devices through the surgical hub from within the sterile field.

For example, a local display, such as a secondary display, may serve as a user interface for displaying and controlling of surgical hub functions from within the sterile field. The secondary display could be used to change display locations, what information is displayed where, pass off control of specific functions or devices. The local display may include a display unit that may be used within the sterile field and accessible for input and display by the surgeon to allow the surgeon to have interactive input control from the sterile field to control other surgical devices and/or displays coupled to the surgical hub. The display unit may be sterile and located within the sterile field to allow the surgeons to interface with the display unit and the surgical hub to directly interface and configure instruments as necessary without leaving the sterile field. The display unit may be a master device and may be used for display, control, interchanges of tool control, allowing feeds from other surgical hubs without the surgeon leaving the sterile field.

The display unit may be or may include an interactive touchscreen display, an interface configured to couple the interactive touchscreen display to a surgical hub, a processor, and a memory coupled to the processor. The memory may store instructions executable by the processor to receive input commands from the interactive touchscreen display located inside a sterile field and may transmit the input commands to a surgical hub to control devices coupled to the surgical hub located outside the sterile field.

The display outside of the sterile field may be or may include the non-sterile display 107 or 109 as shown in FIG. 2. For example, the display inside a surgical sterile field may be or may include a secondary display such as a local display or a display on a surgical instrument. A healthcare personnel may control the secondary display. The primary display(s) and secondary display(s) may have numerous communication levels of operation with the primary hub system. Examples of primary display(s) and secondary display(s) can be found in more detail in U.S. patent application Ser. No. 15/940,671, titled SURGICAL HUB SPATIAL AWARENESS TO DETERMINE DEVICES IN OPERATING THEATER, which was filed on Mar. 29, 2018, which is herein incorporated by reference in its entirety.

Examples of controlling a display outside of the sterile field via a display inside the sterile field are described in a patent application with U.S. patent application Ser. No. 17/062,507, titled COMMUNICATION CONTROL OPTIONS FOR A SURGEON CONTROLLED SECONDARY DISPLAY AND PRIMARY DISPLAY, filed contemporaneously, which is herein incorporated by reference in its entirety:

Secondary displays may include independent secondary displays and/or dedicated local displays that can be linked to the surgical hub 206 to provide an interaction portal via a touchscreen display and/or a secondary screen that can display any number of surgical hub 206 tracked data feeds to provide a status. The secondary display may display force to fire (FTF), tissue gap, power level, impedance, tissue compression stability (creep), etc., while the primary display may display key variables to keep the feed free of clutter. The interactive display may be used to move the display of specific information to the primary display to a desired location, size, color, etc. In the illustrated example, the secondary display may display the instrument proximity displays 6210 on the left side of the display 6200. The local instrument display 6204 on the bottom right side of the display 6200. The local instrument display 6204 presented on the surgical hub display 6200 may display an icon of the end effector 6218, such as the icon of a staple cartridge 6224 currently in use, the size 6226 of the staple cartridge 6224 (e.g., 60 mm), and an icon of the current position of the knife 6228 of the end effector.

A secondary display may be the display 237 as shown in FIGS. 5 and 6. Referring to FIG. 6, the display 237 located on the instrument 235 can display the wireless or wired attachment of the instrument 235 to the surgical hub 206 and the instrument's communication and/or recording on the surgical hub 206. A setting may be provided on the instrument 235 to enable the user to select mirroring or extending the display to both monitoring devices. The instrument controls may be used to interact with the surgical hub display of the information being sourced on the instrument. The instrument 235 may comprise wireless communication circuits to communicate wirelessly with the surgical hub 206, as described herein.

A first instrument coupled to the surgical hub 206 can pair to a screen of a second instrument coupled to the surgical hub 206 allowing both instruments to display some hybrid combination of information from the two devices of both becoming mirrors of portions of the primary display. The primary display 6200 of the surgical hub 206 can provide a 360° composite top visual view of the surgical site 6208 to avoid collateral structures. For example, a secondary display of the end effector surgical stapler may be provided within the primary display 6200 of the surgical hub 206 or on another display in order to provide better perspective around the areas within a current the field of view 6206.

This secondary display could also be used as a control means for adjusting what and how information is displayed on primary displays outside of the sterile field. This would enable them to better highlight for other surgical personnel information they need to track, be aware of or help with.

These secondary displays could be on instruments, positioned over the patient adjacent to the surgical access ports, or even be worn on the user. These displays could change the multi-spectral imaging, control its overlay on the regular scope feed, overlay the pre-surgical imaging based on established location features, adjust the axillary data displayed around the periphery of the display, or its order, or size, it could even allow the user to move one image or dataset from one location to another on another display.

The primary and the secondary display(s) may be controlled via the gesture recognition system as described herein.

For example, the visualization control parameter may be a progression of the surgical procedure. The surgical hub may determine display contents for the primary and the secondary displays based on the progression of the surgical procedure.

Visualization controls can be adjusted according to the step of the surgical procedure being performed. Situational awareness can inform the surgical hub of the current and/or next step of the surgical procedure. For example, based on the previous surgical actions and/or the order of usage of the surgical device(s) and/or generator(s), a surgical hub can determine what particular step of a particular surgical procedure is being performed, such as whether the procedure is currently in a nodal dissection step, vessel transecting step, and so on. The surgical hub and/or generator can determine the procedural specific step or context.

For example, surgical contextual data can include, the type of surgical procedure being performed, the particular step of the surgical procedure that the surgeon is performing, the type of tissue being operated on, or the body cavity that is the subject of the procedure. This ability by some aspects of the surgical hub to derive or infer information related to the surgical procedure from received data can be referred to as "situational awareness." In one exemplification, the surgical hub can incorporate a situational awareness system, as described herein with reference to FIGS. 9 and 10. A situationally aware surgical hub may derive contextual information pertaining to the surgical procedure from various received surgical data. Such surgical data may include perioperative data from the modular devices 5102 and other data sources (e.g., databases 5122 and patient monitoring devices 5124) that are communicably coupled to the surgical hub 5706.

As described herein, the hub can learn and anticipate the procedural specific step or context by analyzing the particular clinician's most common usage at each stage of the surgical procedure and/or after a particular number or type of surgical instrument exchanges. After monitoring the same clinician's behavior over a predetermined number of procedures that include the same steps, the hub may automatically change content displayed on the display(s) based on the monitored and past display interactions with and/or controls indicated by the clinician. In various instances, the hub can provide notice to the clinician when the display is adjusted. For example, the hub and/or the display(s) can provide an auditory notice (e.g., a beep or verbal explanation), a visual cue (e.g. a flashing light and/or words on a screen), and/or a tactile warning (e.g. vibrations and/or movement of the surgical device or a portion thereof, such as the actuator button itself). In other instances, the surgical hub can recommend a display adjustment. Recommendations from a surgical hub are further described herein.

FIG. 208 shows an example flow for a hub operating under a visualization control mode that supports situational awareness capabilities. The hub may obtain a visualization control mode associated with a surgical procedure at 17610. The hub may receive perioperative data from at least one surgical instrument, at 17611. The hub, based on the visualization control mode and at least in part of the perioperative data may determine the surgical progression, at 17612.

Progression of surgical procedure may be determined using a situationally aware surgical system 5100 as shown in FIGS. 9 and 10. For example, a situationally aware hub 5104 may determine what step of the surgical procedure is being performed or will subsequently be performed. The situationally aware hub 5104 may determine whether an event has occurred based on the received data. The event can include, for example, a surgical procedure, a step or portion of a surgical procedure, or downtime between surgical procedures or steps of a surgical procedure. The surgical hub 5104 may track data associated with the particular event, such as the length of time of the event, the surgical instruments and/or other medical products utilized during the course of the event, and the medical personnel associated with the event. The surgical hub 5104 may determine event data via, for example, the situational awareness process as described herein. Situational awareness processes are described in greater detail in U.S. patent application Ser. No. 15/940,654, titled SURGICAL HUB SITUATIONAL AWARENESS, filed Mar. 29, 2018; U.S. patent application Ser. No. 16/209, 478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Dec. 4, 2018; and U.S. patent application Ser. No. 16/182,246, titled ADJUSTMENTS BASED ON AIRBORNE PARTICLE PROPERTIES, filed Nov. 6, 2018; the disclosure of each is herein incorporated by reference in its entirety.

Referring back to FIG. 208, based on the determined surgical progression and the types of the displays, the hub may then determine the display content, at 17613. At 17614, the hub may instruct the display to display the determined display content.

For example, the hub may associate different display contents with different example procedural steps shown in the in FIG. 189. As shown, example surgical steps may include mobilizing the lung, managing major vessels, and removing the lobe. The surgical hub may instruct the display(s) to show information specifically related to a current step in the surgical procedure based on situation awareness and automated control. The surgical hub may determine the type of surgical data for display based on the determined progression of surgical procedure. The surgical hub may select a display among the displays in the OR to display the surgical data base on the determined progression of surgical procedure.

For example, a baseline visualization of an anatomical structure and/or surgical site can be obtained before initiation of a surgical procedure—such as before the manipulation and dissection of tissue at the surgical site. The baseline visualization image of the anatomical geometry can include a visualization of the surface of the anatomical structure and its boundaries. Such a baseline visualization image can be used to preserve overall orientation of the surgical site and anatomic structure even as local regions within the anatomic structure are progressively disrupted, altered, or otherwise manipulated during the surgical procedure.

For example, the surgical hub may update the baseline visualization image upon identifying a particular type of surgical procedure, step in the surgical procedure, type of tissue, and/or one or more specific tissue characteristics. In an example, an updated baseline visualization image can be helpful after a transection or after the application of one or more rows of staples. In certain instances, distorted sub-regions within an original anatomical structure can separately create a new baseline visualization image or update an existing baseline visualization image for the distorted sub-region(s) to properly inform image overlays. For example, a key region of a patient's anatomy can be updated after removal of a tumor or growth therein.

For example, the surgical hub may generate display content using spectral imaging techniques to visualize different tissue types and/or anatomical structures as shown in FIG. 190. In FIG. 190, a spectral emitter 2320 (e.g., spectral light source 150) can be utilized by an imaging system to visualize a surgical site 2325. The EMR emitted by the spectral emitter 2320 and reflected from the tissues and/or structures at the surgical site 2325 can be received by an image sensor to visualize the tissues and/or structures, which can be either visible (e.g., be located at the surface of the surgical site 2325) or obscured (e.g., underlay other tissue and/or structures at the surgical site 2325). In this example, an imaging system can visualize a tumor 2332, an artery 2334, and various abnormalities 2338 (i.e., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system, such as an imaging system display, a primary display, a non-sterile display, a hub display, a device/instrument display, and so on.

The surgical hub may tailor or update the displayed surgical site visualization according to the identified tissue and/or structure types. For example, a margin 2330*a* associated with the tumor 2332 being visualized may be displayed on a display. The margin 2330*a* can indicate the area or amount of tissue that should be excised to ensure complete removal of the tumor 2332. A control system can be configured to control or update the dimensions of the margin 2330*a* based on the tissues and/or structures identified by the imaging system. In the illustrated example, multiple abnormalities 2338 may be identified within the FOV. Accordingly, the control system can adjust the displayed margin 2330*a* to a first updated margin 2330*b* having sufficient dimensions to encompass the abnormalities 2338. Further, an artery 2334 may be identified to be partially overlapping with the initially displayed margin 2330*a* (as indicated by the highlighted region 2336 of the artery 2334). The surgical hub may adjust the displayed margin 2330*a* to a second updated margin 2330*c* having sufficient dimensions to encompass the relevant portion of the artery 2334.

For example, upon determining that the next surgical step is resecting a portion of tissue, the surgical hub may display estimated changes in deformation for a proposed resection on a display. The proposed resection line(s) can be added to the digital model, which can be updated to show the anatomical structure with the hypothetical resection. Referring again to FIG. 13B, in one example, a clinician may intend to remove a wedge-shaped portion from the tissue at the surgical site 2325 to remove the tumor 2332 along with the tissue abnormalities 2338. In such instances, the model can be updated to show the organ with the wedge-shaped portion removed therefrom. The updated model can depict the deformation of the tissue, as well as the computed stress and/or strain in the tissue based on the known tissue mechanical properties and the deformation induced by the surgery. For example, the tissue can be shaded or otherwise layered with the stress and/or strain data so that the clinician is informed regarding how a particular resection may impact strain on the tissue. In some aspects, the stress/strain data may be overlaid on the image as a set of vector lines indicating stress/strain direction and line type or color to indicate the value of the stress/strain. Based on the computed stresses and strains, a clinician may modify the proposed resection and consider an alternative strategy to reduce and/or better distribute the stresses and strains within the tissue. For example, the angles of the resections can be modified. In certain instances, the clinician can reorient a staple line with a preferred strain direction.

For example, upon determining that the surgical procedure is a video-assisted thoracoscopic surgery (VATS) procedure, the surgical hub may instruct one or more display(s) to show example contents shown in FIGS. 191 and 192. A VATS procedure is a surgical procedure whereby one or more surgical instruments and one or more thoracoscopes (i.e., cameras) are inserted into the patient's chest cavity through slits positioned between the patient's ribs. The cameras are utilized to provide the surgeons with a view of the interior of the patient's chest cavity to allow the surgeon to properly position/move the surgical instrument(s) and manipulate tissue/structures within the chest cavity. Because the surgeon controls the surgical instrument(s) based on what is displayed by the imaging system via the camera(s) and because the surgical instrument(s) may not be aligned with the viewing perspective of the camera(s), the spatial relationship between the surgical instrument and the POV displayed by the imaging system can be potentially disorienting, especially for imaging systems that allow users to pan, manipulate, and reorient the displayed visualization.

FIGS. 191 and 192 show example display content associated with a VATS procedure. In this particular VATS procedure, the surgeon may seek to remove a tumor 6506 located within the apical segment of the superior lobe of a lung 6508. As shown, the surgeon has placed a port 6502 between the second rib 6501 and the third rib 6503 to provide an access path 6504 for a surgical instrument 6510 (e.g., a surgical stapler) insertable through the port 6502 to access the tumor 6506 and/or the surrounding area within the chest cavity. Once the location of the access for the surgical instrument 6510 has been selected, the surgeon can place one or more cameras 6520a, 6520b through other ports 6502 that are positioned to allow the camera(s) 6520a, 6520b to visualize the interior of the patent chest cavity in the vicinity of the surgical site. Visualizing the surgical site in this manner allows the surgeon to position and orient an end effector 6514 of the surgical instrument 6510 to manipulate the tissue as needed (e.g., excise a portion of the lung 6508 around the tumor 6506). In the particular illustrated example, two cameras 6520a, 6520b are utilized, although a different number of cameras can be utilized and/or one or more of the cameras 6520a, 6520b can be oriented in a different manner depending upon the particular type of surgical procedure that is being performed and/or the region within the body of the patient 6500 that needs to be visualized.

For example, when operating under an example visualization control mode, the surgical hub may adjust a secondary display, such as a local display attached to a surgical instrument, based on a local coordinate system. The local coordinate system may be a surgical visualization coordinate system. Upon determining that the surgical procedure is a VATS procedure, the surgical hub may send a locally displayed coordinate system to a surgical instrument or other medical device to enable the instrument/device controls to be adapted to control motion relative to a local visualization coordinate system. At least one measurement derived from the imaging system can be utilized to define the local coordinate system. User controls displayed on the local display may be reoriented relative to the local coordinate system, rather than a standard global coordinate system or another coordinate system.

As shown in FIG. 192 and set forth below in TABLE 1, a variety of different coordinate systems can be defined with respect to the differing POVs of the patient, devices, or device components. Further, when operating under a visualization control mode that allow users to manipulate the displayed visualization, "virtual" POVs can be defined that correspond to the virtual or predicted visualization being displayed to the surgeon and coordinate systems can also be defined according to these POVs. The generation and control of such visualizations are further described herein.

TABLE 1

| Coordinate System | Description |
| --- | --- |
| $x_p, y_p, z_p$ | Patient anatomical plane POV |
| $x_d, y_d, z_d$ | Handle assembly POV |
| $x_j, y_j, z_j$ | End effector/cartridge POV |

TABLE 1-continued

| Coordinate System | Description |
| --- | --- |
| $x_{c1}, y_{c1}, z_{c1}$ | Camera #1 POV |
| $x_{c2}, y_{c2}, z_{c2}$ | Camera #2 POV |
| $x_{L1}, y_{L1}, z_{L1}$ | Virtual local POV #1 |
| $x_{L2}, y_{L2}, z_{L2}$ | Virtual local POV #2 |
| $x_{L3}, y_{L3}, z_{L3}$ | Virtual local POV #3 |

The coordinate systems can be defined based upon sensor measurements and/or measurements by the imaging system. For example, a coordinate system with respect to a surgical instrument handle assembly 6512, a shaft 6513, or the end effector 6514 could be defined according to measurements by an accelerometer or another such sensor associated with the respective components. As another example, any of the aforementioned coordinate systems could be defined based upon measurements of the relative distances and/or positions of objects with respect to each other or a global coordinate system as determined by imaging the objects via the imaging system.

In the example shown in FIG. 193, the surgical instrument 6510 has utilized the provided transfer function to determine that the controls 6518 and display screen 6516 should be adjusted based on the updated coordinates. In various instances, situational awareness, as further described herein, can inform when the controls 6518 and/or the display screen 6516 are updated. The display screen 6516 can display a GUI 6517 that is adjusted from a first orientation, shown on the left side of FIG. 193, to a second orientation, shown on the right side of FIG. 193, to ensure that the GUI 6517 is oriented properly for the surgeon controlling the surgical instrument 6510. In one aspect, the GUI 6517 can further include a GUI element 6524 (e.g., an icon) indicating the POV or coordinate system being utilized by the surgical instrument 6510. In this example, the GUI element 6524 shifts to indicate that the POV displayed by the visualization system 2108 has changed from the device coordinate system ("DVC") to the local coordinate system ("Local") associated with the image/video displayed by the visualization system 2108.

As an example, the surgical instrument controls 6518 that are adjusted according to the updated coordinates can include articulation controls. The articulation controls can include a first control 6519a configured to cause the surgical instrument 6510 to articulate in a first direction and a second control 6519b configured to cause the surgical instrument 6510 to articulate in a second direction, for example. The articulation controls 6519a, 6519b can be embodied as a rocker, toggle, or separate actuators and/or buttons, for example. In this example, the surgical instrument 6510 has caused the first articulation control 6519a and the second articulation control 6519b to swap functions in response to the change in orientation of the surgical instrument 6510. In other words, actuating the first articulation control 6519a would instead cause the surgical instrument 6510 to articulate in the second direction, and actuating the second articulation control 6519b would cause the surgical instrument 6510 to articulate in the first direction. Accordingly, the functions of the articulation controls 6519a, 6519b can be set according to the orientation of the surgical instrument 6510 or a component thereof (e.g., the end effector 6514) as displayed to the user.

Additionally, or alternatively, in certain instances, the GUI 6517 on the display screen 6516 can be adjusted. For example, the GUI 6517 can be inverted when the handle assembly 6512 is inverted. In certain instances, the GUI 6517 can include a touch screen such that the surgeon can switch between coordinate systems by interacting with the GUI 6517. For example, the surgeon can toggle between a device POV, local POV, and/or one or more other POVs by interacting with the GUI 6517.

When operating under an example visualization control mode, the surgical hub may fuse images from different sources to expand visualization field scope, for example upon determining that the current surgical step may benefit from an expanded visualization field scope. For example, the surgical hub may generate and send fused images from different sources when upon determining that the current surgical step is dissecting a vessel.

3D representations of objects within the visualization field of the imaging system may be created, and the 3D shapes may be characterized to allow users to alter the displayed visualization with respect to the established coordinate system to better visualize the surgical site. The 3D representations can be generated from images generated from real-time sources or non-real-time sources (e.g., CT scans or MRIs). In one aspect, structured light, or structured EMR may be projected to create structured 3D shapes that can be tracked in real time. These 3D shapes could be generated in such a manner as to allow the POV displayed by a display to be moved or rotated away from the scanning source's local coordinate system to improve the perspective view of the user through the display.

FIG. 194 illustrates an example FOV 6570 of a camera during a VATS procedure. The target of this particular illustrative procedure is a tumor 6506 located within the apical segment of the superior lobe 6580 of a lung 6508. A number of biological structures are identifiable within this FOV 6570, including the thoracic wall 6509, veins 6574, arteries 6576, bronchi 6578, the fissure 6582 delineating the superior lobe 6580, a pulmonary artery 6584, and a pulmonary vein 6586. Non-biological objects are also viewable within the FOV 6570, including the end effector 6514 and the shaft 6513 of the surgical instrument 6510 being controlled by the surgeon. In an example imaging system, such a view, in combination with any corresponding views from any additional camera(s) 6520 being utilized, would be the sole view(s) available to surgeons performing a video-assisted procedure. Although the cameras are placed with the intent to provide the surgeon with an adequate visualization field scope for performing the surgical procedure, the visualization field scope provided by the camera(s) 6520 may ultimately not provide the ideal FOV 6570 for performing each step or task in the surgical procedure, or unexpected obstructions may be present at the surgical site that impede the surgeon's view. Further, intraoperatively repositioning or reorienting the camera(s) 6520 can be impractical or undesirable in certain instances due to the surgical constraints of the procedure.

A surgical system can be configured to expand the visualization field scope provided by the camera(s) by combining multiple images of the surgical site, including preoperative images and intraoperative images, to generate 3D representations of the surgical site or tissues and/or structures located at the surgical site. During the surgical procedure, the user can then manipulate the 3D representations displayed by the imaging system 142 to visualize the surgical site from orientations that are outside the scope of the FOV 6570 of the camera(s) being utilized in the procedure. Such reoriented views can be referred to as "virtual POVs," as noted above. Accordingly, the surgical system can supplement the FOV 6570 provided by the camera(s) and allow surgeons to dynamically adjust the displayed visualization of the surgical site during the surgical procedure to find ideal viewing POVs for performing one or more of the surgical tasks.

Locally displayed coordinate system is further described in U.S. patent application Ser. No. 16/729,747 titled DYNAMIC SURGICAL VISUALIZATION SYSTEMS, filed Dec. 31, 2019, which is incorporated by reference herein in its entirety.

FIG. 209 shows an example flow of a hub operation under a visualization control mode that supports adjusting display based on an adjusted display event. At 17620, the hub may receive data from at least one surgical instrument. At 17621, the hub may detect the surgical context based at least in part on the perioperative data. The hub may determine, based on the surgical context whether the surgical context correspond to an adjusted display event, at 17622. If the surgical context includes an adjusted display event, the hub may then adjust display content for one or more displays based on the adjusted display event, as described in 17623. The adjusted display event may include a stressful procedure step, a critical procedure step, and/or a pre-defined procedural step.

For example, the surgical hub may adjust the display format and/or content at a display to a focused mode, upon determining that the current surgical step is a stressful procedure step, a critical procedure step, or a pre-defined procedural step.

FIG. 200 illustrates example procedural steps and progression that may be detected by example situation awareness capabilities of the system. Certain steps may be considered important to the success of the surgery or may be associated with heightened stress level. For example, ligating IMA branches, accessing plane between omentum and colon, managing major bleeder, freeing splenic flexure from omentum and spleen and colon as shown under segment "mobilizes the colon" may be considered a stressful procedure step by the surgical hub. As shown in FIG. 200, steps such as transecting distal sigmoid colon below recto-sigmoid junction under segment "resects sigmoid" and firing circular stapler under segment "performs anastomosis" may be considered stressful procedure steps that may warrant display content and/or format change(s).

For example, display content may be adjusted by zooming in on a target in an image, removing extraneous information from the first display content and/or emphasizing a portion of a laparoscopic scope image.

The adjusted display event may include a detection of an abnormality associated with the surgical procedure, received surgical data being outside of expected value range, or a system parameter being outside of desirable system parameter range. The display content may be adjusted by projecting a warning, error message, or an indication of the detected abnormality on a hub display (e.g., the main monitor). The display content may be adjusted by overlaying a warning, error message, or an indication of the detected abnormality on the display.

The adjusted display event may include a detection of steps for use being out of sequence. For example, procedural steps for use of a surgical instrument may be displayed on a device screen such as display attached to the surgical instrument. Based on the surgical context based at least in part on the perioperative data received, a situational aware hub may detect that the steps for use of the surgical instrument are out of sequence. Upon detection, the display content on the primary display (e.g., the main screen) may be adjusted to show an indication of the steps for use of the surgical instrument being out of sequence. If an early action is identified, the surgical hub may instruct the primary display to show an indication of a recommended step. For example, upon sensing that firing trigger is being pulled prior to clamp time, the surgical hub may adjust the display content on the primary display to show an indication to direct user to wait or a countdown prior to firing.

In examples, display content may be adjusted by moving certain data to another display. An interactable display may receive a user indication, for example, from a healthcare professional, such as a surgeon, that indicates a selection of where the data is to be displayed. The selection may be indicated for a specific surgical step, for stressful procedure step(s), critical procedure step(s) and/or in the event an abnormality associated with the surgical procedure is detected. The content may be sent to the selected display location for display.

Referring back to FIG. 209, if the surgical context does not include an adjusted display event, the hub may refrain from making additional adjustments to the displays at 17624.

In examples, the hub, in communication with the AR devices and at least one smart surgical device, can provide interactive overlay of a surgical display superimposing information onto another surgical display. The surgical display may connect to an AR device in a surgical suite. The AR device may overlay or superimpose additional datasets or data streams received from the hub onto a display such as a surgical display or a display on a smart device. This interactive overlay may enable the user of the AR device to layer data on a screen when the user is looking at the screen. The surgical hub may adjust the layer data based on the display the user is viewing. For example, the hub may adjust the layer data when the user looks from one display to another display. The AR device can adjust the displayed data on the monitor or the device screen. For example, a display control indication may be received from an AR device. In response, the surgical hub may adjust the content for displaying on the monitor or the device screen based on the received display control indication.

The AR device may provide auditory overlay, for example, in addition to hearing OR sounds rather than in place of them. The AR system may communicate certain information only to the targeted individual within the OR that could utilize the information.

The AR content may be enabled or disabled based on the location of the AR device. For example, the surgical hub may detect that the AR device is outside of the bounds of a surgical operating room. In response, the surgical hub may disable sending AR content to the AR device.

FIG. 206 shows an example flow for a hub operation under a visualization control mode where the secondary display is an augmented reality (AR) device. At 17520, the hub may obtain a visualization control mode. The hub may identify a secondary display that is an AR device, at 17521.

As shown in FIG. 206, the hub, at 17522, may determine whether to generate overlay information associated with the primary display for overlaying via the secondary display based on the visualization control mode. If the visualization control mode does support AR capabilities, the hub may disable generation of information associated with the primary display for overlaying via the secondary display, at 17524.

A secondary display may be or may include an AR device. The AR device may include a head-mounted display (HMD). An HMD may include a processor, a non-transitory computer readable memory storage medium, and executable instructions contained within the storage medium that are executable by the processor to carry out methods or portions of methods disclosed herein. The HMD may include a graphics processor for rendering 2D or 3D video and/imaging for display.

FIG. 185 depicts a perspective view of a surgeon using a surgical instrument that includes a handle assembly housing and a wireless circuit board during a surgical procedure, with the surgeon wearing a set of safety glasses. The safety glasses may be or may include an AR device that may serve as a secondary display. The wireless circuit board transmits a signal to a set of safety glasses worn by a surgeon using the surgical instrument during a procedure. The signal is received by a wireless port on the safety glasses. One or more lighting devices on a front lens of the safety glasses may change color, fade, or glow in response to the received signal to indicate information to the surgeon about the status of the surgical instrument. The lighting devices are disposable on peripheral edges of the front lens to not distract the direct line of vision of the surgeon. Further examples are disclosed in U.S. Pat. No. 9,011,427, titled SURGICAL INSTRUMENT WITH SAFETY GLASSES, which issued on Apr. 21, 2015, which is herein incorporated by reference in its entirety.

FIG. 185 shows a version of safety glasses 6991 that may be worn by a surgeon 6992 during a surgical procedure while using a medical device. In use, a wireless communications board housed in a surgical instrument 6993 may communicate with a wireless port 6994 on safety glasses 6991. Exemplary surgical instrument 6993 is a battery-operated device, though instrument 6993 could be powered by a cable or otherwise. Instrument 6993 includes an end effector. Particularly, wireless communications board 6995 transmits one or more wireless signals indicated by arrows (B, C) to wireless port 6994 of safety glasses 6991. Safety glasses 6991 receive the signal, analyze the received signal, and display indicated status information received by the signal on lenses 6996 to a user, such as surgeon 6992, wearing safety glasses 6991. Additionally, or alternatively, wireless communications board 6995 transmits a wireless signal to surgical monitor 6997 such that surgical monitor 6997 may display received indicated status information to surgeon 6992, as described above.

A version of the safety glasses 6991 may include lighting device on peripheral edges of the safety glasses 6991. A lighting device provides peripheral-vision sensory feedback of instrument 6993, with which the safety glasses 6991 communicate to a user wearing the safety glasses 6991. The lighting device may be, for example, a light-emitted diode ("LED"), a series of LEDs, or any other suitable lighting device known to those of ordinary skill in the art and apparent in view of the teachings herein.

As shown in FIG. 206, if the visualization control mode supports AR capabilities, at 17523, the hub may overlay, via the secondary display, the overlay information onto the primary display upon detecting a user of the secondary display viewing the primary display.

In an example, the primary display may display a livestream of a surgical site in the surgical operating room from a medical imaging device, and the secondary display may be AR glasses. As an example, a doctor performing a laparoscopic surgery wearing AR glasses may see the image of the tumor overlay on the screen. When the hub detects that the doctor is looking down at the patient (e.g., via gesture recognition described herein, via HMD-based motion tracking, via image recognition based on images captured by the AR glasses), the hub may instruct the AR glasses overlay the laparoscopic images with AR content with the orientation of the devices inside the patient. This may allow the doctor to see an overlay with the orientation of the devices inside the patient. As the tumor is in three-dimensional space, although the doctor can only see the outside draping of the tissue, with the help of the AR glasses, the doctor can better orient the surgical instrument.

The surgical hub, communicating with the specific AR devices, can generate and send different overlays based on the targeted displays within the OR. The users can observe different overlays when they look at different displays without interfering with each other. The hub can adjust information contained in the overlays based on different displays within the OR room, the specific situation, information received from surgical devices, specific user requirements, and/or the specific operation procedure.

In an example visualization control mode that supports targeted AR content, individual users may have different display devices that may work in concert with a shared display. Different display devices may be provided with different AR content for overlaying on the shared display. This may allow the users to view personally directed information or overlaid data that only they can view and/or interact with. Example interactive surgical systems are described in detail in U.S. patent application Ser. No. 15/940,671, titled SURGICAL HUB SPATIAL AWARENESS TO DETERMINE DEVICES IN OPERATING THEATER, which was filed on Mar. 29, 2018, which is herein incorporated by reference in its entirety.

The augmentation of the user's perceptions could be visual, for example, via AR glasses or local display. For example, FIG. 195, FIGS. 201A-C provide example visual augmentation of the user's perceptions. Further visual augmentation examples are described in U.S. patent application Ser. No. 15/940,704, titled USE OF LASER LIGHT AND RED-GREEN-BLUE COLORATION TO DETERMINE PROPERTIES OF BACK SCATTERED LIGHT, which was filed on Mar. 29, 2018, which is herein incorporated by reference in its entirety.

The augmentation of the user's perceptions could be audible, for example. An audible overlay may be provided via an ear bud set with pass through noise capabilities and/or via a bone conduction speaker system.

The surgical hub may adjust the visual, audible and/or other types of user perception augmentation based on its situational awareness capabilities as described herein. AR content may be adjusted based on a detected surgical progression, for example. AR content may be adjusted based on the activities the user is conducting, voice command, hand gestures, and/or in a predefined manner. AR devices may be instructed to operate by the user in a manner customizable in advance.

AR content may include pre-surgical imaging, intraoperative imaging, instrument data, or procedural instructions. Intraoperative imaging may be obtained via indocyanine green (ICG) fluorescence imaging. AR content may include real time surgical data received from another connected system. AR content may include steps-for-use, device settings, device instruction for use, device status, operational parameters, irregularities detected, or some combination of data derived from the instrument operation.

FIG. 210 shows an example flow of a hub operation under a visualization control mode with AR capabilities. The hub may obtain an AR control parameter for controlling multiple AR devices, at 17701. The AR control parameter for controlling multiple AR devices may include user role(s), a user's orientation relative to a display, a progression of the surgical procedure, a surgical context, a real-time user input, and/or a preconfigured user preference.

At 17702, the hub may then determine, based on the AR control parameter, different AR contents for overlaying via different AR devices. Based on the determined AR contents for different AR devices, the hub may send respective AR contents to the respective AR devices, at 17703.

The AR content may include a step for use associated with a surgical instrument, a device setting, a device status, a device instruction for use, at least one operation parameter, or an indication of a detected abnormality.

The AR control parameter may be a user's orientation relative to a display, and different AR contents for overlaying via different AR devices may be determined based on the user's orientation relative to the display. FIG. 213 shows an example flow of a hub operation under a visualization control mode with AR capabilities that allow overlays on various displays. The hub may obtain an AR control parameter, at 17730. The hub may determine, based on the AR control parameter, overlay data for overlaying on a display via an AR device, at 17731. The hub may detect a user of the AR device viewing the display, at 17732. The hub may overlay, via the AR device, the overlay data onto the content displayed on the display, at 17733. For example, upon determining that a user is viewing a display, the hub may generate and overlay AR contents associated with that display (e.g., the AR content associated with the content displayed on the display). Upon determining that a user is not viewing the display, the hub may remove the AR content associated with the display from the AR device.

In examples, the AR control parameter may be the user role(s) associated with the AR device(s). Different AR contents for overlaying via different AR devices may be generated based on the user role(s) associated with each AR device.

FIG. 212 shows an example flow of a hub operation under a visualization control mode with role-based AR capabilities. The hub may identify a first user role associated with the first AR device, at 17721. The hub may determine, based on the first user role, a first overlay data set for the first AR content, at 17722. The hub may then identify a second user role associated with the first AR device, at 17723. The hub may determine, based on the second user role, a second overlay data set for the second AR content, at 17724.

For example, the surgical hub may identify a user role associated with the AR device and the display type associated with the display. The surgical hub may determine, based on a display type and the user role, the AR content for overlaying on content displayed on the display via the AR device. The display type may be an instrument display located on a smart surgical instrument, a shared display in a surgical suite, or a personal display. The AR content may be adjusted based on the display type of the display onto which the AR content may be superimposed. For example, when the display is a shared display with a larger screen, the AR content may be sized up to fit the image on the shared display. When the display is a surgical device display, AR content may be sized down to accommodate the smaller screen. For example, when the display is a surgical device display, surgical information that may not fit into the surgical device display may be added to the AR content to make such information available to the user.

FIG. 188 illustrates an augmented reality system that can be controlled by multiple users. As shown, the system may include various OR displays 17100, including an instrument 17100(*a*), a primary display 17100(*b*), other displays 17100 (*c*), a surgical hub 17104 and a smart device 17100(*d*). The hub 17104 and the AR devices worn by users 17120(A), (B) and (C) can superimpose a predefined set of overlay data layers 17110(a)-(e) on various OR displays 17100(a)-(e). Healthcare professional users 17120(A), (B) and (C) may each wear an augmented reality device, such as safety glasses with an AR display, AR goggles, or HMIs as described herein. The surgical hub and/or the AR device(s) can control access to certain displays and the overlay data layers.

AR content displayed on an AR device may be generated based on its user's role, situation awareness-related data, and/or the visualization control mode (such as subscription tier). As shown, user 17120(A)'s AR device may receive overlays 17110(a)-(e) based on 17120(A)'s user role, the operation situation and/or the tier level of the system, while user 17120(B)'s AR device may only receive overlays 17110(b)-(e). A subset of overlay data layers that user 17120(A)'s AR device and user 17120(B)'s AR device receive may be the same, while some of the overlay data layers received at the devices may be different, as shown in FIG. 188. Example interactive set of overlay data layers 17130 may include pre-surgical imaging, intraoperative imaging, instrument data, procedural information and/or data generated based on the aforementioned. As an example, user 17120(A), (B) and (C) may access to different set of overlays based on their different roles and different procedures of the situation.

FIG. 211 shows an example flow of a hub operation under a visualization control with AR capabilities. At 17711, the hub may obtain an AR control parameter as described herein. At 17712, the hub may obtain, from a surgical instrument, a data stream for displaying on a display. The data stream may be or may include video image of a surgical site within a patient. The hub, at 17713, may determine, based on the AR control parameter, a first AR content for overlaying on the data stream displayed on the display via a first AR device. The first AR content may include a step for use a surgical instrument, a device setting, a device status, a device instruction for use, at least one operation parameter, or an indication of a detected abnormality. The hub, at 17714, may determine, based on the AR control parameter, a second AR content for overlaying on the data stream displayed on the display via a second AR device. At 17715, the hub, based on the determined AR contents for the respective AR devices for display, may send the AR contents to the respective AR devices.

In an example visualization control mode that supports augmented reality content, the surgical hub may overlay surgical information onto an anatomical structure model on a display. For example, based on a determination that the user associated with the AR device is a surgeon, the surgical hub may send AR content that includes visualization of the tumor, the tumor margin and possible emphysema to the AR device. For example, based on a determination that the user associated with the AR device is a surgeon's assistant, the surgical hub may send AR content that includes the step surgical step that requires assistance, a device setting and/or a device status.

FIG. 195 shows an example display 5020 that may be viewed from an AR device. Display 2020 includes screen content displayed on a screen overlaid with AR content. Display 5020 can depict an information index 5022 and a model of an anatomical structure 5024 generated by a control system of the surgical visualization system. The anatomical structure 5024 may include unaffected tissue 5026 that is neither diseased, nor occupied by a critical structure. The model of the anatomical structure 5024 can depict detected and/or determined features, such as a subject tissue 5028, a predetermined margin 5030, a resection margin 5032, a first characteristic 5034 of the anatomical structure 5024, and an adjusted resection margin 5036. The control system 133 of the surgical visualization system has designated each of these detected features of the anatomical structure 5024 a specific color, and the display 5020 can depict each of the detected features in its specifically designated color, as is represented via the cross-hatching of FIG. 195. The information index 5022 can depict a correlation of each specific color with information that is relevant to its designated detected feature. For example, the information index 5022 of FIG. 195 correlates each specific color with a textual description of a corresponding feature of the anatomical structure 5024. In other aspects, the information index 5022 correlates each specific color with additional information that is relevant to a corresponding feature.

As depicted in FIG. 195, the surgical visualization system can detect a subject tissue 5028 within the anatomical structure 5024. The information index 5022 of the display 5020 can indicate that the detected subject tissue 5028 is a tumor. An instruction stored in the memory of a control system of the surgical visualization system can instruct the control circuit to apply a predetermined margin 5030 around the subject tissue 5028 based on detected qualities of the tumor, including its size, geometry, and/or type. Accordingly, the control system 133 can designate the resection margin 5030 a specific color, and the information index 5022 can correlate the specific color with additional information associated with the resection margin 5030. The control circuit of the surgical visualization system can determine a resection margin 5032 around the subject tissue 5028, in consideration of the detected subject tissue 5028 and predetermined margin 5030. In the display 5020 of FIG. 195, the resection margin 5032 is depicted in linear segments about the anatomical structure 5024, corresponding to the capabilities of an intended surgical instrument. For example, the surgical instrument can be a surgical stapler configured to staple tissue before cutting it via a linear stroke. However, the display 5020 can alternately depict the resection margin 5032 if other surgical instruments are implemented.

The display 5020 of FIG. 195 depicts a characteristic 5034 of the anatomical structure 5024 detected by the surgical visualization system. The information index 5022 of the display 5020 of FIG. 195 can indicate that the detected characteristic 5034 of the anatomical structure 5024 is tissue 5026 that has been damaged by emphysema. The AR content may include the initially determined resection margin 5032 of FIG. 195, which can traverse through the characteristic 5034 of the anatomical structure 5024. The control circuit of the surgical visualization system can determine an adjusted resection margin 5036 to encompasses the characteristic 5036, the subject tissue 5028, and the predetermined margin 5030. The AR content may include the adjusted resection margin 5036 via dashed lines. Such AR content may allow the operating clinician(s) to select either the initially determined resection margin 5032, or the adjusted resection margin 5036. In other aspects, the display 5020 will limit the operating clinician(s) to the adjusted resection margin 5036 based on an instruction stored in the memory of the control system.

For example, AR content may be generated for surgical planning and/or critical structure detection, etc. Referring now to FIG. 196, a three-dimensional model 5068 of an anatomical structure 5069 generated by a surgical visualization system is depicted. The surgical visualization system can include an imaging device 5070 with a distance sensor system 5071 having an emitter 5072 configured to emit electromagnetic radiation 5074 onto the anatomical structure 5069, and a receiver 5076 configured to detect reflected electromagnetic radiation 5074. The imaging device 5070 of FIG. 196 can utilize the aforementioned spectral light, structured light, and Laser Doppler techniques to identify critical structures, such as a tumor 5078, and generate a fully integrated model 5068 and detailed characterization of the anatomical structure 5069. For example, the three-dimensional model 5068 of FIG. 192 can depict the anatomical structure 5069 as the superior lobe of a right lung, and can depict various characteristics of the anatomical structure 5069 with specificity, such as an artery 5080, a vein 5082, a bronchus 5084, a superior lobar bronchus 5086, a right pulmonary artery 5090, and/or a main bronchus 5092. Although the anatomical structure 5069 of FIG. 196 is a lung, the surgical visualization system can model various anatomical structures depending on the intended implementation. Accordingly, the surgical visualization system can use spectral light, structured light, and/or Laser Doppler to characterize any anatomical structure and display detected characteristics in detail via a three-dimensional model.

AR content may include a proximity alert when the distal tip of a surgical instrument moves within a certain range of the critical structure 5078. For example, real-time, three-dimensional spatial tracking of the distal tip of a surgical instrument may be performed. The distance sensor system 5071 of the imaging device 5070 can be positioned on the distal tip of a surgical instrument. Accordingly, the emitter 5072 can emit electromagnetic radiation 5074 onto the surface of the anatomical structure 5069 and the receiver 5076 can detect electromagnetic radiation 5074 that has reflected off the surface of the anatomical structure 5069. The surgical visualization system can determine a position of the emitter 5072 relative to the surface of the anatomical structure 5069 based on a time-of-flight of the electromagnetic radiation 5074, or the time between its emission from the emitter 5072 and its detection by the receiver 5076. Although the surgical visualization system may use a distance sensor system 5071 and time-of-flight technique to determine the position of a surgical instrument relative to the anatomical structure 5069, other suitable components and/or techniques can be employed to achieve the same effect and include the position of a surgical instrument in the three-dimensional model 5068 of the anatomical structure 5069.

In examples, the AR control parameter may be a progression of the surgical procedure, and different AR contents for overlaying via different AR devices may be determined based on the progression of the surgical procedure. For example, based the surgical progression approaches a transection, the AR content provided to the AR device associated with a surgeon may include a proposed transection path. The AR content provided to another AR device may include a notification that the surgery is reaching an important step.

Referring to FIG. 197, a display of the three-dimensional model 5068 of FIG. 196 is depicted in accordance with at least one aspect of the present disclosure. The AR content may include a resection margin overlay configured to depict user selected transection path 5096 and a system proposed transection path 5104. For example, the resection margin overlay can further depict detected characteristics such as the artery 5080, vein 5082, and bronchus 5084, detected subject tissues such as a tumor 5094, and/or a predetermined margin 5095 based on an instruction stored in the memory 134 (FIG. 2). Having reviewed the AR content superimposed or overlaid on the surgical display, the operating clinician(s) can determine a user selected transection path 5096 to remove the tumor 5094 and predetermined margin 5095. For example, the operating clinician(s) can determine a user selected transection path 5096 that can optimize the residual volume of the anatomical structure 5069, such as lung volume. Accordingly, the operating clinician(s) can provide the user selected transection path 5096 to the surgical visualization system via a user interface.

The surgical visualization system can receive the user selected transection path 5096 via user interface and assess the user selected transection path 5096 relative to the position of any detected characteristics of the anatomical structure 5069. For example, as depicted in FIG. 197, the surgical visualization system can identify that the user selected transection path 5096 interferes with an artery 5080, vein 5082, and bronchus 5084 of the anatomical structure 5069. Accordingly, the combined view 5093 (e.g., surgical display superimposed with AR content) can depict the anticipated interference and issue a notification to the operating clinician(s). The notification can be visual, audible, haptic, and/or any combination thereof. The display can additionally highlight a characteristic or a portion of the anatomical structure 5069 affected by the user selected transection path 5096 and/or a portion of the anatomical structure 5069 that can be rendered non-viable by the user selected transection path 5096. For example, the AR content can highlight a transected portion 5098 of the artery 5080 to represent a blood supply 5100 that would be affected by the user selected transection path 5096. The AR content may highlight a portion 5102 of the anatomical structure 5069 that can be rendered non-viable by the user selected transection path 5096 dude to a lack of blood or air.

Additionally and/or alternatively, the AR content may include a system proposed transection path 5104 that may optimize the residual volume of the anatomical structure 5069, remove the subject tissue 5094 and predetermined margin 5095, and minimize adverse impacts to the detected characteristics of the anatomical structure 5069. For example, although the system proposed transection path 5104 may preserve less residual volume of the anatomical structure 5069, it may not interfere with the artery 5080, vein 5082, and bronchus 5084 and may still remove the tumor 5094 and predetermined margin 5095 from the superior lobe of the lung. In some aspects, the surgical visualization system can allow the operating clinician(s) to choose either the user selected transection path 5096 or the system proposed transection path 5104. In other aspects, the surgical visualization system can allow the operating clinician(s) to decline the system proposed transection path 5104 and input a second user selected transection path based on the depicted information on the display.

Referring now to FIG. 198, an AR content combined with display view 5106 three-dimensional model 5108 of an anatomical structure 5110 generated by a surgical visualization system 5107 is depicted in accordance with at least one aspect of the present disclosure. The surgical visualization system 5107 can include a surgical instrument 5109 with a distance sensor system, a structured light system, a spectral light system, or any combination thereof. Having reviewed the display 5106, the operating clinician(s) can determine a user selected transection path 5112 to remove a subject tissue from the anatomical structure 5110. The surgical visualization system 5107 of FIG. 198 can receive the user selected transection path 5112 via user interface and assess the user selected transection path 5112 relative to the position of any detected characteristics of the anatomical structure 5110. For example, the surgical visualization system 5107 of FIG. 198 has identified that the user selected transection path 5112 can interfere with a portion 5114 of the anatomical structure 5110 that is underinflated. The underinflated portion 5114 of the anatomical structure 5110 can have an adverse effect on the excision of a subject tissue and can lead to post-operative complications, including a less than optimal residual volume of the anatomical structure 5110. Accordingly, the AR content include an indication of the anticipated problem and a notification to the operating clinician(s). The notification can be visual, audible, haptic, and/or any combination thereof.

Additionally and/or alternatively, the AR content shown in FIG. 198 can depict a system proposed transection path 5116 that may be overlaid on the display. The system proposed path may optimize the residual volume of the anatomical structure 5110, remove the subject tissue and predetermined margin, and/or minimize adverse impacts caused by the detected characteristics of the anatomical structure 5110. For example, the transection of underinflated tissue 5114 could complicate the surgical procedure and introduce unnecessary risk. The system proposed transection path 5116 of FIG. 198 directs the operating clinician(s) to the fully inflated tissue of the anatomical structure 5110, thereby minimizes the risk. In some aspects, the surgical visualization system 5107 can allow the operating clinician(s) to choose either the user selected transection path 5112 or the system proposed transection path 5116. In other aspects, the surgical visualization system 5107 can allow the operating clinician(s) to decline the system proposed transection path 5116 and input a second user selected transection path based on the depicted information on the display 5106.

The surgical instrument(s) described herein can be configured with a distance sensor system, or other means to enable the surgical visualization system to detect a position of the surgical instrument relative to the anatomical structure. The surgical visualization systems discussed herein can also issue notifications via the AR device(s), informing the operating clinician(s) if a detected position of the surgical instrument does not comply with the selected transection path. The surgical visualization systems can issue, via the AR device(s), a visual, audible, and/or haptic notification to the operating clinician(s) indicating that the surgical instrument should be repositioned prior to commencing the surgical procedure. In some aspects, the surgical visualization system can, via the AR device(s), prevent the operating clinician(s) from performing the surgical procedure until the surgical instrument is properly positioned in accordance with the selected transaction path depicted on the display.

Display of automatically adjustable tumor margins based on visually identified key structures, anomalies, and instrument sensed tissue properties is further described in U.S. patent application Ser. No. 16/729,778 titled SYSTEM AND METHOD FOR DETERMINING, ADJUSTING, AND MANAGING RESECTION MARGIN ABOUT A SUBJECT TISSUE, filed Dec. 31, 2019, which is incorporated by reference herein in its entirety.

In examples, the AR content may include visualization of obstructed portions of a surgical site. The visualization of the obstructed portions of the surgical site may be overlaid on the livestream of a surgical site in the surgical operating room from the medical imaging device. The visualization of the obstructed portions of the surgical site may be generated using a multispectral EMR source.

FIG. 199 shows an example fused image generated from a multispectral EMR source. The fused image may be generated using image data from at least three different EMR wavelength ranges to generate the resulting image. Multiple images may be used to collectively visualize the surgical site at the corresponding EMR wavelength range. For example, a first image may be captured utilizing the visible light portion of the EMR spectrum and includes a first unobstructed portion, with the remaining portions of the image being obstructed; the second image may be captured utilizing the MWIR portion of the EMR spectrum and includes a second unobstructed portion; and a third image 3042c may be captured utilizing the LWIR portion of the EMR spectrum and includes a third unobstructed portion. For example, a fourth image may be captured utilizing the visible light portion of the EMR spectrum and thus can correspond to the first image, but may include additional image processing to identify a fluid (water) obstructed portion. Accordingly, the corresponding portion of the first image could be filtered at a corresponding wavelength or wavelength range (e.g., the blue-green portion of the visible light spectrum) to remove the obstruction.

A combination or fused image 3070 may be generated from the aforementioned initial images. The fused image 3070 can include a first portion 3072 corresponding to the unobstructed portion of the first image generated from the visible light portion of the EMR spectrum, a second portion 3074 corresponding to the unobstructed portion of the second image generated from the MWIR portion of the EMR spectrum, a third portion 3076 corresponding to the unobstructed portion of the third image generated from the LWIR portion of the EMR spectrum, and a fourth portion 3078 corresponding to the obstructed portion of an image generated from the visible light portion of the EMR spectrum, but post-processed to remove the blue-green portion of the visible light spectrum. Each of the aforementioned image portions 3072, 3074, 3076, 3078 can be fused together to generate the fused image 3070 that provides for an unobstructed visualization of the tumor 3038 and any other relevant structures 3040.

Utilization of fusion imagery is described in detail in U.S. patent application Ser. No. 16/729,807 titled METHOD OF USING IMAGING DEVICES IN SURGERY, filed Dec. 31, 2019, which is incorporated by reference herein in its entirety.

FIGS. 201A-C illustrate examples of a sequence of surgical steps for the removal of an intestinal/colon tumor and which may benefit from the AR content generated using multi-image analysis at the surgical site. FIG. 201A depicts a portion of the surgical site, including the intestines 2932 and the ramified vasculature 2934 supplying blood and nutrients to the intestines 2932. The intestines 2932 may have a tumor 2936 surrounded by a tumor margin 2937. A first light sensor module of a visualization system may have a wide field of view 2930, and it may provide imaging data of the wide field of view 2930 to a display system. A second light sensor module of the visualization system may have a narrow or standard field of view 2940, and it may provide imaging data of the narrow field of view 2940 to the display system. In some aspects, the wide field image and the narrow field image may be displayed by the same display device. In another aspect, the wide field image and the narrow field image may be displayed by separate display devices.

During the surgical procedure, it may be important to remove not just the tumor 2936 but the margin 2937 surrounding it to assure complete removal of the tumor. A wide-angle field of view 2930 may be used to image both the vasculature 2934 as well as the section of the intestines 2932 surrounding the tumor 2936 and the margin 2637. As noted above, the vasculature feeding the tumor 2936 and the margin 2637 should be removed, but the vasculature feeding the surrounding intestinal tissue must be preserved to provide oxygen and nutrients to the surrounding tissue. Transection of the vasculature feeding the surrounding colon tissue will remove oxygen and nutrients from the tissue, leading to necrosis. In some examples, laser Doppler imaging of the tissue visualized in the wide-angle field 2630 may be analyzed to provide a speckle contrast analysis 2933, indicating the blood flow within the intestinal tissue.

The AR content may include an indication of blood flow within a tissue. For example, the AR content may include an indication of which part of the vascular tree may supply blood to a tumor. FIG. 201B illustrates a step during the surgical procedure. The surgeon may be uncertain which part of the vascular tree supplies blood to the tumor 2936. The surgeon may test a blood vessel 2944 to determine if it feeds the tumor 2936 or the healthy tissue. The surgeon may clamp a blood vessel 2944 with a clamping device 2812 and determine the section of the intestinal tissue 2943 that is no longer perfused by means of the speckle contrast analysis. The narrow field of view 2940 displayed on an imaging device may assist the surgeon in the close-up and detailed work required to visualize the single blood vessel 2944 to be tested. When the suspected blood vessel 2944 is clamped, a portion of the intestinal tissue 2943 is determined to lack perfusion based on the Doppler imaging speckle contrast analysis. The suspected blood vessel 2944 does not supply blood to the tumor 2935 or the tumor margin 2937, and therefore is recognized as a blood vessel to be spared during the surgical procedure.

FIG. 201C depicts a following stage of the surgical procedure. In stage, a supply blood vessel 2984 has been identified to supply blood to the margin 2937 of the tumor. When this supply blood vessel 2984 has been severed, blood is no longer supplied to a section of the intestine 2987 that may include at least a portion of the margin 2937 of the tumor 2936. In some aspects, the lack of perfusion to the section 2987 of the intestines may be determined by means of a speckle contrast analysis based on a Doppler analysis of blood flow into the intestines. The non-perfused section 2987 of the intestines may then be isolated by a seal 2985 applied to the intestine. In this manner, only those blood vessels perfusing the tissue indicated for surgical removal may be identified and sealed, thereby sparing healthy tissue from unintended surgical consequences.

The AR content may be generated based on imaging analysis of the surgical site. The surgical site may be inspected for the effectiveness of surgical manipulation of a tissue. Non-limiting examples of such inspection may include the inspection of surgical staples or welds used to seal tissue at a surgical site. Cone beam coherent tomography using one or more illumination sources may be used for such methods. The AR content may include landmarks denoted in an image of a surgical site. In some examples, the landmarks may be determined through image analysis techniques. In some examples, the landmarks may be denoted through a manual intervention of the image by the surgeon. In some aspects, non-smart ready visualizations methods may be imported for used in hub image fusion techniques.

The instruments that are not integrated in the hub system may be identified and tracked during their use within the surgical site. In this aspect, computational and/or storage components of the hub or in any of its components (including, for example, in the cloud system) may include a database of images related to EES and competitive surgical instruments that are identifiable from one or more images acquired through any image acquisition system or through visual analytics of such alternative instruments. The imaging analysis of such devices may further permit identification of when an instrument is replaced with a different instrument to do the same or a similar job. The identification of the replacement of an instrument during a surgical procedure may provide information related to when an instrument is not doing the job or a failure of the device.

In examples, AR content may include anatomical identification information that may be generated based on pre-operative image(s). The AR content may be overlaid on a video image of a surgical site within the patient. The anatomical identification information may be overlaid on the livestream of a surgical site in the surgical operating room from the medical imaging device.

FIG. 202 illustrates an example of an augmented video image 6350 comprising a pre-operative video image 6352 augmented with data 6354, 6356, 6358 identifying displayed elements. AR data may be overlaid or superimposed onto a pre-operative image 6352 via an AR device. A pre-operative image 6352 of an anatomical section of a patient may be generated. An augmented video image of a surgical site within the patient may be generated. The augmented video image 6350 can include an image of at least a portion of a surgical tool 6354 operated by a user 6456. The pre-operative image 6352 may be processed to generate data about the anatomical section of the patient. The AR content can include a label 6358 for the anatomical section and a peripheral margin of at least a portion of the anatomical section. The peripheral margin can be configured to guide a surgeon to a cutting location relative to the anatomical section, embedding the data and an identity of the user 6356 within the pre-operative image 6350 to display an augmented video image 6350 to the user about the anatomical section of the patient. A loading condition on the surgical tool 6354 may be sensed, a feedback signal may be generated based on the sensed loading condition. The AR content, including the data and a location of the identity of the user operating the surgical tool 6354 may be updated in real time, in response to a change in a location of the surgical tool 6354 within the augmented video image 6350. Further examples are disclosed in U.S. Pat. No. 9,123,155, titled APPARATUS AND METHOD FOR USING AUGMENTED REALITY VISION SYSTEM IN SURGICAL PROCEDURES, which issued on Sep. 1, 2015, which is herein incorporated by reference in its entirety.

Radiographic integration techniques may be employed to overlay the pre-operative image 6352 with data obtained through live internal sensing or pre-procedure techniques. Radiographic integration may include marker and landmark identification using surgical landmarks, radiographic markers placed in or outside the patient, identification of radiopaque staples, clips or other tissue-fixated items. Digital radiography techniques may be employed to generate digital images for overlaying with a pre-operative image 6352. Digital radiography is a form of X-ray imaging that employs a digital image capture device with digital X-ray sensors instead of traditional photo graphic film. Digital radiography techniques provide immediate image preview and availability for overlaying with the pre-operative image 6352. In addition, special image processing techniques can be applied to the digital X-ray mages to enhance the overall display quality of the image.

Digital radiography techniques can employ image detectors that include flat panel detectors (FPDs), which are classified in two main categories indirect FPDs and direct FPDs. Indirect FPDs include amorphous silicon (a-Si) combined with a scintillator in the detector's outer layer, which is made from cesium iodide (CSI) or gadolinium oxy-sulfide ($Gd_2O_2S$), converts X-rays to light. The light can be channeled through the a-Si photodiode layer where it is converted to a digital output signal. The digital signal is then read out by thin film transistors (TFTs) or fiber-coupled charge coupled devices (CODs). Direct FPDs include amorphous selenium (a-Se) FPDs that convert X-ray photons directly into charge. The outer layer of a flat panel in this design is typically a high-voltage bias electrode. X-ray photons create electron hole pairs in a-Se, and the transit of these electrons and holes depends on the potential of the bias voltage charge. As the holes are replaced with electrons, the resultant charge pattern in the selenium layer is read out by a TFT array, active matrix array, electrometer probes or micro plasma line addressing. Other direct digital detectors are based on CMOS and CCD technology. Phosphor detectors also may be employed to record the X-ray energy during exposure and is scanned by a laser diode to excite the stored energy which is released and read out by a digital image capture array of a CCD.

In examples, the AR control parameter may be a real-time user input, and different AR contents for overlaying via different AR devices may be determined based on user input. For example, a user interface may be presented for the user to select one or more AR content for displaying at the AR device. The hub may generate and send the AR content in accordance with the user selection.

FIG. 203 illustrates an example of customizable AR content overlay. As shown, AR content options 17410 may be presented, for example, on an interactive display screen. AR content options 17410 may include available overlay layers, which can include pre-surgery tumor MRI, other relevant pre-surgery data, ICG data, real-time doppler monitoring, procedural steps, device status, and other overlays customizable by the users. The overlay layers may be provided by the hub. In this example, pre-surgery tumor data and real time doppler monitoring have been selected, and such data is included in the AR content to be overlaid on the surgical image. Through the AR device, the user may view vision 17420, which shows the two selected overlays: pre-surgery tumor MRI and real time Doppler monitoring. As shown, AR content may include marking the tumor 14733 and the tumor margin 17432. With the help of the overlay, the user can clamp jaws 17436 onto a vessel to verify if the vessel is within, or without tumor margins. AR content may indicate the blood flow of a vessel. For example, whether a vessel is associated with low blood flow or high blood flow may be indicated via color coding in the AR content. To illustrate, the AR content may include changing the low blood flow vessels 17434 to blue vessels, and changing high blood flow vessels 17438 to red.

The hub, in communication with the augmented reality device can provide simulation or confirmation of the intended action. The AR content may include an indication of a predicted outcome if user performs the intended action. As an example, if the user clamps or has the jaws over the intended area to staple, dissect, or seal, the AR content may indicate to the user the change of flow of fluids. This may provide guidance to the user to move in one direction or another. For example, the surgical hub may receive an indication of an intended action on a target area. The indication may include an image captured via a surgical scope indicating a surgical instrument being placed on or proximate to a target area. The indication may include an image captured via the AR device indicating a surgical instrument being placed on or proximate to a target area. For example, the AR content may be generated based on a microwave ablation confirmation, which can show the predicted output based on time and temperature. The surgical hub may receive visual input from the camera(s) in the OR, and sensor input from the surgical device(s) in the OR. The surgical hub may combine and compile the received inputs and generate confirmation and/or feedback of expected outcome for inclusion in the AR content. The hub may synthesize various data streams into a coherent output that can be overlay or shown on the displays, including the primary and/or the secondary displays, AR displays and/or non-AR displays. The surgical hub may obtain a predicted outcome associated with performing the intended action on the target area and may include the predicted outcome in the AR content. The predicted outcome may be determined based on visual data received from the surgical scope and surgical data received from the surgical instrument(s). The predicted outcome may be determined by the surgical hub, or with the help of a remote server. For example, the surgical hub may obtain visual data from a surgical scope and sensor input data from the at least one surgical instrument and send the visual data and the sensor input data to a remote server. The predicted outcome may be received from the remote server and included in the AR content for display at the AR device.

FIG. 211 shows an example flow of a hub operation under a visualization control with AR capabilities. The AR content for overlaying on a display may vary by the AR device. At 17711, the hub may obtain an AR control parameter as described herein. The AR control parameter may comprise at least one of: a user's role, a user's orientation relative to the first display, a progression of the surgical procedure, a surgical context, a real-time use input, or a preconfigured user preference. At 17712, the hub may obtain, from a surgical instrument, a data stream for displaying on a display. The data stream may be or may include video image(s) of a surgical site within a patient. The hub, at 17713, may determine, based on the AR control parameter, the AR content for overlaying on the data stream displayed on the display via a first AR device. An AR device for use by a surgeon may display AR content different than the AR content displayed via an AR device for use by a surgeon's assistant. An AR device with one preconfigured user preference may display AR content different than the AR content displayed via an AR device with a different preconfigured user preference. The AR content may include a step for use associated with a surgical instrument, a device setting, a device status, a device instruction for use, operation parameter(s), and/or an indication of a detected abnormality. The hub, at 17714, may determine, based on the AR control parameter, the AR content for overlaying on the data stream displayed on the display via a second AR device. At 17715, the hub, based on the determined AR contents for the respective AR devices for display, send the AR contents to the respective AR devices.

A powered surgical device may include a processor configured to obtain one or more multi-display control parameter(s) and identify a current multi-display control mode based on the multi-display control parameter(s). Based on the current multi-display control mode, whether to generate visualization control data associated with the display outside of the surgical sterile field may be determined. The powered surgical device may interact with the display inside the surgical sterile field and the display outside of the surgical sterile field based on the determination.

The multi-display(s) control parameter may include an indication from the surgical hub. The multi-display control parameter(s) may include a consumer-controlled parameter, such as a subscription level. The multi-display control parameter(s) may include available data bandwidth, power capacity and usage, processor and memory utilization, and/ or internal or attached systems. The multi-display control parameter(s) may include an indication from a tiered system.

The powered surgical device may operate under various multi-display control modes such as one-way communication mode, sterile field display-based control mode, and/or remote aggregation analysis mode.

For example, when operating in an example one-way communication mode, the surgical device may receive content for displaying on the display inside the surgical sterile field and send the received content to the display. The content for displaying on the display inside the surgical sterile field may be received from a surgical hub.

For example, when operating in an example sterile field display-based control mode, the surgical instrument may obtain, via the display inside the surgical sterile field, the visualization control data associated with the display outside of the surgical sterile field. The surgical instrument may send the visualization control data associated with the display (e.g., to the surgical hub) for controlling the display outside of the surgical sterile field. When operating under a multi-display control mode does not support sterile field display-based control, the surgical instrument may disable generation of the visualization control data associated with the display outside of the surgical sterile field.

The surgical instrument may determine that the current multi-display control mode supports sterile field display-based control and may receive a user indication of changing the content on the display outside of the surgical sterile field. The surgical instrument may generate the visualization control data associated with the display outside of the surgical sterile field based on the received user indication, and send the visualization control data associated with the display outside of the surgical sterile field (e.g., to the surgical hub) for controlling the display outside of the surgical sterile field. The user indication of changing the content on the display outside of the surgical sterile field may be received via the display inside a surgical sterile field. The user indication may indicate projecting content associated with the display inside the surgical sterile field onto the display outside of the surgical sterile field, or removing the content associated with the display inside the surgical sterile field from the display outside of the surgical sterile field.

For example, when operating in an example remote aggregation analysis mode, surgical instrument may request aggregation analysis from a remote server (e.g., via the surgical hub). The surgical instrument may determine, based on the current multi-display control mode, whether to request aggregation analysis from a remote server (e.g., via the surgical hub). Based on a determination to request the aggregation analysis, an aggregation analysis request may be generated. An aggregation analysis response may be received and combined with surgical data generated based on the sensed surgical data for displaying on the display inside the surgical sterile field.

A surgical hub may include a communication array operably connected to a surgical instrument, a display inside a surgical sterile field and a display outside of the surgical sterile field. The surgical hub may include a processor configured to obtain a multi-display control parameter and identify a current multi-display control mode based on the multi-display control parameter. The surgical hub may interact at least one the display inside the surgical sterile field and at least one display outside of the surgical sterile field based on the current multi-display control mode. For example, the surgical hub may determine whether to receive visualization control data associated with a display outside of the surgical sterile field from a display inside the surgical sterile field based on the current multi-display control mode.

The surgical hub may operate under various multi-display control modes such as one-way communication mode, sterile field display-based control mode, and/or remote aggregation analysis mode.

Based on a determination that the current multi-display control mode supports sterile field display-based control, the surgical hub may receive the visualization control data associated with the display outside of the surgical sterile field, and may control the display outside of the surgical sterile field based on the received visualization control data associated with the display outside of the surgical sterile field.

The surgical hub may determine, based on the current multi-display control mode, whether to retrieve aggregation analysis from a remote server for displaying on the first display inside the surgical sterile field. Based on a determination that the current multi-display control mode supports remote aggregation, the surgical hub may generate an aggregation analysis request. The aggregation analysis request may be generated based on an indication from the display inside the sterile field. The surgical instrument may receive an aggregation analysis response, and may combine the received aggregation analysis response with surgical data received from the at least one instrument to generate content for displaying on first display inside the surgical sterile field.

A tiered multi-display control scheme may provide various communication control options for a surgeon-controlled secondary display and primary operating room display. A powered surgical tool may be in operative communication with a local display and at least one main monitor within the operating room outside the sterile field for displaying multiple data and/or imaging sources. The local display may be interactable by the surgeon within the sterile field. The display outside the sterile field may show an image of an aspect of the laparoscopic scope and may contain superimposed other data streams from other devices besides the scope. The secondary display could be used to direct from its displayed content up onto the primary display or remove it from the display. The added or removed data streams may be originated from the secondary display, passed through the secondary display, or be networked with the secondary display.

FIG. 214 shows an example flow 18200 for operating under tiered multi-display control mode(s). As shown in FIG. 214, at 18205, a device such as a powered surgical device or a surgical hub may be connected to one or more display(s) inside the surgical sterile field and one or more display(s) outside of the surgical sterile field. The powered surgical device may be or may include surgical instruments 112 shown in FIG. 1, the surgical instrument 600 shown in FIG. 8, or the modular devices 5102 shown in FIG. 9, for example. The powered surgical device may include a communication array operably connected to display(s) inside and outside the surgical sterile field.

The display outside of the sterile field may be or may include the non-sterile display 107 or 109 as shown in FIG. 2. For example, the display inside a surgical sterile field may be or may include a secondary display such as a local display or a display on a surgical instrument. The display inside a surgical sterile field may be a secondary display. A healthcare personnel may control the secondary display. The primary display(s) and secondary display(s) may have numerous communication levels of operation with the primary hub system. Examples of primary display(s) and secondary display(s) can be found in more detail in U.S.

patent application Ser. No. 15/940,671, titled SURGICAL HUB SPATIAL AWARENESS TO DETERMINE DEVICES IN OPERATING THEATER, which was filed on Mar. 29, 2018, which is herein incorporated by reference in its entirety.

FIG. 183 illustrates an example primary display 6200 associate with the surgical hub 206 comprising a global display window 6202 and a local instrument display window 6204, according to one aspect of the present disclosure. With continued reference to FIGS. 1-11 to show interaction with an interactive surgical system 100 environment including a surgical hub 106, 206 and FIGS. 12-14 for surgical hub connected instruments together, the local instrument display 6204 behavior may be displayed when the instrument 235 senses the connectable presence of a global display window 6202 through the surgical hub 206. The global display window 6202 may show a field of view 6206 of a surgical site 6208, as viewed through a medical imaging device such as, for example, a laparoscope/endoscope 219 coupled to an imaging module 238, at the center of the surgical hub display 215, referred to herein also as a monitor, for example. The end effector 6218 portion of the connected instrument 235 may be shown in the field of view 6206 of the surgical site 6208 in the global display window 6202. The images shown on the display 237 located on an instrument 235 coupled to the surgical hub 206 is shown, or mirrored, on the local instrument display window 6204 located in the lower right corner of the monitor 6200 as shown in FIG. 183, for example.

During operation, relevant instrument and information and menus may be displayed on the display 237 located on the instrument 235 until the instrument 235 senses a connection of the instrument 235 to the surgical hub 206 at which point all or some sub-set of the information presented on the instrument display 237 may be displayed (e.g., only) on the local instrument display window 6204 portion of the surgical hub display 6200 through the surgical hub 206. The information displayed on the local instrument display window 6204 may be mirrored on the display 237 located on the instrument 235 or may be no longer accessible on the instrument display 237 detonated screen. This technique frees up the instrument 235 to show different information or to show larger font information on the surgical hub display 6200.

The primary display 6200 may provide perioperative visualization of the surgical site 6208. Advanced imaging may identify and visually highlight 6222 critical structures such as the ureter 6220 (or nerves, etc.) and may track instrument proximity displays 6210 and shown on the left side of the display 6200. In the illustrated example, the instrument proximity displays 6210 may show instrument specific settings. For example, the top instrument proximity display 6212 may show settings for a monopolar instrument, the middle instrument proximity display 6214 may show settings for a bipolar instrument, and the bottom instrument proximity display 6212 may show settings for an ultrasonic instrument.

Secondary displays may include independent secondary displays and/or dedicated local displays that can be linked to the surgical hub 206 to provide an interaction portal via a touchscreen display and/or a secondary screen that can display any number of surgical hub 206 tracked data feeds to provide a status. The secondary display may display force to fire (FTF), tissue gap, power level, impedance, tissue compression stability (creep), etc., while the primary display may display only key variables to keep the feed free of clutter. The interactive display may be used to move the display of specific information to the primary display to a desired location, size, color, etc. In the illustrated example, the secondary display may display the instrument proximity displays 6210 on the left side of the display 6200. The local instrument display 6204 on the bottom right side of the display 6200. The local instrument display 6204 presented on the surgical hub display 6200 may display an icon of the end effector 6218, such as the icon of a staple cartridge 6224 currently in use, the size 6226 of the staple cartridge 6224 (e.g., 60 mm), and an icon of the current position of the knife 6228 of the end effector.

A secondary display may be the display 237 as shown in FIG. 5. Referring to FIG. 5, the display 237 located on the instrument 235 can display the wireless or wired attachment of the instrument 235 to the surgical hub 206 and the instrument's communication and/or recording on the surgical hub 206. A setting may be provided on the instrument 235 to enable the user to select mirroring or extending the display to both monitoring devices. The instrument controls may be used to interact with the surgical hub display of the information being sourced on the instrument. The instrument 235 may comprise wireless communication circuits to communicate wirelessly with the surgical hub 206, as described herein.

A first instrument coupled to the surgical hub 206 can pair to a screen of a second instrument coupled to the surgical hub 206 allowing both instruments to display some hybrid combination of information from the two devices of both becoming mirrors of portions of the primary display. The primary display 6200 of the surgical hub 206 can provide a 360° composite top visual view of the surgical site 6208 to avoid collateral structures. For example, a secondary display of the end effector surgical stapler may be provided within the primary display 6200 of the surgical hub 206 or on another display in order to provide better perspective around the areas within a current the field of view 6206.

FIG. 184 illustrate an example primary display having a composite overhead views of an end-effector 6234 portion of a surgical stapler mapped using two or more imaging arrays or one array and time to provide multiple perspective views of the end-effector 6234 to enable the composite imaging of an overhead field of view. The techniques described herein may be applied to ultrasonic instruments, electrosurgical instruments, combination ultrasonic/electrosurgical instruments, and/or combination surgical stapler/electrosurgical instruments. Several techniques may be performed for overlaying or augmenting images and/or text from multiple image/text sources to present composite images on a display (e.g., a single display).

As shown in FIG. 184, a primary display 6200 of the surgical hub 206 may display a primary window 6230. The primary window 6230 may be located at the center of the screen shows a magnified or exploded narrow angle view of a surgical field of view 6232. The primary window 6230 located in the center of the screen shows a magnified or narrow angle view of an end-effector 6234 of the surgical stapler grasping a vessel 6236. The primary window 6230 may display knitted images to produce a composite image that enables visualization of structures adjacent to the surgical field of view 6232. A second window 6240 may be shown in the lower left corner of the primary display 6200. The second window 6240 displays a knitted image in a wide-angle view at standard focus of the image shown in the primary window 6230 in an overhead view. The overhead view provided in the second window 6240 can enable the viewer to easily see items that are out of the narrow field surgical field of view 6232 without moving the laparoscope, or other imaging device 239 coupled to the imaging module 238 of the surgical hub 206. A third window 6242 can be shown in the lower right corner of the primary display 6200 shows an icon 6244 representative of the staple cartridge of the end-effector 6234 (e.g., a staple cartridge in this instance) and additional information such as "4 Row" indicating the number of staple rows 6246 and "35 mm" indicating the distance 3248 traversed by the knife along the length of the staple cartridge. Below the third window 6242 is displayed an icon 6258 of a frame of the current state of a clamp stabilization sequence that indicates clamp stabilization.

The local display/secondary display may be or may include an augmented reality (AR device). The AR device may include a head-mounted display (HMD). An HMD may include a processor, a non-transitory computer readable memory storage medium, and executable instructions contained within the storage medium that are executable by the processor to carry out methods or portions of methods disclosed herein. The HMD may include a graphics processor for rendering 2D or 3D video and/imaging for display.

FIG. 185 depicts a perspective view of a surgeon using a surgical instrument that includes a handle assembly housing and a wireless circuit board during a surgical procedure, with the surgeon wearing a set of safety glasses. The safety glasses may be or may include an AR device that may serve as a secondary display. The wireless circuit board transmits a signal to a set of safety glasses worn by a surgeon using the surgical instrument during a procedure. The signal is received by a wireless port on the safety glasses. One or more lighting devices on a front lens of the safety glasses change color, fade, or glow in response to the received signal to indicate information to the surgeon about the status of the surgical instrument. The lighting devices are disposable on peripheral edges of the front lens to not distract the direct line of vision of the surgeon. Further examples are disclosed in U.S. Pat. No. 9,011,427, titled SURGICAL INSTRUMENT WITH SAFETY GLASSES, which issued on Apr. 21, 2015, which is herein incorporated by reference in its entirety.

FIG. 185 shows a version of safety glasses 6991 that may be worn by a surgeon 6992 during a surgical procedure while using a medical device. In use, a wireless communications board housed in a surgical instrument 6993 may communicate with a wireless port 6994 on safety glasses 6991. Exemplary surgical instrument 6993 is a battery-operated device, though instrument 6993 could be powered by a cable or otherwise. Instrument 6993 includes an end effector. Particularly, wireless communications board 6995 transmits one or more wireless signals indicated by arrows (B, C) to wireless port 6994 of safety glasses 6991. Safety glasses 6991 receive the signal, analyze the received signal, and display indicated status information received by the signal on lenses 6996 to a user, such as surgeon 6992, wearing safety glasses 6991. Additionally, or alternatively, wireless communications board 6995 transmits a wireless signal to surgical monitor 6997 such that surgical monitor 6997 may display received indicated status information to surgeon 6992, as described above.

A version of the safety glasses 6991 may include lighting device on peripheral edges of the safety glasses 6991. A lighting device provides peripheral-vision sensory feedback of instrument 6993, with which the safety glasses 6991 communicate to a user wearing the safety glasses 6991. The lighting device may be, for example, a light-emitted diode ("LED"), a series of LEDs, or any other suitable lighting device known to those of ordinary skill in the art and apparent in view of the teachings herein.

Referring back to FIG. 214, at 18210, one or more multi-display control parameter(s) may be obtained. At 18215, a current multi-display control mode may be identified based on the multi-display control parameter(s).

For example, the current multi-display control mode may be selected from multiple multi-display control modes that may be preconfigured, dynamically updated, semi-dynamically updated, periodically updated, or preset. The multi-display control modes may support or disable various multi-display control capabilities as described herein.

The multi-display control parameter(s) may include, but not limited to, systems capabilities such as hardware capability, firmware capability and/or software capability associated with the surgical device(s) and/or systems. For example, if secondary display lacks the hardware capability to receive a user indication, the surgical hub may switch to a multi-display control mode that may disable controlling the display content of a primary display via the secondary display.

The multi-display control parameter(s) may include a consumer-controlled parameter, such as a subscription level. For example, a medical facility may purchase a subscription to multi-display control capabilities. Some subscription level(s) may provide the display(s) (e.g., via the hub and/or surgical instrument(s)) access to surgical data gathered from external systems, while others may limit the display control and connectivity to internal devices.

The multi-display control parameter(s) may include available data bandwidth, power capacity and usage, processor and memory utilization, and/or internal or attached systems.

In examples, the multi-display control parameter be or may include an indication from the surgical hub. The multi-display control parameter(s) may include an indication from a tiered system. With reference to FIGS. 217-219, the tiered system may scale the display connectivity and control communication among the surgical hub 18706, the local display 18725, the main display 18730, the communication between the surgical hub 18706 and external server(s) 18713/18722 and/or the like, based on the available data bandwidth, power capacity and usage, processor and memory utilization, and/or internal or attached systems. The tiered system may determine max communication capabilities the surgical system may operate under.

For example, upon detecting the power capability associated with the operation room, associated with the surgical hub, and/or associated with a medical facility is below a threshold, the tiered system may scale down the multi-display control capabilities. For example, upon detecting available data bandwidth is below a threshold, memory utilization is above a certain threshold, power usage is above a certain threshold, and/or other system conditions that may warrant scaling down the multi-display control capabilities, the tiered system may limit or disable the interactions between the primary and secondary display(s), the surgical hub and the display(s) and/or the communication between the surgical system (such as the surgical hub and/or the surgical instruments in the OR) and external server(s). For example, sterile field display-based control mode 18800 (as shown in FIG. 218) may be scaled down to one-way communication mode 18700 (as shown in FIG. 217). External communication capabilities (as described herein with reference to FIG. 219) may be disabled. In examples, the tiered system may be a module within the surgical hub or may be a system external to the surgical hub.

At 18220, whether to generate visualization control data associated with the display outside of the surgical sterile field may be determined based on the current multi-display control mode. At 18230, the device may interact with the display inside the surgical sterile field and the display outside of the surgical sterile field based on the determination.

The surgical system may operate under various multi-display control modes such as one-way communication mode, sterile field display-based control mode, and/or remote aggregation analysis mode.

FIG. 217 shows an example multi-display control mode such as a one-way communication mode 18700. As shown, surgical instrument 18712 and local display 18725 may be placed in the sterile field. The local display 18725 may be part of the surgical instrument 18712 or may be external to the surgical instrument 18712. Main monitor 18730 may be a primary display as described herein and may be located outside of the sterile field. The surgical hub 18706 may be located outside of the sterile field, as shown. In some examples, the surgical hub 18706 may be located inside the sterile field. The local display 18725 can receive information from the surgical instrument 18712 for display, and/or receive information from the surgical hub 18706 for display. The information from the surgical instrument 18712 and the information from the surgical hub 18706 may be combined for display at the local display 18725. The local display 18725 may provide a place the surgeon can view or access a part of the overall data environment.

As shown in FIG. 217, the surgical instrument 18712 may receive, from the surgical hub 18706, content for displaying on the local display 18725 inside the surgical sterile field and send the received content to the display 18725. In some examples, the local display 18725 may receive display content from the surgical hub 18706. The surgical hub 18706 may send display content to the main monitor 18730. In the example one-way communication mode 18700, generation of the visualization control data associated with the display outside of the surgical sterile field based on indication(s) received via the local display 18725 may be disabled. Generation of aggregation analysis requests may be disabled.

FIG. 218 shows an example multi-display control mode 18800 that may support sterile field display-based control. As shown, surgical instrument 18712 and local display 18725 may be placed in the sterile field. The local display 18725 may be part of the surgical instrument 18712 or may be external to the surgical instrument 18712. Main monitor 18730 may be a primary display as described herein and may be located outside of the sterile field. In some examples, the main display may be or may include display(s) outside the sterile field, such as the display 107 or 109 as shown in FIG. 2. In some examples, the main display may be or may include a display inside the sterile field, such as the primary display 119 as shown in FIG. 2. The surgical hub 18706 may be located outside of the sterile field, as shown. In some examples, the surgical hub 18706 may be located inside the sterile field. As shown in FIG. 218, the surgical instrument 18712 may receive, from the surgical hub 18706, content for displaying on the local display 18725 inside the surgical sterile field and send the received content to the display 18725. In some examples, the local display 18725 may receive display content from the surgical hub 18706. The surgical hub 18706 may send display content to the main monitor 18730.

As shown in FIG. 218, the surgical instrument 18712 may receive the visualization control data for controlling the main display 18730 from the local display 18725 inside the surgical sterile field. The surgical instrument 18712 may send the visualization control data for controlling the main display 18730 to the main display 18730. The surgical instrument 18712 may send he visualization control data directly to the main display 18730. The surgical instrument 18712 may send he visualization control data via the surgical hub 18706. The main display 18730 may adjust its display in accordance with the visualization control data.

In some examples, the surgical hub 18706 may receive the visualization control data for controlling the main display 18730 from the local display 18725 inside the surgical sterile field. The surgical hub 18706 may send the visualization control data for controlling the main display 18730 to the main display 18730. The main display 18730 may adjust its display based on the visualization control data.

For example, a secondary display such as the local display 18725 shown in FIG. 218 may serve as a user interface for displaying and controlling of surgical hub functions from within the sterile field. The secondary display could be used to change display locations, what information is displayed where, and/or pass off control of specific functions or devices.

During a surgical procedure, the surgeon may not have a user interface device accessible for interactive input by the surgeon and display within the sterile field. Thus, the surgeon may not interface with the user interface device and the surgical hub from within the sterile field and cannot control other surgical devices through the surgical hub from within the sterile field.

The local display 18725 may include a display unit that may be used within the sterile field and accessible for input and display by the surgeon to allow the surgeon to have interactive input control from the sterile field to control other surgical devices and/or displays coupled to the surgical hub. The display unit may be sterile and located within the sterile field to allow the surgeons to interface with the display unit and the surgical hub to directly interface and configure instruments as necessary without leaving the sterile field. The display unit may be a master device and may be used for display, control, interchanges of tool control, allowing feeds from other surgical hubs without the surgeon leaving the sterile field.

The display unit may be or may include an interactive touchscreen display, an interface configured to couple the interactive touchscreen display to a surgical hub, a processor, and a memory coupled to the processor. The memory may store instructions executable by the processor to receive input commands from the interactive touchscreen display located inside a sterile field and may transmit the input commands to a surgical hub to control devices coupled to the surgical hub located outside the sterile field.

The local display 18725 inside the surgical sterile field may be a secondary surgeon display within the sterile field and accessible for input and display by the surgeon within the sterile field interactive control displays. Sterile field interactive control displays may be shared or dedicated to a particular healthcare professional.

The local display 18725 may be mounted on the operating table, on a stand, or laying on the abdomen or chest of the patient. The sterile field display 18725 is sterile and allows the surgeons to interface with the non-sterile field display 18730 and the surgical hub 18706 via the sterile field display 18725. This may provide the surgeons control of the system and may allow them to directly interface and configure the non-sterile field display(s) 18730 as necessary (e.g., without leaving the sterile field). The sterile field display 18725 may be configured as a master device and may be used for display, control, interchanges of tool control, allowing feeds from other surgical hubs (e.g., without the surgeon leaving the sterile field).

A surgical instrument such as the surgical instrument 18712 may include the local display 18725. The surgical instrument 18712 may include an interactive touchscreen display, an interface configured to couple the interactive touchscreen display to a surgical hub, and a control circuit configured to receive input commands from the interactive touchscreen display located inside a sterile field and transmit the input commands to a surgical hub to control devices coupled to the surgical hub located outside the sterile field.

A non-transitory computer readable medium may store computer readable instructions which, when executed, may cause a machine to receive input commands from an interactive touchscreen display located inside a sterile field and transmit the input commands to a surgical hub through an interface configured to couple the interactive touchscreen display to the surgical hub, to control displays coupled to the surgical hub located outside the sterile field.

Providing the display unit designed to be used within the sterile field and accessible for input and display by the surgeon provides the surgeon interactive input control from the sterile field to control other surgical display(s) coupled to the surgical hub.

A secondary user interface via the display unit may enable control of non-sterile display(s) from within a sterile field. The display unit may include a display device such as an i-pad, e.g., a portable interactive touchscreen display device configured to be introduced into the operating theater in a sterile manner. It could be paired like any other device or it could be location sensitive. The display device may be allowed to function in this manner whenever the display device is placed over a specific location of the draped abdomen of the patient during a surgical procedure.

The local display 18725 inside the surgical sterile field may generate the visualization control data for controlling a non-sterile display such as the main display 18730 outside the surgical sterile field. For example, the visualization control data may indicate a change of display location and/or what information and where the information may be displayed. The visualization control data may indicate passing off the control of specific functions or devices.

For example, the local display 18725 may re-configure the wireless activation devices within the operating theater and their paired energy device if a surgeon hands the device to another. The local display 18725 may be employed as an interactable scalable secondary display allowing the surgeon to overlay other feeds or images like laser Doppler scanning arrays. The local display 18725 may be employed to call up a pre-operative scan or image to review. Once vessel path and depth and device trajectory are estimated, the surgeon may use a sterile field interactable scalable secondary display to overlay other feeds or images. Examples of sterile field display-based control are described under heading "Surgical Hub with Direct Interface Control with Secondary Surgeon Display Units Designed to be within the Sterile Field and Accessible for Input and Display by the Surgeon" in U.S. patent application Ser. No. 15/940,671, titled SURGICAL HUB SPATIAL AWARENESS TO DETERMINE DEVICES IN OPERATING THEATER, which was filed on Mar. 29, 2018, which is herein incorporated by reference in its entirety.

FIG. 219 shows an example multi-display control mode 18900 that may support remote data aggregation analysis. As shown, the surgical instrument 18712 may receive the visualization control data for controlling the main display 18730 from the local display 18725 inside the surgical sterile field. The surgical instrument 18712 may send the visualization control data for controlling the main display 18730 to the main display 18730 (e.g., directly, or via the surgical hub 18706). The main display 18730 may adjust its display based on the visualization control data. In some examples, the surgical hub 18706 may receive the visualization control data for controlling the main display 18730 from the local display 18725 inside the surgical sterile field. The surgical hub 18706 may send the visualization control data for controlling the main display 18730 to the main display 18730. The main display 18730 may adjust its display based on the visualization control data.

As shown in FIG. 219, the local display 18725 may communicate with a remote server 18713 and/or aggregated database 18722 through the surgical hub 18706. The local display 18725 may access and display of data and/or analyses residing on the remote server 18713. The local display 18725 may combine the data and/or analyses retrieved from the remote server 18713 with locally created content and data for display.

FIG. 215 shows an example flow 18300 for operating under tiered multi-display control mode(s). As shown in FIG. 215, at 18312, the current multi-display control mode may be identified based on the multi-display control parameter. At 18315, whether the current multi-display control mode supports sterile field display-based control may be determined. Upon determining that the current multi-display control mode supports sterile field display-based control, at 18316, visualization control data associated with the display outside of the surgical sterile field may be obtained. The visualization control data may be obtained via a display inside a surgical sterile field as described herein. Upon determining that the current multi-display control mode does not support sterile field display-based control, at 18318, generation of the visualization control data associated with a display outside of the surgical sterile field may be disabled.

FIG. 216 shows an example flow 18400 for operating under tiered multi-display control mode(s). As shown in FIG. 216, at 18412, the current multi-display control mode may be identified based on the one or more multi-display control parameter(s). At 18415, whether the current multi-display control mode supports aggregation analysis requests may be determined based on the current multi-display control mode. Based on a determination that the current multi-display control mode supports aggregation analysis requests, an aggregation analysis request may be generated at 18416.

For example, the aggregation analysis request may include a request for historic datasets, steps-for-use, issue resolution, images associated with the current procedure, videos associated with the current procedure, comparative information from prior patients that present in a similar fashion, and/or procedural suggestions.

An aggregation analysis response may be obtained at 18418 and combined with surgical data generated based on the sensed surgical data for displaying on the display inside the surgical sterile field at 18420. At 18428, based on a determination that the current multi-display control mode does not support aggregation analysis requests, generation of aggregation analysis requests may be disabled.

Examples of aggregation (e.g., remote aggregation), requests and analysis are described in detail in U.S. patent application Ser. No. 15/940,668 titled AGGREGATION AND REPORTING OF SURGICAL HUB DATA; filed on Mar. 29, 2018, which is herein incorporated by reference in its entirety.

FIG. 220 shows an example flow 18500 for operating under tiered multi-display control mode(s). In examples, the steps shown in FIG. 220 may be performed by a surgical hub as described herein. As shown in FIG. 220, at 18512, the current multi-display control mode may be identified based on one or more multi-display control parameter(s). At 18515, whether the current multi-display control mode supports sterile field display-based control may be determined. Upon determining that the current multi-display control mode supports sterile field display-based control, at 18516, visualization control data associated with one or more display(s) outside of the surgical sterile field may be received from one or more display(s) inside the surgical sterile field. For example, visualization control data generated via the secondary display(s) can control to change, focus, or control that data displayed on the display(s) outside the sterile field. This may allow a healthcare personnel to more seamlessly view data relative to other imaging or even pre-surgery imaging mechanisms.

For example, sterile field display-based control may allow data to move back and forth, to and from, the surgical hub. The display in the sterile field may act as a control system that may control display location of information (such as on a display outside the sterile field), the storage location of information, etc.

At 18520, the display(s) outside of the surgical sterile field may be controlled based on the visualization control data from the display inside the surgical sterile field. Upon determining that the current multi-display control mode does not support sterile field display-based control, at 18528, control of display(s) outside of the surgical sterile field from display(s) inside the surgical sterile field may be disabled. In some examples, steps 18512, 18515, 18516, 18520 and 18528 may be performed by a surgical hub. In some examples, steps 18512, 18515, 18516, 18520 and 18528 may be performed by a surgical instrument.

FIG. 221 shows an example flow 18600 for operating under tiered multi-display control mode(s). In examples, the steps shown in FIG. 220 may be performed by a surgical hub as described herein. As shown in FIG. 221, at 18612, the current multi-display control mode may be identified based on the multi-display control parameter. At 18615, whether the current multi-display control mode supports remote aggregation analysis requests may be determined based on the current multi-display control mode. Based on a determination that the current multi-display control mode supports remote aggregation analysis requests, an aggregation analysis request may be generated and sent to a remote server at 18616.

For example, the aggregation analysis request may include a request for historic datasets, steps-for-use, issue resolution, images associated with the current procedure, videos associated with the current procedure, comparative information from prior patients that present in a similar fashion, and/or procedural suggestions. The aggregation analysis request being generated based on an indication from the display inside the sterile field.

An aggregation analysis response may be received from the remote server at 18618. The aggregation analysis response may correspond to the aggregation analysis request. For example, the aggregation analysis response may include, but not be limited to historic datasets, steps-for-use, issue resolution, images associated with the current procedure, videos associated with the current procedure, comparative information from prior patients that present in a similar fashion, and/or procedural suggestions. As shown, the received aggregation analysis response may be combined with surgical data generated based on the sensed surgical data for displaying on the display inside the surgical sterile field at 18620. At 18628, based on a determination that the current multi-display control mode does not support remote aggregation analysis requests, generation of aggregation analysis requests may be disabled.

In some examples, steps 18612, 18615, 18616, 18618, 18620 and 18628 may be performed by a surgical hub. In some examples, steps 18612, 18615, 18616, 18618, 18620 and 18628 may be performed by a surgical instrument.

The invention claimed is:

1. A method for analyzing at least a portion of a surgical field, the method comprising:
   receiving a control parameter; and
   based on the control parameter, operating in at least one of: a first mode of operation or a second mode of operation,
   wherein operating in the first mode of operation comprises:
      determining a first metric which represents a present state of moving particles in the at least a portion of a surgical field, and wherein operating in the second mode of operation comprises:
      determining the first metric and a second metric, wherein the second metric represents at least one of: an aggregated state of moving particles in the at least a portion of the surgical field or a present state of moving particles in the at least a portion of the surgical field at a selectable tissue depth.

2. The method of claim 1, wherein the control parameter comprises a parameter indicative of at least one of: power capacity, memory capacity, bandwidth capacity, or processing compatibility.

3. The method of claim 1, wherein the control parameter comprises a parameter indicative of processing compatibility, and wherein processing compatibility indicates a purchased functional tier associated with any of a user or instrument.

4. The method of claim 1, further comprising:
   displaying the first metric and the second metric as an overlay on an image that comprises the at least a portion of the surgical field.

5. The method of claim 1, wherein operating in the second mode of operation further comprises:
   receiving situational awareness information; and
   reducing noise based on the situational awareness information.

6. The method of claim 1, wherein the second mode of operation differs from the first mode of operation in any of a duration of time or a difference in laser-light frequency.

7. The method of claim 1, further comprising:
   illuminating the at least a portion of the surgical field with laser-light;
   receiving reflected laser-light; and
   transforming information indicative of the reflected laser-light to information indicative of moving particles in the at least a portion of the surgical field.

8. A surgical visualization system to analyze at least a portion of a surgical field, the system comprising:
   one or more processors collectively configured to receive a control parameter and, based on the control parameter, to operate in one of at least of a first mode of operation or a second mode of operation, wherein in the first mode of operation the processor determines a first metric which represents a present state of moving particles in the at least a portion of a surgical field, and wherein in the second mode of operation the processor determines the first metric and a second metric, wherein the second metric represents any of an aggregated state of moving particles in the at least a portion of the surgical field and a present state of moving particles in the at least a portion of the surgical field at a selectable tissue depth.

9. The system of claim 8, wherein the control parameter comprises a parameter indicative of any of power capacity, memory capacity, bandwidth capacity, and processing compatibility.

10. The system of claim 8, wherein the control parameter comprises a parameter indicative of processing compatibility, wherein processing compatibility indicates a purchased functional tier associated with any of a user or instrument.

11. The system of claim 8, further comprising:
- a laser-light illumination source configured to illuminate the at least a portion of the surgical field with laser-light;
- a light sensor configured to receive reflected laser-light;
- a field-programmable gate array configured to transform information indicative of the reflected laser-light to information indicative of moving particles in the at least a portion of the surgical field; and
- a display configured to display the first metric and the second metric.

12. The system of claim 11, wherein the field-programmable gate array comprises an output coupled to an exterior processing device, wherein the exterior processing device is configured to aggregate the information indicative of moving particles in the at least a portion of the surgical field, to calculate a second metric, and to send the second metric to the processor.

13. The system of claim 11, wherein the light sensor comprises a complementary metal—oxide—semiconductor (CMOS) imaging sensor array, and wherein the information indicative of moving particles in the at least a portion of the surgical field comprises a number and velocity of moving particles per CMOS element.

14. The system of claim 8, further comprising a display, wherein the display is configured to display the first metric and the second metric as an overlay on an image that comprises the at least a portion of the surgical field.

15. The system of claim 8, wherein the one or more processors comprises a first processor associated with an image acquisition module and a second processor associated with an external processing resource with situational awareness information, wherein in the second mode of operation, noise is reduced based on the situational awareness information.

* * * * *